US011155884B1

(12) United States Patent
Losert et al.

(10) Patent No.: US 11,155,884 B1
(45) Date of Patent: Oct. 26, 2021

(54) DOUBLE-FLOWERING DWARF *CALIBRACHOA*

(71) Applicant: Klemm & Sohn GMBH & CO. KG, Stuttgart (DE)

(72) Inventors: Dominik Losert, Aspach (DE); Nils Klemm, Stuttgart (DE); Andrea Dohm, Pforzheim (DE); Ulrich Sander, Stuttgart (DE); Anita Stöver, Ostfildern (DE)

(73) Assignee: Klemm & Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/072,837

(22) Filed: Oct. 16, 2020

(51) Int. Cl.

| | |
|---|---|
| ***A01H 5/02*** | (2018.01) |
| ***C12Q 1/6895*** | (2018.01) |
| ***A01H 6/82*** | (2018.01) |
| ***A01H 1/00*** | (2006.01) |

(52) U.S. Cl.
CPC ........... *C12Q 1/6895* (2013.01); *A01H 1/121* (2021.01); *A01H 1/1215* (2021.01); *A01H 5/02* (2013.01); *A01H 6/821* (2018.05); *C12Q 2600/13* (2013.01); *C12Q 2600/156* (2013.01)

(58) Field of Classification Search
CPC .. A01H 6/821; C12Q 1/6895; C12Q 2600/13; C12Q 2600/156
USPC .......................................................... 800/267
See application file for complete search history.

(56) References Cited

U.S. PATENT DOCUMENTS

| | | | |
|---|---|---|---|
| 5,034,323 A | 7/1991 | Jorgensen et al. | |
| 5,107,065 A | 4/1992 | Shewmaker et al. | |
| 5,453,566 A | 9/1995 | Shewmaker et al. | |
| 5,463,175 A | 10/1995 | Barry et al. | |
| 5,500,365 A | 3/1996 | Fischhoff et al. | |
| 5,633,435 A | 5/1997 | Barry et al. | |
| 5,689,052 A | 11/1997 | Brown et al. | |
| 5,759,829 A | 6/1998 | Shewmaker et al. | |
| 5,880,275 A | 3/1999 | Fischhoff et al. | |
| 5,959,185 A | 9/1999 | Streit et al. | |
| 5,973,234 A | 10/1999 | Mueller et al. | |
| 5,977,445 A | 11/1999 | Soper et al. | |
| 6,423,885 B1 | 7/2002 | Waterhouse et al. | |
| 6,453,242 B1 | 9/2002 | Eisenberg et al. | |
| 6,528,700 B1 | 3/2003 | Baszczynski et al. | |
| 6,753,139 B1 | 6/2004 | Baulcombe et al. | |
| 6,785,613 B2 | 8/2004 | Eisenberg et al. | |
| 6,911,575 B1 | 6/2005 | Baszczynski et al. | |
| 7,138,565 B2 | 11/2006 | Waterhouse et al. | |
| 7,151,201 B2 | 12/2006 | Barbas, III et al. | |
| 7,177,766 B2 | 2/2007 | Eisenberg et al. | |
| PP20,201 P2 | 8/2009 | Klemm | |
| PP21,018 P2 * | 5/2010 | Klemm et al. | A01H 5/00 Plt./413 |
| 7,713,715 B2 | 5/2010 | Speer et al. | |
| 7,786,342 B2 | 8/2010 | Stover et al. | |
| 7,788,044 B2 | 8/2010 | Eisenberg et al. | |
| PP21,465 P3 | 11/2010 | Westhoff | |
| PP21,525 P3 | 11/2010 | Westhoff | |
| PP22,600 P3 | 3/2012 | Klemm et al. | |
| PP23,191 P3 | 11/2012 | Klemm et al. | |
| PP24,381 P2 | 4/2014 | Ui | |
| PP29,491 P2 | 7/2018 | Nguyen | |
| PP30,114 P3 | 1/2019 | Nguyen | |
| PP30,803 P2 | 8/2019 | Sakazaki | |
| PP30,804 P2 | 8/2019 | Sakazaki | |
| PP30,835 P2 | 8/2019 | Klemm et al. | |
| 2014/0179006 A1 | 6/2014 | Zhang | |
| 2014/0294773 A1 | 10/2014 | Brouns et al. | |

FOREIGN PATENT DOCUMENTS

| | | |
|---|---|---|
| NL | 238195 | 9/1965 |
| NL | 238194 | 5/2013 |
| NL | 242570 | 5/2013 |
| NL | 242568 | 2/2015 |
| NL | 242569 | 2/2015 |
| NL | 242571 | 2/2015 |
| NL | 242572 | 2/2015 |
| NL | 242573 | 2/2015 |
| NL | 243713 | 6/2015 |
| NL | 246123 | 4/2016 |
| NL | 246124 | 4/2016 |
| NL | 246125 | 4/2016 |
| NL | 246326 | 5/2016 |
| QZ | PBR51562 | 4/2019 |
| QZ | PBR51563 | 4/2019 |
| QZ | PBR51564 | 4/2019 |
| QZ | PBR51565 | 4/2019 |
| QZ | PBR51566 | 4/2019 |
| QZ | PBR51567 | 4/2019 |

(Continued)

OTHER PUBLICATIONS

Aukerman & Sakai, "Regulation of Flowering Time and Floral Organ Idenity by a MicroRNA and Its APETALA2-Like Target Genes," The Plant Cell, 15:2730-2741 (2003).
Baulcombe, "Fast forward genetics based on virus-induced gene silencing," Curr. Op. Plant Bio., 2(2): 109-113(1999).
Burton et al., "Virus-Induced Silencing of a Plant Cellulose Synthase Gene," Plant Cell, 12:691-705(2000).
Creissen et al., "Molecular characterization of glutathione reductase cDNAs from pea (*Pisum sativum* L.)," The Plant Journal, 2(1):129-131 (1991).
Daboussi et al., "Engineering Meganuclease for Precise Plant Genome Modification" in Advances in New Technology for Targeted Modification of Plant Genomes. Springer Science+Business, pp. 21-38 (2015).

(Continued)

*Primary Examiner* — Keith O. Robinson
(74) *Attorney, Agent, or Firm* — Cooley LLP

(57) ABSTRACT

The disclosure relates to *Calibrachoa* plants comprising a double-flowering characteristic and a dwarf growth characteristic, methods for generating said plants, and molecular markers corresponding to the double-flowering and dwarf growth traits.

10 Claims, 23 Drawing Sheets
(22 of 23 Drawing Sheet(s) Filed in Color)

Specification includes a Sequence Listing.

(56) References Cited

FOREIGN PATENT DOCUMENTS

| | | |
|---|---|---|
| QZ | PBR51568 | 4/2019 |
| WO | WO 99/31248 A1 | 6/1999 |

OTHER PUBLICATIONS

DeBloc et al., "Expression of foreign genes in regenerated plants and in their progeny," The EMBO J., 3:1681-1689 (1984).
Dubin et al., "Transposons: a blessing curse," Current Opinion in Plant Biology, 42:23-29 (2018); ff10.1016/j.pbi.2018.01.003ff. ffhal-01713131f.
Ferrie et al., "Review of Doubled Haploidy Methodologies in Ornamental Species," Propagation of Ornamental Plants, 11 (2):63-77 (2011).
Flavell, "Inactivation of Gene Expression in Plants as a Consequence of Specific Sequence Duplication," PNAS USA, 91 (9):3490-3496 (1994).
Fletcher et al., "QTL analysis of root morphology, flowering time, and yield reveals trade-offs in response to drought in Brassica napus," Journal of Experimental Biology, 66(1):245-256 (2015).
Frontes et al., "Characterization of an Immunoglobulin Binding Protein Homolog in the Maize floury-2 Endosperm Mutant," The Plant Cell, 3:483-496 (1991).
Gould et al., "A conserved tripeptide sorts proteins to peroxisomes," J. Cell. Biol., 108:1657-1654 (1989).
Ishino et al., "Nucleotide sequence of the iap gene, responsible for alkaline phosphatase isozyme conversion in *Escherichia coli*, and identification of the gene product," J. Bacteriol., 169:5429-5433 (1987).
Johnson et al., "Vast potential for using the piggyBac transposon to engineer transgenic plants at specific genomic locations," Bioengineered, 7(1):3-6 (2016).
Kalderon et al., "A Short Amino Acid Sequence Able to Specify Nuclear Location," Cell, 39:499-509 (1984).
Koncz et al., "Expression and assembly of functional bacterial luciferase in plants," Proc. Natl. Acad. Sci. USA, 84:131-135 (1987).
Lerner et al., "Cloning and Characterization of Root-Specific Barley Lectin," Plant Physiol., 91:124-129 (1989).
Luciana et al., "Tissue culture in ornamental plant breeding: A review," Crop Breeding and Applied Technology, 1(3):283-300 (2001).
Malzhan et al. "Plant genome editing with TALEN and CRISPR," Cell & Bioscience, vol. 7:21 (Apr. 2017), 18 pages.
Matsuoka et al., "Propeptide of a precursor to a plant vacuolar protein required for vacuolar targeting," Proc. Natl. Acad. Sci., 88(3):834 (1991).
Montgomery et al., "RNA as a target of double-stranded RNA-mediated genetic interference in Caenorhabditis elegans," PNAS USA, 95(26):15502-15507 (1998).
Napoli et al., "Introduction of a Chimeric Chaicone Synthase Gene into Petunia Results in Reversible Co-Suppression of Homologous Genes in trans," The Plant Cell, 2:279-289 (1990).
Needleman & Wunsch, "A general method applicable to the search for similarities in the amino acid sequence of two pioleins," Journal of Molecular Biology, 48(3);:443-53 (1970).
Pandey et al., "Plant regeneration from leaves and hypocotyl explants," Japan J. Breed., 42:1-5 (1992).
Pearson & Lipman, "Improved tools for biological sequence comparison," Proc. Natl. Acad. Sci., 85:2444-2448 (1988).
Petolino, "Genome editing in plants via designed zinc finger nucleases," In Vitro Cell Dev Biol Plant, 51(1):1-8 (2015).
Sander and Joung,"CRISPR-Cas systems for editing, regulating and targeting genomes," Nature Biotechnology, 32:347-355 (2014).
Shah et al.."Engineering herbicide tolerance in transgenic plants," Science, 233:478-481 (1986).
Sharp, "RNAi and double-strand RNA," Genes Dev., 13:139-141 (1999).
Sheehy et al., "Reduction of polygalacturonase activity in tomato fruit by antisense RNA," PNAS USA, 85:8805-8809 (1988).
Smith & Waterman, "Identification of common molecular subsequences," Journal of Molecular Biology, 147(1):195-197 (1981).
Smith et al., "Total silencing by intron-spliced hairpin RNAs," Nature, 407:319-320 (2000).
Sorek et al., "CRISPR-Mediated Adaptive Immune Systems in Bacteria and Archaea," Annu. Rev. Biochem., 82:237-266 (2013).
Steifel et al., "Expression of a Maize Cell Wall Hydroxyproline-Rich Glycoprotein Gene in Early Leaf and Root Vascular Differentiation," Plant Cell, 2:785-793 (1990).
Steinecke et al., "Expression of a chimeric ribozyme gene results in endonucleolytic cleavage of target mRNA and a concomitant reduction of gene expression in vivo," EMBO J., 11(4): 1525-1530 (1992).
Stephens et al., "Agronomic evaluation of tissue-culture-derived soybean plants," Theor. Appl. Genet., 82:633-635 (1991).
Taylor, "Comprehending Cosuppression," Plant Cell 9:1245-1249 (1997).
Teeri et al., "Gene fusions to lacZ reveal new expression patterns of chimeric genes in transgenic plants," EMBO J., 8:343-350 (1989).
Wang et al., "Efficient targeted mutagenesis in potato by the CRISPR/Cas9 system," Plant Cell Reports, 34:1473-1476 (2015).
Zamore et al., "RNAi: double-stranded RNA directs the ATP-dependent cleavage of mRNA at 21 to 23 nucleotide intervals," Cell, 101:25-33 (2000).
Zhang et al., "Exploiting the CRISPR/Cas9 System for Targeted Genome Mutagenesis in Petunia," Science Reports, vol. 6, No. 20315, pp. 1-8 (2016).

* cited by examiner

Figure 2A

CCCTCATCTTTCTCTTTCAGAAGAGCCTACTTTCGCCCATGGTTCGCGTCGCTAT
CGTGCTTGGTCCGTTCGCTACTCTCTTTTCAGCCATTATTGTATGCGTGTAGCCT
AAGTCTACCCTTCGATTGGACTTTCTCCAGATCCTTTGACACCCGCTCATCTTAC
TTCCCATTCTGGTAGGTTGGTGCGTGATGATTCGTGGAGTACAAGGCTCTCTCTG
GTTGGGTACGTAGGCTGGTCCTGCAG [A/C] TTGTGGAGGTGACCAGCGCTGCAT
GCCCGAATGGAATATTGACTATCCCGTAGAACTGACCTAGTCGCTCGT [G/C] AA
GGAGCTGGTCATTATGGAATATACTATATGTAGGCGCAGGTCTTCCTAGAGCGAA
CCTCCATGTGTTTTATATTAAACATATAAAAATCAACAGTGGAAGAGGCACTGGT
TGTGCGAGATCATTATGACTGGAGGAAGCCCATTCGACAACCATAATAGGCTCTA
TAACCGGATCACGCACGCTAAGAACACAGCGGATTAGAGGGGACAAGAGGTTCCA
CT

Figure 2B

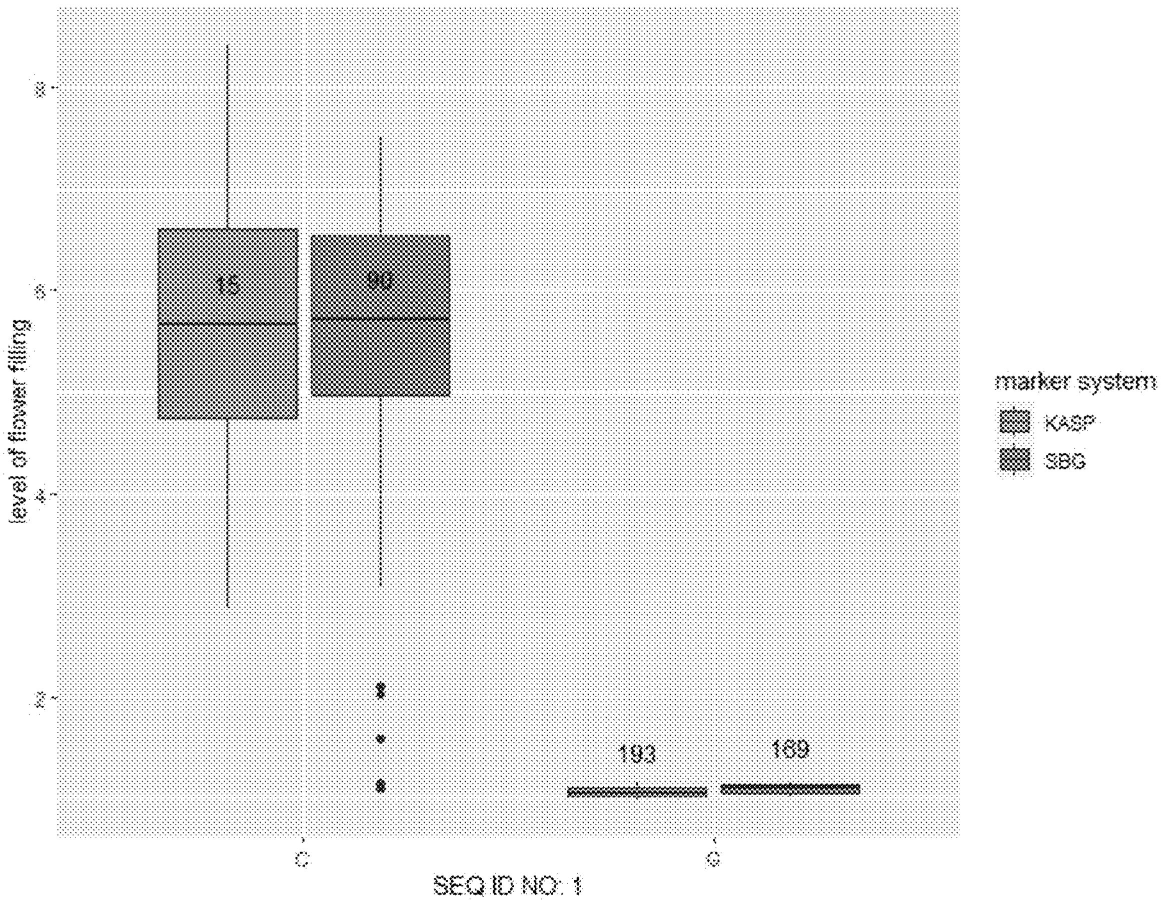

ATRCCACCACTGAACCACCRGCTGCAATGGCGGAGAAGGTGT [G/C] TGATGAAC
CATTTTTGGTGGTGGGACACGGTGGATTCTTGGGCTGAAAAAACAAGAATGGAAA
ACGCAGTG

Figure 5

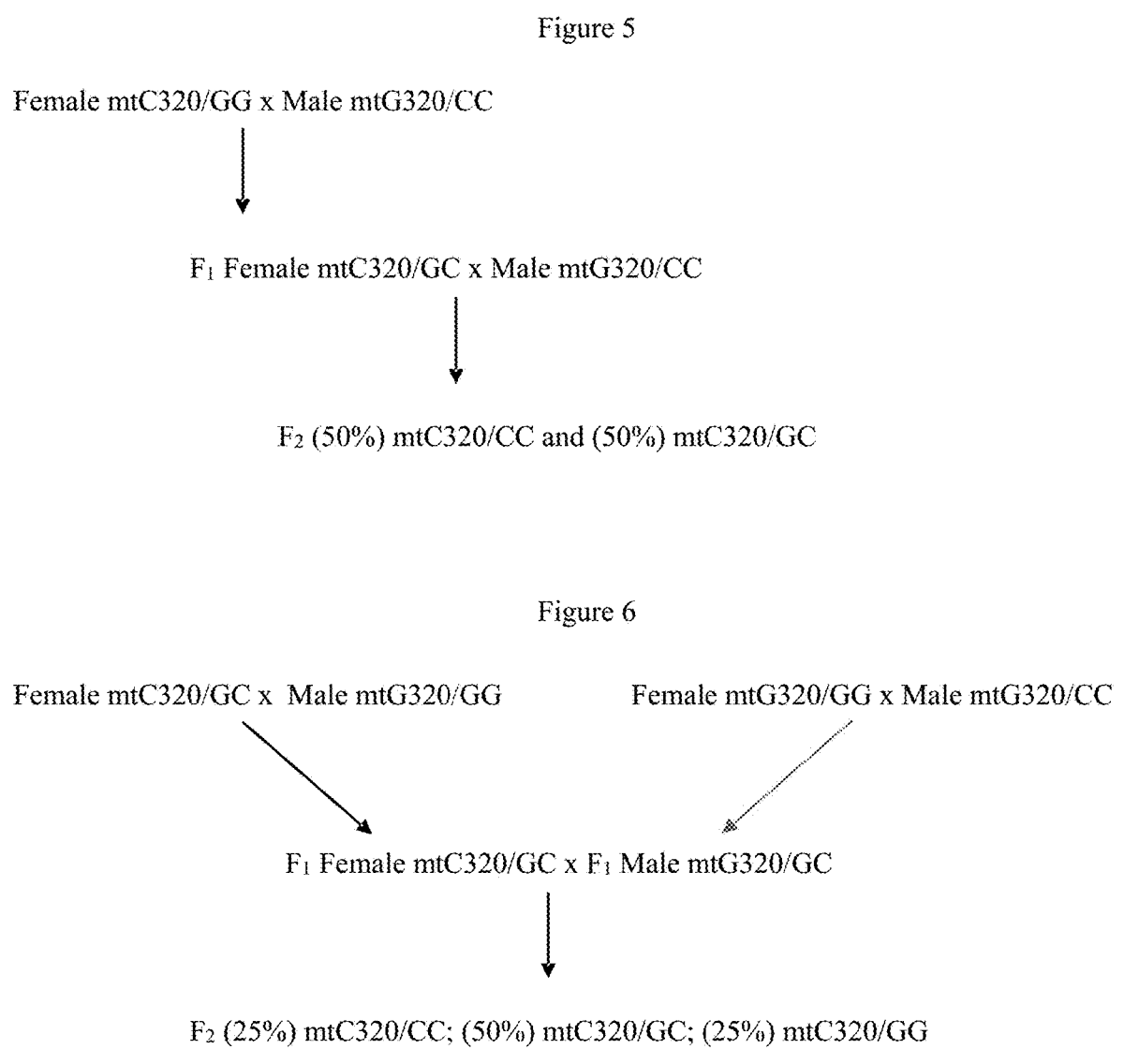

Female mtC320/GG x Male mtG320/CC $F_1$ Female mtC320/GC x Male mtG320/CC $F_2$ (50%) mtC320/CC and (50%) mtC320/GC

Figure 6

Female mtC320/GC x Male mtG320/GG

Female mtG320/GG x Male mtG320/CC $F_1$ Female mtC320/GC x $F_1$ Male mtG320/GC $F_2$ (25%) mtC320/CC; (50%) mtC320/GC; (25%) mtC320/GG

DOUBLE-FLOWERING DWARF *CALIBRACHOA*

The contents of the text file submitted electronically herewith are incorporated herein by reference in their entirety: A computer readable format copy of the Sequence Listing (file name: SELE_003_00US_SeqList_ST25; date recorded Oct. 13, 2020; file size: 596 kb).

BACKGROUND

Double-flowering *Calibrachoa* varieties have been around since at least 2006, when the first Plant Patent Application was filed (PP18,694). Since then a number of double-flowering varieties have been developed, encompassing a wide range of colors and patterns. However as with all *Calibrachoa* varieties, these plants show high vigor and therefore plant growth regulators (PGR) need to be applied in order to achieve a more compact plant shape, which is commercially and economically desired. However, growth regulators are increasingly being banned by regulators. For instance, the growth regulator TILT® is banned in the USA, Canada, Germany and Sweden.

Additionally, the timing of PGR application is very important for the shape of end products, but the correct moment of application is influenced by temperature and development stages of the plants. This means that it is difficult for a grower to apply PGR at the correct moment. Incorrect PGR application regularly leads to economic loss during cultivation. It is therefore also commercially interesting to breed *Calibrachoa* plants in which plants can be grown without PGRs.

Breeding of new plant varieties requires the continuous development of genetic diversity to obtain new, improved characteristics and traits. New genetic diversity can be established by crossing, random mutagenesis, or with the help of modern biotechnology.

The foregoing examples of the related art and limitations related therewith are intended to be illustrative and not exclusive. Other limitations of the related art will become apparent to those of skill in the art upon a reading of the specification.

SUMMARY

The present disclosure relates to a *Calibrachoa* plant comprising a double-flowering characteristic and a dwarf growth characteristic, wherein said double-flowering characteristic is caused by a mitochondrial allele associated with at least one single nucleotide polymorphism (SNP) mutation selected from the group consisting of a G to C nucleotide substitution at position number 320 of SEQ ID NO: 1 and an A to C nucleotide substitution at position number 247 in SEQ ID NO: 1, and wherein said dwarf growth characteristic is caused by a homozygous recessive nuclear allele associated with a SNP mutation consisting of a G to C nucleotide substitution at position 43 of SEQ ID NO: 2.

In some embodiments, the present disclosure relates to plants comprising double-flowering and dwarf growth characteristics, wherein the plant has a petaloid stamina rating of at least 2. In some embodiments, the plant at maturity has a vigor rating of less than 5 compared to plants having a G/C or G/G genotype at position 43 of SEQ ID NO: 2 when grown under the same environmental conditions. In some embodiments, the plant exhibits male sterility.

In some embodiments, the present disclosure relates to plants comprising double-flowering and dwarf growth characteristics, wherein the plant is grown without the addition of synthetic plant growth regulators. In some embodiments, the plant comprises no detectable residue of a synthetic plant growth regulator or a related breakdown of a synthetic plant growth regulator product.

In some embodiments, the present disclosure relates to plants comprising double-flowering and dwarf growth characteristics, wherein the plant further comprises a mutation affecting flower color and/or flower color pattern, wherein said mutation is the result of induced random or targeted mutagenesis. In another embodiment, the targeted mutagenesis is a gene editing tool or technology.

In further embodiments, the present disclosure teaches a method of producing a *Calibrachoa* plant comprising a double-flowering characteristic and a dwarf growth characteristic comprising the steps of crossing a first female *Calibrachoa* plant with a first male *Calibrachoa* plant to produce $F_1$ plants, wherein said first female *Calibrachoa* plant comprises a mitochondrial allele associated with at least one SNP mutation selected from the group consisting of a G to C nucleotide substitution at position number 320 of SEQ ID NO: 1 and an A to C nucleotide substitution at position number 247 in SEQ ID NO: 1 and exhibiting a double-flowering characteristic, and wherein said first male *Calibrachoa* plant has at least one copy of nuclear, recessive allele associated with a SNP mutation consisting of a G to C nucleotide substitution at position 43 of SEQ ID NO: 2, wherein when said nuclear allele is in the homozygous form, plants exhibit a dwarf growth characteristic; screening said $F_1$ plants for the presence of said nuclear SNP mutation; selecting an $F_1$ female plant exhibiting said double-flowering characteristic and further comprising at least one copy of said nuclear SNP mutation; crossing said $F_1$ female plant with said first male or a second male *Calibrachoa* plant having at least one copy of said nuclear SNP mutation to produce $F_2$ plants; screening said $F_2$ plants for the presence of said nuclear SNP mutation; and selecting an $F_2$ plant exhibiting said double-flowering characteristic and being homozygous for said nuclear SNP mutation.

In some embodiments, the first or second male *Calibrachoa* plant is homozygous for said nuclear SNP mutation and exhibits a dwarf growth characteristic. In some embodiments, the method further comprises asexual propagation or sexual reproduction of the selected $F_2$ plant.

In some embodiments, the present disclosure relates to plants produced by the methods disclosed herein, wherein the plant produced is further asexually propagated and grown without synthetic growth regulators. In some embodiments, the plant produced by the methods disclosed herein has a petaloid stamina rating of at least 2 and a vigor rating of less than 5 at maturity when compared to plants having a non-dwarf growth characteristic when grown under the same environmental conditions, wherein said non-dwarf plant has at least one copy of the allele associated with a SNP mutation consisting of a G at position 43 of SEQ ID NO: 2 (i.e., having a G/C or G/G genotype at position 43 of SEQ ID NO: 2).

In some embodiments, the plant produced by the methods disclosed herein further comprises a mitochondrial allele associated with an A to C nucleotide substitution at position number 247 in SEQ ID NO: 1.

In some embodiments, the plant produced by the methods disclosed herein exhibits male sterility.

In some embodiments, the plant produced by the methods disclosed herein further comprises a mutation affecting flower color and/or flower color pattern.

In some embodiments, the present disclosure teaches a method for producing a double-flowering dwarf *Calibrachoa* plant having a desired trait comprising applying a plant breeding technique to the *Calibrachoa* plant produced by the methods disclosed herein. In some embodiments, the plant breeding techniques are selected from the group consisting of recurrent selection, mass selection, hybridization, open-pollination, backcrossing, pedigree breeding, mutation breeding, haploid/double haploid production, and marker enhanced selection. In some embodiments, the plant breeding technique is mutation breeding and the mutation selected is spontaneous or artificially induced.

In some embodiments, the present disclosure relates to a plant produced by the methods disclosed herein, wherein said plant exhibits dwarf growth, double-flowering, and a desired trait. In some embodiments, the desired trait is flower color and/or flower color pattern.

In further embodiments, the present disclosure relates to a molecular marker for distinguishing a plant having at least one allele for a double-flowering characteristic comprising at least one sequence selected from the group consisting of SEQ ID NO: 1, cDNA sequences thereof, fragments of at least 20 consecutive nucleotides thereof, and complementary sequences thereof.

In further embodiments, the present disclosure relates to a molecular marker for distinguishing a plant having at least one allele for a dwarf growth characteristic comprising at least one sequence selected from the group consisting of SEQ ID NO: 2, cDNA sequences thereof, fragments of at least 20 consecutive nucleotides thereof, and complementary sequences thereof.

In some embodiments, the present disclosure relates to a molecular marker for distinguishing a plant having an allele for a double-flowering characteristic, comprising a sequence of at least 20 consecutive nucleotides of SEQ ID NO: 7, or the complementary sequence.

In some embodiments, the present disclosure teaches a method for distinguishing a plant having at least one allele for a double-flowering characteristic comprising using SEQ ID NO: 1, cDNA sequences thereof, fragments of at least 20 consecutive nucleotides thereof, or complementary sequences thereof, and detecting at least one of a C nucleotide at position number 320 of SEQ ID NO: 1 and a C nucleotide at position number 247 in SEQ ID NO: 1. In another embodiment, detecting at least one of a C nucleotide at position number 320 of SEQ ID NO: 1 and a C nucleotide at position number 247 in SEQ ID NO: 1 comprises obtaining genetic material; obtaining a nucleic acid, wherein said nucleic acid has at least a portion of sequence complementary to the molecular markers disclosed herein; and base-pairing said nucleic acid with said genetic material and examining the result of said base-pairing. In some embodiments, the genetic material is deoxyribonucleic acid, ribonucleic acid, or a combination thereof. In some embodiments, the nucleic acid is a primer set, a probe, or combination thereof.

In some embodiments, the present disclosure teaches a method for distinguishing a plant having at least one allele for a dwarf growth characteristic comprising using SEQ ID NO: 2, cDNA sequences thereof, fragments of at least 20 consecutive nucleotides thereof, or complementary sequences thereof, and detecting a C nucleotide at position 43 of SEQ ID NO: 2. In another embodiment, detecting a C nucleotide at position 43 of SEQ ID NO: 2 comprises obtaining genetic material; obtaining a nucleic acid, wherein said nucleic acid has at least a portion of sequence complementary to the molecular markers disclosed herein; and base-pairing said nucleic acid with said genetic material and examining the result of said base-pairing. In some embodiments, the genetic material is deoxyribonucleic acid, ribonucleic acid, or a combination thereof. In some embodiments, the nucleic acid is a primer set, a probe, or combination thereof.

In some embodiments, the present disclosure relates to a plant distinguished by the markers and methods of using the markers disclosed herein, wherein the plant is homozygous for the allele for a dwarf growth characteristic, and wherein the plant is subsequently grown without synthetic growth regulators.

The following embodiments and aspects thereof are described and illustrated in conjunction with products and methods, which are meant to be exemplary and illustrative, not limiting in scope.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1A shows a flower having five single petals and a rating of 1. FIG. 1B shows a flower having a double-flowering rating of 3. FIG. 1C shows a flower having a double-flowering rating of 5. FIG. 1D shows a flower having a double-flowering rating of 7. FIG. 1E shows a flower having a double-flowering rating of 9.

FIG. 2A corresponds to SEQ ID NO: 1 and shows the results of the Kompetitive Allele Specific PCR (KASP) assay of a single-flowering trait and the related sequence with the corresponding double-flowering trait. Two polymorphisms were identified in the double-flowering trait; an A to C nucleotide substitution at position number 247 and a G to C nucleotide substitution at position number 320, both indicated by bold, underlined font within brackets.

FIG. 2B is a boxplot of the level of flower filling (y-axis) of genotypes having a C at position number 320 of SEQ ID NO: 1 compared to those having a G at position 320 of SEQ ID NO: 1 (x-axis). The validation of the findings within the SBG approach (turquoise box plots) is displayed in FIG. 2B with additional box plots for the KASP assay (red box plots). The number within the boxplot indicates the number of genotypes in each group.

FIG. 5 represents an example breeding scheme to produce plants having a double-flowering dwarf phenotype.

FIG. 6 represents another example breeding scheme to produce plants having a double-flowering dwarf phenotype.

DEFINITIONS

Figures 1A, 1B, 1C, 1D, 1E:
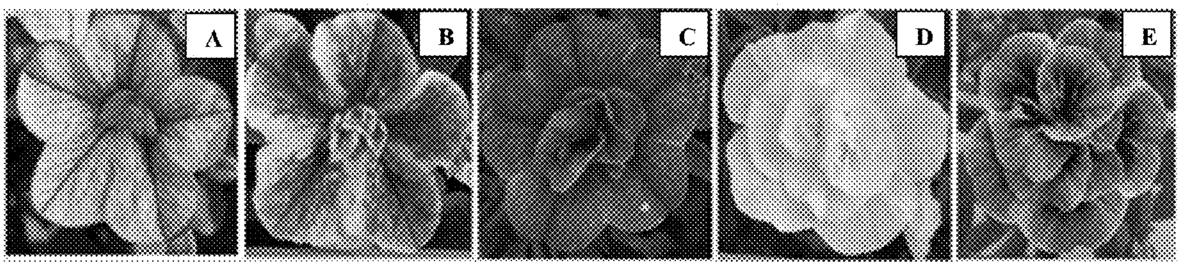
FIGS. 1A-1E shows photographs of flowers having different ratings (1-9) of flower filling (double-flowering), wherein 1 corresponds to single flowers and 9 corresponds to the highest level of flower filling.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art.

Following long-standing patent law convention, the terms "a," "an," and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about." The term "about," as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one or more of the elements to which the "and/or" refers can also individually be present in single or multiple occurrences in the combinations(s) and/or subcombination(s).

As used herein, the phrase "an allele associated with [a particular SNP mutation or mutation]" can mean the actual causative mutation of the phenotype, or a linkage—either physical or functional, for example as a regulatory element or some sort of epistatic relationship. It is a recognizable and/or assayable relationship between two entities. Additionally, the SNP mutation or mutation "associated with" the allele serves as an indicator of whether the allele is present in a plant/germplasm and can be used to predict whether a plant is homozygous or heterozygous for the allele.

As used herein, the phrase "dwarf" as it relates to *Calibrachoa* refers to a plant phenotype (or trait or characteristic) caused by a homozygous recessive nuclear allele associated with a C nucleotide at position 43 of SEQ ID NO: 2. A "non-dwarf" plant would have at least one copy of an allele associated with a G nucleotide at position 43 of SEQ ID NO: 2.

As used herein, the phrase "flower filling" or "filled" refers to the degree of the double-flowering characteristic and is measured herein according to UPOV's scale of 1-9 for quantitative traits.

"Genotype" as used herein refers to the genetic constitution of an individual organism.

As used herein, the term "human-induced mutation" or "induced mutagenesis" refers to any mutation that occurs as a result of either direct or indirect human action. This term includes, but is not limited to, mutations obtained by any method of targeted or human-induced random mutagenesis including for example, irradiation and treatment with mutation-inducing chemicals.

"mtC320" as used herein refers to the G to C nucleotide substitution (SNP mutation) at position number 320 of SEQ ID NO: 1 in the mitochondrial genome of a *Calibrachoa* plant.

"mtC247" as used herein refers to the A to C nucleotide substitution (SNP mutation) at position number 247 of SEQ ID NO: 1 in the mitochondrial genome of a *Calibrachoa* plant.

As used herein, the term "nucleotide sequence identity" refers to the presence of identical nucleotides at corresponding positions of two polynucleotides. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, Calif., United States of America. See also Smith & Waterman, 1981; Needleman & Wunsch, 1970; Pearson & Lipman, 1988; Ausubel et al., 1988; and Sambrook & Russell, 2001. One example of an algorithm that is suitable for determining percent sequence identity and sequence similarity is the BLAST algorithm, which is described in Altschul et al., 1990. Unless otherwise noted, alignments disclosed herein utilized ClustalW.

As used herein, the term "plant" can refer to a whole plant, any part thereof, or a cell or tissue culture derived from a plant. Thus, the term "plant" can refer to any of whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

"Phenotype" as used herein refers to the observable characteristics or traits of an organism that are produced by the interaction of the genotype and the environment.

As used herein, "vigor" relates to overall plant size as measured by their potential to produce biomass and is rated herein according to UPOV's scale of 1-9 for quantitative traits.

DETAILED DESCRIPTION

All publications, patents and patent applications, including any drawings and appendices, are herein incorporated by reference to the same extent as if each individual publication or patent application was specifically and individually indicated to be incorporated by reference.

The following description includes information that may be useful in understanding the present disclosure. It is not an admission that any of the information provided herein is prior art or relevant to the presently claimed disclosures, or that any publication specifically or implicitly referenced is prior art.

Overview

Embodiments described herein relate to *Calibrachoa* plants comprising a double-flowering characteristic and a dwarf growth characteristic, wherein said double-flowering characteristic is caused by a mitochondrial allele associated with at least one single nucleotide polymorphism (SNP) mutation of a G to C nucleotide substitution at position number 320 of SEQ ID NO: 1 and an A to C nucleotide substitution at position number 247 in SEQ ID NO: 1, and wherein said dwarf growth characteristic is caused by a homozygous recessive nuclear allele associated with a SNP mutation consisting of a G to C nucleotide substitution at position 43 of SEQ ID NO: 2, methods for generating said plants, and molecular markers corresponding to SEQ ID NO: 1 and SEQ ID NO: 2, cDNA sequences thereof, fragments of at least 20 consecutive nucleotides thereof, and complementary sequences thereof.

History of the Double-Flowering Trait, U.S. Pat. No. 7,786,342

Double-flowering *Calibrachoa* varieties were generated by Applicant through an intensive breeding program which began with screening 17,500 first generation plants. A handful of sections from these $F_1$ plants exhibited some flowers having more than 5 petals, and were then the subject of extensive breeding which included, for example, intercrossing siblings or half-siblings, back-crossing, out-crossing (to increase diversity and circumvent inbreeding depression), and open pollinations through the third and higher generations. Since then a number of double-flowering varieties have been developed, encompassing a wide range of colors and patterns (see Table 1 below).

TABLE 1

Double-flowering *Calibrachoa* varieties

| Denomination | Trade name | Patent No./ PVP No. |
|---|---|---|
| KLECA20428 | Superbells ® Double Amber | |
| KLECA20459 | Superbells ® Double Orange | |
| KLECA14275 | Superbells ® Double Orchid | |
| KLECA19067 | MiniFamous ® Neo Double OrangeTastic | |
| KLECA18085 | MiniFamous ® Uno Double PinkTastic ® | |
| KLECA07162 | MiniFamous ® Double Blue | PP20,201 |
| KLECA08164 | MiniFamous ® Double Pink Blush | |
| KLECA08182 | Compact MiniFamous ® Double Yellow | PP21,018 |
| KLECA09204 | Compact MiniFamous ® Double Lemon | PP23,191 |
| KLECA09207 | MiniFamous ® Double Hot Pink | |
| KLECA09208 | MiniFamous ® Neo Double Amethyst | PP22,600 |
| KLECA10220 | MiniFamous ® Double Pink | |
| KLECA11225 | MiniFamous ® Neo Double Yellow | |
| KLECA11226 | MiniFamous ® Double Nostalgia | |
| KLECA12231 | MiniFamous ® Double Blue | |
| KLECA12233 | MiniFamous ® Double Purple Red | |
| KLECA12234 | MiniFamous ® Neo Double Pink Vein | |
| KLECA13242 | MiniFamous ® Uno Double White | |
| KLECA13255 | MiniFamous ® Neo Double Dark Red | |
| KLECA13257 | Compact MiniFamous ® Double Red | |
| KLECA14261 | MiniFamous ® Double Orchid | |
| KLECA14264 | MiniFamous ® Uno Double Pink | |
| KLECA15269 | MiniFamous ® Neo Double Blue '15 | |
| KLECA14272 | Can-Can Rosies Blue | |
| KLECA14273 | Can-Can Rosies Dark Yellow | |
| KLECA14274 | Can-Can Rosies White | |
| KLECA14275 | Can-Can Rosies Pink Vein | |
| KLECA14276 | MiniFamous ® Double Purple | |
| KLECA14277 | Can-Can Rosies Magenta | |
| KLECA14283 | MiniFamous ® Double Apricot | |
| KLECA15290 | MiniFamous ® Neo Double Lemon '15 | |
| KLECA15332 | Compact MiniFamous ® Double Rose | |
| KLECA16356 | MiniFamous ® Uno Double PinkMania! | |
| KLECA16364 | MiniFamous ® Neo Double Light Blue | |
| KLECA19508 | MiniFamous ® Uno Double Blue | |
| KLECA20509 | MiniFamous ® Neo Double light violet 098 | |
| KLECA18510 | MiniFamous ® Uno Double LavTastic | |
| KLECA18511 | MiniFamous ® Uno Double White Pink Vein | |
| KLECA18514 | MiniFamous ® Uno Double Red | |
| USCAL81302 | Superbells ® Doublette Love Swept ™ | PP30,804 |
| USCAL83901 | Superbells ® Double Ruby | Can4591 |
| USO8CJ0202 | Superbells ® Double Rose | |
| USCAL51505 | Superbells ® Double Chiffon | PP30,803 |
| Duealdubcit | Aloha Double Citric | NL238194 |
| Duealdublav | Aloha Double Lavender | NL238053 |
| Dueldubstra | Aloha Double Strawberry | NL238195 |
| | Aloha Double Orange | |
| | Aloha Double Pink | |
| | Aloha Double Purple | |
| | Aloha Double Cherry Red | |
| DCALNOADBZ | Noa ™ Double Bronze | |
| | Noa ™ Double Pineapple | |
| WESCADOBL(U) | Celebration Double Blue | PP21,525 |
| WESCADODARE | Celebration Double Dark Red | |
| WESCADOFU | Celebration Double Fuchsia | |
| WESCADOLEM | Celebration Double Lemon | |
| WESCADOORE | Celebration Double Orange Pink | |
| WESCADOPI | Celebration Double Pink | PP21,465 |
| WESCADOSOPI | Celebration Double Soft Pink | |
| WESCADOWEIM | Celebration Double White Improved | |
| WESCADOYEL | Celebration Double Yellow | |
| WESCACHADOPIYE | CHAMELEON ® Double Pink Yellow | |
| WESCACHAMTIPI | CHAMELEON ® Double Ticld Pink | |
| | COLIBRI ™ Double Copper | |

As with all *Calibrachoa* varieties, these plants show high vigor and therefore growth regulators need to be applied in order to achieve a more compact plant shape, which is commercially desired.

History of the Dwarf Growth Trait

*Calibrachoa* varieties naturally show high vigor and therefore plant growth regulators (PGR) need to be applied in order to achieve a more compact plant shape, which is commercially and economically desired. However, growth regulators are increasingly being banned. For instance, the growth regulator TILT® is banned in the USA, Canada, Germany and Sweden. Additionally, the timing of PGR application is very important for the shape of end products, but the correct moment of application is influenced by temperature and development stages of the plants. This means that it is difficult for a grower to apply PGR at the correct moment. Incorrect PGR application regularly leads to economic loss during cultivation. It is therefore also commercially interesting to breed *Calibrachoa* plants which can be grown without PGRs.

*Calibrachoa* plants with dwarf phenotypes have been described and are known in the art (see Table 2a below, for example). These example varieties, while sometimes labeled "compact" are in fact distinct from other compact varieties and are herein referred to as dwarf varieties. The dwarf trait is recessive and breeding with the dwarf trait has been difficult, thus there are a limited number of commercially available lines. Examples of compact varieties are shown in Table 2b.

TABLE 2a

Dwarf Varieties

| Denomination | Trade name | Patent No./PVP No. |
|---|---|---|
| | MiniFamous ® Piu Pink | |
| SAKCAL106 | Calipetite ® Blue | NL242570 |
| SAKCAL105 | Calipetite ® Red | PP24,381; NL242571 |
| SAKCAL104 | Calipetite ® Rose | NL242572 |
| SAKCAL108 | Calipetite ® White | NL242568 |
| SAKCAL107 | Calipetite ® Yellow | NL242569 |
| Balcongraniss | Conga ™ Orange Kiss | PBR51567 |
| Balcongcink | Conga ™ Pink | PBR51563 |
| Balcongite | Conga ™ White | PBR51565 |
| | Conga ™ Peach Kiss | |
| Wescaebreim | Early Bird ™ Red | |
| Wescaebsu | Early Bird ™ Sun | |
| | Pocket ™ Lilac | |
| | Pocket ™ Yellow | |

TABLE 2b

Compact varieties

| Denomination | Trade name | Patent No./ PVP No. |
|---|---|---|
| KLECA17002 | MiniFamous ® Piu White | |
| KLECA17038 | MiniFamous ® Piu Red | PP30,835 |
| KLECA17288 | MiniFamous ® Piu Light Blue | |
| KLECA17338 | MiniFamous ® Piu Yellow | |
| KLECA17340 | MiniFamous ® Piu Yellow + Red Veins | |
| KLECA17343 | Calitag Scarlet Red Eye | |
| | MiniFamous ® Piu Orange | |
| | Calita ® Compact Lemon | |
| SAKCAL114 | Calipetite ® Pink Vein | NL243713 |
| SAKCAL110 | Calipetite ® Plum | NL242573 |
| Balcongetiss | Conga ™ Sunset Kiss | |
| Balcongarlu | Conga ™ Dark Blue | PP29,491; PBR51562 |

TABLE 2b-continued

| Compact varieties | | |
|---|---|---|
| Denomination | Trade name | Patent No./ PVP No. |
| Balcongcriss | Conga ™ Coral Kiss | NL246124 |
| Balconglow | Conga ™ Lemon | NL246125 |
| Balcongor | Conga ™ Orange | NL246126 |
| Balconginkiss | Conga ™ Pink Kiss | NL246123 |
| Balcongosiss | Conga ™ Rose Kiss | NL246326 |
| Balcabscarim | Conga ™ Red | |
| Balconglipar | Conga ™ Light Pink Star | |
| Balconginar | Conga ™ Pink Star | |
| Balconglav | Conga ™+0Lavender | PP30,114 |
| Balcongrissm | Conga ™ Rose Kiss | PBR51568 |
| Balcongdel | Conga ™ Deep Yellow | PBR51564 |
| Balcongosiss | Conga ™ Rose | PBR51566 |
| Wescaebblim | Early Bird ™ Blue | |
| Wescaebli | Early Bird ™ Lilac | |
| Wescaebpi | Early Bird ™ Pink | |
| Wescaebwe | Early Bird ™ White | |
| | Pocket ™ Apricot Eye | |
| | Pocket ™ Dark Pink | |
| | Pocket ™ Light Red | |
| | Pocket ™ Rose | |
| | Pocket ™ White | |
| | Aloha Nani Yellow | |
| | Aloha Nani Cherry Red | |
| | Aloha Nani Blue | |
| | Aloha Nani Dark Red | |
| | Aloha Nani Tropicana | |
| | Aloha Nani Red Cart Wheel | |
| | Aloha Nani White | |
| | Aloha Nani Golden Girl | |
| | Colibri ™ Malibu Pink | |
| | Colibri ™ Mellow Yellow | |
| | Colibri ™ Pink Flamingo | |
| | Colibri ™ Yellow Canary | |
| DCALCOLBL | Colibri ™ Blizzard | |
| | Colibri ™ Lemon | |
| DCALCOPILA | Colibri ™ Pink Lace | |
| DCALCOCHLA | Colibri ™ Cherry Lace | |
| DCALCORANG | Colibri ™ Orange | |
| | Colibri ™ Pink | |
| DCALCOPULA | Colibri ™ Purple Lace | |
| DCALCOFUCH | Colibri ™ Fuchsia | |
| | Colibri ™ Plum | |

Thus, in order for the double-flowering and dwarf traits to be combined, one would require the underlying molecular mechanisms and/or markers for any successful breeding program.

Detection of Single Nucleotide Polymorphisms (SNP) Associated with the Mitochondrial Allele that Causes a Double-Flowering Phenotype A diverse collection of *Calibrachoa* plants, were phenotypically and genetically analyzed. The experimental trials for this analysis were grown in multi-location sites worldwide over several years. The plant cultivation tests were conducted in an experimental design containing several sub-experiments to capture the crop growth performance affected by different or no inhibiting substances (Paclobutrazol, Daminozide, no plant growth regulator). In total, 464 plants were analyzed (343 single flowering and 121 double-flowering).

For the phenotypic analysis, the level of flower filling, or the petaloid stamina rating, was scored visually on a 1-9 scale, based on the UPOV scale for quantitative traits, where 1 means single flowers having five petals per flower and a score of 2 or higher means flowers containing converted anthers. See for example FIGS. 1A-1E and Table 3 below.

TABLE 3

| States of Double Flower Expression | |
|---|---|
| Approximate percentage of flower diameter covered by additional petals or petaloids | Scale |
| >1 | 1 |
| 1-10 | 2 |
| 10.1-30 | 3 |
| 30.1-40 | 4 |
| 40.1-50 | 5 |
| 50.1-60 | 6 |
| 60.1-70 | 7 |
| 70.1-80 | 8 |
| >80 | 9 |

As shown in FIGS. 1A-1E and described above in Table 3, a plant having a petaloid stamina rating of 1 exhibits single flowers with five petals (FIG. 1A). Plants having a petaloid stamina rating of 2 have rudimentary converted anthers, while plants scoring 3 (FIG. 1B) or higher covering a bigger size of the total flower diameter by additional petals or petaloids.

For the genotypic analysis, an applied Sequence Based Genotyping (SBG) approach for the simultaneous Single-Nucleotide Polymorphism (SNP) discovery was conducted to genotype 288 plants (186 double-flowering, 102 single flowering). SBG libraries were prepared on the basis of genomic Deoxyribonucleic Acid (DNA) including both nuclear and mitochondrial DNA of 288 *Calibrachoa* samples and subsequently sequenced using the Illumina HiSeq. The resulting alignments were subsequently mined for SNP mutations (Truong et al. 2012). Quality checks were performed, leading to 11,641 SNP mutation markers. A Genome-Wide Association Study (GWAS) implemented with the high-quality data revealed a major Quantitative Trait Locus (QTL) in which one of the alleles is responsible for double-flowering phenotypes. The nucleotides between brackets in FIG. 2A indicate the position of the SNP mutations: an A to C nucleotide substitution at position number 247 in SEQ ID NO: 1 and a G to C nucleotide substitution at position number 320 of SEQ ID NO: 1. Genotypes having the "G" allele at position 320 displayed in all cases the single flower phenotypic trait. Genotypes having the "C" allele at position 320 displayed in all cases the double-flowering phenotype.

Other than for the SNP mutations described above, the sequence shown by SEQ ID NO: 1 is identical in the single and the double-flowering lines. The findings were confirmed with a Kompetitive Allele Specific PCR (KASP) assay (Chunlin et al. 2014). For the validation with the KASP, 234 plants were genotyped (210 single flowering, 24 double-flowering). 58 genotypes were analyzed with both SBG and KASP parallel.

Scoring and Genotyping the Double-Flowering Trait

The data from the SBG and KASP assay was further evaluated using linear mixed model analysis adjusted for influencing factors like genotype-environment-interactions (Best linear unbiased Predictors).

The results of the analysis are shown in FIG. 2B, which depicts a boxplot of the level of flower filling (y-axis) of genotypes having a C at position number 320 of SEQ ID NO: 1 compared to those having a G at position 320 of SEQ ID NO: 1 (x-axis). The validation of the findings within the SBG approach (turquoise box plots, 259 of the 288 plants analyzed) is displayed with additional box plots for the KASP assay (red box plots, 208 of the 234 plants analyzed). The number within the boxplot indicates the number of genotypes in each group, while the outward lines indicate the minimum and maximum values. As shown in FIG. 2B, plants having a C at position number 320 of SEQ ID NO: 1 have transformed anthers to additional petals or petaloids a flower filling rating of at least 2, while plants having a G at position 320 of SEQ ID NO: 1 exhibited a flowering filing rating of 1.

Thus, an embodiment of the present disclosure provides a molecular marker for distinguishing a plant having an allele for a double-flowering characteristic comprising at least one sequence selected from the group consisting of SEQ ID NO: 1, cDNA sequences thereof, fragments of at least 20 consecutive nucleotides thereof, and complementary sequences thereof. As will be understood by one skilled in the art, fragments may comprise lengths of at least 30, at least 40, at least 50, at least 60, least 70, at least 80, at least 90, at least 100, at least 125, at least 150, at least 175, at least 200, etc., nucleotides and upwards to the entire length of the sequence.

As will be understood by those skilled in the art, the SNP mutations shown in SEQ ID NO: 1 may be detected by any number of mechanisms, including but not limited to, Restriction Fragment Length Polymorphisms (RFLPs), Dynamic Allele-Specific Hybridization (DASH), molecular beacon, SNP microarray, PCR-based method, Flap endonuclease (FEN), Single-strand conformation polymorphism, temperature gradient gel electrophoresis, Denaturing High Performance Liquid Chromatography (DHPLC), DNA mismatch binding proteins, or sequencing.

Another embodiment of the present disclosure teaches a method for distinguishing a plant having at least one allele for a double-flowering characteristic comprising using SEQ ID NO: 1, and detecting at least one of a C nucleotide at position number 320 of SEQ ID NO: 1 and a C nucleotide at position number 247 in SEQ ID NO: 1. In another embodiment, detecting at least one of a C nucleotide at position number 320 of SEQ ID NO: 1 and a C nucleotide at position number 247 in SEQ ID NO: 1 comprises obtaining genetic material, obtaining a nucleic acid, wherein said nucleic acid has at least a portion of sequence complementary to the molecular marker for the double-flowering trait disclosed herein, and base-pairing said nucleic acid with said genetic material and examining the result of said base-pairing. The genetic material may be deoxyribonucleic acid, ribonucleic acid, or a combination thereof. The nucleic acid may be a primer set, a probe, or combination thereof.

Another embodiment of the present disclosure relates to double-flowering dwarf *Calibrachoa* plants having a petaloid stamina rating of at least 2. Another embodiment of the present disclosure relates to double-flowering dwarf *Calibrachoa* plants exhibiting male sterility.

Detection of Single Nucleotide Polymorphisms (SNP) Associated with the Dwarf Phenotype The diverse collection of *Calibrachoa* plants described above (464 plants total), including a wide range of growth vigor from very dwarf to very vigorous varieties were phenotypically and genetically analyzed. The experimental trials were grown in multi-location sites worldwide over several years. The plant cultivation tests were conducted in an experimental design containing several sub-experiments to capture the crop growth performance affected by different or no inhibiting substances (Paclobutrazol, Daminozide, no plant growth regulator).

Figure 3:
FIG. 3 is a photograph of nine plants corresponding to the 1-9 rating scale for vigor (level of compactness), wherein a rating of 1 corresponds to very dwarf and 9 to extremely vigorous plants. In the foreground, from left to right, are plants exhibiting ratings of 7, 8, and 9, respectively. The middle row, from left to right, shows plants exhibiting ratings of 4, 5, and 6, respectively. In the background, from left to right, are plants exhibiting ratings of 1, 2, and 3, respectively. All plants shown are the same age.

For the phenotypic analysis, growth vigor, or the determination of biomass, was rated on a 1-9 scale, where 1 refers to very dwarf and 9 to extreme vigorous plants. Plants representing each rating are shown in FIG. 3, specifically, in the foreground, from left to right, are plants exhibiting ratings of 7, 8, and 9, respectively. The middle row, from left to right, shows plants exhibiting ratings of 4, 5, and 6, respectively. In the background, from left to right, are plants exhibiting ratings of 1, 2, and 3, respectively.

The genotypic analysis described above further revealed a major Quantitative Trait Locus (QTL) in which one of the alleles is responsible for a dwarf phenotype. The nucleotides between brackets in FIG. 4A indicate the position of the SNP mutation comprising a G to C nucleotide substitution at position number 43 of SEQ ID NO: 2. Genotypes heterozygous or homozygous for the “G” allele at position 43 displayed in all cases the normal, vigorous plant growth. Genotypes homozygous for the “C” allele at position 43 displayed in all cases the dwarf phenotype. The confirmation of these findings was conducted with a Kompetitive Allele Specific PCR (KASP) assay.

Scoring and Genotyping the Dwarf Trait

The data from the SBG and KASP assay was further evaluated using linear mixed model analysis adjusted for influencing factors like genotype-environment-interactions (Best linear unbiased Predictors).

Figures 4A, 4B:
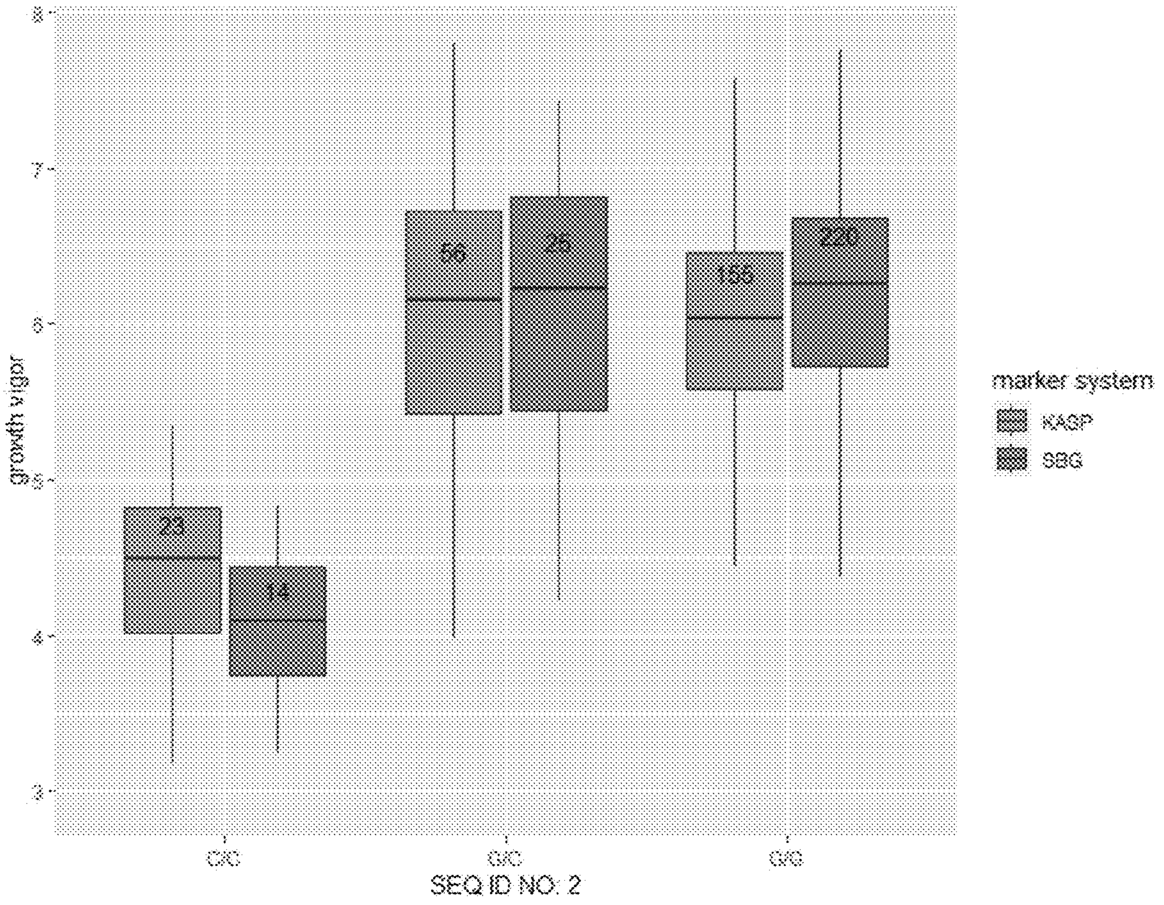
FIG. 4A corresponds to SEQ ID NO: 2 and shows the results of the Kompetitive Allele Specific PCR (KASP) assay of wild-type and the related sequence with the corresponding dwarf trait. A G to C polymorphism was identified at position 43 of SEQ ID NO: 2 indicated by bold, underlined font within brackets.
FIG. 4B is a boxplot of the level of growth vigor (y-axis) of genotypes carrying different allele composition for the detected nuclear "dwarf" polymorphism (x-axis) represented by SEQ ID NO: 2 (see also FIG. 4A). The validation of the findings within the SBG approach (turquoise box plots) is displayed in FIG. 4B with additional box plots for the KASP assay (red box plots). The number within the boxplot indicates the number of genotypes in each group.

The results of the analysis are shown in FIG. 4B, which depicts a boxplot of the level of growth vigor (y-axis) of genotypes homozygous for C at position number 43 of SEQ ID NO: 2 compared to those heterozygous or homozygous for G at position 43 of SEQ ID NO: 2 (x-axis). The validation of the findings within the SBG approach (turquoise box plots, 259 of the 288 plants analyzed) is displayed with additional box plots for the KASP assay (red box plots, 234 plants analyzed). The number within the boxplot indicates the number of genotypes in each group; while the outward lines indicate the minimum and maximum values. As shown in FIG. 4B, plants homozygous for C at position number 43 of SEQ ID NO: 2 exhibited much less growth vigor, while plants having at least one G allele at position 43 of SEQ ID NO: 2 exhibited a significantly stronger growth vigor.

Thus, an embodiment of the present disclosure provides a molecular marker for distinguishing a plant having at least one allele for a dwarf characteristic comprising at least one sequence selected from the group consisting of SEQ ID NO: 2, cDNA sequences thereof, fragments of at least 20 consecutive nucleotides thereof, and complementary sequences thereof. As will be understood by one skilled in the art, fragments may comprise lengths of at least 30, at least 40, at least 50, at least 60, least 70, at least 80, at least 90, at least 100, at least 125, at least 150, at least 175, at least 200, etc., nucleotides and upwards to the entire length of the sequence.

As will be understood by those skilled in the art, the SNP mutation shown in SEQ ID NO: 2 may be detected by any number of mechanisms, including but not limited to, Restriction Fragment Length Polymorphisms (RFLPs), Dynamic Allele-Specific Hybridization (DASH), molecular beacon, SNP microarray, PCR-based method, Flap endonuclease (FEN), Single-strand conformation polymorphism, temperature gradient gel electrophoresis, Denaturing High Performance Liquid Chromatography (DHPLC), DNA mismatch binding proteins, or sequencing.

Another embodiment of the present disclosure teaches a method for distinguishing a plant having at least one allele for a dwarf characteristic comprising using SEQ ID NO: 2, and detecting a C nucleotide at position 43 of SEQ ID NO: 2. In another embodiment, detecting a C nucleotide at position 43 of SEQ ID NO: 2 comprises obtaining genetic material, obtaining a nucleic acid, wherein said nucleic acid has at least a portion of sequence complementary to the molecular marker for the dwarf trait disclosed herein, and base-pairing said nucleic acid with said genetic material and examining the result of said base-pairing. The genetic material may be deoxyribonucleic acid, ribonucleic acid, or a combination thereof. The nucleic acid may be a primer set, a probe, or combination thereof.

In another embodiment, the present disclosure provides for a plant distinguished by the markers and methods disclosed herein, wherein said plant is homozygous for said allele for a dwarf growth characteristic, and wherein said plant is subsequently grown without growth regulators. In another embodiment, the plant comprises no detectable residue of a synthetic plant growth regulator or a related breakdown of a plant growth regulator product.

Another embodiment of the present disclosure relates to double-flowering dwarf *Calibrachoa* plants having a significantly smaller growth vigor rating of less than 5 at maturity, when compared to plants having a G/C or G/G genotypes at position 43 of SEQ ID NO: 2 when grown under the same environmental conditions.

Plant Growth Regulators (PGRs)

Plant growth regulators (PGRs) (herein also called synthetic plant growth regulators) are widely used in the ornamental plant business. PGRs consist of a large group of synthetically produced organic chemicals and considered as helping tool in the actual production system of ornamentals. The application of them is exercised by the commercial growers as a part of cultural practice. There are many methods of application of PGRs, most common used is drenching, foliar spraying and pre-plant soaking. According to professional experience and literature research, one or more PGRs have been used in *Calibrachoa* cultivation (Table 4 below).

TABLE 4

Widely used Plant Growth Regulators (PGRs) for *Calibrachoa* (modified according Wipker 2013 and 2019)

| PGR | Active Ingredient | Application rate | Method |
|---|---|---|---|
| Dazide (B-Nine) | Daminozide | 2,500-5,000 ppm | Spray |
| Citadel (Cycocel) + | Chlormequat + | 1,500 ppm (Citadel) + | Tank-mix |
| Dazide (B-Nine) | Daminozide | 2,500 ppm (Dazide) | spray |
| Concise (Sumagic) | Uniconazole-p | 10-25 ppm | Spray |
| Piccolo (Bonzi, | Paclobutrazol | 3-8 ppm | Drench |
| Paczol, Downsize)) | Paclobutrazol | 3-50 ppm | |
| Piccolo (Bonzi, Paczol) | Spray | | |
| Florel | Ethephon | 300-500 ppm | Spray |
| Toplor | Flurprimidol | 150-300 ppm | Spray |

The dangerous effects on both grower and end consumer health have increasingly become the focus of awareness worldwide. Various countries and international organizations have issued regulations by setting up the maximum authorized residue levels of PGRs in various plants and this will likely intensify in the future.

A large number of analytical methods for the determination of PGRs or residues of them have been developed. The methods of detection are enzyme-linked immunosorbent assay (ELISA) (Qian et al. 2009; Jiang et al. 2011), gas chromatography (GC) (Brinkmann et al. 1996; Xu et al. 2011), liquid chromatography-diode array detection (LC-DAD) (Das and Prasad 2015), gas chromatography-mass spectrometry (GC-MS) (Müller et al. 2002; Du et al. 2015), liquid chromatography-tandem mass spectrometry (LC-MS/MS) (Riediker et al. 2002; Ma et al. 2013; Kim et al. 2016), and high-performance liquid chromatography coupled with tandem mass spectrometry (HPLC-MS/MS) (Luo et al. 2019). Accredited laboratories (e.g. Analytisches Insitut Bostel, https://bostel.de/) analyze plant material for residue level conform to legal requirements (e.g. German Federal Office of Consumer Protection and Food Safety, § 64 LFGB).

Figure 4C:
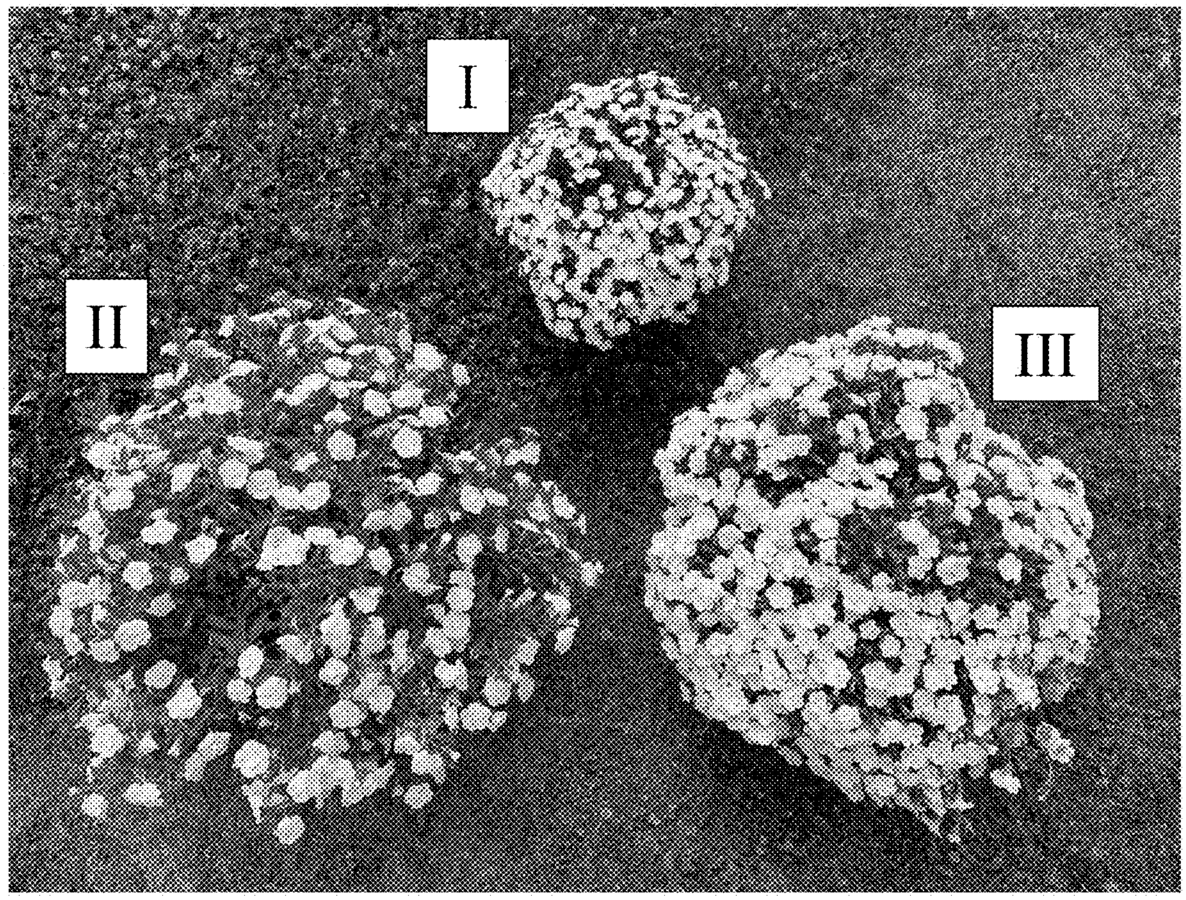
FIG. 4C shows three *Calibrachoa* plants of two different genotypes. *Calibrachoa* plant I is a genotype with a combination of the double-flowering trait (SEQ ID NO: 1; "C") and a dwarf growth trait (SEQ ID NO: 2; "C/C"), not treated with any plant growth regulators and has a vigor rating of 3. *Calibrachoa* plants II and III demonstrate the same genotype with the double-flowering trait (SEQ ID NO: 1; "C") but do not comprise the dwarf growth trait (SEQ ID NO: 2; "G/G"). Plant II is untreated with any plant growth regulators and has a vigor rating of 7. Plant III was growth inhibited according to good horticultural practice (5 treatments of Dazide/B-Nine) and has a vigor rating of 6.

The double-flowering dwarf *Calibrachoa* plants of the present disclosure inherently exhibit a significantly smaller growth vigor, therefore another embodiment of the present disclosure provides for double-flowering dwarf *Calibrachoa* plants grown without the addition of synthetic plant growth regulators. FIG. 4C shows three *Calibrachoa* plants of two different genotypes. *Calibrachoa* plant I is a genotype with a combination of the double-flowering trait (SEQ ID NO: 1; “C”) and a dwarf growth trait (SEQ ID NO: 2; “C/C”), not treated with any plant growth regulators and has a vigor rating of 3. *Calibrachoa* plants II and III demonstrate the same genotype with the double-flowering trait (SEQ ID NO: 1; “C”) but do not comprise the dwarf growth trait (SEQ ID NO: 2; “GIG”). Plant II is untreated with any plant growth regulators, and has a vigor rating of 7. Plant III was growth inhibited according to good horticultural practice (5 treatments of Dazide/B-Nine) and has a vigor rating of 6.

Another embodiment provides for double-flowering dwarf *Calibrachoa* plants which comprise no detectable residue of a synthetic plant growth regulator or a related breakdown of a plant growth regulator product.

Methods of a Producing Double-Flowering Dwarf *Calibrachoa*

An embodiment of the present disclosure provides a method of producing a *Calibrachoa* plant comprising a double-flowering characteristic and a dwarf growth characteristic comprising the steps of: crossing a first female *Calibrachoa* plant with a first male *Calibrachoa* plant to produce $F_1$ plants, wherein said first female *Calibrachoa* plant comprises a mitochondrial allele associated with at least one SNP mutation selected from the group consisting of (i) a G to C nucleotide substitution at position number 320 of SEQ ID NO: 1 and (ii) an A to C nucleotide substitution at position number 247 in SEQ ID NO: 1 and exhibiting a double-flowering characteristic, and wherein said first male *Calibrachoa* plant has at least one copy of a nuclear, recessive allele associated with a SNP mutation consisting of a G to C nucleotide substitution at position 43 of SEQ ID NO: 2, wherein when said nuclear allele is in the homozygous form plants exhibit a dwarf growth characteristic; screening said $F_1$ plants for the presence of said nuclear SNP mutation; selecting an $F_1$ female plant exhibiting said double-flowering characteristic and further comprising at least one copy of said nuclear SNP mutation; crossing said $F_1$ female plant with said first male or a second male *Calibrachoa* plant having at least one copy said nuclear SNP mutation to produce $F_2$ plants; screening said $F_2$ plants for the presence of said nuclear SNP mutation; and selecting an $F_2$ plant exhibiting said double-flowering characteristic and being homozygous for said nuclear SNP mutation. In another embodiment, the first or second male *Calibrachoa* plant is homozygous for said nuclear SNP mutation and exhibits a dwarf growth characteristic.

As will be understood by those skilled in the art, the first and/or second male *Calibrachoa* plant may be homozygous for the nuclear dwarf growth characteristic. As shown in FIG. 5, a first female *Calibrachoa* plant comprising a mitochondrial allele associated with a G to C nucleotide substitution at position number 320 of SEQ ID NO: 1 and (ii) an A to C nucleotide substitution at position number 247 in SEQ ID NO: 1 and exhibiting a double-flowering characteristic (mtC320) with vigorous growth G/G) is crossed with a male exhibiting single flowers (mtG320) and a dwarf growth trait (C/C). An $F_1$ female progeny from this cross having a double-flowering characteristic (mtC320) and vigorous growth (G/C) is then bred to a second male exhibiting single flowers (mtG320) and a dwarf growth trait (C/C). While FIG. 5 depicts this as an outcrossing, those skilled in the art will understand that this may also be accomplished via backcrossing to the first male *Calibrachoa.* 50% of the $F_2$ progeny from this cross will exhibit double-flowering and dwarf growth, and the other 50% will exhibit double-flowering and normal, vigorous growth as they will be heterozygous for the dwarf allele (G/C).

As will be understood by those skilled in the art, additional crosses may be conducted to produce the parental lines described above. Shown in FIG. 6 is an example wherein a double-flowering female (mtC320) carrying the dwarf allele (G/C) is crossed with a male having single flowers (mtG320) and no dwarf allele (G/G) but may comprise some other desirable trait (not depicted). An $F_1$ progeny is selected for having double-flowers (mtC320) and carrying the dwarf allele (G/C) and additional desired trait (not depicted) to be used as the female parent in a cross with a male having single flowers (mtG320) and carrying the dwarf allele (G/C). This male parental line may have been produced to carry, for example, the same desirable trait as the $F_1$ female parental line, or may carry a second desirable trait, and may have been produced as depicted in FIG. 6, from a cross between a single-flowering (mtG320) vigorous female (G/G) with a single flowering (mtCG20) dwarf male (C/C). As will be understood by those skilled the art, the $F_1$ male parental line carrying the dwarf allele shown in FIG. 6 may have been produced by any number of crosses, for example, by one or both parental lines being heterozygous for the dwarf allele.

As shown in FIG. 6, all $F_2$ progeny will exhibit double-flowering (mtC320) as this is inherited from the mitochondria of the $F_1$ female parent. Additionally, approximately 25% of $F_2$ progeny will also be homozygous for the dwarf allele and exhibit the dwarf growth trait (C/C).

Additional Breeding Methods

Any plants produced using the double-flowering dwarf plants and/or markers of the double-flowering and dwarf traits disclosed herein are also an embodiment. These methods are well-known in the art and some of the more commonly used breeding methods are described herein. Descriptions of breeding methods can be found in one of several reference books (e.g., Allard, "Principles of Plant Breeding" (1999); and Vainstein, "Breeding for Ornamentals: Classical and Molecular Approaches," Kluwer Academic Publishers (2002); Callaway, "Breeding Ornamental Plants," Timber Press (2000).

Breeding steps that may be used in a plant breeding program can include for example, pedigree breeding, backcrossing, mutation breeding, and recurrent selection. In conjunction with these steps, techniques such as RFLP-enhanced selection, genetic marker enhanced selection (for example, SSR markers), gene editing and the making of double haploids may be utilized.

In another embodiment, the present disclosure teaches a method of producing a double-flowering dwarf *Calibrachoa* plant having a desired trait comprising applying a plant breeding technique to the double-flowering dwarf *Calibrachoa* plant produced from the breeding methods disclosed herein. The desirable trait may be for example, a mutation affecting flower color and/or pattern. Thus, in another embodiment, the present disclosure provides for plants produced by the breeding methods disclosed herein and further comprising a mutation affecting flower color and/or pattern.

In another embodiment the present disclosure provides for plants produced by the breeding methods disclosed herein, wherein said plant has a petaloid stamina rating of at least three and wherein said plant at maturity has a vigor rating of less than five compared to plants having a G/C or G/G genotype at position 43 of SEQ ID NO: 2 when grown under the same environmental conditions.

In another embodiment, plants produced from the breeding methods disclosed herein may be asexually propagated or sexually reproduced. In another embodiment, the plants produced are grown without plant growth regulators.

Recurrent Selection and Mass Selection

In some embodiments, the plant breeding technique is recurrent selection. In some embodiments, the plant breeding technique is mass selection. Mass and recurrent selections can be used to improve populations of either self- or cross-pollinating crops. A genetically variable population of heterozygous individuals is either identified, or created, by intercrossing several different parents. The plants are selected based on individual superiority, outstanding progeny, or excellent combining ability. The selected plants are intercrossed to produce a new population in which further cycles of selection are continued.

Recurrent selection is a method used in a plant breeding program to improve a population of plants. Double-flowering dwarf *Calibrachoa* plants disclosed herein are suitable for use in a modified recurrent selection program. The method entails individual plants cross pollinating with each other to form progeny. The progeny are grown and the superior progeny selected. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties. Once a desired plant is obtained with improved traits, it can be used as a breeding line in crosses to generate double-flowering dwarf *Calibrachoa* plants.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. In addition to self-pollination, directed pollination could be used as part of the breeding program.

Open Pollination and Hybridization

In some embodiments, the plant breeding technique is open-pollination. Open-pollination is when pollination occurs by insect, bird, wind, humans, or other natural mechanisms. This can yield greater variation and more genetically diverse plants. In some embodiments, the plant breeding technique is hybridization, Hybridization is a controlled method of pollination in which the pollen of two different varieties or species is crossed by human intervention. For example, *Calibrachoa* can hybridize with *petunia* to produce *petunia-Calibrachoa* hybrids. Thus, an embodiment of the present disclosure are *petunia-Calibrachoa* hybrids exhibiting the double-flowering and/or dwarf traits disclosed herein.

Backcross Breeding

In some embodiments, the plant breeding technique is backcrossing. Backcross breeding has been used to transfer genes for a simply inherited, highly heritable trait into a desirable homozygous variety or inbred variety which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent. This is also known as single gene conversion and/or backcross conversion.

In addition to being used to create a backcross conversion, backcrossing can also be used in combination with pedigree breeding. Backcrossing can be used to transfer one or more specifically desirable traits from one variety, the donor parent, to a developed variety called the recurrent parent, which has overall good commercial characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selection. This approach leverages the value and strengths of the recurrent parent for use in new *Calibrachoa* varieties.

Pedigree Breeding

In some embodiments, the plant breeding technique is pedigree breeding. Pedigree breeding starts with the crossing of two genotypes, such as the double-flowering and dwarf alleles disclosed herein, and another variety having one or more desirable characteristics that is lacking or which complements double-flowering dwarf *Calibrachoa* plants. If the two original parents do not provide all the desired characteristics, other sources can be included in the breeding population. In the pedigree method, superior plants are selected in successive filial generations.

Mutation Breeding

In some embodiments, the plant breeding technique is mutation breeding, wherein said mutation breeding selects for a mutation that is spontaneous or artificially induced. Mutation breeding is another method of introducing new traits into the double-flowering dwarf *Calibrachoa* plants of the present disclosure. Mutations that occur spontaneously or are artificially induced can be useful sources of variability for a plant breeder. The goal of artificial mutagenesis is to increase the rate of mutation for a desired characteristic. Mutation rates can be increased by many different means. Examples of mutagens that may be used with the method disclosed herein include: radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (for example from 250 to 290 nm), temperature, long-term seed storage, tissue culture conditions, or chemical mutagens (such as base analogues (5-bromo-uracil)), related compounds (8-ethoxy caffeine), antibiotics (streptonigrin), alkylating agents (sulfur mustards, nitrogen mustards, epoxides, ethyleneamines, sulfates, sulfonates, sulfones, lactones), azide, hydroxylamine, nitrous acid, or acridines, proflavine, ICR191 and ethidium bromide. Other techniques such as gene editing are also possible and lie well within the scope of the skilled person.

Once a desired trait is observed through mutagenesis the trait may then be incorporated into existing germplasm by traditional breeding techniques. Details of mutation breeding can be found in Allard, *Principles of Plant Breeding*, John Wiley & Sons, Inc. (1960) but may include, for example, crossing, recurrent selection, backcrossing, pedigree breeding, marker enhanced selection, haploid/double haploid production, or transformation.

In another embodiment, the double-flowering dwarf *Calibrachoa* plants of the present disclosure further comprises a mutation affecting flower color and/or flower color pattern, wherein said mutation is the result of a gene editing tool or technology.

Breeding with Molecular Markers

In some embodiments, the plant breeding technique is marker enhanced selection. In addition to the sequences disclosed herein which may be used as molecular markers for the double-flowering and dwarf traits, molecular markers can be used during the breeding process for the selection of other traits. For example, markers closely linked to alleles or markers containing sequences within the actual alleles of interest can be used to select plants that contain the alleles of interest during a breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms, may be used in plant breeding methods. See Vainstein, "Breeding for Ornamentals: Classical and Molecular Approaches," Kluwer Academic Publishers (2002).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See for example, Fletcher, Richard S., et al., "QTL analysis of root morphology, flowering time, and yield reveals trade-offs in response to drought in *Brassica napus*" *Journal of Experimental Biology*. 66 (1): 245-256 (2014). QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Molecular Techniques Using Double-Flowering Dwarf *Calibrachoa* Plants

The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See Vainstein, "Breeding for Ornamentals: Classical and Molecular Approaches," Kluwer Academic Publishers (2002). Expression vectors can be introduced into plant tissues using a direct gene transfer method, such as microprojectile-mediated delivery, DNA injection, electroporation, and the like, or by using either microprojectile-mediated delivery with a biolistic device or by using *Agrobacterium*-mediated transformation. Transformant plants obtained with the protoplasm of the present disclosure are intended to be within the scope of the embodiments.

Expression Vectors for *Calibrachoa* Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. Positive selection methods are also known in the art.

One commonly used selectable marker gene for plant transformation is neomycin phosphotransferase II (nptII) which, when under the control of plant regulatory signals, confers resistance to kanamycin. Another commonly used selectable marker gene is the hygromycin phosphotransferase gene which confers resistance to the antibiotic hygromycin.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.,* 13:67 (1987); Shah, et al., *Science,* 233:478 (1986); Charest, et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri, et al., *EMBO J.,* 8:343 (1989); Koncz, et al., *Proc. Natl. Acad. Sci.* USA, 84:131 (1987); DeBlock, et al., *EMBO J.,* 3:1681 (1984)).

Expression Vectors for *Calibrachoa* Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., *Plant Mol. Biol.,* 20:49 (1992); Knox, C., et al., *Plant Mol. Biol.,* 9:3-17 (1987); Lerner, et al., *Plant Physiol.,* 91:124-129 (1989); Frontes, et al., *Plant Cell,* 3:483-496 (1991); Matsuoka, et al., *Proc. Natl. Acad. Sci.,* 88:834 (1991); Gould, et al., *J. Cell. Biol.,* 108:1657 (1989); Creissen, et al., *Plant J.,* 2:129 (1991); Kalderon, et al., *Cell,* 39:499-509 (1984); Steifel, et al., *Plant Cell,* 2:785-793 (1990).

Foreign Genes: Transformation

Various promoters, targeting sequences, enhancing sequences, and other DNA sequences can be inserted into the genome for the purpose of altering the expression of genes.

Many techniques for altering gene expression are well-known to one of skill in the art, including, but not limited to, knock-outs (such as by insertion of a transposable element such as Mu (Vicki Chandler, The Maize Handbook, Ch. 118 (Springer-Verlag 1994)) or other genetic elements such as a FRT, Lox, or other site specific integration sites; antisense technology (see, e.g., Sheehy, et al., PNAS USA, 85:8805-8809 (1988) and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, *PNAS USA,* 91:3490-3496 (1994); Finnegan, et al., *Bio/Technology,* 12:883-888 (1994); Neuhuber, et al., *Mol. Gen. Genet.,* 244:230-241 (1994)); RNA interference (Napoli, et al., *Plant Cell,* 2:279-289 (1990); U.S. Pat. No. 5,034,323; Sharp, *Genes Dev.,* 13:139-141 (1999); Zamore, et al., *Cell,* 101:25-33 (2000); Montgomery, et al., *PNAS USA,* 95:15502-15507 (1998)), virus-induced gene silencing (Burton, et al., *Plant Cell,* 12:691-705 (2000); Baulcombe, *Curr. Op. Plant Bio.,* 2:109-113 (1999)); target-RNA-specific ribozymes (Haseloff, et al., *Nature,* 334:585-591 (1988)); hairpin structures (Smith, et al., *Nature,* 407:319-320 (2000); U.S. Pat. Nos. 6,423,885, 7,138,565, 6,753,139, and 7,713,715); MicroRNA (Aukerman & Sakai, *Plant Cell,* 15:2730-2741 (2003)); ribozymes (Steinecke, et al., EMBO J., 11:1525 (1992); Perriman, et al., *Antisense Res. Dev.,* 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); transposable elements (e.g. Dubin, M. J., et al., Transposons: a blessing curse, *Current opinion in plant biology*, Vol: 42, Page: 23-29, 2018 and Eric T. Johnson, Jesse B. Owens & Stefan Moisyadi (2016) Vast potential for using the piggyBac transposon to engineer transgenic plants at specific genomic locations, *Bioengineered,* 7:1, 3-6) and other methods or combinations of the above methods known to those of skill in the art.

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular *Calibrachoa* variety using the foregoing transformation techniques could be moved into another variety using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene.

Likewise, by means of one embodiment, plants can be genetically engineered to express various phenotypes of interest, including, but not limited to, genes that confer resistance to pests or disease, genes that confer resistance to an herbicide, genes that confer or contribute to a value-added or desired trait, genes that control male sterility, genes that create a site for site specific DNA integration, and genes that affect abiotic stress resistance. Non-limiting examples of particular genes and corresponding phenotypes one may choose to introduce into a plant include one or more genes for insect tolerance, such as a *Bacillus thuringiensis* (Bt.), pest tolerance such as genes for fungal disease control, herbicide tolerance such as genes conferring glyphosate tolerance, and genes for quality improvements such as, environmental or stress tolerances, or any desirable changes in plant physiology, growth, development, morphology or plant product(s). For example, *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety. Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.,* 9:207, 1991). The RNA could also be a catalytic RNA molecule (i.e., a ribozyme) engineered to cleave a desired endogenous mRNA product (see for example, Gibson and Shillito, *Mol. Biotech.,* 7:125, 1997). Thus, any sequence which produces a phenotype or morphology change of interest may be used with the double-flowering dwarf *Calibrachoa* plants disclosed herein.

Tissue Culture

Further reproduction can occur by tissue culture and regeneration. Tissue culture of various tissues of ornamental plants and regeneration of plants therefrom is well-known and widely published. For example, reference may be had to Valla Rego, Luciana et al., *Crop Breeding and Applied Technology.* 1(3): 283-300 (2001); Komatsuda, T., et al., *Crop Sci.,* 31:333-337 (1991); Stephens, P. A., et al., *Theor. Appl. Genet.,* 82:633-635 (1991); Komatsuda, T., et al., *Plant Cell, Tissue and Organ Culture,* 28:103-113 (1992); Dhir, S., et al., *Plant Cell Reports,* 11:285-289 (1992); Pandey, P., et al., Japan J. Breed., 42:1-5 (1992); and Shetty, K., et al., *Plant Science,* 81:245-251 (1992). Thus, another embodiment is to provide cells which upon growth and differentiation produce *Calibrachoa* plants exhibiting, or carrying the alleles for, double-flowering and dwarf traits described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Production of Double Haploids

The production of double haploids can also be used for the development of plants with a homozygous phenotype in the breeding program. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. For example, see, Ferrie, Alison M. R., et al., "Review of Doubled Haploidy Methodologies in Ornamental Species" *Propagation of Ornamental Plants.* 11(2): pp. 63-77 (2011).

Protoplast Fusion

Also known as somatic fusion, this process can be used with the double-flowering dwarf *Calibrachoa* plants of the present disclosure to create hybrids. The resulting hybrid plants have the chromosomes of each parent and thus the process is useful for incorporating new traits. The protoplast fusion technique is well known in the art; see for example Hamill J. D., Cocking E. C. (1988) Somatic Hybridization of Plants and its Use in Agriculture. In: Pais M.S.S., Mavituna F., Novais J. M. (eds) *Plant Cell Biotechnology*. NATO ASI Series (Series H: *Cell Biology*), vol 18.

Gene Editing Using CRISPR

Targeted gene editing can be done using CRISPR/Cas9 technology (Saunders & Joung, *Nature Biotechnology,* 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system, for example petunia, a close relative of *Calibrachoa*. See for example, Zhang, B. et al., "Exploiting the CRISPR/Cas9 System for Targeted Genome Mutagenesis in Petunia" *Science Reports, Vol.* 6, February 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:237-266, 2013; and Wang, S. et al., *Plant Cell Rep* (2015) 34: 1473-1476.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing in double-flowering dwarf *Calibrachoa* plants. The technique is well known in the art; see for example Malzahn, Aimee et al. "Plant genome editing with TALEN and CRISPR" *Cell & Bioscience* vol. 7 21. 24 Apr. 2017.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in *Advances in New Technology for Targeted Modification of Plant Genomes*. Springer Science+Business. pp 21-38 (2015).

EXAMPLES

The following examples are provided to illustrate further the various applications and are not intended to limit the disclosure beyond the limitations set forth in the appended claims.

Example 1: Breeding with Purple Double-Flowering and Dwarf Traits

Figure 7:
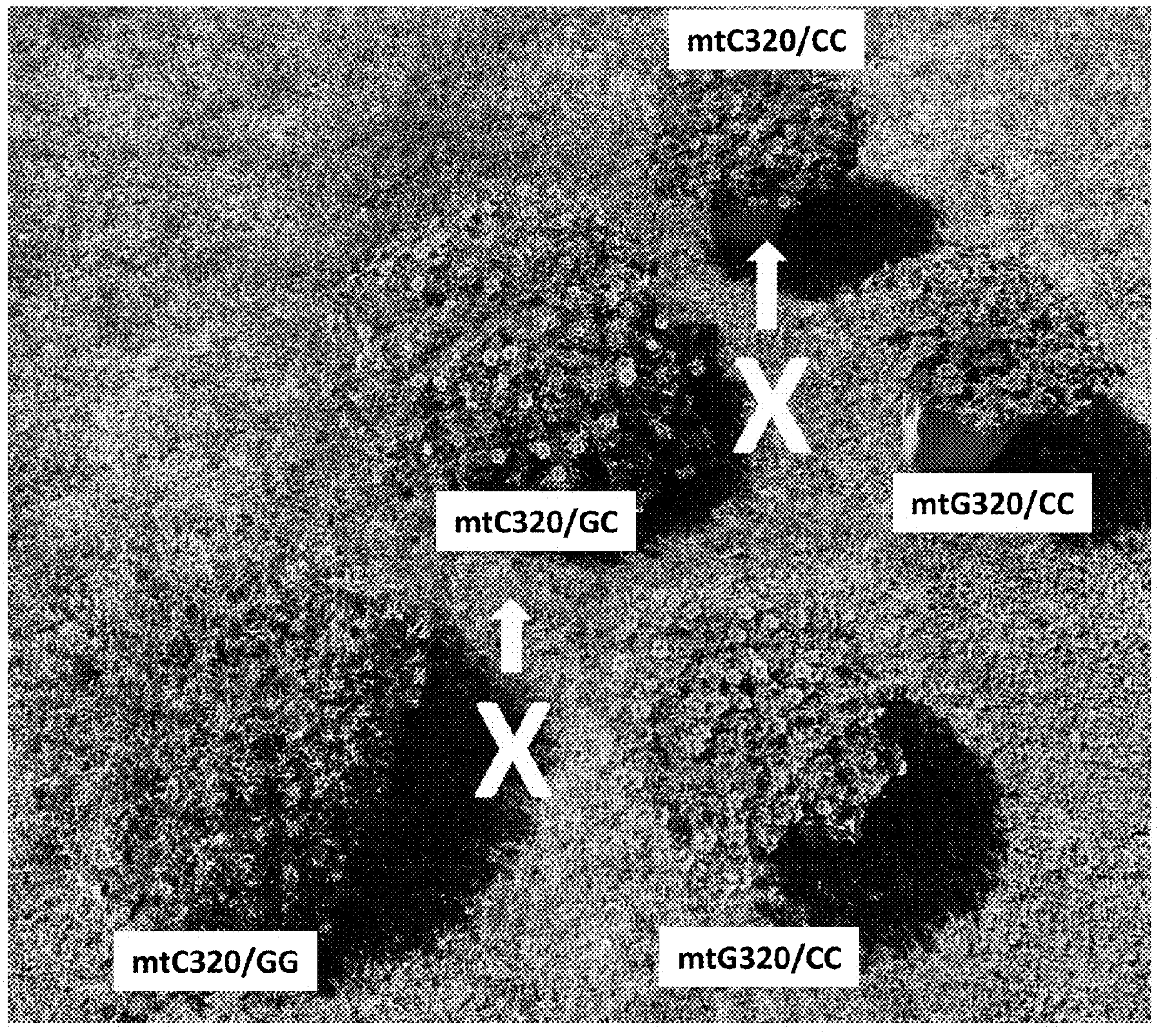
FIG. 7 is a photograph of parental lines and progeny plants from a breeding scheme to produce a purple double-flowering dwarf *Calibrachoa* plant.

*Calibrachoa* plants having both the double-flowering and dwarf traits were bred using the molecular markers disclosed herein. As shown in FIG. 7, a purple plant having double-flowers (mtC320) and normal vigorous growth (G/G) was used as the female parent and crossed with a purple dwarf plant (C/C) having single flowers (mtG320) as the male parent. The $F_1$ progeny exhibited purple double-flowers (mtC320) and normal vigorous growth as it was heterozygous for the recessive dwarf allele (G/C). This $F_1$ progeny was used a female parent in a cross with a male purple dwarf plant (C/C) having single flowers (mtG320). While an outcrossing is shown in FIG. 7, those skilled in the art will understand that this progeny could also be backcrossed to the first male parent. $F_2$ progeny were genotyped for the molecular markers disclosed herein using methods well known in the art. A selected $F_2$ progeny from this cross is shown at the top of FIG. 7, a purple double-flowering (mtC320) dwarf (C/C) *Calibrachoa.*

Example 2: Breeding with White Double-Flowering and Dwarf Traits

Figure 8:
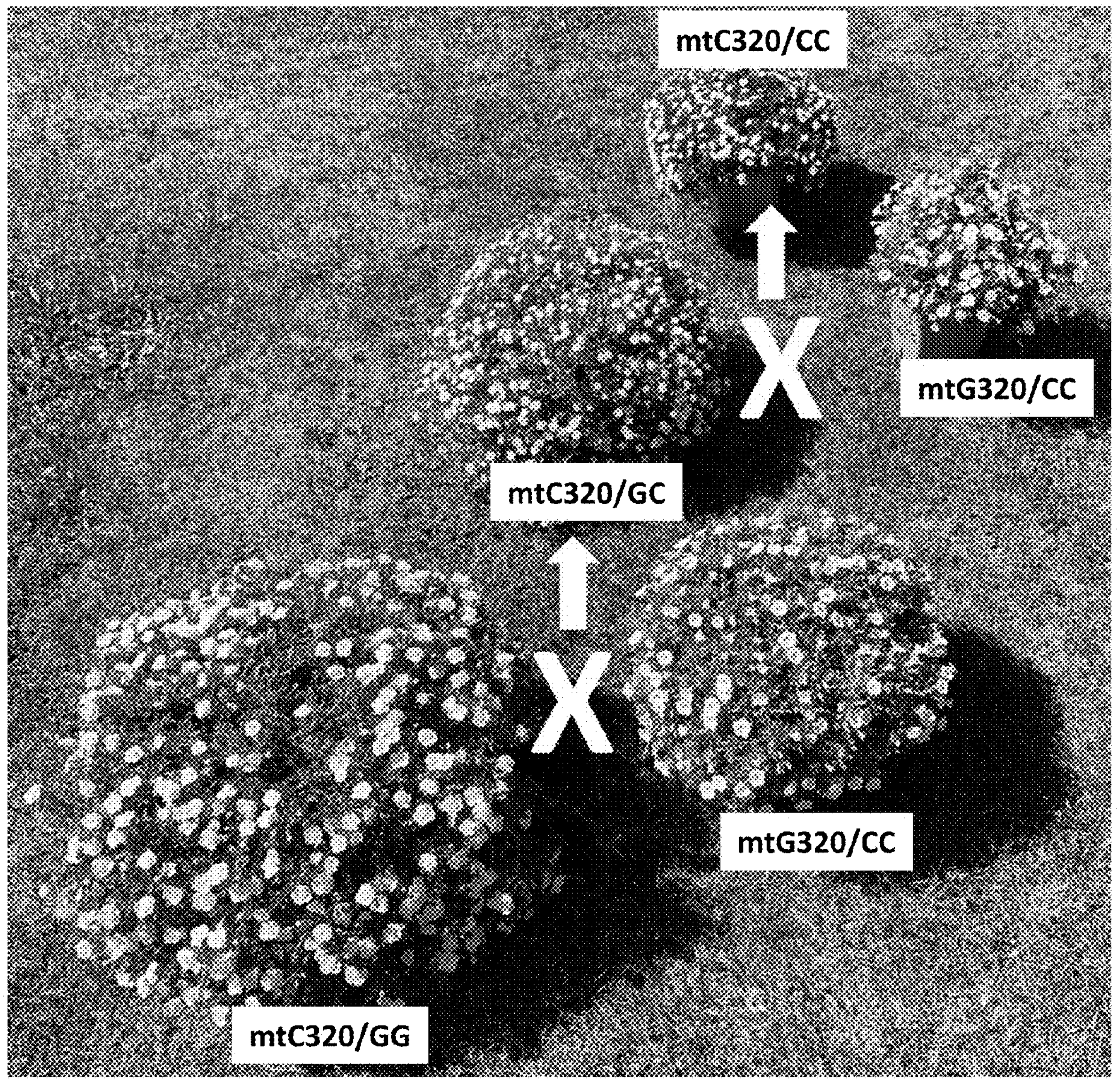
FIG. 8 is a photograph of parental lines and progeny plants from a breeding scheme to produce a white double-flowering dwarf *Calibrachoa* plant.

As shown in FIG. 8, a white plant having double-flowers (mtC320) and normal vigorous growth (G/G) was used as the female parent and crossed with a white dwarf (C/C) plant having single flowers (mtG320) as the male parent. The $F_1$ progeny exhibited white double-flowers (mtC320) and normal vigorous growth as it was heterozygous for the recessive dwarf allele (G/C). This $F_1$ progeny was used a female parent in a cross with a male white dwarf (C/C) plant having single flowers (mtG320). While an outcrossing is shown in FIG. 8, those skilled in the art will understand that this progeny could also be backcrossed to the first male parent. $F_2$ progeny were genotyped for the molecular markers disclosed herein using methods well known in the art. A selected $F_2$ progeny from this cross is shown at the top of FIG. 8, a white double-flowering (mtC320) dwarf (C/C) *Calibrachoa.*

Example 3: Double-Flowering Varieties with and without the Dwarf Trait

Figure 9A:
FIGS. 9A-9E show plants of different colors all having the double-flowering trait combined with either a wild-type allele for growth, (plant pictured left, "G/G" or "G/C"), or homozygous for the recessive dwarf allele associated with the nucleotide polymorphism shown in FIG. 4A (plant pictured right, "C/C"). Shown in FIG. 9A are yellow varieties. Shown in FIG. 9B are red varieties. Shown in FIG. 9C are pink varieties. Shown in FIG. 9D are pink-purple varieties. Shown in FIG. 9E are purple-red varieties.
Figure 9B:
Figure 9C:
Figure 9D:
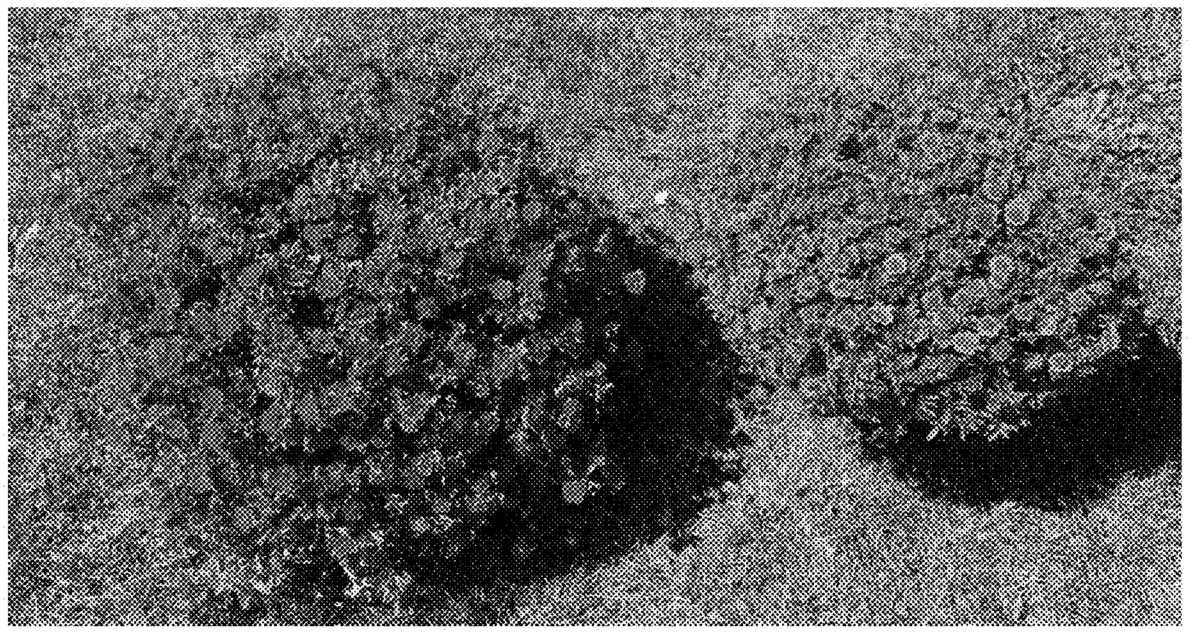
Figure 9E:
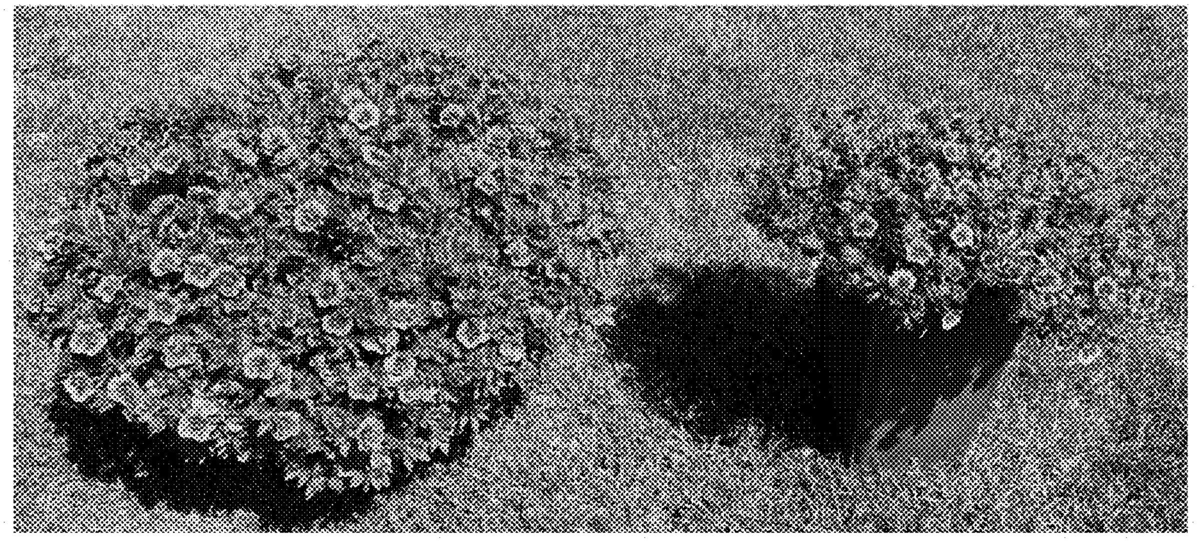

FIGS. 9A-9G show plants of different colored varieties all having the double-flowering trait combined with either a wild-type allele for the dwarf trait (plant pictured left, G/G or G/C), or homozygous for the recessive dwarf allele (plant pictured right) associated with the nucleotide polymorphism shown in FIG. 4A (C/C). Plants were bred using the breeding methods and schemes disclosed herein. Shown in FIG. 9A are plants of yellow varieties. Shown in FIG. 9B are plants of red varieties. Shown in FIG. 9C are plants of pink varieties. Shown in FIG. 9D are plants of pink-purple varieties, and shown in FIG. 9E are plants of purple-red varieties.

Figures 10A, 10B, 10C, 10D, 10E, 10F:
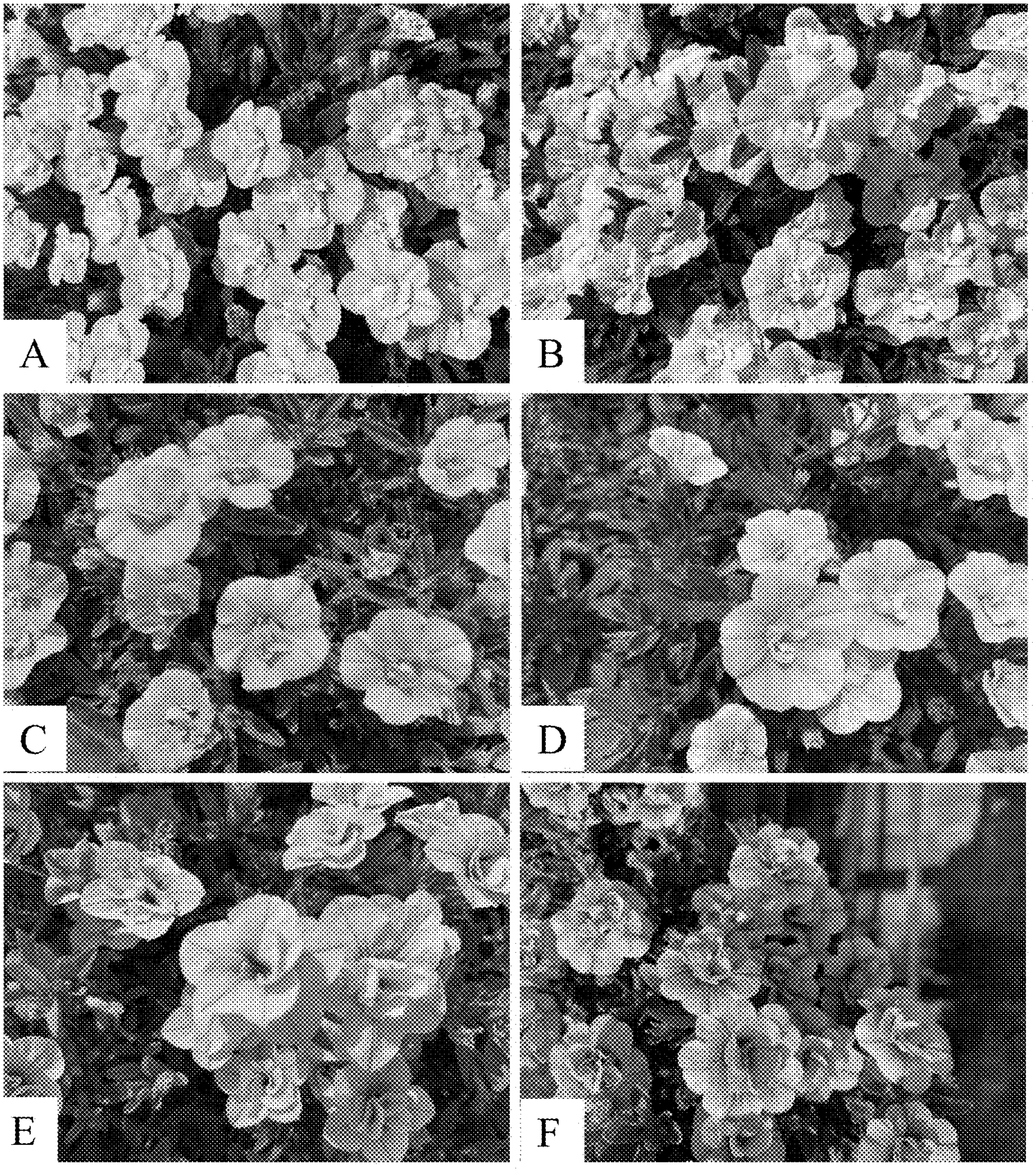
FIGS. 10A-10F are photographs of double-flowering dwarf *Calibrachoa* plants of the present disclosure having varying shades of white colored flowers (FIGS. 10A and 10B), yellow colored flowers (FIGS. 10C and 10D) and yellow-orange colored flowers (FIGS. 10E and 10F).

Example 4: White, Yellow, and Orange Double-Flowering Dwarf *Calibrachoa* Varieties Generated Using the Methods Disclosed Herein FIGS. 10A-10F are close up photographs of double-flowering dwarf *Calibrachoa* plants of the present disclosure having varying shades of white colored flowers (FIGS. 10A and 10B), yellow colored flowers (FIGS. 10C and 10D) and yellow-orange colored flowers (FIGS. 10E and 10F). Shown in FIGS. 10A and 10B are plants of white varieties designated CA-2020-0723 and CA-2020-0710 respectively. Shown in FIG. 10C is a plant of a yellow variety designated CA-2020-0743. Shown in FIG. 10D is a plant of a light yellow variety having a large area of yellow at the transition to the corolla tube designated CA-2020-0735. Shown in FIG. 10E is a plant of a light orange variety having strong red veins, designated CA-2020-0611, and shown in FIG. 10F is a plant of a yellow-orange variety having strong red veins designated CA-2020-0931.

Figures 11A, 11B, 11C, 11D, 11E, 11F:
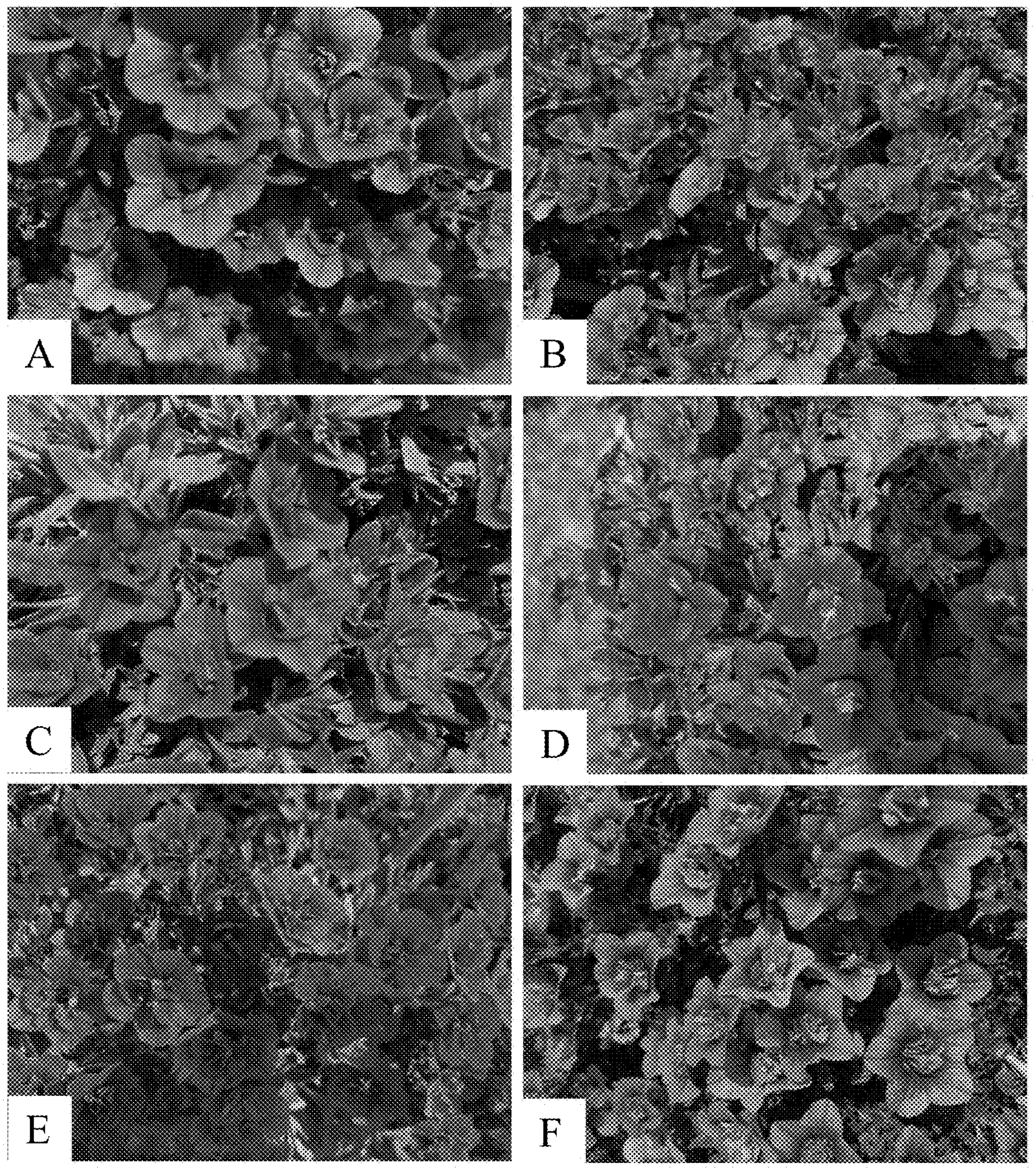
FIGS. 11A-11F are photographs of double-flowering dwarf *Calibrachoa* plants of the present disclosure having varying shades of orange colored flowers (FIGS. 11A and 11B) and red colored flowers (FIGS. 11C-11F).

Example 5: Double-Flowering Dwarf *Calibrachoa* Varieties in Varying Shades of Red and Orange Generated Using the Methods Disclosed Herein FIGS. 11A-11F are close up photographs of double-flowering dwarf *Calibrachoa* plants of the present disclosure having varying shades of red and orange colored flowers. Shown in FIGS. 11A and 11B are two plants of orange varieties, designated CA-2020-0825 and CA-2020-0833 respectively. Shown in FIG. 11C (CA-2020-0810), FIG. 11D (CA-2020-0805) and FIG. 11E (CA-2020-0697) are three plants of red varieties, and FIG. 11F shows a plant of a light red variety designated CA-2020-0809.

Figures 12A, 12B, 12C, 12D, 12E, 12F:
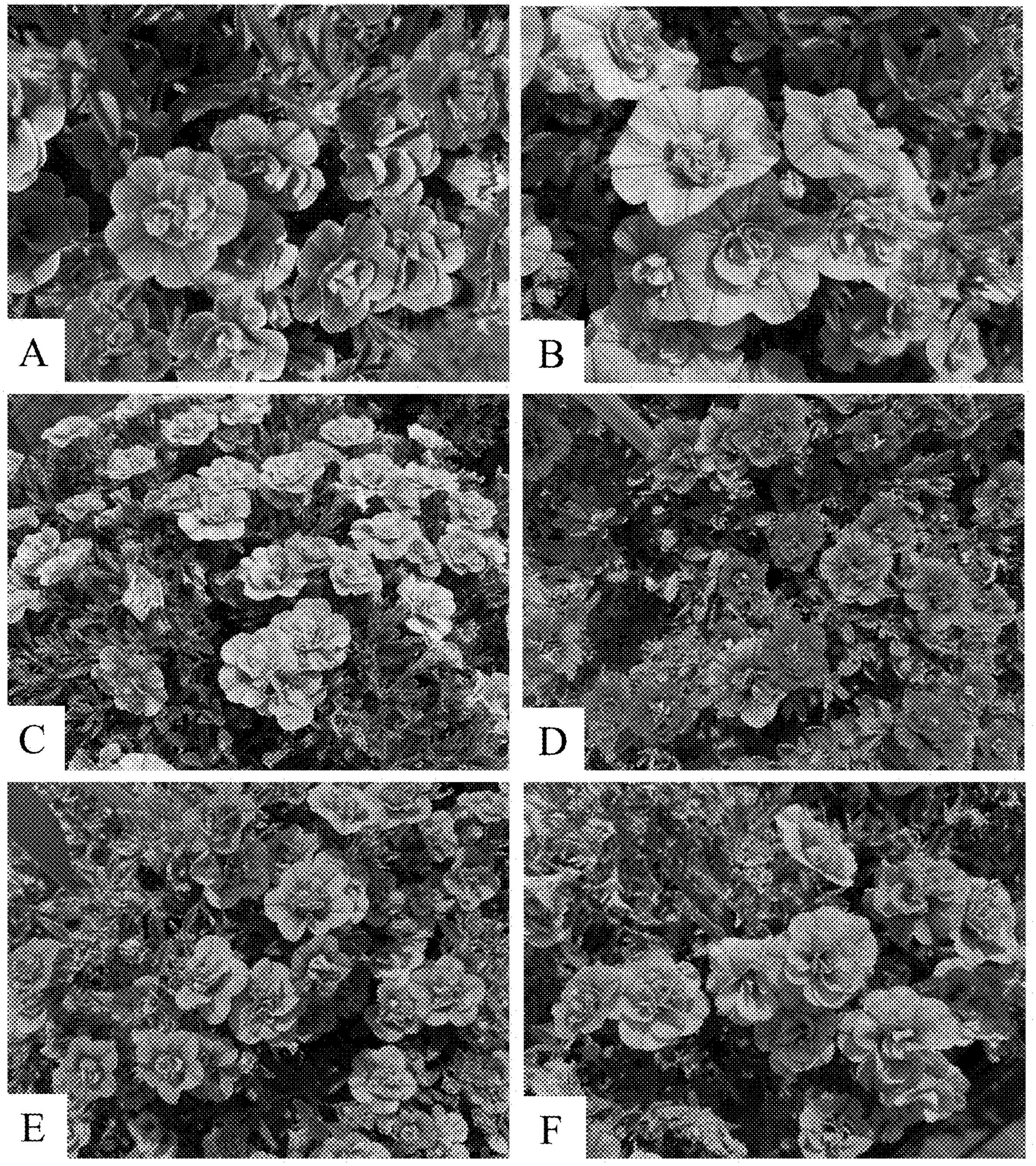
FIGS. 12A-12F are photographs of double-flowering dwarf *Calibrachoa* plants of the present disclosure having varying shades of pink colored flowers.

Example 6: Double-Flowering Dwarf *Calibrachoa* Varieties in Varying Shades of Pink Generated Using the Methods Disclosed Herein FIGS. 12A-12F, FIGS. 13A-13F, and FIGS. 14A-14D are close up photographs of double-flowering dwarf *Calibrachoa* plants of the present disclosure having varying shades of pink colored flowers. In FIG. 12A, a plant of a pink-purple variety is shown having a white color at the margin of the corolla lobes and designated CA-2020-0766. FIGS. 12B and 12C show plants of two purple-pink varieties designated CA-2020-0604 and CA-2020-0748 respectively. In FIG. 12D a plant of a dark pink-red variety having irregular magenta and yellow colored petaloids, designated CA-2020-0775, is shown. FIGS. 12E and 12F show plants of two dark pink varieties having strong veins, designated CA-2020-0772 and CA-2020-0762 respectively.

Figures 13A, 13B, 13C, 13D, 13E, 13F:
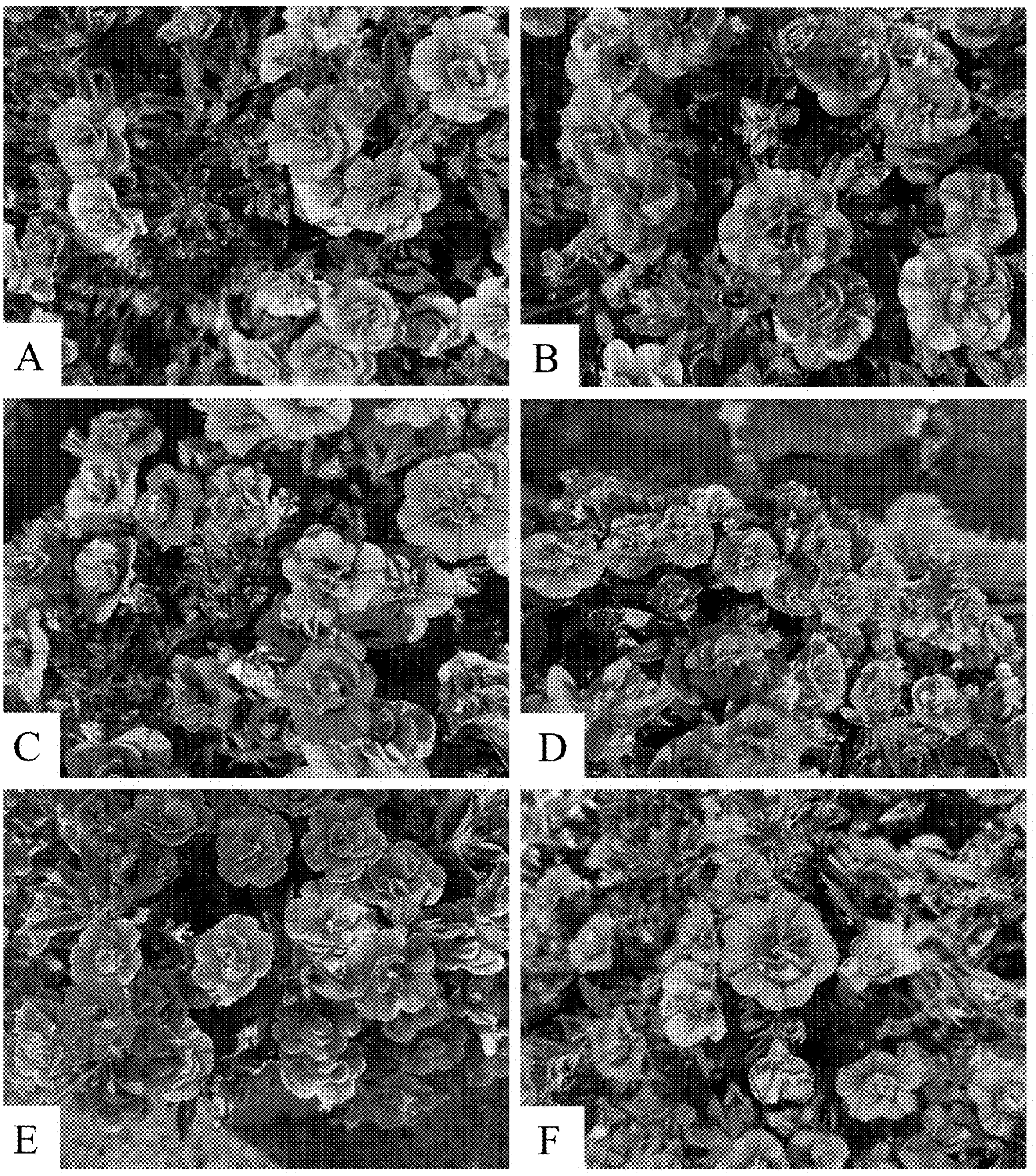
FIGS. 13A-13F are photographs of double-flowering dwarf *Calibrachoa* plants of the present disclosure having varying shades of pink colored flowers.

FIG. 13A (CA-2020-0784), FIG. 13B (CA-2020-0782) and FIG. 13C (CA-2020-0780) show plants of three purple-pink varieties. FIG. 13D shows a plant of a dark pink-red variety designated CA-2020-0778. In FIG. 13E, a plant of variety CA-2019-5055 is shown having pink flowers with a white color at the margin of the corolla lobes, and FIG. 13F shows a plant of a pink variety designated CA-2019-4954.

Figures 14A, 14B, 14C, 14D:
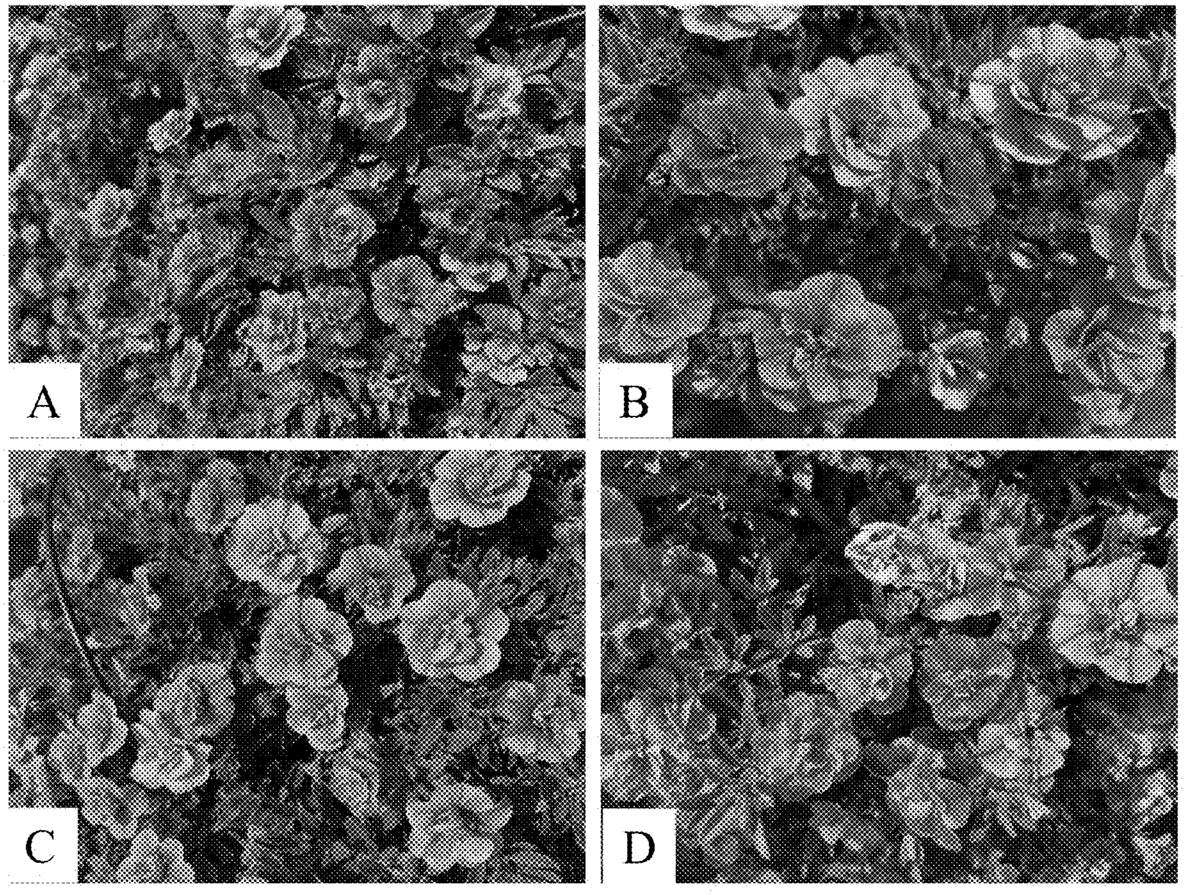
FIGS. 14A-14D are photographs of double-flowering dwarf *Calibrachoa* plants of the present disclosure having varying shades of pink colored flowers.

FIGS. 14A and 14B show plants of two purple-red varieties designated CA-2020-0763 and CA-2020-0755 respectively. FIG. 14C shows plants of a dark pink-red variety designated CA-2020-0788 and FIG. 14D shows a plant of a purple-pink variety designated CA-2020-0797.

Figures 15A, 15B, 15C, 15D, 15E, 15F:
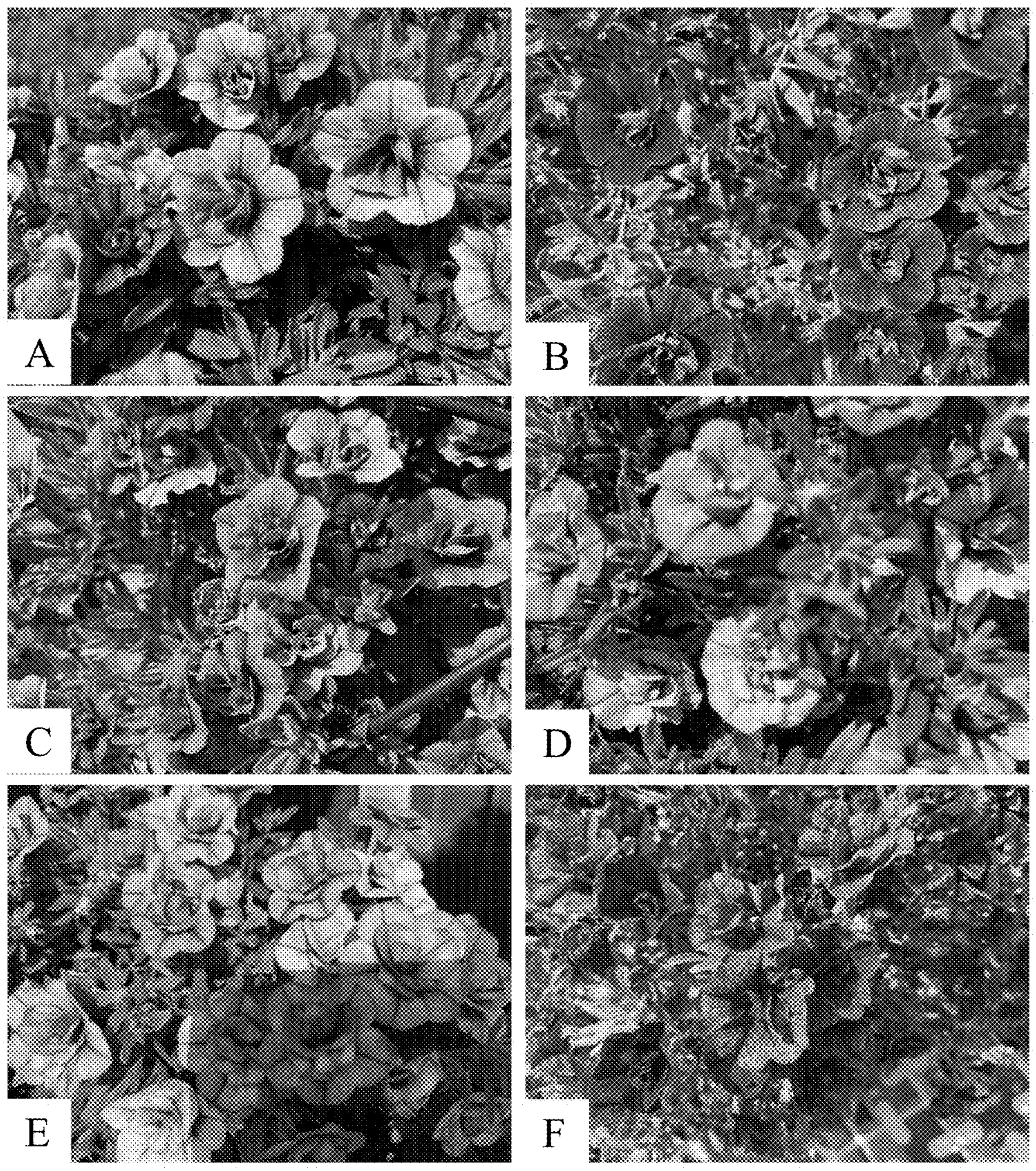
FIGS. 15A-15F are photographs of double-flowering dwarf *Calibrachoa* plants of the present disclosure having varying shades of purple colored flowers.

Example 7: Double-Flowering Dwarf *Calibrachoa* Varieties in Varying Shades of Purple Generated Using the Methods Disclosed Herein FIGS. 15A-15F are close up photographs of double-flowering dwarf *Calibrachoa* plants of the present disclosure having varying shades of purple colored flowers. FIGS. 15A and 15B show plants of two dark pink-violet varieties having strong veins, designated CA-2020-0842 and CA-2020-0708 respectively. FIG. 15C shows a plant of a brown-orange variety with strong purple veins designated CA-2020-0837. FIG. 15D shows a plant of a light violet variety having medium violet veins, designated CA-2020-0843. FIG. 15E shows a plant of a violet variety designated CA-2020-0846, and FIG. 15F shows a plant of a purple variety with strong veins, designated CA-2019-5258.

Figures 16A, 16B, 16C, 16D, 16E, 16F:
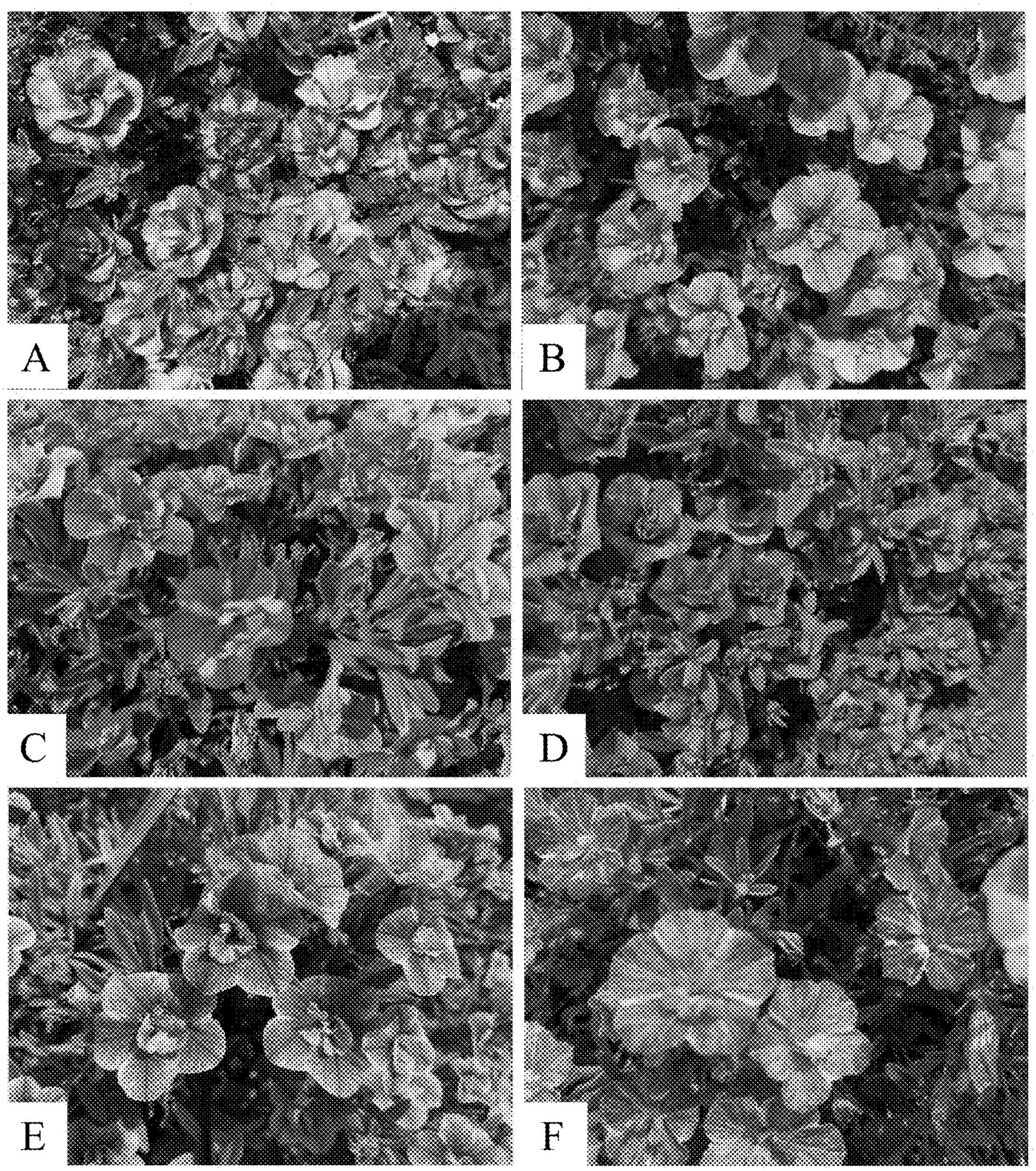
FIGS. 16A-16F are photographs of double-flowering dwarf *Calibrachoa* plants of the present disclosure having patterns in different main and secondary colored flowers.

Example 8: Double-Flowering Dwarf *Calibrachoa* Varieties in Varying Colors and Patterns Generated Using the Methods Disclosed Herein FIGS. 16A-16F are close up photographs of double-flowering dwarf *Calibrachoa* plants of the present disclosure having varying colors and patterns. FIG. 16A shows a plant of a variety designated CA-2019-5264 having light purple flowers with a darker purple color at the distal part of the corolla lobes. FIG. 16B shows a plant of a variety designated CA-2020-0900 having red-pink flowers with a broad yellow color along the fused parts of the corolla lobes. FIG. 16C shows a plant of a variety designated CA-2020-0765 having pink-purple flowers with irregular light-pink color distribution. FIG. 16D shows a plant of a variety designated CA-2020-0812 having orange-red flowers with irregular yellow color distribution. FIG. 16E shows a plant of a variety designated CA-2020-0680 having pink-purple flowers with a small area of black at the transition to the corolla tube and a white margin on the corolla lobes. FIG. 16F shows a plant of a variety designated CA-2020-0589 having pink-purple flowers with irregular white color distribution.

Figures 17A, 17B, 17C, 17D, 17E, 17F:
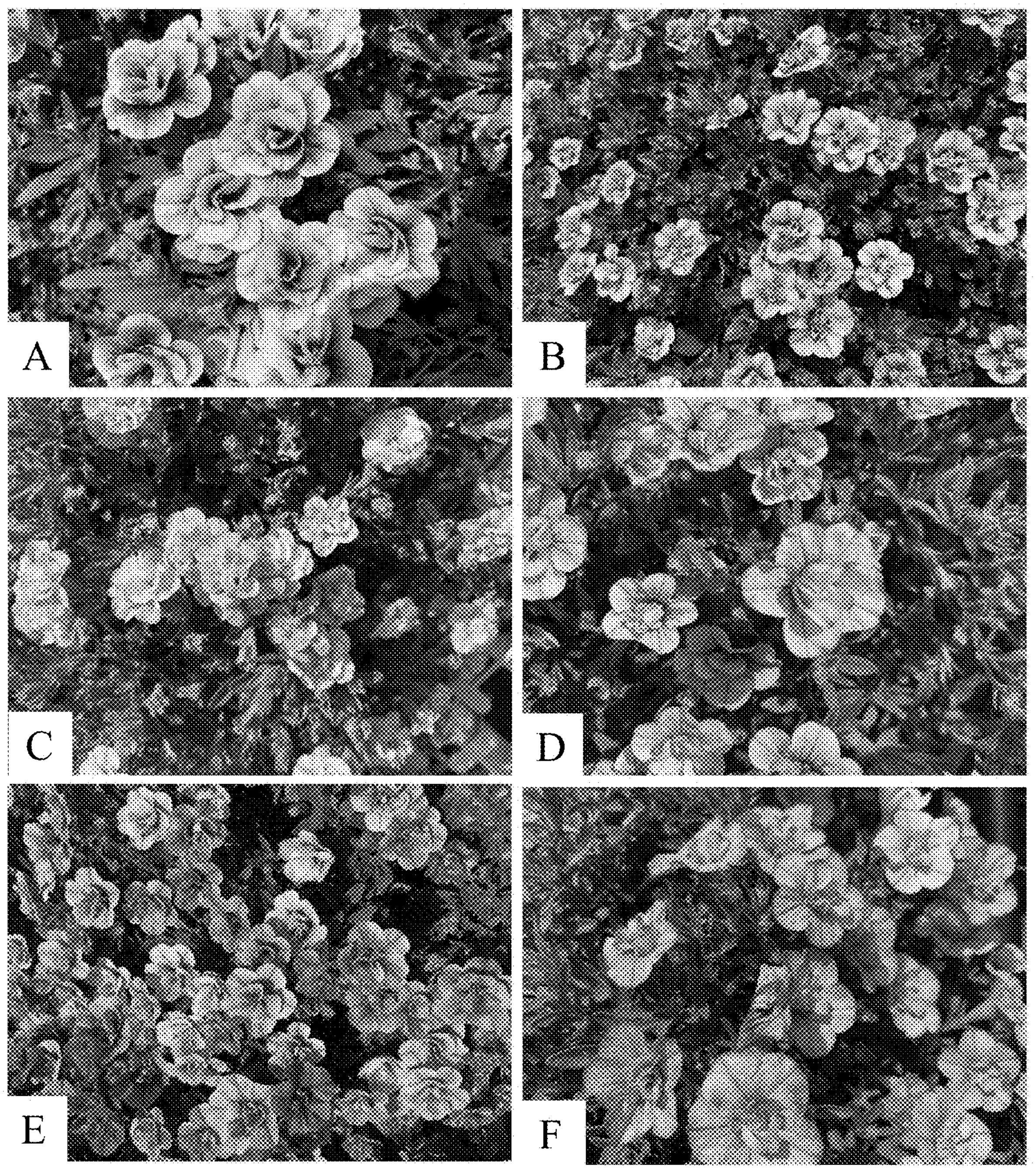
FIGS. 17A-17F are photographs of double-flowering dwarf *Calibrachoa* plants of the present disclosure having different colored flowers with contrasting veins and flowers with color change during growing season.

Example 9: Double-Flowering Dwarf *Calibrachoa* Varieties in Varying Colors with Contrasting Veins Generated Using the Methods Disclosed Herein FIGS. 17A-17F are close up photographs of double-flowering dwarf *Calibrachoa* plants of the present disclosure having different colored flowers with contrasting veins. Shown in FIG. 17A is a plant of a purple variety with white margins on the corolla lobes and dark purple veins, designated CA-2020-5194. Shown in FIG. 17B is a plant of a light yellow-orange variety with strong red veins, designated CA-2020-0773. Shown in FIG. 17C is a plant of a light yellow variety with very strong purple veins, designated CA-2016-8659. Shown in FIG. 17D is a plant of a light yellow variety with very strong red veins, designated CA-2020-0612. In FIG. 17E, a plant of a purple-red variety with strong pink veins designated CA-2020-0790 is shown, and in FIG. 17F, a plant of variety designated CA-2020-0923 having light yellow flowers with strong red veins and a red color at the margin of corolla tubes is shown.

Figures 18A, 18B, 18C, 18D, 18E, 18F:
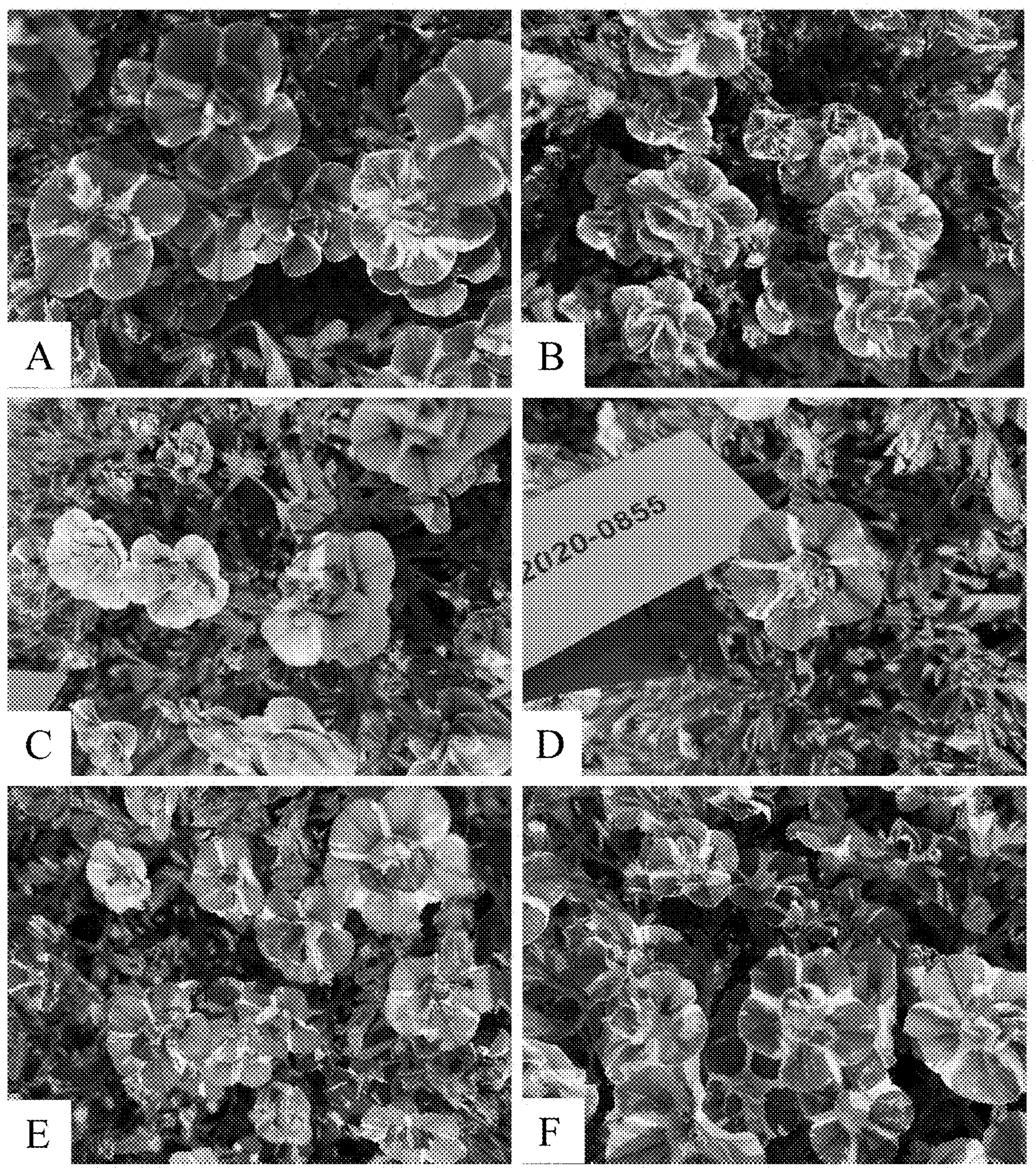
FIGS. 18A-18F are photographs of double-flowering dwarf *Calibrachoa* plants of the present disclosure having different main colored flowers and variations of secondary flower color distribution.

Example 10: Double-Flowering Dwarf *Calibrachoa* Varieties in Varying Colors with Variations of the Star Pattern Generated Using the Methods Disclosed Herein FIGS. 18A-18F are close up photographs of double-flowering dwarf *Calibrachoa* plants of the present disclosure having different colored flowers and variations of the star pattern. Shown in FIGS. 18A and 18B are plants of two varieties, designated CA-2020-0579 and CA-2020-0581 respectively, having pink-purple flowers with very large yellow markings at the transition to the corolla tube and a white color along the fused parts of the corolla lobes. In FIGS. 18C and 18D, plants of violet and dark violet varieties designated CA-2020-0854 and CA-2020-0855 respectively are shown having a white color along the fused parts of the corolla lobes. FIGS. 18E and 18F show plants of two varieties, designated CA-2020-0856 and CA-2020-0857 respectively, having dark pink-violet flowers with a white color along the fused parts of the corolla lobes.

Figures 19A, 19B, 19C, 19D, 19E, 19F:
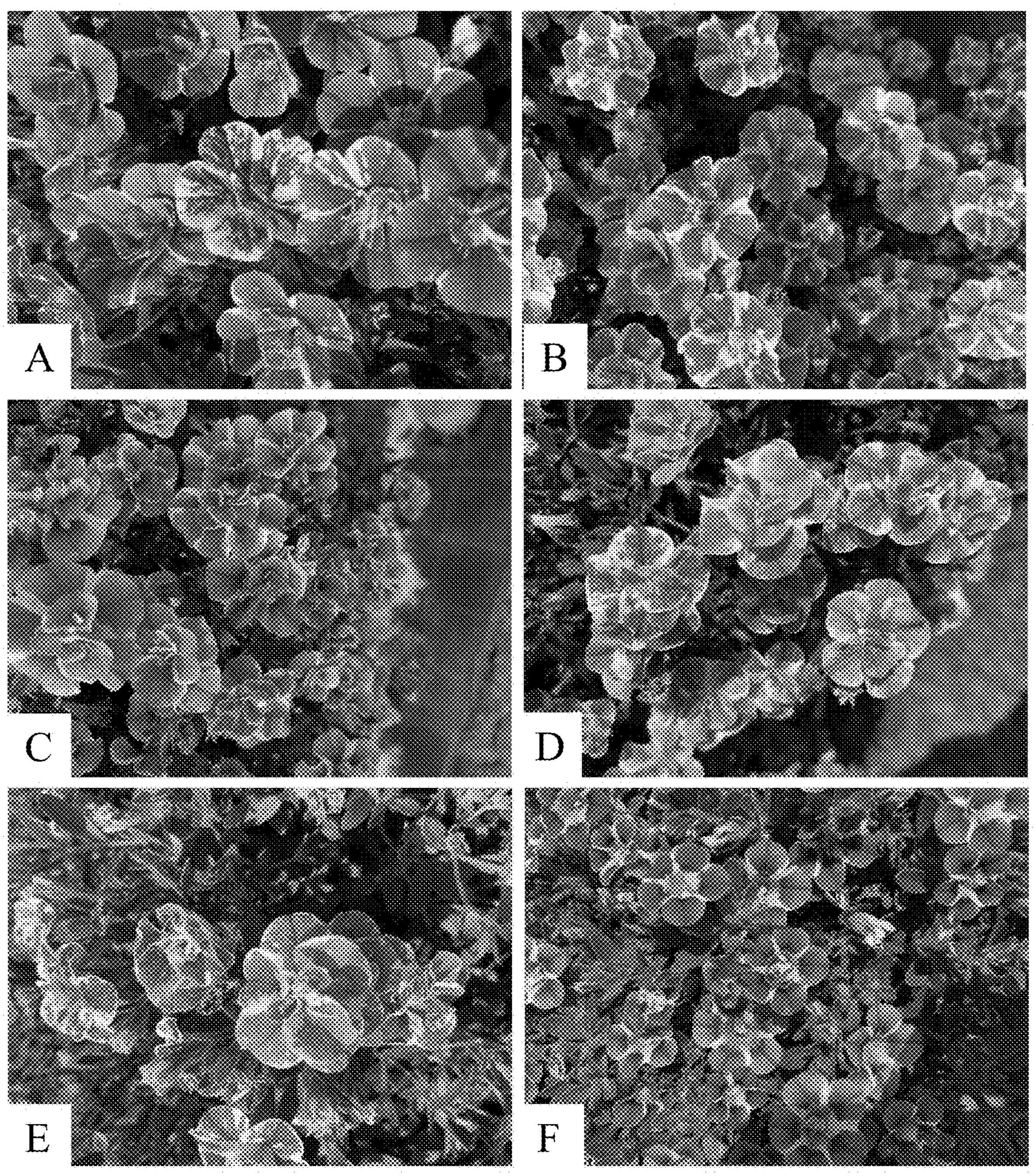
FIGS. 19A-19F are photographs of double-flowering dwarf *Calibrachoa* plants of the present disclosure having different main colored flowers and variations of secondary flower color distribution.

Example 11: Double-Flowering Dwarf *Calibrachoa* Varieties in Varying Shades of Pink-Purple with the Star Pattern Generated Using the Methods Disclosed Herein FIGS. 19A-19F are close up photographs of double-flowering dwarf *Calibrachoa* plants of the present disclosure in varying shades of pink-purple with the star pattern, all having some degree of white coloration along the fused parts of the corolla lobes. FIG. 19A shows a plant of variety designated CA-2020-0862, which also exhibits some irregular white color distribution in addition to the star pattern. FIG. 19B shows a plant of variety designated CA-2020-0864. FIGS. 19C and 19D show plants of varieties designated CA-2020-0870 and CA-2020-0883, respectively, and FIG. 19E shows a plant of a variety designated CA-2020-0875. FIG. 19F shows a plant of a variety designated CA-2020-0889 having a milder double-flowering phenotype, with an additional darker color at the transition to the corolla tube.

Figures 20A, 20B, 20C:
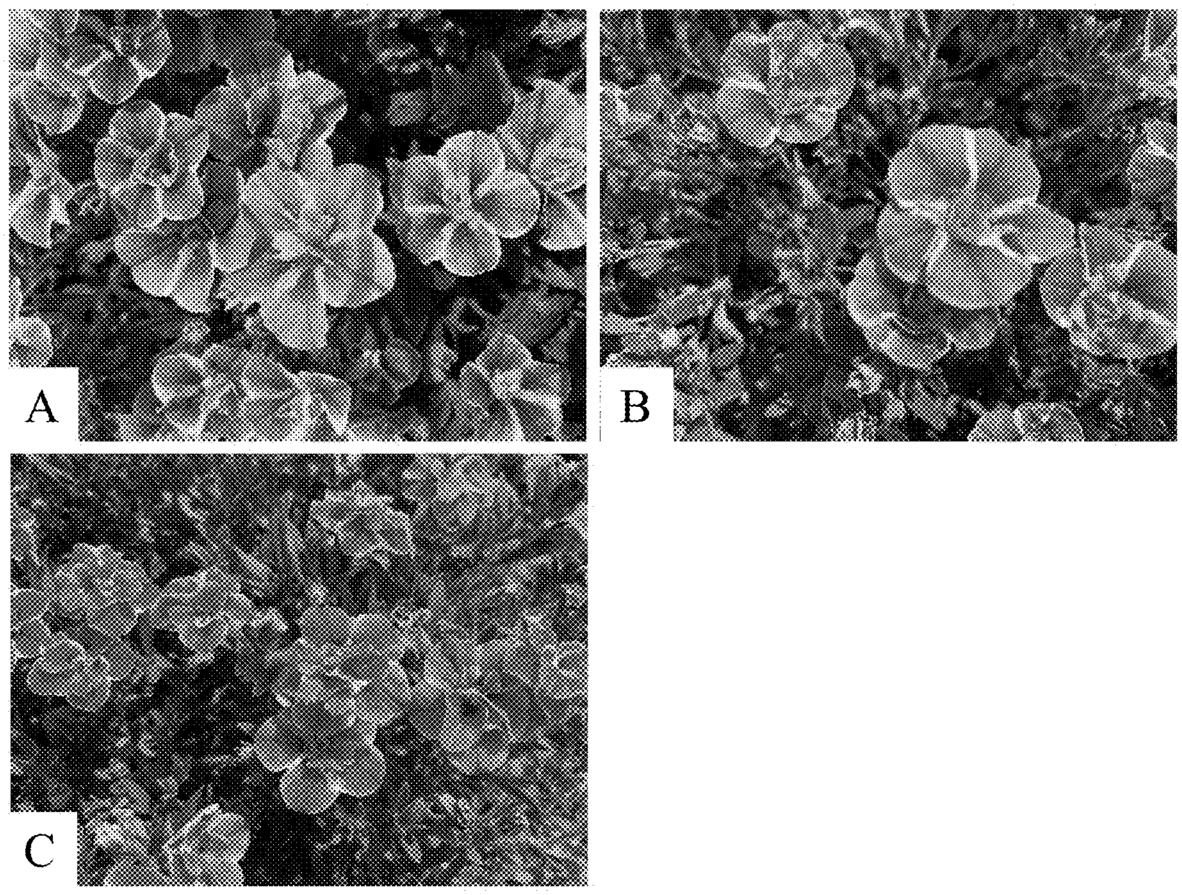
FIGS. 20A-20C are photographs of double-flowering dwarf *Calibrachoa* plants of the present disclosure having different main colored flowers and variations of secondary flower color distribution.

Example 12: Double-Flowering Dwarf *Calibrachoa* Varieties in Different Colors with Variations of the Star Pattern Generated Using the Methods Disclosed Herein FIGS. 20A-20D are close up photographs of double-flowering dwarf *Calibrachoa* plants of the present disclosure having different colored flowers and variations of the star pattern. A plant of a red variety having yellow along the fused parts of the corolla lobes, designated CA-2019-5092 is shown in FIG. 20A. A plant of a purple-pink variety designated CA-2020-0678 with medium white color along the fused parts of the corolla lobes is shown in FIG. 20B. FIG. 20C shows a plant of a variety designated CA-2020-0750 having purple-pink flowers with white margins of the corolla lobes.

Figures 21A, 21B, 21C, 21D, 21E, 21F:
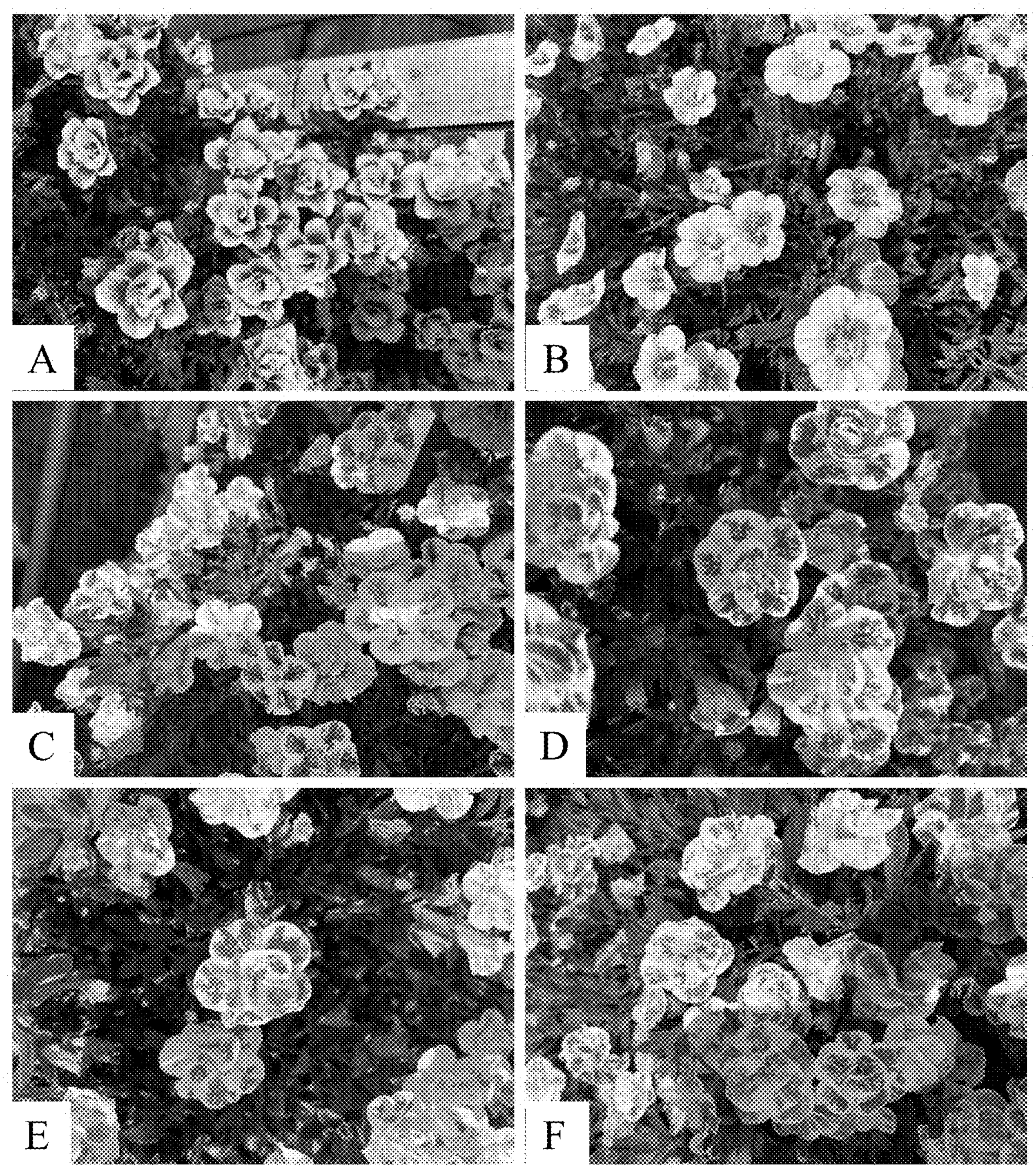
FIGS. 21A-21F are photographs of double-flowering dwarf *Calibrachoa* plants of the present disclosure having different main colored flowers showing variations of secondary flower color distribution and flowers with color change during growing season.

Example 13: Double-Flowering Dwarf *Calibrachoa* Varieties in Different Colors with Variations of White Margins Generated Using the Methods Disclosed Herein FIGS. 21A-21F are close up photographs of double-flowering dwarf *Calibrachoa* plants of the present disclosure having different colored flowers and varying amounts of white coloration at the distal portions of the corolla lobes. Shown in FIG. 21A is a plant of a purple variety designated CA-2017-1140 having a white margin of the corolla lobes. FIG. 21B shows a plant of a variety designated CA-2020-0907 having purple-pink flowers with white at the distal part of the corolla tubes. FIG. 21C shows a plant of a violet variety designated CA-2020-0899 having a white color at the margin of the corolla lobes. FIGS. 21D-21F show plants of purple-pink varieties having a white color at the margin of the corolla lobes designated CA-2020-0868, CA-2020-0869, and CA-2020-0894, respectively.

Example 14: Generating a Double-Flowering and/or Dwarf *Calibrachoa* Via a Gene Editing Tool or Technology In the event that the SNP mutations disclosed herein are the causative SNP mutations for the double-flowering and/or dwarf trait, single flowering vigorous *Calibrachoa* plants may be converted to a double-flowering and/or dwarf phenotype by targeted genetic engineering. Such methods may include, for example, the CRISPR system. Many plants have already been modified using the CRISPR system, for example *Petunia*, a close relative of *Calibrachoa*. See for example, Zhang, B. et al., "Exploiting the CRISPR/Cas9 System for Targeted Genome Mutagenesis in *Petunia*" *Science Reports*, Vol. 6, February 2016.

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing in *Calibrachoa*. The technique is well known in the art; see for example Malzahn, Aimee et al. "Plant genome editing with TALEN and CRISPR" *Cell & Bioscience* vol. 7 21. 24 Apr. 2017.

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in *Advances in New Technology for Targeted Modification of Plant Genomes*. Springer Science+Business. pp 21-38 (2015).

Example 15: Double-Flowering Dwarf *Petunia-Calibrachoa* (Petchoa) Hybrids

*Petunia* and *Calibrachoa* are closely related. In the 1990's, several species of *Petunia* were crossed with *Calibrachoa*. The resulting hybrid offspring was named Petchoa. The double-flowering dwarf *Calibrachoa* plants disclosed herein can be used in a plant breeding program to produce double-flowering dwarf Petchoas. For example, a female double-flowering dwarf *Calibrachoa* may be crossed with a male *Petunia* carrying at least one allele for a dwarf trait. Embryos may be rescued and cultured by techniques well known in the art, and the plant(s) can be grown and further propagated by tissue culture and cuttings.

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Further, European Application No. EP20202350.3, filed Oct. 16, 2020, and entitled: Double-Flowering Dwarf *Calibrachoa* is hereby incorporated by reference.

NUMBERED EMBODIMENTS

Further embodiments contemplated by the disclosure are listed below.

1. A *Calibrachoa* plant comprising a double-flowering characteristic and a dwarf growth characteristic,
   wherein said double-flowering characteristic is caused by a mitochondrial allele associated with at least one single nucleotide polymorphism (SNP) mutation selected from the group consisting of (i) a G to C nucleotide substitution at position number 320 of SEQ ID NO: 1 and (i) an A to C nucleotide substitution at position number 247 in SEQ ID NO: 1, and
   wherein said dwarf growth characteristic is caused by a homozygous recessive nuclear allele associated with a SNP mutation consisting of a G to C nucleotide substitution at position 43 of SEQ ID NO: 2.
2. The *Calibrachoa* plant of embodiment 1, wherein said plant has a petaloid stamina rating of at least 2.
3. The *Calibrachoa* plant of embodiment 1, wherein said plant has a petaloid stamina rating of at least 3.
4. The *Calibrachoa* plant of embodiment 1, wherein said plant has a petaloid stamina rating of at least 4.
5. The *Calibrachoa* plant of embodiment 1, wherein said plant has a petaloid stamina rating of at least 5.
6. The *Calibrachoa* plant of embodiment 1, wherein said plant has a petaloid stamina rating of at least 6.
7. The *Calibrachoa* plant of any one of embodiments 1-6, where said plant comprises both the G to C nucleotide substitution at position number 320 of SEQ ID NO: 1 and (i) the A to C nucleotide substitution at position number 247 in SEQ ID NO: 1.
8. The *Calibrachoa* plant of any one of embodiments 1-7, wherein said plant at maturity has a vigor rating of less than 5 compared to plants having a non-dwarf growth characteristic when grown under the same environmental conditions, wherein said non-dwarf plant has at least one copy of the allele associated with a SNP mutation consisting of a G at position 43 of SEQ ID NO: 2.
9. The *Calibrachoa* plant of any one of embodiments 1-6, wherein said plant at maturity has a vigor rating of less than 4 compared to plants having a non-dwarf growth characteristic when grown under the same environmental conditions, wherein said non-dwarf plant has at least one copy of the allele associated with a SNP mutation consisting of a G at position 43 of SEQ ID NO: 2.
10. The *Calibrachoa* plant of any one of embodiments 1-6, wherein said plant at maturity has a vigor rating of less than 3 compared to plants having a non-dwarf growth characteristic when grown under the same environmental conditions, wherein said non-dwarf plant has at least one copy of the allele associated with a SNP mutation consisting of a G at position 43 of SEQ ID NO: 2.
11. The *Calibrachoa* plant of any one of embodiments 1-10, wherein said plant exhibits male sterility.
12. The *Calibrachoa* plant of any one of embodiments 1-11, wherein said plant is grown without the addition of synthetic plant growth regulators.
13. The *Calibrachoa* plant of any one of embodiments 1-12, wherein said plant comprises no detectable residue of a synthetic plant growth regulator or a related breakdown of a plant growth regulator product.
14. The *Calibrachoa* plant of any one of embodiments 1-13, wherein said plant further comprises a mutation affecting flower color and/or flower color pattern, wherein said mutation is the result of an induced random or targeted mutagenesis.
15. The *Calibrachoa* plant of embodiment 14, wherein said targeted mutagenesis is a gene editing tool or technology.
16. The *Calibrachoa* plant of embodiment 15, wherein the gene editing tool or technology is selected from the group consisting of homing endonucleases/meganucleases (EMNs), zinc finger nucleases (ZFNs), transcription activator-like effector nucleases (TALENs), and CRISPR/Cas enzymes.
17. A method of producing a *Calibrachoa* plant comprising a double-flowering characteristic and a dwarf growth characteristic comprising the steps of:
   (i) crossing a first female *Calibrachoa* plant with a first male *Calibrachoa* plant to produce $F_1$ plants, wherein said first female *Calibrachoa* plant comprises a mitochondrial allele associated with at least one SNP mutation selected from the group consisting of (i) a G to C nucleotide substitution at position number 320 of SEQ ID NO: 1 and (ii) an A to C nucleotide substitution at position number 247 in SEQ ID NO: 1 and exhibiting a double-flowering characteristic, and wherein said first male *Calibrachoa* plant has at least one copy of a nuclear, recessive allele associated with a SNP mutation consisting of a G to C nucleotide substitution at position 43 of SEQ ID NO: 2, wherein when said nuclear allele is in the homozygous form, plants exhibit a dwarf growth characteristic;
   (ii) screening said $F_1$ plants for the presence of said nuclear SNP mutation;
   (iii) selecting an $F_1$ female plant exhibiting said double-flowering characteristic and further comprising at least one copy of said nuclear SNP mutation;
   (iv) crossing said $F_1$ female plant with said first male or a second male *Calibrachoa* plant having at least one copy said nuclear SNP mutation to produce $F_2$ plants;
   (v) screening said $F_2$ plants for the presence of said nuclear SNP mutation; and
   (vi) selecting an $F_2$ plant exhibiting said double-flowering characteristic and being homozygous for said nuclear SNP mutation.
18. The method of embodiment 17, wherein said first female *Calibrachoa* plant comprises both the G to C nucleotide substitution at position number 320 of SEQ ID NO: 1 and (i) the A to C nucleotide substitution at position number 247 in SEQ ID NO: 1.
19. The method of embodiment 17 or 18, wherein the first or second male *Calibrachoa* plant is homozygous for said nuclear SNP mutation and exhibits a dwarf growth characteristic.
20. The method of any one of embodiment 17-19, further comprising asexual propagation or sexual reproduction of said selected $F_2$ plant.
21. A plant produced by the method of any one of embodiments 17-20, wherein said plant is asexually propagated and grown without synthetic growth regulators.
22. A *Calibrachoa* plant produced by the method of any one of embodiments 17-20, wherein said plant has a petaloid stamina rating of at least three and wherein said plant at maturity has a vigor rating of less than 5 compared to plants having a non-dwarf growth characteristic when grown under the same environmental conditions, wherein said non-dwarf plant has at least one copy of the allele associated with a SNP mutation consisting of a G at position 43 of SEQ ID NO: 2.

23. A *Calibrachoa* plant produced by the method of any one of embodiments 17-21, wherein said plant has a petaloid stamina rating of at least 4.

24. A *Calibrachoa* plant produced by the method of any one of embodiments 17-21, wherein said plant has a petaloid stamina rating of at least 5.

25. A *Calibrachoa* plant produced by the method of any one of embodiments 17-21, wherein said plant has a petaloid stamina rating of at least 6.

26. A *Calibrachoa* plant produced by the method of any one of embodiments 17-21, wherein said plant has a petaloid stamina rating of at least 7.

27. A *Calibrachoa* plant produced by the method of any one of embodiments 17-21, wherein said plant at maturity has a vigor rating of less than 4 compared to plants having a non-dwarf growth characteristic when grown under the same environmental conditions, wherein said non-dwarf plant has at least one copy of the allele associated with a SNP mutation consisting of a G at position 43 of SEQ ID NO: 2.

28. A *Calibrachoa* plant produced by the method of any one of embodiments 17-21, wherein said plant at maturity has a vigor rating of less than 3 compared to plants having a non-dwarf growth characteristic when grown under the same environmental conditions, wherein said non-dwarf plant has at least one copy of the allele associated with a SNP mutation consisting of a G at position 43 of SEQ ID NO: 2.

29. The *Calibrachoa* plant of any one of embodiments 17-28 further comprising a mitochondrial allele associated with an A to C nucleotide substitution at position number 247 in SEQ ID NO: 1.

30. The *Calibrachoa* plant of any one of embodiments 17-29, wherein said plant exhibits male sterility.

31. The *Calibrachoa* plant of any one of embodiments 17-30, wherein said plant further comprises a mutation affecting flower color and/or flower color pattern, wherein said mutation is the result of an induced random or targeted mutagenesis.

32. The *Calibrachoa* plant of embodiment 30, wherein said targeted mutagenesis is a gene editing tool or technology.

33. The *Calibrachoa* plant of embodiment 32, wherein the gene editing tool or technology is selected from the group consisting of homing endonucleases/meganucleases (EMNs), zinc finger nucleases (ZFNs), transcription activator-like effector nucleases (TALENs), and CRISPR/Cas enzymes.

34. A method for producing a double-flowering dwarf *Calibrachoa* plant having a desired trait comprising applying a plant breeding technique to the *Calibrachoa* plant of any one of embodiments 21-29.

35. The method of embodiment 34, wherein said plant breeding technique is selected from the group consisting of recurrent selection, mass selection, hybridization, open-pollination, backcrossing, pedigree breeding, mutation breeding, and marker enhanced selection.

36. The method of embodiment 35, wherein said plant breeding technique is mutation breeding and the mutation selected is spontaneous or artificially induced.

37. A plant produced by the method of any one of embodiments 34-36, wherein said plant exhibits dwarf growth, double-flowering, and the desired trait.

38. The plant of any one of embodiments 34-37, wherein the desired trait is flower color and/or flower color pattern.

39. The plant of any one of embodiments 34-37, wherein the desired trait is tolerance or resistance to a disease or pest.

40. The plant of any one of embodiments 34-37, wherein the desired trait is tolerance or resistance to abiotic or biotic stress.

41. A molecular marker for distinguishing a plant having an allele for a double-flowering characteristic comprising at least one sequence selected from the group consisting of SEQ ID NO: 1, fragments of at least 20 consecutive nucleotides thereof, and complementary sequences thereof.

42. A method for distinguishing a plant having a mitochondrial allele for a double-flowering characteristic, comprising: using the molecular marker of embodiment 41 and detecting at least one SNP mutation selected from the group consisting of (i) a C nucleotide at position number 320 of SEQ ID NO: 1 and (ii) a C nucleotide at position number 247 in SEQ ID NO: 1.

43. A method for distinguishing a plant having a mitochondrial allele for a double-flowering characteristic, comprising: using the molecular marker of embodiment 41 and detecting at least one of a G nucleotide at position number 320 of SEQ ID NO: 1 and an A nucleotide at position number 247 in SEQ ID NO: 1.

44. The method of embodiment 42 or 43, wherein said molecular marker is detected by Restriction Fragment Length Polymorphisms (RFLPs), Dynamic Allele-Specific Hybridization (DASH), molecular beacon, SNP microarray, PCR-based method, Flap endonuclease (FEN), Single-strand conformation polymorphism, temperature gradient gel electrophoresis, Denaturing High Performance Liquid Chromatography (DHPLC), DNA mismatch binding proteins, or sequencing.

45. A molecular marker for distinguishing a plant having at least one allele for a dwarf growth characteristic comprising at least one sequence selected from the group consisting of SEQ ID NO: 2, fragments of at least 20 consecutive nucleotides thereof, and complementary sequences thereof.

46. A method for distinguishing a plant having at least one allele for a dwarf growth characteristic, comprising: using the molecular marker of embodiment 45 and detecting a C nucleotide at position 43 of SEQ ID NO: 2.

47. A method for distinguishing a plant having at least one allele for a dwarf growth characteristic, comprising: using the molecular marker of embodiment 45 and detecting a G nucleotide at position 43 of SEQ ID NO: 2.

48. The method of embodiment 46 or 47, wherein said molecular marker is detected by Restriction Fragment Length Polymorphisms (RFLPs), Dynamic Allele-Specific Hybridization (DASH), molecular beacon, SNP microarray, PCR-based method, Flap endonuclease (FEN), Single-strand conformation polymorphism, temperature gradient gel electrophoresis, Denaturing High Performance Liquid Chromatography (DHPLC), DNA mismatch binding proteins, or sequencing.

49. A method for distinguishing a plant having a mitochondrial allele for a double-flowering characteristic comprising obtaining genetic material;

obtaining a nucleic acid, wherein said nucleic acid has at least a portion of sequence complementary to the molecular marker of embodiment 41; and base-pairing said nucleic acid with said genetic material and examining the result of said base-pairing.

50. The method of embodiment 49, wherein said genetic material is deoxyribonucleic acid, ribonucleic acid, or a combination thereof
51. The method of embodiment 49, wherein said nucleic acid is a primer set, a probe, or combination thereof.
52. A method for distinguishing a plant having at least one allele for a dwarf growth characteristic comprising obtaining genetic material;
    obtaining a nucleic acid, wherein said nucleic acid has at least a portion of sequence complementary to the molecular marker of embodiment 45; and base-pairing said nucleic acid with said genetic material and examining the result of said base-pairing.
53. The method of embodiment 52, wherein said genetic material is deoxyribonucleic acid, ribonucleic acid, or a combination thereof.
54. The method of embodiment 52, wherein said nucleic acid is a primer set, a probe, or combination thereof.
55. A plant distinguished by the marker of embodiment 45 or the method of any one of embodiments 46-47 or 52-54, wherein said plant is homozygous for said allele for a dwarf growth characteristic, and wherein said plant is subsequently grown without growth regulators.
56. The plant of embodiment 55, wherein said plant comprises no detectable residue of a synthetic plant growth regulator or a related breakdown of a plant growth regulator product.
57. A method for producing a double-flowering dwarf *Calibrachoa* comprising providing a double-flowering *Calibrachoa* plant and crossing it with a dwarf *Calibrachoa* plant.
58. A method for producing a double-flowering dwarf *Calibrachoa* comprising providing a double-flowering *Calibrachoa* plant, wherein said plant is heterozygous for a dwarf allele, and producing a double haploid.
59. A method for producing a double-flowering dwarf *Calibrachoa* having a desired trait comprising providing a double-flowering dwarf *Calibrachoa* and applying a plant breeding technique to introduce a desired trait.
60. The method of embodiment 59, wherein said plant breeding technique is selected from the group consisting of recurrent selection, mass selection, hybridization, open-pollination, backcrossing, pedigree breeding, mutation breeding, and marker enhanced selection.
61. The method of embodiment 60, wherein said plant breeding technique is mutation breeding and the mutation selected is spontaneous or artificially induced.
62. A method for producing a double-flowering dwarf *Calibrachoa* plant having a desired trait comprising providing a double-flowering dwarf *Calibrachoa* plant and applying a gene editing tool or technology to introduce a desired trait.
63. The method of embodiment 62, wherein said gene editing tool or technology is random mutagenesis, targeted mutagenesis, transformation, an engineered nuclease, or a natural nuclease.
64. The method of embodiment 63, wherein the engineered or natural nuclease is selected from the group consisting of homing endonucleases/meganucleases (EMNs), zinc finger nucleases (ZFNs), and transcription activator-like effector nucleases (TALENs).
65. The method of embodiment 62, wherein said gene editing tool or technology is utilizing a clustered regularly interspaced short palindromic repeats (CRISPR)-Cas nuclease.
66. The method of embodiment 65, wherein the nuclease is selected from the group consisting of Cas9, Cas12a, CasX, CasY, and Cas12J (Casϕ).
67. A plant produced by the method of any one of embodiments 59-66, wherein said plant exhibits dwarf growth, double-flowering, and the desired trait.
68. The plant of embodiment 67, wherein the desired trait is flower color and/or flower color pattern.
69. The plant of embodiment 67, wherein the desired trait is tolerance or resistance to a disease or pest.
70. The plant of embodiment 67, wherein the desired trait is tolerance or resistance to abiotic or biotic stress.
71. A mitochondrial genome of a plant having a double-flowering characteristic, wherein said genome comprises SEQ ID NO: 7, or a sequence at least 90% identical thereto, and complementary sequences thereof.
72. The mitochondrial genome of embodiment 71, wherein said genome is isolated.
73. A fragment of at least 20 consecutive nucleotides of the mitochondrial genome described by SEQ ID NO: 7 or its complementary sequence.
74. The fragment of embodiment 73, wherein said fragment is isolated.
75. A method of using an isolated sequence of embodiment 72 or an isolated sequence of the fragment of embodiment 74 in a *Calibrachoa* breeding program.
76. A method for identifying a plant comprising an allele for a double-flowering trait comprising using a fragment of at least 20 consecutive nucleotides of SEQ ID NO: 7 or the complementary sequence thereof, as a marker for said double-flowering trait.
77. A method for generating a plant having a double-flowering characteristic, wherein said method comprising using a fragment of at least 20 consecutive nucleotides of SEQ ID NO: 7, or the complementary sequence thereof, in a gene editing technology.
78. The *Calibrachoa* plant of embodiment 1, wherein at least one of the SNPs selected from the group consisting of
    i. the G to C nucleotide substitution at position number 320 of SEQ ID NO: 1 and
    ii. the A to C nucleotide substitution at position number 247 in SEQ ID NO: 1, and
    iii. the G to C nucleotide substitution at position 43 of SEQ ID NO: 2 is not exclusively the result of the sexual crossing of plants.
79. The *Calibrachoa* plant of embodiment 1, wherein said plant further comprises an additional trait in its genome, which has been introduced or modified by a step of a technical nature so that the introduction or modification of that trait is not exclusively the result of the mixing of the genes of the plants by sexual crossing, said step of a technical nature preferably being selected from the group consisting of spontaneous mutagenesis, induced random mutagenesis, and targeted mutagenesis and/or
    said additional trait being an additional mutation affecting flower color or flower color pattern and wherein preferably said mutation is the result of an induced random or targeted mutagenesis.
80. The *Calibrachoa* plant of embodiment 79, wherein at least one at least one of the SNPs of embodiment 78 or the additional trait of embodiment 79 is not exclusively obtained by essentially biological processes.
81. A method of producing a *Calibrachoa* plant comprising a double-flowering characteristic and a dwarf growth characteristic, comprising the steps of:
    (i) crossing a first female *Calibrachoa* plant with a first male *Calibrachoa* plant to produce F1 plants, wherein said first female *Calibrachoa* plant comprises a mitochondrial allele associated with at least one SNP mutation selected from the group consisting of (i) a G to C nucleotide substitution at position number 320 of SEQ ID NO: 1 and (ii) an A to C nucleotide substitution at position number 247 in SEQ ID NO: 1 and exhibiting a double-flowering characteristic, and wherein said first male *Calibrachoa* plant has at least one copy of a nuclear, recessive allele associated with a SNP mutation consisting of a G to C nucleotide substitution at position 43 of SEQ ID NO: 2, wherein, when said nuclear allele is in the homozygous form plants exhibit a dwarf growth characteristic;

(ii) screening said F1 plants for the presence of said nuclear SNP mutation;

(iii) selecting an F1 female plant exhibiting said double-flowering characteristic and further comprising at least one copy of said nuclear SNP mutation;

(iv) crossing said F1 female plant with said first male or a second male *Calibrachoa* plant having at least one copy of said nuclear SNP mutation to produce F2 plants;

(v) screening said F2 plants for the presence of said nuclear SNP mutation; and (vi) selecting an F2 plant exhibiting said double-flowering characteristic and being homozygous for said nuclear SNP mutation, said crossing with said first male *Calibrachoa* plant preferably introducing at least one copy of a nuclear, recessive allele associated with a SNP mutation consisting of a G to C nucleotide substitution at position 43 of SEQ ID NO: 2 into the genome of the resulting *Calibrachoa* plant.

82. A method of selecting a *Calibrachoa* plant comprising a double-flowering characteristic and a dwarf growth characteristic, comprising the steps of:

(i) crossing a first female *Calibrachoa* plant with a first male *Calibrachoa* plant to produce F1 plants, wherein said first female *Calibrachoa* plant comprises a mitochondrial allele associated with at least one SNP mutation selected from the group consisting of (i) a G to C nucleotide substitution at position number 320 of SEQ ID NO: 1 and (ii) an A to C nucleotide substitution at position number 247 in SEQ ID NO: 1 and exhibiting a double-flowering characteristic, and wherein said first male *Calibrachoa* plant has at least one copy of a nuclear, recessive allele associated with a SNP mutation consisting of a G to C nucleotide substitution at position 43 of SEQ ID NO: 2, wherein, when said nuclear allele is in the homozygous form plants exhibit a dwarf growth characteristic;

(ii) screening said F1 plants for the presence of said nuclear SNP mutation;

(iii) selecting an F1 female plant exhibiting said double-flowering characteristic and further comprising at least one copy of said nuclear SNP mutation;

(iv) crossing said F1 female plant with said first male or a second male *Calibrachoa* plant having at least one copy of said nuclear SNP mutation to produce F2 plants;

(v) screening said F2 plants for the presence of said nuclear SNP mutation; and (vi) selecting an F2 plant exhibiting said double-flowering characteristic and being homozygous for said nuclear SNP mutation.

BRIEF DESCRIPTION OF THE SEQUENCE LISTINGS

SEQ ID NO: 1 is a sequence from the mitochondrial genome of *Calibrachoa* (SEQ ID NO: 7) identifying the location of two single nucleotide polymorphisms at positions 247 and 320.

SEQ ID NO: 2 is a sequence from the nuclear genome of *Calibrachoa* identifying the location a single nucleotide polymorphisms at position 43.

SEQ ID NO: 3 is a sequence from the mitochondrial genome of *Calibrachoa* comprising two single nucleotide polymorphisms at positions 247 and 320 associated with an allele for double-flowering.

SEQ ID NO: 4 is a wild-type (single flower) sequence from the mitochondrial genome of *Calibrachoa.*

SEQ ID NO: 5 is a sequence from the nuclear genome of *Calibrachoa* comprising a single nucleotide polymorphism at position 43.

SEQ ID NO: 6 is a wild-type (non-dwarf) sequence from the nuclear genome of *Calibrachoa.*

SEQ ID NO: 7 is a whole mitochondrial genome sequence from *Calibrachoa*, and shows the single nucleotide polymorphisms of SEQ ID NO: 1, here at positions 224,919 and 224,992.

While a number of exemplary aspects and embodiments have been discussed above, those of skill in the art will recognize certain modifications, permutations, additions, and sub-combinations thereof. It is therefore intended that the following appended claims and claims hereafter are interpreted to include all such modifications, permutations, additions, and sub-combinations as are within their true spirit and scope.

What is claimed is:

1. A *Calibrachoa* plant, comprising: a double-flowering characteristic and a dwarf growth characteristic, wherein said double-flowering characteristic is caused by a mitochondrial allele associated with at least one single nucleotide polymorphism (SNP) mutation selected from the group consisting of (i) a G to C nucleotide substitution at position number 320 of SEQ ID NO: 1 and (ii) an A to C nucleotide substitution at position number 247 in SEQ ID NO: 1, and wherein said dwarf growth characteristic is caused by a homozygous recessive nuclear allele associated with a SNP mutation consisting of a G to C nucleotide substitution at position 43 of SEQ ID NO: 2.

2. The *Calibrachoa* plant of claim 1, wherein said plant has a petaloid stamina rating of at least 2.

3. The *Calibrachoa* plant of claim 1, wherein said plant at maturity has a vigor rating of less than 5 compared to plants having a non-dwarf growth characteristic when grown under the same environmental conditions, wherein said non-dwarf plant has at least one copy of the allele associated with a SNP mutation consisting of a G at position 43 of SEQ ID NO: 2.

4. The *Calibrachoa* plant of claim 1, wherein said plant exhibits male sterility.

5. The *Calibrachoa* plant of claim 1, wherein said plant is grown without the addition of a synthetic plant growth regulator.

6. The *Calibrachoa* plant of claim 1, wherein said plant comprises no detectable residue of a synthetic plant growth regulator or a related breakdown of a synthetic plant growth regulator product.

7. The *Calibrachoa* plant of claim 1, wherein said plant further comprises a mutation affecting flower color or flower color pattern, wherein said mutation is the result of an induced random or targeted mutagenesis.

8. A method of producing a *Calibrachoa* plant comprising a double-flowering characteristic and a dwarf growth characteristic, comprising the steps of:

(i) crossing a first female *Calibrachoa* plant with a first male *Calibrachoa* plant to produce $F_1$ plants, wherein said first female *Calibrachoa* plant comprises a mitochondrial allele associated with at least one SNP mutation selected from the group consisting of (i) a G to C nucleotide substitution at position number 320 of SEQ ID NO: 1 and (ii) an A to C nucleotide substitution at position number 247 in SEQ ID NO: 1 and exhibiting a double-flowering characteristic, and wherein said first male *Calibrachoa* plant has at least one copy of a nuclear, recessive allele associated with a SNP mutation consisting of a G to C nucleotide substitution at position 43 of SEQ ID NO: 2, wherein, when said nuclear allele is in the homozygous form plants exhibit a dwarf growth characteristic;

(ii) screening said $F_1$ plants for the presence of said nuclear SNP mutation;

(iii) selecting an $F_1$ female plant exhibiting said double-flowering characteristic and further comprising at least one copy of said nuclear SNP mutation;

(iv) crossing said $F_1$ female plant with said first male or a second male *Calibrachoa* plant having at least one copy of said nuclear SNP mutation to produce $F_2$ plants;

(v) screening said $F_2$ plants for the presence of said nuclear SNP mutation; and (vi) selecting an $F_2$ plant exhibiting said double-flowering characteristic and being homozygous for said nuclear SNP mutation.

9. The method of claim 8, wherein the first or second male *Calibrachoa* plant is homozygous for said nuclear SNP mutation and exhibits a dwarf growth characteristic.

10. The method of claim 8, further comprising: asexual propagation, outcrossing, or backcrossing said selected $F_2$ plant.

* * * * *

SEQUENCE LISTING

```
<160> NUMBER OF SEQ ID NOS: 7

<210> SEQ ID NO 1
<211> LENGTH: 544
<212> TYPE: DNA
<213> ORGANISM: Calibrachoa x hybrida

<400> SEQUENCE: 1

ccctcatctt tctctttcag aagagcctac tttcgcccat ggttcgcgtc gctatcgtgc      60

ttggtccgtt cgctactctc ttttcagcca ttattgtatg cgtgtagcct aagtctaccc     120

ttcgattgga ctttctccag atcctttgac acccgctcat cttacttccc attctggtag     180

gttggtgcgt gatgattcgt ggagtacaag gctctctctg gttgggtacg taggctggtc     240
```

ctgcagmttg tggaggtgac cagcgctgca tgcccgaatg gaatattgac tatcccgtag 300
aactgaccta gtcgctcgts aaggagctgg tcattatgga atatactata tgtaggcgca 360
ggtcttccta gagcgaacct ccatgtgttt tatattaaac atataaaaat caacagtgga 420
agaggcactg gttgtgcgag atcattatga ctggaggaag cccattcgac aaccataata 480
ggctctataa ccggatcacg cacgctaaga acacagcgga ttagagggga caagaggttc 540
cact 544

<210> SEQ ID NO 2
<211> LENGTH: 114
<212> TYPE: DNA
<213> ORGANISM: Calibrachoa x hybrida

<400> SEQUENCE: 2
atrccaccac tgaaccaccr gctgcaatgg cggagaaggt gtstgatgaa ccatttttgg 60
tggtgggaca cggtggattc ttgggctgaa aaaacaagaa tggaaaacgc agtg 114

<210> SEQ ID NO 3
<211> LENGTH: 544
<212> TYPE: DNA
<213> ORGANISM: Calibrachoa x hybrida

<400> SEQUENCE: 3
ccctcatctt tctctttcag aagagcctac tttcgcccat ggttcgcgtc gctatcgtgc 60
ttggtccgtt cgctactctc ttttcagcca ttattgtatg cgtgtagcct aagtctaccc 120
ttcgattgga ctttctccag atcctttgac acccgctcat cttacttccc attctggtag 180
gttggtgcgt gatgattcgt ggagtacaag gctctctctg gttgggtacg taggctggtc 240
ctgcagcttg tggaggtgac cagcgctgca tgcccgaatg gaatattgac tatcccgtag 300
aactgaccta gtcgctcgtc aaggagctgg tcattatgga atatactata tgtaggcgca 360
ggtcttccta gagcgaacct ccatgtgttt tatattaaac atataaaaat caacagtgga 420
agaggcactg gttgtgcgag atcattatga ctggaggaag cccattcgac aaccataata 480
ggctctataa ccggatcacg cacgctaaga acacagcgga ttagagggga caagaggttc 540
cact 544

<210> SEQ ID NO 4
<211> LENGTH: 544
<212> TYPE: DNA
<213> ORGANISM: Calibrachoa x hybrida

<400> SEQUENCE: 4
ccctcatctt tctctttcag aagagcctac tttcgcccat ggttcgcgtc gctatcgtgc 60
ttggtccgtt cgctactctc ttttcagcca ttattgtatg cgtgtagcct aagtctaccc 120
ttcgattgga ctttctccag atcctttgac acccgctcat cttacttccc attctggtag 180
gttggtgcgt gatgattcgt ggagtacaag gctctctctg gttgggtacg taggctggtc 240
ctgcagattg tggaggtgac cagcgctgca tgcccgaatg gaatattgac tatcccgtag 300
aactgaccta gtcgctcgtg aaggagctgg tcattatgga atatactata tgtaggcgca 360
ggtcttccta gagcgaacct ccatgtgttt tatattaaac atataaaaat caacagtgga 420
agaggcactg gttgtgcgag atcattatga ctggaggaag cccattcgac aaccataata 480
ggctctataa ccggatcacg cacgctaaga acacagcgga ttagagggga caagaggttc 540
cact 544

<210> SEQ ID NO 5
<211> LENGTH: 114
<212> TYPE: DNA
<213> ORGANISM: Calibrachoa x hybrida

<400> SEQUENCE: 5
atrccaccac tgaaccaccr gctgcaatgg cggagaaggt gtctgatgaa ccatttttgg 60
tggtgggaca cggtggattc ttgggctgaa aaaacaagaa tggaaaacgc agtg 114

<210> SEQ ID NO 6
<211> LENGTH: 114
<212> TYPE: DNA
<213> ORGANISM: Calibrachoa x hybrida

<400> SEQUENCE: 6
atrccaccac tgaaccaccr gctgcaatgg cggagaaggt gtgtgatgaa ccatttttgg 60
tggtgggaca cggtggattc ttgggctgaa aaaacaagaa tggaaaacgc agtg 114

<210> SEQ ID NO 7
<211> LENGTH: 465789
<212> TYPE: DNA
<213> ORGANISM: Calibrachoa x hybrida
<220> FEATURE:
<221> NAME/KEY: misc_feature
<222> LOCATION: (24511)..(24511)
<223> OTHER INFORMATION: n is a, c, g, or t
<220> FEATURE:
<221> NAME/KEY: misc_feature
<222> LOCATION: (24513)..(24515)
<223> OTHER INFORMATION: n is a, c, g, or t
<220> FEATURE:
<221> NAME/KEY: misc_feature
<222> LOCATION: (24518)..(24519)
<223> OTHER INFORMATION: n is a, c, g, or t
<220> FEATURE:
<221> NAME/KEY: misc_feature
<222> LOCATION: (24521)..(24521)
<223> OTHER INFORMATION: n is a, c, g, or t
<220> FEATURE:
<221> NAME/KEY: misc_feature
<222> LOCATION: (42971)..(42977)
<223> OTHER INFORMATION: n is a, c, g, or t
<220> FEATURE:
<221> NAME/KEY: misc_feature
<222> LOCATION: (148862)..(148863)
<223> OTHER INFORMATION: n is a, c, g, or t
<220> FEATURE:
<221> NAME/KEY: misc_feature
<222> LOCATION: (157905)..(157905)
<223> OTHER INFORMATION: n is a, c, g, or t
<220> FEATURE:
<221> NAME/KEY: misc_feature
<222> LOCATION: (293054)..(293054)
<223> OTHER INFORMATION: n is a, c, g, or t
<220> FEATURE:
<221> NAME/KEY: misc_feature
<222> LOCATION: (293985)..(293985)
<223> OTHER INFORMATION: n is a, c, g, or t
<220> FEATURE:
<221> NAME/KEY: misc_feature
<222> LOCATION: (294064)..(294064)
<223> OTHER INFORMATION: n is a, c, g, or t
<220> FEATURE:
<221> NAME/KEY: misc_feature
<222> LOCATION: (294372)..(294372)
<223> OTHER INFORMATION: n is a, c, g, or t
<220> FEATURE:
<221> NAME/KEY: misc_feature
<222> LOCATION: (294386)..(294386)
<223> OTHER INFORMATION: n is a, c, g, or t
<220> FEATURE:
<221> NAME/KEY: misc_feature
<222> LOCATION: (294412)..(294412)
<223> OTHER INFORMATION: n is a, c, g, or t
<220> FEATURE:
<221> NAME/KEY: misc_feature
<222> LOCATION: (298184)..(298186)
<223> OTHER INFORMATION: n is a, c, g, or t
<220> FEATURE:
<221> NAME/KEY: misc_feature
<222> LOCATION: (417943)..(417944)
<223> OTHER INFORMATION: n is a, c, g, or t
<220> FEATURE:
<221> NAME/KEY: misc_feature
<222> LOCATION: (465621)..(465621)
<223> OTHER INFORMATION: n is a, c, g, or t
<220> FEATURE:
<221> NAME/KEY: misc_feature
<222> LOCATION: (465754)..(465754)
<223> OTHER INFORMATION: n is a, c, g, or t
<220> FEATURE:
<221> NAME/KEY: misc_feature
<222> LOCATION: (465764)..(465764)
<223> OTHER INFORMATION: n is a, c, g, or t
<220> FEATURE:
<221> NAME/KEY: misc_feature
<222> LOCATION: (465770)..(465770)
<223> OTHER INFORMATION: n is a, c, g, or t
<220> FEATURE:
<221> NAME/KEY: misc_feature
<222> LOCATION: (465776)..(465776)
<223> OTHER INFORMATION: n is a, c, g, or t

<400> SEQUENCE: 7
wymytrtyst ykhhgtvggt aghswhavat stdhawtgta tatagkwdah cymaawratc 60
cgahvcctcv ratkcawyay catatcatgg ccgtbyctaw sadttgctyt ttgtgatgca 120
gcggaaccat ggcaattagg atctmaagmc gcagmammry cwmtmaykyw wgrmakwwmw 180
rmswtacmws amgatgttty wghattcgtt attctgattt tgggtttcgt atcatggatc 240
ttgggtcgcg ctttatggca tttccactat aaaaaaaatc caatcccgca aaggattgtt 300
catggaacta ctatcgagat tcttcggacc atatttccta gtatcatccc tatgttcatt 360
gctataccat catttgctct gttatactca atggacgagg tagtagtaga tccagccatt 420
actataaaag ctattggaca tcaatggtat cggagtgcgc ctcttcacga gggtgattaa 480
agtgcaacga aatgccttaa agttgaatat ggttcgcgaa gcatctggct taccggtaat 540
ctcccattcc cgccgtcgag agactttaat aactatagca tgccagaaac ggggagttga 600
ggtggttaga cctataccccc gaaatgctcc cagcatagga gcctatggtt ccattcttgt 660
tgttgctgga ggtacacatc cctcttctcg gtgtggaacg atatacgaga aatagatgct 720
cagcctgcaa tgtccgataa cggcgctgaa gtagtgaatc tatcggcacc atagcagtgg 780
tatacaactt tggacctaac ggccggccta gtaacctttc ggaatggggg atccccgttg 840
gcaacaacca cggtagtagt tgcggaacta ctgggccggg agaggacaac ctcttgttcc 900
tgctcctctt tcttcgcttc ggggacggag gtcctacggt aggtaacagc aggcacaagc 960
aagttgaccg aaggggacca gcgcttctac tcctccaccg aggagccgtt cttgcgagaa 1020
gcaagggatg tcgtgaacgg tgggaggtca cagagaattg acctattcat agagtgatcc 1080
tatgatcgat acaggatata gactatctca ttctttattc tattctattt ctgaaaaaaa 1140
aaagaagggt gactcaactt ctcagctaga gttggtggtg ggacctcttg gcataatgca 1200
cgctggaacg tgggaattcg aggtctcatg aactactact aaaaaccgac tttgtttttg 1260
ttttgtttgt ggacaaacga tatccggtca ggcctatggc tggatccttt tagatctacg 1320

-continued

```
ggccggccgg ccccggccgt ttacatgagc atagggaatc tatactcgag cgttccactg   1380
ggcccctgac aggataggtg aggaatcact ctggatcttc tttttttggg ctacaacttc   1440
gccgagccga ctagcatccc tttccactgt gcatttttcg aacaaagaag acgactatag   1500
gatcgaattc gctcttcaag aaactgctcg tcccatacct tctgcctgtc tcatatgtgt   1560
ggaacctggt ctttttcggt tccagcctct ccctcgaata catagggtag gtagggctgg   1620
gtgataaagg gttccctctt gccaataaac tttccccggc cttcgattaa ccttactcat   1680
aaagggtctt acggtcggga gaactaccta actaaagaaa aatagtgttc tttctaagag   1740
taggcgtgga gagcttttg cggggaaact tgcaagtaca gtttgggggg aggcgggcgt   1800
cgaccctacc ttatgagtat tcggactata acagttccga tgaacagtca ctcacttttg   1860
acagttatac gattccagaa gatgatccag aattgggtca atcacgttta ttagaagtcg   1920
acaatagagt ggttgtacca gcaaaaagtt atatacgttt tattgtaaca tctgctgatg   1980
tacctcatag ttgggctgta ccttccttag gtgtcaaatg tgatgctgta cctggtcgtt   2040
taaatcagac ctctatttcg gtacaacgag aaggagttta ctatggtcag tgcagtgaga   2100
tttgtggaac taatcatgcc tttatgccta tcgtcgtaga agctgttcct aggaaagatt   2160
atgggtctcg ggtatccaat caattaatcc cacaaaccgc agaagcttct ccagtcttcg   2220
tcggttcccc aaaagaagac actattcttt ttgggagacc cgtcgtcgac gaagatgagc   2280
tctacgaagc ggcttaccac cccttctacg cggccaacgt agtccacatc cctggggaaa   2340
ttgaagaccc ctttactctg gctaaattaa gtaaattaaa tgggactctc ctagccatag   2400
cggatctctt tttcaacggc cagataaggg gatcgtacac taaagagctg caacttgaat   2460
tgaatgcgac cgaagaaggc gagctggcgg ctaagctgga agagctgcgg attagggaaa   2520
agcggcgcta taatttacgc tagggtgagc aagcgctagc tctttctctt gcggtgaaat   2580
aaccgccgta tagaggcgaa cagcccttat agcaatagca aacggcctac ttatagcctt   2640
tcaacaggtc agtcaatatc agtaagtagg ggtcctcttg cctaacggag tcagcccaac   2700
atggacaatg ataggcagac caaagattta cgcagtcgtt gcgtgcttgc tttgcgcacc   2760
ggcatagcag aattagaatc cgctggctca gatgagtggc tcttggcttc gtaaacatat   2820
ctatgttgtt gctttttcac taccaatgag taggcagctt tggatgctta tggagatatg   2880
gcttggccca ggactattgg ctttccgtca agtgtcagtt cagccataga cattcaattc   2940
aatctcggag atagtcaaaa tgccattgtc cgttctaaat gaaaggaatg agataggccg   3000
cttacacacg cttcaagtct tcttttgctg attcaataac agtctggaaa ttcgactgaa   3060
taagtcttag tgtggttaag ccggggccag ggtcagaagt tcttccatct cctgagataa   3120
gatcagacag agcctatacg ccttcttgct ttgctgcagc taccgggtat tcattcaaaa   3180
agaatgcatt tacctttttct ccccccttcct tcggcatccc tgactcgggc atccctttca   3240
ggtgcagttg acgtacaatt taggtaattt ataaggacta aacgtactga tgaaagggaa   3300
aacttaggaa agaatagcta aggagaatcc ttcgtttgag gaaagagatg ataaaataag   3360
tcatgaaaaa aacccagttt gttttaaggc tctcatgaag ccttagggcg aattcctctc   3420
acattggaaa cttcgctcac ttcctatatt attcgcgcac ctacctacca caatccggtt   3480
ccaagtcctt tattttaaaa tcgaggagta gttcaacttt tctctcttcg ggactaagag   3540
aacttactta ctaattgaaa aaaaaagaca actagaacga ggtttttttt tacgtgatcg   3600
gaaatcaccc gtcggtgatg aaccagtacg cacttaggat agcacttcgg gagagtgaga   3660
tccaggtggc atatcaaaaa gacttatcaa aatcgccacc atacgagact tgcagggcat   3720
```

-continued

```
gcccgccaga aagtgaagag aggtttataa gcaccccgac ttaggaatca tgacccaccg   3780
aagaaaagaa gactcgagga aaactattga tccctttgat gactctcctc ttcatcttcg   3840
cgggttgcag agaagaatcc gaactgagga aatgaaaaaa aaaaagaaaa gtatctcttt   3900
ctctttctac gatcacctgt agcgtcctta aaaagtctta gaaggagaat ctaactattc   3960
tcgaagagat tcttgccaac accattagga agatgaggga aaggggaaaa gaagtcaaat   4020
tcgctatttc cgacagctac ggtagtagag aaggagaggg actacttatg agaaagagga   4080
gttctctctt ctactcccgg gtattgaacc gggatgcttt ggtactagac tgggcgggcg   4140
agccataatc acagggggag aaaggcgcag atcttttcat cctccgccaa caagcagagc   4200
cgacaccgag ctacttcgta ccttttttcat tcaaacggga atgactccac tctcagtccc   4260
agtgtggctt agactagtag aaggcgtaag gatgctagac cgctgctcaa tactggataa   4320
tccacgttca tcggtctgca gcaagcactg acttttaggg ggcggcaact aaagaggtag   4380
cgagactaag cgcaatttca ggaagagttg gacccttgcc tctaagcttc cttctaccct   4440
tgtgctaaag gacaggaaaa acaacttctt tctttctttt tttttaatat attgaataat   4500
ggaataactc gaaccctact aaagagtggc tttcagctcc tccccccttct ttcattcagc   4560
gactgggtac gcacttcgcc atgaaagatc ttggtgatct tcatttcttt cttaggaatc   4620
gaagtcaaag gtacatcgac ttctctagtc ttgactcaga ctaaatacac cttggaatta   4680
ctcgaactca tttgcaagac tccaagccat gtcccacacc ccttgcgtct ggcttaaagc   4740
tctctgcata cgatggtcct cctctctctg atgcaacgga atatcgtagc attgttggcg   4800
cccttcaata cctcactctc accaccgtat atctccaggc tgtaaaaggc atcttacggt   4860
atatgaaggg ttttcttggg cttggcctaa ccatcactca gggactttaa accaccttct   4920
ttgcattctc cgatgccgac tgggctggct gtcccgatag cagacggtcc actacttgct   4980
tctgcgtatt tctcggaaac aacctactga cttgggtttc aaaaaaaaaa aagaaaccga   5040
ttctttccag gtctagtgcc gaagcagagt acaaggcact cgctcttact acctctgaac   5100
tcttatgact ttcttactta ctacgcgatc tagcggtgcc gtttcgctat caatttttcg   5160
tgcactgtga taatgctagc gctacacact tggtggccaa tcctgtgttc catgtccgct   5220
ctaagtacat agaagttgac taccacttcg ttcgtgacct cgtcgtcgca ggcaaattgc   5280
tcattcgact tgttcgtagc aacaatcaag tggcggacct tttcactaaa ggattacctg   5340
aaccccccctt ccatcatttt ctgctgtctc ccgcctgccc ttctcgaaag aatgggctcc   5400
tggccgtcct atctcattga aaaggacaaa aaccatttac ttttccaatc aaagaaagtg   5460
aagccaccaa aaaaaaagaa aaagggtata gtaatatata tataaagtca aagttcaatg   5520
gtaacgactt cttccattga cttcaggatt gcttggtttc agggaaagtc tctcgctcct   5580
ctccttatag cgctggcctc tgtctttgat cttggctcga gctctgtcct ctcctctccc   5640
tatgtgagag tggctgcttg aagcttttcg tatgaatagt caaagctcgg acttaggagc   5700
tgctggcctt tgttgatccg cttgaagaga gttctcacga ccctgctaca tcgcgatcgt   5760
ttattcccaa ggaatagaga atacaaagca cacaaggcgc atgatgaaca agagtaactt   5820
cccgtccctt actccatttc ttgtcttaaa tagacaaaat agtgggcttc ctgccccctt   5880
ctcaaagaga ggaggacggg ttattcattc atatttcatt tgatggtcag aggcgaattg   5940
aaagctaagc agtgggaatt ctaaagattc cccgggggaa aaatagagat gtctcctacg   6000
ttacccataa tatgtggaag tatcgacgta atttcataga gtcattcggt ctgaatgcta   6060
```

```
catgaagaac ataagccaga tgacggaacg ggaagaccca ggatgtagaa gatcataaca   6120
tgagtgattc ggcagatttg gattcatata tatatccacc catgtggtac ttcattctac   6180
gatatatata agatccatct gtatagatat catcatctac atccagaaag ccgtatgctt   6240
tggaagaagc ttgtacagtt tgggaagggg ttttgattga tcaaaagaag aatctacttc   6300
aaccgatatg cccttaggca cggccataca taacatagaa atcacacttg gaaagggtgg   6360
acaattagct agagcagcgg gtgctgtagc gaaactgatt gcaaaagagg ggaaatcggc   6420
cacattaaaa ttaccttctg gagaggtccg tttgatatcc aaaaactgct cagcaacagt   6480
cggacaagtg gggaatgttg gggtgaacca gaaaagtttg ggtagagccg gatctaagcg   6540
ttggctaggt aagcgtcctg tagtaagagg agtagttatg aaccctgtag accatcccym   6600
kmcmtgtggg tcgagcctcc ttttcagtcg ccctctacaa ctaagtcagt tgagctctct   6660
cggctcctag accagctgtg atctttcctc ctgttggttt gcttagttaa atatatgcat   6720
ccttagagtc agtccctttt tttggagaaa aattccgagc cggtaagcaa gacaaagcaa   6780
gtcaacgtgg gaaaaagctc tcgatggcca tagacctgaa tggttggagt gtggaggatc   6840
actcctgaaa ctttcttcct ttatataagg aatcctcttg gttggtcgaa gctagaagac   6900
ggctggacga actgctattt tgcatagggg gagtaagata ggctaggtgc ttttactcaa   6960
ctcgtgaagg ttcatttcta gttagcaagg ataaggaagc aaaggtagag tcctttaata   7020
atatgtctgt cattacgtgc gactatctcc actatagaaa gaaaaaaagg aaagaacaac   7080
attttcagca catttatacg aaaaagtctt tattattata ttagcataag taggaaacat   7140
tttccactag ggtttttccc atacatgcaa acataaaaaa gaaaagcaaa caaagataat   7200
tagcatagat aggagtctat ctccagtaag catcggagta gatctccact aaaaaagaca   7260
aagaacaccc taaattaaaa cacattactt tgcgtctaca gacacttatt taaaccttct   7320
aaaactaaaa agagtcgacg gactcttcta ttctagtctc cctggcgacc acgggtgaca   7380
gcacccacaa ttaggtcttc ctgtttttgg aggagggccc gtttcctgtc ttccaggacg   7440
ctaatgcggt cccggatccg ctgcatggct gcagccacaa gtgcaggatc gatgggaggc   7500
aggtgctccc aaaaggcagc cagggtttgc tccgattgga gcttctcctc ttccacttga   7560
gagatttctt gcgaaatttc ttgaagtctt ataaaagaat ccatggctac actcaaagct   7620
ttttttgcc gacttctaag ttcctctccg tctccctttg ccaaatagag actgaaagaa   7680
gcttctattt ataggcgttg gaggccctta accctttctt attattagta agataggttg   7740
tcttggttcc gtaacatgga tcatttcaaa cctggctttt catgaatatg gaaccccctc   7800
cactagattt tagtgtgctg aataattatc ttcgtactcc aatccgtacg aagggcccct   7860
ttcttttggc gggtatcgcc acgtggctta atcccggatc actccttaag gaataggaca   7920
caataatata gcgcacatca gagaagagag tacccccttt attataagac aggccccacg   7980
cgtcctttct taagagatgg agcaatcgtc actcgacagc tcaaagctga ccggtacaac   8040
ccgcgtgctt gcctactcgt ctttcaccgg cctatttgta cccagctaca atctcttccc   8100
ttagaaaaga aaaagggccc ctcggccaat cgtcactcga cagctcgaaa gcggatcagt   8160
acaaaaccat gtgatctgta cttgtttacg tactgcccct taggcctagg gcttcgtcgt   8220
accctgctta ctcctctttc actttcactg gcttctactt gtcttttttt tttttattgg   8280
cttatttaga aaatggtatc agcatttgag acgactctcc ccggccaatc ctcagtcgtc   8340
cgtccttgct taggagaaaa ccgaaccact atctcttgat agatctgttt ttttctacct   8400
ttacagctcg ctctgtaagt tcactagcaa tacagcacta gcactagcta tagcagtaac   8460
```

-continued

```
tagtacaatg agttaggggt cgggtcgggt gaattcaata atagacgcct gttggcattc   8520
cagccttcct atccgaaaga gaatccatta tttcttggtc gtgaatatct gaactggttg   8580
ttcactgttc aagaattctt gtttagacaa ttcagaccat ccatacatag tcttttaatc   8640
taagattgaa attcttccat attttattgc taaaatattg ttccatggag ctaaggtcca   8700
aaatatggaa gaaagaagtg tttccacgac tctccagtca attctgttcc acttaatccc   8760
tctttcatgg caacatctct ttccggctaa ggaatgggaa atctttctcc tgttacatga   8820
atcaagtttt cattttatcc ggaaaagccc ctttccagct gacgctgtca gtccactaac   8880
agcggtatac agtaagtcag tataagtcag tacaggaagg gcacgcgaaa tagacaacta   8940
cttactaggc tagggtagta gtttttttcat cttccctta ttttacttta ccctagtgga   9000
aattcatttt taaaagtgac taggtaatta gtgaagaggt ttataaaagt gacaagcttg   9060
gtggaaagct cttatcttag gaggaaaagc taagtatgcc cgagtagtct tgatattggt   9120
tggtttgagg tttcgttagt tttatactaa caagcaagct tcggttcggc gaccgctcga   9180
cctagcgcct tagccccagt actataggga aggcctatgc gaagaaaagg cctgcccatc   9240
atcaaagcaa gcccaagtcc atgcaagaag gccctccaga tctgtccaaa ttcaaagccc   9300
gtcaaaggca tatgaaatca tgcaaaggat ccgagcccat ccaaatgatg ttcagcgggc   9360
taaacccaag tagctctggc ccatgatcca agagacccga aactagttaa tcactccgtg   9420
ccttaccttc taaccaatcg gccaatcacg ctatccttac ctttcaacca accccttcga   9480
ttcagtttct gcagcagtat agaatctcgg acccgatgga tgcctacaga aaaatgagtt   9540
ttccagcagt gatggcaaga atccgcgaaa taatgttctt tctccttttt gtgttctttc   9600
tgaatggagc tacgcgaggg aaagctcagc tttctactct gccgcaaaag gggccgctt    9660
tcttcccccc caaaatgcca gttccgccat cagggcctag caagaagcat aattctgttc   9720
caaagcttcg tttcattcca gcaacagtag tctatggttc gaagcgccgt gttccatccg   9780
gcgcgaatcc tctccataac tagtatagtg gaggtcttac ttgtattgca ataatgaaaa   9840
aatgtacgaa cacaaataat gagcagacca gcccactttt atatgtgggt tcatttcaga   9900
atgttttttt gttttgaata aagaagcgcg tgaactttta gtgtaaggca ggtgtttttc   9960
tcggtggatg gatgggataa atgcctatat tgctttataa tgttattgtt atgttgatgt  10020
tatattaaag aatgaaatct aaaaaagttg cttagtccca ttctttataa ttgtctttct  10080
catactgtgt aaacaaactt caagtctgaa ttgtgtactg tactcaacag gaagcgtcac  10140
agccaccccc gatgtcgatc tgcagtatta gtttgagaaa gtcgtttggt ttttaaccta  10200
gagcgattgg tttacctgta tcatgcaaat gtccaacact taggtgcttt ctaagatcat  10260
cctatatgaa agatgtatga catgtgtgga taatgaatga cttgcagggt atgcaatatc  10320
ttaagtacaa aaggtaagac ctaaaaagag aaatgagctt agcacaacac gggatagaaa  10380
gctaatccta gaaggagaaa acccatcaca gaacaatcat aggaaaagaa gaaatgggtt  10440
cagaccaagt gacagaactc tctatgagtt gggctacata aaagatcctt ttctactaaa  10500
atggatgtag gcttaactaa agcccaatgc aggttgaact ctatggaatc taagcctcac  10560
taccccttacc ctcttagagg gttacaagga attttaggcc ggccccatat agattcagct  10620
taggggttta tgagagattg attgatggac ctaagctaaa caactaagat tgaacctaaa  10680
ccaaaaccta tagactgaat taggagagca gaggtttaat tcaagaccag gaaagcaagt  10740
tatatcgaag cccaatgcca agcaaagccc tagactacaa gtgaagaaat tgggttcaac  10800
```

-continued

```
taagccctta acccaagatg aggtggagcc ttaacccgac acaagagggg ccctgtagga  10860
tagtgggctt agtcagccca acataggttg ttaaccaaaa aggagaagtt cccgtgaaaa  10920
cagaaaaaga cctccccctt aacccccccc ttacttggca gattcacatt cgtaggaaag  10980
gtctgttctt ttgtctcttt ccctcaagcg aaggaaccta ttaataagat aataatatct  11040
ctctgcttcc tagatcgata acgaatcctt cggttgctta tcctgtcatc cgagcccggc  11100
gttccgaaca acaatgattc ggaaagataa ggtctacgaa agaaaagaaa atttacaatt  11160
tgccctactc ctcaagaaat actgcgagcg gtattgtaaa ggtatgggct ttttcggtcg  11220
atttgctca agagggtggg gggacttcga ctttatcgaa gcagcacatg agattgccca  11280
gaaggattac tttttatta acctagtgcg gatgtggact ccctaaaaaa cctgctccac  11340
tttgtacgaa aaacatagta atgcagctaa gtgggagtct tacatgaacg cgcacttgat  11400
ctttgacttg gtccgccgcg atccataagg aaggggtttt cgttcgcaac aaggtagccg  11460
tagggaaacc cctatgggct ggattgaatc tttcctttcc ttctccctct cacctgatcc  11520
attaaaggaa aacagactca aggattgggc cattttccat atgtctctag aaagatagga  11580
gctaatcaaa attcttatta cttatgtaaa tgtaactctc aaatttgata ttactccatg  11640
tgtaacgcca aaggggcctt gtattcaatt gaaacagagg atctcccaca ttgatataca  11700
catccttcac ccaatctgct caaagtattt tcaactcttt catggtatca gagcactagc  11760
tcttgggaaa ggttcagttg gttcgtgtga agtgtggtct gaataccttc ttcttaggtg  11820
ttttctcttt ggcgctgtcc accgctctgt ctctatcctt ctcctcagca cttagttagt  11880
atcccgtcca tcgaaattga gttttccata gcgtctgttt caattttatg gaaaactaag  11940
aaaattgctt tttttgaagc acaagatctt ctcagtttcg ttgatggaac tggaaaagaa  12000
ccaaagaaag gactttcttg agactgatca caaaggtaag ataatgaatc ctgagtacgt  12060
cccctggaga agaacagacc gactactcaa aagtttaatg atgcacacca tgccctttcc  12120
caggcgtcga ggttgcctag ccgtaatcca caggctggct tcgacagatg tcagagtgaa  12180
tccgattctt cgattcaatt acttttccaa ttccaacccc gcgcgtggat gtagaaaagt  12240
gtgtgaatgg catacgtaag attggggatg gacaacatca attcatttag tatagtcagc  12300
taggaagcac tagctaggca agtcatactg ggaatgctgt tccacacatt ggctcaattc  12360
taccttccac atccaattct tccttcatta caaggcccag cttcgctaaa ctcgcaccga  12420
cccttagtta aatatgcggg tagcttttca cgaaagattg ttggcatgcc tcccataaga  12480
agtaggataa aaaaacctat gagacccccct tgttctaatc tttttcctaa agagcaatcg  12540
attactatac tagtgcatgc aaactgaaat cttagagaac cttgatccta ttgatcagaa  12600
agagctcggg cgagaaggtc tgcggggtca gaagagttca gagaaagctg gatccgggaa  12660
ggcttacgcc gataacgaag gattttgaaa ccgatcgata tgcagacgct gcaaaagcaa  12720
atgacttcgc ttcctcaatc aaggtaaggt aatttgagaa gctatcgaaa ctattccgaa  12780
gttgatgatt tcgttctagc tagggcaatt taaaagagag aagtttacgc tctccaacaa  12840
agaagcactc acctcctaat agaagagata acgtaagaaa gactagcaga tgcggacgat  12900
gtaagcggtc aatcaattga gactacttag agtccgctaa ctaggggaaa gagaagcact  12960
aagatgaaaa gatataacta gattcccctt acataatgct cctgttgaaa ctaaaaaaag  13020
ataagaaggg acttgaagct tacagtcctt actcaactac aagtacatag agaaatgctt  13080
ccacctatta gactatgcat tgacgttgca gatgttaaat tgcagttggc attaggagat  13140
agagagcaaa aggaatgaat ctagtatact taaggcaatc caaaaaaaga aagcgcttag  13200
```

-continued

```
tccttatgca actaaagcac aggcaggaaa taaagctaca tccacaaaga aagagatggt  13260
tgcatctaag ggcttcttat cttattgggt ctagcttctt agaaagccat agggagagac  13320
cgaacaatct gatgatatat acttgtgatg tcagaaaaaa gttccgaaga gtggaggcag  13380
ctttttcctc tccaattttc tgttggattc taataggatt caggaaaaaa ataggaattc  13440
gacagagcgc aaaaagatag tcgagcaatc agcgggcagg cataggtagt cgacagcagc  13500
aatcgaccat cttgagcaac aagagaaaga aggaccaacg acgatcaagg aaagaaagac  13560
taagtaaagg cagacaacga gacgaagata gcagacttgc ctcgaaacag gaacatagca  13620
taggggcatt tctccggact agttaagtag ttgagcccgg ctcccccgct tggctcctct  13680
ttgctcctag tagactacta gacatcttgt ctactctgct tttatggaag agctcagtcc  13740
aagaagggct ctcaaaaaaa gaaaattgtc aagctttcga actcgccttg aagttgatga  13800
atgattgcaa ggctagcaac aagcaggctc gcttatgatc tgctgaaaga gtacatcagg  13860
tttttttatt aatccctcac attcatgaag cagattgtcg aaaagggctt tctgcaagca  13920
ggaaaacgac ctttttttacg atccacaggg tctagcttga tcccggtctc gggacttccc  13980
aagtcacgga gtctttgatc aagttgtaaa ctaaaggagt ataacctatc caatatatat  14040
atattttcgc ttattgttag taagaaaggt gtcactaaca aataaatcct taatcagtag  14100
tggactacta gttaacgcac tactaaagca gagtagccag catgcgcaca taattttttg  14160
ccagaggatt tttcagcgaa tggaagaagc aggcagggat agatataatt ttttagggaa  14220
aaagtgcttt gtttgatttg ttcccaggtg agatccaaga tctttcaacg cgttgatttc  14280
ctactaaaga aactgggctt ctatcaggag tttgatcatt ggaaagggtc gaaaactctt  14340
gctttatgct tgagaaagag ccttcccggc gatctgcttc atttatggag ggtttgcaag  14400
gaagacaact gaatagcggg aattaaaaga gaaggatttc cagaggtcaa tatctggcat  14460
tgagcctgcc tatcctaagt atgagttggg agagcgagat agagacaaag acccaatgga  14520
cgttcccctg ctctctctct cgatgtggta cctttcagtc tgctctgtca aaactttctc  14580
gcaatgccga aaggtagagc agcttcaagg tcttcggcaa cgagatcaac tgctgaccca  14640
agaaggtagg gaagagagga ggaagggcca atccccgagt caggggcatc tatctttatt  14700
tacgcaaagc tattttcgat ttagatatgt tcattggcct gcgactgatc tcatcgtccg  14760
ttttcccccct ctttcctatt caagagttct cctccctaac ggcacactgt atataatctc  14820
tctagatggc caatgtgaac agttcaatca aacttgtatg tgtgaagcat attgaaagtg  14880
acattgacaa agcaaagcac agattcccta gaatgttaga actcagacat gacagagaag  14940
gtagtcaaaa acggtacgct aagctccttg cttcgtcgct tctgttttca gttattcaaa  15000
gaatgatgtt ttaagcatct ctatatgcca gtcatctatc tgacctgaca aggaggtcga  15060
ctttgatatc tcacccctga tctctacggt tggttgaagg tgtcttggaa gacgggtcga  15120
aatcagatct ggatagaaga ttcatctacg ctggcaaaag ggctatcaga aagagtccaa  15180
tcccgaggag agttcatgtg tgaaatttct ttgttgaatg gaggtgagtt caagggcttc  15240
tttgatcggg aaatgcacgc acttcttttg ttgtcattaa ggtcccttcc ccctgagttc  15300
aagatgtccc ttccgcttct ctttcactac tttcctcatt gggattggtc aagctccttc  15360
acttattgct cgatccgatc cggaacctat tgggatagca ccctttcctc ctatttatta  15420
gtaggtcttc ttgcccgttc agttcctcta ctggtagtct agttgtagtt ttgagcgggt  15480
gaacccatgt tctatctcgt agtcacctaa gcggcagagt ctgtaaactc aaatggtctg  15540
```

-continued agagttgcct ttggcttctg aacctctgaa actggactgg agcaagctac caagctcctc 15600
ttcccccttc atcactctct atctccggcc cttgccatta gttagcttgc acttcccttg 15660
cttgcccttt gagttttcaa agtcaaggtg cctttccctt ttctgcctta cctcttactg 15720
aagtgaaaga actgactgtt gtctaccttt gattctgtct tccgggtgaa ggtcctgcgg 15780
aggtcttttt tagtgatcaa aattgattag ggacagtgac ccatgatgaa aggagctatt 15840
gacctaagtg gttttctatt tgtatttgaa aagcaaggta ggtttgttaa cgaaaggata 15900
aggttaggct ggaatgggat atagtaagtg tgccacgagt gctcccttct aaggcttctg 15960
cttctctcta ataacgagaa aatgactctt tcagaaagca aagctacaac tcttcagtct 16020
aagctatcta agctagaact taaggccgac ctcttttcca gggatacccc acttcccggt 16080
ctagcttcac taactgtatt cacagctttc cagatctcgg aaccagatct actttctcat 16140
cggcattctc taaatgaatt acgttatggt cttgaactct cgatatatca tatgtaatga 16200
atgatcgagg ttgtcttttc ggaagaggtg ggtgggagtg gggcagggca agaaagtaac 16260
aatcataccc gatattcaga gcgccggaga tagaagcggc ggcagccata aagtggagaa 16320
tttccatcca tttgctgtct ccttcgctac cgctccgtgg ggtcaacatt acgaaattag 16380
ccaggttcag ttctgactat agctgcaacc tatctcatat ttggccgccc tcgatcacaa 16440
actcgaaatt ttggaagata aagtaaagaa agaatttcgg gctaggttca aggtatgccc 16500
aaaggtatgc cagttgattg aaaaagaaac tcaactttca agattcaaga ttaggtaagt 16560
gttcagtgta ctaaggtaca agatcgaaaa aaaagcgcgg atagcaaatt ccttaggcta 16620
gatagagtgg tggttgtaaa ttactaggta gccatacaac actcggccca agcaacgccc 16680
aaaagcccat gcctttcttg gtcggaccaa cccaaccggc gatttccgac aagtctttct 16740
gaattggaag agcaagaagc ggaacttgaa gaaaactttc tttctcttta tggatagaca 16800
gtctttttca aattctcctt ctaattcatc ttccccggtg gatttaggtt tatctctgag 16860
gtcccacgaa ggttcgacta gtagcactct gtcggacgcc aattcgggtg atattactag 16920
cactcaagtt ttgagtgata tcaccgctct ttttgagcaa cgaatggaag tgggaaagaa 16980
ttcacaccag aatggagccc aatagagttc tgccaagcgg tttttgggga agaagcggtg 17040
aatgacctat ctttattgaa agacatctat tgtgatctag cggaccatgg aatgctaagt 17100
tggtattggg aaccagcttg gggctttcta aatctcatta gcaatagtcc aggaatgaca 17160
tagccttcct gtgcaatggg tgtcttaacg tactaagtaa ggtggttttt tctaaagcgg 17220
cattctccct tctatctatc aacaatagaa ttatggaact ttctccccga gctgcggaac 17280
taacgagtct gatcaataga gtccgtcatt ttttctattc cttcctactt cttcttcctc 17340
tattatgtgc ttttattcta tttgcctgaa actcgagaaa atagagttgt ttgagaccaa 17400
atgttataga gttgggggct ctctggggag gcacaccttc acttccttct taatgaaggg 17460
gttccccggg agtctgacct tgtcctttct tttaattgtc ggggccgtca tgagtgccga 17520
aacctatttc ggtaagatga tgatggctcc ttcgggcgca tcaagctctg aagatccaaa 17580
ctggacggaa gccctgagat cttctaaagg gcagggagag acttcagaaa gggaaagcac 17640
aggcacatcg tcgtccatca acctacaaaa agaaagagca cgtccggcgc ctgccccaaa 17700
tgaagtagct tcccctgccc ctgtcgtccc ctttccatat caagaagatg agatcatagg 17760
gggcgacagt gtagaaagca tccaagagcg tttaatttga ggagaaaaac ccctccttct 17820
gccgaggtca tacatcatac aacaggcccg aattgaagcc gaagacctat tcgaggtcaa 17880
ggtcgatatt ttcaggggca tgtctggcct tgatccagaa ggagattggc tgggacgggg 17940
agctcgggcc ctcgagaatc cgcgtaccgc cacgggggag cattccttgg agaaactcca 18000
tacccttctt tcggatctcg aatcgagggg agtcaattcc gagtccttct ctcaattaaa 18060
agggaaggta cccctgcgaa ggggtgggga cgaacactct accacatagt ggagtggata 18120
gctaggacta ctaaaatgga gatcgtgtac aacaacaatc ctatatttga tgtcgattca 18180
tccacacttc cattccttgt agaggaaggc taactgcttg ctggctggga gctgtatgag 18240
cggtaacgtc cacgtacagc tccgtgagaa gggcggtgga cagaaatggc cttgttgtac 18300
ctcactctcg tcttcaatgg ggtctgctct ttcttttttg ggagagtatg ccaatatgat 18360
cttaatgagg tgcggggctt tgcatctgac attcgttggg cttctctctt cgggagcctg 18420
cgccccggcg tttttgtgca ataaacccct ccggccgaag actagtggta ggtggtcctg 18480
cggagctttc ggaaaagggt agccttgtgt gtaagcacag caatgaaccg cggcgaaccc 18540
tcagacgacc tatctaagat taggggggga tcctcagtag tggtgaccct ttcactcttc 18600
cacggactga tacatgtacc gaatgctcat acgggaaagt tgactcctgg gtctggaacc 18660
tggggggttg ctccgagaaa acctttcttt ctcgtccact caggggggtg cggacacacc 18720
tgcgcggatt acaggtgaca gttacaagaa tggcggggaa gttaacagta cccgacgaca 18780
ttcagggatg gatgtagacc catcgggcag ggataatcat tccggtcctg ggagaagtgg 18840
cgaccattct caagaaccaa aaagactgag ctgagggaag ccctatgagt cactgaaacg 18900
acggcaggag tgcccttttt ctatcaatag agggagcaaa aaaggggcct tgctcccctt 18960
tacaatatga agaaagaaat aagggtcgaa gtttagaccg ctcacagtag ttctacctat 19020
agaaaggatc atgaaagagg cgatcagaat ggtactcgaa tccatttacg atctcgagtt 19080
tccagacaca tcgcacttcc gctcgggtcg aggcttccac tccgtcctaa gacggatcaa 19140
agaagagtgg ggaacctctc gctggttttt ggaattcgac atcaggaagt gttttcacac 19200
catcgaccga catcgactca tcccaatctt taaggaagag atcgacgatc ccaagttctt 19260
ttaccccatt cagaaagtct tttccgccgg acgactcgta ggaggtgaga agggccctta 19320
ctccgtccca cacagtgtat tactatcggc cctaccaggc aacatctacc tacacaagct 19380
cgatcaggag atagggagga tccgacagaa gtacgaaatt ccgattgttc agagaataag 19440
atcggttcta ttaagaacag gtcgtattga tgaccaagaa aactctggag aagaagcaag 19500
cttcaacgct ccccaagaca acagagccat cattgtgggg aggttaaaga gcatccaacg 19560
caaagcggcc tttcattccc ttgtttcgtc gtggcacacc ccccccacaa gcaccccccg 19620
gctcaggggg gaccagaaaa cgcctttcgt tttccaccct tcgtcggccc ttgccgcctt 19680
ccttaacaag ccctcgagcc tcctttgcgc cgccttcttc atagaagccg ccgggtttac 19740
ccggaagtcc gaattctatg gtagagaacg ctgtaataat aattgggtca tgagagactc 19800
ttttaagtat tgcaaaagaa agggcccgct gatagagctg ggcggggagg cgatacttgt 19860
tatcaggtca gagagaggcc tggcccgtaa gctggccccc ttaaaaacct attacttaat 19920
aaggatttgt tacgcgcgat atgccgacga cttactactg ggaatcgtgg gttccgtcga 19980
gcttctcata gaaatacaaa aacgtatcgc ccacttccta caatctggct tgaacctttg 20040
ggtagactct gcaggatcaa caaccatagc tgcacggagt acggtagaat tcctcggtac 20100
ggtcattcgg gaagtccctc cgagggcgac tcccatacaa ttcttgcgag agctggagaa 20160
gcgtctacgg gtaaagcacc gtatccaaat aactggttgc cacctacgct ccgccatcca 20220
ttccaagttt aggaacctag gtaatagtat cccgatcaaa gagctgacga aggggatgag 20280

```
cggaagaggg agtctactgg acgcggttca actagcggag actcttggaa cagctggagt  20340
aagaagtccc caagtgagcg tcttatgggg ggccgtcaag cacatacggc aaggatcaag  20400
ggagatctcg ttgttgcata gctcaggtcg gagcaaggtg ccatcggacg ttcaacaggt  20460
agtctcacga tcgggcactc atgccccgac attgtcattg tatactcccg cgggtcggaa  20520
ggcggcgggg gaaggagggg gacactgggc gagatctatc agcagcgaat tccccataca  20580
aatagaggca cctatcaaaa agatacttcg aaggcttcgg gatcgaggtc tcattagccg  20640
aagaagaccc tggccaatcc acgtggcctg cttgacgaac gtcagcgacg gagacatcgt  20700
aaattggtcc gcgggcatcg cgataagtcc tctgtcctac tacaggtgct gcgacaacct  20760
ttaccaagtc cgaacgattg tcgaccacca gatccgctgg tctgcaatat tcaccccggc  20820
ccacaagcac aaatcctcgg cgcggaatat aatcctaaag tactccaaag actcaaatat  20880
agtcaatcaa gaaggtggta agacccttgc agagttcccc aacagcatag agcttgggaa  20940
gctcggatcc ggtcaagatc cgaacaagaa tgagcactca actactagta aaaagggaga  21000
aagttgactt tgagaaagaa ggtgcttctt gccgctttat tagtaagtaa gcttgtttta  21060
tatctcctca ataaaggcga aagatcactc ctaaaagcaa gctttctctt atatacgata  21120
ccataccaca gaatttcatt tgccttcctg cttaaggcac tagttcggat ggaaaccctg  21180
atcaggcagg tggcctagct aacatagcta tccgtcagaa atagcagcat tccattgcag  21240
gctactatag aggcatataa ttttccgggt gttaagaaag atattgaatc gaaagcggac  21300
atgcttgctc actggctaga tcgggctgtc tgtacctttg ctaactcttc tgcctgtaag  21360
gaagcttgaa agagggaatt ctctgatcta tgaccccgaa agaaagatag tctttttttcg  21420
attccgcgca ttggaactga aaagggctat tcataaacag tcttccttgc ttcttacctc  21480
ttatcttatt gtaggagata atcggagaga gaaaagtctt cctatcaatt ccttttgaat  21540
aaggctacgc tcctccaagc ctttgaaact attgaaaatc gaatctttgt tttcaggcgg  21600
gttttcttct ccaccaacaa ccaagacgca tgaaagcggt ttccagcgct gctgggcaga  21660
aagacatgat ggcatgaaac tcgattacgt acgctgattg ttcgtccact tcaaaggctc  21720
aaaacagacc attttccgtg tgaaatgaca gggattggtt tggttactta gggaatccca  21780
agcaaagcaa tctacgcaat ttccgggttc agtagtagga aagaaaggga cctctcactc  21840
aattcaataa catgttctag ggcatccttt tctaataata atgttcgcat ttgaccaggc  21900
tttttggacg ttccatgatt aaaccgacta gcggcacttt cgagatgcca ccttgtttct  21960
aaaaagagtc ttttcaattc catttgactc ggggcgtcag ggaccctcca acagaaacct  22020
cgtctttttt gtcgtcgata agttctccct cagtgcccta ctattcataa gaaagactga  22080
tttaaaagag actgatttat taaagcccgg tgaggcctca accgacagct aagcttcgtt  22140
ctgcggcggt tttcaagcta gcaccccttt cagcatatca tctcgctcga ttccaaaaaa  22200
aaaaagagac gcagtttttg attatccagt tctatatcga aaacgagcag ttgatcccac  22260
gaaagcaagg ctggctttgt tgcgggttca actggaattg taagaagtga ggtaaattgc  22320
ctttctcccc accgcatatg cctcctctgc ttatgccact ggtgatgaac tcactatggc  22380
tattcaacgt caaactcaga gtttttctac tacataggcg gctaaacgaa gccccagtct  22440
tttttagtaa aaccccaacc ccettattag tagccgaagt aaaggccagc atgagatcaa  22500
agtcacttgc cgtccgttcg ctctctgttc aacaaaggcg atcgatattc ccttacttct  22560
caagttttga attttatgag cccttcgatt gtatcccata agaaaatctc tctgataaac  22620
atcttgtcga tgattcgatt atattattta gaatcttcgt gtgcgctttt cgcctgaggc  22680
```

tttcggacaa gactacttac tccagtaggt tagtaagcta cctcttccgc tttcaggcaa 22740
gggtagctct gaagggagag ttgagcggaa ccaggcataa ggagcaagaa tcgctattga 22800
gagttccccc gctaggggaa cgtcaggagg gggacatgct ctatgtccac tgattctgtt 22860
tagtacagta taggaagccc ttgtttgagt gagagcttct agaatgccat tcatttcgca 22920
ataagaaact tttccacata gaggtttcag ctacttaaag cgagagtgca tccaaaaatt 22980
cgagaagagt gctcggcctt ggttgaaaca attataggtg tcaatggacc gatttcacta 23040
gcagagcact ttctccaatg tgcgcaaaca gagatgccac tttcaatgat ggacaccggc 23100
ccttgtgtta aagtagcatc gagtttcgct tggaaaccgg caagtttcta gtttccaaat 23160
aagtggtacc ctttctttag agtccggtag gtcaattaag ttgcctaaat ctcttcctta 23220
tctgctgctc tgtagctgcc ttcctcgctt cgtcttcggc tttcagagtt gtgaactaac 23280
ctcttccttt tacagccaga caactggcag ataagctggg catctaaaga acataagatc 23340
cgagttgccg ccaggcataa aagtcatatt gtcaactagg gaaattggca caaccaggca 23400
tctcaaacat tgataaggga agaatcaggc tttcattagg atgatattcc tttcatccga 23460
atggcaaggc ttgctagttt cctgaagtac actcgcatct gtctatctat gtcatagttg 23520
cttggaagga aggtctcaga tgtaccttcg gcatgtatga gattttcttt cctctatcta 23580
tgtcatactt gggattcact gacagccaat tccaagtaga tcctccctcc ccctcgctcc 23640
acttcgtttc gctcgttttc tctttccttc tgcctgcaaa aaaagtgatg agattggttt 23700
tgtgtgcgtt agcgatcatc aaacctgtga catagataag attggagttc atgcagttgg 23760
aatgcctgag accacttttt gccttgctgc tcttgcttct ctggctactg ctccggctaa 23820
ggctttcttt ccgctttgac ttgccttcct tatctttcaa tctggacttg catgtgttcc 23880
gcatatgact atttcgagtg attgctgcta tctggcttga gttagacaag cagagaagga 23940
tcttatgcca ccggtgaccg gcctgcctat ctagtatcta gtactaggac tagtagagta 24000
gaggcactac tgggcggggc ttcctcgatc acagcttctc gcttagctaa ctgccagaca 24060
aggatgcaaa tcaactcctt atatagaatg cagatcgaca cattcaatga agcagccagt 24120
acggcagaca agctactttc ttattctagg actggaagat cctctatcta ttagcatacc 24180
cgtaccggca gttagactag cactctctcc ccaatcaatc gcagtaactg gctgtaagag 24240
agctgactgt ctactatcta tgtcatgcct tggcaggtga atatgagaga gaggctgtaa 24300
gtgcattctc tccttctcca tcttctggaa agcactcttt gagcatgctg acagaatgat 24360
tgacactcac atctctctca tttccagtga tttcgctaca gtttactagc gcattcctag 24420
actaagacta cggcattgaa gaagcaagct cactctcatt ccaggaatca gaggaaggca 24480
ttctgtccgg taatgaagtt agaagtttcc ngnnngcnnt ntctcttctc ttgcagttgg 24540
tccggccagt caaccttgtt ccgggccttc tcttctactc tatctgctta ttggattggt 24600
aggtacagtc tttcttctag gcttctgatt gaactttaag gtaatgggag agaaggcaat 24660
cgacagataa ctggtaagta aagctatgga ctgggttctc actctaagcc agtaccagta 24720
atttgaaaaa acgatagaca tctagcgcat tcactcgttt tttctttctg atcggccaac 24780
tcaaagaggg aaatgcaagg ggcgttagcg gtctttttttg cctcgcctgc tactgggaag 24840
agagagccgc tgtcattctt cgcttcgttc gagaatcaac tgcacatgaa taggctcctc 24900
cttaggcctt caaggaggaa gcggcttttt tccaaaattc ccgggaaaat gaaacttttg 24960
aaattctttt cgtaaggcaa gaaagttgcc taaggaaagt agaagtctat gcacactaac 25020

-continued

```
cgaatctttg gggaaggatg gtggtgctgg ccttttccct tctcctttct aaagcaaaaa  25080
agaatgtcat cattctgatc gtgacttgaa aaaagaaaga agagaaggaa cttggagttg  25140
gcgcccacat aacggattgc ttgcttacca agccatcctg gcttttcgct cctctcctta  25200
cagtcaagtg gctttcactc ctccagttct attattattg acttgactta ttattaaaaa  25260
aactactcac tatccaaatg aaagacgatc gattatctac ccaagaagat agagagtccc  25320
acatacgaga aaaggtcaca aatagagttg aaccaagtaa cattgcaaag gcataatgat  25380
agtagggtcg ggatatcccc gccctccgaa ccggacgtga gggtctcccc tcatccggct  25440
ctctgcaggg gaatctccac tcactgcttc ccctaatatc ctccccttac cacatcatgg  25500
gggtttacag gagatcccag aggctcgctc ggaaaggctg ctataccata ccttttgact  25560
taactctact ctagtagtca ctagactcac tatagtagtc cgtctggctg ctcttgctga  25620
aatcattact cttaattctc ccgtgctcta gcaattgcgc tccctagacc actaccatgt  25680
agttaggtag ggacaatcag tccgtagtga cgggaatcta ggaatgaatg gggatcccta  25740
tcaatataaa aagaatatct aattrgakwt tthtttttty bmrmvsagda vgvgatatvh  25800
gagdtbcght abdgtcbhgt gcdctvvgag atgtdtaaaa gctatgggat agatggtaga  25860
gggctgcctg cgcccaaaag cgatgattca cttgtcccct tgtccatagg gacctcgtgg  25920
catacaaccg aaacgactcc cgctagatag ccgccccttt ctctcttttt acagcctcgt  25980
ggacggacga aagaagggaa gttacagaac ggggcagtga aggctcgcga agtagacagc  26040
aagcagcaag caacagcttc tcagcccccct aacctttctc tttttaata atactttttt  26100
tatcaggtaa gctttgaagc tggctgctct gctatactat actagttgta gggcgctagc  26160
gcttgactaa tataatagaa agtaaaggga ctctattatg atcttacgaa tctaaagatc  26220
tcaaaatgga agaacgagct cttttgctcg cccctatctc taaaggggcg taagcacttc  26280
actcgctagg ggatgggatt cattcacttg cattcctgct agcactacaa aaagctccgg  26340
tcttaacgcc cctactactg ctgtgcagcc tttcctcggg ttcgtagagt cgggtttccc  26400
gtttacccac aacggaggag ccgcccccac caggcaggcg gccacgggtc ataacgcact  26460
cttcgcacaa caaatccact ttgaagttga cttattcgct cggccaatcg tcggaatgtg  26520
tacgagatac cataagggcc caatatctca atagcacctt tgtctaaagc ttcgaaggag  26580
acttcatatc cgaaacgcag gaacgatctg actagaaagt cattcaaaac ttgatcgaaa  26640
aaccagcgtt tattgaagaa gctatagagt cgattactaa tagtactagt ttgaaaggct  26700
cgttggaatt gatccgctac gggattaaca ttatacgcaa cataagcacc tgaagtacta  26760
aacagaatag gtattagttt ggtaatggtt ggagcagcaa actcggattc ggcaagaatc  26820
tcatttttttg gtagtacgaa gggggaattg gcccaaaaat tggatggggg tcaagacgct  26880
gtcgggcgcc ggcggctgac tcaagtgccc cccgaaccgc gcgaaatggt cgcctattac  26940
acggctcact aactctgcct ggggtgtggg tacctattat tcgtcggcgg tccggcgcac  27000
ccctactata caaagccgcc cccccaactc acttaaagga tgctggttaa ttacgaagga  27060
aattctttct taatcgaggg acttcctttt cgttaagcgc atcgaaccag gagtggacat  27120
tatcatcatc tgcagaaaaa tccagattct ctttcatcat tagcgaaagt ggaatagtat  27180
gactggcttt ccggaaaata agacgaaacc cgctttatcg atatgataaa catgcgctca  27240
aaaagacctc ctaaaccccc ctgccaagcg atcgagttta gtctgaattt gctctagaag  27300
tagctcccgc tccagactga cttcaaggaa agaaagggtt gggcaattcc gccggttctg  27360
gagcttacct tattattaag gggaaaggga ttttttatag atgttgaggt gagtaagggg  27420
```

gggcgtagct tgaggcttct cagccgcagg aacagggaac gaatcctcca aaaatggaat 27480
gagttcgcaa ttaataccac aagaaagccg ccaccctcgc cctttagaga taggggcgca 27540
acaaaaagta ttcaaaaagg gcgccggagg cctcaaactc atccggagtt ggagaatgaa 27600
ataaaaaaaa aaagattctc aagaggaatg tatcaacaaa actgcccttc catatagatc 27660
gtcgtggcat gaactttgtc aatagattcc tagcttccta ttgatcttga ttagttctag 27720
cttcgttttt tttgttgaga gttatctttc tggaccggac ccacttttat accgtctcct 27780
gaaacacctg cttatcctgc atgtgctttc ggggccccca ctcaaaaaat cacttgcttg 27840
tgattgcagc cattccccga aaagggggag ggtggatgta attcagctcg aacgaagtga 27900
gaggggtaat agactattac cgttcagttc atgtgacgaa ccgaacatcg ttaggtcccg 27960
aattctgcga agcaccggat ctagatcaag atctccatta cgtcgtacga tatatcgatc 28020
cggagaactt actttcagtt taagtcatcc attctgctcc tatctaaagt gatgctaggc 28080
tgcttcacag aggtgcgctt cgctcgacca catgatgaac atgttttaag ctaactgcat 28140
gtcgagcgct taagcggagc ttgtggtcac tcgttcctcg cttgttcgaa agagcttcag 28200
attggattct acactacata cgatattcca ttccggccct cactagctct ttgcttgctt 28260
gtacaaagag catgcccgag ggggctacta cgctcaccgc gcacttgcat taccacctga 28320
gcttcgctac cgttccgccc agctcctacg cctaccacga acttgaatca tcacatggct 28380
gctaaagcaa gctaagcttc acacggccct gaggaagcca aaagaccctc tcacggccga 28440
aggctccgca acacgttgga gagcttttag atcccgccct aaaacgccca ttcccctaga 28500
gttccgaagt gattctcatt ctcaccgcag ccttcttaag ccgaaagaaa gccgggcaag 28560
aatctcatgg tagtacgaag ggggagcgga atcgtatctg ggagtggttc ttcggatcga 28620
tcacagattc tcggccccgt cctttggctt ccactccagt tgacctctct tctttccatc 28680
ccaccgtgag aaggtagaga gcaaaaccaa cccagcaaac aactatgact atgcccctat 28740
tagtaaagca tgtacttctt gcaaggcttg ctgagcttct tcatgtgaca gacatcgcaa 28800
aagtagtccg ttgaacgatc gccgatcgag ggcatcgtaa tagtatacta tttttgaacc 28860
ctgatgggtt tcgcagtcga ccatttgata gccctgttcc tgaatataca cagaataggg 28920
cttcgatgag ccctagatgt aaaggggttc ttgaaccctt ctaagcaatt agaagagcgc 28980
ggaattggac ctccctcaaa tagatggatc tgggattgat tgtggaaccg agcatagaga 29040
accgggggcg ggcaggaaga taggctaggc ggagtagtcg ctctggagca ggttcttcga 29100
ctggatcaat gcatgtatga accctaaaaa aatcccgaag gtctagtcta gaaaaaaccc 29160
ggattttgtt gggttagctt tttggtagga aaggcggtca caggaagaaa tgccctacca 29220
atgaatagat tagtctacta acgtcaacaa tctctttctt catatacgag accgtctgct 29280
tttatatcct aaactataga tatgaaacaa aaaagaaaga aaggaaaaca ggcagggagg 29340
taagagcgag taagactagg ttatagcaag acaacagagg ttagatagct cttaccggag 29400
gaagagggtt caggtcaccc gtccccttga cccagacacg aactaatcct tctctctctc 29460
gaatgtatgc ccggttttcg tcgaatcttt ttgatcacct tcaaaaacaa accggaattc 29520
cgtcttgaca tgataaatag tgatgcccac ctgcagagcg tagccctccc tgcagccttg 29580
aagtagacta tttttcgagt ctgatcttat ccccaaagcc tttttgcaaa aggagtaggt 29640
agcgagatag atgactaaaa gctgatgatc tttgcctctt actagtaaag ggaaaagccc 29700
tatatatctg attagtcaag cctaaaggcc ctttactaat ataatagaag gtaagaccgg 29760

-continued

```
ctttcgcgca gctgctgcgc ccttgcttct tgcccataga gagttaggat attttgtgag  29820
ctccttcgcc tagcggaaac ctccgctttt cggccgtaat cccgtgcttt accaacgcat  29880
tcaatggatt ccaccatgaa ccgggagcgg gcgaagacat gcagcttcca ttttcggggt  29940
acacagtcac gtgctgagca aagaggtata tatcacactc attcacaagc gcaaggtgcg  30000
gcatccgcct gaacggggag aggatttccc taaaacaaag ataggcgtgt caggaaagaa  30060
tgtgaagtca cccctatttc gctgtccagg gagctgttga ctaatgacct aaaaaatgcg  30120
tgacgtttgg gaagcatgag caacccttcg cgcacgagat agcaatgaca ggagattgac  30180
cggtcggggt cgagtgatct caggggttta ggggtgcttc tcctgctgcg actacctctc  30240
tattttcaaa agtatataga aatggtaggc actgggagtg agtgaactac ccggggagaa  30300
aggggcaacc tctctataga agggaaggga aagggttctc cgctcataat gattgtagag  30360
tctctcgggg ttggaggtct aatagtagtc acatcaagtc ctccccctct tactcagaat  30420
agctagcgag aggaagacta ctgattatct atgaaagaag gcttttaaga atgaaaaaaa  30480
tcttatctta aggatagaga gccccccgcc tgcgttttca gatacgagtg agtgagcgct  30540
ttttctgcta tgaatgaatg acctctccat ttattttcaa gcttgctctt caaaccggcc  30600
tatcgctctc ctctatgaaa aggttcttcc gtaatcactc tcaataagac atccattccc  30660
ctttcaaatg aaaagagaac tagacttttc tcttcatcat tgaaatccgc cattcaatcg  30720
cagtgcggtg ctctcaaaag gctcaatcct ctaaggctga aacgaatagg tcaggaattc  30780
gacctgggat ccgcccgttc cgatccttgc ctactaaaca gttgcacccc cggatatgta  30840
tgttgggaga accccatgat ccttccgtgt ggaagggaag gaagaaagaa ggcgaacacg  30900
aatactaaaa agcggttcat ggggaccccc caaaaagggg atagagagcg cggaacgggc  30960
tttccaagca taaaacaatc cctacctata cattccatgg caacagacag aaggcagttt  31020
tgtcgttgtt cttaacccca ggcacatttc cgttcccaat aatctccatg aaaagactac  31080
catgatttcc gaacgaaccg agggagagtc gaggcatgaa aaaacttatc tatgatctgc  31140
ttatttccaa gtacgtatca tccgctgcct tatccgccgt ctctgcggcc gccaaaagcc  31200
taccctctct cggatattga gtgggttgac cggggaagag atccggacga accttccaac  31260
aagcagaata gaagttgacc acaaggccat ctctgtggga ggctgctacc cataaggcca  31320
tctcgggcat gggaaagaaa ggcggcggac aaccgactta actggagagc ctaaacggca  31380
tagaggatga gtccaccggt cgacaaacgg cttctatcta caggtgcttt cattatggat  31440
cggtcgactt gtcacgattg attgctcaca cacaattagg ttaggcaggc ttggggaggt  31500
gatctgaatc gctatcgata cgatgcgggg ctgatttgct gaccgtaacg aacttgactc  31560
tgcccctgaa aaaaaagggc gggaagacct ttgacctggg ctggggaggg attggggtcg  31620
cttttcttta ggactttagt ccgtaacaag gctcgaagac ctccggctgg atttgaaatg  31680
gatcaggtag ggcatccgtt tacgacgtgg gtgggattag cagttttctc tattttcttc  31740
aatggtagga aatacgcatc agcgggggta tatgggagga aaccagtctg cagtaattca  31800
aattgctcct tcggatcact aagtaaaatc ttgactcaca cataccgcgg tgtattgttg  31860
tcaactcaca tagtcgcacc taccagcaac aagacgacta ctccctgcac gccactaaac  31920
ggcgctattt aacgcttggg ttcgcccaat acaagaacta cagcccaacc tagcttaagg  31980
ctaaagccgt ggactacacc cccgtgagag ccctctattt tactaacata ctcccttttg  32040
atctccccca taccttcata tcaaagctgg gaatgattga ctttcggatt aaaataatag  32100
cgcataatgg cagtactcct tcccatttct tcttttatga tcttatctac ttgaaatgct  32160
```

```
tacctgtaag tgcggagaag gtacccaggg gaccaaacga aagggcactg aaaggtcttc  32220
aattaaagct tcgccagtac ttgaaagact cgaaagacct acttgatgag tttccttatg  32280
agtgagttcg taggtgcctt taagtcgagt gtagcgaagg gattctccta agagaagctt  32340
tagcccttga acctgaaacg acttttatga gctgtctcag tagtgaccga ctttatttta  32400
ttagctgtat gattagtggc ttagctctta gctgtctaaa agctacggta aaaaaaatcc  32460
cttttgaaaa taaaccacta atccgcctta ggtactcttt taagtccgtg taaggcggag  32520
ggaatgaagg gacctgcagg aggctgaaaa gccgtagtgc gctagcgcta gcgagttagc  32580
gcaacaactt agtgtcttgt tttcttcgct gctttttttg tccgcaggaa agcggttgct  32640
aaggcttgta gcttgcttct gtccttagtc aattttggac tgaagctgtt ctgactgccg  32700
tatctttttt gaaccgaata ccttcctctg tcatctctgg tctgtctctt tttgagagaa  32760
gattttctac cccgcctgcc tatgaagaac ttcaagtcta tcgggaaagg atgtggtggt  32820
aacccccgca gctttgtcta gaaccgggcg tccagccgtg taggaagact caccctagcc  32880
actatagcga ccccaccccc aaccctagct gagaagcacc ctyvdgccac tcccdthttt  32940
ccgtgtgccc aaaagcccgc ccgcccggtt tttgagaccc tttctgattc cctcacccaa  33000
tctcatgaga agcaagccca gcaggccctg ccttaacctg tcctcagaca gccagccctc  33060
accaggctgc tggcattgct aaatgctccg ccacgaagca agctttcccg aatacgacag  33120
atgcggaagt ggctaaagaa gtcggaggaa gaaagttgtt ggacaactgt atacacgagg  33180
gtacattagt attctgggaa ttggcaacat tgacagaaag ggtaaggggt aggaagaaac  33240
ttttttaggt cttgctctac taaagtagtc ggcctaacct tcggttcccg taaccaagtt  33300
tttctttctc actccttatg tacttttttt tacttcatcc atactttttt actttttctg  33360
aagtgtgggg caaacggcgc cctctacttc tacttctaac taaaggcgaa cagccggcat  33420
tgcaagcaaa tagaaagccc ccgcccgttt gagccggaaa gcgtaccggc tgtttgagtc  33480
gcgaaagggc cgcttgctta atattattta tataataata atagatagat aatattatat  33540
tatataacta tctataaaga taaataaaaa actacagaaa atactttttt ttttataaaa  33600
ttcttcattc ctgggaagag gaagaagcag atagggcaaa ggccttctct ttccgtccgc  33660
tcttcccgaa gtgagcgaat tgcatgtaga gatccgtagg ggcttatagt ttaattggtt  33720
gaaacgtacc gctcataacg gtgatattgt aggttcgagc cctactaagc ctaccacccc  33780
cttctcttca cctgatacaa ggcagtcgaa gtacccgcca ccctgcagat ctcaatctag  33840
cgacggcatc tggaaccaca ctgctgccgc tgcccttcgg gcacgcctcc tatgcttatc  33900
actcacctac gctcttgcag catgccccct tcgggcaata cggtgtaata cgcgaagcag  33960
ctgagccata gctcttcgat cgctatattc ttgcggcgtg gttcatcctc taagagagag  34020
tagatgcgaa ggttcggatc gaagatcttc gcgagacagc cccggggcac catagcatgt  34080
cgggaataag ggggacatag tgaacactcc cttggttggg ggctgtgact cccctatcct  34140
ttcaattttt tgattcccag gtctttttta ttatcactgt tggaatcttt tttaagacga  34200
cttggtcagg gcggttcaca atttctttgc tgaaggcgct gttaagccct aagtttgaat  34260
tcaaatttca ttgcccttct tccgaaagtc taaagtcctt caaattttca ccaattccga  34320
cctaccttta tttatgggat atttgaagga gagctttgta actgtttcta gaaaattctc  34380
tctagctcga agaatttgtt tgattctccc tataaaaata gttaaggaaa aaggggcgct  34440
tttgttaaag gactaactat tgtagagaag atctccttgg ctcacgaggt ggctttaagt  34500
```

-continued gataggggat tttaacctaa agacaacata ggagggaggg gggtcaaaag aaagtcagga 34560
tatggcaaaa gcatcttttt ggatcgaatg ggcttttgtg ataaatggcg gaatttgata 34620
catggatgtt tatgtaatga agactttgga gtgcttgtgg atggtgtgcc acatgggtac 34680
tttccagctt ctcgagggct gcgacaaggg ttccaaacct agcctgttga ttttagctga 34740
agaagtgcta agccgggact tggtatcatt gaaaatgata acatcttacc atgcttcgag 34800
atcgtgccca gcactctcct actttctctt tgataacgat gttctaatat tatataatag 34860
ccataaacgg aatcttaaga agcagaaaat ctttctggaa agaagtaaga agctgattgt 34920
aatgttgtaa tggccaaaag gtcaatttcg ataagagcca gtgcttcctc tcgaacagag 34980
ctcctcgcag aaattccaga tcattgaaga ggaatcaaaa aaggtagttt tcctatcaag 35040
tacctggaag ttttcttgtc cctcaagaga ataaagagag aaccttcctc tactggagaa 35100
aatgaaaaag agaatctcag attggaaaag taaattgttg tcctccggag gtcgactaag 35160
gcttattaaa catgttatag tcttcctatg cacatgtgca agtttttttcc ttaattagcc 35220
ggcccacact tcggctacta ataatgggat aagaccttac tactatatag gatatgttac 35280
cctctctcca gtgagtgcag tgaaggactc tcgcctcacc cgcccgtttg acttatggca 35340
tcatcgactt gcttttcaat caaagcgatt tcataaccat aaagaaagac ctctccttcg 35400
ggatcagtcc cgtccctaga tgtagtagtc aatcagcggg acattcaaag aagctatgca 35460
ccttcactga atgttaatga aagaaagccc tttcatccta atctcatcta ctgaaaaggg 35520
ggccgggcgt agcacgttct tttttgggac acataggcta ttacagacgc atcaaaaaag 35580
acttttcgaa gcgcggaatc cctgaatgga atcattgcag aagaaaggta taacggttgg 35640
gaaccggaac aggattaagc ctttaagcat gcagatgagt gtttgctgtc agccccaatc 35700
cttcggtttc cggattggaa taaggagttc catgttcata ctgacgcatc actctatgcc 35760
attggatgta tgttggcgca agaagggccg cttgatcact ccatctactt ttaaagtata 35820
cgactttccg ctttggaatt atagaaccac cgaaccttct ttatcatgat tcgacccata 35880
cctcagaccc aagatcgagc accagagctg ctcataacaa ggtaccaaaa agaagaatgc 35940
gagaagttca tattctccag attcgactat aaaccaggta gtgaggatga aaaaaagcat 36000
aagctacctc gttcgtgctc ccgtctttct cgctgccatc ttcggtggat gcgccccttc 36060
acttaaaggc ggccaaacca acccactgag ccaacctttt agattgaaaa aagttactaa 36120
gctagtcacc tcacctctct ttcttacccg cccttattag tagtaggcaa cctttctttc 36180
tcgcctttct tccagctttt tccagataaa gatctaatag agttgcgctt tcttagtaca 36240
ttgcctttca ttaccaatct gtcgttttac agcacgaagt tacctgatgt tcgctactac 36300
taataagggc ggagagatgt taacctttcg ctattagtaa gcactcccct agttttgacc 36360
taatgagctt tctttacgtt gagttaatta acccggcggg ttcgcctaga tgcctagtaa 36420
agaacgagct ggtgggaaag agctggagat catgaaaaag atttccacac aaggaggcag 36480
gcgaccggga agctttgctt ctcgaatgcc gactacatgg gaacagatgt tatataggtt 36540
gattctcatt cttgctgccc gctcgattcc gaggaataaa gggagggctt taccacaatt 36600
tcccaagtaa gagatagaat ctcactaatt ggaaggaaaa ggagggcttc gatccattgt 36660
gattcgcttt cttggtatgg agagatctct gccataaaag agagagctcc taagccttat 36720
tctgcagatc aaagagcgag gtaattcccc attcatccga aatagtcttt tagtaaagaa 36780
gagaggcatt ctgggccgac tactacgact acatgcccat ctagtgcagt ggcttggaag 36840
caagctacct tgaccatctt ccgaagttct aaataattta ctgatcaaag gctgtaaggg 36900

-continued

```
cggactgctc tacattcagc cacaccacag tgaccccgaa gcgatcttct tctagttgcg  36960
ggacgaaatc cgacagccaa ttgctggctc tgaataacca gcccagcaat aagctcaatt  37020
cttccataac ataagggggc gggcttgcgc gcgagccgaa tgacgtaggt gcacaagagt  37080
acttcgcgcc acaaccatct cctttttata ggttctacgg accgatgcct gctgcttcat  37140
ctgggagaaa agaatcatag atatgccggt cattagaagg aagaaccgcc ataaaaagat  37200
tcctcgtgta tcatctgtag caaaactatg aacgggagct agcaatccgg accgtattga  37260
aaaggttcct gagacacagc atggaaaagt aacaatatta agaaacgagg tccaagaatg  37320
aagaaggggt tgaattactg aatgaatacg agctgtggct aatacccgag gcataaaaga  37380
agcattttct acgggatccc gaaaccacca gccaccccga cctaattcat gataagccca  37440
ccaacttcct ggcaaaatgc ctacggttaa aaaccaccga catgtcaaga tccaaattcg  37500
aattggttcc tggtcctggt cagagaccac tgtgttcgcg ccggcggtcc aacaaagagg  37560
cgaagtagtg gtatctttct ttccattacg aacgacacgc ttcgcctgct ccctccccgt  37620
gtccactagc gctcctgtcc agagcgaaga gaaggcgaaa aagcgccgcc gaagcagcat  37680
aagcaggctt ctattgctac gtaacaataa agcaggatag cattttgcgc ccacatgttt  37740
gaatttgagg gtaaagagct cgcttgttat acgggatccg acgcatccaa cagagcgaaa  37800
cagtgttcca ttcttttcgg cggcatcctt ccgcattggc ggcgagtgga gtgccacaat  37860
cccattcatc atttttgatc tacataagcc aaagcccata gcactggcga cgtctccggc  37920
ataaatgcaa ggaggatgta tagctgatat aggatcttgt ggaacaggat ttgattctgc  37980
aagcggttca gtacaaacga agaaatttcg aacaaaaggg tcggaactcg ctgataggaa  38040
aggagagaaa aacaaagcaa tgccaagagc tccgtcaatc cgctgttcat cgatagacga  38100
agctctctct ttatcatctc gtgccagatg caacatcctt tttccttctc gcgaaccacg  38160
ggagcgccta gcgcccagag gagcaaagct catttccctt tcagggtaaa gcggcgcata  38220
aaaaagggct ggcccgtcaa aagtccggtt ccttcgcgaa cgaagttcag aatcaacaag  38280
ggttcgtaga acgaagggag tgtataactg gggcgcagcc ccactttttt gttcgtaacg  38340
agggagagat agaatggagt tcttcacgaa gttcgaaaca aaggaataaa aaaaagtttc  38400
tctatggcct cctcgttttg agacattatg gcttaggggt cgaccccggt aacaaagaag  38460
gaatccataa aaacttagga tccaacacca tgataaaata ctaccctcat gattagacca  38520
tgtccctgag atttgataaa agaaaggtgc attagcggtt aatacgttgt aattggataa  38580
gttattagga atatgacgga acgaaagacc aaggaaagaa agaagaatac accaaaatgc  38640
aagtgctgca ccaaagactg gtggttgttt cttgttgtaa gtgaatgcaa cgaaaagacc  38700
cggaaataac gaataatgaa acaattcata tattgacatt tcgtgctcat ttccaaattt  38760
atgctttgtt attcccatca tccggtaacc acaggatgat ccacaagaaa ggtggcagga  38820
ttcgaaccta tggccggcct gcccctgacc tgctgggttg ggtggccggg ttagcacccc  38880
tcgtcgcctc tgtacccgaa acagatgcgc tgcgctaccc agcgcctaac cttgtctccc  38940
ctactcctct tctggttgtg ccattaccaa tcgcgggtaa cccccggtcc ggccgcccct  39000
gacctaagaa gaactattat ccttatgacc aaacaaggac cagcttactt acttctcgag  39060
cgatagttcc acgatcccga ccagcaactt cttgggagta ggggcatcaa agcttgccca  39120
acctagtaaa ggggcttggg gatagagggt tttctggggg agagaaagtt tccaggttgg  39180
attttttgag atcaaatagt actagttggg tagatagagg tggtgaaatc taacctttgc  39240
```

-continued atcgatcttc tttagcaggg cgggtcgctt gagtgtcaaa accaagcggt ggttgttttt 39300
ccttggctta tcgaaccagc gtatgcccat tcctcctttg atgactccca gtagagaaag 39360
cctaaatttt ccgatgtgga ttgaaaggaa gttggggatg gacatagatc cttccgccta 39420
tccggagtgt tggaaatata gcaatgtttt ttgtattttt gatttcccga tcattggaag 39480
caatcttcac tggcacaagg atctcctcac agcaacctcc actacgatag aaaccgacaa 39540
tgagtttacg aaggcttcga gtagtgcggg ataggctaat caccagactg ctctggaata 39600
ggttaatcgc tggagacaag aacgagtgaa tctagtttcg agagcatgcc ttactctaat 39660
agggggcgta gagtttctaa gtgaaggcaa gcgctactat atatgtaata tcctagctgt 39720
cagcaaggca ggtccgctat aaagcctacc ggccagaaag tccttaagaa cgagaaagcc 39780
gactaaaagg ctattccata accgactctt gttgccgagt cgagggggct tggctggtac 39840
caggctctaa aagagtttc ttcgagcgag cggtctttct atctttttgg gttgcatgcc 39900
caaggcaatg ctttttgtag attgagatgg attgatcttc gctatcgtgc ctcctccttg 39960
taccagttga tgctggggca gtgcttaatt aatatgagtt ttctcctgcc ccagacagct 40020
tcgaggttcc catcgatcga ttacagaggt ttctaccact gaacttgctt atgctcccct 40080
ttgatcgagt gctatttcta taaataagat tgagtaggaa aatgttgaat tggcttcaat 40140
cgagattgcc tcggcttctt aggcacatga ggaaccggcc taacatcttt tcaatcgaaa 40200
tcccaatcaa agacaagttc taccaaggcc aggatctgaa agagaggatt cactttccga 40260
aattccaagt gacatgattc ctccttcaga agctaaagtt gaatgatcga agtctccttt 40320
aggttcagtc gaagagatcg aagcgaagtc atcaattcaa ccattcgaat ggtctcccca 40380
aagattgacc tcttttccaa ataaaccgaa cctcgatacc agattcatca aaaagatatg 40440
gccatctctc taggttgcac aacccccttta gatcgttcta ttcgtgcttg aaaaacgacc 40500
ccatcggtcc gctcctttta atggacattc ttagccgtcc tccgagggtt aacaccccat 40560
agatcagatc gtgaactctt tcagaccctt agtttcactt ggttggggca gagtttcagc 40620
ctgccttcca ccgaatataa aaaaccttag agctgcctaa cctgctgaca tcccggcgaa 40680
gagagtcatt atttgtgtta catcttcgaa ttcgagagaa ggctttcctc ttatctctca 40740
aattataggc attgaagcga tcgagagaaa gtaagaaaac tattgcacac gccccccatt 40800
cgccctttac taatataata gaaggtaagg caaaagcaag agtgaaacta cgagctaaaa 40860
gcaggcgtgc ctctcttata agagaatatg ataccatccc ccacttttgg cgcacttctt 40920
tgatgagcta agcctaagcg ccatagaagt caaaagctag cctgagacct aaaaaagcaa 40980
ggtcgaaatc catccctctt tttcctgtat ttgactagta gggctaatga acgacccttt 41040
gatctatgtc gttccaagtt cagccaggtc tgattagaag ttcaaaaatg agtggagcga 41100
ggggctttag agggaaaaaa ggggggcgga gctttaattg aagtaggggc ggagctcctc 41160
atagagagtt agaaagcgtc agttctcata gcgaggctta ggccgacggg gtagggcgcg 41220
gccccccaat tctcaacccc gacctagaca agtggttttt taacccacat tttgaaaagt 41280
tctgttaggt tcttagtagc aatcggcgac cttttcctct tttacttcac atagcttttc 41340
gtctccttga tagctggaag ttctccaaaa gtatgaaaag ctggaggact ttgtaccatc 41400
cattccggtg tggttggatt ctgttcaaca gcccaaggac ttggagcaca tcttttgttc 41460
tttccactgc ttgaagtgat tgttacgacc acgaagaaac gacaaatccc aactacggat 41520
atataagagc caaaactgct aagggcattc catccagcgt aagcatctgg ataatctgga 41580
atgcgacgtg gcatacccga aagccctaag aaatgcatag gaaagaaggt catattaacc 41640

-continued ccgaaaaaag tgatccaaaa atggatttga cctaaagttt cagggtatgt ccgaccaaag 41700
attttaccta cccaatagtg aaatcctgca aataaagcaa aaacggctcc catagaaagt 41760
acataatgga aatgtgcaac cacataataa gtatcatgta gagcaatgtc tagcccagaa 41820
ttagccagaa ctattccagt gagtcctcct atggtgaaca aaaagatgaa ccctacagca 41880
aataacatgg gtgttttgta ttgtatcgaa cccccccaca tggtagcgat ccaactaaag 41940
attttgattc cagtggggac agctatgatc atggtagctg cggtgaagta ggcacgggta 42000
tcaacgtcta agcccacagt aaacatatga tgagcccaaa caagaaatcc aagaacacct 42060
atactgatca tggcataaac catgcctaga tacccgaaaa ccggttttcc cgaaaaagta 42120
gaaacgatat gacttatgat accggatcca ggcagaatgg gaatatacac ctctggatga 42180
ccgaagaacc aaaagagatg ctggtataat atagggtccc cccctccagc gggatcagaa 42240
aaggttgtat taaagtttcg atcggttaat aacatggtaa ttgcccctgc cagtaccgga 42300
agtgataata aaagtgggaa tgctgtcact agaacggacc acacaaatag aggtgatcta 42360
tgcatagtca ttccaggtcc acgcatgttg aagatagttg ttataaaatt aatagaacct 42420
aaaatggatg aaacaccaga tagatgaaga ctagaaattg ctaaatcaac agctcctcca 42480
gaatggctgg taataccact taagggcgga tagaccgtcc acccagtgcc gctacccact 42540
tctactaagg ctgggcttaa taggagcaag agacttggag gcaacaacca gaatgaaata 42600
ttatttaatc gtggaaatgc catgtcaggc gcacctatca gaatcggaac agaccaatta 42660
ccagatccac ctatcatcgc cggcataacc ataaaaaaga tcattaaaaa agcgtgagcc 42720
gttattaaaa cattataaag ttgatgattc ccaccaagaa tttgatcgcc gggtcgtgct 42780
aattccatac gaatcagtac tgagaagcat gtgcccatca ctccagcaat ggcaccgaag 42840
atgaaataaa gagtccctat atccttgtgg ttagtggaga acagccatcg gaccggattt 42900
gtcgtaaaat tgagattatt tcgtttcctt ccttatcaga gaggggcccg cggggcttat 42960
ttattgaaaa nnnnnnnrgg ggrgkgrggg gggaaggaag aatggaaagc cctcacttta 43020
ttgatgggac attttgatcc ccttttcctc tcatcctccc ccggttctgg ttcaggaaag 43080
ggtcaacgca aggatcttat ttcgaagcaa tctctggagt tttcccttat ccgaacgggt 43140
cttgcaagaa aataggattt catattgagc tccaaatata cgctattggg atgggatggc 43200
tcctactagc tctccccccc taagaaccgc acgtgcgagt tccccccgcat acggctcaag 43260 tggcgaaggc cctttccttc gcgcttggta agcgcttcgc tgtagccaag cttactgcta 43320
gcctatcggc tagagccaag cttcgaccgc gactgctcgt cgcttctggc cgccttattc 43380
cgtcacccga gatccaagtc agcaccggca aagatctctt gattcctcgc ggtcgggccg 43440
gcttggaagc aagctacctc ttgcctatct cacctccttc cttcagctgg gtgagccttc 43500
gctttttgga tcgtcttctg cccaatgcgg taccccccgt tttttggttc ccattgggtt 43560
taccttgttc acaggtcgac cccatggcag caagaaaagg cgatcttgtg ctatactccg 43620
gtgatctctt tcctaccgag acacgcaaac tcccatcgtg tcccagatca cattccgtga 43680
atcgaaaggg gaagcctact catctatcag ctcctctcgt agatcggtgt ggttttacga 43740
agcgtctaag cacagttcac tcgcgttgat caatcaagag ggttgccgcc actccttaag 43800
gttatctgtt gtatcataca cttcttgcat tctgtcccac gcttcatacc tcctctttct 43860
tcttaaggta agataaaggg ccaggcatgg tggggtagga gcatccagtc ggcaatcttt 43920
ttggcttgac caagaagtct tatgtcctcc gagtcgcacg gcgttttaac cgaaagaact 43980

-continued

```
tcttgcgcaa ttcatgcctt tctgttttta tgaccagaaa ttctttcttt attttcatat  44040
aaaattgttc tctggacttt ttatcaatat gaggtgatcg taacacagta tataagactc  44100
gtgattcagg caatccaatc ttccgtgtgt aaggcggaag cccccaaaaa tggttttcaa  44160
aaaatgggtg atcaaaagat cgaattacta tgcctatctt ggtggtcgtt acttttggtg  44220
gtctttcttt ttggctgact cctatagacg aagtgcttcg tttcagatca attcttcgct  44280
gcaatcgctt cgatccaccc cctcggtgaa aaaccgtaat acgccctgag gaattcctac  44340
cagcagactt ccctgtactc aaagtgaatt gtctaagtgc tctcctttgt ctcattgttt  44400
atctcgtaat cattcgattc cgcccctaaa gctagcgcct actcctcctc cttctcctcc  44460
tgaatcctcc ttggtccttt ttacataaca ctctcggccg cccaagagga ctggctatct  44520
ttctctttat acgcacaata tcttgaaagg caaagaaaaa gatctacctt ggcaacgaag  44580
acgtcattga ctgatagttt atcttccgaa ccggttaaat acctataaca aaaaaaggcc  44640
aaagcccgct gaagcactgg aaaaatgttg accacgattt ctaacgcttt tcaaaaacca  44700
tttgcttgca acgccttgag tggacagata attacggcca ctagatcctt catactctta  44760
ctaaagtaca cttaagactc aaccaatctt gaaagtggag tggacaactg gcataccttg  44820
aatctagcct gcaatccttt cgcacttctc ttatcaaatt tctagttaga gagagagcta  44880
accgctgcca aaatgcagca gtttttctta tatacgatag cacccccctgc cctccttgtt  44940
caagtagttc aagagtgaaa gggcgtagtg aaagaaggga aagatctctt tcaaagatat  45000
tctacccata aaggcagttc tcttatatgg caatactaga ttggcgagac aagagagaaa  45060
gcttataaag tagtaaggtg tctatggggc ttgccttaca ggtagtgact ataccactta  45120
catatcgaac agatcttact ctcaatggag tcatttcgat atgacctagg aacttacaga  45180
ataccgaact tggataatcg gtagaagaat gattggctag atcatttgct tcactgcgga  45240
agaacccctt tctacgctac gttcccaata aaaagccgtc atccttctgt cgcctgttag  45300
ccacaccaga ccaagaaaag gcaaactaat caaccaagac tcagtcacga cctttgtaac  45360
ctcacggcca ctttctttcc tagagcttgc agccattatc ttcgcttttc agatatggtg  45420
acattacttg tatgggggga agtgccagat ctttacggat cataagagct tgaggtactt  45480
gatgacacag aaggagttga accttcgcca ggatggcaca cttctattcc ggggacgagt  45540
atgtgttcct caggacagtg acctgtgcca tgatatcttg gaggaggcgc atagctcacc  45600
ttttttcctg cacccaggga gcacgaagat gtacaggacg atccgcccac actattggtg  45660
gaaaggtatg aagagggatg tcgctgagta tgtggctaaa tgcttagtgt gccagctggt  45720
taaggctgag caccagagac cagcaggacc cttacagcca gttcagatac cacagtggaa  45780
gtgggacgag atagccatgg actttgtctc tggattgccg aagactgcga ggcaacatga  45840
cgccatttgg gtgattattg atcggctgac caagtcagct cacttcctgc cgatcagtat  45900
gacttactct acgggcaagc tagcccagat atatattgat gagatagtgc gcctacacgg  45960
gataccatca tccatagtat cagacagaga tccacggttc acttcagcct tgtggcagag  46020
cctacagaag gctttgggta gcagagtgag tcttagcaca gccttccatc ctcagaccga  46080
tggccagtct aagaggacca tccagacatt ggaggctatg cggaggtaat cccttgattt  46140
tcgaggttgt tgggacagac atctaccctt ggtggagttc gcctataaca agagttatca  46200
ggcgagtata ggcatgccac cttttgaggc actctatgga cgcaagtgca ggactcccct  46260
atgctgggat gaagtagggg agagacagat tcttgggcca gagattgtac aggagacctc  46320
ttccttcggt ccggttagta caaggttctg tcgtttacct tgcgcctatc tattccttta  46380
```

agcttatatc ttataccatt gcaatcagac tcattggata tcttcctttt ctcttctact 46440
atcgagagtc gtacgggtga ggaggtgagc tctaagcgta tacacataga taggtctggg 46500
taagcgacca tcagcggtat gggtagcagc tactatcagt acgccagtct aaggctgttc 46560
gtagaggtag gtcgtagaga tctatgaagg gctatattta gcataaatag catggttaat 46620
tatagaatag cgtgatggcc gtaagaagat cataaataag gtaaatagtc tggagtggat 46680
gtctagatca gggtgtcggc atcacacata tagcatgtgt gccgtgagtg agagggtggt 46740
cgtagatcag ccctcagctc ttctttcgaa attctcgaac atgatgactt atcggcttga 46800
ggcttctttt cttttcaagc tgagtagaaa tttcataaga gaagaaaagt tcacagaagg 46860
ttcttcaata gtatgcctgg ttcacgaggt tctaccactg cagggcccag ttgccattcc 46920
cccattactc aagtcgtcca agggacagga cccccgcact gtaaaaagtt tcctttttat 46980
acaactcatg atatctttct tctgtgcata tctcggtttt aataacttct gggtttatac 47040
caaatcgacc gtagagagag ttcattagta tcttgtagat atataccata gctgcatcat 47100
cctttatctt tgcttcttgt cttctagcga agatgtctga tacaaagcct tcgaaaggac 47160
tcttcttttt ctcatacaag tagcccctta gcgggaaaat tctataaccc aagtttcggg 47220
cataaaaaaa ttcttcgcta aaatagacgc ctacgaattt acctgttggg aaggttaaag 47280
cattatgtct atccttatag ggtaagaagg ctttctctat tgtagagagg acacactaca 47340
aaagcctcaa taaagccaaa gaagttatcc aattccgcct tttctaaatt attatgccag 47400
acgggtacac cccctggcat cggataagtt ttcattataa atggatataa ggagttcaca 47460
tcgtaatagt ctaaattttc accatagggc ttatagacat cggcatgtcc tccataataa 47520
ccacgccgaa tgaagcgttc ttggtttcga gttggtatat ggatgggcca actctttggg 47580
tcgtaatagt gcatacgaaa gattgataga gctagcgatg acaacgttat tgtatcaacg 47640
atgtctattt tgtacagatt ccaataaatc tcttgtgcct tcagcataac gccacctaag 47700
agacgaatat cttgtttcag ataagccaac aattgttgac ctatctccgg aagatactca 47760
agtcgtaatt tctcataggg aatggtgcct ttagaaccca atttcgggca taaatcctgg 47820
gccaagttat ttagcgcagc ggcaaggaga aggtaggaat ccccttatacg gaacaataat 47880
ttcttttttt catttccacg atagactttt aactcgtaca ttttatgctt cctcatcacc 47940
gtttggaagg agtacttgcc gatctgagaa ggaaaagctc tcgttactat aatgccatcg 48000
tatcgtgaaa agttatggaa atagaccgtt cgaatttctt tttcatctga taccacagcc 48060
gctaaacgtt ctataaagtc gagcatcata cgttcacttc gttttttgaa atcagatatt 48120
gagaaatcct tatcttcact gaaatatgtt tcaatataat attcagactt ggaagcaaga 48180
tcttcacccg gcttaaccac taagaacccc actgcgcaag gaacatgaac atcgtcgtgg 48240
agagcagcct ctatatcggc aacaatgaat gggctccttt ttattttatt aattgctttc 48300
agtgcgggta tatgatcggg acgacgactc ttcttaccca tagctaccac ttctacaggt 48360
tcatcactca ttgtcccgcc atccgttaat tcatcacaaa gttgcttaaa aatttcctct 48420
aggctaaaag ggtggacttc acggtgttca accctatcga agagatagat tcgaacccct 48480
actcggtcta gctgcccctc ttcgtatttc tcagcctttt cacagacttg tttcaaaatt 48540
tcattatata cacgaagcgg gggtacttct gcgttatcgg cctttactaa aattgcattt 48600
cctgctgtaa agtcggctcg ttcgttattt gtatgtatca gaccataatg gatagtgaat 48660
ttaatagaac gaaatccgct attgtatgca tattttatta acagtatcat taccgctaat 48720

-continued

```
gagataactt caatttcgac acatttaagg taaggttttt taaagcggaa ttctgctatt  48780
cttattgact caagggggct atgatatttt tcctcagcga tcaacttgta gagaaatcca  48840
gactggaact attgatgatt ctacgttagc tctaaagtaa ggagaccact taaaaaccct  48900
catcggataa gaaaagatat accagataga gcttcccttt gaggcatgcc tgagagcaaa  48960
gatagatgca ctctcttccg aagcggattc cgcgcttata ccttctccgg agacagctga  49020
ctcggactcc gttcctgcct tctgactttc aataaccatg cgcgtacttt aattaggaat  49080
gaaccaaaga gttaccttag tatagagaaa tggaagccag ggtcttctat aaataataag  49140
tatttcacct aggtgactcg ttcacctatc acgaataaat aggtgggtgg ctgcgtaata  49200
gaatagaacc tgctgaaact acctcatcca gggaagctgc ccggatttcc ttaagttaag  49260
tctttttctg agctgtctta cttaaggtgt taccagtctt taccctcttt gtatggcgct  49320
aaagcgacta gtctatgacc caattccgga tggcgtctca gggtccctgc tcacctatcc  49380
tatttattgg aggtagcagc cacaactgaa cgctttcaag cacagtttca ttacgtgata  49440
ttgagttctt tcagctctaa cagagctaag acttcggttt catcaatcct gtttcgggat  49500
cgaattcgaa ctggtccaat ccacgtactc catcgcaact ggttaaactc tcatgatcga  49560
tgtaattgag agaaatgcca ccagagctca tatccggcaa tggaggattg aactttcaaa  49620
gaactcctaa ttcgaatagg aaatgcctgg caaaggaaga atagttcatt ggacaaggtc  49680
gcgtaagctg aaaggtcagc agagtcaaca actacatcgg aagctttttc ccgaagaggt  49740
ctttaagtgc tcgaacgaat gtgagaggag tgaatgtggg aagtgaaaat aaatcctcta  49800
agaattccct ctccttgctc gcagcaagta ttacgctcgc tggatagacc tatttctctc  49860
tttataatca gcaagggcct cagcgtattg aatggccgtc ctgaggtcag ggatatcatc  49920
gccaccattt cgttgcgagc ccaatctttc aaccctctta tgaaatagaa cactttttcc  49980
ttctcagtta catcatccac atgagcaaga ttatcaaggt actccttgat atattctttt  50040
atggtgccag tatgctttgt atcaacaaag cgcattttag cctcaaagta agccgttttc  50100
ggatagaact gcttcttaag ctcacgcttt cactcgcccc aatccacgat agggtcggct  50160
atgccttcat cagcatccat tttcaatcta cgccaccatg acgctgcgcc atcttgcagc  50220
caatatgtgg cttgtttgat tttcaagagg tcatcctcta tgttttgccc ctcaaagaat  50280
tgctcgcatc cccaacgcat caatctctcg ggcatccctt gcgcctttat atggcttggg  50340
cttgggtgcc tccagcttgt tttgagccac agaaatggtg gtagagcctt tggttaggcc  50400
tagcaccgtg gtcttcaaaa gaccaagctc attctcagct gccgtcaacc gattcaaggc  50460
ttcagtcaaa tcagccctca gagagttatt ctcagccact aacgagttaa tcctcccagt  50520
gagagattca tttccctcgg tcacagtttt gccaagctct tcaacagtct ttcccaaggt  50580
cttcaagtca tcctccacgt cggagactcg gtcttcaacc ttttcctctt ctttcttctc  50640
gttcttggga ctctatttag gattgattga ttcccgttag gtggattggt tgctgcgcag  50700
ctaactacca accccgaaat tacgtacaga gaaagggctt gtggaactac ctttcttcat  50760
ggtcaggatt cactgctacg gcgggtagcc tggatctcat ggattagcca gaacagtgga  50820
gaagcaagga cctgctagct acatcttcag tctgtagtga ctcattcatc gggagcggag  50880
ggaattgctt ccccgtgggt cgtaaattga atatgcagaa accctgactt cctgtcttct  50940
cacagctctt tatccatcat gctagcgaaa aaagtgaaag tgcgacgggc tcctccatga  51000
gaaaagggat tccttagtat ataggatatg tcctttaagt tggaagattg gaaacccttg  51060
ggcgtccttc ggactttagt tagcatcgag ccctcttttt aggaagaata ggaaaagagt  51120
```

-continued

```
ttcaatattg aaacagcatt ggataaagga agtcttcgtt cattcaacgg cattaccgac  51180
cggcctaggc tcttcgggag cagagaatag gataggctgc tggtaggact ggcttgttgg  51240
gataggtcag gcaaattcct ctagtggaag gaatatgccc atagagaaaa agcctattag  51300
taagtaagat cgaaagagca gggacagcta gccctactcc ttctccttct cttactaatg  51360
ttaaatcatt cccttccttc tttgctcttc gaatggcgct tgccttgcat tctatgcatc  51420
ttatttacta ctagatgtaa tttccttgtc cgattcaagg ccatcaccag attcaatagc  51480
cggggattcc ttctttcgat ccatgtcatc tggcatacta gctctgacga cgagtcttct  51540
gttaattatt aattaaatct ctcctgcgaa tccttatcct tcaaaaagct tcttctcgac  51600
gcaggagatt cgtgaacaag cccatctaag agcctagcaa gcagccttta gtgcgacaga  51660
gagagcttcc aacaatacaa taaaagatct atcccatctc gtgccctgta agaaggaact  51720
tcatcagtcc cagagcctat tcgacgtcat cttccctgtc ctcttccgat tcaacctcat  51780
attactcgta caacaactat ggcaaccaag agctcggagt cgacaatagg aattaaagca  51840
tcatcaaaat gaagagtgag cactttttgt gacggaattc cttcgttccc tttctcaaat  51900
gcaataggaa gatagccttt ttttcgtaat agaagaaagc tctcgtcttc ttctagggct  51960
gtcaggaagt ctcgttcttt gttctttaca attagaagct cttcctttaa ttacaggacc  52020
agaacaatct aagaagaaga ggaaaagggg ctaaggttga taggtagata ggttacgtag  52080
ctcaacgaaa gcatatacat aatatctttt cttttctctt gcctacaaag tttttggcgg  52140
tatatcgtat ataaagaaga tcacggtttt aggagtgatc ttttctttc ctctcactcg  52200
aaatatcata agagaacaga aaggttttga ttcgaggttt ctagccgtct tcactgactg  52260
gaacccaaac caaataaagc aatggcgtct gtttacgtca gggtccgaag gaacgaagtg  52320
ctcgaccgga agggaagtag tatgtccggt tcactaggtt ctaccactgc agggctcaat  52380
catgctagtt gggctatatg cttaacacat gcaagtcgaa tgacgttttc ttggaaacgg  52440
gagtgaacga aggaccaacg acgatgaagg aggagttggg gaagacgcgg ggtagaggaa  52500
ttggtcaact catcaggctc atgacctgaa gattgcaggt tcgaatcctg tccccgccta  52560
atcagtggaa cactgttcac cgggatagaa ggccggtccc aacccgtcta caaaatgggg  52620
ctagtgttca gtcttggttg gttccacctc tttgcagggt gatgacacca gtagctgtgg  52680
agcacagatg accatttctt agactattga attccaactt agagctcctt ctactctaaa  52740
ctactgtgtg cctatttgga gcttttcaca gtcaaagtca aaggtttctt ggtggcaaga  52800
tcggcatgcc ttctagttgt agttgacttt aagcgcacct gaactaccca tagtcgtcta  52860
tttacgggct tgcactcaat agtcaatcaa ttcgtttttc cgctttctat cgcacgcttc  52920
aactatttgt ttatatagtc taactaatgg aaagtgccta tgaattagtt ccaagaaagc  52980
gtccgttcac gtcaggaata gaggccgtta aggatgtact tgcttttcct tttttgcgtc  53040
gagattgggt tggtgttcag tgtaccgctt gtctagccta tgctttgcaa gcctacatag  53100
ggtacaagat cgaaaagaat gcattggatg gatgcccggg cattgagaag gaaggacgct  53160
ttcagaggcg aaaggccatg gggagatacc gtctgtgatc catggatctc cgatcgggaa  53220
accgtatcca agctccgtgg ctagtctgcg ctctttggac ttttcaaact tagcgaactg  53280
aaacatctta gtagctaaag gaagggaaat caaccgagac cccgttagta gcggcgagcg  53340
agagcggatt gggggtttga agaaaaacaa agacgaagct tcgttcctca gcaaagtgtt  53400
cacttctttt tcgccaggtt tcattcgatt tgttgtggat tggatgatgg aaaaaccagc  53460
```

aagctacggc ttcaaagctt accttattta gaaaagggga aagggctttt ttatagatgt 53520
tgaggttgag taaggggggc ggagcttgaa gagcgaagcg agccgcgcta gcctagcaac 53580
gtttttcagc agcaagctac ggtctaacga ccccctaacc taggttgggg cgaaaactcc 53640
aaaatccaaa acgttggtta gggttccaaa cctttctcta agaataaggt aagctttcaa 53700
gccgccgccc tttaaaggag cgggcgcagt gaactgtaat tgtgaaaaga ttggaagatc 53760
tggccaaaga aggtgatagc cctgtagatt cgttcccatg gttcgatcct tcccagtaaa 53820
acgcggcgtg ttcgaattct gatcgctttt acgcgagaaa gggggaccac cctctaagcc 53880
taagtattcc tcaatgaccg atagcgtaca agtaccgtga gggaaaggtg aaaagaaccc 53940
tatttaggga gtgcaataga gaacctgaga tccgatgcga acaatcagtc gaaggagcgg 54000
agcttagagc ctttacttta tgtaaagcgc actcactcta acggcgtacc ttttgcatga 54060
tgggtcagcg aggaaatggg aacagcggct taagccatta ggtgtaggcg ctttccagag 54120
gtggaatctt ctagttcttc ctatttgacc cgaaaccgat cgatctagcc atgagcaggt 54180
tgaagagagc tctaacaggc cttggaggac cgaacccacg tatgtggcaa aatacgggga 54240
tgacttgtgg ctaggggtga aaggccaacc aagatcggat atagctggtt ttccgcgaaa 54300
tctatttcag tagagcgtat gatgtcgatg gcccgaggta gagcactcaa tgggctaggg 54360
tggccccatt tcgccttacc aaccccaggg aaactccgaa tacaggccta gatcgtttgt 54420
acagacagac tttttgggtg ctaagatcca aagtcgagag ggaaacagcc cagatcgtac 54480
gctaaggtcc ctaagcaatc acttagtgga aaaggaagtg atcgagcgat gacaaccagg 54540
aggtgggctt ggaagcagcc atcctttgaa gaaagcgtaa tagctcactg gtctagctcc 54600
atggcaccga aaatgtatca gggctcaagt gattcaccga agcgacgaga ccttgaaagc 54660
tgctttttca agtgtcagta gcggaacgtt ctgtcaatcg gggaaggttt ttggtgacaa 54720
gacctggaga tatcagaagt gagaatgctg acatgagtaa cgaaaaaatcc tgtgaaaaac 54780
acgatcgcct gccagtggaa ggttttctgc gttcagtcaa tctacgcaga gtgaatcggt 54840
ccctaaggaa cccccgaaag ggctgccgtc cgatgggtac acgaaagtga cgaagttgct 54900
ttgactacag aaccatgcct gtctgttgga gcgaattgga tgatcgggcc gagggctgcc 54960
ccctcttccc ctcactctcc tttccctaat atgaaccttg agtcatcaaa gcctttctga 55020
ctcggcctgg cccggtcgcc ctacgcgact ggcgcttcaa aaggcgaaac tctcggtcgt 55080
agtttggcga cctatcttca gtaggggcct ttagtctttt gattagagta ggggtcgcga 55140
gagagcagag cgtaccgccc tgccatagtc acgagtctgt ttatagtcgc gactgttgtc 55200
atagtcaaca aggttgaaac ttccaggaaa aaacttcgaa ttgggagggc gatcctcccg 55260
gtgaactgac cgtaccccaa accgacacag gtgaacaagt agagtatact agggcgcttg 55320
agagaaccat gtcgaaggaa ctcggcaaaa tgaccccgta acttcgggag aaggggtgct 55380
ctcctatctt ttgattagga aagcggcaca taccaggggg tagcgactgt ttattaaaaa 55440
cacaggactc tgctaagtgg taacacgatg tatagagtct gacacctgcc cggtgctgga 55500
aggtcggaag gagaagtgtt ataagctttg aatggaagcc ccggtaaacg gcggcagtaa 55560
ctctaactgt cctaaggtag cgaaattcct tgtcgcataa gtagcgacct gcacgaatgg 55620
tgtaacgact gccccgctgt ctccgacatg gacccggtga aattgaattc tccgtgaaga 55680
tgcggagtac caacggctag acggtaagac cccgtgcacc ttaactatag cttcgcagtg 55740
acaaccttaa tcgaatgtgt aggataggtg ggaggtggtg acacacaacg accaatcctg 55800
aaagaccact ctttcgtcta aggatgccta accgccgcac cgatcattcg gggggaggcg 55860
ggacactgcg aggtgggtag tttatctggg gcggatgcct cctaaagagt aacggaggtg 55920
tgcgaaggta ggctcaagct aagattctgc tcgtgagcgt aatggtataa gcctgcctga 55980
ctgtgagacc gactggtcga acagagacga aagtcggcca tagtgatccg ggagtcccgt 56040
gtggaagggc tctcgctcaa cggatcaaag gtacgccggg gataacaggc tgatgactcc 56100
caagagctct tatcgacgga gtcgtttggc acctcgatgt cgactcatca catcctgggg 56160
ttgaagaagg tcccaagggt tcggttgttc gccgattcaa gtggtacgtg agttgggttt 56220
agaacgtcgt gagacagttc ggttcctatc taccgttggt gttaaaggga gaactgcgag 56280
gagccaaccc tagtacgaga ggactgggtt gggctaacct atggtgtacc ggttgttatg 56340
ccaatagcag cgccgggcag ctaagttggt atggaagaac tgctgcgccg cgggaaatcc 56400
ttctctatac aagttctcgg acgaggtttt tgaacagaac ttcgataggc gagaggtgta 56460
agcaccgcga ggtgtgaagc gatctcgtac taaacgaaac gactttcact ttccataaca 56520
aaaatgaaag aaagtcaacc tattcctgaa attgcggtca gtctcgctac ctctttagtt 56580
gccgcccccct acttgctcct ttctctaata ataaggtagc cccaacctat acaagggggt 56640
cgttagaccg ccgcttacta agcgctggtt ctatcccggc caagcaacca aagccgggga 56700
cctggcaaaa taggaagcag aaaaccgctt ataccgagtt ccccaacagc agcttagctt 56760
agtaacaaca ctctttctac cggcggcgtg gccctgctgg atgcatttga tcaatagaac 56820
acgaagagga ggaagaagaa aagaagcttt gttatgaaaa agtttccatt tctttcccaa 56880
ataataagaa cttttggtgc tgtagtcact tttgcctttg gacgttttct ttttttcggg 56940
gcagaaagaa cgatcgcgcc tagctggatc cttctctttc tcttttgtct tatacttatg 57000
attcgggcaa aagaaagaac aagaagaaaa aggagtgtgg ttcatttttt cgttgagttc 57060
ttcctccttt ttctttttct ttcccttctg cgcctactca tcatggacgg gatttcttcc 57120
tttctaggcc tgaccctggg cctgaccact tcttttgttt cttatgtttc gtctggatcc 57180
aatgaaagtg ggaattcggc tcctgaatca gggggtcctc cccctttaga atccgagtcg 57240
agttcggcgt cacttaacac ctttcgaaac cagatcgctg cggataatga agccgatata 57300
tatcggcgca tacaaatttt agaaaaccag gaatactaca accttcctcc ccagaacagt 57360
cctggtgact acgaaaggct ggttcgcgag aacttcgatt cagccataaa tgtcaatcat 57420
tttcggacga tttttgatag ggaatacttt gaccttcgag tcttagagag gaagggcgtc 57480
gtacaagacc aactccaaga tctaatgctt cgggaggaga atatttcaca gattctagag 57540
aaatctcctt attcgaacat taggaaagaa gcctattact atcttgagca caagctcaac 57600
cccgttagcg atccacgcca tgcctttcag cgagacattc ttgacaccag tctcgacttc 57660
tttcaacgag atttgaatct gagaggcaaa gattcaacca tttacaagga gtttaagacg 57720
tattttatgg acgaatgatt gggaggagta gtcttcttga cataaaaagt caagagggcg 57780
aggcccctag caatgggggg aaaggggagt gggtaagggg gccccctttca cttgactgct 57840
tagttaggag tgatcttttt tcatctccac tctttttcct attcaataag agagcaacta 57900
cgattgcgac aaccatcgca tagctattca gagttgcact cggagactta cgattcctcg 57960
aactcgctga acactttcta tatctatctg tcttcatcga atttccgcta tctgtcttga 58020
gttagacaag cacaggccta tcttagctcc cggtgaccgg cttcgcgaga ccttttcgct 58080
ccacactgga gaagtcctct ctcgggctag gctctattgg gcggaggatc acctttcttt 58140
actagaggag caggaaagaa gagacttaca tacgtaattc tagaggtgaa ccagcttggt 58200

-continued

```
cggtagaatt ttttcgaatc tagcaaaagg aaggaaatga tgcttttctt aaggcaatcc  58260
ataagtcaga aatagaatga ggaagagaga ggaccccacg gaatggtatg tgggccctcc  58320
tcaagcaatc ccctatgact caacctttgt tcttgtgcaa aagcgtcctc cccttccttc  58380
ctgtttttcg agctcactaa ggcaagcggc gccccatttg tgtctgtctg cgatcgtgcc  58440
tagctgggca gttcatcagg agctgctatc tgggaccaag cactaagcac tcttgatttt  58500
ctttcttaat tggtttctaa caggattggc aaatgtcact gtgcgtaaca catctaattg  58560
gaagtggaat gaagataatg cgcttgactc tttcatttgt agctggatta ccccttgttg  58620
ggttgggcta acttaacttg aatctgttct gtttagtttt tcactaagcc tcatctgagt  58680
gctatataca tagctccttg attacttatc aaataaaatg aacattcttt aagaactttt  58740
tctcccgatc ttattagctt agtagcatgg aagtcacaat agttgtagca gagtaagcta  58800
gaagatgacc aatcccgccc catcatgatt ggtgtcgagt ccattgtgag aggcgcttaa  58860
aaggccgtta aggcattaga ctcaggggtg aacccacagg ggaggggaga ggttgcttcc  58920
tatcctaaaa acaactggct ttggctcgtt gcctttgatt ccttacccat agcataagat  58980
aaagggtgcg tgcttcaaca tctaagtttc acacaaggaa cctcctgctc ttaaggataa  59040
actacgatat ttgatggact gacaggtcag ccacgtaatt tatccctcaa gctgaacgaa  59100
cttgacctgc tcctttattt agtttagggc tatagagttt acttgcttct cactaagggc  59160
agaatcatga gcttcatcac tcgactctaa accaaattaa aaagactcgg ctataggatg  59220
acaatccttc actccggaag ggtaggttcc ataccgacaa gacctcctat cccagaatcc  59280
gctcatttca caccaactaa agcggaactt aatcaccaag gtagagttgt ataaaaccct  59340
aatgtaactg aacgaagtgg aaaacccgca atacgagagc aaaaaccttc tgtgtgtaag  59400
aagaaaagca acatcgagtt aggtaggatg tagatcgagc gcaataagct acaggagtta  59460
ttatttcgct ttggaaggaa aaaagcatct caaacaattt cattgcctca ctcagctctc  59520
aggctgtctg ggaatagctc caccagacat agaagaaagg agtataggat tggtaagctt  59580
tgccggaaag aagctactcg actaattcag gaggctacta ccggcgaagc ccgcttgctt  59640
cggagcgtgc tattgcgtga agcggaaagg gacagcggaa tctaagacca caccagacag  59700
ggaaaaggag gattagatat ttcgtcaacc accacttgag cgcgattcgc ttatctgttg  59760
aaaagtacca tccagacagt aaacctttag ggcatatgac tagtaaggta aatcaaccta  59820
tcgtatcgac gagatgcaac agaatcaatt accagacgga ctggctttcc aatttctctg  59880
tcctaacagc gttcgaagcc taacatcctt gcaagctttg gattctttcc tatctctgac  59940
cgggaaagag gttaccaagc aagtgaaact gaagtgaaac tgtactcgcc tcttctcctt  60000
cttgtcctct tgtacttccg ttcttcttat tctcgtatcc ggaaccggaa caagctcttc  60060
tttagcagcc tcgctttgtt agcagtacta gtttgtactc tttattgacc tggaacacaa  60120
gctttaccag ccaacccgat ctgaccttcg aaactctctt ctcatactcc tcgttcgtcg  60180
ttccaggcgt actccagtta gctcttctct tacagagcct tgtctgttcg attgctttcc  60240
tagtcttctt cctgcttcat tagataaagc gtcttcacta atagatagat aggattgttt  60300
gcttcaaagt gtctttatat caaataaagg cccttgaaag gggatgaaac tcttatttta  60360
acgcccaaag ataggcctct gcagcccttt ctaatgaaga tgatgcatag gaaaggtcct  60420
atcgaaaagg ctgttgtcgt catttttgct ctttgcatct tccctgaccc ctcgtcactg  60480
ctttctgatc atgtctcttt tcgaatacgc gaaaggaaag gacaaagtga gggctgcttc  60540
ttcgcgtcag tagttgaata tgaatgaaaa cacagaaaat ccaagtatgg ccctagcaac  60600
```

agttctaaag gcagttgaaa gaccgtaagc caggcaaggg ttaggggcaa gctcccataa 60660
aaaacttcta aaggagagag ctccggaggc aaggcgaaag gcatgcactg ggtaccgccg 60720
aaacgaatag ctaacatagt tatcccggtg attttgcccg aagagtttag ggcagagtct 60780
gattatgctc ctccaacagt tcacgccaaa cgttgtactt cacaaaaggt agaaaacaaa 60840
gaaccaaatc ctgagactag ggtgatatgc ccactctcca gaaaaaagaa gaggtggctc 60900
atgccggtga aagaagcaaa aaaagaaaag tctgattcct gatccaaaac cggtttttg 60960
aatgaagtta gaaagaagtt ctattgctcc ggaaggaagg cggtaggtgg gcttagataa 61020
gaaatctagg aattttttct atatatcaat ccttcgataa agcaagagac gactataaaa 61080
aaaactgact tttccattta ccggaagaaa cgtcgtcaaa ctgagcgtct gaataaaagg 61140
actcagtccc cgtgaacggc ctaatgtccg ccgcctctag ccgatgcgca ctataatgag 61200
caaaaatgct ttcctttctc catacctcct accctctgaa cttcctggat tgagctggtc 61260
caaagtgttt ccggcaaagc taggaacgtg cgtcaaacct ttcggccccg tgttaaccac 61320
ataaaagaga cgattcattc tattccctcg gttatatttg actaagaccc agaggatatc 61380
ctaaagtggg cattcgggct catccctccc ttcacggtcg cagtcctctt agccataggg 61440
ttttcttgct cgcccgtaac tcctctgttg gcattggttc attttcggta tggctactga 61500
ggatttgatt caattcataa acgaagctcg caggatctaa agtggagtct ggctacaagt 61560
cgagttgaaa tggaaagaaa aatggactca acctctcaac gaaagagaga cgcaggtctt 61620
ttcacggctt cgttcgataa agcactcaaa ccaacgagta aggaaaggag gccttgagtt 61680
gatatttaaa agaaggagtt cgtcctggtg tgctgcttcc tttcctgcca ctactttttg 61740
agtcaaaaag tcctctattg gtttaattca tattcaagtt tctctagcgg aattagactt 61800
tcatttctat ttcttcaaat ccagcatgac atgtgtcaag aagcgaccca tcaaagaaaa 61860
gttagaaaat cctgttttgg cgaattcaat gtttccatat agatgacctt ccctccggac 61920
aggaaatcat atattgaata gagggtactc cacctctgta gaggatacaa cacattgaaa 61980
taaaggaatt ggtggatctc tcccatcaga cagatcaacg gcaccgggca tgggatacac 62040
aggcaggaga gccgatttga ccgcgcagac caaatgagcg aaattttttt aaagcgaaag 62100
cgctgtgcca acttgcgtac aagatttata tgtggatttg atacaatagt caaatcctct 62160
tcataagtcc tttcttacag gctattcaag gtctattggc tttcttgctt atgcggtact 62220
tcgaaggcta agcctcgttt atgcaccgag aaagatcgtc ggtaggaaag ctctgttatg 62280
caccaacgac ggccccttct ctttaccttt cccgtgccct acttcattcc tttgctggct 62340
tgaattccat ctcttttctt ctttgtttga aaatggcttc aattgatttc tttcaggccc 62400
tacttgaaaa ggttgggttc tctgtggggg gtcgagccct ctcctttgca ttatgtaagt 62460
tgggctgctc cagctggatt gcattagaaa tcgcttttgc tgtgcgtggg attgccgggg 62520
aaccccccga tttggctcat tctatgttgc ctgggtcctc tcaccaaccg cacgaacctc 62580
aagatgacga agactcgccc tcttcgagaa aaagaagaat ggatgaggat cgagacgggg 62640
atgtcggccc ctcctcagta cgaagaaggg tgggttccag agaggattgc gccaaccaaa 62700
gctttgactc tgagagtgag agttggcgtc aatctcacgc cttgtcatca gataacaaag 62760
tagatttcgc cccagaaccc tccgcagccc ggggcccccc cttaggggag gccgaccaag 62820
agcaaggaac ccccggcgcc ggcggcttag gcacttctga cgcgcggacg gggaaagatc 62880
ccttagaaag tcaacaatct ttttctgcga gtgaaaaccc taaaaaaaaa tgcgaaggga 62940

-continued

```
tccttatgct caattagttg aggacgcaca acaaaaaact atcaaaatcc agggtgtaat  63000
agacgaattg gaagaagaaa cgtcttccat ggacaatgtg gatgagatca taaggaagtt  63060
ctcaaataag ctaagaatcc aaagttcctc ttcctcctat aaggaaggcg attcgccgac  63120
agaaccagaa tgaaccgccg ccgtgaaaga ggtaagaaaa gagtttgcaa tgtcgagaat  63180
gaaacttatg atcttttagt tgagggcccc ttcacttgag ctaattccgg ctttccagcg  63240
gaggctgcaa agcaaaggtt aagatactaa cccacggagc ggtaggctaa gcgggaaagg  63300
gagagagtgg agttagatcc gatgccattg attctgttgg aggaaggtca gcaggaaaga  63360
gaattgcttt tgttgaagaa gcaacaataa aataagctct tgctcaccga atccctttca  63420
ggtgcagatg aatatgctgt ttagcttggg actagggctt atgatccttc tcttaacggt  63480
agaacaaaaa taacaaagga gctctcctaa cctaagcaag ccgcggagtc gtagaccatt  63540
gctttaaaga cgggatggaa tctttctttc tgatcctaag ctgtgaactc atggtcaaat  63600
ggcttccgag gtgggctttc ccttctctat ggtagtactg tgaaaacgga gattgcttgt  63660
cctgctcgag ccattaagga gggagctgag ggagaggagt ggctccttac gctgggaccc  63720
cttggctcta gttattggtc ggcagagggt gcttgggatg accgggatta gtggattcct  63780
tttttttatg cttttctttc gtttcggctt tcctgcagct cttttcccga tctctttttc  63840
ttcattaaat ttacaagccg cagacatata gccagggagt gccatcccta aaaaagaaaa  63900
aaatcactct tttagagcta tgacttactt agtttaatcc tactagaaga gcagtgagtg  63960
acctacattg agtaggaata aggcaatatc ccctctaagc ctaggagctc ttggaggcat  64020
tacccccatc acattggagt tgacggtccc agtcttttct gtttgcgtag gagttcttcc  64080
tcttgctcca tcgaatgcac tgagaaaagt agctgtgagg aataaagagc gtattctgtg  64140
gcatttgatt ccattcttgc taacagctga ttctatagat tctcgaacag cgggtacgca  64200
aacaagggca ccaacggata ctgtcacacc ggttacgaga acagctataa gagtaggagg  64260
gaattcaata ccaattgaag ttttctaaga catttgggat ttgtcttgca aacaagcctt  64320
ccctccctca catctgattc aatagcactg gtaattcctc caacaccatc caccgcggat  64380
acgatagatg attctatgcc atcctcttcc cttcttgtct atctccttcg atcagatagt  64440
tctgcttccg gtgccggagg aagggtagtt tcagagttcg agatgtctga gcttgggggt  64500
tccgcttctc taatgttata ataaagctgc ccagatcttg cgtcttcttt tgctggctag  64560
atgcgtaagt caaggttcac gcttgggccc ttgacgagta ctttgatttt agttagacca  64620
taggtgctaa agggtatagg aagatattac ggaggagtgt catacacatc catcggcaaa  64680
tgcggataga gtagcagatc aaaatccgga agcaggggtg ggaggatcat ctgaccctag  64740
catgatcctc taccggacca agctgataga gaaggttgga ccaatcgagg gagggagtga  64800
ggctttcaac cggaccgggg gggggtcggg tagagctgta tttgccgagg caaggttgga  64860
ccggaatcaa cagagattgg tgctgcgagg gcgaagcgaa aataactccg tgccgcttgc  64920
tgcgcgaagt caaacttcgc gacggaagca agaaaagaaa gaaattacga cttcaccaac  64980
cacttcggcc taatcatccc acttctttcc tcaatcccaa taaaggatat cgatttacga  65040
taaccacttt cgcccgatcc aattcacctc catcgaggca gcgaactagt agatcatctt  65100
tcctgaggaa tggaaggatg gagtggtatt cgaattctcc ggctacacga tgagaaaaaa  65160
acatccgtga actccttatt aagactttct tctatctgct acttaattaa gatgaaagcc  65220
actaagaagt gcatcttgct tggacgttgc cgaagaaagg gctattagat gggcgattcc  65280
cccctttcca ttgaaatagg gaaagcggga tgaaagctct aagcccgcat cttcagcttc  65340
```

tattagaggg gctgtggatc caatccattc gaagggggag cagagcagca ggcaggcaaa 65400
gcaggggaag agatatggat tgcaccgaaa gcaatgccct tcggagcgca ttgcttgggc 65460
taagtcaaag ttgctgatct ctttttattg tattctcttc cttgggaaac aaacctccca 65520
catcatctgc tgtctcgcat ccatcgggat gagtcttgcg tctgtcttat cttcccctaa 65580
ggtctattgt attgaaaggc catctctcga atccgagcaa tgaaaggagg aagaaccata 65640
tagatattca gtaatgaata cgatgtggat ccgttccaaa gcccctaatt caaaatatag 65700
tgtgaggggg gcagagcttc catttccagg gacaatcctc cgcctcaggg cgttcttttt 65760
tccaggaatc tgtcaatcgg aggagcgcaa ccaagtttca aacctcaaag cccttcaagg 65820
gatgtgaagc ccttctcaat gtcttccact cgccaggagg caaggggaat ccgttgattg 65880
aatccattcc tgatgatgtg ccgctaacaa ggcctaccta ttctcccaat gcaacccggc 65940
tttttagggg catggcattc aatcctatct caatatatgc tcctccaagg cctgagggtg 66000
gattgaatcc aatcccatcc agcataggcg ggtagagttc actcatccgg tagttagagg 66060
atgatgaaca atgatgctat atctgctcac ctttcctaat ctgccttgtt gtgatagggg 66120
gcttaacggc ccaccaacca atctttcttt ctatctcgaa ttcttgatct ttggtgccag 66180
tggagcaaag gaagcggggg acgaactcct ctatttaccc tagaaatggg ttggatctat 66240
tgaatgaaat cctggagaca gggctgggag gtatgagtcg atcggatgca gggaagccca 66300
ggcaatcttt tcctatcaat cattcgtcag gaagcagtgg agaaagaatc gtcttttgaa 66360
atctcattgt tgaaggcgta gagagggctg aaaaaaaaat aggatcattt ttgatagcca 66420
tctcgttaat caaaaattgt gtaattaatt ggacccctct gcccggcagg caatttctgt 66480
gcaactagac tttctctagt ccctgctatg ccagcaatag ggaatcctta gaaaagcgga 66540
atgcaagttg cgtgatagtt ttattcccca caaatgagaa gtccccaagc ttgacccctc 66600
ccacacaggg gcgactggct ggggccctgg tggatttctt tctcagttaa taaatgtctg 66660
gaatcttggg ttactaattg gtggaatact gggcaatccg aaattttttt gaataatatt 66720
caagaaaaga gtcttctaga aaaattcata gaattagagg aactcctctt cttggacgaa 66780
atgatcaagg aatactcgga aacacatcta gaagagtttg ggataggaat ccataaagaa 66840
acgatccaat taatcaagat acaaaatgag aatcgtatac atacgatttt gcacttctcg 66900
acaaatatca tctgttttat tattctaagc gggtattcaa ttttgggtaa tgaaaaactt 66960
gttattctta actcttgggc tcaggaattc ctatataact taagtgacac agtaaaagct 67020
ttttctattc ttttattaac tgatttatgt atcggattcc attcacccca cggttgggaa 67080
ttaatgattg gctctatcta taaagatttt ggatttgttc ataatgatca aattatatcg 67140
ggtcttgttt ccacctttcc agtcattctc gatacaattt ttaaatattg gattttccgt 67200
tatttaaatc gtctgtctcc gtcacttgta gttatttatc attcaatgaa tgactgataa 67260
aggatccgtt gatattaatc taatccaatt agaatgcttg gtactttgta gttgtacata 67320
agcaaagtat tgaaaatcgt atttactctt tctatttcta accatcgggg agattcatcc 67380
tatattattc ctagattatt ccagcaaata gcagaatcgt ggctagggaa ctatattagc 67440
gacctaccca atttattgta gaaattttcg cgatcaatga ttggaccatg caaactagaa 67500
atgctttttc ttggctaaag aaacagatta ctcgatctat ttccgtatcg ctcatgatat 67560
atatcttaac tcggacatcc atttcaagtg catatcctat ttttgcacag cagggttatg 67620
aaaatccacg agaagcgact gggcgtattg tatgtgccaa ttgccattta gctaataagc 67680

-continued

```
ccgtggagat tgaggttcca caagcggtac ttcccgatac tgtatttgaa gcagttgttc  67740
gaattcctta tgataggcaa gtgaaacagg ttcttgctaa tggtaaaaag gggggttga   67800
acgtgggggc tgttcttatt ttgccggagg ggtttgaatt agctcctccc gatcgtattt  67860
ctcccgagat gaaagaaaag attggcaatt tgtcttttca gagctatcgc cccaataaaa  67920
aaaatattct tgtggtaggc cctgtccctg gtcaaaaata tagtgaaata accttcccta  67980
ttctttcccc ggaccctgct actaagaagg atgtttactt cttaaaatat cctatatacg  68040
taggcgggaa caggggaagg ggccagattt atcccgacgg cagcaagagt aacaatacag  68100
tttataatgc tacagcggct ggtatagtaa gcaaaatcat acgaaaagaa aaagggggat  68160
atgagataac cataacggat gcgtcggatg gacgtcaagt ggttgatatt gtccctcccg  68220
gaccagagct tcttgtttcc gagggcgaat ctatcaaatt tgatcaacca ttaacgagta  68280
atcctaatgt aggcggattt ggtcagggag atgcagaaat agtacttcaa gatccattac  68340
gtgtccaagg acttttgttc ttcttagcat ctgttatttt ggcacaaatc tttttggttc  68400
ttaaaaagaa acagttcgag aaggttcaat tggccgaaat gaatttctag attcgcagat  68460
ttatcgacat caagttcgta aaaagaacca aattcttctt ggcgattatt tatgatcaaa  68520
aaaataaaat tatgaaaacc cctttgtctt atttatactc ttcgccaaaa tctacatact  68580
atgtggtaca aaggattccc agcgggaatc ccgttgagtt cttacgattt catgttgaca  68640
actcaattca ttcgattact acagggatga acccaatccg gaatatgaac cataaaagaa  68700
aatacctact aaaccgatta caagaatacc agctacagta cctattatcc aaagaggaat  68760
ccttccagta gtatcggcca tttaccccac ttccctccag atttcatcaa gtggtcatgc  68820
tagagacata aacagtcatg gataatttaa ttatgagatc cttccgaatg agctaagaga  68880
atcttattta ttctctttca ttttcttaat tgaagaaata attggaaaat aaaacagcaa  68940
gtacaaaaat gagtaataac ccccagtaga gactggtacg attcaattca acattttgtt  69000
cgttcgggtt tgattgtgtc gtagctctat aattcggatt aagtttatcg ttggatgaac  69060
tgcattgctg atattgatcc caaaaaaaag acggtaggta cagctaggcc gtgaacagcc  69120
aaccatcgta ctgtaaaaat tggataggtt cgatctatag tcattagggc ctcctaaaac  69180
gatctactaa attcatcgag ttgttccaaa ggatcaaaac ggccagttat taatggaatt  69240
ccttgtcggc tctctgtaaa atactcgttt ggccgagggc ttccaaacac atcgtaagct  69300
aaaccggtgc tgacaaataa ccaacccgca atgaataggg aaggtatagt aatgctatga  69360
atgacccagt atcgaatact ggtaataata tcagcaaacg aacgttctcc tgtgcttcca  69420
gacatgctga gctccacata ttcttgtaca gtcaaagagg atcgattccg taaaagatga  69480
gatcagtaaa tgacaattca ctgaaattta atctttgtga gatcgtcaat attgtaccga  69540
gggcgtcttt agagtatacc gaatcagtat agctatcctt cttctgacac agcaacgcaa  69600
tttgaattag tatcaaaagt aagtactaaa taatttcttt tttcctttac ttgttgatgt  69660
aaaataatct tccattcaat agaaaattct ttcaattcaa cgaaagagat tctaaaattc  69720
ccacaattta agtagatccg agatatagaa attttctttt cgtagttgtg gaagcggttt  69780
tgttgttgga atccttttt taaagaagag gttaatggtc gagtaagaaa taagagtagt   69840
agatcatatt cgatgaaagg aaaaatagaa taattggaat ccatagttgt gatgcattgt  69900
tgtggatctc gacccaaagg ttctttcttg atctagctac aagggtgggg cggtatggaa  69960
agataaaatg tggaacctaa tagaaattac tagttttaga atctagttgg acaaaaaaag  70020
attttttcaa gcaattgtgt gataccettt tcttcttctc catcattcaa aatattatgt  70080
```

gaatttatat attactgaat ctaatgagtt aaacttaaat taaagtaaaa agaaaaggtt 70140
ttataaggta actgttcgct ttaaaatcga aaatggattc gatacaattc aacagaatct 70200
aagaaatgat caaattcgaa agtcatttct attttgattc tataaaaatt aaagtttcat 70260
ttttgaatga agttagacga tacagctctt attagtttaa tagtttaccc aagagttact 70320
caatgaatcg gttgattgga attgcgagat agatagatgt tacagatgat gaatcaattt 70380
attttatatg tctgtcactt tatctttgtt agtgctgtct gcctataatg atagatgaat 70440
caaaaacttt tcattcaact tattctttca attgaaattg agatttttgc ctatcctcct 70500
attttatttt gcaaaaattg aaacttaggt aagtgctttt taaacatatg tataaaaaga 70560
acatatttca tttaatttag ccccctcatg cttactataa ctagttattt cggttttcta 70620
ttagcggctt taactataac ctcagctcta tttattggtc taagcaagat acgacttatt 70680
taaactgaat atttaaaatg aagaattcat aaaaataaat ctttctgtgg gattacgtgt 70740
attctatatt tacttacgtt acctattctc aatttttgtt cattgtcatt gagattcatg 70800
gcaattcgga ttaatattta ggtatcaata ttacttcttt tttttctcct ttcaaacaaa 70860
taaaaatgat tgaagttttt ctatttggaa tcgtgttagg tctaattcct attactttgg 70920
ctggattatt cgtaactgca tatttacaat acaggcgtgg tgatcagttg gacctttgat 70980
taattaacat atctttttga ttgacctcct cctttcttta attcacaggc acaggaggtc 71040
aaattccgat tgttgtgaaa gttacggaat gcatttattt ggttctaatt cgatctaaga 71100
agaaaaaaat cacgctctgt aggatttgaa cctacgacat cgggttttgg agacccacgt 71160
tctaccgaac tgaactaaga gcgctttctt atcagaatag ataagactgt aaacaaaagg 71220
attcttttca gaaccccaat acattttgta tgcatatact agaatagcgt gataaaaata 71280
aaagattatg tccagtttga ggcgatctca attgatccct cgttactgct caaaggagca 71340
gtaataggta gggatgacag gatttgaacc cgtgacattt tgtacccaaa acaaacgcgc 71400
taccaagctg cgctacatcc cttcaattgt tccacagtgt aattgtagag aattcctgtc 71460
ttgttttcca catggttatt ttctccattg atatatacaa attttctgct catttcgtct 71520
ttttggtctc atttaacata taatagtaaa aggaaaagac ttctcttata gacttactta 71580
cttataagca aaaaaaaggg ttctaaataa gaagcccttt gaataagcga ggctttcccg 71640
atagaaagat ttgcatgcaa cagagatccc aattccgtgt atccggttaa gcaagccctg 71700
cccgccagct tccacccaga caaaaaaggt gagcgcctag cgcgaaaggt tgctttacta 71760
agtaagataa ggcaagaagc aagggcgtag cagctgcgcg aaagccgttg cgccttagcg 71820
catccgtttt cttgctcgtt agcgctcttt tttgaaagaa ggggcggagc ttgaagaagc 71880
gaagcgagcc tagagtagca gcctattacg ttttttcagg cccctttgat atgttattag 71940
tcaagcgcta gcgccccttt agagtaagtc ttttctgtta tcaatgaaac cgaaagaaag 72000
aaaaaagacc agtgcctttc gtatagatcg agacttgtag cttgattctt tactcattcc 72060
atactgggaa gaattgcagg aaatcgttcg ataacacttc ttcctatttc tttctcaatg 72120
atatccgacg atcaagacaa ttcccgtgaa actctttcat ttcatagaag tgaattctta 72180
ttcttacgaa gcaaatagca tttcctattg atttgtcccc tggactggac ctattctgat 72240
tctgaattat ccgtcgctac gctgttccca aggactagca aaatcgaaat agcgaaattc 72300
ttgggtcatc tcaatgggtt cagaaaccac acgtttctct ggatcatcat agcgtacttc 72360
cacatatcca ctcagaggaa ggtcttttcg taatggatga ccctcgaaac cataatctgt 72420

-continued

```
tgatatacgg cgtagatccg gatgattgat ggaagaaaca ccaaacatat cccaaacttc  72480
tcgctcccac cggccggctg atggaaatag actgactacc ggagatattc gtgttacttc  72540
gtctgcactg gtttgtacac gaatgcgtga gttataccga atactcagta aattatagac  72600
cacttcaaat ctttgttttc gagagggata atcaactccg caaatatcga tcgaaacttg  72660
aacccttgta taggtatgca atttcagaaa gcacaacaat tgaaataggt agtccgtatt  72720
ggtatcagat ctattcccat gttccgatct ttccattttt ttgacccatt tcttgggtaa  72780
agtctcccaa ctatatttga aaatgaattg gttatccata aagagaaaga aagttttctt  72840
caagttccgc ttcttgctct tccaattcag aaagacttgt cggaaatcgc cggttgggtt  72900
ggtccgacca agaaaggcat gggacttttg ggcattgctt gggccgagtg ttgtatggct  72960
acctagtgat ttacaagcac cctcactgca cactttctat atatctgtct ccatccaatc  73020
aaagacgtcc atgccataga gaatcaggct cggcaaaaac gagactaggg accatgctcc  73080
ccgctttctt cctgtggtta ctattagaac acaagccaag gaactcaaaa ccacaacaca  73140
agcacccttt atttactagt tttggagttt tcgccctttg cttccggctt taatgaaggt  73200
aaatagtcaa aaaagttccc cgtagaacgc gagcgttgag gctttcatcg aaacaaagag  73260
agaggcccgg ctggtgcttt tttctgtgtt agccaggtga aaggcttgct tgactctaaa  73320
tagattagtg tattaagtaa ggaactacta aaacctctat tcccgttttt gggctataag  73380
actcttagct tccagcgagc taggtgcata agcttttttt actacaaaaa cgattcctcc  73440
cccggcaaaa agtggtccgc caactgaact tgccttgttg tgataggggt accgcctttt  73500
cattcccacc aaggagccgt agctttactt agatagggct tgactgcctt accttctatt  73560
atattagtaa agggccttta ggcttgactt tactaatata atatcaagta aaggggcatg  73620
tatccttttt ttgtaaagaa agagggctac ttcacgagcc gctactaata atcgaaaagg  73680
ttcacagcga gttcagtcta tagtgacaaa gggaacgttt ccgccggagg ggtttgtctc  73740
catggaaaaa gtattcacta ctgcttacag caccttcatt cactcgtctt gctacttcgg  73800
aactgttcag cggacacgtg gagtcgaacg tctctctaca atgttgcgta ggtagactga  73860
ttattgtagg tgactgtctc tagtggttta gaaagagttc tgttgctacc aacttctttc  73920
tttgtagtct agtagatcta catgctctag tggatctaaa gtaggtttat gttcagcaac  73980
agaaagaggt gaggttctgc tttcttacct gagaatattt acaaggggga agcctcgaaa  74040
ggcatacgag tgcgcctctc gtagacgaat accgactcag tccgctccta ctgcgcggga  74100
gtatcagccg gtcggtgtcg ggtcggcccc tagggcacta ttcgccttgg gagtggttcg  74160
gccatcaagc tactttgtgg ggtaggggac cagactggtg actgctgcgg ttgttgtctg  74220
cagggtatgt gacaccccac aagttgacta gtgctgagcc aggagatttt cctttggatc  74280
gttacaacgc tcgttgaacg gttcaagtag aagtgaatag gtaagaagta gaaacccccca  74340
tatcaatcca tctccatagg agacaatatg agcaaaagac aggaatccct aaatcccgca  74400
gaaaagaact cactccgggg gagtggagtg aggggggtat tcaaaaaggg gagccgcggg  74460
ttctttcttt ccttgtagga aaggtcttgg tttggtatgg cattagagaa aacttgttat  74520
ggttatgcgg ctatatagaa aaggcgggtg gggcttcagg cggctttttt tatgaatata  74580
atcaatcaaa attccatcga ttgtagctag tgattgcccg ggtcggtgtg tgatcaccaa  74640
aggtgaagta acccttcaga tgctctctcc gcccatgccg aatacccccg gccggttccg  74700
ccgggtaagg ccaggagctg gtttggggaa tcacggggcc ttacttattc agggggggact  74760
tgattctgaa atggaatgat tgatagaatc gagatttcat agaagaatga ccgagaccat  74820
```

```
aaaatccttt cacacccgca catgtggctg aatatataag gaagttcaca caccctggaa  74880
aaatccatcc tgtatccctg acttgccagc ttgatcgctt gtcttattta cccttttctt  74940
agcgggtggt ttatgtctgg tcctttcggg tcgcctgacc tgggctgatg gcgcttcgta  75000
acggcttgtc tggagtccag cggctctcta aggcttcgat gtactagtac ctgccaccaa  75060
aacatcgtga aggattcagt gaacgtcttg aaacttagta acacaagaca attcactgaa  75120
tggttgttgg ctctaccgga ggagtctgaa atcaacaacg tgtaactgct tgggcattga  75180
gtgttccgct gcttgaggaa gtatgtgaga ggatcgatgt tgagcagaag tggggttaaa  75240
gcagccaaca acgcatcccc ctttacttag tagggcttga aaggctggac agtttgtttt  75300
cctttcctgt ccagtatttt caatccaagc cgaaatagga aaagccgcaa gcaccactag  75360
gcccggtcgt cggttgaacg tcagtagggt ccgatattca ttccttactc aaataggaag  75420
gtggcagtct caatctagcg gcgtggtcca gaacaagcct ttgctgatcc atggggtttt  75480
cgttttggtt acaagaagtg cttctttgct cgcttgcagc gcctcgactc gagtttccgc  75540
tgtaggattg agtgaggtga cgagagctga agccaaggtt ccttgctatg ctccatagat  75600
gttcgtacga ttcttgtgga ttttgggtgt gtttgaattc agcctctcgt taggtcttca  75660
ctgaaggatt gtccaccttc tcaagcctct ctaccatacc cttagaaagt gacaacggat  75720
gacttccatt actaaatgga agaacttttc aaactagttg atagttgttc cctggttgca  75780
ccccacaatg ggttctaatt tactaaatca catgtttctg ttttcggaac atcacatgta  75840
gagtttttttg ggggagaatc actcggcgcg gggcctcccg tgtgaggtca ggtgatggtc  75900
aacaactcag gcaggaaatg ctgaaaagcg gctaacgatg caagagctct tttcccctta  75960
tacgctctaa aaaaagggta tgtcgggttt ttggacccta tgttgagtaa gggttccaaa  76020
ccttccaaaa gtgataggta tgtgttcttt cttggcactc tctttctata ttatgccaac  76080
ctaaaaagag cgatggaaag tggatttcag gttcgatagt ctcgagaagg tattagccac  76140
cggtgaccat actttcgtaa aagcaccatt gggcggtggt tcctctcctt cctcttgaac  76200
ctcgaacaaa aaatcgatct cgccatcagc tcgactaaga gttccgaatc gaaaaagtaa  76260
acttcacttt acttaagacg aaggaagcga gtgccgaaaa aaaccgcttt cttaaggctt  76320
caaactacta gtcattaaga ctactatgaa tgaaaaggca aggaagtcct tttcttgact  76380
tggcctgcgt gcattatacc taacctttta acttgatttc aatctcaaca aagaaatgaa  76440
agcataactc tttgctcgct tgcagcgcct cttagtcttt tattttagcc tgccttgtga  76500
agatctctcg agtgtctacg gcagatccga tcagtctcgt gatgaagaga agtcttttcc  76560
gatgttgaaa ggtatcgtca cgacaactca atttgtccgg taaactactc ggggctcccc  76620
atggtttagt aaaagggagg ggagattttt gcttcatccg gggggttcatt cattatgaac  76680
taaaaagtgg ttggctgatt agtgaggtct taaaaacgtc atagaattca tgatcggcca  76740
ttccattttt gctttcagca agtaggcgac gcgaatctat gctttctatc tttcaatcgg  76800
ataccaattg cttggatgcg tttgaaagcc tcgagatgac ttgcagaaaa aattctttct  76860
aggtttgtct tgtgtctccg aaacaaaggg tccatttatt gatgggcgaa cgacggggat  76920
tgaacccgcg cgtggtggat tcacaatcca ctgccttgat ccacttggct acatccgccc  76980
ctacccccgc acaggttgaa gtctctatct acgatcagat cctttctgaa ctcccctatg  77040
accgcttatc aaagagaagc tttttcctat actatagtgg caagtctatt gttgtgtttc  77100
ggaattaggg gaaacaaagc ttcaacaagt agaagcttcc tggcaaagct tcaaacaaag  77160
```

-continued aggttgggct gttcacttca ttgatttgac ttcactttac ttaagattaa agataggggc 77220
cgggcgggca gtgaaggctc atttagtaga cagcgagcga gctgcaagca cctactccta 77280
tcaaaatgaa aagctgcaag cggaacttga acttgaagaa gcgagcctct atcagagaaa 77340
gccattgcgc gctagcccct tgtatagggt tccaaacctg cgcacccccta aactacaagc 77400
tttctttgaa gcccctacaa catgggatat ttgaagaatc ccctttctat tagtaaggtt 77460
gtcaaaaggc tttcctttag ttcctttata actagaatct aaataatagg ggtagggggg 77520
cgctaacgag caaaaaaacg gatgcgctaa ggcgcaaggg ctttcgcgca gctgctacgc 77580
ccttgcttct tgccttatct ttgactaaga aactaatcta aatagaagcc cttctttctc 77640
aaagtcaact ttctcccttc ttgctttagt gaaataaggg gcgctaacgc gaccttcctt 77700
cagctggctt cgccctatct attcatctat tttctcaaat ggatatttag ggatctctct 77760
tgttcataga tcttgaaacc agatcaatat ccatttctca atagatctat ttatcgatag 77820
aaagatctag atctctatat ggatctatct ccatatctaa atatggaaga accgacactt 77880
aaagggcgta accaacggaa ggttctcacc ctgtccccga cattgttctc cgacgatgtc 77940
ccctgggcga aaggagccac cattctcttt ctttcttcaa tcgttccgat caggacaagt 78000
gggttggttc gtttcgtcct cctatctacg caattctctg tcttcgttcg tgatcatgtt 78060
gggcgaaagg tagttgtaga ggagcggctg tgaaagggcg attccccccct ttccattgaa 78120
gtagggaggg cctccttccc caccattccg gcctattatt gatagggatt ttaccgatgc 78180
tgaagatagc ttgcttacca agccgcccac ttgagaagct agtcgccagg aaagaagcga 78240
ggaggaagcg aagctgtcta cgaagctttg cttctccccc tgtagtcgta atactcggct 78300
tgtcgctact ttgattcaaa aggtaaccga cggttcccga ctttctccgc tttccgcaac 78360
cgtaaccact tgtcattccg attacttcat ccataaacct ttttttttatt tcaaaatagc 78420
gatacgctct aaaaaagtaa aggagaagct tccattctag aagcggtagc ttcccgcctc 78480
cctcggggtg agaagttccc ttccctttttc taaaatgcct gagtggtctg ctcagcaaac 78540
gtacaaagtg gaccgcagtt tggctgaccc tcttcttccc attcgggttg ggttgaccca 78600
gaagtacagt aagaaggaat ggaaccactg gagagtcgtc tgcagttcac acttgggcaa 78660
agacgactga ctttggaagc ggaacacgaa cctatttccg ctattccggg ttcttattga 78720
gcgtagcgaa atcaaggttg atgataaagt cagcgaagtt tccatggtct tctacctttg 78780
cgtagtctcg gtccacagtg gaaggctccg cacctgagcc tcgttagact cagctgaagt 78840
gtaaggtgta agtgaagaaa atagaagaga tgaagtccgt cccttagcct agtctatatc 78900
cacagctgac gcaactccgt accgacgcct cactactact ttcatttttc ttttattttg 78960
aaattcatta acggctaagc gatttcataa cctgagcttt ccttaaccag ctgaccttac 79020
ttcgtaacct tagcctccct ttctttatag ttttctagtt cgactaagtg acttcgtaac 79080
ctcaacgtac ttttttttctt actgtagcat aggccttcgc cacttcaaac ggcttcaaag 79140
aagcccctct tttttttgaa ttagaaagag cggggtctga cttattcagg ggggatgaaa 79200
gacaaataaa gggatcaggg ggctttatga tcggagaaag agagggggcg tggttggtgt 79260
gtcactgggt cggtgggggga acccgtagga agggggggacg acccgccgaa ttcacatcag 79320
aaatcgccaa catgaacaca aacgaaatct tgaattgcgt atagaaacaa aacgaaccac 79380
ttctattctc ggagctgagg tatatgaaga atggcttttt ggtccctttc gtccagtggt 79440
taggacatcg tcttttcatg tcgaagacac gggttcgatt cccgtaaggg ataggtactc 79500
attcccggcc gctttcagtt agtgttcatt gctgagtgat cgctcgctat ctggctggaa 79560

```
aagatggtcc ggaagcttcc tctctcccag caagcaagac gagatcacca cttctctcag  79620
taatggactt cctttacttc gtaaccttag ccttagatgt cctttcatag attctcgaac  79680
ctccgacaga cagaatctcc atgcatgcgt tctttctctc ctcccctccg ccatacatcc  79740
ctttttttct tttggccgtt tttgttaggc attgaacccc accttaggtg ctgagtggtg  79800
tcctcccctc cctaatacct aaacagagtt ccgtctatgg agcctaaagc ttaaaccatg  79860
gcatggcagt aagcagtaag ttggcctagt ctctcgccca gccttcgcct tcttcagtgg  79920
ccaagttgaa gcgttcaacg tcggcctacc accctttttt tttcaaggtt gagcttgttc  79980
aattgaagct aatgctatgc tgcccttccc ttgttcaaga gaaagcgagg actttctttt  80040
agctaccggc ccaaacaaaa gagattagcc tcttgatcga tcgattgatt ggatcgaagt  80100
acgaaggggt tgattgaagt ctgagatcag cccaagacta aggccgagca actagctgct  80160
gcaggattgg acgtctatct atctcaccac gctcccctac tcctataaag gccggcggaa  80220
ggaatgctct gctcatcttt cttacggctc gttaccgcag cgctcgttca ccccttcggc  80280
ttcttccatt caaaaaaaaa ggtagtgttt ccttggtaaa tagcgtcttg aagtgaagcg  80340
aaggcattat tgaaggaaag aaatggcggg tcggtcaatt gcattaggta ggagatgcag  80400
gacctgtctt aaccgcaagt gcattcgcta ttcgattcca tcctaaatcc caccgaattt  80460
ggattccaaa gtgtgtatct cttctttact tttaagtgac aagggggggtg acaaagggta  80520
tactttcttc tctatgtcgc cgtctcatta atgagcgtag attaatagcc aagcctaccc  80580
ttttgtgctt gtcaatctgt atcccattct tcaggtatag ttttctttta tcacagatcg  80640
acaggtgatc cgtcctttct ccccctttcg tcataaggcg tggtctgact ctgagaaaga  80700
aaattcctgt gtttaggtcc ctactaagca gaattcgtaa actatgcaaa ggctctttga  80760
atactttttc aaaagttttt agcaaaaaca attctcaacg cccttacgag gtagtgatga  80820
gttaaactac tcgtgttggc atggaagtca gcccggtaaa ctgattccat tctgctacta  80880
gggttccaaa ccttcccctg agctctagaa tctagaaata ccttttcaac tcaagaaatg  80940
ctaaagctat ttagagttgg tatttctaac taagtcggaa ggagggcttt gggcaaagag  81000
caactcgaaa gtactttact tcagtcccag tactgaaaga cgtgacttca ggagtggatt  81060
tcggaaggaa agacttcgtt tacttcctgc aaattgctta tgtaagaact agtagaaaga  81120
aaggcatttt gaaaaaaaaa agaaggcagc attgacattg aatgagaatg cttgaatggg  81180
aatcatctta gcaactgact atagacatga gtctaagccg ccgggagagg agagaccatt  81240
ttcatgagag agggacgagc aagtgacaga ttgggaaaaa aaagaggtag gccttatgag  81300
cggtcattta ggggtcttgt tagcgaccca tcattcttcc ctaagctgtc agagtccgat  81360
cgaagcgagc aagagataga ggaatcctcg ctcatagatg tgaattgaaa aagcaagccc  81420
gaattctttt gaattaggct ctatagtctg gtccctgtcc ctggtaaggt ctgattgtta  81480
tccgtaagtc ttgttttgac cgcgggaagg tgaactttgc aaaagtgctt atttggttgg  81540
gaagaatagg acttctgact ccaagcctac cctacccgaa aaaaagtttc cgctattgat  81600
gtagcctctt gtcgatacta ctagtcttct cgctacctac tagaaaaatc ccatcaagat  81660
agattgaatc gacgacctat acttcaacta aaggcacaag ggcgtagcga gcacagaaca  81720
gaggaaatgc acatgggtct ccttgaagaa cgaagtctag ggtaaagaaa gaaaggtaga  81780
gtgggcgcac tttgactgtg cttggattgg catggctgtc ccccttttgct ggttgaggct  81840
cggcctttga ctccgcttgc ctctactttt catgtcaagc gtacaagtct agtttagtgg  81900
```

-continued

```
gatttacttc taaagacagg aattcttttt catctcccct gtcaaagtcg acgtcttaac  81960
ctgacttcct gagctcagtt gattcttgaa gcagtagctc tggatcgaga gctggatgct  82020
taccttatta ttatgaaatg aaaaggagaa agagcttttt ttatagatgt tgaggtgagt  82080
aaggggggt ttgctggctt gctggctagc tcgtgcaatc aaggaaaaaa gccttcgcct  82140
tctttttaa aaatgaaaaa gtaaactacc ttagtaagct agctttgtaa gctaagcaag  82200
ccgggcacta ggctaggacg tggatcgatc atgacgagaa tggacttctc cgtaatgtaa  82260
tgtaaatgta atagaagagg cagagtccag ttcccctccc ttctcgacca gacgaaggag  82320
atatgaattc catttaggcg ggtcagggct tggcttgacc ctgtgttctc ccgggtcgga  82380
ggcgagaact tgaaagtgaa tcattcagtg gtggggtgtt catagaacag aaggcctcgc  82440
ccaaggagtg atttggatgg agtctcgctt tgatgctggg gagatgagat ccatagatct  82500
ggatagagtc tcgctcatag aggaagagta cgcgcgctag cgcgctacgg cttacgtagt  82560
tgatcggatc agatagccct tccttcgggc aagcaaccaa acccggcaca tccaattcca  82620
ttccgatcaa gaacttggag gtatggctga gtggcttaag gcattggttt gctaaatcga  82680
catacaagaa gattgtatca tgggttcgaa tcccatttcc tccggtacgg aaatgaaacg  82740
ggcgggcgaa attacgtgag agaaagaacc tcttggtgga gtccagtccc ccggaggaca  82800
gaatagcact tcttagtgac taggagcgga gagcccgttg caccttgttt ttctttgacc  82860
ggcctatctt ctttctataa gcaagctccc tccggctgtc cagtccctgg gcggctttcg  82920
gttcttgagc atgttgggag attaggcggc agttgaaaga gctgctcgaa agcttgacga  82980
agaagcgaaa aaagcctatc tattcgattt tcttagttta gtaaagggct tttcccttac  83040
tagtcaagtg gtaaggtagg gcgctattcg atgaagaaaa cagactttag gaaagtggtt  83100
caggtagctc agctggttag agcaaaggac tgaaaatcct tgtgtcagtg gttcgaatcc  83160
acttctaagc aggcgaaagg tccaaaccgt agccgggagc gagccggatt tggaaatgaa  83220
agtgaaagag taagcaaaaa aatgtgagcg ctcctgcact atacggacgg ctttttggcg  83280
gtagggttgg ggtggcttgc ttgaggcaga ttcaaaaaaa agcggttgat tactcggatt  83340
ggttctcgca tccctgtgcc caaaaggatg ggcgagttcg gttcgagtct tcatagatcg  83400
ggtagatcta tatgcttcgg agggtgagac gaggtgtagc gcagtctggt cagcgcatct  83460
gttttgggta cagagggcca taggttcgaa tcctgtcacc ttgatgtggt agccttctcc  83520
gtggtcggac agtaaggcaa acagcgcaaa gcataaagta aagacatgat gcctcgacta  83580
agtaaagtct ttttgcccct tatcggtagt tccgtagcag gttgtttcgt acgttttcta  83640
ggatcagata gaagcaccac cccagaatgg atccttcttt tcttcttact tttactaagt  83700
ttgactcttg tttctcgttc aacaaaaaga aaaaggagtg tgattctttt attcctaata  83760
ttttgcatct ctttcttttt ctattttctc ctgatctact tactttctcg cttagatgtt  83820
cttttttttg gctgatcttt tctcttttgt tttgcttttg agtgtggggg gagggcaagg  83880
acttcctctt ccgggccctt caaactcctc atcggaagat ttattcgggc tccaggtcct  83940
gtcggagcct tggcccccga ctcacaatat agccttggag tcatcgatga taaataggat  84000
attggcaatg gaaaatacca atagcatttt tttgatggat aaggataggg gggtctattg  84060
ggcagaagta aaacattcac tctaaaattc ttcctcccaa aaggaatata accaattgat  84120
cgagttcgag aatagggatc ttcggatccg tgagaaaaag cattcatgct attctctttt  84180
tcaacaaata cttacttcac atcctgcctt ggccgaaaat gccgcctaca ccccccaaga  84240
agccttttgt gactttttgg atgagaaacg aagtgaactt gaccaacaag gcgggaatgt  84300
```

attagtaaag gaccagagag aactcgaatt ttggaatcta ctgtctcgcg atatacgaac 84360
acatggccaa aactcagcct atataaatag aatactcggt ggatgataat gaattggatt 84420
tgcactgaga agtccctatg gcgcggttga gggcagctga acgaaaggaa agcgggtagg 84480
ccgcctgggt gagacaaagc agaataatct aactggagga gtgaaagcca ggatggcttg 84540
gtaagcaagc aatccgttat gtgggcgcca actccaagtt ccctctcttc tttcttttt 84600
ttgtcacgat caaaatgaaa ggttgttctc tgggcctgtc ttttgctccc agagatgctg 84660
gttcgagtcc agctcgtgaa agagtttgtg agtatacctc gggatgactt tttatccact 84720
actcatcctc gaaatctagt ctagttcagc catagaggac ttgatactta tcttcgacaa 84780
acctcaagcg ggacgagtca atagcagatg cggattttat ttaatagctg cgcttacgcc 84840
ttcaaccccg aaaaggtcgg attcgtgcaa aaaagtaaca tccgagattt gtgaacagac 84900
cggcttggga cagagaaatc cggatgaata ccgcaagggg ggggcatagg gctgtgtgaa 84960
cgcggctttc actaagagaa agatgtgcct acaatgaaac tgttagacct ttgttgatgc 85020
acatgaatta tctttccagc cggtgaagct aagaaaagaa gcccttagaa agcagagcta 85080
gacccacaca aatgcttaat cgaaagctct gtcctccttc ccctcctacc agatcgaaaa 85140
gaagaagctt gctcttccga cccaaaaggc ttttgccgtg atattacttc cccctattcg 85200
acgattcact cttcctggac ttgcttgact cgtccgaaaa aagagggaaa gtgctaagac 85260
cgctaatgca gctaggggag tttaaggact catttccaag gctagaagcc tagactagac 85320
tagaaaggag attgctttgg tcttcagtca gctctactag atgcagttgc ccaggaatcc 85380
aatgcactaa ctcctggaag ctccattcat gcccacctac cgaccgagga agacgctacc 85440
gatccctgaa tcgagggact acgcgctttc aatcccttac agctgccttc caagccccga 85500
actaccaatc gccccactat ctgctagtct ggttcgactc gaacttctgt catgtcaagc 85560
ttcctgacct gctttgtacc agccggtatt ttgtgtactt cggggcgctg actagccctg 85620
ctcaacgccc tacacccttc tcttgagcgc ttcattgagc atttctcttt cctatcccgt 85680
ccttaggcta cgctatccat aaggttgacc tagccctctc ttctctctct ttgtccacgc 85740
gaagattcca ttcctttcct agcctattca atgtggtcat gtatgtaata gaattcaatg 85800
ggaagacctc ctagttggac ccagactgcg atggtagtga atgtggcctc agctcccaca 85860
aatgcaggct cccaaagcct tagactgaga tagtaccaca aagcaggggt taacataaat 85920
gactctatgg aagtcctctc ccacttgaaa gctaaataag gagaagaagt gccccaaatc 85980
aatgcattcc attctttgca gaggttcctt ccatagaatc cctcgaagta cttcgctcac 86040
cttcgaagag tgaaaggatc attcaaagca gactaaaggc atagggcaaa ggagcttaga 86100
agggtgacgg aggggagtag taaggtatga aatcacttag atagaagcat gttggatgac 86160
ggaacgatga cttcatgctt caattcgaaa ttttagattt ctgaccttga gaaatgacgt 86220
aagtgataga tggaatcgtt cagtaggcta gtttccattt tcgattgaga aagcggcggg 86280
cccagtgagc tctccaatag tgcaccgaaa cggggccgga gagacggtaa accttagatc 86340
ggctaagatc gaattgaact gtctttgatt gagcgaatcc tgcccgattt tgatttccgt 86400
ccccgcggga gacatcgtaa atagtgaaat gtttgattcc cctattgaat tgaattagga 86460
atcgattgaa tgggacttgc ctatccctta ttcatatccg atttttctct ctttcttttt 86520
gatacttggt tggcagggtc agggcctttc tcactgggcg agcgaatccg tatttttcta 86580
tgtaaatgtg accttaacgg cctttatttt aagcaattat tcgctccaag acgcacgaca 86640

-continued agaccttcga tctctctctc tccataattg atatggaagt tggaaaaaat caaccactca 86700
aagctgacct caaaatgttc caaacacgca taagtgtgaa gattgaagac cttctattct 86760
atatttcata gagttgatta gtgcaaaaga aaagggcact ggttcacgca ttacgggtag 86820
attcctcttg cctaagaaat ggaagggggc acttcaccga atgataggta aagtatggga 86880
cgttcagtaa acaatccctt agctcaagtc ctcggagata cccaaggcag ctccccgtgt 86940
cctttatacc caacaggaca agagtctaca ggtctgccag gggcgaataa gagctcgtcg 87000
aaccgtcatt ctttacttcc ggggtcaatc aataggtagt cctcaaattt cttctcgaaa 87060
gcctgtttat aagaaatagc ttatgccact cgtattgccc cggattgaca aaataggctt 87120
ggattggaga ttcttgtgta aacattcaag ttgacaatcg ggtttctaga cagccagtgg 87180
actctgaaac caataccaat gatttcgctg gatctaagaa taacgtagca cagaaaagcg 87240
gactcaccaa ggatggcgaa tgggcaatac gtagagcttg ctccgcttcc tatggattgt 87300
tttatagcgg tacgattacg atgcttgctc cgaatggaag agagacggct ttcctttcgg 87360
atgttgcaaa cgcacaaacg aaagacctta gtcagcggaa gaagtcactc tcaatccgat 87420
ctagcaagaa atgctttacc ggtaaagtaa agcgagagac agtcgattct ttcttagggt 87480
tccaagtaat tcaactagtg ccaagaaaag tatccggttg tagagcgagg cagcaaaggg 87540
gagttggcac aatatgtaat ccctagggta tcggtgtcgg agaaggggat cactcaatgc 87600
tgctacaggc actcattagt tcggattggg tagcgtgaag gagataatag aaggacccgc 87660
cgaaagtagt tccgtctttc caggtcttcc ggagtcaaaa tttcctcatc caatagcatt 87720
cttagttagt accattcaac taagcctgtt tttgacgagt gaagcggcta ggctacatgc 87780
ttagcctagt attcccggat tggtattgga taagaaagat tttgctttct tcccactcat 87840
gaagaacaat aaagtgaggg gagggcttcc gtggaaaaag ggtaagtttg ggatgagagg 87900
gtgaacacta aaatagtagt caccaaaccc aaagaaattt gactcttttt ttttatgaag 87960
gcgaattgat aagaaaaggt acttccatgt gtataaaagc acaagggaag ggggccccta 88020
gtccaagtat aatagcatag gggggtgcaa gggtgaagat actagagtgg tttggcactc 88080
ctggtcagct ttctttcgtt cgggctttct ttcttctgcc tttacgcgag ccaattatgc 88140
gtggcgctga agaggaaggc gtcacttact gtactactat cggccataca atgatggcat 88200
tgtggatctc attcgtattc cagttttttt ggacaaagtt agagtagtca tttagggaat 88260
aagtcttttt taattattct attagcatag cattaagtgg taaacatttg acactagagg 88320
ttttaccata ctatacatgc aaacataaca aataaaacca aacaaagata gttagcatag 88380
ataggagtct atctccagta ggcaccggag tagatctcca ctagaacacc agacatgaaa 88440
acaaatgtct caagacactt atggaattta aaccttctaa aactaaaaag agtcgacgga 88500
ctcttttagt tttctcgggc accaaggaag attgcctcca cgatcagtgc ctgctgctcc 88560
tggcgtagtc cctggagtct ttcttctagt tcccgaattc tttgacggct tgcttccatt 88620
cgggcttcaa tagcagccgg gttcacggag cgaagatgcc tcaagaaacc atttaacatt 88680
attcgagtat ttcgaagata attttctact ttttgtattt caacgttaat ttcagcaagt 88740
cgctggggaa tgtcgagaat ttgagcaggg agggccatgg cttctcgata tacactggta 88800
gaaaactctt ttctcttttt tgttttttttt tgtagaacac gaaggcttat cgagcctctt 88860
tttttagagt gtatagcaat tcttccaatg cagtacgaat tgcatggctg gcacaatatg 88920
agtactataa ccacgctgcc tgtatgaaaa aacaaacttt gcagaaccct ttcacctaat 88980
cgatcgtggt gaagtcagca atggattcgg cggatcatac accttacgct aggatttggg 89040
aaggacattt acgagactga ggtgagtttt aagagaaaga cgggggtgga ttttttttgct 89100
ctaactggct gtgagcatgg gaattgcgtt gccgagcaga gggcggagag gaatttggtg 89160
ttgcaggttt gatgactgtg agaggggttg aaaattgatt ggttttttttt agcaggtata 89220
ttggtatttt tgaacatatt aaagattata gaatgtagaa gaatctcgcc atacggcacg 89280
agcagttgag tacagtacta tcatgccttt gttttgtttt gtgaagaaac taaaaaactt 89340
gcgaagcacg cacctcaatc accctgcctg tgtgaattga acgaacttaa aagtacaacc 89400
agcttaagct ggttttccac ctattttttta gtgttcggcc atttctagca aagtataaag 89460
gacatattcg ttgccgattt ggggttctga tggaagatac tgctgaggtt atacaccaag 89520
tacacacgtg attctgctct ggcagaagtg cacgcgcaat tcagctctgg aaaaactccc 89580
tgaggtccag agagagatga agtttatagt aaacctctgc ctctcagata gctttctttt 89640
ccaacacttc tatgtggaga tggatgtaat attaatatga ttgatagttt cagtttacta 89700
tttgcagttt tccaaagtct caaatttagg acttggttcc ggccttgttt cgtagtgaat 89760
ttatggattt gaatacttct aagactgaat tcttttttgt aaattcaact tgacttgtac 89820
ctggaacaga gaaaaagggt atccaattga aatccaggca ctttttttcta tttttcgctt 89880
agatgtgctc ggcagatgct aaagccagag cgtgatggca agaattgatc ggggagatgc 89940
ccttgaagat cacttaccca gctctggaag gacatgagtg gagaattgtc accggatttg 90000
atccaaaaaa cacagggcgg agttacctta ttggtgagtc ttggccgggt tagtgtttaa 90060
ggaagaaaac cttattgtag gttatttttt atttaaagag tgccaaattc aaaaagaaaa 90120
ggaaaaagat gcttgtacgc acattagatt tgctaactca attgatccta ctgtgtctag 90180
atcagggttc ccgtttaaga aagcttgtta gctttgtatt ggctcccatc ttacttaacg 90240
gggcccttag ttgaataccg atcaaaattg tttgaaattt tgaaactttt ccaataaaga 90300
attattcgtt atgttaaata ccccgaaaag ccgaaacctc ttattctggt ccttagaaaa 90360
actacgacta gtcaggaatt gcgtaagaga agagacgtcg caagtaacaa tagcgcaaaa 90420
gcaggcggcg gagatccgca aaggtaaccg gatgcctggg gcttaggaca aggggcgtcc 90480
ggagtctctt aagaaaggac aaagactaat taatatcatg tttacaccga tcggatttaa 90540
aaaagtgctt cgcccccttat cttctcgtct atcttctatt ttgcatcgat ggtccattcc 90600
tttcctaatc ctcacctcta cctttttttg tgtctatctt ctttatcttc tgatcggatc 90660
gcctggcttc tttcaagccc tacttgaaag gcttgctttc ttaaaaaatg ctttctttat 90720
taagagtcct ttaagaagct aagctccttc agatagtaag attcgcttaa cttcatacct 90780
ctaagcgctc gtgactatcc gatgatagtc acttcgcttt ccttttagac tgaaaaagga 90840
aaactgaaag attgagcata aaaaaaatat agagaatgag ctattacgtg caaacaatgg 90900
aaattcaata ataagagtct gatcttctcc cttaagaata tgcgattcct ccggagtgaa 90960
gttgttgggg ggaagagaag atgaggaagc tagtttaatt gaggaagcca ctttctttaa 91020
tgtatactag ctggtctaca aaagcatgac gcatgacgct tctccttttt ttagtccact 91080
ctcccttaga aaacggagct ccttgaaagc agatttctaa attacatagg tgaatgtaga 91140
gatcaccggt gtcctactcg agacgaagta cttgtcgtcc ccaaaccaaa agggatgagg 91200
gaaaaaggct cgagaaagcg tccttggaag ggggaataag atcttaaaaa gtgttagcgg 91260
ggagcccatc cctctcgttc ttacagaaga cataaggggg aatacacgac ggacgaaaag 91320
cggggaaaca tccttttcct gtcttctctc cacagaggaa ggaaagcacc gccaagccaa 91380
caagaaagca gaaactgcat gaggtaagac taagggcctt gtgcgccctg caagagatta 91440
ccgggggtct cggtaccagg ggggcgcggg aacaagaaac tccagtaaat aaaagaaaga 91500
caataggagt cctctcaata gccgagggcc cacttcccta tatgcgctta cggaagggga 91560
aaagcttgat tctcatagat tagacaatac acatgtgcaa acaagaaaat caaactatct 91620
tcttattgat actatatatt tatcctttcc cctatagatc cacgtttctt caaaataaag 91680
atatagcaac taaaagaaag ctaaatcgag tcggaatagg ataaagaacg cacgaaggat 91740
cagagagaaa gaggattcta aaagctaaaa gcctagaaga ctagattgtc agactcggag 91800
gtagcagtaa gatctctgtc tccagagaag gcatgagggg tttctaaaag tctcctctca 91860
ttacttatgg ataaagctct taagcttaag cttttacgaa cagaaagatc ttcccattct 91920
aaataagaat gagagtcttt caactagatg tgctcctttg gctgggtttg agagagagag 91980
cctgagatag ttggtctcct tactagtcca acttccttgt atctgaaagc gatgacagga 92040
tgttaggtct agtaaggaga ctttttggag aattgacttc cacgaataga ctgttaggct 92100
aagaagaata ggttgggatt gatcccacct ttgaaagagt ggttttgttc tgtcaataca 92160
gcttatcgag ttatcaagct gaactgcctt ctgtaaggag cttgaatcgt tcgtttactc 92220
taagtcttat taccgacgcg atggattgct atttgaaaac actttcaata caaaaagagc 92280
tccttccggc tatactctag ttggacagtc tttgttcagt ttgagaagtc aaggaggcac 92340
gaagagctaa caaagagtct ttctatttga ctgtccgaaa tcaagtggga gattgaattg 92400
aaaaggcccc ttactataga tagggtgtta gcgctgtttt ttgaaataag gacgtttaga 92460
tttgactaat aagaaagaaa ggggcaagcc aaaacccact ctgctgagtt cggctttcgg 92520
ggctacctac tttagggctt atgtaatata taaagaagaa ccctcttagg gcctttttgt 92580
ttaagggctg ctcgcctttt gaatagaagg aagtggggga gcagaggtta tttcggtaaa 92640
ccgatgcatg agctgaggct cccatgtccc gccgaccctc cgaaaaagta agggctcata 92700
gggagtcaga agcaagcaga gtaaaaggcg ggtaaaactc acataagcag agggggagac 92760
acattcatga aaagcgagaa gccctgccgt gggggactga ccaactatga atagatctta 92820
cttatgctta cgggtaagaa catatattag tccgtatcgt gggtctattt gttacaaaag 92880
gcgaacatcc cctttccaaa acattaacat aggtcctcag gcagacatcg aaaagggggc 92940
gaaaagagtc tatttacctt tacaatattt cggaatgtat catggctcta tctattcatt 93000
aaaaaaaaaa agagttctgc atctctccgg ggctgggtga acaaataggc gtggggaaga 93060
gtgagagggg gggctacgag ccctctctcg ttgttgttcc cggaccaccc atctcttcct 93120
tccccttcgc ctggcccggt gagatctgat ttatagaacg aagtgaagtg ataggaagag 93180
aagactgctg gcgggaaatc cctattcatg aaagcccctt gttaaggtta aggggaaaac 93240
gaaagtgcgc tcctgcgcac cagctgaaga aaggagcttt ggaagcttac cttattatta 93300
tattaaaagg ggaaagggtt ccaaacctat ctgactaata agaagaaagg ggcaagccaa 93360
aacctactcc taacaagttg ctggatcgaa gtagtacatt atacatctgc ccgccagcag 93420
cagagggggt tcgattcccg ttatacgcga tgtggcgaaa aagactgatt caacgagata 93480
tgccttgcct gcattaagat ttaaaacttg tcgtctactt tcaggaaatg tttggaacag 93540
agaacttaca ataatacaac gccgtattct ccgaagattg aggaacaaga agagatctat 93600
taagagaaag atttattcta gagaaaatct taacagttac atccaatcac aaactacacg 93660
aaagttgtcc ctttttttatg gagatttacc catcacagag atgcacagag gaagagaacg 93720
aacttcatat atccctttc tactcaatcc agaaacaaga tcggacgtta tcccggttcg 93780
tctccatttt tgtgaaacta ttcctcaagc aaggcagccg ataagtcatc gaagggtttg 93840
tgtgaataat ggaatggtta acattactca ttttaaactc tcccacggtg atataatatc 93900
ttttcaagaa aatgatgcga gaacccgcgg tgaagaaata aagagatcct tctatatcga 93960
aatctcagtt gaaaaaataa taggaaaatt cctggatcac ccgtggagaa gaaccaaaac 94020
agaatgcttc cgcctactca aaactaagag gggatgccgc ctactactaa aatcccggtt 94080
tttgcaacag ttgcgttctt ctatgcaaaa agaagactta gaaagaacaa agaagtttgg 94140
atccgaaaaa gtatgcttag gcagttcttt cactgagcac aacagaatga agaggaattt 94200
gtatcatttc aaatccctat tcttatcgaa gagaaggaac gagaaaaacc gaaatattcc 94260
tactcgaaca agaagtccta tagtttacaa ctcttcttta tatagtaatt cgacctattg 94320
ctccgcatcc ccccatcggt ttactaaaaa gatcaaaatc aaaaggatcg aactacctac 94380
tcattattcg gaggtgaatc atagaacacc aaaagctgtg gtatcttatg gacctaacat 94440
aggtcacata cctcacgaca taagattgaa agatccaaac cttcttcttc ggagcggaaa 94500
gggacgtggc caaaacatat aaagatcggc gtagtcgctc atagggacat atctatccgg 94560
atagaggata gtctaggccg attcatagat agatctctct ccatatagat aggtatctcc 94620
gtgaatagag ataaagatag ggatccatct agatcttgat tcactatttc catatttttt 94680
cttgattctg attgattgcc tttttttga cgacaagttt taaatcttaa tgcaggcaag 94740
gaaagatcgt ttttcaatta ttacttgctg ggtcggagcg tagacgagcg agcagagcca 94800
aggaaagagg gaagcccgtc atagagtagt cgactagaag tagaagactg ctggcctgag 94860
agaaggcggc ctctctcggg aaagatggcc caatttctct tctttctttt tgatttcagc 94920
tttctttttt ttttttcagg ggtccagaag gctaaaaggt gggggagaag gaagccgaac 94980
ctctaatcga cctggacaca taaaaaattc tcggcgtcga gagagatttg agattccgta 95040
agtaactcag tgactgcttt ctaagaaggg cttggaagaa gaaaatgaaa taggaacaac 95100
cgcgctggtc gtaatagatc gactttcatg ctagttcttg ctccagcatg aaagttccat 95160
ttcagggaag gacgacgtac tatgatactt tctgttttgt cgagccctgc tttggtctct 95220
ggtttgatgg ttgtacgtgc taaaaatccg gtacattccg ttttgtttct catcccagtc 95280
tttcgcaaca cttcaggttt acttcttttg ttaggtctcg acttcttcgc tatgatcttc 95340
ccagtagttt atataggagc tatagccgtt tcattcctat tcgttgttat gatgttccat 95400
attcaaatag cggagattca cgaagaagta ttgcgctatt taccagtgag tggtattatt 95460
ggacttatct tttggtggga gatgttcttt attttagata atgaaagcat tccattacta 95520
ccaacccaaa gaaatacgac ctctctgaga tatacggttt atgccggaaa ggtacgaagt 95580
tggactaatt tggaaacatt gggcaattta ctttatacct actatttcgt ctggtttttg 95640
gtttctagtc ttattttatt agtagccatg attggggcta tagtacttac tatgcatagg 95700
acgacgaagg tgaaaagaca ggatgtattt cgacgaaatg ctctggattc taggaggact 95760
ataatgagga ggacgacaga cccactcacg acaataagga gaagcagtgg ttcgaatcca 95820
catcgtgaga ccaggacagt gtggagaagc atcgataaat gctattaaca ttgatgatac 95880
ggcttagagg aattcctctc ttgctgccgg actgattcct ttccttttga tgtggacaaa 95940
tgggcatccc tagaatcagc tgctctcctt cctgttggag gaagacaatg cgaaaaaatt 96000
cataaataag taaggcaagg tgattgttcg ttgacaacat tggggcgtag cggattgact 96060
attgggatct ctttagcttt agtatgacta ttactatagg cgctggagga agcttgtcat 96120

-continued agtatgtaaa ctttgtggtg gatacgacaa caaaaaagcc tttctcccca accgaggtga 96180
tagaccacct tatggccgat gtgattacca gccaaagggc aaaaagacgg ggttgaatgc 96240
gactctacca ataccaatct cctctggagc aaggaaaggc aactctgcct ggtatcggta 96300
acgattaaca tattcttttt ttttagagag gggaaccctt acttaagaac agagagtggc 96360
cgagcaaaaa agcaaggcaa gggataaagg agaagtaccc ggcccggcaa agaagggtct 96420
cccattaaca ggtttttcct tagtaagcta gctttgtaag ctaagcaagc caggttctct 96480
ttcactcctg gaatgagcct tttggcgact ctctctcaac acaaagaaag aagagatgaa 96540
aggatcttca agtagccctg actaaggttt gaaaagattc ccgggggtac tacagcttgc 96600
gtggaaggct agggtggttt ttagaaagcg cgaagacaga agacgtcgta gggaaccaat 96660
ttctatcgct ttccccctct agtggtcatt cattcttttg atgactcgca gtcgaaagag 96720
ttggttggca gttcaaacct cagagggagt tgaagagagg cctttcagtt cgttcaaagg 96780
cactagggac gagccattac agacggtctg atgcttctgg agttcgctca tatcgaattg 96840
tccaaaagct catcaacctg tccgagggat gatgaaggcg atgccacaat tgagggaacc 96900
gcccttttac tctttttag ataagaatgc gaaagaccct gaccctgcca accaagccca 96960
ctcagataga ctaagtagac taaaaaaagt gcacaagaaa gactaaggaa acaaaacctt 97020
ttctcgataa ggctgggcca agtagcgaca cttcacccag attcgatcat cacgtcaact 97080
tgctttattc aacaaagtga tcaagcttct tagccaccgg ggaccggcct cgtgaacgca 97140
ttcgctaaag gcactactgg ccggctttct caatcttcaa tctaacttca gaaatagaag 97200
aagcccactt gacgagattt gatctaattc tctttctaac atttttggat tgacaggaag 97260
ctttcttgct gtgtgattct gccccccact ctgccagcag cctatgtgtc gatctatacc 97320
cagttgatct accactattt tactttgcac gttctggata ggcgcgcatc ctcatagagc 97380
gaggggtaga aaagatcaat gaaagactag agcgcgagct agctgatcta ccgacaagtc 97440
cttgatttct tatccgcgaa ggcagacttg gactcattga agaaagcact tgaggtgaag 97500
actaatgagc gattgcgaca actacggacc ccttaactag gtttttttact aaaaaaaacg 97560 aataggcttt cagaagcttt tccacacaaa gaggagagga agtgcttgct gccaacttgc 97620
cagacgagcg gacatctgag ctcagcagcg catttactat ttgatcgaag ggatggctaa 97680
aaggccaaat ccggctaaaa acaaaaagaa gagatcaagg agagggagct agacgagcac 97740
ttgcaagaga gcgaccggca gatctaaaac tgctatagta aagtagaacg aaagtacctc 97800
ccaaaggttc taccttttct tgtgcgttcg ggaataaata gaaagttttt aaatgtatag 97860
aagactctcg attgattggt tgtaatgttc acgaggttgt atataatcca atgttcagtg 97920
atatgacttt cctactgact gaattgcttg aattagttga aggtgcggag tcttcttctt 97980
ttgatttgag acgaattcat ttttctactg aaagtgcttt tgatagggaa tagggaaaag 98040
ccttgcctta ttcaagagta ccaggaagga gaagaataag cattacctct gttgaaggga 98100
gaagcccctc cctttgctta tttattcttc ctggtcttcg ggtctcatct gaacggctcg 98160
ctgcctattt agttacattt tttgttttga ttccagaaca gaactagaga tcctggcccc 98220
ctcccttgaa agctcctggt gctgcgacta tcaccggtaa gttgcgtcgg atcaacatcg 98280
ggattaaaat aaactgcaaa agcaactaag tcaacgccta tttgctgtgg atctactggc 98340
ccggacgctt gaatctattc caccgcaaac aaccgaatat actactgcag gatcttctgc 98400
tgcttttgtt gttattgctc tcacctgtca ctacgccacc tcagcagctg ggactcccta 98460 acctttttcta tctatcttta gaagtagggc gagtgagtcc gttcctttcc cgtgaaggtt 98520

```
ttgggatatg tgaccagatg cttcctccag atctaacgtc tctatcaaca aaattctctt  98580
ttcttcaccg gatcgatact aacttaccta ctcctgctcc taccggatcc aagagggccg  98640
atgcccgatt ccccgaccca ttactcattc cttcccgact cgatagggat tgcaatctcg  98700
agagagggag caacaattga cctccgacaa taggtagatg ggtgggctc cgatggatac  98760
agtgaaatct atccttattc cgcactccct ctcaccggcc tgaaacatat ataaatcatg  98820
aattcttcag agcgggccgg caggccgggc gtacggggac cgtcgaagaa gtgcctcaac  98880
gcgccgcagc cactactttg actcctttta tgcaattatg aactccacgg aactttatca  98940
attccaacgc aacttatcct tttggagctg acgtaacaaa ctacgcgagc ctcccaacga  99000
agccaacata aatccgatcc gaataaaaaa aagaaaagga agtttgatta ttgtggtata  99060
ccagccacca gttctggaac ttccagttcc aatcgaagca tatagatccg taaatagatt  99120
tgtatgtata gccacttcag tcgtgctcgt cctttctcta aagtatcttt tttctgggaa  99180
catggtcaac cagaaattat tatgttcgcg attcttcatc caccgatgga aaaaatgctc  99240
cagttttcca ttctcatatg aggccggaaa gtggattggc aacaggtcgg cacgaagtga  99300
ttcatcatgc tcaaacatga gccgatcgct cgttagggac ggtttataga tcatcaaatt  99360
cccacaaatg gaatgaaaag tgggtccatg taaatgatca agacctcgca aacaacaacg  99420
ctccttcccc atatggagtt cggaacccaa aggcaatcgt tgagtgaact gtatcttttt  99480
tgtgttagtt gacctaagcc gcacccttac tgctggggtg gggctcggcc tccgaaccgt  99540
acgtgggacg agtttttgcc tcatacagct cgggccgaag accgggggaa gtttagaaga  99600
gatggggaaa cctagcagct gccggtcggg gcggggataa gcttgcttct tcacaagcct  99660
atccccccaa aaaaaccgac cctgtagcgc tagcgcttcg ccttctttct attccatccc  99720
attccattcc gggataggcg gctaatacta aaataataag tgaagtagtc gtcgtctgac  99780
caatcggctc ggacaccaga ccgcccgtgc ccgcccattt tgtctcgccc taaatggaat  99840
ggctctctta gttacgctgc gccccgaccc gagtccccac gtccgctttt ctccgcccgc  99900
aacccaataa gttggcaaag ccaacacaag attagggccg tccccttcat tctatgctga  99960
ccccggcccg ggctggcttc ttgggaagcc cgttcccacc gcgctcacgg cccggctggc 100020
ctgccagcgg tagtgggaat tctcccgttc cctggtcaaa gacttggttg gatgcgggat 100080
ctactccacg aggagcggta cggacgtaga tgatatcatc acgacccctc ttttcgtacc 100140
gctagggatg cttaacgcca cttcgccaac tggcgttacc tgcgctttcg tgtctctcag 100200
tgtggtcagc actgggtgtt tccgagcagc gaggcttaca cccattcgca ttagttcatc 100260
caaagttcct taccccttatg cacgaattat tgaataagcc atcttcctat caaggttaag 100320
gagtcaactg agcatctcag cggcgggatt gaatacccgg atcgaatcag agttcacgcc 100380
gcccgccctg aacaaatagg aggcgtgggc cacaggtcgc acataagccg ccgggtcgca 100440
cgacagaaga acacccaaca taaagatgca cactcctcca tgtgaaatat tcatcttcat 100500
agaagctttt tgatagtagt cgtgaccaac agccatcagc tctcggcttg ttggtaaggt 100560
gagagcttca agcccgattt caggtggcgc accctccaca caagcaccgc ccgacgaagg 100620
ggggacgggg aaagctacag gcccaaaacc ttcgaccctt ctttctaaat gggggtgccc 100680
gaggcacctc atcttctcat ttcgtcgttg ctcattcccc ttaggccgaa gtctttggcc 100740
tttccttctc cgcgcccgct caggcttcgc tgacctatcg cgtggtaaaa agaagaaagt 100800
acgaaagaat agtaaacgga gcacaccgca gaaagattct aaatatgaga agtcccccctt 100860
```

ggattcgaga agaaggaaat gaagaacggg aacgaaacga aataaagcgt ttctagctct 100920
agtttcggat gagcttctcc taattatgtc tggtaataga atagggggc ttgctctgac 100980 caagactcca ctttttgctc cgtccgcgga gcgtatgaat ttcctggaat gtagatagac 101040
caaaagaggg aatgaagaga taggaatagg aattatagta ccattggaaa aaagggcacc 101100
tgtgggaaca tctctactga cgaaccattt caatagtacg ggtgctgccg tgccacgagg 101160
cacgaccatg gaagtaatga aaaagaaaaa gttatgtagt tggaccatct gttctatccg 101220
ttcgagtttt gcttctctag agaagatgag aggctaaaaa tgaaagtgtt cgcaacacat 101280
accgaaaggg tactaattaa gccgaccatt aatgactagt taaaacacca ggagtggtct 101340
gatcccctat ttgatcagac cgctctgaga aagagaaaaa gcaaactctc ataattcgga 101400
gcccagctcc aacaacttct tcgtaagtga ggtgaggtac ttcctttggt ttgaataggg 101460
ggtcgccctt tttttggttg aagtagccac gactttggtc gtagtcagtt taaccccata 101520
aacccagtcc acttgcagcc atgttgatca aaatgactaa gtttaatgac ttgaccagtc 101580
acaagccctc gtattataag attctctcac cctgtggtcg acattccatt ccccttagtc 101640
gtaggtgctc gttctatttt gatttgaatg ggccggggct cccgaggtac atatggccgt 101700
cccttcgggt gtctcggtga tacaaagaaa gaaaagacga tggtttttaa catacccttg 101760
aacaaaaggc caatccttac caaaggagga aatagaatag aataatctac cttctttttt 101820
ccttcccgtt gattcccccc gacaataaag ctgcacttcc ttctaacaag tggctgagag 101880
ttagcaagca accttggcct cttggcagga ggttcgctgt ccccctcctt tccggtccgg 101940
ccgcagtacg gcacctgaac tcgaagctac gatcagatcc gattggatct ggtcctatcc 102000
gacccaaccc cggaacttag aacggccggc ctgtttggac ggtagaacgg ggagaggggg 102060
agtcgtgccc attctctatc cgggcacgag caggaacata aaaaaaaaat ggaaaaccga 102120
atacatgtac atgatctaac gacatattca aaaatacgtg atccgatttg ataggctgcc 102180
cgcagaaagg aaagagttta ccgaccgcat aacaattcat tcttgtgtgt agcgcgtggg 102240
cccatgtctc tcgaacgatc atagtacggc cgctcatcta atataaaatc aatgagtaga 102300
tctcacctcc ccttccccat accatagccg gaagggatag cgtatccaca gaagagagag 102360
tacgggccct tgcccaacat ttagtttaga cgcggctcga atgcctttat gctataggct 102420
gtgttaagca tgcttctttg acagaaaaca aactcttttt ccatgacaac agtcgcgact 102480
ataaagggcg gggcggtaag ctctctatca acaatagggg gctattcata gtaaaaaact 102540
actagactat atggattcca actgaacttc aacttctact tggttgatta attcaggggc 102600
agtgctccaa cataatgttg gacgatctcc atttccatat ggtaattgaa gtcaaacagg 102660
agcaaagcag gtgcaattca atccttattc ctagcacaaa aaagcaaaac ctcactagac 102720
cgaggcccat tgctatgggg actacactat ataagagaat gactaaggta attgccaata 102780
gtttctattg aaagacaggc tggctcttta aaaagggcgc cctcctaatc tcattttgat 102840
aggaagagat attgaaaatt ttcccaagga ggcttactac tcagctgata gatcaggtga 102900
gccagccatg atcactaaac tcaccaaacc tgcagcatat tcaaattgga atcataggtt 102960
tctatatgct taaggaaaat gggatttgca gagtaggata cgaaagttta tttatataca 103020
atggaaagcc cctataatcc atggacgacc agtggagttc ataaaagaaa ccaaagaaag 103080
gtccgcgaca aagctgtccc ctctctccat atctctactt actggctggg tgcagataac 103140
actgtaataa taacaaagcc agatagagat actgttcgtt cagaattgat tcagatggcg 103200
aggacccacg gaaaaatcca ccttattcat gctccgcaca gcaacttgcc cggtcaatat 103260

-continued tatatgtcta tgctaaactt ggtgatctat tttcgttgcc ccctttaagc gtatgtgata 103320
taatcattct tatctcagaa gagaagtatg cattgtcccc acttaagtta ttaagtattc 103380
ccaaagacga ggcgatttct ttttatgttg aaactttatg tcagccaggg gaccctgatc 103440
ataaatgggt tgtttgtccc ggtgaaaggg acgctctcgt tttaatcgct ctggcgcata 103500
tgtttaatag ttgttttatg cgttcatcta tctttcagga gctgtcgtgt ggttttccca 103560
gagatcgccg tcagttcttt gccaaattag gtggagtggg gaagattaga actattttca 103620
tcttgaatct agcaccctca caaggtacta ttcctcataa aagaatttta cgaaagctgg 103680 caccccttggt gcgtgatagc tacgtaatat ccttagtttc atcctttttta aagatagcag 103740 tttatgacca aaatggaatt aattgttcta ttacggaagt tgggatccca cacgctgggt 103800
taatcaaaaa ggtcttatac aattttatgt tggatgattt cgaccgggga tttaaacagc 103860
tataccctag tctttcttat tatcgttact tggctgactg ttacgtatta tttccattgt 103920
ttagtctcta aagcgagcag cagtgtgaag aagaaatgaa tagtatcctc ttagagttag 103980
atcttgatgg ggatatcaca actattctac ctggtggggg tgcccatgtg actcgtgatg 104040
ggcctttgat tattctaagt cgagattgca gtcttcacgt tgtcgaacag tcaacattct 104100
ttctttagtt caatttgtag tcaatatgtt ttatacaaaa aggaacccat gcttagatag 104160
gaaatccttt ttttagagag ccaatgcctt aagacagacc ctaatagcag ttgtcgccta 104220
cttcactgag ttgtggttct aaaaagagga tttttcttgg tatattccat caagagaaag 104280
ccatatctat atatataaag aaaaatcgaa attgtataca ggtgcttaca ctctcctgag 104340
gattctaaga cccgatcacc cgtcaaagaa atatccttag gtcttaagtc tacagctccg 104400
tagcttgtgt cgcctacata gggtagaaaa gaatgctttg cataaacatc tcaatgtcca 104460
agataaaagg aacgagggga agaatcgacg aggccagtgt tctcgaagag aaaatcgtga 104520
tggaaaaagc gtgaggagaa ttcgaaagtc gagatatgca aaataaaaag actccctggg 104580
agatggtatt ctttgtttta ggtcttgata gatttttcta ttgattgaag ttattacgct 104640
ggctgattaa atctcttcct aacgccttta ggggctgtga agagagccca gttccaggcc 104700
ctcttttaga aagaaaaaaa tggtacaaaa agagggcttg gggtatata tactataaaa 104760 attgatgatg gtttatcatc atcagaacta agatcagtct aggtcgagat gaatggaaga 104820
tgcttctgga actagttttt gatagggtct atcttagctc gaaggaaaga acaaccaaag 104880
ttacaccccc aaagaatatg gattcaaatc agttagtatt tgacaaagaa cctaacggaa 104940
tttaacaagc agtaaccgga atcaaagttt tcaaaaatgg tgtcaaccgg taatagaatg 105000
tagctagata actgatgcca cagcatccaa aatatgtggg atggagttca tggtacacta 105060
acttaacctt caaggtcaga tagtgctaca gtgaacatca atccactatc tagctcaaaa 105120
ttagcctcac gaactactaa cactattatt cgcgtagccc ttttgtgtgc tatttcatca 105180
taggctgtcg gaacttgctt cttagcgcta cgtgggaaga gaatttctct attcagcccc 105240
cccctattac aaactttaac ttctcggtct aacttggact aatcccttag caggcaagaa 105300
attcctacta accagacaga aagtaagttt ccactcacta ccaaagcgct gtcgcacctc 105360
tactattttc ggcgtaacga ggttttagtc tttacgaggg caccccctag ccagattcaa 105420
tcccaagggt caatcaagcc tttgaaacta gtgaaaatag tcgtcacagt ctgagttcct 105480
gctttcaacg agactttctt agcttgtcaa actttctctc cttcaccagg aaagttatcc 105540
ggtaagcaag atctttgatt gatgtgcctg aataaggttg atcaatggta gctgcttgga 105600
gctttctcta taccttaatt gaactaccct gctctttctt agctcgggtt cttgcttaat 105660
gaggcgtcct tgtttgctct tggattggac taagcggcaa tccttactgt ggaagcagac 105720
cttgtcattc ttctccttca atgccagtgg ataagtacac tagggctgga atgctctttt 105780
atcatgtatg tggattactt ggtcgattac ctgattgcac tagtctcata gccatctctt 105840
tagcgtcccg ccattccttc ttgttaacac aggaaatcta actcattcta aggtagagct 105900
cttagagtcc tacttaaagt taaaggtagt tctttagtta aagcaaggag agcagaaagc 105960
agctaccggc catcaggaga tccacgactt taagatccgc atgcatgcaa gggaagattc 106020
tttatagaag attctcttta ttcccacctc aagctcggtc attggctgtc ctcctcaatc 106080
gattagacta tggcgaatca cttgtgtatt ggtctttggg aaagtgtaag acgctattgc 106140
tcgcaactgg gtcttgagtg tcgatctaac aaaaaagtaa actctagttg cttctcttgt 106200
ccgatcggaa actggtcttc tttttatggt gtaagggtcg gcaacagctc cctttggaag 106260
gaatcgatcg tcaacgtctt tggttccctc cacccgccgc cttcggtcaa ctcaaacaag 106320
aggccaggaa ggacattgtt gaaggctcac tgagtgctta taggttaaag ggttgcacta 106380
gactcactcc acgggaacta gcttttcggt ttgcttaaga tttggcattc attccccctc 106440
cccttcctga atttcgcctt attgcttatt gtctgctatg ctagcctatg atgaagacct 106500
ttcattttgg ctctgtaggg ctaccctatg gtatgggctg ttatctcaag ggccaggtta 106560
ggctcttctt gttggagtat cctcgctcag aggctaaaat gaatttcatt ctctcttttc 106620
ttttgggagt gcctgaagag acctgcttac tggaaggtac cattctaaaa gaatggtgaa 106680
aaggttacct accctatgat cctccttatc ttacagaggt ttactacgag ccatacccag 106740
cgggatacat attgcccaaa tggaacctaa aagatgggat gggtgatcca taagatcatt 106800
tggcgaggtt catccctcag cgtggggatc cttctggaaa taaaaacttg ttttgttgag 106860
gcaatttccc tcgtcgctta cccgcatttc tcttggtata cccacctgtg tgcctcctaa 106920
ttccgtgaag tccttggagc atgtgcgatt tattcaggat ccttgtcaag aaagaagtca 106980
gtcccttatt cttgatttta tgttaaaagg tctggactcg aagagggagt cgattcacgt 107040
acttcaccat ttcctgggtc gttatcgcct ttccccggtt cagggtatgg gttctttctc 107100
tattaagaaa gtcccggtgt gaactcccct actgatctga ctccagcgga ttctcgagaa 107160
gccaattctc tctctcgatc tactttaccg acaagagctc ttaatgaatg agcaatgagt 107220
ttgattctaa ctattcaaag cagaggaaat agaatattat atagcctata gctatagggc 107280
taggctccgc tcctcgctcg agctaccagc tttcttagat ttcattcctg ttgactaatc 107340
cgagtccttg agagcttaga cgtcagcggg gaagaactcc gaaagaattt catcggctcc 107400
tcctctcttg ccctcttgat ggtatccagt tgaaatggtt gctggattgc ccctagttca 107460
agctctaagt caggcattca cgcaccaaag acctctgact acgctcctca gcctaggaaa 107520
gaaaattccc atttgcctaa tacgtactac tgtgcagcag atgatttagc tgccgttatt 107580
cctccaccag cttcttcttg gcatcaagcc agcccttatt ccttgcatca acaggcaatc 107640
ccgcataaaa gaaaggctac tgacttggct gattcaacaa gggaaaaagg catccattca 107700
aactgctccc attcctatgt tgacaccaaa ccaagagaaa gaaaccctgg agccttcctc 107760
tctatccatt cctttttcat aatcataaag gatggaaatg cttagcttac taaaccagca 107820
acagcggagt aagctcccat atccgtgaag gactgctttc cagcagagga aaacttctcg 107880
ttgctgagct tgccgttaaa gagtaagatg ctgattctat agcagctccg attccttcac 107940
cgagaacgag aaggaagtct tatagaacga acaagcgcta aagaaggggg tgggatctct 108000

-continued cctaaaagaa agaattgacc tcgagcctgt cctactcatt ctccttttcc cgttcctgac 108060
cctgagtgtc gaggggttag ccttgagcca ggtcttgatt gtttattcca ttttgtcagt 108120
ttaagtactg gaatgggagt tacggatatt cattcctaaa ctatgtcacc gattggtgac 108180
ctgatcccgc taagcaagaa cagctaccga caccgactct atcttaacga ccggtaaagc 108240
cctctctcta ggatatggca cttcactgct cggagaggaa agaattcttc tccaaatcat 108300
ctcttccttt atttaagtta agaaagaagt caattacgtt cgagcttttt gtcaactgat 108360
tcaactcaag caatagaaag aaaagctatc tcctctaatc tctaagtatg cagagttcaa 108420
tcaagctaag aactagtcga cctccttact tttttaccgc tagaaccttc ctttcacgag 108480
tgaacccggg cacgagccta ccttgtaaga accaaaaaag gggtaccggc gtacctacca 108540
ttaccatata gggaatgaac tgagttagag gcatatgctt cctttaccga tagccggtac 108600
cgaactatcc gaaagccctc taaaaggctc aagaagaagg attggatgat ctgcggaacg 108660
gaatgagaaa gagcaacaat tgtctgacca aagtcttacc ctttctttcc ctttcgactg 108720
gcattatcac accgccatca ccagattcaa tagctgctcc tagcccgatt ccaagacctg 108780
accaggtttg aaagttcaag cagccttgat caactatagg aaagtaccag ttttccacag 108840
tgacaaggac ttcttagaaa gcattgattg gaggtctcat ggtggcaaag aaaaagaaag 108900
aggaagcgct cttgttcttg ttgcgcggac cccacaataa agaaagatgg aagacaagaa 108960
gctcagtagc aaggccgtct catagtcacc acttgtctgt cgtttcaagc ttccaaaaca 109020
agcagaaaaa cacgttgtcg gttcagcagc tcgaagttca tctcaataaa atgttaggtc 109080
aatcacatga ctcatcctgt tagtcgagca tagctaacgc taccaggacg ctacgctgcg 109140
cctgcactga cgtgacttgc aaacaaggct gacgccttat agccatatac gcaacgctcg 109200
ggaccacctc ccttcgcttc agagtcttag gcgcagctct tctagtcaga gaagagtcca 109260
gttgcgaacc tgtgcgctcc tatcctattg ttgcttctat cacgataggg aatcgtgtga 109320
ttctttctat ccccgtactt tctcgctctt atggagttgt attccctagg ttatgcagtt 109380
atcttccctg gcctgacagt agtcaaggga aaatcacttg agctttttcg cctttgctcc 109440
ttctttccgg agcgcactaa cggaaaacct gagataaggt atggaagcag tctgattatt 109500
tccacttgag tcgacttaag tctttctctc ctcgtacagt cttggctcta gtaaagagaa 109560
agaatctctc cttaccctac tgcgggaaaa agcactttct atccccccgt gctacaaaac 109620
aaacttatct aagcactaaa agcaaagcaa caataaggaa tggaatggga gaagctatag 109680
tgcagatcac ttttcacttt ctctagagtc cagaccttgt ccttggttct atcagctatg 109740
gagtcttcct ctggttcttc ccgtctctag tacagatcaa atcacaggat ctctgtatgt 109800
atgcgctgag gagctatatc tcccggacga aagactttta aaccctgatt tccggaatgg 109860
cagcaatcga cttctttctg tcttacagct ttcttgtagt actgctctct tttcaagcga 109920
atctctattt caactgcatt ccctattgca aagaaatcaa cctcggttct ttctgttgat 109980
aggttagttt gattccaggt gtgagcctct tcagttgcag tgaaagttcc cgactctcta 110040
gtgctatccc cccttttca gcctgacatt acaaaggtag acttcatcca ccggacgccc 110100
tggctttctt tttcgttttc caatcttctg tcctttcctt cattcttgca gatgcaaatc 110160
atagatgacc tagtggcatt tatgccagac cagagcattc ttctcaagaa aagaaaagaa 110220
aggggagagg gtgactgaat ttcactcttt atcattcctt actactcctc aattcccatc 110280
aagtgttgtc ttatttccca agccactgct caatcctcct tttctgattg attgaaagta 110340

-continued gcaaggaaag acaagcaaaa actttgttgg ctcaagaagc aactgaggag agacaaagag 110400
tagtaaagga aatacaagta gcagtctcag gtcaaaggaa tcaaggaaga atttcttctg 110460
atattgcggt tactcttcca gaatctcatc ctgagaccta agtatgccat tctcttcgtc 110520
aagaaagatc gagcagcata gaagccttga cttcaagctt aggtcttttt tttgaaaaag 110580
ggaactaagg caacttttag gtgcagggaa agaggttcgc tagccttttc cctagctttt 110640
tttgtcaact atctatcttt ccgaactaga ttagacggac ttacttaaaa tgaaaaaagg 110700
gctaaaaaag aaggacgaag taatttcgta tataaagata tggctttccg ggtttagatc 110760
gaaatggaat ccccgaaaac cagggctgga gtcttagact tcttctgctt cgatagaggg 110820
actgacagcc taagtggaat aagaatcatt cggccgattg ctctgactct tatccttcct 110880
tcgctgacag agaagagaga gagcactccc caagccaagg atgagtgcca aagagaagat 110940
gggcaagcta gtctatcaga aggagaaagc gagggagtga gattttcgct ttcattaggg 111000
tagactgaag accaagccaa tctcgattca aaaaagaaaa cttattgcaa ctacgaaggt 111060
gaagagatgc tttctcatta gactatttta accgaaaaag tctttatgtc gaccctaggc 111120
tacgattctt cttctcttat gaaatttata gttagatgaa gactgctctg ctgcatgacg 111180
gagtgatctt tccctcttat gaaaggcgct atctcacttt cgaaagagag tctcgacgtg 111240
gcggtctaga cctagctcca tagctgggct agtcactggc tagaggtcga gggacctagc 111300
ggaccggagg gagccgagaa tgttatgtaa aaaggaccaa ggaggattca ggaggagaag 111360
gaggaggagt aggagctagc tttaggggcg gaatcgaagc gaagaaatta gttcatgcca 111420
cgacgatcca tatggaaggg cagttttgtt gatgcattcc tcttgagaat gaagaagaag 111480
agagatcttc tttttaacag gaaaatttgg tcacgtagat cttctatttc gccggaattc 111540
gttgattgct ccgtacgaat ttacaatgga aaaactcctg ttcgttgtaa gattactgaa 111600
ggaaaggttg gtcataaatt tggagagttt gcttctacac ggaaacgaag accttcgaga 111660
acaaatattg gaccgggaag aaaaaggggg aaaaagtaaa gtctaagcgc atatggcacg 111720
aaaaggaaat cctatttcgg taagacttga tctgaatcgt agttcagatt caagttggtt 111780
tagtgagggc gaccgcgaaa gtcaccgaat gggtcagtct tttagttctc ccagattcga 111840
atctcaaagg aggacgttgc agatgcccgg ggcggacacg acttcttctt aggctagaag 111900
accactggaa gacacccagg actatagcat gtcgtgaaag aagcacactg gacgggcgtg 111960
cttcgaccgt gtctccgggg cacagttgaa tgtagatatc atgaacgcga ggtgcaggat 112020
accaggccga gaaacccggg caaccattcc cctatgtgcc aatcgctagc gcatccaggg 112080
ccccggcgcc cagctcagct ggagaggcct agcctgatct gagaagtgct aattcggttc 112140
ggatagactt cattcaagaa tgccaccgcc ccgggaatca ataagaaaac aagtgctaag 112200
tttcagatca gtgaataaac cgaaaggaaa gaagagacgt ttctcgctca gcgcctaaag 112260
cgcactatgc tccgcttcaa caaatgagag ttttcggtgg aaccggtgaa ccacgcgagc 112320
tggttagatg cgtgggacag agggctcgta gtacctgcta gcgcggctac gcagtggaag 112380
ggaaggagcc taaatcgacc cccttctttt tttctttgaa aaaagcagta aggagtaagg 112440
agattaaact ctcggatgag actaagcagc taccgaccgt tccgacgcgc ccttgaccta 112500
ttttgattaa gaccaaaaac ctatctctaa agtggagcct agtttaagct gtcaaacaag 112560
tgatgattga atgaaagaaa aaccactagt agggatatgg atggagtctc gctcagtaaa 112620
gagagttgta ggattcgtaa aacaggagaa gagcctttac tttcaaatga caactgcttc 112680
ttcctgctgc gagggccttg cacgaaacca aaccgccccc cgcccgatca agtaccagtt 112740
gcttcgctgg taggcctact taggttaggt ttggaaccct cagttcttac caacctccgg 112800
tgtgtaatct acatctttct agctagaact aggtcgaata agaatcattg actccctctg 112860
ctgtcaattt cttattcatt cattgcgttc ggccggtgct cctttctcat ctcaaaccat 112920
aactactctg aaccttaggg aagataaggg aagaccgcct gagcgaagcg accgaaggaa 112980
cttgacttat ccgaaccgaa cgatagcggc ttaaagcgtt gcctatcacg agcagcctcg 113040
ctccttgatc ggcggggagg agcatctcaa agtatggggc aaaggatgtt gcgttttgac 113100
tttgtctccc gggatccacc acaggttggg tttgagagcc gtgtgatagg tgactatcca 113160
gcacggttcg gagagcactt ttagtctgcg ctggtgaatg gaagcccccc ctatcaagca 113220
agaaggaagc ggctcttccc acggcggagt caccattgac tctatttatt attatggtaa 113280
atcagtgtat caagatgtca atctgagatc ttatttcggt tcgatacgtc cacctacgag 113340
actcaccttt ggctttcgtc tcggtaggtg tattattata cattttccca aaagaacatt 113400
cattcatttc tttcttcccc gtcgaccacg acgactgaaa cgacgcgaaa aatccagacc 113460
cgtaaaggag aagggccggt ggggggcatt tgggaaagtc gggccgatcg ggtgtcttca 113520
ttcaagcgac ggtacagaag aagaacgaaa cgaagtgaga ggccgggggg cagggaaaag 113580
agtcgagtcg atcaggctcg acgatcggga gaagcaaaac gaaatcagga tttggccgaa 113640
aaagaagcaa ggctatggat accatgaccg atcaccatcg ataaagaaaa atctgtctaa 113700
atcacttcgt gtcagcgggg ccttcaagca tccgaaatac gccgggattg aaaatgacat 113760
agccttcctg atagaaaatg acgactcctt cagaaaaaca aacttattca agttcttttt 113820
cccaaagaag tcccgctccg accgcccgac gagtcatcta cttaaaagga ccctccccgc 113880
agtccgccct tccttgaatt attcggtcat gcaatactta ttgaatacaa agaacaaaat 113940
acatttcgac cccgtcgtag ttctcaatca tttcgtggca ccgggcgtgg ctgaaccatc 114000
tacgatgggg ggagctaatg cacagggaag aagcttagat aaaagaatac gttcttgcat 114060
cgcttttttt gtagaaagct cgaccagcga gaaaaagtgt ttggccgaag ccaaaaagag 114120
ggtgacccac tttattcgcc aagcgaatga tcttcgcttc gcgggaacaa caaaaaccac 114180
catctcgctc tttcctttct tcggtgctac cttttttttt ccaagggatg gggttggggt 114240
gtataataac cttttttttg aggatgcccg ggaacaactc ctaggtcaat taaggagaaa 114300
atgttggaac ctcatgggta aggataaggt aatggaattg atagagaaat tcatagacct 114360
aaataggata ggagaattga taaggggaat agagatgatg atagagatca tactgagaaa 114420
cagaagaatt ccgtacgggt acaactatta tttgaacgaa gtgaaaaaaa tgcgatcttt 114480
gttgtataat agaacaaaca ctaatacctt aattgaatcg gtcaagatca aatctgttta 114540
tcaaagtgct tctccgattg ctcaagacat ctcttttcaa ccgaggaaca aaacaagatc 114600
atttcgttcc atttttagta aaatagtgaa ggatattcca ttagtaatga aaaaaggggt 114660
ggaggggatc cgtatatgtt gttcaggtcg attagaaggt gcagaaatag ctagaactga 114720
atgcggaaag tatggaaaaa catctcgtaa tgtatttaac cagaaaatag attatgctcc 114780
tgcggaagta tctactcgtt acggaatctc aggtgtcaaa gtgtggattt cttatagtaa 114840
aaaaaaaaag ggacgtgcta tatccgaaac gtacgaaata tagtaaatat cgtaaaggca 114900
gatgtagtag gggttgcaaa ccggacggta cacaacttgg ttttggaaga tatggcacta 114960
aaagttgtag agctggtcgt ctttcatatc gagccattga agcagcgcgt cgtgctataa 115020
tcgggcactt ccatcgtgct atgagcggac aattccgaag aaatggtaag atatgggtaa 115080

-continued gagttctcgc agatatccct attaccggga aacctacaga agtaagaatg ggaagaggaa 115140
aaggaaatcc tacgggttgg attgctcgtg tgtccagggg acaaatccta tttgaaatgg 115200
atggtgtgag tttgtcaaat gctcgacaag ccgctacatt agcggcgcat aaactatgtt 115260
cgtcaaccaa gtttgttcag tggtcgtaag cttattaatc tgacccaaat tccccatttt 115320
ggtacacgcc aaagccttcc atttcggcgg attgaaagag ccatcaatga ctagaatctc 115380
cttttagatt cgaaattctt cgttttttc tcccatgctt tccgttggtc aacaaccaac 115440
taaagtgctc tatacttctt cactactcgt acagggaagg tggaagaaat tcagtctctc 115500 tttttttgg ggggagcaga gcagtgaaag aatgaaccaa accaaatgat tgttctagaa 115560
tggctattcc tcacaattgc tccttgtgat gcagcggaac catggcaatt aggatctcaa 115620
gacgcagcaa cacctataat gcaaggaata acagacttac atcacgatgt ctttttcttc 115680
gttattctga ttttggtttt cgtatcatgg atcttgggtc gcgctttatg gcatttccac 115740
tataaaaaaa atccaatccc gcaaaggatt gttcatggaa ctactatcga gattcttcgg 115800
accatatttc ctagtatcat ccctatgttc attgctatac catcatttgc tctgttatac 115860
tcaatggacg aggtagtagt agatccagcc attactataa aagctattgg acatcaatgg 115920
tatcggagtg cgcctcttca cgagggtgat taaagtgcaa cgaaatgcct taaagttgaa 115980
tatggttcgc gaagcatctg gcttaccggt aatctcccat tcccgccgtc gagagacttt 116040
aataactata gcatgccaga aacggggagt tgaggtggtt agacctatac cccgaaatgc 116100
tcccagcata ggagcctatg gttccattct tgttgttgct ggaggtacac atccctcttc 116160
tcggtgtgga acgatatacg agaaatagat gctcagcctg caatgtccga taacggcgct 116220
gaagtagtga atctatcggc accatagcag tggtatacaa ctttggacct aacggccggc 116280
cthgtaacct ttcggaatgg ggatccccgt tggcaacaac cacggtagta gttgcggaac 116340
tactgggccg ggagagkaca acctcttgtt cctgctcctc tttcttcgct tcggggacgg 116400
aggtcctacg gtaggtaaca gcaggcacaa gcaagttgac cgaaggggac cagcgcttct 116460
actcctccac cgaggagccg ttcttgcgag aagcaaggga tgtcgtgaac ggtgggaggt 116520
cacagagaat tgacctattc atagagtgat cctatgatcg atacaggata tagactatct 116580
cattctttvt tctatgcbat ttctgramaa aagarrahvb cgkactcaac ttctmascwa 116640
gagttkgkgg tkggacckct tggcataatg cacgctggaa cgtgggaatt cgaggtctca 116700
tgaactacta ctaaaaccga ctttgttttg ttttgtttgt ggacaaacga tatccggtca 116760
ggcctatggc tggatccttt tagatctaca ggccggccgg ccccggccgt ttacatgagc 116820
atagggaatc tatactcgag cgttccactg ggcccctgac aggataggtg aggaatcact 116880
ctggatcttc ttttttgggc tacaacttcg ccgagccgac tagcatccct ttccactgtg 116940
catttttcga acaaagaaga cgactatagg atcgaattcg ctcttcaaga aactgctcgt 117000
cccatacctt ctgcctgtct catatgtgtg gaacctggtc ttttcggttc cagcctctcc 117060
ctcgaataca tagggtaggt agggctgggt gataaagggt tccctcttgc caataaactt 117120
tccccggcct tcgattaacc ttactcataa agggtcttac ggtcgggaga actacctaac 117180
taaagaaaaa tagtgttctt tctaagagta ggcgtggaga gcttttgcgg ggaaacttgc 117240
aagtacagtt tggggaggcg ggcgtcgacc ctaccttatg agtattcgga ctataacagt 117300
tccgatgaac agtcactcac ttttgacagt tatacgattc cagaagatga tccagaattg 117360
ggtcaatcac gtttattaga agtcgacaat agagtggttg taccagcaaa agttatatac 117420
gttttattgt aacatctgct gatgtacctc atagttgggc tgtaccttcc ttaggtgtca 117480

```
aatgtgatgc tgtacctggt cgtttaaatc agacctctat ttcggtacaa cgagaaggag 117540
tttactatgg tcagtgcagt gagatttgtg gaactaatca tgcctttatg cctatcgtcg 117600
tagaagctgt tcctaggaaa gattatgggt ctcgggtatc caatcaatta atcccacaaa 117660
ccgcagaagc ttctccagtc ttcgtcggtt ccccaaagaa gacactattc ttttgggaga 117720
cccgtcgtcg acgaagatga gctctacgaa gcggcttacc accccttcta cgcggccaac 117780
gtagtccaca tccctgggga aattgaagac ccctttactc tggctaaatt aagtaaatta 117840
aatgggactc tcctagccat agcggatctc ttttcaacgg ccagataagg ggatcgtaca 117900
ctaaagagct gcaacttgaa ttgaatgcga ccgaagaagg cgagctggcg gctaagctgg 117960
aagagctgcg gattagggaa aagcggcgct ataatttacg ctagggtgag caagcgctag 118020
ctctttctct tgcggtgaaa taaccgccgt atagaggcga acagccctta tagcaatagc 118080
aaacggccta cttatagcct ttcaacaggt cagtcaatat cagtaagtag ggtcctcttg 118140
cctaacggag tcagcccaac atggacaatg ataggcagac caaagattta cgcagtcgtt 118200
gcgtgcttgc tttgcgcacc ggcatagcag aattagaatc cgctggctca gatgagtggc 118260
tcttggcttc gtaaacatat ctatgttgtt gchbtccaca hccacbcagb tggcagcght 118320
ggatgcttat ggagatatgg cttggcccag gactattggc tttccgtcaa gtgtcagttc 118380
agccatagac attcaattca atctcggaga tagtcaaaat gccattgtcc gttctaaatg 118440
aaaggaatga gataggccgc ttacacacgc ttcaagtctt cttttgctga ttcaataaca 118500
gtctggaaat tcgactgaat aagtcttagt gtggttaagc cggggccagg gtcagaagtt 118560
cttccatctc ctgagataag atcagacaga gcctatacgc cttcttgctt tgctgcagct 118620
accgggtatt cattcaaaag aatgcattta ccttttctcc ccttccttcg gcatccctga 118680
ctcgggcatc cctttcaggt gcagttgacg tacaatttag gtaatttata aggactaaac 118740
gtactgatga aagggaaaac ttaggaaaga atagctaagg agaatccttc gtttgaggaa 118800
agagatgata aaataagtca tgaaaaaaac ccagtttgtt ttaaggctct catgaagcct 118860
tagggcgaat tcctctcaca ttggaaactt cgctcacttc ctatattatt cgcgcaccta 118920
cctaccacaa tccggttcca agtcctttat tttaaaatcg aggagtagtt caacttttct 118980
ctcttcggga ctaagagaac ttacttacta attgaaaaaa aagacaacta gaacgaggtt 119040
tttttacgtg atcggaaatc acccgtcggt gatgaaccag tacgcactta ggatagcact 119100
tcgggagagt gagatccagg tggcatatca aaagacttat caaaatcgcc accatacgag 119160
acttgcaggg catgcccgcc agaaagtgaa gagaggttta taagcacccc gacttaggaa 119220
tcatgaccca ccgaagaaaa gaagactcga ggaaaactat tgatcccttt gatgactctc 119280
ctcttcatct tcgcgggttg cagagaagaa tccgaactga ggaaatgaaa aaaaaagaaa 119340
agtatctctt tctctttcta cgatcacctg tagcgtcctt aaaagtctta gaaggagaat 119400
ctaactattc tcgaagagat tcttgccaac accattagga agatgaggga aaggggaaaa 119460
gaagtcaaat tcgctatttc cgacagctac ggtagtagag aaggagaggg actacttatg 119520
agaaagagga gtctctcttc tactcccggg tattgaaccg ggatgctttg gtactagact 119580
gggcgggcga gccataatca caggggagaa aggcgcagat cttttcatcc tccgccaaca 119640
agcagagccg acaccgagct acttcgtacc ttttcattca aacgggaatg actccactct 119700
cagtcccagt gtggcttaga ctagtagaag gcgtaaggat gctagaccgc tgctcaatac 119760
tggataatcc acgttcatcg gtctgcagca agcactgact tttaggggcg gcaactaaag 119820
```

aggtagcgag actaagcgca atttcaggaa gagttggacc cttgcctcta agcttccttc 119880
taccccttgtg ctaaaggaca ggaaaaacaa cttctttctt tcttttttt taatatattg 119940
aataatggaa taactcgaac cctactaaag agtggctttc agctcctccc cttctttcat 120000
tcagcgactg ggtacgcact tcgccatgaa agatcttggt gatcttcatt tctttcttag 120060
gaatcgaagt caaaggtaca tcgacttctc tagtcttgac tcagactaaa tacaccttgg 120120
aattactcga actcatttgc aagactccaa gccatgtccc acacccccttg cgtctggctt 120180
aaagctctct gcatacgatg gtcctcctct ctctgatgca acggaatatc gtagcattgt 120240
tggcgccctt caatacctca ctctcaccac cgtatatctc caggctgtaa aaggcatctt 120300
acggtatatg aagggttttc ttgggcttgg cctaaccatc actcagggac tttaaaccac 120360
cttctttgca ttctccgatg ccgactgggc tggctgtccc gatagcagac ggtccactac 120420
ttgcttctgc gtatttctcg gaaacaacct actgacttgg gtttcaaaaa aaaaaagaaa 120480
ccgattcttt ccaggtctag tgccgaagca gagtacaagg cactcgctct tactacctct 120540
gaactcttat gactttctta cttactacgc gatctagcgg tgccgtttcg ctatcaattt 120600
tcgtgcactg tgataatgct agcgctacac acttggtggc caatcctgtg ttccatgtcc 120660
gctctaagta catagaagtt gactaccact tcgttcgtga cctcgtcgtc gcaggcaaat 120720
tgctcattcg acttgttcgt agcaacaatc aagtggcgga ccttttcact aaaggattac 120780
ctgaaccccc ttccatcatt ttctgctgtc tcccgcctgc ccttctcgaa agaatgggct 120840
cctggccgtc ctatctcatt gaaaaggaca aaaccattta cttttccaat caaagaaagt 120900
gaagccacca aaaaaaagaa aaagggtata gtaatatata tataaagtca aagttcaatg 120960
gtaacgactt cttccattga cttcaggatt gcttggtttc agggaaagtc tctcgctcct 121020
ctccttatag cgctggcctc tgtctttgat cttggctcga gctctgtcct ctcctctccc 121080
tatgctattg atttacgtaa ttggaaataa ccaattaggt ttacgacgaa acctagaaat 121140
cgatcatgat ccaatttgag tacctctgca ggatagacct caacagaaaa ctgaagagta 121200
acggcagcaa gtgattgagt tcagtagttc ctcatataaa attattgact ctagagatat 121260
agtaatatgg agaagacaaa attgtttcaa gcaccgacag aaccggaagc gccccttctt 121320
tcaaagagag gaggacgggt tattcacatt tcatttgatg gtcagaggcg aattgaaagc 121380
taagcagtgg gaattctaaa gattccccgg gggaaaaata gagatgtctc ctacgttacc 121440
cataatatgt ggaagtatcg acgtaatttc atagagtcat tcggtctgaa tgctacatga 121500
agaacataag ccagatgacg gaacgggaag acccaggatg tagaagatca taacatgagt 121560
gattcggcag atttggattc atatatatat ccacccatgt ggtacttcat tctacgatat 121620
atataagatc catctgtata gatatcatca tctacatcca gaaagccgta tgctttggaa 121680
gaagcttgta cagtttggga aggggttttg attgatcaaa agaagaatct acttcaaccg 121740
atatgccctt aggcacggcc atacataaca tagaaatcac acttggaaag ggtggacaat 121800
tagctagagc agcggatgag ataggagcag agtcgtgaaa agagctaaaa gcattctata 121860
catacgaaag caccaagcac atttgcttat gaaagaagag cagcttattc tgtaacagat 121920
tttcaacctc ccttcgggaa gtaagagcaa ttttcccttg ccttgagcca gttccagtca 121980
tgagatgact tttcccttac tcttttcatt cacaatctct ctctgcccat cgctctccct 122040
gtgggtcgag cctccttttc agtcgccctc tacaactaag tcagttgagc tctctcggct 122100
cctagaccag ctgtgatctt tcctcctgtt ggtttgctta gttaaatata tgcatcctta 122160
gagtcagtcc ctttttttgg agaaaaattc cgagccggta agcaagacaa agcaagtcaa 122220
cgtgggaaaa agctctcgat ggccatagac ctgaatggtt ggagtgtgga ggatcactcc 122280
tgaaactttc ttcctttata taaggaatcc tcttggttgg tcgaagctag aagacggctg 122340
gacgaactgc tattttgcat agggggagta agataggcta ggtgctttta ctcaactcgt 122400
gaaggttcat ttctagttag caaggataag gaagcaaagg tagagtcctt taataatatg 122460
tctgtcatta cgtgcgacta tctccactat agaaagaaaa aaaggaaaga acaacatttt 122520
cagcacattt atacgaaaaa gtctttatta ttatattagc ataagtagga aacattttcc 122580
actagggttt ttcccataca tgcaaacata aaaaagaaaa gcaaacaaag ataattagca 122640
tagataggag tctatctcca gtaagcatcg gagtagatct ccactaaaaa gacaaagaac 122700
accctaaatt aaaacacatt actttgcgtc tacagacact tatttaaacc ttctaaaact 122760
aaaagagtcg acggactctt ctattctagt ctccctggcg accacgggtg acagcaccca 122820
caattaggtc ttcctgtttt ggaggagggc ctgtttcctg tcttccagga cgctaatgcg 122880
gtcccggatc cgctgcatgg ctgcagccac aagtgcagga tcgatgggag gcaggtgctc 122940
ccaaaggcag ccagggtttg ctccgattgg agcttctcct cttccacttg agagatttct 123000
tgcgaaattt cttgaagtct tataaaagaa tccatggcta cactcaaagc tttttttgc 123060
cgacttctaa gttcctctcc gtctcccttt gccaaataga gactgaaaga agcttctatt 123120
tataggcgtt ggaggccctt aaccctttct tattattagt aagataggtt gtcttggttc 123180
cgtaacatgg atcatttcaa acctggcttt tcatgaatat ggaaccctcc actagatttt 123240
agtgtgctga ataattatct tcgtactcca atccgtacga agggcccctt tctttggcgg 123300
gtatcgccac gtggcttaat cccggatcac tccttaagga ataggacaca ataatatagc 123360
gcacatcaga gaagagagta cccctttatt ataagacagg ccccacgcgt cctttcttaa 123420
gagatggagc aatcgtcact cgacagctca aagctgaccg gtacaacccg cgtgcttgcc 123480
tactcgtctt tcaccggcct atttgtaccc agctacaatc tcttccctta gaaagaaaaa 123540
aggcccctcg gccaatcgtc actcgacagc tcgaaagcgg atcagtacaa aaccatgtga 123600
tctgtacttg tttacgtact gcccccttagg cctagggctt cgtcgtaccc tgcttactcc 123660
tctttcactt tcactggctt ctacttgtct tttttttttt tattggctta tttagaaaat 123720
ggtatcagca tttgagacga ctctccccgg ccaatcctca gtcgtccgtc cttgcttagg 123780
agaaaaccga accactctgg taaaatgccc gcccgtaacc cagcagataa agtacattac 123840
atagtccagg gattggcgac ttacccattc agtgactttg gcactggacg ttcccaaaat 123900
ggggactatc gggtaaattc aatataatag acgcctgttg gcattccagc cttccttctc 123960
ctttcagggc ctatccgaaa gagaatccag tacttcttgg tcgtgaatat ctgaactggt 124020
tgtttgctgt tcaagaattc ttgtttaggc agttcatacc atccatacat agtgttttga 124080
tctaagattt caattcttcc gtgtttcagc agtaacatat tcttccatgg agctaaggtc 124140
caaaatatgg aagaaacaag cgtttccacg actctaccac ccagtcaatt ctgttccact 124200
taatccctct ttccggctaa ggaatgggaa atctttctcc tgttacatga atccaatttt 124260
catttcatcc gggaaaagcc acctttttct caacaatgtc tttgtcattt gatccaatag 124320
cgttccgtta gataggaaca gatttgataa atactgaata actctcggat agagtattag 124380
aacggaaaga tccattagat aatgaactat tggttctaag ccatctctga cgattcattt 124440
taaaagtgac taggtaatta gtgaagaggt ttataaaagt gacaagcttg gtggaaagct 124500
cttatcttag gaggaaaagc taagtatgcc cgagtagtct tgatattggt tggtttgagg 124560
tttcgttagt tttatactaa caagcaagct tcggttcggc gaccgctcga cctagcgcct 124620
tagccccagt actataggga aggcctatgc gaagaaaagg cctgcccatc atcaaagcaa 124680
gcccaagtcc atgcaagaag gccctccaga tctgtccaaa ttcaaagccc gtcaaaggca 124740
tatgaaatca tgcaaaggat ccgagcccat ccaaatgatg ttcagcgggc taaacccaag 124800
tagctctggc ccatgatcca agagacccga aactagttaa tcactccgtg ccttaccttc 124860
taaccaatcg gccaatcacg ctatccttac ctttcaacca accccttcga ttcagtttct 124920
gcagcagtat agaatctcgg acccgatgga tgcctacaga aaaatgagtt ttccagcagt 124980
gatggcaaga atccgcgaaa taatgttctt tctccttttg tgttctttct gaatggagct 125040
acgcgaggga aagctcagct ttctactctg ccgcaaaggg gccgctttct tccccaaaat 125100
gccagttccg ccatcagggc ctagcaagaa gcataattct gttccaaagc ttcgtttcat 125160
tccagcaaca gtagtctatg gttcgaagcg ccgtgttcca tccggcgcga atcctctcca 125220
taactagtat agtggaggtc ttacttgtat tgcaataatg aaaaatgtac gaacacaaat 125280
aatgagcaga ccagcccact tttatatgtg ggttcatttc agaatgtttt tttgttttga 125340
ataaagaagc gcgtgaactt ttagtgtaag gcaggtgttt tctcggtgga tggatgggat 125400
aaatgcctat attgctttat aatgttattg ttatgttgat gttatattaa agaatgaaat 125460
ctaaaaaagt tgcttagtcc cattctttat aattgtcttt ctcatactgt gtaaacaaac 125520
ttcaagtctg aattgtgtac tgtactcaac aggaagcgtc acagccaccc cgatgtcgat 125580
ctgcagtatt agtttgagaa agtcgtttgg ttttaaccta gagcgattgg tttacctgta 125640
tcatgcaaat gtccaacact taggtgcttt ctaagatcat cctatatgaa agatgtatga 125700
catgtgtgga taatgaatga cttgcagggt atgcaatatc ttaagtacaa aaggtaagac 125760
ctaaaagaga aatgagctta gcacaacacg ggatagaaag ctaatcctag aaggagaaaa 125820
cccatcacag aacaatcata ggaaaagaag aaatgggttc agaccaagtg acagaactct 125880
ctatgagttg ggctacataa aagatccttt tctactaaaa tggatgtagg cttaactaaa 125940
gcccaatgca ggttgaactc tatggaatct aagcctcact acccttaccc tcttagaggg 126000
ttacaaggaa ttttaggccg gccccatata gattcagctt aggggtttat gagagattga 126060
ttgatggacc taagctaaac aactaagatt gaacctaaac caaaacctat agactgaatt 126120
aggagagcag aggtttaatt caagaccagg aaagcaagtt atatcgaagc ccaatgccaa 126180
gcaaagccct agactacaag tgaagaaatt gggttcaact aagcccttaa cccaagatga 126240
ggtggagcct taacccgaca caagaggggc ccwgtagrat agtgbghata gtcagcccaa 126300
cataggttgt taaccaaaag gagaagttcc cgtgaaaaca gaaaagacct ccccttaacc 126360
ccccttact tggcagattc acattcgtag gaaaggtctg ttcttttgtc tctttccctc 126420
aagcgaagga acctattaat aagataataa tatctctctg cttcctagat cgataacgaa 126480
tccttcggtt gcttatcctg tcatccgagc ccggcgttcc gaacaacaat gattcggaaa 126540
gataaggtct acgaaagaaa agaaaattta caatttgccc tactcctcaa gaaatactgc 126600
gagcggtatt gtaaaggtat gggcttttcg gtcgattttg ctcaagaggg tgggggactt 126660
cgactttatc gaagcagcac atgagattgc ccagaaggat tactttttat taacctagtg 126720
cggatgtgga ctcctaaaaa cctgctccac tttgtacgaa aacatagtaa tgcagctaag 126780
tgggagtctt acatgaacgc gcacttgatc tttgacttgg tccgccgcga tccataagga 126840
agggttttcg ttcgcaacaa ggtagccgta gggaaacccc tatgggctgg attgaatctt 126900
tcctttcctt ctccctctca cctgatccat taaaggaaaa cagactcaag gattgggcca 126960
ttttccatat gtctctagaa agataggagc taatcaaaat tcttattact tatgtaaatg 127020
taactctcaa atttgatatt actccatgtg taacgccaaa ggggccttgt attcaattga 127080
aacagaggat ctcccacatt gatatacaca tccttcaccc aatctgctca aagtattttc 127140
aactctttca tggtatcaga gcactagctc ttgggaaagg ttcagttggt tcgtgtgaag 127200
tgtggtctga ataccttctt cttaggtgtt ttctctttgg cgctgtccac cgctctgtct 127260
ctatccttct cctcagcact tagttagtat cccgtccatc gaaattgagt tttccatagc 127320
gtctgtttca attttatgga aaactaagaa aattgskwky kwgrrgsrsv agawskwchc 127380
vgttdcgbtg abggaactgg aaaagaacca aagaaaggac tttcttgaga ctgatcacaa 127440
aggtaagata atgaatcctg agtacgtccc ctggagaaga acagaccgac tactcaaaag 127500
tttaatgatg cacaccatgc cctttcccag gcgtcgaggt tgcctagccg taatccacag 127560
gctggcttcg acagatgtca gagtgaatcc gattcttcga ttcaattact tttccaattc 127620
caaccccgcg cgtggatgta gaaaagtgtg tgaatggcat acgkaagatt ggggatggac 127680
aacatcaatt catttagtat agtcagctag gaagcactag ctaggcaagt catactggga 127740
atgctgttcc acacattggc tcaattctac cttccacatc caattcttcc ttcattacaa 127800
ggcccagctt cgctaaactc gcaccgaccc ttagttaaat atgcgggtag cttttcacga 127860
aagattgttg gcatgcctcc cataagaagt aggataaaaa acctatgaga ccccccttgtt 127920 ctaatctttt cctaaagagc aatcgattac tatactagtg catgcaaact gaaatcttag 127980
agaaccttga tcctattgat cagaaagagc tcgggcgaga aggtctgcgg ggtcagaaga 128040
gttcagagaa agctggatcc gggaaggctt acgccgataa cgaaggattt tgaaaccgat 128100
cgatatgcag acgctgcaaa agcaaatgac ttcgcttcct caatcaaggt aaggtaattt 128160
gagaagctat cgaaactatt ccgaagttga tgatttcgtt ctagctaggg caatttaaag 128220
agagaagttt acgctctcca acaaagaagc actcacctcc taatagaaga gataacgtaa 128280
gaaagactag cagatgcgga cgatgtaagc ggtcaatcaa ttgagactac ttagagtccg 128340
ctaactaggg aaagagaagc actaagatga aaagatataa ctagattccc cttacataat 128400
gctcctgttg aaactaaaaa aagataagaa gggacttgaa gcttacagtc cttactcaac 128460
tacaagtaca tagagaaatg cttccaccta ttagactatg cattgacgtt gcagatgtta 128520
aattgcagtt ggcattagga gatagagagc aaaaggaatg aatctagtat acttaaggca 128580
atccaaaaga aagcgcttag tccttatgca actaaagcac aggcaggaaa taaagctaca 128640
tccacaaaga aagagatggt tgcatctaag ggcttcttat cttattgggt ctagcttctt 128700
agaaagccat agggagagac cgaacaatct gatgatatat acttgtgatg tcagaaaaaa 128760
gttccgaaga gtggaggcag ctttttcctc caattttctg ttggattcta ataggattca 128820
ggaaaaaata ggaattcgac agagcgcaaa agatagtcga gcaatcagcg ggcaggcata 128880
ggtagtcgac agcagcaatc gaccatcttg agcaacaaga gaaagaagga ccaacgacga 128940
tcaaggaaag aaagactaag taaaggcaga caacgagacg aagatagcag acttgcctcg 129000
aaacaggaac atagcatagg ggcatttctc cggactagtt aagtagttga gcccggctcc 129060
ccgcttggct cctctttgct cctagtagac tactagacat cttgtctact ctgcttttat 129120
ggaagagctc agtccaagaa gggctctcaa aaaaagaaaa ttgtcaagct ttcgaactcg 129180
ccttgaagtt gatgaatgat tgcaaggcta gcaacaagca ggctcgctta tgatctgctg 129240
aaagagtaca tcaggttttt tattaatccc tcacattcat gaagcagatt gtcgaaaagg 129300
gctttctgca agcaggaaaa cgacctttta cgatccacag ggtctagctt gatcccggtc 129360
tcaggacttc ccaagtcacg gagtctttga tcaagttgta aactaaagga gtataaccta 129420
tccaatatat atatattttc gcttattgtt agtaagaaag gtgtcactaa caaataaatc 129480
cttaatcagt agtggactac tagttaacgc actactaaag cagagtagcc agcatgcgca 129540
cataattttt gccagaggat ttttcagcga atggaagaag caggcaggga tagatataat 129600
ttttaggaaa aagtgctttg tttgatttgt tcccaggtga gatccaagat ctttcaacgc 129660
gttgatttcc tactaaagaa actgggcttc tatcaggagt ttgatcattg gaaagggtcg 129720
aaaactcttg ctttatgctt gagaaagagc cttcccggcg atctgcttca tttatggagg 129780
gtttgcaagg aagacaactg aatagcggga attaaagaga aggatttcca gaggtcaata 129840
tctggcattg agcctgccta tcctaagtat gagttgggag agcgagatag agacaaagac 129900
ccaatggacg ttcccctgct ctctctcgat gtggtacctt tcagtctgct ctgtcaaaac 129960
tttctcgcaa tgccgaaagg tagagcagct tcaaggtctt cggcaacgag atcaactgct 130020
gacccaagaa ggtagggaag agaggaggaa gggccaatcc cgagtcaggg gcatctatct 130080
ttatttacgc aaagctattt tcgatttaga tatgttcatt ggcctgcgac tgatctcatc 130140
gtccgttttc ccctctttcc tattcaagag ttctcctccc taacggcaca ctgtatataa 130200
tctctagatg gccaatgtga acagttcaat caaacttgta tgtgtgaagc atattgaaag 130260
tgacattgac aaagcaaagc acagattccc tagaatgtta gaactcagac atgacagaga 130320
aggtagtcaa aacggtacgc taagctcctt gcttcgtcgc ttctgttttc agttattcaa 130380
agaatgatgt tttaagcatc tctatatgcc agtcatctat ctgacctgac aaggaggtcg 130440
actttgatat ctcacccctg atctctacgg ttggttgaag gtgtcttgga agacgggtcg 130500
aaatcagatc tggatagaag attcatctac gctggcaaaa gggctatcag aaagagtcca 130560
atcccgagga gagttcatgt gtgaaatttc tttgttgaat ggaggtgagt tcaagggctt 130620
ctttgatcgg gaaatgcacg cacttctttg ttgtcattaa ggtcccttcc cctgagttca 130680
agatgtccct tccgcttctc tttcactact ttcctcattg ggattggtca agctccttca 130740
cttattgctc gatccgatcc ggaacctatt gggatagcac cctttcctcc tatttattag 130800
taggtcttct tgcccgttca gttcctctac tggtagtcta gttgtagttt tgagcgggtg 130860
aacccatgtt ctatctcgta gtcacctaag cggcagagtc tgtaaactca aatggtctga 130920
gagttgcctt tggcttctga acctctgaaa ctggactgga gcaagctacc aagctcctct 130980
tccccttcat cactctctat ctccggccct tgccattagt tagcttgcac ttcccttgct 131040
tgccctttga gttttcaaag tcaaggtgcc tttccctttt ctgccttacc tcttactgaa 131100
gtgaaagaac tgactgttgt ctacctttga ttctgtcttc cgggtgaagg tcctgcggag 131160
gtcttttta gtgatcaaaa ttgattaggg acagtgaccc atgatgaaag gagctattga 131220
cctaagtggt ttctatttgt atttgaaaag caaggtaggt ttgttaacga aaggataagg 131280
ttaggctgga atgggatata gtaagtgtgc cacgagtgct ccttctaagg cttctgcttc 131340
tctctaataa cgagaaaatg actctttcag aaagcaaagc tacaactctt cagtctaagc 131400
tatctaagct agaacttaag gccgacctct tttcagggat accccacttc ccggtctagc 131460
ttcactaact gtattcacag ctttccagat ctcggaacca gatctacttt ctcatcggca 131520
ttctctaaat gaattacgtt atggtcttga actctcgata tatcatatgt aatgaatgat 131580
cgaggttgtc ttttcggaag aggtgggtgg gagtggggca gggcaagaaa gtaacaatca 131640
tacccgatat tcagagcgcc ggagatagaa gcggcggcag ccataaagtg gagaatttcc 131700
atccatttgc tgtctctttc gctaccgctc cgtggggtca acattacgaa attagccagg 131760
ttcagttctg actatagctg caacctatct catatttggc cgcccdcgat cacaaactcg 131820
aaattttgga agataaagta aagaaagaat ttcgggctag gttcaaggta tgcccaaagg 131880
tatgccagtt gattgaaaag aaactcaact ttcaagattc aagattaggt aagtgttcag 131940
tgtactaagg tacaagatcg aaaaaaagcg cggatagcaa attccttagg ctagatagag 132000
tggtggttgt aaattactag gtagccatac aacactcggc ccaagcaacg cccaaaagcc 132060
catgcctttc ttggtcggac caacccaacc ggcgatttcc gacaagtctt tctgaattgg 132120
aagagcaaga agcggaactt gaagaaaact ttctttctct ttatggatag acagtctttt 132180
caaattctcc ttctaattca tcttccccgg tggatttagg tttatctctg aggtcccacg 132240
aaggttcgac tagtagcact ctgtcggacg ccaattcggg tgatattact agcactcaag 132300
ttttgagtga tatcaccgct cttttgagca acgaatggaa gtgggaaaga attcacacca 132360
gaatggagcc caatagagtt ctgccaagcg gttttgggga agaagcggtg aatgacctat 132420
ctttattgaa agacatctat tgtgatctag cggaccatgg aatgctaagt tggtattggg 132480
aaccagcttg gggctttcta aatctcatta gcaatagtcc aggaatgaca tagccttcct 132540
gtgcaatggg tgtcttaacg tactaagtaa ggtggttttt tctaaagcgg cattctcctt 132600
ctatctatca acaatagaat tatggaactt tctccccgag ctgcggaact aacgagtctg 132660
atcaatagag tccgtcattt ttctattcct tcctacttct tcttcctcta ttatgtgctt 132720
ttattctatt tgcctgaaac tcgagaaaat agagttgttt gagaccaaat gttatagagt 132780
tgggggctct ctgggaggca caccttcact tccttcttaa tgaaggggtt cccgggagtc 132840
tgaccttgtc ctttctttta attgtcgggg ccgtcatgag tgccgaaacc tatttcggta 132900
agatgatgat ggctccttcg ggcgcatcaa gctctgaaga tccaaactgg acggaagccc 132960
tgagatcttc taaagggcag ggagagactt cagaaaggga aagcacaggc acatcgtcgt 133020
ccatcaacct acaaaagaaa gagcacgtcc ggcgcctgcc ccaaatgaag tagcttccct 133080
gcccctgtcg tcccctttcc atatcaagaa gatgagatca taggggcgac agtgtagaaa 133140
gcatccaaga gcgtttaatt tgaggagaaa accctccttc tgccgaggtc atacatcata 133200
caacaggccc gaattgaagc cgaagaccta ttcgaggtca aggtcgatat tttcaggggc 133260
atgtctggcc ttgatccaga aggagattgg ctgggacggg gagctcgggc cctcgagaat 133320
ccgcgtaccg ccacggggag cattccttgg agaaactcca tacccttctt tcggatctcg 133380
aatcgagggg agtcaattcc gagtccttct ctcaattaaa gggaaggtac ccctgcgaag 133440
gggtggggac gaacactcta ccacatagtg gagtggatag ctaggactac taaaatggag 133500
atcgtgtaca acaacaatcc tatatttgat gtcgattcat ccacacttcc attccttgta 133560
gaggaaggct aactgcttgc tggctgggag ctgtatgagc ggtaacgtcc acgtacagct 133620
ccgtgagaag ggcggtggac agaaatggcc ttgttgtacc tcactctcgt cttcaatggg 133680
gtctgctctt tctttttgg gagagtatgc caatatgatc ttaatgaggt gcggggcttt 133740
gcatctgaca ttcgttgggc ttctctcttc gggagcctgc gccccggcgt tttgtgcaat 133800
aaacccctcc ggccgaagac tagtggtagg tggtcctgcg gagctttcgg aaaagggtag 133860
ccttgtgtgt aagcacagca atgaaccgcg gcgaaccctc agacgaccta tctaagatta 133920
ggggatcctc agtagtggtg accctttcac tcttccacgg actgatacat gtaccgaatg 133980
ctcatacggg aaagttgact cctgggtctg gaacctgggg ggttgctccg agaaaacctt 134040
tctttctcgt ccactcaggg tgcggacaca cctgcgcgga ttacaggtga cagttacaag 134100
aatggcggga agttaacagt acccgacgac attcagggat ggatgtagac ccatcgggca 134160
gggataatca ttccggtcct gggagaagtg gcgaccattc tcaagaacca aaagactgag 134220
ctgagggaag ccctatgagt cactgaaacg acggcaggag tgccctttc tatcaataga 134280 gggagcaaaa gggccttgct ccctttacaa tatgaagaaa gaaataaggg tcgaagttta 134340
gaccgctcac agtagttcta cctatagaaa ggatcatgaa agaggcgatc agaatggtac 134400
tcgaatccat ttacgatctc gagtttccag acacatcgca cttccgctcg ggtcgaggct 134460
tccactccgt cctaagacgg atcaaagaag agtggggaac ctctcgctgg ttttggaatt 134520
cgacatcagg aagtgttttc acaccatcga ccgacatcga ctcatcccaa tctttaagga 134580
agagatcgac gatcccaagt tcttttaccc cattcagaaa gtcttttccg ccggacgact 134640
cgtaggaggt gagaagggcc cttactccgt cccacacagt gtattactat cggccctacc 134700
aggcaacatc tacctacaca agctcgatca ggagatagga ggatccgaca gaagtacgaa 134760
attccgattg ttcagagaat aagatcggtt ctattaagaa caggtcgtat tgatgaccaa 134820
gaaaactctg gagaagaagc aagcttcaac gctccccaag acaacagagc catcattgtg 134880
gggaggttaa agagcatcca acgcaaagcg gcctttcatt cccttgtttc gtcgtggcac 134940
accccacaag caccccccgg ctcaggggac cagaaaacgc ctttcgtttt ccacccttcg 135000
tcggcccttg ccgccttcct taacaagccc tcgagcctcc tttgcgccgc cttcttcata 135060
gaagccgccg ggtttacccg gaagtccgaa ttctatggta gagaacgctg taataataat 135120
tgggtcatga gagactcttt taagtattgc aaagaaaggg cccgctgata gagctgggcg 135180
gggaggcgat acttgttatc aggtcagaga ggcctggccc gtaagctggc cccttaaaac 135240
ctattactta ataaggattt gttacgcgcg atatgccgac gacttactac tgggaatcgt 135300
gggttccgtc gagcttctca tagaaataca aaacgtatcg cccacttcct acaatctggc 135360
ttgaaccttt gggtagactc tgcaggatca acaaccatag ctgcacggag tacggtagaa 135420
ttcctcggta cggtcattcg ggaagtcctc cgagggcgac tcccatacaa ttcttgcgag 135480
agctggagaa gcgtctacgg gtaaagcacc gtatccaaat aactggttgc cacctacgct 135540
ccgccatcca ttccaagttt aggaacctag gtaatagtat cccgatcaaa gagctgacga 135600
aggggatgag cggaagaggg agtctactgg acgcggttca actagcggag actcttggaa 135660
cagctggagt aagaagtccc caagtgagcg tcttatgggg ccgtcaagca catacggcaa 135720
ggatcaaggg agatctcgtt gttgcatagc tcaggtcgga gcaaggtgcc atcggacgtt 135780
caacaggtag tctcacgatc gggcactcat gccccgacat tgtcattgta tactcccgcg 135840
ggtcggaagg cggcggggaa ggaggggaca ctgggcgaga tctatcagca gcgaattccc 135900
catacaaata gaggcaccta tcaaaagata cttcgaaggc ttcgggatcg aggtctcatt 135960
agccgaagaa gaccctggcc aatccacgtg gcctgcttga cgaacgtcag cgacggagac 136020
atcgtaaatt ggtccgcggg catcgcgata agtcctctgt cctactacag gtgctgcgac 136080
aacctttacc aagtccgaac gattgtcgac caccagatcc gctggtctgc aatattcacc 136140
ccggcccaca agcacaaatc ctcggcgcgg aatataatcc taaagtactc caaagactca 136200
aatatagtca atcaagaagg tggtaagacc cttgcagagt tccccaacag catagagctt 136260
gggaagctcg gatccggtca agatccgaac aagaatgagc actcaactac tagtaaaagg 136320
gagaaagttg actttgagaa agaaggtgct tcttgccgct ttattagtaa gtaagcttgt 136380
tttatatctc ctcaataaag gcgaaagatc actcctaaaa gcaagctttc tcttatatac 136440
gataccatac cacagaattt catttgcctt cctgcttaag gcactagttc ggatggaaac 136500
cctgatcagg caggtggcct agctaacata gctatccgtc agaaatagca gcattccatt 136560
gcaggctact atagaggcat ataattttcc gggtgttaag aaagatattg aatcgaaagc 136620
ggacatgctt gctcactggc tagatcgggc tgtctgtacc tttgctaact cttctgcctg 136680
taaggaagct tgaaagaggg aattctctga tctatgaccc cgaaagaaag atagtctttt 136740
tcgattccgc gcattggaac tgaaaagggc tattcataaa cagtcttcct tgcttcttac 136800
ctcttatctt attgtaggag ataatcgaga gagaaaagtc ttcctatcaa ttccttttga 136860
ataaggctac gctcctccaa gcctttgaaa ctattgaaaa tcgaatcttt gttttcaggc 136920
gggttttctt ctccaccaac aaccaagacg catgaaagcg gtttccagcg ctgctgggca 136980
gaaagacatg atggcatgaa actcgattac gtacgctgat tgttcgtcca cttcaaaggc 137040
tcaaaacaga ccattttccg tgtgaaatga cagggattgg tttggttact tagggaatcc 137100
caagcaaagc aatctacgca atttccgggt tcagtagtag gaaagaaagg gacctctcac 137160
tcaattcaat aacatgttct agggcatcct tttctaataa taatgttcgc atttgaccag 137220
gcttttggac gttccatgat taaaccgact agcggcactt tcgagatgcc accttgtttc 137280
taaaagagtc ttttcaattc catttgactc ggggcgtcag ggaccctcca acagaaacct 137340
cgtcttttgt cgtcgataag ttctccctca gtgccctact attcataaga aagactgatt 137400
taaaagagac tgatttatta aagcccggtg aggcctcaac cgacagctaa gcttcgttct 137460
gcggcggttt tcaagctagc accctttcag catatcatct cgctcgattc caaaaaaaaa 137520
aagagacgca gttttgatta tccagttcta tatcgaaaac gagcagttga tcccacgaaa 137580
gcaaggctgg ctttgttgcg ggttcaactg gaattgtaag aagtgaggta aattgccttt 137640
ctccccaccg catatgcctc ctctgcttat gccactggtg atgaactcac tatggctatt 137700
caacgtcaaa ctcagagttt tctactacat aggcggctaa acgaagcccc agtctttttt 137760
agtaaaaccc caacccctta ttagtagccg aagtaaaggc cagcatgaga tcaaagtcac 137820
ttgccgtccg ttcgctctct gttcaacaaa ggcgatcgat attcccttac ttctcaagtt 137880
ttgaatttta tgagcccttc gattgtatcc cataagaaaa tctctctgat aaacatcttg 137940
tcgatgattc gattatatta tttagaatct tcgtgtgcgc ttttcgcctg aggctttcgg 138000
acaagactac ttactccagt aggttagtaa gctacctctt ccgctttcag gcaagggtag 138060
ctctgaaggg agagttgagc ggaaccaggc ataaggagca agaatcgcta ttgagagttc 138120
cccgctaggg gaacgtcagg aggggacatg ctctatgtcc actgattctg tttagtacag 138180
tataggaagc ccttgtttga gtgagagctt ctagaatgcc attcatttcg caataagaaa 138240
cttttccaca tagaggtttc agctacttaa agcgagagtg catccaaaat tcgagaagag 138300
tgctcggcct tggttgaaac aattataggt gtcaatggac cgatttcact agcagagcac 138360
tttctccaat gtgcgcaaac agagatgcca ctttcaatga tggacaccgg cccttgtgtt 138420
aaagtagcat cgagtttcgc ttggaaaccg gcaagtttct agtttccaaa taagtggtac 138480
cctttcttta gagtccggta ggtcaattaa gttgcctaaa tctcttcctt atctgctgct 138540
ctgtagctgc cttcctcgct tcgtcttcgg ctttcagagt tgtgaactaa cctcttcctt 138600
ttacagccag acaactggca gataagctgg gcatctaaag aacataagat ccgagttgcc 138660
gccaggcata aaagtcatat tgtcaactag ggaaattggc acaaccaggc atctcaaaca 138720
ttgataaggg aagaatcagg ctttcattag gatgatattc ctttcatccg aatggcaagg 138780
cttgctagtt tcctgaagta cactcgcatc tgtctatcta tgtcatagtt gcttggaagg 138840
aaggtctcag atgtaccttc ggcatgtatg agattttctt tcctctatct atgtcatact 138900
tgggattcac tgacagccaa ttccaagtag atcctccctc cccctcgctc cacttcgttt 138960
cgctcgtttt ctctttcctt ctgcctgcaa aaaaagtgat gagattggtt ttgtgtgcgt 139020
tagcgatcat caaacctgtg acatagataa gattggagtt catgcagttg gaatgcctga 139080
gaccactttt tgccttgctg ctcttgcttc tctggctact gctccggcta aggctttctt 139140
tccgctttga cttgccttcc ttatctttca atctggactt gcatgtgttc cgcatatgac 139200
tatttcgagt gattgctgct atctggcttg agttagacaa gcagagaagg atcttatgcc 139260
accggtgacc ggcctgccta tctagtatct agtactagga ctagtagagt agaggcacta 139320
ctgggcgggg cttcctcgat cacagcttct cgcttagcta actgccagac aaggatgcaa 139380
atcaactcct tatatagaat gcagatcgac acattcaatg aagcagccag tacggcagac 139440
aagctacttt cttattctag gactggaaga tcctctatct attagcatac ccgtaccggc 139500
agttagacta gcactctctc cccaatcaat cgcagtaact ggctgtaaga gagctgactg 139560
tctactatct atgtcatgcc ttggcaggtg aatatgagag agaggctgta agtgcattct 139620
ctccttctcc atcttctgga aagcactctt tgagcatgct gacagaatga ttgacactca 139680
catctctctc atttccagtg atttcgctac agtttactag cgcattccta gactaagact 139740
acggcattga agaagcaagc tcactctcat tccaggaatc agaggaaggc attctgtccg 139800
gtaatgaagt tagaagtttc cggcttgctt tctctcttct cttgcagttg gcagtctcag 139860
tcaaccttgt tccgggcctt ctcttctact ctatctgctt attggattgg taggtacagt 139920
ctttcttcta ggcttctgat tgaactttaa ggtaatggga gagaaggcaa tcgacagata 139980
actggtaagt aaagctatgg actgggttct cactctaagc cagtaccagt aatttgaaaa 140040
aacgatagac atctagcgca ttcactcgtt ttttctttct gatcggccaa ctcaaagagg 140100
gaaatgcaag gggcgttagc ggtctttttt gcctcgcctg ctactgggaa gagagagccg 140160
ctgtcattct tcgcttcgtt cgagaatcaa ctgcacatga ataggctcct ccttaggcct 140220
tcaaggagga agcggctttt ttccaaaatt cccgggaaaa tgaaactttt gaaattcttt 140280
tcgtaaggca agaaagttgc ctaaggaaag tagaagtctm tgyacdbthb thbatghgba 140340
tgabggcada vtggttbhgv cttabtcccb tctcctytca aawgaawaag aawgwcatca 140400
ttctgatcgt gacttgaaaa aagaaagaag agaaggaact tggagttggc gcccacataa 140460
cggattgctt gcttaccaag ccatcctggc ttttcgctcc tctccttaca gtcaagtggc 140520
tttcactcct ccagttctat tattattgac ttgacttatt attaaaaaaa ctactcacta 140580
tccaaatgaa agacgatcga ttatctaccc aagaagatag agagtcccac atacgagaaa 140640
aggtcacaaa tagagttgaa ccaagtaaca ttgcaaaggc ataatgatag tagggtcggg 140700
atatccccgc cctccgaacc ggacgtgagg gtctcccctc atccggctct ctgcagggga 140760
atctccactc actgcttccc ctaatatcct cccccttacca catcatgggg gtttacagga 140820
gatcccagag gctcgctcgg aaaggctgct ataccatacc ttttgactta actctactct 140880
agtagtcact agactcacta tagtagtccg tctggctgct cttgctgaaa tcattactct 140940
taattctccc gtgctctagc aattgcgctc cctagaccac taccatgtag ttaggtaggg 141000
acaatcagtc cgtagtgacg ggaatctagg aatgaatggg gatccctatc aatataaaaa 141060
gaatatctaa ttagagtttt ctccctttct ctcactcaat agatctatct ggtctgatac 141120
ggcacagtac aatacgagac gatggaatgc tatgggatag atggtagagg gctgcctgcg 141180

-continued

```
cccaaaagcg atgattcact tgtccccttg tccataggga cctcgtggca tacaaccgaa 141240
acgactcccg ctagatagcc gcccctttct ctctttttac agcctcgtgg acggacgaaa 141300
gaagggaagt tacagaacgg ggcagtgaag gctcgcgaag tagacagcaa gcagcaagca 141360
acagcttctc agccccctaa cctttctctt ttttaataat actttttttta tcaggtaagc 141420
tttgaagctg gctgctctgc tatactatac tagttgtagg gcgctagcgc ttgactaata 141480
taatagaaag taaagggact ctattatgat cttacgaatc taaagatctc aaaatggaag 141540
aacgagctct tttgctcgcc cctatctcta aaggggcgta agcacttcac tcgctagggg 141600
atgggattca ttcacttgca ttcctgctag cactacaaaa gctccggtct taacgcccta 141660
ctactgctgt gcagcctttc ctcgggttcg tagagtcggg tttcccgttt acccacaacg 141720
gaggagccgc ccccaccagg caggcggcca cgggtcataa cgcactcttc gcacaacaaa 141780
tccactttga agttgactta ttcgctcggc caatcgtcgg aatgtgtacg agataccata 141840
agggcccaat atctcaatag cacctttgtc taaagcttcg aaggagactt catatccgaa 141900
acgcaggaac gatctgacta gaaagtcatt caaaacttga tcgaaaacca gcgtttattg 141960
aagaagctat agagtcgatt actaatagta ctagtttgaa aggctcgttg gaattgatcc 142020
gctacgggat taacattata cgcaacataa gcacctgaag tactaaacag aataggtatt 142080
agtttggtaa tggttggagc agcaaactcg gattcggcaa gaatctcatt ttttggtagt 142140
acgaagggga attggcccaa aattggatgg ggtcaagacg ctgtcgggcg ccggcggctg 142200
actcaagtgc ccccgaaccg cgcgaaatgg tcgcctatta cacggctcac taactctgcc 142260
tggggtgtgg gtacctatta ttcgtcggcg gtccggcgca ccctactata caaagccgcc 142320
cccccaactc acttaaagga tgctggttaa ttacgaagga aattctttct taatcgaggg 142380
acttcctttt cgttaagcgc atcgaaccag gagtggacat tatcatcatc tgcagaaaaa 142440
tccagattct ctttcatcat tagcgaaagt ggaatagtat gactggcttt ccggaaaata 142500
agacgaaacc cgctttatcg atatgataaa catgcgctca aaaagacctc ctaaaccccc 142560
ctgccaagcg atcgagttta gtctgaattt gctctagaag tagctcccgc tccagactga 142620
cttcaaggaa agaaagggtt gggcaattcc gccggttctg gagcttacct tattattaag 142680
gggaaaggga ttttttatag atgttgaggt gagtaagggg gggcgtagct tgaggcttct 142740
cagccgcagg aacagggaac gaatcctcca aaaatggaat gagttcgcaa ttaataccac 142800
aagaaagccg ccaccctcgc cctttagaga taggggcgca acaaaaagta ttcaaaaagg 142860
gcgccggagg cctcaaactc atccggagtt ggagaatgaa ataaaaaaaa aagattctca 142920
agaggaatgt atcaacaaaa ctgcccttcc atatagatcg tcgttgcatg aactttgtca 142980
atagattcct agcttcctat tgatcttgat tagttctagc ttcgtttttt ttgttgagag 143040
ttatctttct ggaccggacc cacttttata ccgtctcytg awacacmtgc tymkmsysca 143100
tgtgctttcg gggccccact caaaaaatca cttgcttgtg attgcagcca ttccccgaaa 143160
ggggagggtg gatgtaaktc agctcgaacg aagtgagagg ggtaatagac tattaccgtt 143220
cagttcatgt gacgaaccga acatcgttag gtcccgaatt ctgcgaagca ccggatctag 143280
atcaagatct ccattacgtc gtacgatata tcgatccgga gaacttactt tcagtttaag 143340
tcatccattc tgctcctatc taaagtgatg ctaggctgct tcacagaggt gcgcttcgct 143400
cgaccacatg atgaacatgt tttaagctaa ctgcatgtcg agcgcttaag cggagcttgt 143460
ggtcactcgt tcctcgcttg ttcgaaagag cttcagattg gattctacac tacatacgat 143520
```

-continued attccattcc ggccctcact agctctttgc ttgcttgtac aaagagcatg cccgaggggc 143580
tactacgctc accgcgcact tgcattacca cctgagcttc gctaccgttc cgcccagctc 143640
ctacgcctac cacgaacttg aatcatcaca tggctgctaa agcaagctaa gcttcacacg 143700
gccctgmgga agccaaaaga ccctckcacg gccgaaggct ccgcaacacg ttggagagct 143760
tttagatccc gccctaaaac gcccattccc tagagttccg aagtgattct cattctcacc 143820
gcagccttct taagccgaaa gaaagccggg caagaatctc atggtagtac gaagggggag 143880
cggaatcgta tctgggagtg gttcttcgga tcgatcacag attctcggcc ccgtcctttg 143940
gcttccactc cagttgacct ctcttctttc catcccaccg tgagaaggta gagagcaaaa 144000
ccaacccagc aaacaactat gactatgccc ctattagtaa agcatgtact tcttgcaagg 144060
cttgctgagc ttcttcatgt gacagacatc gcaaaagtag tccgttgaac gatcgccgat 144120
cgagggcatc gtaatagtat actatttttg aaccctgatg ggtctcgcdv ttaavcabat 144180
ghtcghvcbc hbbctdctda tdcaaatctc vdadvccabv hgagccctag atrtaaaggg 144240
ttcttgaacc cttctaagca attagaagag cgcggaattg gacctccctc aaatagatgg 144300
atctgggatt gattgtggaa ccgagcatag agaaccgggg gcgggcagga agataggcta 144360
ggcggagtag tcgctctgga gcaggttctt cgactggatc aatgcatgta tgaaccctaa 144420
aaaaatcccg aaggtctagt ctagaaaaac ccggattttg ttgggttagc ttttggtagg 144480
aaaggcggtc acaggaagaa atgccctacc aatgaataga ttagtctact aacgtcaaca 144540
atctctttct tcatatacga gaccgtctgc ttttatatcc taaactatag atatgaaaca 144600
aaaaagaaag aaagaaaggc aggaggtaag agcgagtaag actaggttat agcaagacaa 144660
cagaggttag atagctctta ccggaggaag agggttcagg tcacccgtcc ccttgaccca 144720
gacacgaact aatccttctc tctctcgaat gtatgcccgg ttttcgtcga atcttttgat 144780
caccttcaaa acaaaccgga attccgtctt gacatgataa atagtgatgc ccacctgcag 144840
agcgtagccc tccctgcagc cttgaagtag actatttttc gagtctgatc ttatccccaa 144900
agccttttgc aaaaggagta ggtagcgaga tagatgacta aaagctgatg atctttgcct 144960
cttactagta aagggaaaag ccctatatat ctgattagtc aagcctaaag gccctttact 145020
aatataatag aaggtaagac cggctttcgc gcagctgctg cgccttgctt cttgcccata 145080
gagagttagg atattttgtg agctccttcg cctagcggaa acctccgctt ttcggccgta 145140
atcccgtgct ttaccaacgc attcaatgga ttccaccatg aaccgggagc gggcgaagac 145200
atgcagcttc cattttcggg gtacacagtc acgtgctgag caaagaggta tatatcacac 145260
tcattcacaa gcgcaaggtg cggcatccgc ctgaacgggg agaggatttc cctaaaacaa 145320
agataggcgt gtcaggaaat awwrkrrast ccccctattt cgctgtccag ggagctgttg 145380
actaatgacc taaaaaatgc gtgacgtttg ggaagcatga gcaacccttc gcgcacgaga 145440
tagcaatgac aggagattga ccggtcgggg tcgagtgatc tcaggggttt aggggtgctt 145500
ctcctgctgc gactacctct ctattttcaa aagtatatag aaatggtagg cactgggagt 145560
gagtgaacta cccggggaga aaggggcaac ctctctatag aagggaaggg aaagggttct 145620
ccgctcataa tgattgtaga gtctctcggg gttggaggtc taatagtagt cacatcaagt 145680
cctccccctc ttactcagaa tagctagcga gaggaagact actgattatc tatgaaagaa 145740
ggcttttaag aatgaaaaaa atcttatctt aaggatagag agccccccgc ctgcgttttc 145800
agatacgagt gagtgagcgc tttttctgct atgaatgaat gacctctcca tttattttca 145860
agcttgctct tcaaaccggc ctatcgctct cctctatgaa aaggttcttc cgtaatcact 145920
ctcaataaga catccattcc cctttcaaat gaaaagagaa ctagactttt ctcttcatca 145980
ttgaaatccg ccattcaatc gcagtgcggt gctctcaaaa ggctcaatcc tctaaggctg 146040
aaacgaatag gtcaggaawt ssmscykksw kccgcccgtt ccgatccttg cctactaaac 146100
agttgcaccc cggatatgta tgttgggaga accccatgat ccttccgtgt ggaagggaag 146160
gaagaaagaa ggcgaacacg aatactaaaa gcggttcatg gggaccccaa aaggggatag 146220
agagcgcgga acgggctttc aagcataaaa caatccctac ctatacattc catggcaaca 146280
gacagaaggc agttttgtcg ttgttcttaa cccaggcaca tttccgttcc caataatctc 146340
catgaaaaga ctaccatgat ttccgaacga accgagggag agtcgaggca tgaaaaactt 146400
atctatgatc tgcttatttc caagtacgta tcatccgctg ccttatccgc cgtctctgcg 146460
gccgccaaaa gcctaccctc tctcggatat tgagtgggtt gaccggggaa gagatccgga 146520
cgaaccttcc aacaagcaga atagaagttg accacaaggc catctctgtg ggaggctgct 146580
acccataagg ccatctcggg catgggaaag aaaggcggcg gacaaccgac ttaactggag 146640
agcctaaacg gcatagagga tgagtccacc ggtcgacaaa cggcttctat ctacaggtgc 146700
tttcattatg gatcggtcga cttgtcacga ttgattgctc acacacaatt aggttaggca 146760
ggcttgggga ggtgatctga atcgctatcg atacgatgcg gggctgattt gctgaccgta 146820
acgaacttga ctctgcccct gaaaaaaaag ggcgggaaga cctttgacct gggctgggga 146880
gggattgggg tcgcttttct ttaggacttt agtccgtaac aaggctcgaa gacctccggc 146940
tggatttgaa atggatcagg tagggcatcc gtttacgacg tgggtgggat tagcagtttt 147000
ctctattttc ttcaatggta ggaaatacgc atcagcgggg gtatatggga ggaaaccagt 147060
ctgcagtaat tcaaattgct ccttcggatc actaagtaaa atcttgactc acacataccg 147120
cggtgtattg ttgtcaactc acatagtcgc acctaccagc aacaagacga ctactccctg 147180
cacgccacta aacggcgcta tttaacgctt gggttcgccc aatacaagaa ctacagccca 147240
acctagctta aggctaaagc cgtggactac acccccgtga gagccctcta ttttactaac 147300
atactccctt ttgatctccc ccataccttc atatcaaagc tgggaatgat tgactttcgg 147360
attaaaataa tagcgcataa tggcagtact ccttcccatt tcttctttta tgatcttatc 147420
tacttgaaat gcttacctgt aagtgcggag aaggtaccca ggggaccaaa cgaaagggca 147480
ctgaaaggtc ttcaattaaa gcttcgccag tacttgaaag actcgaaaga cctacttgat 147540
gagtttcctt atgagtgagt tcgtaggtgc ctttaagtcg agtgtagcga agggattctc 147600
ctaagagaag ctttagccct tgaacctgaa acgactttta tgagctgtct cagtagtgac 147660
cgactttatt ttattagctg tatgattagt ggctthgctc dtagtggttb aavagctacg 147720
gtaaaaaaaa tccctttgaa aataaaccac taatccgcct taggtactct tttaagtccg 147780
tgtaaggcgg agggaatgaa gggacctgca ggaggctgaa aagccgtagt gcgctagcgc 147840
tagcgagtta gcgcaacaac ttagtgtctt gttttcttcg ctgctttttt tgtccgcagg 147900
aaagcggttg ctaaggcttg tagcttgctt ctgtccttag tcaattttgg actgaagctg 147960
ttctgactgc cgtatctttt ttgaaccgaa taccttcctc tgtcatctct ggtctgtctc 148020
ttttgagaga agattttcta ccccgcctgc ctatgaagaa cttcaagtct atcgggaaag 148080
gatgtggtgg taaccccgca gctttgtcta gaaccgggcg tccagccgtg taggaagact 148140
caccctagcc actatagcga ccccaccccc aaccctagct gagaagcacc ctccacccac 148200
ttccattttt ccgtgtgccc aaagcccgcc cgcccggttt ttgagaccct tkctgaktcc 148260
ctcacccaat ctcatgggaa gcaagcccag caggccctgc cttaacctgt cctcagacag 148320
ccagccctca ccaggctgct ggcattgcta aatgctccgc cacgaagcaa gctttcccga 148380
atacgacaga tgcggaagtg gctaaagaag tcggaggaag aaagttgttg gacaactgta 148440
tacacgaggg tacattagta ttctgggaat tggcaacatt gacagaaagg gtaaggggta 148500
ggaagaaact tttttaggtc ttgctctact aaagtagtcg gcctaacctt cggttcccgt 148560
aaccaagttt ttctttctca ctccttatgt actttttttt acttcatcca tacttttttta 148620 ctttttctga agtgtggggc aaacggcgcc ctctacttct acttctaact aaaggcgaac 148680
agccggcatt gcaagcaaat agaaagcccc cgcccgtttg agccggaaag cgtaccggct 148740
gtttgagtcg cgaaagggcc gcttgcttaa tattatttat ataataataa tagatagata 148800
atattatatt atataactat ctataaagat aaataaaaaa ctacagaaaa tacttttttw 148860
tnnataaaat tcttcattcc tgggaagagg aagaagcaga tagggcaaag gccttctctt 148920
tccgtccgct cttcccgaag tgagcgaatt gcatgtagag atccgtaggg gcttatagtt 148980
taattggttg aaacgtaccg ctcataacgg tgatattgta ggttcgagcc ctactaagcc 149040
taccaccccc ttctcttcac ctgatacaag gcckgyctct tatacacawc tccgarcmcc 149100
hcaadctagc gacggcatct ggaaccacac tgctgccgct gcccttcggg cacgcctcct 149160
atgcttatca ctcacctacg ctcttgcagc atgccccttc gggcaatacg gtgtaatacg 149220
cgaagcagct gagccatagc tcttcgatcg ctatattctt gcggcgtggt tcatcctctt 149280
vgcghdtada hvcgtattbb ccvvcaggag actgcdgcga gadtcbhbtt vdgtbaghdg 149340
catbbcdgvd gtdtvbggga babagtgaac actcccttgg ttgggggctg tgactcccct 149400
atcctttcaa ttttttgatt cccaggtctt ttttattatc actgttggaa tctttttttaa 149460 gacgacttgg tcagggcggt tcacaatttc tttgctgaag gcgctgttaa gccctaagtt 149520
tgaattcaaa tttcattgcc cttcttccga aagtctaaag tccttcaaat tttcaccaat 149580
tccgacctac ctttatttat gggatatttg aaggagagct ttgtaactgt ttctagaaaa 149640
ttctctctag ctcgaagaat ttgtttgatt ctccctataa aaatagttaa ggaaaaaggg 149700
gcgcttttgt taaaggacta actattgtag agaagatctc cttggctcac gaggtggctt 149760
taagtgatag ggattttaac ctaaagacaa cataggaggg aggggtcaaa gaaagtcagg 149820
atatggcaaa agcatctttt ggatcgaatg ggcttttgtg ataaatggcg gaatttgata 149880
catggatgtt tatgtaatga agactttgga gtgcttgtgg atggtgtgcc acatgggtac 149940
tttccagctt ctcgagggct gcgacaaggg ttccaaacct agcctgttga ttttagctga 150000
agaagtgcta agccgggact tggtatcatt gaaaatgata acatcttacc atgcttcgag 150060
atcgtgccca gcactctcct actttctctt tgataacgat gttctaatat tatataatag 150120
ccataaacgg aatcttaaga agcagaaaat ctttctggaa agaagtaaga agctgattgt 150180
aatgttgtaa tggccaaaag gtcaatttcg ataagagcca gtgcttcctc tcgaacagag 150240
ctcctcgcag aaattccaga tcattgaaga ggaatcaaaa ggtagttttc ctatcaagta 150300
cctggaagtt ttcttgtccc tcaagagaat aaagagagaa ccttcctcta ctggagaaaa 150360
tgaaaagaga atctcagatt ggaaaagtaa attgttgtcc tccggaggtc gactaaggct 150420
tattaaacat gttatagtct tcctatgcac atgtgcaagt ttttccttaa ttagccggcc 150480
cacacttcgg ctactaataa tgggataaga ccttactact atataggata tgttaccctc 150540
tctccagtga gtgcagtgaa ggactctcgc ctcacccgcc cgtttgactt atggcatcat 150600
cgacttgctt ttcaatcaaa gcgatttcat aaccataaag aaagacctct ccttcgggat 150660
cagtcccgtc cctagatgta gtagtcaatc agcgggacat tcaaagaagc tatgcacctt 150720
cactgaatgt taatgaaaga aagccctttc atcctaatct catctactga aaaggggccg 150780
ggcgtagcac gttcttttgg gacacatagg ctattacaga cgcatcaaaa aagacttttc 150840
gaagcgcgga atccctgaat ggaatcattg cagaagaaag gtataacggt tgggaaccgg 150900
aacaggatta agcctttaag catgcagatg agtgtttgct gtcagcccca atccttcggt 150960
ttccggattg gaataaggag ttccatgttc atactgacgc atcactctat gccattggat 151020
gtatgttggc gcaagaaggg ccgcttgatc actccatcta cttttaaagt atacgacttt 151080
ccgctttgga attatagaac caccgaacct tctttatcat gattcgaccc atacctcaga 151140
cccaagatcg agcaccagag ctgctcataa caagstacca aaagaagaat gcgagaagtt 151200
catattctcc agattcgact ataaaccagg tagtgaggat gaaaaaaagc ataagctacc 151260
tcgttcgtgc tcccgtcttt ctcgctgcca tcttcggtgg atgcgcccct tcacttaaag 151320
gcggccaaac caacccactg agccaacctt ttagattgaa aaaagttact aagctagtca 151380
cctcacctct ctttcttacc cgcccttatt agtagtaggc aacctttctt tctcgccttt 151440
cttcmagctt tttccagata aagatctaat agagttgcgc tttcttagta cattgccttt 151500
cattaccaat ctgtcgtttt acagcacgaa gttacctgat gttcgctact actaataagg 151560
gcggagagat gttaaccttt cgctattagt aagcactccc ctagttttga cctaatgagc 151620
tttctttacg ttgagttaat taacccggcg ggttcgccta gatgcctagt aaagaacgag 151680
ctggtgggaa agagctggag atcatgaaaa gatttccaca caaggaggca ggcgaccggg 151740
aagctttgct tctcgaatgc cgactacatg ggaacagatg ttatataggt tgattctcat 151800
tcttgctgcc cgctcgattc cgaggaataa agggagggct ttaccacaat ttcccaagta 151860
agagatagaa tctcactaat tggaaggaaa aggagggctt cgatccattg tgattcgctt 151920
tcttggtatg gagagatctc tgccataaag agagagctcc taagccttat tctgcagatc 151980
aaagagcgag gtaattcccc attcatccga aatagtcttt tagtaaagaa gagaggcatt 152040
ctgggccgac tactacgact acatgcccat ctagtgcagt ggcttggaag caagctacct 152100
tgaccatctt ccgaagttct aaataattta ctgatcaaag gctgtaaggg cggactgctc 152160
tacattcagc cacaccacag tgaccccgaa gcgatcttct tctagttgcg ggacgaaatc 152220
cgacagccaa ttgctggctc tgaataacca gcccagcaat aagctcaatt cttccataac 152280
ataaggggcg ggcttgcgcg cgagccgaat gacgtaggtg cacaagagta cttcgcgcca 152340
caaccatctc cttttatagg ttctacggac cgatgcctgc tgcttcatct gggagaaaag 152400
aatcatagat atgccggtca ttagaaggaa gaaccgccat aaaagattcc tcgtgtatca 152460
tctgtagcaa aactatgaac gggagctagc aatccggacc gtattgaaaa ggttcctgag 152520
acacagcatg gaaaagtaac aatattaaga aacgaggtcc aagaatgaag aaggggttga 152580
attactgaat gaatacgagc tgtggctaat acccgaggca taaagaagca ttttctacgg 152640
gatcccgaaa ccaccagcca ccccgaccta attcatgata agcccaccaa cttcctggca 152700
aaatgcctac ggttaaaacc accgacatgt caagatccaa attcgaattg gttcctggtc 152760
ctggtcagag accactgtgt tcgcgccggc ggtccaacaa agaggcgaag tagtggtatc 152820
tttctttcca ttacgaacga cacgcttcgc ctgctccctc cccgtgtcca ctagcgctcc 152880
tgtccagagc gaagagaagg cgaaaagcgc cgccgaagca gcataagcag gcttctattg 152940
cbacgdaaca ataaagcagg atagcatttt gcgcccacat gtttgaattt gagggtaaag 153000

-continued agctcgcttg ttatacggga tccgacgcat ccaacagagc gaaacagtgt tccattcttt 153060
tcggcggcat ccttccgcat tggcggcgag tggagtgcca caatcccatt catcattttt 153120
gatctacata agccaaagcc catagcactg gcgacgtctc cggcataaat gcahgdaggh 153180
tgtatabctb atvbagbatc ttgtgkaaca ggatttgatt ctgcaakcgg ytcagtamaa 153240
acgaagaaat ttcgaacaaa agggtcggaa ctcgctgata ggaaaggaga gaaaacaaag 153300
caatgccaag agctccgtca atccgctgtt catcgataga cgdctctctc tttatcatct 153360
cgtgccagat gcaacatcct ttttccttct cgcgaaccac gggagcgcct agcgcccaga 153420
ggagcaaagc tcattttcct ttcagggtaa agcggcgcat aaaaaagggc tggcccgtca 153480
aaagtccggt tccttcgcga acgaagttca gaatcaacaa gggttcgtag aacgaaggga 153540
gtgtataact ggggcgcagc cccacttttt tgttcgtaac gagggagaga tagaatggag 153600
ttcttcacga agttcgaaac aaaggaataa aaaaaagttt ctctatggcc tcctcgtttt 153660
gagacattat ggcttagggg tcgaccccgg taacaaagaa ggaatccata aaaacttagg 153720
atccaacacc atgataaaat actaccctca tgattagacc atgtccctga gatttgataa 153780
aagaaaggtg cattagcggt taatacgttg taattggata agttattagg aatatgacgg 153840
aacgaaagac caaggaaaga aagaagaata caccaaaatg caagtgctgc accaaagact 153900
ggtggttgtt tcttgttgta agtgaatgca acgaaaagac ccggaaataa cgaataatga 153960
aacaattcat atattgacat ttcgtgctca tttccaaatt tatgctttgt tattcccatc 154020
atccggtaac cacaggatga tccacaagaa aggtggcagg attcgaacct atggccggcc 154080
tgcccctgac ctgctgggtt gggtggccgg gttagcaccc ctcgtcgcct ctgtacccga 154140
aacagatgcg ctgcgctacc cagcgcctaa ccttgtctcc cctactcctc ttctggttgt 154200
gccattacca atcgcgggta accccggtcc ggccgcccct gacctaagaa gaactattat 154260
ccttatgacc aaacaaggac cagcttactt acttctcgag cgatagttcc acgatcccga 154320
ccagcaactt cttgggagta ggggcatcaa agcttgccca acctagtaaa ggggcttggg 154380
gatagagggt tttctgggga gagaaagttt ccaggttgga ttttttgaga tcaaatagta 154440
ctagttgggt agatagaggt ggtgaaatct aacctttgca tcgatcttct ttagcagggc 154500
gggtcgcttg agtgtcaaaa ccaagcggtg gttgttttcc ttggcttatc gaaccagcgt 154560
atgcccattc ctcctttgat gactcccagt agagaaagcc taaattttcc gatgtggatt 154620
gaaaggaagt tggggatgga catagatcct tccgcctatc cggagtgttg gaaatatagc 154680
aatgtttttg tattttgatt tcccgatcat tggaagcaat cttcactggc acaaggatct 154740
cctcacagca acctccacta cgatagaaac cgacaatgag tttacgaagg cttcgagtag 154800
tgcgggatag gctaatcacc agactgctct ggaataggtt aatcgctgga gacaagaacg 154860
agtgaatcta gtttcgagag catgccttac tctaataggg gcgtagagtt tctaagtgaa 154920
ggcaagcgct actatatatg taatatccta gctgtcagca aggcaggtcc gctataaagc 154980
ctaccggcca gaaagtcctt aagaacgaga aagccgacta aaggcwwtyy ywtarscgrc 155040
ycttgttgcc gagtcgaggg gcttggctgg taccaggctc taaaagagtt ttcttcgagc 155100
gagcggtctt tctatctttt gggttgcatg cccaaggcaa tgcttttgta gattgagatg 155160
gattgatctt cgctatcgtg cctcctcctt gtaccagttg atgctggggc agtgcttaat 155220
taatatgagt tttctcctgc cccagacagc ttcgaggttc ccatcgatyk attmcagagg 155280
tttctaccac tgaacttgct tatgctcccc tttgatcgag tgctatttct ataaataaga 155340
ttgagtagga aaatgttgaa ttggcttcaa tcgagattgc ctcggcttct taggcacatg 155400

-continued aggaaccggc ctaacatctt ttcaatcgaa atcccaatca aagacaagtt ctaccaaggc 155460
caggatctga aagagaggat tcactttccg aaattccaag tgacatgatt cctccttcag 155520
aagctaaagt tgaatgatcg aagtctcctt taggttcagt cgaagagayc gaarcgaart 155580
catcaattca accattcgaa tggtctcccc aaagattgac ctcttttcca aataaaccga 155640
acctcgatac cagattcatc aaaaagatat ggccatctct ctaggttgca caaccccttt 155700
agatcgttct attcgtgctt gaaaacgacc ccatcggtcc gctcctttta atggacattc 155760
ttagccgtcc tccgagggtt aacaccccat agatcagatc gtgaactctt tcagaccctt 155820
agtttcactt ggttggggca gagtttcagc ctgccttcca ccgaatataa aaccttagag 155880
ctgcctaacc tgctgacatc ccggcgaaga gagtcattat ttgtgttaca tcttcgaatt 155940
cgagagaagg ctttcctctt atctctcaaa ttataggcat tgaagcgatc gagagaaagt 156000
aagaaaacta ttgcacacgc ccccattcgc cctttactaa tataatagaa ggtaaggcaa 156060
agcaagagtg aaactacgag ctaaaagcag gcgtgcctct cttataagag aatatgatac 156120
catccccact tttggcgcac ttctttgatg agctaagcct aagcgccata gaagtcaaaa 156180
gctagcctga gacctaaaaa gcaaggtcga aatccatccc tcttttcctg tatttgacta 156240
gtagggctaa tgaacgaccc tttgatctat gtcgttccaa gttcagccag gtctgattag 156300
aagttcaaaa tgagtggagc gaggggcttt agagggaaaa aagggggcg agctttaatt 156360
gaagtagggg cggagctcct catagagagt tagaaagcgt cagttctcat agcgaggctt 156420
aggccgacgg ggtagggcgc ggccccaatt ctcaaccccg acctagacaa gtggttttaa 156480
cccacatttt gaaaagttct gttaggttct tagtagcaat cggcgacctt ttcctctttt 156540
acttcacata gcttttcgtc tccttgatag ctggaagttc tccaaaagta tgaaaagctg 156600
gaggactttg taccatccat tccggtgtgg ttggattctg ttcaacagcc caaggacttg 156660
gagcacatct tttgttcttt ccactgcttg aagtgattgt tacgaccacg aagaaacgac 156720
aaatcccaac tacggatata taagagccaa aactgctaag ggcattccat ccagcgtaag 156780
catctggata atctggaatg cgacgtggca tacccgaaag ccctaagaaa tgcataggaa 156840
agaaggtcat attaaccccg aaaaagtgat ccaaaatgga tttgacctaa agtttcaggg 156900
tatgtccgac caaagatttt acctacccaa tagwgaaatc ctgcaaataa agcaaaaacg 156960
gctcycatag aaagtacata atggaaatgt gcaaccacat aataagtatc atgtagagca 157020
atgtctagca cagaattagc cagaactatg ccagtgagtc chcctatggt gaacaaaaag 157080
atgaaaccta aagcaaataa catgggdgtt ttgtattgta tcgaaccccc cacatggtag 157140
cgatccaact aaagattttg attccagtgg ggacagctat gatcatggta gctgcggtga 157200
agtaggcacg ggtatcaacg tctaagccca cagtaaacat atgatgagcc caaacaagaa 157260
atccaagaac acctatactg atcatggcat aaaccatgcc tagatacccg aaaccggttt 157320
tcccgaaaag tagaaacgat atgacttatg ataccggatc caggcagaat gggaatatac 157380
acctctggat gaccgaagaa ccaaaagaga tgctggtata atatagggtc ccctccagcg 157440
ggatcagaaa aggttgtatt aaagtttcga tcggttaata acatggtaat tgccctgcca 157500
gtaccggaag tgataataaa agtgggaatg ctgtcactag aacggaccac acaaatagag 157560
gtgatctatg catagtcatt ccaggtccac gcatgttgaa gatagttgtt ataaaattaa 157620
tagaacctaa aatggatgaa acaccagata gatgaagact agaaattgct aaatcaacag 157680
ctcctccaga atggctggta ataccactta agggcggata gaccgtccac ccagtgccgc 157740
tacccacttc tactaaggct gggcttaata ggagcaagag acttggaggc aacaaccaga 157800
atgaaatatt atttaatcgt ggaaatgcca tgtcaggcgc acctatcaga atcggaacag 157860
accaattacc agatccacct atcatcgccg gcataaccat aaaangatca ttaaaaaagc 157920
gtgagccgtt attaaaacat tataaagttg atgattccca ccaagaattt gatcgccggg 157980
tcgtgctaat tccatacgaa tcagtactga gaagcatgtg cccatcactc cagcaatggc 158040
accgaagatg aaataaagag tccctatatc cttgtggtta gtggagaaca gccatcggac 158100
cggatttgtc gtaaaattga gattatttcg tttccttcct tatcagagag ggcccgcggg 158160
gcttatttat tgaaaagggg agtgagggga aggaagaatg gaaagccctc actttattga 158220
tgggacattt tgatcccctt ttcctctcat cctccccggt tctggttcag gaaagggtca 158280
acgcaaggat cttatttcga agcaatctct ggagttttcc cttatccgaa cgggtcttgc 158340
aagaaaatag gatttcatat tgagctccaa atatacgcta ttgggatggg atggctccta 158400
ctagctctcc ccccctaaga accgcacgtg cgagttcccc cgcatacggc tcaagtggcg 158460
aaggcccttt ccttcgcgct tggtaagcgc ttcgctgtag ccaagcttac tgctagccta 158520
tcggctagag ccaagcttcg accgcgactg ctcgtcgctt ctggccgcct tattccgtca 158580
cccgagatcc aagtcagcac cggcaaagat ctcttgattc ctcgcggtcg ggccggcttg 158640
gaagcaagct acctcttgcc tatctcacct ccttccttca gctgggtgag ccttcgcttt 158700
ttggatcgtc ttctgcccaa tgcggtaccc cccgtttttt ggttcccatt gggtttacct 158760
tgttcacagg tcgaccccat ggcagcaaga aaaggcgatc ttgtgctata ctccggtgat 158820
ctctttccta ccgagacacg caaactccca tcgtgtccca gatcacattc cgtgaatcga 158880
aaggggaagc ctactcatct atcagctcct ctcgtagatc ggtgtggttt tacgaagcgt 158940
ctaagcacag ttcactcgcg ttgatcaatc aagagggttg ccgccactcc ttaaggttat 159000
ctgttgtatc atacacttct tgcattctgt cccacgcttc atacctcctc tttcttctta 159060
aggtaagata aagggccagg catggtgggg taggagcatc cagtcggcaa tctttttggc 159120
ttgaccaaga agtcttatgt cctccgagtc gcacggcgtt ttaaccgaaa gaacttcttg 159180
cgcaaytcat gccrwgcasw aggttktrkd cgaattcttt ctttatbtcg agatadcvdt 159240
gdtctctgga cttttatcaa tatgaggtga tcgtaacaca gtatataaga ctcgtgattc 159300
aggcaatcca atcttccgtg tgtaaggcgg aagcccccaa aaatggtttt caaaaaatgg 159360
gtgatcaaag atcgaattac tatgcctatc ttggtggtcg ttacttttgg tggtctttct 159420
tttggctgac tcctatagac gaagtgcttc gtttcagatc aattcttcgc tgcaatcgct 159480
tcgatccacc cctcggtgaa aaccgtaata cgccctgagg aattcctacc agcagacttc 159540
cctgtactca aagtgaattg tctaagtgct ctcctttgtc tcattgttta tctcgtaatc 159600
attcgattcc gcccctaaag ctagcgccta ctcctcctcc ttctcctcct gaatcctcct 159660
tggtcctttt acataacact ctcggccgcc caagaggact ggctatcttt ctctttatac 159720
gcacaatatc ttgaaaggca aagaaaagat ctaccttggc aacgaagacg tcattgactg 159780
atagtttatc ttccgaaccg gttaaatacc tataacaaaa aaaggccaaa gcccgctgaa 159840
gcactggaaa aatgttgacc acgatttcta acgcttttca aaaccatttg cttgcaacgc 159900
cttgagtgga cagataatta cggccactag atccttcata ctcttactaa agtacactta 159960
agactcaacc aatcttgaaa gtggagtgga caactggcat accttgaatc tagcctgcaa 160020
tcctttcgca cttctcttat caaatttcta gttagagaga gctaaccgct gccaaaatgc 160080
agcagttttt cttatatacg atagcacccc tgccctcctt gttcaagtag ttcaagagtg 160140
aaagggcgta gtgaaagaag gaaagatctc tttcaaagat attctaccca taaaggcagt 160200
tctcttatat ggcaatacta gattggcgag acaagagaga aagcttataa agtagtaagg 160260
tgtctatggg gcttgcctta caggtagtga ctataccact tacatatcga acagatctta 160320
ctctcaatgg agtcatttcg atatgaccta ggaacttaca gaataccgaa cttggataat 160380
cggtagaaga atgattggct agatcatttg cttcactgcg gaagaacccc tttctacgct 160440
acgttcccaa taaaaagccg tcatccttct gtcgcctgtt agccacacca gaccaagaaa 160500
aggcaaacta atcaaccaag actcagtcac gacctttgta acctcacggc cactttcttt 160560
cctagagctt gcagccatta tcttcgcttt tcagatatgg tgacattact tgtatdggga 160620
agtgccagat ctttacggat cataagagct tgaggtactt gatgacacag aaggagttga 160680
accttcgcca ggatggcaca cttctattcg gggacgagta tgtgttcctc aggacagtga 160740
cctgtgccat gatatcttgg aggaggcgca tagctcacct tgdgayasac ccagggagca 160800
cgaagatgta caggacgatc cgcccacact attggtggaa aggtatgaag agggatgtcg 160860
ctgagtatgt ggctaaatgc ttagtgtgcc agctggttaa ggctgagcac cagagaccag 160920
caggaccctt acagccagtt cagataccac agtggaagtg ggacgagata gccatggact 160980
ttgtctctgg attgccgaag actgcgaggc aacatgacgc catttgggtg attattgatc 161040
ggctgaccaa gtcagctcac ttcctgccga tcagtatgac ttactctacg ggcaagctag 161100
cccagatata tattgatgag atagtgcgcc tacacgggat accatcatcc atagtatcag 161160
acagagatcc acggttcact tcagccttgt ggcagagcct acagaaggct ttgggtagca 161220
gagtgagtct tagcacagcc ttccatcctc agaccgatgg ccagtctaag aggaccatcc 161280
agacattgga ggctatgcgg aggtaatccc ttgattttcg aggttgttgg gacagacatc 161340
taccettggt ggagttcgcc tataacaaga gttatcaggc gagtataggc atgccacctt 161400
ttgaggcact ctatggacgc aagtgcagga ctcccctatg ctgggatgaa gtaggggaga 161460
gacagattct tgggccagag attgtacttt ytttwtytta wkcagaagrc ttagtacaag 161520
gttctgtcgt ttaccttgcg cctatctatt cctttaagct tatatcttat accattgcaa 161580
tcagactcat tggatatctt ccttttctct tctactatcg agagtcgtac gggtgaggag 161640
gtgagctcta agcgtataca catagatagg tctgggtaag cgaccatcag cggtatgggt 161700
agcagctact atcagtacgc cagtctaagg ctgttcgtag aggtaggtcg tagagatcta 161760
tgaagggcta tatttagcat aaatagcatg gttaattata gaatagcgtg atggccgtaa 161820
gaagatcata aataaggtaa atagtctgga gtggatgtct agatcagggt gtcggcatca 161880
cacatatagc atgtgtgccg tgagtgagag ggtggtcgta gatcagccct cagctcttct 161940
ttcgaaattc tcgaacatga tgacttatcg gcttgaggct tcttttcttt tcaagctgag 162000
tagaaatttc ataagagaag aaaagttcac agaaggttct tcaatgtatg cctggttcac 162060
gaggttctac tgcagggccc agtavdmsdw tmgctctaaa gtaaggagac cacttaaaaa 162120
ccctcatcgg ataagaaaag atataccaga tagagcgcaa ccaagtccat ttttgaatga 162180
taagggtaaa tcatcacctt atttgaggaa gtagctatgg aagattgggt ctgtatggct 162240
tcctggggtc gaaagatctt ccttcagcct tgaaagtatg ctgctgcttt agcgcgaatg 162300
aaaccatttc tcaaaatcaa aaggaatcct cctcttgagg ttggtaacct agcccaaaac 162360
catgctcatg ggaaaaaaaa gtatggggaa atgaaaagag accttgatgt cttcgcccta 162420
agcgcatgcc aggaaactca ttcctctcat gattcccatg acacgaatct tactctaggg 162480
atcgaaataa aaggtaaaat actccttact cgtaattaaa cccactaatc atcatatctt 162540
ttttaccttg ttcgatttgc agaatgggga tattcgaatc cggtccttct gacatatctg 162600
catccccatg tatagtaaga gtctttccaa cgaggaactt cactatcgta tagttgactc 162660
gactcgaatg ccctcttagc aatagcatcc gtaaccgcag ctattgagtc tgctgtggga 162720
ataagcgccg cagaataggc agctattgac tccgctctaa gcctaggcac tctggggtga 162780
attaccggtg cgagaagtct gatgtcaatc tatctaatag tataaagatt acaacgacat 162840
agccagagac tgaaacttat tgtttagtat aggctaagcg cttacctaaa catatggtaa 162900
tgcaaccacc ttagtcagtg attactaagc tagcgcctag cgctaaatcg ttgaaagaga 162960
ggtcccccat ccctaagcta acgagaaggg aatctctctc acaagccacg atcagcactt 163020
agcctaaaag cctcttcaac gaataatgaa ttaccgaaag cctcaatctc ttactgctta 163080
cctggtaatg ccacttttcg ctccgtatac tctagcaagc tagtactggt cgactaagtg 163140
gtctcatgcc caagtcaaat ccaatgacga gttgagatca tacaagagta ctttaccaat 163200
caagggatag acctatcttg actaagtaag caacctttct cagacctctt ggaatagacc 163260
tttatttacc aagtttttac ccttttgtcc actcactact gatcgcaacg aagattagtc 163320
tcattacggt atcaccagca aaccttcttt ttattaggat cacaagaagg ttacgaaatc 163380
ttcttttctt tttgcattct tacaaatgaa cattcccaat ggaaataatt gagactaacc 163440
atcttatttt taggtaatat tgaattcccg tgcctattgt ttagcctaag aatggaatgg 163500
ggggcaaagc tgtgaataca gttagtgaag ctagaccgcg gaactcaagg gcattctttg 163560
aggtattata aaaacatcgt tccatttgat agtaaattct agcatctttg aagaatcata 163620
ttgagaaaaa gaaagaaggc acgaaaggag ttgagcaaga gctataagaa gaaggtttac 163680
ctcgtaaata tgtaaagtgg aagacaaggc aatctcatag gtgaagcttc gtttttctat 163740
aagcagactt tgagaaagtt gaatacccca aaagtcaaag tcaaccttcc gctatgaaat 163800
gaaggaagaa aacaagggct aacgcgctca tcccttgctt ggttctcccg tgagggaagg 163860
ggaaggtcta gtatacaatt atcttcttcg ggaaggtcta gtatacaatt ttcttcttct 163920
tgatcgaagc tctatctctc attcagcaag cttccttcaa aaggggagtc cataggcgcg 163980
aatactcgga ttggacttgg aaccccccgc ggagttgaag actgacttcg gccaggagat 164040
tgatagagac catccttttg ctttgattga gagagccaga gccagagccc ttcagtggta 164100
gaaggatcta aaattcccaa tgggagagca tgcgcccaga gaagagaagg gcttaagcaa 164160
agaaggttga cttggaagac cgaaaagcac cttttaaaag caccttttt tgggttctat 164220
cgaagacttt tagtgtggaa agcaagcctt taagccagaa gtgccgctgt gccagtggaa 164280
atctaccagt acccgttgaa gtgaaatccg cttcagcatc atcaagaaga aatggaaaaa 164340
atgggatttg tggactcgcc tcaggatgga ggggaagcta ctgtggaaaa aggcagttgt 164400
tgagcaagtg acattggttg aagttcaata tgaatatgca tcatcaactg gagaagaaag 164460
atgaagattc cgctgaagat gtcgaagatt tagaagaaag atacgatcta atatgattaa 164520
gacgaatatg tcgagttaga gcacggattg aaattgttct cttacagttc ctccaccgaa 164580
ctgtagtaca gaaggaatgg aatagccgtg atgcggtctg tcgccaagcc cgcctctctc 164640
tctcgttgtt gcgcggccat tactctacag aaccagcata gctcgcagac gagcacgcta 164700
atgaggccct gagccgatag atgaagatgg gaaggtcaga cttctactgt ctcgaaggtt 164760
ccgatagaaa gaatgattga ttgcttgaat gccgggccat ctactcgcga aatcaccccg 164820
gtccgaaccc tctcagctcc ttcctaaaga agtgaattaa tgatcgatca acggagggaa 164880
aggaatatca gaattgggac acctggactc ggtctttctg gttccattgg ttggtaggtc 164940
ttaacttctg ggctaggtct cgatacggaa ggaatataga gggcgggcgt cgaaacccca 165000
tgctttgaga gttcctttct gccagcactt tctctacccg ggagtcactt catcagtacc 165060
tggggctact gtcccaggat gccaaaggta tgatccacac attgaaagtg tcaacgttga 165120
ctcacacgcg ccaccctcac cgggtaaatc cggagaaggg gaacttattc taagatagaa 165180
taagaataag cagaattgct taagtaaggt agtggccata aggcttttct ttttttcggt 165240
ataccgctct gctcgcagag cgaatgaaga taaatcttac ctaatctcat gaatatcctt 165300
cgccccttat ctcctcatct tcctatttat aagccacagc ttacttcgac gttttcaatt 165360
tcccatagaa tctccggagc tttcctagcc actatagttt tcttttttta tcttctttgt 165420
ctgaaaatag gtttgatttg cttcacctat gagaatttct accaattctt cttttattca 165480
tcaaagctca tcctaatctc cgtcgagatt actgccttag ccctgtccta tcatctgtat 165540
aatggagttc gtcatttatt gacggatttt tcgggatttt tctttcttag aattggaaga 165600
aaaagattga aataactgtt ccaaatttca cctatacctt tctttgagat ttaaacaaaa 165660
aattattctt tttttatgaa atgtttctta ttcgttgata gatctaaagc ttatgccgta 165720
gaagctgaca tcaggctatt ggccttttat ctgcatcttc cctcgtagag tggcgtcttt 165780
tataagaaaa gactttctca gtggaactaa aaaaaaaaaa aagagtttga gctctttttt 165840
ttgctttact tttagccacg cgcggcggct atgcgcatgt gtcccaaagt gacgtatatt 165900
ttttggtaat gggtatactc gagagaaaag gtttggaatt cgacctcccc ttatacgctc 165960
taaaaagggg tcatggactc cttttttgta taggatcccc tttctacatt caattattta 166020
ttgagcctgg tgtggaatca ccatcattac acattcattc ttggtctggc tgctggtcta 166080
gcgagccttc ctagccgcct agagtgcagc ctgcctgctg aagaccgtaa cgtaagtaac 166140
tcagtgctcc atacggggga aatgaaagca gaattcgttc ggatcctccc acatgttcaa 166200
tctttttta gcggtttccc cagagatctt tatcattaat gcaaccttca ttttgctcat 166260
tcatggagtt gtatttagta cctctaagaa atatgattat ccaccgttag tcagtaatgt 166320
gggttggctt ggattactta gtgttgcgcg cctaggaggg cagcgcgctt tgggatgcgg 166380
aggagctatt atcgtccagc tccctaacct aaagcggcac cgggtttgga ccgcagggaa 166440
ccgtagcatg gggggacgtc taatcctttt gccgccgcaa ggctggctaa tcgtacgcag 166500
caggctcgaa tacccctggt tctggaaggc acatgagtcc gaacgctatg ttgaatgtgc 166560
gaccgagact acactacgta ggtacccgtg caggtgaggc gtcggtcggt cctagaaacg 166620
gcggcagcgg cgcgaggagt taacgaccgg acgtgctgca acctagggat caccaggcag 166680
ctctttcgct ctatagggat cgggggggca tagcacaatt cttcttggag gagggttgtt 166740
tgcccgggtg actgatcctg ccataatgta cttctaccta ttatagcacc ggcaaccgaa 166800
gtcgagcata catacgacga tcttcatgcg tgaatagccg ggaggaaaga aagggcggta 166860
gatgataatg agaaagggcg ccgcgtctgg acgggcggaa tggatgagcg aaaggtgtca 166920
tgccatggag tggggaagag ccctcgtctc atgtaagaca actaaatgca cctcgaggtg 166980
ctgccgagga actgagggac cttctcgagc acaggatagg taattgagag atagagctag 167040
cctattcgtt atgggaaatc aatgctccgg gccaaataga gcttacctac ggcacctggc 167100
tttctccggc gagctttcta tcgtaaagcc aaagacgccc caagacaagg tacaactgtt 167160
gggaagggga catgatcaat agaacctggc tggatccggg ctgggatagt ggcgcccatt 167220
cttaaccagt tccgagaggg ttcgctcatg ctggagggag catccccact tagtgatcgg 167280
tccgctagtt cacgcaaatc cgaagaagtt atcacggacg agccacatgc agggaaactt 167340
gcacgtgtgg ttctggccgg gctttcctga ggtatctaat aaccttgctt ctgctcgccg 167400
ctggcgcacc tctcctaact attgcccatt tattctggaa taatcttttt aggagggaca 167460
attttacata tttctgccaa atccttctat tattaagtac ggctggtacc atttcgatgt 167520
gtttcaattc tttcgaacaa gagaggtttg atgcttttga atccattgta ttaattccac 167580
ttcctactcg cggtatgctc tttatgatct cggcttatga ttcaattgcc atgtatttag 167640
ctattgagcc tcaaagttta tgtttttatg tgatcgcagc atcaaaaaga aagtctgaat 167700
tttctacgga agccggctcg aaatatttga tcttaggtgc atttccctct ggaatattat 167760
tgtttgggta cgaccggaca actaccgata tctattaata tcttttctta gaatgttctt 167820
tagaaatata tatctatcta tctatatcgt aaactatcgg atcgggtatt acttagatgt 167880
gaaacttgca gacctcatag gttgtaagat ttttcttacg gggggaacga aatcaaagaa 167940
tatatagact agtagagacc ctctatgtag tttctatcta gggcgatcga tctacatctt 168000
tccccatagc cctggggctg tgtctcgatc tcctatgtgc taaatataag ggactagttc 168060
ctatagagat tccccttggt ctaattccac gccttatgac gaaaggggag tcggcgtggc 168120
gtaaagtgaa gattgggggg agtagaaaaa attcccttat ggggtattcc gaaggtgtaa 168180
cctaggcaac gaaaaagggg cccgatactt caactagagg agcgaccagt tggttcacca 168240
aaccccgacc cagcgtcaca cattctccag gtccgaaggg atccagtgcc caactaccga 168300
ctcctcccgg aattgcgtta tcggagccga gccaggaatg gccgttagtg gacacccacc 168360
acttttcacc ggttagagag gccctcttta atacattaag aaaagatgtt cacaggggcc 168420
agaaagactc ggtcatagga atttagaaca cctacgtgct ggtaaacgaa aaccacctcg 168480
accggatcag agtaaacaac aatgtcgaat caggccgccc tttgccttga aagaattcac 168540
acgcggccgc cagctttccc aaaataaggg gagatctgct gcttactgct cacggaaaca 168600
tccgacctat actatagtca agtcgttcgc ctatctttct gatctccttt ccttctattc 168660
atcatctttt ttgctttgac ccagtgaaaa atggggttga tggtgttggc taaaaaaggg 168720
ggagagagga gagccttagg gtacgctcac ttctgcattt ttgtttaggt tctcgagatt 168780
ctcaatcgtt ctttttagtg gggaggaata gtacgtgaat ggcggttctc agacgaggga 168840
atcattcctc tataaataaa aaaaagctag aatctttcta ttgatagagc tttcacgtct 168900
gcgcatagaa tccttttttg cccttccatt ctgttcttac ggtagttggg tcggaatccg 168960
tgtgatggtt cgaaagtcgt ttcaaatatt cttcgcatcc ccagagagat agattgttgc 169020
cattgtgcct tggtcgtcaa aaggggcacg aacagcctta aagtactgtt ccatgtccca 169080
gaggtcttcg agccttggca tttcgaatcc cgttgaatgg ctgtggttcc gggactcaag 169140
tctggagtcg ccaggtgaga cattcggttc acgaaccgga aacctatctc cacagcaagc 169200
tcctcaattt gacccggtcc gtcacgcttt ggacatcgcc accgggatcg ttgaggcccc 169260
atgaagacgg ctctacttca cagggaagac gcggtactca ttagcgagcg tctggtgacc 169320
aaggattccg gattcccctg cctttccgct atagtctaca cttgtccgtc caaatggtcg 169380
accttgccat caagttaagt tgggtcactc gatccttgag tgtttcctta acaacagccg 169440
ccgctgacag cactccactg ctatcgtcat gtacatggta caacaagaag agaattagca 169500
gaaatcgaaa ggtttttacc caaaactccg ctctgatacc tcctaaagcg aaataggcac 169560
gcgcacgggt agagagtctg cctgagtcgt gcggccccag gtaacgccta gtttagtgta 169620
gcacctgggt tccgccttct ccttgccgag ttttgcttct gatctctctc tgagtctcta 169680
gttcgttacc ttctactacc gatcttctcc ctctgctgct actggatatc gacctaagag 169740
atactagacc aggtgcgaga ggaagggatg ctgctattga tggaccggtg ctacctctgg 169800
atctaagaat catggaagac gtaattgaaa tatgcacctg gaattgaatc acattggtat 169860
aaagagccgg aaaggaaaaa gaggaggaaa gaagcaaggg actgagcgac gaagcgaggt 169920
ttggaaccct tcaattacaa agtggaagat gcctctcaca atgggtagga ttactgcatt 169980
tcttatattt gactcttcta tttgataata tagggagttg gggcaggttg aaggggaggg 170040
gaagtcaatt taaacatagt gccaccataa ccctaagaaa acgagattgg gtttgtgtgt 170100
gtagactatc cttggaagtg tctattctac caaaccacgg gacgcagccg tagatcgagc 170160
cctggaagtc ctctcctcgc ggctccctgc gttgatattc gaggaagtag ctctcgacac 170220
gagggatata caagaaagac ctgctctaga tccccaagtc tccatggtcg ttctttttaa 170280
catctctttc tattcttcta atgtaatgct atcagtcacc tcgtactacc ccccattgcg 170340
catcctgtgt aacatcaagg aaagggaagg ctcatactac cccggcggga ggtcgtctcc 170400
caacacattc cccctatagt agatctgcca cagattgagg catatctttt ggagatggtc 170460
acgtcagcgg cggcaagtgg atcattcatg cgaagactta actgaaaaag aaagattccc 170520
ttttgttacc gaccttcttc ccttgactgg tgttttaggt cttcttatcc aagaggacac 170580
tttaatcttg ctttagaggc cgaatgctta tcattcttgc cttctaaact tctttatatc 170640
gagggatgag gaaccatatt atcctgcatt ccttaaacct atgtagtgag tcgtgtaggt 170700
ggcgtgttta aattaggacc atacattggg attcttttcc cctcatcgct agccagtcgg 170760
gatgctatct ctcttctcct tcgtcactca accatcaaaa tatggtatat aataatctct 170820
ttttttata tttacttaaa actatactga accacctatc tattcgtttt ttggcgctgt 170880
cccgacactg atgagcatca cttaggcctt cattcatgag actctgctag gatctgcagc 170940
gcttcagtag gccctaggca ctgatgtgag gttaaagttt taaccaatgc ttaatactat 171000
ccataaacat tgtactccca taataataat aaggcaagaa agcggaaaat ttcaaaaaaa 171060
aagtaaaatg gaaaaagtgc cccctttga ttagccagtt tccaagaggg agaaggtctt 171120
atggcaatct caggcatact caaaatcggt tatttggcct gatcgagcaa cctatgaaca 171180
gttgtcgcct acataaccta cctcccagac caagggaaga aggtatcaga tcacttttga 171240
gagcccttta gttaaaccag ttcctttact ctttttgaat gaattacagt cagtaaagta 171300
atctggtgga aggggtccat agaataaaaa ttggcttctt tttcttttt ctattttgag 171360
ttttagaata gagaaagagt cgaaactaag ggtacgctct ctagaagatt tgctcggagc 171420
ttttttttc acttggtcgc ctggtatctt gaaacctctt tgcttgcggg ggcaggagtg 171480
gaaagagcgc ttcgcgaaag aatcgtgtgg cgcggtgaaa ggtttcccgt tggggtttcc 171540
gaccctccag gtctccacct acttgtggaa taggggggg ttccttgata ttaaggtgtc 171600
aaggcggtcg aagaaggcca caggtggaag caaccgatgc tttgatcatt caattgactc 171660
cttgctgcca gtccgtgctt gctgtcatgc tggcaaaagc aggggttgcg gtcggtttta 171720
cctactattg gatttgaacc aatgactctc gccgtatgaa agcgatactc taaccgctga 171780
gtcaagtagg tcaagctgag tcaagtcacc ctataagaga aagccgcgca accaaagtag 171840
cccttactat acaaggggg cagagcgcta agaaagagaa agccttatca ctatacgaaa 171900
tgaagcagcg gttagcacgc taagctaaga tcaaccaatg ttcgaacgcg gagcctttct 171960

-continued ttctcggtcc tctgtcttaa taagtggatt ccgattcatg cagtcgttct ctgctgcatt 172020
ggtcttttca ctccccactc tccaccataa caaaatgttt ccactatatc tcaggagtag 172080
tcaaaggaag tacggcgggt ccgagtagga ataaattgac taagaagtag ggcatacaac 172140
aatggatcaa ttcattcaac aagatctgtt cggatcagac caggatgaat gggattggtc 172200
tgacctctcg ctcggatgta agactcccgc cgctgacaga tgtcccatgc cacctttcgt 172260
gaacagctat gcccgagaat gaatgaattg tgatatagcg ccgaataagc cacagctcta 172320
ttcccgactc gaaatccata aaggacttta agggagataa aatagggggc cctataccat 172380
acatcctgct gccttgggac gactgcacgt tacatcatag cagcacgacc aaatggaggt 172440
ggaaagccct tgtataggtt gggcgctagc tagcgccttc cttatactaa tcaaaaatgt 172500
tgggccttcc ccttatttat tagtcttagt aaagttgctc gaggacttct actgggaatg 172560
aaagttcctt attataggat ccctagtaaa gccaatttaa tgatggccgc ttatctgagt 172620
aagaagacga tggctcctat tattggtgag cgatctcctc tacacgttat ctttgggcgt 172680
tttactctct ttcaaagaga tgactattca aacctcagag tattcggatg cacgtgcttt 172740
gttaaaattc catctcctgc acaagacaaa ctgagcccta catctcactc tatgtgtttt 172800
cttgagtgag gttggggtac ccctctctca aaagggctac aagtcttaat gatccttcta 172860
cacgacgatt ccacctttct cgacatgtca cctttttcga acatgtgcct tactacggag 172920
ctcggggctt tgagattccc tgtgatggtg ggccattatg ttcccttgtc tccccttaga 172980
ggggaggggt ggaactattg aggagtttat gtgagacagc atcagaattc tccgatttaa 173040
tagagtcagc aagatccggg tgaccagagt gatcagcagc ttgatcagct taaggggaag 173100
tttcgcaggt ttgtgaagac agattctcgt cactcagttt tcagagctga gccaactgat 173160
tcagtggtct ccctctctcc ctatacttcg aaccaagact cttcttcaga cttaggttct 173220
ctagcttcta ttctcggggt acgtagatcc acccgtcttc gttttcctat tcataggttt 173280
gtatcaacta agtctctgtc tacttcccac gagtcttttt tgcaatttca tccatctttt 173340
ttaacctgat acctttgcag aggccatatc tcaaccctgc tggcagctct atgcagaaag 173400
agatcgtagc actagaatgg tttgctactt gggattgagt ctctcttcct ctagggaaat 173460
ctatagtggg ctactagtgg gtctataaag taaacaaaaa gctgatggag cagttgaggg 173520
gttgaaggct agattggtgg ccaaaggata cacacaagag tattgagtcg aacccccttta 173580 gagatagggg aaagatttgc cccagcttgg cgaatcgcat ccccgcgcaa cgaattgcat 173640
tgccaacctc ttgattgtct tcttatcatt ctccgttgca tgttagggat acgtttggtc 173700
ttcaatatat tccctgatgt cagtaaacca tggtttaccg ttgggtgccc tttcaatggc 173760
caaaagatca ctattgaaca tgccgggagt caactcaaaa atttctatta gtttgcaata 173820
caccgggctg cttctttgtt ctatcatgat tgggcggact ttccctcagg aatgtttatc 173880
atggaggcca gtgttgccaa tacatccgcg aacttatttt ttctctgggt agtggagaga 173940
aacttatttt cttgaattgc tcagtgagct tttcaagata agcatggtat gtcaaatttc 174000
atatttattt ggtttttcat ttcttttgag tttggcagat gataagcgtc gaatccctaa 174060
atacttcgat ttcttatatt cccagggtca acgcagtctt taatccatgg atacatgctt 174120
catcttctgt ggtattctta gttccttaaa agtggagctt aatggcaatg ggggtgtgcg 174180
attcatcagg tgcaatcagc aatgccccta ctccgtaccc attttgatta gtcgtgccat 174240
caaagtcaaa tttccatgcc ctcctcttct gtgacagcta tttcctcgtc tgggaagcaa 174300
tccttaaact catgttcctc cttgataggg tgcaaggtgt tctgctatcg cccttccttt 174360
ttggttacat acgtgatgtc gaattcagac agaagcagta accatcttgc ggtccttccc 174420
gttacgttaa ggcgggtttt tcgaacaaat actttttttg taggtccatg gaagctatta 174480
aatgtactgg gtaagacagc atgtaatgcc tcaatttccg ccttacccaa accaaagcca 174540
agcaggtttt ctccaaattg gtatacctgg tcttgtagtc agtaattttc ttactaaggt 174600
agtatatggc cctttacttc cgtctgtctt catcgtatta agccaacata gaccccatag 174660
tggtttcagt gactgatagg tatagtaata aaggcttcct ggcgttgtag gcactagaat 174720
ggaggtattc ctgtattttg tcaaaagctt tctggcgggc ttcatcccat tttcctgcta 174780
aattttgatt tcgaaatttg tgtatcggct cgcaagtggt tatacaagag aaagtcaaag 174840
tctgatggga ctattgatcg ctacaaggct cgcgtggtag ccaaaggcta caaccagcaa 174900
tagggtatag actatgatga gacattcagt ccagttatca agatggcatc aagggcgatt 174960
aggtgttact tgcttgataa gggaaagaga agacgtccct caaagcccca ttaacgcaaa 175020
agaagtcgat tcctacgttt ttaaattacc agaagctctt agctactcag ctatactata 175080
ggctctaaag gcattacttg actgaaagag tgcttatatt atgggggctt ccctttccaa 175140
catctgactt atatacaggt caacatcgac ttaaaaagca cgaaaaaaaa aagtagctac 175200
ctcgggagag ggatgagact agtctttttc caataggcta gctgcctatt gcaggagttc 175260
ctgacctgaa aggacaccag caagctgcta ctgaatgtga acaaagtcaa ggagatggaa 175320
tcaactcaat agaattaggt ttttttatg actgctgaag cgaccgaacg aaattaagga 175380
ttgattcaat accgaatccc agatctctat agacgactaa tggtaggggc tgcatttttc 175440
ggaaagaaag atagtggcaa aaggaagact gttaatcaag aaccgacgtc tcatgccgac 175500
cccgtctgca gttgctacta cactgttaca tccggataaa gtgatccgta ctggtggaat 175560
aattgcaatg cgactatacc gtctgctgat aaagggaaga cagtatacca agcttgtccc 175620
agcagtcagg tttggtcctc cgggcagcaa cccggccggt atacactcca cagagcaaat 175680
tgggctgtga ggtgagtaac tatattcaac aatcatttgc caacatcgtt cctaagccct 175740
actaagtaaa gggggatgtg ttcaatccca agcatcttcg tcaatactcc atctgccccc 175800
cgccgggggg gttaaggggg aggatgtcaa aaccttaccc ataaaaaaaa gtacatagac 175860
ctgctcacaa agagctacaa gacagccaaa aaaattacag ctaataaaat gaaagtgaac 175920
aaagccaaat caatatgata ttcaataagc ccactttttt gagagaaaaa acctgaattt 175980
gttgaggaag atcagctgta gaggaaaacc tatagtcaaa ctgagaatcg cagccgaagt 176040
ttgctaaaga gtctgccact ttgttgtttt ctctaaatgt atagacgatt ttgaaatggc 176100
cagccgagaa tttggatgaa atgaagctcc accatgagtc taggtatggg taattttagg 176160
ggcttcttta ttttcattga agcaatcaac aatgattttg gagtcaattg cgagtttacg 176220
agcttgatga atgtagagcg catccagaag aatagaatca gtaaacgtcc aagatgatct 176280
gatgtcaaga agctgagaac agtctttcag ccagtccgta atttgttgaa taatagcagc 176340
cggttgagat attgggcttt ctaatttact gctattgcct tccttccaga gttcccaaac 176400
tgaaaaaata gtaagcatag acgtgacgta gccaacttgg gatttcctgc gagatctgtt 176460
aaaccgccgg gactgaatgg aatccgtttg gaaggatctt atattgaaaa ggcgatcaaa 176520
atggttccaa acctccatag caagctcact cttgatgaag aggtgatcaa tactttattt 176580
atcatgctcc gaacagcaca agcatttgct tgctaatctt atacctttcg tttgaattta 176640
ttcccttaac tgattctgaa atccccgcat acaaagtaaa ataagagctt ccacgcaaaa 176700

-continued

```
atgcttcgat atcattgaaa aagcagtttc catgtgcgtc aagcacatct atgattttgg 176760
agaaataact agtaaaggag ttggcctggt caataagagg gagtcatact ttggactgct 176820
tttttcaaaa gaaactatct gaaagcccct atggtttgct gcttccaaac ctggttgtca 176880
ggacttggag tgaaatcagt tctattttca ggcaacccca ccaatactta agggctaaaa 176940
atggtggatt ggaaatggag ctagcactga tttctggttc cacccctggc tctctgatat 177000
tcttctcatt gaaagtaccc ccctcttatt gaccaggtaa acttcatacg aaaagctttt 177060
gaaagctctt gaaaatgtct tgtagtagga ggacccaaag ccccttcctg aataggtagg 177120
cacatagtat caaaaaatat ccagtgaagc tttcttttgt cttcatcacc gcctcaccaa 177180
aagttagcta acatttttc ctactggtca agaactccct ttgaaactgg aatccctgca 177240
agaaggtgta taggcatcga gaaaagaaca tgtttgcaaa ataagccgcc ctccactgga 177300
taacaatgct ttcatctcct accactttat tttagactct atccagaaga tgagcaattt 177360
tttttttaag atttaaatag aggtagtcct agataaaaat attaggaatc aaagcaagga 177420
aagttgcatt gatggaacgg gggatcgcac cttcagcgaa gaaataaggt gaccagctgg 177480
aagtttttga aatcccaaca agattttcta tataaaaaga atccggaaag ccatcaggct 177540
ttaaaggata ggggagacct ttttttgggt tagtgcgcgc cgacatgcta aaaatgacct 177600
tttgaacttc ttccatatta ggagggctcg taagcatctt attatcttcc tctgtgacta 177660
gagaggggat ggtctcaagg atctcatctt caagcaccga accttgagaa gaaagtaatg 177720
tatgaaataa attgagagct tcctgtcata cagagacaag ttctgaattt ggttcaaggt 177780
gcttattctc tatctttctt cgtaaagcag aagtttttca aggttactct tggccgaatc 177840
taactccatt ttcttatcag cagaccaact ctgttcaaga gcaaattggc cttcttcgtt 177900
ttcggcattt ctatattctg aaatagttcg ccaattcagt gctttatttg tcgagtcaat 177960
cttcctggag aagacttgaa aaggatttcc cgagcatggt tgagatcaat gtgaaaataa 178020
gaatgccgaa tccacattct ttggaaacga aagaccccag gcctgcgagt attagaatct 178080
tctaagaaga ttactagagg agagtgatca gaggatactc taggcaaatg gtcaactctg 178140
gtggaagcaa aacggctttt atatagaagc gggcagtccc cattcaaaag gattctatct 178200
agtctggccc agatacaatg ttgaccgctt tgattattgc tccaagtcaa tttgctgtca 178260
ttgaaagccc aatcaaataa tccaaacgag aaaatcatat cttcaaagct catcacttca 178320
ataaaggcat tgaagtcagg aggccgaccc ccaagttttt tctaatggat ccgcaattac 178380
attaaagttc cccctactag ccacgccacg ggaagttaat gcaagtcgat aggtccttca 178440
atcatcgagt acactatcga cttcccacac ttatcatgac aacatcaccg atctttggcg 178500
cttatggggg gccctatcat acacatgcac caccagagtc ttcataagaa ctctggggcg 178560
agggccaagg tgaacccgga ttaacgatga gaagcggtca aatcagtagc aaaggcacca 178620
ggacggacgg ttggttgaac cgggcgatag cttcgcgatc gatagctcag tgaggtacgc 178680
cacccgccct acttctaatg atagatagaa aaggtgggag aggtgctgag ggacggcaaa 178740
ggtacaaaaa caaaaactac atgacatacg tacgttaaat ggtaggccca ttacgaacaa 178800
tcattaaggc ggtctccaat ctcgctcggc tcggggcgat cacttgaaca gggcgggatt 178860
gatcgatcta catcaaaaat tctgccttcc cttcccagga gcgcatctac agaataaaga 178920
gagcacgcac cacactccta ctataccagg gcctttagct ttcactgaga agaagagatt 178980
acttccagct agcttttttc cctaacccta accaatgaat gataggccgg cttaggataa 179040
tcgaaaacga attcactttc agtaatcgga ggcaggtcag gggccggcgg gcacgccccc 179100
```

agcttcttaa gtttgggaat tgtgcatgac ctatgcaagg agcttccgga atccaatgga 179160
atcttcgtaa agtcgatcat tacgagtgtt acgattcatt cgattggcag gtccaatcgt 179220
tcatagcctc tcgagcacaa cccatattca tgcaaggatt ggtgattgag gatccataca 179280
gagttttatg aaatatctta gagatcaagg aacagatgct ttcttcagga aatatgaata 179340
ctttttggta gggacaagaa attttttggc cttgaatcgg gtcaggaaga acaacttgtt 179400
ccagctccgg ggaaaagatt catcttccaa ttttcccttc cttccaatat tttggatttt 179460
agcttccctc attcctttta ttgagcataa tgatgcgaat cgggcttgtt gtatttagta 179520
tacagcgtca agcagttccg ctttccccta ccgatgatgt gccgagaagt gcattgttgg 179580
aactgggttg gaacttaaga ccataagctc tagattcggg ggtttacgct atagccgaac 179640
acaagggaaa gatcattttt ttaccggaaa agatcgtttt atcaggtaat ggatacacta 179700
taagcattcc tttggttatg tataagcttt ccaacaaaga gaaagacttg tatgcatcag 179760
gttcataggg gtaaatacat tcaaaaggga aaaattttag cggctcatat ttcaaataaa 179820
gatcgccgcg tggaaaactc gtttttttgg ggggttgtcc ccactggttt gcgaaagcaa 179880
tgggagactt gctccataga accccccccc agagactttc gtccccagta ttctctatgg 179940
gcaaaggcgc tcaggtgcgc ttaaagtctt attgcctata tcttatctta agacgaggtt 180000
gccaccccgc ctgctttagt ctcaaatagg gcgcaaattg aggtgaacag actggaccga 180060
acctccctac gtcaagagct tttggctctt cacaagaaag caccaggtcg taacaccgga 180120
agactgcgcc gttattagtt attattaaaa tgatataatt tttttgtatg gttagtcacc 180180
agtggcacaa cctacgggct aagtagcgcc tcaatgggag tatttttttc ctccgcgata 180240
gtgtaatacc aagaccagta agagagaatg gacttcatcc attcggacaa aacccatgcc 180300
cccctaacca gtcgtactct gaccaggctt cgaaaaactt cgagatcacc gagtttctcg 180360
ggaatcgagg ggtcaagagc ctaatcaggt cccctcacca taccttgttg ataagaggtt 180420
aagtgtttac cagtggttgc gcttaaccag atccaaaagg ggagaggaca cacaccgttc 180480
ggtgagtgaa agacgaggaa atgccgattc cagtgtctcc taggaggcgc cgtgcgtcga 180540
gtatacaccc ggtacccagc ttcccgtaaa cgatacgaca atgtaagatc cttatacata 180600
agagccctca ttacaggaac aagggatatg gaactaacta aggatcttaa catgtgacag 180660
gagacaggaa aaaagtcctt agtcactccg cgtacgaaga accgcttagc aaactccaaa 180720
gcaccaactg acgagactaa cgatttctct aacgaaaatg gaacattcag tggcgaaatt 180780
agctcgcgat aacgctcagc cacccgctca tctccgatga cgatatcgtc gccgaggata 180840
gcctagcgtg taaaaggaac tcctggatat acttgggctg ctacgaacca aatcaccaaa 180900
tggtgagtta atgcgaaagc aggccaagct ccgtaaaagc ccaacggggc tcctgttaca 180960
aaacgaactc tacctcgagg aagccgacga cgagaatttc gaatcgtcag aaaagagtag 181020
taggcatact ttcacaatag tcttgtccac aagcaaatca atgttcggca gcggaaaatc 181080
atctttggga acatgcttta ttgagatttc aaaaatagat gcatacgcga acacgtccat 181140
ccctcttggg catggggacg atgttcgaaa tccaatcaga ataatctact gccttaatga 181200
aatcagtata atagtaacaa gacagctgaa gagaggatga cgtagacaag aatcaacctc 181260
ttcccggtga ggttttgatg tatcgcagaa tccgaaaagc agcttctaag tgagatgatc 181320
tcggcttgtc catataaaaa tcggctgatc actccctcct atgttgtaag tgtaagcaat 181380
gtctgggcga taattagtca ggtagaaaag agtcccaaca agtctccttg caagtagatg 181440

-continued ggtcatccaa tagctctcct gcatctaagg ctaattttag atcttattcc ggtttgcatg 181500
cagaaagacc agcttttgac aataaatcca atgaatactt gcactgggtt ccaaaactct 181560
ttgtgacctc atcactttaa tctccagaag agactttgag tctcctaaat ctttcatatc 181620
aaactgggtt cttaatcttc tcttaagctc atttatcgaa gctaagtcat tactagagaa 181680
agcaatgtca tccacataaa gcagaagaag gacaatacct gatgtcgacc tccttataaa 181740
cattgaatga tccgatttac ttatttgaaa accggctcct tcctctactc ctatttcggc 181800
tcttatacat gctgctgtca cctttcaaac caagctcttg gtgcctgctt tagcttgccg 181860
gaggccgtaa cataaatcgc tttcttgagc ttgcatacca agttaggatt cctaggagaa 181920
gagaagcctg gagttggagg aggctgaata gaaacttatt cttgcccccct tcccttatgt 181980 tgttgaaagg cattctattc ttcacgtcaa attgaaataa ggccaccttt tgattgcagc 182040
caaggcaaga atgccacgaa tggtgtttag caacctgaag caaatggttt ccctatctct 182100
aaaggggttc gactcaatat tcttgaagga atcctttagc tactaatcta gccttgtatc 182160
tatctaccga gccatctgct ttatgcttga tcttgtaaat ccacttgcag ccaatggctt 182220
ctttccctgc aggcaatgag actaagtctt attattatta tttttttcct gggcattgat 182280
ttcttcctgt atagcatctc tccagcaaga atgattggag gcttcagcaa atgattcagg 182340
ttcatgagaa gattgaactg agatgaggta agctcgatct tttggggaaa acgattcata 182400
agccttcaac aggataagaa acttgagagg gtcgacgaag ctgagagcgg gatccagaat 182460
ttgaggaagc gactggaagg gaagcaactg ggctagactg ctgatcttct ggagtagcct 182520
gaccctggga aagagactgt aatcgccgcc gagaataaac atgctgtgcc gggtgacagg 182580
aatcctctga ggtcagctga acaggctgac aatcggcaga aaatgctgag caaagctgct 182640
ggcctgaaga gtgaggctaa tccgtaacat caactgcaga agaatgaggt tcgagttgat 182700
gaacaggaga aggccgcaat acatctccat catcattctc ccccggggct gattaattag 182760
gttaaggaaa atatgaggcg accctattaa agagagcatt aaggatacat cgactctctt 182820
ggatttcacg tcatagcata tatatacccg gactgagcat atccaagaaa gacacaagtg 182880
gttgccttgg ggacaatttt tctcttaact gcgcaggaat atgaacaaaa cacgtgcatc 182940
caaacactcg caaatgccta ttatagtact gccccagtaa gaagttcgtg aggtgccgct 183000
gcagcttgga ttatcgtaga ataagaggag ccgtcttagg aaatgactta acttaaaaga 183060
cagatgccgc cgctgcgagg cgagggagca acttgtctgg tcttgcggtg cactcattcc 183120
cgttacgaga atgaaatgag gccccagctt gactcgagac caagactcct tacaactcgc 183180
accaatagcg gcactgagcg gccggagatt gattgaaaag gcaggcccag ccgaccctct 183240 cccccccctaa ccgcctatct actcgtgttc gtagctcgat cggaggtcaa gactgtggtc 183300
cggcggaaaa acagaagtcg tccgtatcaa gtgatacgtg aattgctcag tagtgcttcg 183360
ccactaccct agctggcgga aatagcttaa tggtagagca tagccttgcc aaggctgagg 183420
ttgagggttc aagtccctcc ttccgctcct ggcttcgtcg tttagtggta acaagtgggg 183480
tgcataagcc actttagaga taggggcgag cagcaagcag ccccttgtat agggttccaa 183540
acctatctga ctaataagta agaggaaagg ggcaagccaa aactgactcc taacaagttg 183600
ctggcttttc atcagccgtt gcgcgctagc gcgctagcct tttcccaacc tagtaaaggg 183660
gctgctagtt gtagcgcgca gtgtactagt gaataggaaa agcgaattga gattactaat 183720
gacggatgga ggttgagggt agaacatgtt cggtgcctcg cccttgtctc cttcgccgta 183780
gactgaaaat gatgggaatc ctatcgataa agaagaggca taagcatcgc ctctcgatcc 183840
aatccatctt ccctggcctc cccagcacac tcttgatacg aaagaaacct cccgccatag 183900
agaagagatc gaaagtctgg gtcccctcga tcaccctccc ttgaacctga actggtcgag 183960
agagatgaac ccgcaccaca ttttctcgaa tcgaaacccc caactagaga tggaattcca 184020
gaacctaaac aactcagttg agagctccgt gactggttca agggaaggtc aaccaatgat 184080
tgataggcca ttccctccct atccgtctct tgatccctca ttccactaat ccgttgttac 184140
tgattcattc aaggcataga ctctccattt ctttgtctta ttagcgcagg tgttcgtcaa 184200
cgatgaaagc cgctgaactt cagactcgag tggagaaaga gggctaggcc cccggagggc 184260
tttcagggac tggggaagac gggtggatta tagaactagg gtaggggcaa atcgaaggtt 184320
ttgcccatcg ggattgggca tggacgagcc tcgactgggc cagcattgat gaaaaaagaa 184380
aaacttcccc catcgcatca ttaaccggtg taggattcaa gatcaggtcc aggattcgag 184440
tcaaatcgac cttccctctc atctcagggt gaggcaagga attgtttcaa atgttcgttg 184500
ttgggacggg ttcaaactgg actgaaggga ggaggataaa aagagtcctc tcttcctggg 184560
gattcatcac tggctagggc tttcgaatca aagcatgggc atccgctatt aagagggagc 184620
agtagatcgt cgattgaaga gccaggtcag tcaacttcta ttgggacttc tattgattat 184680
taattcgact ctagggactc ctagcagcaa actagtataa aaaaaggggc cccatagaga 184740
tgcaggagcc gccagccgga tcgaccaaga aatgataggc cagagagatg ggctcattcg 184800
actaatcagt gatccctggg cctacctaac acagatgtcc ctgaaatagg ggattggttg 184860
atcggaaagc tcaggcagga gtaggacatt ccatacaaat ctttctgatc cgctagctgg 184920
tggtcctctc aaatcccatt ttttcatcga caggtagggt gaattctaag gttccttatt 184980
ccggttgtaa agcggaagaa gagggagaat gggcacagcc ccactagcag cccgcgtttc 185040
cgacccgaaa ggaatggaaa atgaaagaag aatctgtgtg cactatctat ggagtggagt 185100
gactatcctg aatctcctct tccctatctc cccctttttt gccttcggct attaccggct 185160
ggcaaggctt ggcccaacat tggatttgtt tgaaaactac caaggtggca ttcattcaat 185220
caaatctttt atgcctatgc cagcccaaac taattgactt tttttggaaa ggaaggaatg 185280
cagggaagaa gtctttcctt tccactggtt cttgaaagct atcaatcccc gcttctccct 185340
ctcgcatcgg ttctgcatca gatgatgagc ccatgcgaaa actttctctt ttattggcgc 185400
ccgataggta ggctattaga ttgagtcgaa agcctaccaa cgcataaaag ttccgattcg 185460
agcgagagcc caaacgggtg aggcgagaag atcttgatcg aaagctccac tgttctgaat 185520
agtgagaaag atttttggaa attcgatcaa atcgatcgag aatctcatca tctgttaggt 185580
gggccaaccg accgaccgag ttgggctggg cgtccatgtc acagaacctt tctctagcca 185640
agaatcccat tattgatcga atcggggcgg atccaattca ttggcaaatg aaaaatctat 185700
cgttttaaca ctcagaaaaa aaacctagaa aagaggaaga gtcactaaga caagagagct 185760
ataggtaagc aagcaagaag gataggtgca aaaaggcgag gcaaggggct ctccatctct 185820
aggaagattg tgtccaggat ctggtaatct aagccttgtt tcttctggtc ggctcgtatt 185880
agcctgtgct ttattacagg tagtcattcc cccgttcctt tagtcttttc aagggtactt 185940
ttttcttaag tcgcggtcat gtcttgcccc cccagtatag tgaccgcttc catgttttcc 186000
ccgaatttca tcagttccag gctcaagtgc ctgttcatcc atcttcattc caaacaaagg 186060
cgaacatctc cattgagtga ctgtaactgc tatggtttac agtcaatagt tcttaaccaa 186120
ccctttcttt tttgaattat taattaatta attcattaca ttattatatt atgtctttct 186180

-continued ttctgaaggg cttgcggttt attacaccaa aggctttcag tgaactattg aagctatcga 186240
gagagtacca aatgctgacg gtgacgaagg ttaccgactt tcggtggacg cggagccaac 186300
aagttcagtc gaacagcgta acgagtctaa ggttacagaa gccttcgcca actttgatag 186360
ttatagcatt gcaagcaaat agagcagaga gcttaccctt tctttctatt agagtcgcga 186420
gcttgttgta gtcggtccta aggggagaac cttgctgctt acttgctata tccccgcgtc 186480
cttgcacggc tcggctcgtt cttcgagccc tgcttctccc ttccccctct ccccgttcct 186540
accgtccaaa acaggtctat ggagtatagc caagtggtaa ggcatcggtt tttggtaccg 186600
gcatgcaaag gttcgaatcc ttttactcca gattatgaac acccgatcgg atctgtcaag 186660
aacgagctga cgactacaag ggaagcagct gactgcagtc cctgagcccg caagccaaaa 186720
gtttgacttg aacctacctt tgctaagaga agagagagaa gggaaagaca gatggcagaa 186780
ataaatcctt ccaaccgcgg aattgaacac aagactgact tcggccaggt tcttttatca 186840
atctcctggt ccttgcttaa ctccttgttc cgtaaaccgg tcgctggtag atctgatcgg 186900
atcccggaca cgcgagagcc cagcccggga ggaatgcatg gttccctggc gcttcatggg 186960
acggacgttc gcagtcctcc tccatctaat ctaaccctac ctcgttcgcc caggcctgcc 187020
ggcacaataa gagaatgagg gagctaatct gcttgcttgt gcaggcgagg accgctcggc 187080
tagggcgcgc cagaggagct tcgagtgact tttttctttg ctcttcgaca gccctaacaa 187140
gtcacttgaa gctctgccct ttgctttgcc ccgtgctgtc ttcctccagt tgcccccacc 187200
caatagccaa taggccgaaa aaggttgcag tcaattgccc ttcccgttat catcaaacaa 187260
aagactacca tacacgctgc cggcaagcta ccctcgccta cctcatctat aggcatttct 187320
atccgcccgc gcgcgagatc agatcgacta ctctactacc atcattccga aggttttttt 187380
attcaaaagg acggagaatg aatagcttat tcataatctt ataggccccg caccgcttca 187440
ttcaattgct ctgtcataaa gaaagggaag gaaatctttt tttgatcaat cgcctgaacc 187500
tgcctttctt tctttgccag gaggggtggc ccaatcacta atagatctct caacgggagc 187560
ctcattctgt ctagaggaaa tagcttcggt ggatccggtt gattaagtcg ttgtgtctgt 187620
cgatacccac ctgctcggag tgcgggtaag ggctcacctg ttgattgtgt cgttgcatgc 187680
tttttggtag agcccccacc tcccacggct acagccagca ccaggagcct agaaaggtat 187740
aggcacccgt tcattcagtc aatgaagctg cagtcggttc tgatgattat gccgtttcaa 187800
gtggatgttc agttggttca gcgatagatg tagtcgatgg ggtagagggt ctgcagatac 187860
tcgtctagct cctcattgcc ccaaccttcc ctgtaggctc cctgctccgc cagcgcgaca 187920
actgtccaaa tcatttgacg cttcttctca ctgagcagcc cctcgacttc cacttcaggt 187980
tcggggagct ccggcagggg gacttgagtc tcagcagaac cttccctttt cttctctctc 188040
ctttccctca tctcccgggc ctcaaccgaa tttgctccat tttgctcagt tggggagcgg 188100
aggtaccctc gagcggtgta tgggctgtga tatttgtggt agcgggggta gaactcggaa 188160
ggctggccaa ggttgtgtcc ttccgagcgg acgaggtcgg ctcggtgacc gagggcttgc 188220
gtggaggcgg cattgcgacc acgggcttgg acgtcacttc aacatttctc tgcttttttg 188280
aggcccgagt gaaggcatat atgtcgaacg gattcacaat aaacaaaggc gattgaaaaa 188340
cataaaaaaa agaaaggggg cttactcgtg acgatgtcgg gcagggtgtc atagaaagat 188400
gtttggggta gtggctgtaa gttcgaaggc ttttgtgtta ttcgagtgag gatgtgaata 188460
agtagaaaag gaaataatta ggctttgaac ttaccttctc tggatggaag gggtgaccgg 188520
ggtaagtgat gtgcgaaaag cgatatgctt tacacgtccg cttccaggac gtcacgccca 188580
cgcgtctcct gactgtaatg gttgggcttg gctctgctcg ccggttgtgc tgcgtgagcc 188640
ttcagatgcc tccaagcaag cgaaggtttt cggggtaatc gccgcgcgtc cttcccatgc 188700
tccgtgacaa cggcggtacc ccgaaacaaa ggggccagtc ttcgtcgtgc cggggtatcc 188760
cgatccggat gccacgaaaa tttagggaag ccttttttctt aaaagacttt ctgcgaccgg 188820
tgagaaagcg gacgacttta gggcttaaag gaacaccttt ctctttcata ttgagtcctc 188880
agaggtgcgg cccacttggt gtcggatcag ctcgacaggt cactcaatag tctttcgcgg 188940
agtatccccc gttttagtga accctgggag ttgtcggcgg ctcgacgatc tttattccaa 189000
aggtttaccg aggtgaagct tttgacaggt attcttttat ttgtaggttt ctctacttca 189060
ggctcttccg agggcctttg tttgaggtga ggttctatag tttgatggtt acttatgttc 189120
tcctctcccc ttccccggta gctaggaaag atttctaaat atatttcctt ccttccgttc 189180
aggggcactc taaaggcttt gcaaccttca gagctggttg acagccgtct agtcagtccc 189240
tctcgctctt tgatagacat ctttcggttc tcggtctcat ccgacgaaca acttgaggtc 189300
tttattctgt gtcctatcct tccttgcgga ttcccggttt ctgaaggagt agcggcctgt 189360
gtctccggct ctgggagaac tttacctata gctaacctag agagctttac tttaagatag 189420
ctcgggcagg cactcttctt cggaaagagg agttgcttgc cttaccacac caaccacctt 189480
agcgctggaa gttctagcaa tgggcagcta ggcaaaggaa tattatatag caatttcata 189540
ttcattagat aagagattgt ggatctgttc ttagtgagga caaccggatt gggacgatca 189600
ggtcggttga gggcagcagc acaccaatag gtggattgcc attcttgtac tgtttgggta 189660
aagggcagga gcgctctttc cctctcacca gtacttacta taaggggtgg ggcaaccggt 189720
taaaaccaaa tatccaacag ccgctttcct taatggctac ccgctttcga gtgaactgaa 189780
ctcttggact ggctgaaagg gaaaggggaa actgtacaag gtctttttca ctcgtttacg 189840
ggaccagtgt caaaggaaag gattgttgca ctctcttgct tgaatgaatc gacatttgtg 189900
gatgcttgtt cattcgggat tcttctatct atatttagaa ctactggatc aactactccg 189960
gcttttagcc tttggaacct gtggaaccct aaagtcactc gcccgttcaa actcttctgt 190020
ccatcccatc taaaaccctt gaatcagtga atccggggac agagacctag cccctgcttt 190080
atttaaacag ctaagataag gtctaagacc gtttcttctt ttccacatcc tccttcctcc 190140
ttctttccgg atacttaagc ttctaatgct acggaacctg ctttcccaat caatcaattc 190200
aaattaatgt gtaggaacct gccctcatcg aactgaatgt ctacccttcc cgcatttgaa 190260
gacagactaa tgtttaagac ctcctgcttt catggagatc ctttcttctc tgaccgccgg 190320
agattaccca tatatggatg aataaccgtg aagttcgaca atcttttgag ggaggggagt 190380
cgactgactg acaaggaact gacagaaggg gaaaagagga gtgaaaccat tcgacggagt 190440
tggaaaggac ttcgctaatc ataataaggt tggtctcacc ttcgtccggg gactcgaacg 190500
aggagatcgc tgatgccgac caccctctgt gtctttgtca gtgaagtaaa tcaccccgag 190560
gctaagcgat ccgcagtgtt caatggttgc ctaagcaccc gactttaata gtaggagaaa 190620
ggaaagcgct cgatccatgg aatccgtcat cggatctccc cattgacaga tagagtagaa 190680
gaatcaatta gcccgggatt taagatttag atcttcaact acttccgaga gggtctcatg 190740
ctacgatacg agtagaatac atagggggtat agttcgggta aagcaaatca gattttgacg 190800
tataccttttt attggaaacc tacaaagtcg caatcctggc agaccttttt gagattcctt 190860
cttgcatccc agtctaactc ccctttctgt ctgtcactgg atctacacta cttgacttgc 190920
gacttgagct agcagactga gctttagctt gagcgagaac gaaggcagac atctcttttt 190980
tggacttttc tgcttgagct ggagctttgg actcgacgag gtattttgtg cttgccctat 191040
tgagagtctc ttccattctc tcttcaccag acagatagac aaataggcaa tccgatagat 191100
agattatggc ttcctcacta tcagcaagct cccacaggcg atgaactgct tccgacttct 191160
tcattcggtt tgtagccata ccgtatagag tgaaaaattc cttttaatgg gagtagctat 191220
attcaagcaa gcattccagc gaaacgatcc tttgacaatg ggctctgccc aacactggga 191280
ctgactttat acagagagag gaaaatcagc aaaaaaagct ctttttgaat cgaatattgg 191340
ataggctaag ctaggtgtag cccgctctct ctacggtttt gcttgaactt gtcaagcccg 191400
ggtgcctatg cgattattaa ggcagggtgc tattgtacca gtggtggagt ggcttgaatc 191460
aaatcgtttg tctagagagg gtgtagcgat aaccaaagtg gactctacta gaaagtcaag 191520
atgctgtata ggcaactggc cttagagtag tgtatcgaac taaaggacag gagcgaccca 191580
taatcattga cgaagaggaa ggcttggaaa gggatcaaac atattgagga ggagctttca 191640
caaaggccaa tagccgatag ctgatgtcac tagccttaac ttctttatct acttgaaagc 191700
tgatgggagt acggctttct tcaaggaagt gtcccatatg atattatatt agtaaagagc 191760
ccttgatcct agataagtaa gcagatatgc ctatggctgg aaagatagcg agcgctattc 191820
tcaacttagt ctctcagagg ccagctcgtt gtaaccctaa aacacggcgt tagcggggtt 191880
gggctccccc tgcagaaata caacaaacat gggacagccg ggaacgatga cccttctcaa 191940
gcctgaggcc taagttggac tttctctttc tgcaacttgc cactccgaag tttaggattt 192000
cgtttcgaac cgatgggatt tttcgaatgg taatgaagct tgccattctg tttatttggc 192060
cgaatccgac tctgggcctg cccttttgct agctttttca ttatgctggt tcaactactg 192120
cttatgcttg aaatatctaa acacctgaaa tccactctca atagatgctg ccccttaaac 192180
agtgtgaaag ggtggtaggt agaactaagg gaataatctt ctttggttcg gtaatggaat 192240
caatagcttt cccgaacagg gatataggaa gaagccaata gcctacaggc ttgccagcgg 192300
acttgcttga cctattgaaa tgccagtata gacttctggc acatggtcgg ctagctaaag 192360
gtcagcttcg gttctaggca aagatccgcc agtagcagtt cctatcccag ttcccattca 192420
acattcattc aaagtattct ccccttgcca tgcttcaacc agctgctttg cggactgctc 192480
ttgctcttac tgctactgct ctttcctatg cttcctgctt ctgactacta tttaaaatag 192540
tttagaaagc tattcctaca aggaaaggcc tcctttcttt catctaaaag ctggctggtc 192600
tcttttcata ttcaaaaaag gaagccccat tccattctat cataagataa gggggaatga 192660
atctcttcaa agaaaagaag gaaactatcc tgacatccta agagctaccc cagtctggag 192720
cacagctaag gctatacttc cgattctgaa ggtaatccca tttttcttt cttttccgga 192780 accccccgaa aacctaagtg agagcgaaaa ctacataccc taagatctcg tcccttactc 192840
ttctttagag gaagcgacct tacctatatt ccaaaaaagag gataggagcg aaactgcctc 192900
ttcaagtcca ctccttttcc tatgcttcac acagggctcg aagaatcatc ttatagccta 192960
gaggttaagc ttaaggttaa ggttaaggtt aaggaccttc cagtcttcct cgagttcgtg 193020
ccttctatcc cgccaagcta tagctatagc tagtgtcagt gagttcaacc tcccactcgt 193080
gtggatttgc tttctgttct aatcccctac tagacctcct tgcaaaagaa aagagaaggc 193140
ttacttctta gcttctctaa gattctttat ttacctttga ttcaatcctt tcgcttctct 193200
cacattccca tcccatggta gtcttttgcc ctcttctagt cattctcttt tcctccctca 193260
gaaggtgaag gagaaggaga agggacctag aaaagcctca aagaggtatg ccgagtcctc 193320
tatcttaaaa cttcctctaa tgtcccatcc cgtcgatgtt gatttcacac aggatgatcg 193380
attggatacc ttgataccgc tctttcgcct tgattgatcc tattactcga cacatctact 193440
cttatgatat gaaattttac cacattgacc gctttctgaa gcgaatcaca tttgcggatg 193500
gaatgtccta aacctccacc tactcctgtg gaaaggcttc cccttcggct tggggataaa 193560
gcaaaaggga gaatttactt tctgcagcta ccagcacacg atcccacttt tggcctgggc 193620
tacaagccaa aagtcaaata ctaaatcagt agaaaaggag agtcagaaga gcgctggaac 193680
agggttgact cctaaaaagc cgcacgagta catgcctacg ccaccgccca actatgtctc 193740
ctttccgatc cacatgccgc tacgagaccc ctgtaaacca cccttagcca agaaagacaa 193800
gtccgtcccg tccatagaaa gtccacaccc aaatgtctct atccctagtc ccacagtact 193860
ctcgactgct gaacaggcat tattatcctg atctttcttg tctgttcttg agtgaggacg 193920
gtcagcttga tgcagacccc gagtctgagt ctagttcgtc aagcacggcg gaggaggtac 193980
ggagagaagg agacgtcgag atggattaag taggggtgac tctgaaccac tcgcgctcga 194040
aggaagaaaa tggagacagg aatcactagc cttagctaga agcccgaaag gcactctagt 194100
cttcgttgac tctgagacct tcgatctagt ggaattagtg gacgactctg aatgcggagt 194160
aagaaagtac gggtttcttt gatcgacaac ttgctagtcg acagaaggat tttcaaactc 194220
gatagcctac tggtttaact agtttctgga actctgatag cactatcctt cgccttccaa 194280
agtctttagt agggcactca agacttcaat cgcgaattct cagttggaat cttctttgga 194340
agagaggtag tataccgggc tagcaggact gaatgcttag taagctaccc ggatagaggg 194400
atgtggtaag gaagcgtagc agttcaattt caaaggttag gtaagtgcta gctcgatcat 194460
cataagatcc accagcaact ctcttatcta cccaattgga aaatctttat gttaagatta 194520
tatagtgaag tagatcgctc gctctttcct tctactttgg acttacattc agcttgcctt 194580
ccgtggagct aacagaccgt gccactatta tacctccctc cccttactcg tccattcact 194640
atgtcagttg ctttagctgc tccttctgta ataggctgct gcttgatcta tatcattaac 194700
tgcagaatcc ccatgagtgt acttacagct agcaaaagac tacttcttgg actgtggccg 194760
acaccagaga agactatttc gagatttgct aagcgaacga gggactgtct tgactcactg 194820
gatcgcaagc acctattcgt tcagctgaat cgacatagca agcatgggcg agaaacttat 194880
ttctttatta aaccactgga caagaggaca atatgtgtaa agcatatact tggctgtccc 194940
cgcttcttcc ccccctttct attagaccgg tacgccaagg aacaagtcca taggtcatgt 195000
caaacttaac acttgatgtc ttcaagtcca tgtgatagga cccaacccgg acatggtcgt 195060
acgtcctcta ccttcggtgc acatagggga aaacgtggaa tactgttata aggacacctt 195120
atcttttcca agaccttacc atctctttcc ttgtctctct gtgctctctt tgtactttag 195180
ggtataggag agagaaggag tgcatacgag gggttgaaa gggcaacgaa tgaatatagg 195240
caggctgatg ctgcccaagc agacgcttta tctgatacaa ctcagacctc cgggtttggt 195300
taagtaatct gtctattcat cagtcagttc ggacaagatc tctatctctt gaggacaatc 195360
agatgctttc gaagaatcgg accaaagagg atatccattg gaaaatcagg cagatcgcag 195420
gagagctccg ttacacggaa agtccttttt tactgatgga gatcctctag cgggatcaga 195480
ccttccacaa gatagcatcc cgtaacaaga gaccttctct caagaatatt ggttgcggag 195540
aagagagtgt gtcaagccgt aaaggggcag agtaccagcc acgtggcatc ttgacaagga 195600
aatcgaatgc ttaacgcgag caattccaag atcggattct gctacggaat cggataatgt 195660

-continued ttgtgatacc acatccgctg tctcctaatc ttcttctgac agagagtctg ccgttggaaa 195720
atcaactgcc tcggttcggt tatcttatat aagatagcgc attgatgttc gcggatggtg 195780
ttcgtagaca gcaggagttt agtcagagtt atcgcaaata agataagagt ttggtaggta 195840
gaatgcctcc ctcttgagag gatgcatttt tagaacccgc ctcttttact caagtcgaat 195900
tccccctcat ccatgttgta gtatcccttg cccaaagcat caggcaagac agacacgata 195960
gaatatccga tgttgttcgt agggaatccg agagggtcct tctattcttc ccatagaagt 196020
cagacgatcc taagcttacg tacttagttc cggaaaccga tctccagaaa gtcatcgagg 196080
ctagtaaaca agacatccaa gcgtcccaag gcgaatgcaa agaattggcc ctaaggaaag 196140
aatggcatac ctacctcatt tcttcaaagg gggggtacga ggaatggaat gagggacaaa 196200
aaggagtgaa aagctatcag cgcttaccac gattctctca aaaaaaggaa ggagatgaat 196260
ctgcctaagt aaggagcccc tccggggctt agtgtgagtc acttcactcg ggaaagaaca 196320
aagaaggggc aatcaattgt ttaagctgtc aagaatttct ttaaattagt aatttgactg 196380
cggaaaagcc tactaaggtc cgctcgaggt tatcttcttc ctgattcaat caatagcagc 196440
tccttccttt cttgctaaca gggcaagggc attcgatgca tctgattcaa ttcctgatcc 196500
gccctctctt tcacagccta ggagtacaca tcgatgagct taagtaagcc tttttgacta 196560
aaaaactttg ttgatgcaag gaactctttc tattccacga gcagaacacc agagatgcac 196620
agcacgtggg ccttgtctaa cgaacgacga ctttcgattc ttaatcgaca taggtttctc 196680
tttttgtgta attgaattgg atgggcttgc aacccttagg cctgcctctg tcactgcaag 196740
aagctcgaag ggatgaaatt gctcctttaa tcaacaataa gagggaagcg cttgagcgaa 196800
aggagaaggc agaaaaaaag atgcacaaag gaaaaagggc taaaaaagaa ggacgaagta 196860
atttcgtata taaagatatg gctttccggg tttagatcga aatggaatcc ccgaaaacca 196920
gggctggagt cttagacttc ttctgcttcg atagagggac tgacagccta agtggaataa 196980
gaatcattcg gccgattgct ctgactctta tccttccttc gctgacagag aagagagaga 197040
gcactcccca agccaaggat gagtgccaaa gagaagatgg gcaagcaatg cccactccca 197100
tgctttccgt tggtcaacaa ccaaccaaag tgctctatac ttcttcacta ctcgtacagg 197160
cttgacggag ttaagctgta ttgagggaat cgttttgtct caatcaatca atatgtttcc 197220
gaaaattcca cgtatctttt tctttgatga agagagtcta aattccagtg ctacatcctc 197280
tcaaactccg agtcaatcca cgacaactat tagcgatttt agtcttcaat cgtccgatac 197340
tcaaggttct tctaatggta tttttgagga tcatccaggt cttaaccctt ccagtgaacg 197400
tatagtagag cttcaatgtt gtatacgcga aagattcgaa gagttgctgc ctaacaacaa 197460
tgccgaagcc caagcccaag aggctctggt agcggccgaa gttttacatg gcgaaagcaa 197520
cgatatcgcc gagctggaac accttttgac agatttgaat cttcacggag tactaagtga 197580
agcctttcta gaggcgatgc atctagtgaa ggagctcacc agcccccccca acccacctac 197640 cgtccccagc ccacttgaac aatttgaaat aatcccattg attcctatga aaataggaaa 197700
cttatatttc tcattcacaa atccatcttt gtttatgcta ctaactctca gtttggtcct 197760
acttttggtt tattttgtta ctaaaaaggg aggaggaaac tcagtaccaa atgcttggca 197820
atccttggta gagcttattt atgatttcgt gctgaacccg gtaaacgaac aaataggtgg 197880
tctttccgga aatgttaaac aaaagttttc ccctcgcatc tcggtcactt ttactttttc 197940
gttattttgt aatccccagg gtatgatacc ttatagcttc acagttacaa gtcattttct 198000
cattactttg ggtctctcat tttcgatttt tattggcatt actatagtgg gatttcaaaa 198060
aaatgggctt catttttttaa gcttcttatt acctgcagga gtcccactgc cattagcacc 198120
ctttttagta ctccttgagc taatccctta ttgttttcga gcattaagct caggaatacg 198180
tttatttgct aatatgatgg ccggtcatag ttcagtaaag attttaagtg ggttcgcttg 198240
gactatgcta tgtatgaatg atcttttata tttcataggg gatcttggtc ctttatttat 198300
agttcttgca ttaaccggtc tggaattagg tgtagctata tcacaagctc atgtttctac 198360
gatcttaatc tgtatttact tgaatgatgc tataaatctt catcaaagtg cttatttttt 198420
tataattgaa caaaagcgag tctgaatggg tatacttagt cgtggagcat tccgagtatt 198480
tgctttaggg atcgttcctg cgcatctcct tactttatag cagttattgc tccggttcca 198540
gaaggtatag ctcttggctc agctttttct tagaaattgg agactgttcc aatttcctac 198600
tgagataggc aagcggaggg agaactagac gtatcttgct aggcaaagac aggttagaat 198660
ggatagctcg cgggtgggat tgacgggata gatcactatt gcagaaggag gtagaaccgg 198720
gggaagaatt atggctataa aggtcctcgc cctcttaggc acatggttct aaagattcaa 198780
tctcaaagcg gtactaaaga ttaggcagaa gcagaactag aactagaatt cttcgcccct 198840
ccccttgtac caagaagcaa gttcagaaca taaggataat gggctcgtct attagaagtt 198900
attagtttac ggagctatct cagatatctc gagtaaggag acggggcggg tttgatagtt 198960
agagttctat ttctaggaag gaagagacta tcgggaagct cactctcggc cgggctcgaa 199020
gcagaaggta gaacgtaata tctcttgttg gttcagctca tcaagctatt acaaaagagt 199080
ccagcggaga caaagaaaga agccattttt acggtatttt cgcttccagt ccgtaattag 199140
atcttcaagc ttagtccagt ccggatccat cctaaaccaa agagcggggc taagcgaggg 199200
gcatagcgat acagtgttca tactcgagtt gctcaaatcc agtaggaata tcaggaatag 199260
taggatctag taggagcttg ccttggaatg cagtgaggga gcccggagct attgaattct 199320
ttcataaccc aaggagaaga ataggactct ttaccagtat cataacctct cgatgggaaa 199380
tggaacttag atcacgatgt gaacctactt atgagtggaa tttcgttgac aagcaaattc 199440
cccgggaaaa cgaacttttc tccaattgag atgctttctt catttatgga ttctatgcga 199500
gattcggtta gtgtgaagtg tgatcctggc tcagaaggaa gagctatatg cttaacacat 199560
agagttcgat gtaggtaagg atgtgctcca aagttttcaa ttccacctta tcaacctgaa 199620
aagagctaat acgggcttag cctgcctttt atcttatcct tctattctag gcgaggaggt 199680
ttatttttaa atagtaaata gccccataaa aaacaacaaa ctagtcaaag gacagcctgc 199740
cttattcttc tcccgttcgg gacccctatt ttctcggaga tagcctggtc tgagctagaa 199800
cagcagattc gtgagcaaga gcgtatttca cagctgattc aacaacagcc atttttctg 199860
gggaactttc atatgagtct gttctttctt ttaatccact ataaaggttc ttaattttct 199920
ctttaatatg aaggagaatt acattcttga aaggatcaag ggctctaccc tctcgcataa 199980
agtcttacgc tcttatcgtc aaccttcgtg gctttttgct cctttggtct cgctatttca 200040
ttcctggttc tctctttcaa gcttctttcc atcctgggga tttcttctca ttccgtccgt 200100
tctgctagct ggtgtcgcct tctctcttac ttatctattc ccatccatct ttacctctcc 200160
tactccacta cttccctcct tcaaagcgtg attaatgcgc cttaaacctc tctcttgaaa 200220
aagagcattt tttagtggag ccttagcacg tgaacccata ggaacagggc ccttcttctt 200280
tgcaaaaaag cttctgaatt atcatcacat cagtaggcgc agaaagcaaa tcttggtatt 200340
gacttattga aaatctcttt gagattgctt agacaaatct ttttgtgtga ggccgctgtt 200400
ccccaccttt cttaccttgt tttttgggct taaaattctg tgactcataa gccctccata 200460
tctaaagata gatggctaaa gggcgggttc cgcagttaac taagaaggcg atcgattggc 200520
ttggagagga aacgaaaccc gggactgaaa acaaaaagga taggaatgaa ttgaataaag 200580
aaagaatata tagaaccttg agcattttct cttctcggca atggttgaga gtaaaaaagg 200640
ggtatccgca tagaaggatt gctggtatac cgggtagatg tttatctttt cgacttcagc 200700
gaaaatgtaa aaagcacaaa tttcgtaaat tttctttctg tcgaaaggga agaggacagg 200760
gtcttactta cttaaaagta aaaaaaaaaa atggaagttt cctgtcttag tttcacttcc 200820
ttgaactggc tactaccgcg caacgtgccc ttgcttggtg ggtcgttaat taatcagttt 200880
taaaaagagg gatggatttc gaccttgctt tgagtcgtca ggctagtaaa gcgctacttc 200940
taaaacgatc gttaaggtca ttcactcgat tccctcggtg gctctgctac cgatggatca 201000
agatatgctg cctgcctatc atgccaaagg cgctgctggt ggatatgcca aagatgtcct 201060
ggctctgaac cgggtacttg aaatgctaaa ggtacttctt atggtcctgc ttcaaccacc 201120
cttccttctc taccttttc ttcaaaaact taagctactt agactgatgc tggcgatctc 201180
gaagggagat atctggacct ggagctactc atcttgatct ttattatatt aggatgcgag 201240
gaaagggaaa gaaggtgata agcaagaaga ggaaagaaga atgttaaaga agtccctata 201300
agtacttcac ttagcctttc tatagtctgt ctttcttccc ctcttccctc aaagcgcgct 201360
ctttcatcca tgcgcatggt tcttactttc atttcccccc tcctcacgta ggagcgcatc 201420
ttgttttcaa agatgagttg tagatgagtc ggttcgatca ccccacatat cgacggtttt 201480
ttaatgcctt atcctaagcc catctagttg atcgagggat agacgagtat aaagaaggga 201540
tggagaatct tttatttgat cttgatttga tgtatatgtt acgatgcctt cgtattcagg 201600
aggattgggg gtacggcaga taagaagagc gacccaaaaa cggaaagaag agtatgaggg 201660
gcagcggctc accgataata agaagaactc acattctcgt cctgacagat gaccaacctg 201720
ttaaggcatc tttctcaatg accatcctct cccattccag ttcttttctc tttttttagg 201780
gacaagttca ttttcattcc ctcgatatgg ccaggtgtga agcaacttca cgatccaatg 201840
aattccctaa aatcggatga cacaaggcga actagaatag gctgatttat ccacaagaat 201900
gtcataaagg ttttctccgg tcttcctcaa aaagacagct ttagagcgca agtcaaactc 201960
atgataggcg agaaatcacg cgcacatggt ttagcggttt gctgtgctct gtgatcttat 202020
tcttctccaa gacccgatgc ttcatctgct tctttagttt agtaggactt ctttcacgct 202080
attgcgtgaa acatttgttt ggtctcccac tgctactgct atctatgcta acttgaaagg 202140
tatggctact ctcttgtttc ctgctgaacc tccttcccaa tacaggcttc gcagccatcc 202200
ctgcttgcat tttttaaaaa agtttggtag gggctgccaa gcttgactaa tagaataggg 202260
gtccccttaa aaggagaatg cctgccctgt gccaccttgg tagcacaaac aaaggtcctg 202320
tgtaccaggg atgtacgaat catagtaata aactttacaa actttattag ttgcaaggcg 202380
actttgctgt aaagtttatt atactcttaa agtatattct aaagtaaaag tcttcttagt 202440
attcaaattt ttgactatga atattcctac ccttgcagtg ctaatatatt cattagtctg 202500
agtcttagtc tactaaaagc ataggaaagg aagagtcaac tcttatgttg caaggttcca 202560
ccccaaccaa gtaataagca ctaaactgaa ctctataagg atagacgggg tgatttctca 202620
ctacaaagaa aaaggctgag gatttgaaat agatagaaag gagtccaatc taagcaagcg 202680
tagtggagga aaaaaatcct aaaagtaagc aagtagttga attagtccct gctagtattg 202740
gttggtctta ctttattata caaaggattg tggcaagcaa cagaaagtca agtgagtgtt 202800
atggtgcagc ggaaggcccc ctcgaatctt ccttgagttg acgtcactgg gacatctacc 202860
gcttggatcc tgccttgtta gtcatccgta gagctaaagg gaatttttttg aagccattcc 202920 cattcccaca caccaatacc aaccagggtg gctgttcagt aagtcctacc cctaatagaa 202980
aggataaatt gcttgcgcgc ttcgtcaagt aagagagagg atcttaggcc gaacagatca 203040
ccggctccga aggcctgcaa tcgtgacttt agttccggtg gttcgctttg ctgccggggt 203100
gcaacagcct tttgtgacac ttcgaatgga gtggtccgta cgcccctccc cctcgccaag 203160
cctgaagaaa ggagcaactt agatacctct ttgttaacta gattcctggt ttgctaaaag 203220
ggtccttggg cccaatcaat ctctatactc ttgatgcaat ggactcccca aagccactaa 203280
accgctctct tccacccgat ttgaacagaa cctcgttcta gtgagatttt atcccttttt 203340
taaacggaaa ctcagttgcc tatctgatcc ttggtctaat tgggcctttc tctatagctc 203400
gaatcgaata gctgggctac cccttccctt ggcttggttg gttatataag agaatcccag 203460
gagaaagcaa gttagacctt acttagggcg aaagattttt tggatggttc attccagtct 203520
gaagtcagtc aagtcatgga attggcagaa gttccccctt aaccaaccct aagagggaat 203580
tcttctattc attaagatga agccattcag tcagctctga atctgaactc aatgattgct 203640
tttcaagaag ggcatgaagc tttggctcag tacagtagca tttgactttg ggaaagagaa 203700
tcgatagaat cgatcgctta ccttgctttg gcatgccaga agcatttcgc tgtggttctc 203760
attgattgag tcgatcccga gacaaagcaa agggagttcc gtgggttcag tttgcttaga 203820
ggcagaaagc ctagaagagg cctagaagtc ataaggaata ggcaatgtac cggcaactct 203880
aaggtttggc tttttctttt attgactttt ttgagtcaat gtcgcatttc gcgtgcttgg 203940
ttagatctcc taacctaatg taatgaagga gaaggcagaa aaaaaagatg cctttatccc 204000
tagagatgca ggagcttgcc ttaggacaga aatgatatcc gaatggcgta cggagctgct 204060
taccctaaga cttcaactcc atcttacatc gaagtcagtt cggctggatc gagagaatct 204120
ggataggcat gatcgaaaga gggggcaact ctgtctccgc ctctgctcgt gcactcgtta 204180
aagtcatggc ctagcctagt tggtgaagga gcctacaagt ggtaaccgct ctgtatccgt 204240
catctctttg aagaagcagt tgggctacaa gcggcgcttt caaaatcccg tgactctcag 204300
tcatctatct tcttttcacc tgaaaatttt ggattggggg aagcagagaa tcaaaaaaaa 204360
aaaaagaaag tcatgcttac tataagaagg aagcgggcgg agacccgtgc gtgcagcagg 204420
tgtagagtca gtcgaactag tcctgcgaat atgcgaaaat gttctttatg aatggagacc 204480
agacacaatt gctttagcgg ggactgaaat cgtgactatg tgttcatgct ttcgaaaaga 204540
aaacaaccat ctacacgggg cgctatttgt ctacttattg cattagtcac gtctattttg 204600
aagtcttatt taactcgttc gatgtgaagc ccttccacac ctgtatgaag catctcctct 204660
cgggattcac cggacttcgt agcttgaaac aacctgtcct tttccctatg ctgaggcagc 204720
accaacaaat caatccatcg aagttcctat tgacatacat aaaaatatag ggatgccctt 204780
gatgattcgg atcatctcaa tcaattgatt gggaagagat tacttatgag caaaagggga 204840
ggacgaagtc gcaggagatt aggtattatt taaactgtca aaataaggga tatcgttgac 204900
tggtacaaga atagaattcc ttgcttacac tttctttcta ctggttggct taccctgtat 204960
ttcaagagta aataccgcag tgaggaatag cggttcctct ctttgtttgg tctaataaaa 205020
agattattca tcaccgcaac cactctcgct tagctaccac ttgtctttgc ttgcttactt 205080
ctaaagcaaa ccagactgaa gacagtagag aaagactttt tattacgtta tccagaatgc 205140

-continued gatgccccaa ggcaagaaag tagcaatcgg ctttcaatcc tatgatttta ctcgaatagc 205200
taatatcaga gtagcagata tggttttagc ggaagctgct ttccccggat gcggaattga 205260
aagaaccatg cctttttttct tataaaagcc tcctcatcaa ctctctatct ttcgaaccca 205320
cctcaccgag cttaacgccc tgtggacttt tttacgaagg cctaacttga caggcccgga 205380
cggccgattc ataagggtct gagccttggt cggctgccct actaggtaag gcaagcgctc 205440
accgatttct ttacgtcttt tcgatcgtgc tttccgtgaa ttgaaagggg ggaattaatt 205500
atccagcaga gatggcatcc attagcttat tgtcggctct cactctggct catcatccag 205560
aggcgggttg agccccttgc acagcttttt agcagatgat tccaggcaag acaagatcag 205620
ggtcaatgaa gtgtttaagg acaatcaatg gcactgggat tgtctgcaca ctcaacctcc 205680
agactttgtg aagaacatca tctcctctat gcagcttaca ctcagtccag atgaagatga 205740
tttggcaatt ttgtctccaa ctgcatcagg taaattctct cttgcttcag cctggaatat 205800
gcttaaacat aaaaaagggg tgtccttttt agattcaaag atatggcata aggatgtgcc 205860
ttttaaaatg gcatttctta cctggagagc agtccatgat aaactcccaa ctgatgggag 205920
agtgtccagg tttggtcatt ctctttcccc taaatgttat tgctgtgttg actctactgt 205980
gaactcaagc ttagaatctg ttgagcatct cttttgctct ggtgtttttg ctcaactggt 206040
ttgggaacat caattgttga atgctacttc ttaattggtg gaaccacaag gtccttaatc 206100
ctgtggcttc atatattact aaggtcatgc ctcctttggt ttgctgggag ctgtggaggt 206160
ccagatgcag caataaatat ggttctgaga aaccatcact caatagatcc aaggcattga 206220
tcacatactc cttatctcac ctgctgcatt ctcagtttgg caaggttaga gtaggtgaga 206280
gctgggagag tatctgtcat ctgtgtgatg cttcaatgac ttagaaatct gtggctttgg 206340
ttaggtggat caagccacca ctgctttttg tcaagcttaa tagtgatggt agctgtagag 206400
atggtatttg tggaggtggt ggtgttgtca gagatagtat gggtgctctt attatggctt 206460
actccattcc cttgggtgct ggaaccagca actgggcaga agcaaaggcc atgcttttttg 206520 gccttaaatg gtgcattgaa agaaggtaca ggttggtgat aggggagact gattccttat 206580
tgctgtcaag ctgcatttca ggagaagtga agtgatcccc acccgggaat cacgaacggg 206640
aatctaaata gaaaaagaag gccctggcaa agcctctcct aggcacctaa gggcggataa 206700
tagcagcgga tatatcgctt tctgtttccg ctctatctgc caaggggaaa tcccggtaaa 206760
gggaaccccg accccgagaa gaccgtactc atgtgcaact aattcaatag gaccggttat 206820
gaacccaaga gaagagcgga taggagtact catactcaag gacaggaagc tctcacagcg 206880
tgaaggcaaa gaataactcc tattggaaga agagcgttta cgatcagagc tggaagagtg 206940
ggagggaatg aaatagcaat agccgctact tctgtctgcg gctatcttct cctattgatt 207000
aagcccttca aaggaatttc ttctatttct tctttctaaa ggcaaggcta agccatccgc 207060
ccttcattgc tgggtaaaag gggagacggt tcccaagggg tggctagttc gagtaagaga 207120
gacggataca gataaggtcc ttttttctga gagacccgct cttgactttt atcataccca 207180
ctagtaagcg cagtggatgc tccttcatac agggacagag aggcgagtga tgggcactac 207240
tcatcataag aaagcagtca tgcagataga aagagtaaaa caatgactct gactaagtaa 207300
agagatgagg tttttttttct catctatttt ccataccaca gctctagaca tgcgccccga 207360
ttcaaactat gtttcaatca taccaccctt gtggggtgtt cgcaattcac attaaagacc 207420
ctttccaaag gttgagtacc ttggctcggg taggtggtgc tgggttccgt gtccttggca 207480
ggctcgacca tcggagatcc gttcattacg aacgtttttt ctcgatgtgg accaagctcc 207540

-continued gacttccttt ttagctttgg ctcggaagag gccggccttt gagcccgtat tggaagggga 207600
tcttggtttc ttttttaga aaagaaaccc caagagttac gtcttattcc cgaggagatg 207660
tttgatctcc ctagtctagg gacttcttgt aagggcccct tatttatgga atgggtaatg 207720
tgttaaagga tagcttaggt actgcagtag gtttggaatt agactacctt aatatcagac 207780
atcaaagaca acacagaatc caagtccaag acttgagtga taatgctaga gaacgtatcc 207840
ttcttggcaa ggcaaacaac ctttgccaag gttccgaagg aaagatagat ctgaactaac 207900
acaatcacta taatcatccc tcttgtatgt atataagttt ttcgatgaaa agaggggatt 207960
atcctacgat accctaggag cgtgtcagaa agatgggtac gcgaagtgag taatggtgaa 208020
attctccgcc acaagccctc tgaagcgagg atgcacactg ctttaaatag aaagcgcaat 208080
gcaacatccc cgaacgtcgg gccgtcctca ttaccgtaag agcaaacagg taagctccaa 208140
tacagaactc cttagtaaga ccgtcagcgg ctatcaagat cgctttgtta agcagtgacc 208200
ttaagaaccg agagtcttct aaaactctct gccacaaact aaagaattga attaccttgc 208260
gccggtatca tttcgcttga gccgggaact cctgtttacc ttgcgacagg tattccttct 208320
tatagatacc accgaaaaag cggaagacta agaagacttt tctttgtctc gtccacaccc 208380
aggaaagaaa agatcagatc agcaacggct ttcgagtaga ggattttttt gcttttaatt 208440
attccctcgg agttgagtta gagttagcag atgggatcta attcattaga ggaagggatg 208500
gtgattaact gatagaacct cttctcttct ttcaaatcgc atctctcaag tgagaagaaa 208560
aggcccccca cggagcggtg ggaaagcaag ggcgtagcag gaagaagaag tatgaaagca 208620
gcaaatcttt cctcctcggg ctgggatcac gaacgggaat ctaaatagaa aagaaggccc 208680
aggtcgagag ttcgctccct ctctctcagc taaggaaaga gatagagaat tcatgtacat 208740
cgctatttcc tgcggatcta tcgtatcctt acttctctct gattgtgatt tcccttgtgc 208800
cgtactatac cgctaaggaa aacaaacaag aaccaggcta ggctactcct cttccccttt 208860
ctgaatcaac ttgtccttgc gcttaccact tcttaaaact tgcgagcgag tgtcgatcgc 208920
tcctttgcct gggcaagatc tgacgactcc tgcccaaggc gggttacgaa ttcagattag 208980
ctactgccaa agaggccagg aacgagcttc cgctttatct aaagaaaaaa cctcttcctt 209040
tctctcttcc tgatcagcgg attcagagtg atcaggtgaa gccccccttc tcgttggatg 209100
accggccctt tcttagactt ggtgaactcc tgtcgcgatg aattaaactc cgttccatgc 209160
cccgctgctt gtcaatcaca tcggaaagtc gttgggtcgg cggagacctc tttcggcaaa 209220
gaattatatc acaaagaaag ccccaactag ggactaccac ttataggagt cttctttgct 209280
agtagaatgc cccccacgag aagaaagaat agtgggatgc tcacgctctc gttggacgtg 209340
acagtcagtt acagtgggta aactaacgaa gggaagaatt ttatttcatc acagaattga 209400
atcgggtctc atcccttcga ttcctcgctg catacttcaa tgagaaagga aaagagcttt 209460
gttgcgtgct tcttcgggtg tggttgcaag atctcgcttt cagttcgaaa atgtgtacgt 209520
agcttccttg tacaatagct ctctctctct gagagagtga tcgggaagca ttctctcttc 209580
ccctccgtat ctgaccctga cccacgctct agccctcttt cgtcgtccaa gtcgcatacc 209640
tcctaaacag tctatttggt ttttaaacgc gatctattta actgattaac tgtgaactag 209700
gtgggacttg attctttttt tgctgaaaag agaaggtacg taggcagctc tcctaaaaaa 209760
gagtgaagtt ccgcccgcgt ttgaaggcta gctcctgctt cggagcttca tccccacatc 209820
tcacatattg gaaaaggcaa acaaaaaagg ggaactcagt caatagacaa agaaaaaaac 209880

-continued ggatatgtta cacaaaaaca atccaatctt tgtctttcta aggattgatt tttcttgtcg 209940
tagttcatat tcatattcaa gttggaaaaa ttcttctttt tcttcttatt gtggaaacgg 210000
agggaaggca aaggtccgta ggaggacaac tatcaatatt agctgacagg tgacgaggat 210060
catatagttt gagagctgga tcgagtttga aagcgtggtt atggcggaat ggaatgtgcc 210120
ctatcccgcg aaggagagga acgaagtaac tcgacaaaaa gtagaggaac ctgtcatgtg 210180
aggaacttag gtcaaaacta cgctctttca gccggtttag tatagtagta gtttcaaatc 210240
aatgcaagcc aatggaaacc ccccttcac ccccaaaacc tatactcatt cgtcttttac 210300
ttgtgcgttt acaacatcca ttgcttctga ctatgtcgat gaaatgggac cgcgaagaca 210360
acccaccact agagcttgct ttgctctcgc tccgctcgct cccacctgtc ttctttccca 210420
ctatagtgaa agatctttca cttcaccata gcaggaacct cgctaacctt ctcggccagt 210480
tactctaatc taaccacagg gatcccctat gagaactctg tcaagccctc gctaagaggt 210540
agaattggct aaaagcatcg tacttcttcc catagctaag gatgtatcat tatcagaatc 210600
ttggtcttcc gtctacggct tgtagaagta gttttaggat gaggttagac ctcgagcttg 210660
ctgacataac tacttcccta aatctagctc ttgagggaac gagcgaaatg aaatgaagcg 210720
agtgataacc aaaaggaacg agcggaattc tgtagcgata gggacatgta gctaagggag 210780
cgcggggtgc tggttctaat cccttcttcc gactgttata gatgctaaat gctaaagaag 210840
aggagttcta aatttatatg gcatcctttg tgacagacga ttcccactct ttcttatact 210900
attatatctg gccatctatc tctacttctc ttatatactc gcctttcggt aactcgttat 210960
actagttaga cttacttcaa acgaacggaa taaatgagtt gaacgaatag ctcttcgagc 211020
tattcgttca actcatttcg tttattccac tcgcttcatc ggatagtgtt ctaattccaa 211080
ggctagtgtg gcctgcctta cctgaatcta tctcttcggg tcgttgcaat ctttctgttg 211140
aaaagtatcc ttcttcgggt attattgata ttggcataga acagagcttc aggtcgaact 211200
agtgggttgg gtggcaagga gactattagg gaaaacatac attcgttgga taggtagctg 211260
gatttaatct aattgctgat tccgacggaa gccataggag ttgtattcga gtaagagcgc 211320
gggaacccga agagaaatac ggatgagtgc aaaaagggca aacgaagggt acgagtgaaa 211380
tgaaattcaa tgcccgtagc gagtcaaaaa gcaggggccg aagacttggt tcttagccgt 211440
gaaaaaatag gcgaataagc atcctttgcg gcgcttgccc ttaggaaagt ctattcagtt 211500
cgattccgcg atgaggccat gcatataaaa acaaagcaag agaagctaca gaaagcgaat 211560
tctttaataa tattttagac cggcgtaaca agaacaagct gaagaataga atttagatct 211620
ttcctccgct tcggattcat tcattagaaa gagttcccta cgccgcctag tcgctatagg 211680
agacacgtgt acaccgccgc gtctgaaatc aaagaacgga ataccttctg cggctatcat 211740
ggctagggta ataattcgta tatggaaacg ccgcttcctc tttatccttt attcgattta 211800
aggatagaag aaggataggg aatacggcct tgaaggcgat gaaaaaagat gataatatag 211860
gaacgcggca aactctttca agaaattagc atcctcagct acagtggtaa aatctctata 211920
ggcaagtagc ccatgatttt ccaattatag ctcgggccga atgccctata gctttggagt 211980
ttccaccctt ctctgaaggt ggtgatttgg ctgtagaagc ctaggctaat gaattgggga 212040
ggtacgcaag cgagggaaaa agctttgatg aagcaaagtg taaagctgag gcatattttt 212100
aaaacttgca attccgactc ttctctcaaa gggtcttggt ctcggtccgg tcttttcttc 212160
cttggtctga cgcttgcgtc ttcctttcag cgaagaacat ccatccttgg ggaggtcacc 212220
tctaaaggcc tataggtccg tctatcgata ggcagtcttt cttttctttc tcttacgggt 212280

```
cggcaaagtc tgattctatt ggaaaaaagg gccggtctct tcggcgaggg cttgacgcca 212340
tctgaagcgt cagacgatgc ttggcattcc tgaaatctat ctctttgggt gatgatgcta 212400
aaagcacagg tctatacttc ggcacagacc tcttttgaga tttaatgtag gaaagtaaag 212460
tgctagtatt tcttagagct tggctttctc cacaaccagt cttctattgg ggcaccatat 212520
agaggttcta gaggaaagaa gggagctaaa ggagtacgaa gtccgatcag cgtcttcaag 212580
agcatgattc tataggaaag catttaagag ggcaaaaggt ctgatgaagt tgtgcaactg 212640
acctctatcc tttgagaacg atgtcaaggc cttgaaaggc cctttatggc taatgctgca 212700
tccgaagcta ggaaaagggc gcccttgact acgtcttttc tttatttctc attgccatct 212760
tccgcgtctg aaataagaca ataatccttg gaaaggtcac aagtccccaa gggaaggaag 212820
tcgtgggata ttcaagaaaa gcatcctaag cgaattcatt gtctagggaa gtttctcttt 212880
gggggctgcc tatcggtact cccatgaact gaacacatac ctattcgatc taatggtgcg 212940
aggtcaaaag tcgataaagg caggggtagg agaaggagag agaggtgcgc tttacccttt 213000
gagatatcca agaagtttcg actttcaaga gattgaaaga ttttagtctt atttcatagg 213060
ctgcaacaag ggattattaa aagaatgccg tgctttcatc tattagagaa gtatgcccct 213120
agggaaggga gaactgatct tttcaaacga aagccttaga gttggaaggg actatcctaa 213180
acttttatta ataatcttct tttggccctt gattggactt agagttgggg atagaagacc 213240
cgccgcttta ccttgaaatt ggaatcggaa agggcgtaat cgaagaaatt tcaatcacaa 213300
gaaagaaaga ctttcggaac aaaagacaaa gcttcaatta aacactcctt ttagctacag 213360
gaactcctat tacatttgaa ttcaaaatat cttctataag ggtatgactt tttctcaagg 213420
atgggaagcc ctcacttgac ataatatctt agtgggaagg taaaagactt agctgaacgt 213480
tagcgaagcg ctggtacaat gagattcttc atagaaaaga aagaaggaat gcaccgagag 213540
cccttcctct tccacggatt ccattagagc cattttgaat ggtatggcct tagaccaatg 213600
cgctttcagg tcgggtaaat ctagccgtaa cagtcagttc aataggactt agaaaaaaaa 213660
gcgaaaacga aagccttcat tcagctccgg cataagaagg agcgagaagc cactccgact 213720
aaaaggaaag gatcacttag ggagcgggta aagcaaagag tggaaagggc aagcttcaca 213780
aatcatgctt tcaaacttgc cgaagttctt ctaaaaaaat aatttatagt aaaccaaggg 213840
aatcgtatca tccatggcga gtgctatcgt atactttcga atgcttgctc agagtcttcg 213900
ttctaggtta gggttacttt cactcgcttt cgagaaccta atctctttca tggtgaaaat 213960
tgcccgagtg catcaaacaa ctcttggagg agaacaaaga catcatgccg gacgagttgc 214020
ccatgcgtct accactgagg cgggagatag accatcaaat tgagttggaa cctggtacga 214080
aaccacccgc ctttgcacca tataggatgg cacccccgga atttgaagag ttgaggaagc 214140
aactcaaaga gttacttgag tccgggcaga ttcgaccatc caaagcacct tttggcgccc 214200
cagtactctt ccaaacaaaa gaagcatgat ggatcattac gactgtgcat cgactatcgc 214260
gcactaaaaa agataactgt gaagaaaaaa tatcctattc ccttgatcgc cgacttgttc 214320
gatagattgg ggaaagccaa gttcttcacg aaggtagatt tgcgcaaagg atattatatt 214380
accaagtgcg catagccgaa ggagatgagc ccaagaccac gtgcctaaca aggtatggag 214440
cgttcgagtg gctcgtgatg ccgttcgggt taactaacgc accagccacg ttttgcactc 214500
ttatgaataa gattttccag ccataccttg atgagttcgt ggtggtatac ttggatgaca 214560
tagtcatttt tagtaaaacc ctggaggagc acgtggagca tctacgtaaa gtcttccaac 214620
```

-continued tactaaggga gaatgaactt tacatcaaga aagagaagtg ctcgttcgct aaggaggagg 214680
tacacttctt ggggcatgtc ataagccaaa tcaagatgga cgaggccaag gtgtctgcca 214740
taagggagtg ggaggtgcct acttccgtga ccgagttgcg gtcatttctg ggctcgtga 214800
actactatcg tcgatttaga aaggggtatt ccgccattgc tgcacccta accgacttgt 214860
tgaagaagaa ccgtccttgg gagtggacgg agagcagcca aagagccttt gaagagttga 214920
aggccgcctc tatgtgccaa aatgggggaa cttaaggcgc actcttataa agcagtgtca 214980
tgatacaaag tgggctggtc atccggggca acaacgcacg cgagcactct tggagtcggc 215040
atattattgg ccgcaaatga gagacgagat cgaaggctac gtgcggactt gtcttatttg 215100
ccaacaagac aaagtggaga acaaggagcc cggtggactt ttggaacctc taccagtggc 215160
ggagcgacca tgggatagtg tcacgatgga cttcatcacg gcactaccat tgtccgaagg 215220
gtatggttcc actatggtcg tggttgatag attctcgaag tatgcaacct tcattcccgc 215280
accaccggat tgcaaggccg aagaagcagc tcgtttgttc cttaagaacg tggtaaagta 215340
ttggggacta aaacggacta tcataagtga ccgagacccg cgcttcacgg gtaagttttg 215400
gacggagctg tttcaactct tgggttcgga gttgcacttc tccacgagtt tccacccaca 215460
gacagatggc caaaccgaga gggtaaatgc catacttgag tcttacttga ggcactttgt 215520
gagtgcaaac cagcgggatt gggctaggct tcttgatgtg gcacaattct cctagaactt 215580
gcaaaggagc gaagctacgg ggcgtacacc gttcgagtta gcaacggggc aacaaccaca 215640
tactcccctt tggtgagttc ttacaaagga agaagtcccg gagcatatcg cttggcaaag 215700
acttgggaag aatataccga caccgcccgc tcatacttat agaaggccgc atacaagatg 215760
aggaagttcg cggataagaa gaggcgcccc gtggactaca aggtaggaga ctttgtgatg 215820
gtgaagctta ataggacaca attcaagaca cttcgaaaac atcacaaagg gctcttacgg 215880
aggtacgaag gaccattcga gatcgtggca aaagttggta agatccctta tcgactcaaa 215940
tagccaccac acttaaaggt ccaccctgtc ttccatgcaa gtcttttcaa accttatcat 216000
gaagacaagg aggatccaag ccgagggttg tcatcgcgcg cacctatggc cgtaaccgca 216060
tcatatgaca aggacattga agccatcatt gacaagaggg tcgtccgttc aagtggcaag 216120
aagccaagca cggagtactt ggtcgtatgg aaggggttgc cggcgcgaga agctacttgg 216180
gagaaagaaa gagactattg gcaattccga gaccaagtcc aagcatactt ggggagtact 216240
tgcgccgagg acgtcgcaac aataggtggg ggagagtgtc acaacccgct caaaacaccc 216300
caattttccg accaacacaa tgtgccaaag atagccgacg ggagcgcgac ttatgtccgt 216360
ggccgtatgc ccgaccatgc cgaggtgagc acggatggca tggaacatgt tcacaaggat 216420
cttggcatga tggaaggcct aggagtatcg tgggagcacg agggtgcatg tggaagagtg 216480
gccaagacaa tgccaagaac actagaggcc atggaagcac aatgttgcgc tatggaaggt 216540
tctagaatgg cctagcgtgg ccttgccctt gggcaatagg ggctgcccaa tgccccaccg 216600
acttaggggc ctattccacc gactttaagg cttcaagaac tctcctataa aaagaaggat 216660
agacaaagaa aagagaaagg gattctatcc tcgtccaacc aagataatat cgattgctcg 216720
cccgacatca gcctcttcac ccaccggggt ggaacgactc ttaacgaggt tgatggactt 216780
gactttttct ttagcctctc ggcttcgaga agccgtgggc ccagtagtgc tttcttaaag 216840
ccggtaacct gatcgacgta agaaccgatc tcaagctgga tgagaaggca aataaagact 216900
agtgagaata gccgtaattc aactaggcct tgaatcagtg gtttacagag agaattagtc 216960
atctgcttac ggctaatctg ctcttcgaat cttatcttag aataggttgg aactttttaa 217020
acatgagagg cttcttcaga aagtacgcat ttcttgctct aagtccgctg ggttggatcg 217080
aactagttgg tttggcagga agataatggc ataaaagaag cattccactt ttggaaagag 217140
aagagtcagt ctgattctag atccctctgt cttgcattgg gttaactgga gcttagataa 217200
agcgataggc agaagagaga gaattagtat gtctttatag actgactttc ctcgcatcaa 217260
agctttccag ttctcttcct ttatgaagaa aggaaaggct tgttatcgac gaagaagatc 217320
tttatactgt tcatcctaag aaaagaagtt ttcttttcac tcggtacaac tattcttatt 217380
ctatgctagc atagcatgct tctacttatg ttgcaaattc cggatcagga agaatccttt 217440
cttattcgtt gatgccagtc taaaaatccg tacttgttga ctaaaaggct ttcggctttc 217500
tttctagctt gaagcttaag ggctaaggga aattcatcct tggatcaatg aaatagttga 217560
attagctaag atgcaagaag gaacctcttc tcttattgaa attactttag ctttaggaag 217620
tgccaaagct ttctccttcg atccgatcct ttctgtgacc catggtctgt aaatgaactt 217680
attctctctt cgtctcttgc ctttgaatcg gatattccga tgaaagcgga ttctctttcc 217740
gtccctcgtc atcgagagga agagtcgcta tctatctatc catataccta tcaacaaatg 217800
tggttccagg gatcggtcga ttgcccctca ccagcagcta gaggaggaga aaggaatgat 217860
gtcccggcct gggcacctat cagccaacta ttccttttag gaatggaaag aagaaaggat 217920
ggtcgtagat cactgatgtc gaattcagga aaaagatcat atgtgaaaga atcgtcagat 217980
tatgggttcc cggagtagac ggttttgaat ggagaatgaa tgaaatagaa tagtctggga 218040
gaatcgtatg atagggaaag tgcggagcct cccacttgtc tgggttacca ggctggctaa 218100
agtgactatg aatttatatc aatgtcggga tagacagagg tctaggatag tacgctgtcg 218160
gagtgagacc ggggtagagt aaggaagtta gaccgaaatg aacgactcaa ttcctctaga 218220
agaaaggaga gagaaagaag aaccaattca atgaaagaat atcttattta ctagaatcgg 218280
ttgctactag tccgggttac ctcagagata gagccattag gggagaaaaa agaacctagt 218340
tagtgcacga aatgtcctgc taacatagga gcactcctac taagaaatgg aagagcaaat 218400
ttctttcttt ggggtcaaag ggctattcta ttacaaaaaa agttatggac tcggatatga 218460
tccttctaat gagagttcct tggggatata tgaattagtg gacatataca agaacgaccc 218520
attttcttac acaagcattt ctgtactcag atcggtaggt atggaggtct ttcctaacct 218580
ctttagttag acaatcagtt atatacggac attcaacaag ataaccccga aaggaggcaa 218640
ccccgttcac tccgacaaga aaggtgtcaa gtctgaaagc caagccctcg taccagagcg 218700
ctctcataag tcaaataaag tattcattcc ttcatttatc catatattaa acaccctgtc 218760
tttgaagctt cttgcaaaaa gtcgttcgac gacacaatgc ctcacctgcc ctctgctaca 218820
catctctttc gttcgcccta gacccaccca ccaaagggaa ctctgccctt ttcaaccaag 218880
gaacgagcaa gaacgctttg ctcctggggc tcgtctacac cacatcgact agcgcttagg 218940
cttctcttta tgttccaacg cggcctttga ttgattcgta aacctttccc cgatcgaggg 219000
cttcctatct cctcagacgg tgggaaaagg cgattctctt tagtcaaaga ggccttctcg 219060
tggatttcgc cttttttgat ggctatctcg tgcctctcaa ttcccactgc aagcttggga 219120
agtgccttgc tttctcgatc agccaagccc ttgcttttga atagcaggaa ttcgaaaggg 219180
gaaagacctt gctaatacct tttaggcact agacagaggc tgctaggaag attacataaa 219240
aaagtgccga gttggcagct ctggaagcgc tgatagcttt tcactccctt tccctcatag 219300
ctgaatagta ggtaataaaa cctagtaact gaaataccaa gtaatctcag gcctaaaggg 219360
tactcagtta agggaaatta cataagtagg aatataagcc gaaacatccc cgattgagtt 219420
tcaactattg gtaaggcggt catacttcct tcacctaaac tagaacctaa tttagcggct 219480
ctttccaaaa ggcgtgaatg caaataaaaa acatctcctg gataagcttc acgcccgggc 219540
ggtcttcgta atagaagaga catttggcga taagcttgtg cttgtttgga gggatcatca 219600
taaatgatta aagtgtgtcg ttcacgatac ataaaatatt cagccagagc tgctcctgta 219660
taaggagcaa ggtattgtaa tgtagcaggg gaatctgccg cttcggctac cacaatagtg 219720
tattccatcg ctcccctttc ctgtaaagta gttactacct gggccacaga agatgctttt 219780
tgcccaatag ctacataaac acatattaca ttttgacctt gttgattgag aatcgtatct 219840
gtggctactg ctgttttacc ggtctgtctg tccccaataa ttaattctcg ctgaccacgt 219900
cctataggga tcatcgaatc aatagcaata agcccggttt gaagaggctc atatacggaa 219960
cggcgcgaaa taataccggg ggcggcagat tcaattaatc gaaattcgga agctggaatt 220020
tcacctctac catcaatagg tttagccagc gcatttacaa cacgacccaa ataggcctca 220080
ctcacgggga tctgtgtcgg ggattgaata taggaagacc aatagtggaa ttgaatcgga 220140
ttctcgctca aagcctattc tcgaggcagt cttttctctt ctagcggaat tccccttcac 220200
ttccattgag attacgacag attacacact gccactgacc tgagccatgt aaaatattgc 220260
aataaagatt tgcatacgct ccacaattat ggcaacgatg gggatcgcgt tgtatcatct 220320
gaggcccagg tgacatctcc cttccagtgg aaactaatgc accaaagccc aaacttggaa 220380
tatttgcaag ttttttctgt ttcaacacct tgtgagcgga gaatagaaca tttggagatt 220440
ccgtagcagg tgtccaatct tcagtagcat cagaactttg gtgatgcagc tcgacagacc 220500
catttgaaaa atggggaggt gatgatgtgg gcagagatga agccgacgaa taggcaagag 220560
gctgaggggt ggctggagaa gttctgaatg gcacggcagc aggttggagc ggcgacgaaa 220620
atacaggagg accaggtgga gtgctgagat gaggtgcagg gcttccagtt ctaactccat 220680
tagccggtga tggtaaattg gggtcttga tggacggaga aggaatctgg ttcggttgta 220740
caattggtgg aggaaatatg ggacctgttg atgacgggaa aggaggagga ctaaatactg 220800
tttctgggcg aggtgactga gtcccttgct gagagggtgg aatggtgaca gagtacccaa 220860
ctgaggattc aggttgcttc gccatcaaaa tggcatcaaa caccagcttt tcaagaattt 220920
caaaaaaaaa aacgaaaaat aaagccaaga acctagagga ttgaaaattg gaaagaggcg 220980
aagccctcag cagtcacatc caagatctcc tcggagactc agaatcgatc gcacccaagt 221040
cagaattaat cgagatgggc ctttgctcca ggatgattaa tctgatgaca aataatgaaa 221100
gggaaagctt atattttggc atcaaaaaag tgaagatcgc cctgaattgg atcctttgag 221160
ggtctcagag agagggcaag tacaagagga actcaaagta aaaactagac tttgtcttgc 221220
aaactgactt cagccatagt gaatagggga agctgctcac tttgatagcc ctaccctagt 221280
gtatgcactc aagcagagta gacggcacgc gtcaccaagc ataccgcccg aggttaaggg 221340
ttcatcagcg aatggagtta ggcccatttc ctagcctagt tttaagcaga acagcaccat 221400
cctagtccag agcagtactt ctcttatggg ctcgaggcaa gacaagcagc ccgcttcgct 221460
tcctcaattg ctcaaggaac aagatgaaat aatgcttttg tggaacgtct tcaggcgagg 221520
ctttgggatt aaaccaatat ctttctattt gaagcagtgt gcggtatgcc ttcaattcaa 221580
caagcatacg ctggccagaa tagtactgag atttccgtct ctctttagct gactcgctcg 221640
ggatatcctc gcatcattcc ggcatttcac cgtaagagga tccttaaagg tgattccaaa 221700
agtgatttgc tagtggtact tgtcgctttt ctccgaaggc tattgaatta gctaaaccac 221760

-continued gtgggtggcg gttgtccatg gatgtccctt gggcctattc ttcatcggat acgagagcag 221820
gaagagcttc tattccatca acacaagtta ttccagcaac agctcttact ctaacagaac 221880
taggaccgtc aactccaact gtccttatag ataggcgaaa gccacctcct tgacagatta 221940
cggagctacc cagcttctct taatgccaag tagtagaaaa accgctttcc cgagctggct 222000
ttatcgagtt aacgaggtaa caagcggaac cttgcgcaaa gacatacccg gcatactaag 222060
atgaatcatc taagttcccc gccgtcttga ttgatgagct cgaacagccg gttgatggca 222120
atgaatgggt gaagcaggga aggctctgac tttgaagccc gggctcaggc aataaagata 222180
aagaggcgat caagaaagtc acgactgtct gtcccttcct caaagcaagg agcggaaccc 222240
tatgatgact cactttaggt tgaacctgat ctgagatctc tcccgtcttc aaaaaacaag 222300
caatgaagac aactctcacc ttcgattgat agatgaagag ccccgccaaa ccaatgaaag 222360
ttgagaaaga tttggcatct tgaaaggcag ctaagagcgc atctggtctt ccacaacaca 222420
ctggggatat tctcatggac gccagctgga gaggttctta atagtttgtt ccgagatgtc 222480
agtctgcaaa gcatcatctt catctctttc atcgcacgta ggctcaacat ccaagttagc 222540
gtaacgaggc ccaaactatt ctggttggat gaaccaactt gagatgttaa aatattccat 222600
cggcatccct ggtatagtga tagaataata ttaggcacat caagcctaac taggcttgct 222660
tctatcttta tagatcggtg tatgacaaag atatatatgg tctaacagct ccctcaagct 222720
tcgtgtagtt cctccccttc agcttggacc gaagaggact tagcagaaga taaagccttg 222780
gtttggtaaa gacatctgcc aattggtaca tgctggaaac atagcatacc cgaacttcac 222840
cacgcgacac tctcaccggg taaatccgga gaaggggaac ttattctaag atagaataag 222900
aataagcaga attgcttaag taaggtagtg gccataaggc ttttcttttt ttcggtatgc 222960
cgctccgcga gcaaggagtg ccacgcacga gcggagcaaa aagaaagcaa ggggaattct 223020 tctcttttt ggggagaaat cctttgattg cgtattgaat atggatccat gtctttcttg 223080
ttccactagc taagaccaaa ttctcacatg tccctttcct tattacaacc ttcttttttg 223140
atgtcaaaga ccagaagcta cgcgcaaatt ctcattggat ctcggttgtt cttaacagcg 223200
atggctattc atttaagtct tcgggtagca ccactagatc ttcaacaagg tggaaattct 223260
cgtattccgt atgtacatgt tcctgcggct cggatgagta ttcttgttta tatcgttacg 223320
gctataaaca cttttttgtt cctattaaca aaacatcccc tttttcttcg ctcttccgga 223380
accggtacag aaataggtgc tttttctacg ttgtttacct tagttactgg ggggtttcgg 223440
ggaagaccta tgtggggcac cttttgggtg tgggatgctc gtttaacctc tgtattcatc 223500
ttgttcctta tttacctggg tgcactgcgt tttcaaaagc tttctgtcga accggctcct 223560
atttcaatcc gtgctggacc gatcgatata ccaataatca agtcttcagt caactggtgg 223620
aatacattgc atcaacctgg gagcattagc cgatctggta catcaataca tgttcctatg 223680
cccattccaa tcttgtctaa ctttgctaac tccccttct caacccgtat cttgttcgtt 223740
ctggaaacac gtcttcctat tccatctttt ctcgaatctc ctttaacgga agaaatagaa 223800
gctcgagaag gaataccaaa acctatttca ctcgctgagt ctttttgcat ccatggctga 223860
atggttaaag cacctttcct agtaaagggg caaattcgta ggttcgattc ctgctggatg 223920
tttttatagg atcgggaaag aatatacatg agagtcagtg tgaggagaaa gagctttccc 223980 ttttttgtt cttctagacc ttgccttttc agctatcact tcttagatgg agctctgacg 224040
ggagacctat gaacgccttg gctctaagcc gtacgaaccc cctttcaatg ccgtattaag 224100

-continued

```
ccaggcggaa actttctttc atgctatagc gtgcttttga gcgcattcat tgctttgagg 224160
gattggttgt gataagcaaa caaggaagcg ttgagttggg cgcgtatggg ttcccggcct 224220
tgattgcttt ttaccttaaa aaaaaaagaa atattcgttt ataccattga cattgataat 224280
tatagaaagt tggatagtat gctttgatga atagcaatgg tagttaaaag cattcctttc 224340
ctagggtcaa gataggtctc ttcccctctt cccttattcc tgctcttccc gcttcagttg 224400
atggaaaagc attgaataag gcaaggaagg ggtcgagaca gtgttagcta caatctctgc 224460
ccttagctta gctaaaagga taaagtgaag ctctataact cgaacgcttg gattcgtcta 224520
tcttagagta ggttggcttg ttagatctat atgaactagg agtcatttag ttggcttctc 224580
cgtcgttaga gctttctgtc cgaactttct tactcttgta agctcgtctt gtcctatcta 224640
tgctcactac ctcgttgtct gacaagcagt ttccctcatc tttctctttc agaagagcct 224700
actttcgccc atggttcgcg tcgctatcgt gcttggtccg ttcgctactc tcttttcagc 224760
cattattgta tgcgtgtagc ctaagtctac ccttcgattg gactttctcc agatcctttg 224820
acacccgctc atcttacttc ccattctggt aggttggtgc gtgatgattc gtggagtaca 224880
aggctctctc tggttgggta cgtaggctgg tcctgcagmt tgtggaggtg accagcgctg 224940
catgcccgaa tggaatattg actatcccgt agaactgacc tagtcgctcg tsaaggagct 225000
ggtcattatg gaatatacta tatgtaggcg caggtcttcc tagagcgaac ctccatgtgt 225060
tttatattaa acatataaaa atcaacagtg gaagaggcac tggttgtgcg agatcattat 225120
gactggagga agcccattcg acaaccataa taggctctat aaccggatca cgcacgctaa 225180
gaacacagcg gattagaggg gacaagaggt tccactcatc aaagtgtgag acgcaaggct 225240
tctgcctgga agtaagctac cctctttgcc actttcaaat caataataac gatgtcatcg 225300
atattccaat ccgatctttt ctttcttcac ccaagtaggt aaggtgctct ataggtatcc 225360
ccccgtagcc ctaaaatcga aaaaagccca tggttgagtg agcatagagc tctgcccttt 225420
tctttccttt tgaagccgct ttcctccttt ccagctttag tgttttgcta tacattttaa 225480
tgtgttaagc atagtggcat gctctgtagc cggagtaaga aagattcaag gagcgcaggg 225540
ggatctgctt ttacgagtga tctctctcgc tttcttaagg aatttctaga gtcatatggc 225600
atggctatgg tttccactct tgtgagttcc aatttttttct ttggttcgct ttcccttggg 225660
ctcggttgcc cttctttcta tttgctgcag taaatgagac tgggagttgg atttccttta 225720
tgactttcgc tccgctcttc ccacggatat ttcaaagacc ggtaattccc ttgcatcgga 225780
ttcctcgttc tattcctcca aggctcaaag acctcacagc tgattctcaa gaacttgcta 225840
tttcatattc tcttagatag gctatcttcc gattcaatgc catcaaaatg tacttagcat 225900
gcctactttt ccttattagt tcaaatagcc ctagctagat tctcaagctc ggattcaccc 225960
gcaaagcaaa gatcaaaaag ctctttttca agctgcttat tcgaaaacag taagagcttt 226020
tgagtgcaca acttattctt tcactcctgt tctacgatta ccagtggtct cagcgctaac 226080
tggcaaaggc aaacttcttt cagggcatct tagttccttc ccttaggtct aggctaagcc 226140
ttaacaatcc cttcttgaag aaaaacgatt ctgtaacaac tcaacctaag agctgatatg 226200
tctccaaccg cggatacgag acctctaaga acggttattt cagttattcc caaagctaat 226260
tcaattgcaa agagaacagc ggcaacagat atggcaacaa gaggatgata aaccttctcc 226320
ccttaaccgc tggactcgaa ccctaactct acaccgtcgc cttcaactgg cacaaaagga 226380
ataggaaagt catgacctga caaaaatgga aagacttttc ttctttatcg ccagactcga 226440
tcacaagcag gggaggttca attgatctat ctacgtaaag ggagctaatt caatattcct 226500
```

cggtgagagg aaagaagcct cggacaacat tagcctttct tgtctttctt cactgcaaga 226560
tatccaaata agtttatcgc tcgttcgtgt ggggagccac tcaataacgc ggctagggca 226620
atcttcaacg atcagcccgg tgcttcagga tatggatcac ggatacccgt tccccttcaa 226680
gaagattagg atatgtcgtc taggcctcca ggatgcaagg agggggatag gaatggatta 226740
agagttcgag aatgcctctc attacgacta tgatcaagtt tgtacctctt attgtgtcgc 226800
ggaacagcaa gagtcatccg actcttagga acctccatac gaggatgcta aaaaaaagtc 226860
ctattgaggt aagccaatat aaggatccca tacttagcaa ccaagaacaa acagacttcg 226920
gtcaggagtc ggcggatgat gccggatatg cctcgaggac ggcggccaac ctacagtaga 226980
cgaatttaaa gaaagaaaga tgggcgatga gactgaccag cgacctatat tcatcgcgaa 227040
ggctctcccc gatagagtat cagaaagccc taagctaagt agaagaaaga aatgaggtta 227100
gagctgaacc ggaaacatct tacactacac taggtacccc atatagagtg ccaaggagaa 227160
aaggattgag aaaggcagtg atcatcatca attccaaatt tctttcaatg gcccttcttc 227220
ctaaacgaaa ccttgctttt tagaccaaag atgttggata atctgagctg cttatcgagg 227280
gtttttcttt aattcccttt tcgccccttt tttatattat ataggatatt caaaaatgag 227340
ttcaaataag actcatacct atctcctcgc tctctttctt tatctgtctt aaaagtggta 227400
aattttagct atttggggag agtccagtcc cgctggaaga ggtagtagca tccccgtgct 227460
atgaacaaca aatgaatctc aatgaataaa gttgagtacg ttgacaaaaa atccacttta 227520
atagctggac tctacgccaa ccttatctta cgatctgtct ttctcctatc tacgtaatta 227580
catattttgt ttggtccagg agtagttcgt gagacatgga aagccttctt tggccccata 227640
cgcgtgaatc atagcgatag ggaagctggg tactgcttcg ctttcaatta cgactcgagg 227700
tcgggtgcaa aggccgtggg caagatacat acctcgctag ttgaacgaaa tatagaattt 227760
cttatctaaa taaaaaggag ttcaaacttt tgagaggcgg aatcgatcct gcaccttagt 227820
ctacaggtgg gtcaaaatct gaccttgttt tcgccttaaa cccccgcgct ccatctatca 227880
ttgatgctat caaaaactag atttccaata tccaaaattt ccatagaaag agttttgctt 227940
cccttgtgtg tgaaaatgaa gaatccatac tagtaagagc tccgtcgtat cctgccaaga 228000
caggactccc ctttactcgt aaatagttca atgccttttt ttaagaagat tctaaaggcg 228060
ccgctatagc ttaatacaaa gaaatccatt cacatagtaa atggaagatg cctctgtaac 228120
tctacaatgc ttggggcttc aaagcttagt gcgaatggtg ggaaaattca tagcttttta 228180
aaatcaaacc aagagtactc agtccgccct cggtcaggag aattttgcga aatcaatgct 228240
cggagaaaac taccgaatga aggttcagct taaattgaga gggaaggagg tgctgatcaa 228300
ggctacttgg atcttgagag tagtaaagta ctctgcttac cgctaaaagt acgttagttt 228360
tcggacttaa tctgaatgca cagcgtgctg ttggtgccat tcatgcagct tcttcctctt 228420
attcttcccg aataggacgg aaacgagaaa atgttagacc caggacgagg ctactgccac 228480
tgggaaggtt aaatatatgg atagtcttct tattaatgag gagtgatcga cttggtgatt 228540
ataatagatg ccactactta ttattctttt tgcggacact tgcaaaacct tcgataaaca 228600
gcgcctatgg actttgagac atggagcgca ggaaagaagg acaggagtgg ttccactagc 228660
cgatgcttaa gcgtcagccc ttgcttccac ttcaatgttg ctaaaccgct agccgcttcc 228720
tatgctgcat tgctcacttt gacagagttc cctcgtgctt ttcctcaacg ggaagcacat 228780
cgagatctct gtggttgcac tctttaaaaa attctttttt tgtttagaat gtcccacagt 228840
tactctctct caaatttgtg atttgagttg ctgtaccata cagtctttcc gcttaaagaa 228900
ttctattttc tctagctacg tcacagtgtc ctttcctttc gcgtactcct ctgtcttttt 228960
cctatcctct ctcttcaatt accgagaccc gtacatacta agatctaggt agctcatctc 229020
cttctaagaa gtcagatctc cttcctatat tctaaaaaga ataagagccc tttttaaccc 229080
ttcaattgta aagaaaggcc tcatttagga gcgctgtttt catccaacta tcaatctcgt 229140
aagagaataa agcgtggaaa agaaaggttt tgattcgctt tataaagaag aaagcttttt 229200
ccggttctaa caggctaatt aaattagaaa gcgtctgttc acgtcagggt ccgaaggaga 229260
tgtacttgct tttcctttt tgcgtcgaga ttgggttggt gttcagtgta ccgcttgtct 229320
agcctatgct ttgcatgaac atctcaatgt ccaagataaa aagaacgagg ggaagaatcg 229380
acgaggccag tgttctcgaa gagaaaatcg tgatggaaaa agcgtgagga gaattcgaaa 229440
gtcgatatgt tagaaggtgt cacaaatgaa gaatgcgttg gaggttggtt gaagatgatc 229500
ttacgcggcg ttcagaacca gtcttgaagt gaatgaagaa aagaagcgtt gttatgaaaa 229560
agtttccatt tctttcccaa ataataagaa cttttggtgc tgtagtcact tttgcctttg 229620
gacgttttct ttttttcggg gcagaaagaa cgatcgcgcc tagctggatc cttctctttc 229680
tcttttgtct tatatttatg attcgggcaa aagaaagaac aagaagaaaa aggagtgtgg 229740 ttcattttt cgttgaattc ttcctccttt ttctttttct ttcccttctg cgcctactca 229800
tcatggactg gatttcttcc tttctaggcc tgaccctggg cctgtccact gcttttgttt 229860
cttatgtttc gtctggatcc aatgaaagtg ggaattcggc tcctgaatca gggggtcctc 229920
cccctttaga atccgagtcg agttcggcgt cacttaacac ctttcgaaac cagatcgctg 229980
cggataatga agccgatata tatcggcgca tacaaatttt agaaaaccag gaatactaca 230040
accttcctcc ccagaacagt cctggtgact acgaaaggct ggttcgcgag aacttcgatt 230100
cagccataaa tgtcaatcat tttcggacga tttttgatag ggaatacttt gaccttcgag 230160
tcttagagag gaagggcgtc gtacaagacc aactccaaga tctaatgctt cgggaggaga 230220
atatttcaca gattctagag aaatctcctt attcgaacat taggaaagaa gcctattact 230280
atcttgagca caagctcaac cccgttagcg atccacgcca tgcctttcag cgagacattc 230340
ttgacaccag tctcgacttc tttcaacgag atttgaatct gagaggcaaa gattcaacca 230400
tttacaagga atttaagacg tattttatgg acgaatgatt gggaggagta gttctaccta 230460
tagacaagac catcagagag gagacaaccc atttatgatt ccagccgaga agactagtaa 230520
aaggaaggat caagaatgtt atatatttca ggagctagat tagttggcga tgaacaagta 230580
agaattgcct caaccaaaat tgatggaatt ggacctaaaa aagccattca ggttcgttat 230640
cgattaggta tcagtggaaa gataaagata aaagaattaa ctaagtatca aatcgaccaa 230700
attgaacaaa tgataggtca agatcatgtt gttcattggg aattgaagag gggagaacga 230760
gcagacatcg aacgattaat ttcgatttct tgttatcgtg gaattcgtca tcaagatgga 230820
tcgcccttac gcggtcaacg aactcatact aatgctagga cttgtcgcaa gctaattcgg 230880
aaatgaaaga agtctaccga aagcccttgg tacttgtctg atcaatcaca ctgatagctt 230940
caatagttca ctgaaatttt gtgtagtttg ctatttcacc ggttactaat ccagtatacg 231000
tatagtaggc ctccttcgcc acgacattag tggcttagcc cttcgcgctt cccttcgccc 231060
gcctatcgta tcggctcggc ttcgtcctcg aagctactgc ttccgcctct ctaggcatga 231120
gagatagctc atgactggta tatggatctc tctatgtagt ggtcggcctt ctagaagctt 231180
cgccagaagc gactagtcgc ttcccgaatg cctctttact ttagtatagt ctaatttctt 231240
tttgcctcct tccttgccgc caacgtacgc tactaggaaa gtaagcaagc tagcttgctt 231300
gcattctcga aacggtagct tccgctacct tcctgcctac tgaaatttat gtgaatgatc 231360
gtgacagctc ttcaaatcct attcagtctg attagatatg tcactgaaac aaagtgattc 231420
cgttctgtct ctgttttctt ttcggattcc gaggatgagc cggccgatcc taacatcatt 231480
tatgaggagc cggacgacga agcctcctcc tcagataaag atgtctccga cgctactctc 231540
ccggcaagaa caactttttc aattgtgatt tttttggcga gttcggtcag gagggacaaa 231600
agagagatgc tttctatcag tcaaaagcgg atatcgcccc ccatgctccc acggtccgct 231660
taccgaggaa tagaagggaa ggacccgggg ccagagcaag ttgggttggg gtatagagcc 231720
gtaagcgcgg tggggggtga cagaggacgt gctcgtacgg ttcatagaag gatatgaaaa 231780
agtacttatt tgttgggaac tttcactcct ctatattcga aatatgcctt tctaggagca 231840
ttacgatctg cagctcaaat ggtcccttat gaagtctcta ttggtcttat tcttattgtg 231900
cgccttgtga gcgcgtttgg atccgcgaag gcaatcgctc ggatgttccc ctaacccaac 231960
ccgggaacgg accggaggga accgcagcat ggggaatgtc cgcgtctcgt cgcaaggctc 232020
attttgagtt gtgggtcata aggcgggcag ctttatctga gcaagggccg gggcacaagg 232080
gtcctggtac tatccaggtg cgaagaaccc cggaggtgac tgcaatgagc agaaatctca 232140
ctcacgggcc taaacgacga gcaaacactc gaacgtgaga gcaagggatc acccaacgaa 232200
tggacgagct caaagggggg agggaggcaa gaaccatgct ttcagagacc taacccaacc 232260
cggtccgaat cttatctgaa ctgcgagaat aactgactaa gccgtgccat aaggggtcat 232320
tctccaaacg ggacggggcc aagcctttag gttgtttaag taggttgggt gacagatcgg 232380
ccataggagt actccgggat ataaaccagg gcaacaaaag tggagcatac gacgatgccg 232440
cccgttttca tttcgtggaa gtgcccggca gaggaaaggg ctgtaggtga tggcgcgttc 232500
tgcttcttat ctagagaggg gcgtcgaaat cctttctatt ggttcttgcg tggcagctgg 232560
tatagatgat gaaaggcggg ccgctttttc gggacctatt ctcttaatag gcggcaaagc 232620
gaaataggaa aggggccgag ctgactgatg agtgcctttt tagcctttat tttaaaggct 232680
ctcatgtgga gctaacatgg ctggctacat acaagtatag ccaaatcaag atgagatggg 232740
acggccgttc agaggccgca gcgggactac cattggaaag cccgcccccct tctcccatgc 232800
tgagtcacag gcagcgcctc ggaaagcacg gacgagccac atgcagggaa acttgcacgt 232860
gtggttctgg ccggggaccc cggtatactg tactaatatg tgtaggttcc cgtaattcga 232920
gtgagattgt catggcgcaa aagcagatat ggtccggtat tcccttgttc cctgtattgg 232980
ttatgttctt tatatctcgt ctagcagaaa ctaatcgagc tccgtttgat ctcccagaag 233040
cggaagctga atcagttgca ggctataatg tagaatatgc gcgggatgcg atccttaata 233100
gttcactgtt ggcggaagcc aatgtcccgg ggtctcgggg actcattctg actgaaacaa 233160
ggggcgggtc tttaccaact tccaaatatt cgattttagg gaagccaaaa aaggtgagcg 233220
cctagcgcga aaggttgctt tactaagtaa gataaggcaa gaagcaaggg cgcagcagct 233280
gcacgaaagc ccttgcttct tagcgcatcc gttttcttgc tcgttagcgc ttgactaata 233340
agatagaaag agcctttctt gcttgtttag taaagtctcg ctttttgata ggagtaggtg 233400
cttgctaggg cggggcactt ttcattcttc attcgaaact aacaagtgtc gggtcgggga 233460
tttctgcctt gttatcaaaa agggagttgg gtaaagcaaa ctctctcctt ggaggagcac 233520
gggcttagtc aagtagaacc gggttgcgct gcttgatgct ccgatcgaaa acaaatcagt 233580
ggggccatgc cggtacgact gaatatgcgt tagaaaggtc aatccctccc ctacgacacc 233640
aaaaaaaccg ggccgaactt ctaacccgcc cgcttccata gaacaatatc gtggcaacgt 233700
agatctaagt ggtcatattg gatccttggg aaccatcaca agtacggccg gcctatatat 233760
atttgaacga aaatgccgtg tcgtccagcg gagcctagaa gaaggtgact cgcgcagaca 233820
gctgactcct tttcaataga aaagaatagc caaaccaacc cagctggctg gtcaatctca 233880
gagatcttat cggccggcaa accggagacg gacgaccacg gtcccggcct taccagcacc 233940
ggaggtgtac taatcaatga acccacgaaa ccaactttct tttatgacaa aataaaccaa 234000
gcctaagcgg tcacgacatc ttgttgatat tgattgagtt ggagggactt tcgctgactg 234060
aatccatcca taaacctaga ccgcggtaac cttcgtaacc aaagcgtcac gacaacatcc 234120
aaaggtgacc tttggattct taagtagggg ggcaaggagg agcacgtagg aatgccgacc 234180
actacataag ccactagtgg ctgagagaaa gcgagcagca ccttgtatag gttgggcgga 234240
gcttaaagaa gcaagcccct atcagagaaa gccattgcgc gctagcctag ctagctaacg 234300
tttttctttc agctggctgt tatgttagtt gtagcgcgcc ttccctcctt ctctcacttt 234360
ggaaagattt ttcagtattt tcttatgatg acctggtcga gagagtacga tacatcggtg 234420
taaaagattg actttttttct gtgagcttga ccgaagggtg cagtagaacc tgaaggagag 234480
gaataaaaac ctggtctata attttgacaa aaggaggatc actattggga aatatcttcc 234540
tcctcttggt cgtcatcaaa gaagttgacg tccggggctt cctctttccc tttaaaaccg 234600
gtgaagtcca tcctaaagtt ccaaatctac atccttaacc agaggttcct ggtgagaaca 234660
aattgtaagg cgttgaaaga aactaaagaa agaaaatatt tgaaactcgg gaaaggagaa 234720
taagcctctc taagggaaga agacctagcc cagctttctt tccgagccat caataactgc 234780
cggctttcaa cgggtccggc tatcctttca ccggtcggta agtgcatcct attcctatta 234840
agtggggcgg cagttgctaa ataaaaaggt ggcgccattc ccgctaataa agaaaaagca 234900
attcttcatc caatctctgt tccagattct ggtcttacca agtcaccttt ctctaaggct 234960
aaatagctaa atatccccgt actttttttc ctattttctt tattctttca tgtcgagctt 235020
tcgaaagcca ctggggaggg agaatgaacg atcgactgct aaagatcttg aataaagcat 235080
tgatagcttt gcagaggaga aaaactttga ttcttcccga aggtcttcct tgcatgctga 235140
agtgaacagg ggcggtacca actacgacta gaaagcggtc actcctgtca atgaatacca 235200
ttcatagttg tctatgttag taacatagcc ataacgactt tgttttactg cttgaggtgg 235260
tgatagcttt tatatattta ctaaattata agcttgcata gtgctcttcc tatttgtttt 235320
ctcggctttc ttctgccgaa ccgaacgaag acagtttctc gtacctctgt acctattgca 235380
ctgatatctt ctctttcact ctctttcttc attcaggaaa ggtgaagatt gaatcgggaa 235440
ccgaaaacga agcaggaaca gacttgtcct ttggtcgaaa agtcttgtac ggttcctcag 235500
tccgggggca ctgcaagaac ccctatgaca cttggagatt gcttgcctat gtcacttgta 235560
cagtcctcta acatggtaag tgtgccatat ccatcttggc ttcaaagtct gattctgaag 235620
agagagacac cgaccctagt cagtctaaat gatgtagaca gaacccgctc cgggcttgat 235680
taccaccgaa aatttcccga gacggtagaa tgtaaactct agggtgaaga agaaagcatt 235740
gcatagaaag catttttgta taaggttccc acatccaata gataagggat cttgccctat 235800
aacctagtga agagggaaaa taagataaaa atatatgact tttttaactt ctaaatctat 235860
ttccaaatac cctgaaagca gcaaagaaag cagcaagtga agagataagg cctctcattt 235920
ccattagggc ggatgcattc cattcccatt gtaacggcgg cggagggtgc ctccgggtcg 235980

-continued cagcggttct tccatgtcaa cttaattgaa aagcatccta gagattgatt ggcttttcca 236040
gtactaggct tttgctttct tgtagttctt ctctttacat ctaccttcaa aacaaacaaa 236100
aaggacgacg aaattactat atctatatat agaaagatgt ggactggaga gtttggattg 236160
agatccatat gcttaacaca tcgtagttgg acagcttatc gaagagagga gaaaaaaact 236220
atgttttgtc ggcatcacac atatagcatg tgtgccgtgc cgtgagtgag aagtcaatca 236280
ctttcagctt ttctttaaaa attctacaac atgatgaaga actcttttcg gctcgaacct 236340
tctttttgag ctcggtcaaa atatcaagag gaaagatcgt agcgtagaaa agaaaggaga 236400
aatcgttttg attcgaggcc gatcccttcc ttaaacaagt aagcaagtaa actacccccct 236460
tttttttctt tacgggttga gtaaacaaaa gaaaaaaaaa gctttttcgt aatttttaac 236520
tctaatgaca aagcgtccgt tcacgtcaag aatagaggcc gttaaggatg tacttgcttt 236580
tcctttttttg cgtcgagatt gggttggtgt tcagtgtacc cctgaagaat ttcaagtaac 236640
tgtctttagt acgaagtgag ttgatcgaga aagcggcagg accgtaaagc aacgccttga 236700
gttggactgt ggtcccgcga agctggtatc ctcagaccgc ctaagagact ttccgactgt 236760
cgaaagaagt gaacataaat tgactagttt atttaattga cttaaagatc tttcttctat 236820
gcctgtgaga ttggcgtaat accttttcac taaaagtgat ccttattatc attctaatta 236880
tctaatatat attattaatc tcaaataatt aaagttggaa tttgtttaag taattcgatt 236940
aaatctttcc aagctaaatt gagaatgaaa tttcattcaa ttaagaacaa agatcaatat 237000
ggaacgcttt ggcgtcatcg ttccccatta ccattacttt gttaagacga ttcgctttaa 237060
tcattatttt gttcagacga tcgatatgga ataataaata ttatctaata agagtcgctt 237120
tttccctaac ggtcgagtga cttcttacct ctccaaccac tcttagctac gcccctcttc 237180
tcgtaacttc gtacctttct gtgtctaaag acgctcataa gcgattcttt gacttgtgaa 237240
cccatttgcc ttgagtgtat agaatgaata gataagaagg ggtggagcta gttagaccat 237300
taccgatata tgacaactct tacttaaaga agtagtccgt atcgaatcta ttttctattt 237360
tggaacgaac aacgaccaac taacactttg actttacttt attagattca gaaacattaa 237420
ttgcaataat atctcgaatg agaagaaaaa aagtatcgcg cgatcgctcg aagaaatcaa 237480
acctttattt cggtctaacc cgattctaag actagtcatt cctatgttct tttcctttta 237540
ggttatttca cgatggtgtt tttcgtagca gtctaagggg ttggtttact tttggacata 237600
cttcatttgc ttttcttatt cggacacatt tggcatggtg ctagaatctt gttcagaggt 237660
gtttttgctg gtagtgaccc agattttcaa gtatataaaa aaacatggat ccaacagatt 237720
tattcattac tactacataa agcactacat tacataaaca accacatatg ccttttacta 237780
gagctttaaa agcattaggc ctactacatt actaaactta ttttcgaaac ataaagatag 237840
gccttaacaa gtagaaagtc actattttta taattttttt tctagtggtt ttccgggaca 237900
ccgaaggtgg caacccgcac aacgagttct tccttctccg tccgcagcgc ttgcagcctc 237960
ctctccaaat cgcttatgtc ctctctggca gcggcaatgc gcgcttcttt tcttgcagga 238020
tcctgtgttc taacacttag caaaagcgcg tttagcgttc tacggcgccc ttgaattgca 238080
ttttgcaggt tactcatttg gacatcaatt tgagaaatcc tgtttatatc agctatatcc 238140
atacgtgcta ttactcaatt tctttgcttt gatatttgat gaagtgaaga agcctctatt 238200
tatagagtgg tagagtaatc tcgccatgca gtacgaattg catggctggc acaatatgag 238260
tactataacc acgctgcctg taacaaactt tgcggaaccc tttcacctaa tcgatcgtgg 238320

-continued tgaggattcg gcggatcatc cacgtcacgc taggatttgg gaaggacatt cacgagattg 238380
aggtgggaat tgcgttgcag agaggaatct cgccatgcgt caccgaattt gatggcaggc 238440
acaattctta ctagttctcc gcacaacttt tctgcagttg aagactatca tgcctattta 238500
gtgaaaaact ggctggctct ggctaccaca aaagatcccc aaatcacact gcctgtatga 238560
acaaacaaac cttgcacaac cagcttacgt agaaaagatt ccatattcta tgccaataga 238620
ctcgtgacat ccatgtactg agtcgtcaaa tgagccacgt taagaaagcc caagcttata 238680
cgcattggcc cacagggtgc cccaataggc cccgaatgaa agacccaagc ctacatgaac 238740
catccaagaa agtcctacaa atgaagactt gtgcgtgcct gtttcgatga aagcaggctt 238800
acatgcttat caaaaatgta atcattttaa gggtttggga tgtattttac gtgaaactga 238860
atctatttcc cacattctca agatcctgat ccagccttct tcgctaacgc tcaacctcgc 238920
atcgcatcct taccttaggc tatcgagctt cgaaaggact atattaatat taatttctaa 238980
tattaatagg taagattgcc tttaagggaa tgtgactctc tttccacggg cattttctga 239040
ctcttgaaag aatgtgattc aaagaattga cggtaaccaa ggtgcctact cttcctaacg 239100
agcctgctta ttaagcatgg tcggtcaatc aggtaatacc ccaaaggctg tctccagaga 239160
tataacattt cttgagatcc aaaactaccc cgagaaatgc tctagatcaa acgaaaaggg 239220
gaccagaaaa ggaatcccac atgaggaaat tacttaaaaa aacttattgc taataaagat 239280
gctaattggt atcctggaag ccatctttac atagaccaag gtacatgttc ctcgacgctt 239340
agggcatcct tattttgctt tgttagagcg cttatttcct agtttagtca gtcagtagac 239400
ctacgtccac cggtgaagct ccactatgga gatcacaaga ttagacaaca aaccttccac 239460
aagtaagaaa accccctgatc agacgttggt ggattgtgta atcaagctcc catttcctcc 239520
aaatctcctt ccactctgaa agatccctct tttacacctc cggaagacct acccgatcgc 239580
aaatcaatca acttgactcc acccttgcaa acacagaaga ctaatggagg accgcccatc 239640
ccatcgacta tatctcccca ctcccagagt ctacctccgc tacaaaaccg ccctcttcct 239700
tttcctagcc ttcattgata tcgtatgcgg tttatcggaa tcagaaagat catatattca 239760
attacttaat ccgtgaacgg aacctttggc ttaccctcat tttccaggga atggaccatc 239820
attcaatgca tattgattta gaatctgtgt tggatcgcga accttctctt ctctcaggtc 239880
cagaggggaa ctcctagtta agtccctcat gatgcctatc ggtaagagga aactcgggat 239940
tcgtgccatg tatgtggcac acaactggtt ttatcgatgt gaatcaacaa atcacaggaa 240000
aatttggtca catagatctt ctttcctaca gtagcagatt cggctagtga tcagtaccct 240060
ctctttattc ccatagaaag actcttatct taaacaaact ctcggattgg ctgagctttc 240120
aaagattgaa gaggacaaga aagggatcga actcatgtaa ctaagaaaag aaatccttag 240180
ctttagtgca gtgacccaat gaaaacgagg agaagaaggc caagggtaag aataacccta 240240
caggctaaga tctctcctgg gctttcctca caataattct gctgttggga taggtgaatc 240300
aatgggctca tttccttttt acgggatgaa gagatgatat agcgtgtgtg ccacaagtgc 240360
gtagtctcat tgaagttcag ttcgataagc aggtcttttt cgtaggctag aaggtaagta 240420
agcagggtta gagaatccga tagcataaga tagactcctc agattatcat tatctaaggt 240480
tgtagccgta aatcatgctc tctactcttg gaaatatgtc tttgcctaag atggtaatag 240540
cgtatgaaat tatataggtc cctttctagt aggagtaact tatctcttcc ttttcttctt 240600
cagaaccgct gacactccgt tcaggcggaa caatcagcga gagaccgtct ttcacctaca 240660
cactgggcag tccattgcta aggactcggt gctcaaccgt gcccatatgc tagttgaaac 240720

-continued caatcttacc ttaccttatt tacgataaac cccgaagaca ctgctcagtc tatgtcctcc 240780
aacgttaggt agtatcttgc gcttaaatgg actggccctt cttttaggga aactatatgc 240840
ttgtcttccc ttagatctga gggcggcaat gttgagaggg cgaaagcaca caaagggggg 240900
gcacgtcagc caaaagaagg gtatggagtc ggaaatcgaa ccccttgttg ttgacctgtg 240960
acagcctcaa tgctcttatg gcagggcagt agcaagaaca cgatctctcg gaaaagaaaa 241020
aaaaagacta aaccctatcc aagatgcccc accaatcaaa taaggcactg cagagccagg 241080
ccccaaagta cgcttttgct cgctccgcaa gtaagtacga accaggcaaa gaagcaatgt 241140
cgaccacccc taaaggtaaa aaaacctgat gcatgggaca agggcggaga gtataaagac 241200
tataaacgca cgcagccctc aggcaaacct ctaaccaggc tgatgaaacc taaccaaaat 241260
gttaaatcaa ttacgtcggt cgttgtgatc cttctttccc ttccagctca tcttgactat 241320
tcctcaaaag aaagaaagga aagaactcga tcacactgca cggaaagaaa ggcttcatta 241380
tatcaaaagg ggcgagcgta tcgattgcag aaaggctggc tgtacccgag agtcgttatt 241440
ctcccttact tcgtccttgc tgctattgta gcagtagtgc cttttggaat tgtatcagaa 241500
cagaagtccc tggcttctta atactactct aagtcatttc gtcccttgaa tgctgatcta 241560
agcgagcgcg aatagggtcc agctagtagg ttgtagttgc atagttccta ggccatccat 241620
cctgccttgt cccttctcgc gtaaaccgct gtattaaagg aggtgagtaa gtaagccagt 241680
tagaaagcat gataaaatag cccccttaaat atcccttctct tttatcgagc tagcctttta 241740
gtatgattac caggagtgaa agaaagctac gaaaactctg aagttaagga gaagagtgaa 241800
ccccttttac tacccgtaaa aatacgagta cctgttgcaa atgaatcaac cccgcttgtt 241860
ttttctgttg ataggttaga ttctcggttg aacgttagga aaccctacca aaaatggagt 241920
ctttccccta tatcccagtg cctcgactag tgcttttcct aagtggtgga tattttttttt 241980 aggcttttag tcatatgtat tcccctcttt gagtgtgcta gtaataagct gggaaagtca 242040
aatccatcaa ggcgaggaaa aactagtttg aaagtagtcc tccttgaagt tccttttaat 242100
tgaatgtggt aaggataaat agaaatgcaa tctctgaatc tcttacatcc cgcctagtac 242160
ctttttgaat cgagggggcg aaagcttaat atcaagtagg agttctggat tgaggtccag 242220
ttggttggat aaaggttgga gttctaaggg catcatctcg aaaaattgcc tttcctggag 242280
tttcttttta agtcttttct ttcttcttct atatctgctt tctctccgct ccgggcaagt 242340
cctaagcttt gcctttcccc ccgtctcctt accgccctac tcgcaacttg attttgacca 242400
tatcccgttc ggggctctct ggtctaaatg ctcgaaatga gcgatattca ctcggaacct 242460
agagattcaa acaggcacag gtcaaccaaa agcatattgc cgagctaagg tggaagataa 242520
aaaagctata tttaaaataa taaagagaat ctcttcaaat tcatattcaa aaatgggatt 242580
ctcaactata cttgactgga aaaaccagcc aatctactct cctttttttg gtctcccccc 242640
tgtaacttta taaatcataa gagaagaaga aatcgttgcg tagaaagtcg tgcttactat 242700
ctcctccatc taagttatgt aagaggaaaa gagcgaaaag cttactttta ggtagtggcc 242760
taagcgctaa gaagctccaa tcatgctact cagactatat gcttaacaca tgcaagtcga 242820
accttggttt tcggagttcg aaagagaagg ggaagaagcg gggtagagga attggtcgac 242880
tcatcaggct catgacctga agactgcagg ttcgaatcct gtccccgcct aatccatctg 242940
aggcccggcc tcaagatttg agattccgta agtaactcag tgactgcttt ctaagaaggg 243000
cttggaagaa gaaaatgaaa taggaacaac cgcgctggtc gtaatagatc gactttcatg 243060
ctagttcttg ctccagcatg aaagttccat ttcagggaag gacgacgtac tatgatactt 243120
tctgttttat caatctccgc tgggttgatt cttcttcgat atccatagat tttagatatg 243180
cttacttatg ttgtaacaaa cattcaaaat agcaggttcc tgatagacgg caatccacag 243240
ttacattcgg agttgaagta catcttagtc tcgctttgcc tttatttttt tgtttattca 243300
ttcgttacaa tgagaagatg tcattggtat tatttttaga agaacacaag taatattcta 243360
aaaaaaagtg ctttctgctt tgcttttcct tttctattga taacggcatt cgccccttca 243420
gtagcctttt gcgcagatcc tgcgcctgcg cttccagacc agacctcaac gagattccag 243480
taggcctttc tcctgctgaa atagcccaat tgcatcggga gactgaagag aatgccgccc 243540
agtgtgggtg tggcaggctc ttgcaagaaa tctgtgtgcg ggcaaaagaa gttgcccgtc 243600
aggcaggagt gcaggacgaa ctcaagctgg aaaaactcgt cgacgccgtc aagtttcttg 243660
ccgacgtgga cgagttggac gaagaggacc gaatccccac tctcattgag ttcagggcca 243720
aaatcgagaa taaagactcg acaattttgt ttcatataga taaagaaatg aagaggtggg 243780
gtggccgtgg tctatgatgc atttttttttc ttagatagaa tgaatggaaa aggggtgctt 243840
gtgttgtggt tttcgtagtt gcaagaattt tcttttcgag aaaaggtccc ctccttcaat 243900
atcatgattg ggtcgaccag gctagatcat gagtgaatag aaaatcgaaa atgtacatag 243960
ctgttccagc tgaaatactt ggaataattc taccacttct actaggagta gcctttttag 244020
tgctagctga acgtaaagta atggcttttg tgcaacgtcg aaagggtcct gatgtagtgg 244080
gatcgtttgg attgttacaa cctctagcag atggtttgaa attgattcta aaagaaccta 244140
tttcaccaag tagtgctaat ttctcccttt ttagaatggc tccagtggct acatttatgt 244200
taagtctggt cgctcgggcc gttgtacctt ttgattatgg tatggtattg tcagatccga 244260
acatagggct actttatttg tttgccatat cttcgctagg tgtttatgga attattatag 244320
caggttggtc tagtaattag ggggcggccg ttcggtcgcc tatgatacta ggaccaatag 244380
gttcaaaatg ggtttgtgcc gcaggtgttg aacgatctac tctacacagg tgtgggctta 244440
cagggctagg gctcataaac cccttctttc atttatcaat agggccccgg tcggtcactt 244500
ttctggaccg ggatcgataa gtggaagtca taaaaaagag atctttctct tcgcacctca 244560
gatcaagagg aagggttgct tgtcaagctg gcctatatat aatataataa taataaatag 244620
aaagaaattt ctttctattt attattatta tataatagat tatataagaa aaatggaaag 244680
attcgctttc ttttaaccgg ctccttcttc tttgtcaacg ctactaagga cctataggtt 244740
tgcctacttt acttatcaaa gataatgata atggcttatt caaacaaaaa ggaaaaggcc 244800
ctacttagtt tcgcaagcct ttgtcattgt cagtcaacta agtagggcct gaggccccct 244860
gcgaatccgt aaatctgagg agcatgccgc aacaaaagga tggtccccta tgcatatgca 244920
tttcattttt tccttaagga aaaaaaaagt accccccatc atagtgaacc tctccttgtg 244980
atcgggatga ggtagatgcc tcccagccgg ggggcggatc gaatcggagt ttccttaggt 245040
agccaccgac ctacagttat ccttaaactt ccgtgcttgg tggagaagaa gcgaacaaaa 245100
gtacgctcgc ttgctgtctt gttctctgtc gcgaactggg atcgctcgcc agctaggtca 245160
gattggagca agattttatg agaacatatt ccccatattc ggggacaagg ggcggaacga 245220
cctctcgatc tacttactgc agcccaggaa gaaaaacgtc gtctaggcgt tccctgttgc 245280
tccgatctac cctacgccta ggacgttgtc tgggccaaga gccatagtta gttgctgttt 245340
ccatttggtt gtttcttcct cgttgttgat accggcaaga cccagccaga tgatgtccgc 245400
tggttggtag tgagaggact cttagtacct gcatacccaa aagagggcgc tggttaaaaa 245460
acaatcattt gattttgttt cttgctctcc cttagcagcg ggaaaggagt ctatctatct 245520
gcctagcttt ggtagatttc ccccaacgca atccacagaa attccacgaa tcccttggtg 245580
gataagtccg acgactcagc agcagtgcgg aattgagttt cttgtctggt ggatctgatc 245640
tatagttagg gggcaataca taccaaaagg ttcgaagaag gaaggcgcat aagagtatat 245700
aaccaaccta cccttctgta taacctattc acattagtga agcggttgga tgcataaggg 245760
aagtgcacgt ttgtgagacc ttagtcggga tgcataggtg agtcaaccta cgagcacgga 245820
agagcgtggt accgctaccc ctctctaagt aaaggtaaga ttcttagccc tgtagatgac 245880
tccatctaaa atacaatagg gacagccgtt ttcggctgct cgtttcgtat cttgaagaaa 245940
gagtaggctt aagtaatagg ggtcaggtca ataatagcta tgctattgcc ctagtgattt 246000
aaggcctccg cccgatcccg aatgcacatt ttttcgggtt catcttcaat tgatgttttc 246060
ttaacctttc gaagaccttg cgtaaatttt cgatgtggtc ggttctttct tttgaaaaga 246120
ctaccaaatc gtccacgtaa ggctcgcata tgttatgtag gaggtcaatg agaatttgtg 246180
tcatcgctct ttgatatgtt gcactttctt tttctttttt tggggcatat cgtagtaagg 246240
aaaggaagtg agggcactca ttcgaatcga atagctgaaa ctactataac tcctattttt 246300
ctgctttaag agaagccttc tagctcgttt taaagcgttg aagagagaga taggacattc 246360
taaagatagt tgttgaggaa gcatctgatt tctaactacg agtccgtttt caagctaact 246420
gaatgcctat ctgctgctag ttctgttcca ctatctgctg ttactgctct cgttgccggt 246480
gtgacagtct gagtagacgg tgctctcttt cctgtagttt ttggggttca taaccggtgc 246540
tattgaatct gcagttaagg gaatatcact agttcttgga ataagagctc tgggacttca 246600
tggctttgag ggagggttag cctagcccta agccttttcg gaatagaatg ccccgttaga 246660
atgggcaggg acagtcgatc atcggcttaa tttcctgggt tttgggactc tagtatcaaa 246720
aattcccggt atttcgtcgt gaaagtgtca catttagatt gaacttatta aaggaaagag 246780
ccgaatagac aaagggttta catgaccgct cgctttggac aagatgccat agtctaagaa 246840
gaaggccttt gtttgcaaag atgactttcc cgctttcctt tgtgagggag gtttgtgcac 246900
atgaattaat agtcaaagta taaggaagat ggcatagagc atagaatgag attgatgctt 246960
cgaatgccct gttttcaggg gttgtgatag aaggagctgt ggcactttcg gaagggggaa 247020
tcagactagg ctgtcactgt tctagaagag gaagcgtagc tggcacgttg aaccatgtct 247080
gtcaacggtg aaagatagcc ctaaagtgag ggcccccggag atagtatttc tcaactgtcg 247140
atcgacgtga caatcatgcc tgcttgacaa atccttttttc attcagtctc ccaataaacg 247200
aaaaaggatt tctggtgaca cgaaagctgt gctcgacgct ctctttccta ttccactgtg 247260
ctaagtggtc tttcccttta ttgctggatg actactatgg aaaaagatga cgactactcc 247320
cagtctctgg tcaatccatg ctgatgcatg aagagctatt cccgccgccc acccgaaaga 247380
gacgaggaag actaaccgcc atcctgctcg aacctttgct gcctgagtta tatagctgac 247440
tgcgagaagg aaggttcaag ctatggctgc cccatgggat gctcatttga aacctttgtc 247500
cggtcaatgc gagaaagaga gaagtgatgt aaacataaga atggaaggtt tgcttgtcag 247560
ctgtcgggcc aatgatgctc ttctagcttt acctacacgg caagggaaag atcaaaggcg 247620
aggtgggaaa tgccccgcac gaactatctg atcaagtttt ctttttccta tcacaggcag 247680
ctggcaaagc cgtgtttgat cgtcgcgtac atgctccgtt acagcttcgt tcatgcgcca 247740
atcaattgac agtgaagcag agaaggaaga gttttgatca ccgtgtgggt agtctctatt 247800

-continued agggtttccg tttcatgtgc actaaaaagg aaggaagact ggtgcgacta tagtaatgcc 247860
aagcatacga gcaaaggact ctacctaccc catactgacg aatgaaagaa gctcatcgcg 247920
gatgatagga caagcgatag cggttccatt cttgctcttc ctattccata ccataaacag 247980
acacctttga ttcatcgaca ttggcgcgtc aggctctacc cccacccccc agccctttat 248040
ggagttagcg gaccaagaga aagaattccc cgatataata aagaaagtaa gaagggttcc 248100
aaaccattga aacagaaagc actaaagact gatatgacgt ggcagagatg atcaccgtca 248160
agcacaagat tcaaagctgg aatcttccta ctcttcttag ttgggacaga gcatcctatc 248220
ttgttgattc tcctttccca ccgcctcgag ctctcgcttt cagggtagat acgcaagaaa 248280
ttcactagga aaattgacat gacacaatcc ctgaagagta tgatgtgccc ggccttgctt 248340
ctcttgatcc ccacccacct cccgtagagg cgggccaata tcaatatcta taccagagat 248400
tgcttttagc tttctctttt cagagacagg agaattcctt ctgtacttac aagaatgcta 248460
cttagggaga agaatctctt gactcaggag cacctgaatc tattctttct gtgtcccaca 248520
tccgcctatg ttaaagcatc cgcccattcc tcagtgaaag gaaatgctac tcagggatca 248580
aaaaagaaag ctggtgcctt gtcagaaaga cttggttcgt agagtagagg cctttcccca 248640
agatattggt tttaagctcc tctccttaca gtcaagtggc tttccgctcc tgcgggttac 248700
tttttgtctt acgacacggc atggtaattg atcgagtgcg ctttcctttc tcctactccc 248760
acttcgggaa gggaagtgct aaagggcggg catgctcgac tgcctaaaag aaaagaaaga 248820
aagcccggta tggatattca ttccgctaga gcaaaggcat gaagtgaagg aggccgctaa 248880
ggttgagcct tacaaatttt aaagagtcat attcaatcac ccggaaatat ccgcatctgc 248940
gaatagaagc tgtggaggga gatccatgca atggcatttc atcaacagat accacttctt 249000
cttccctgct tgggcatttg gaactcttag cagttgagga cgaacttcag gctttctatg 249060
agtagaaatc ctattagcga accctctttc gtacctccgc ctttcccttc taggtcatgg 249120
tcaccatttt gtgatcaccg ctacagacta cttcaccaag tgggttgaag caataccaat 249180
agccttaaca ttggaaagtc gcttttaagc ccaagtgcaa ccaaactagc aggaaatgaa 249240
agaagaaatg gatctgtgtc actgtctgta tgcttgtctt cataaaggtt tgagtttgat 249300
tgtttgttgc caaagagaaa agttcattgt ttaggtccta ctctgggtct gtagctgaca 249360
gcggcagtta ttttcttttc gatttttgtc gattaataat acccaaaaac ggtagcgagt 249420
agaataaaga agttgcttct agaatgccga ttgctaggta aatcgcccac tatatatagc 249480
acctatcggt gtagaaggtt caagcaaggg atgtggattg agtccaagtt ctggagaaag 249540
agggggcctt tttttttcat ctttcctaaa tcgatcgatc aaattcttca tatccgaagc 249600
gcaggaagga tctgactaga aagtcgtctt gctgatgcaa tagtcctctg ggtatggcca 249660
cattcgtctc gacaatagga tagggaaaga aaatccatag acgagaccaa cagggaccga 249720
acccttctat cttcttcttt ctctttttgt tcccgcctgc cgaggaccta tctttcaata 249780
acgatgaagg gctactagaa gggaaagggc ttcaggagag atacttagat tggatgggcc 249840
tattcccatt tatgggacag tatcccaagc agtaaggctc tgtagagcta gtctcccttg 249900
agacctgctg ccgcaaaagc tctttctgct gctccttcgc ctgcggatta agctgtagaa 249960
ggcaagcaag caaaccttgg caactggcaa tttcaaggat caggggaggt atgaaatggt 250020
tatctcggct gggaatcaag ccccaacaca aagagctgtg ggccaggttg ctttgcttta 250080
tcggatcaat cagtgtgcag tgggcaagct ctttcccaag tcgctgagct gtttaacaga 250140
gggaaggtca aagagctgtg ggctaggag tgttctcaat cttagcattc cgagacaaag 250200
cctgggtcgt cgaactaaag aatctcagca ttggccataa aaacgcgttt gaaggcctgt 250260
ttctgggact gatagggagg ggtctaaaac ttgaatttct gctatatcaa ccttccaaac 250320
caaaagggga ttctgctcct accgctaaag cattgtttcg gcccctgctt ccagaagagt 250380
tggtgcaaaa gtcattgtag tccaaatagc gtatttccgg ttaggggcct aagactcact 250440
aaagcaattg tagctattca ctccttctag ttctagtgaa tttcgctcca aatagcataa 250500
aaagaagctt gagttcaatt agggggggaac cctctgtagt caacctgctc ccaatgaaga 250560
ggtaaggggc gtagcgatga agtcgaacag ggttggtaaa ttcaccgggt gactcgaaag 250620
caggctctta aagaccactc ctagcgcgtc agtcatttcg ctcccaaaga gctccctaaa 250680
aacgttgcca atatcgacag cagctcctgt tcaagctctt gtttcggttc ccgcaaaaga 250740
aattgttgca gtctcaactg gataaatgaa cagcttcgca tctatttcct attgtaatga 250800
caaaggtttt tctactgatc cagtgtcaga taattgggaa ttcgctttca gctcttaatc 250860
ttcttcggga gacatggaaa aaggcaaggc tcgagagacc tagcgctaaa gcaattgtag 250920
cggcccttgc gtacagaatt gtagcgactc cttctagcat tcatttaaca ccttcgggta 250980
ttctggtatc gaaaactgga gaaaggaagg aagtctttgc ccgagaaagg aaagaggttg 251040
actcactcgc ttggcgaact cataggtcag tagctcccgt taaagctaaa gctattgttg 251100
ggccccctgc gtacaaaaag aaaaaagaca tctttccccc ctcagcactc gaaatctcat 251160
taagagaagt aacgtagaaa agaggacatg aaaaatggct tagattgtaa gagcaggtgt 251220
aagcttatag gcggtagcta agaagttctt tcttgcactt tgcttaacac atgaaattcg 251280
agcagtgatc cactaacaga cacgcgtcaa aaccaaatga ctcagggcat ctccaatcgg 251340
tggcgttggg agctcctggt cgaggtgtgg agttttctgc ttcctgccct gcggaagtct 251400
aaggctgatc cctgctgcta gtgtaattta ttctaaggct cttcgagttt attcactctc 251460
tggtaatccc ttacgagtct caagactctt cggtcaccgg aaagtagttg ttttctatcc 251520
ttctcgatag ggctggcccg ctatagagag gtattgtcgg cttatggggg tataggatat 251580
gacttaagaa tccaccttcc ctttctcttt gtctgagcac aagtgttaag ggtacggtga 251640
ttacgcagca agatcttttc cccactagat ctctgaggga caactccttc acttggaaag 251700
cggatggaga ggatggcgta gctttcaaac ttagcctagc cgatttgctt tttgggtttg 251760
ttgtcttcct ccctaagact ttcgttcagt gacatcacaa gggttggttt gagcgcttag 251820
ggccattggg agggggcttt ccgatagggc ttccttcgct aggaaatcgg actattctac 251880
cgctactgac tgactggact tacaaaaagg gagttcatta tctaggtgag ctctttgctc 251940
ctggtagacc ggttggtgtt catcagtcag tttgcttctt tttttgactg acgtaattga 252000
tttgcccttc cttccgattc ggatggagat gcggaatctt cttctctgta ttaaccaccc 252060
ttcttcacag aaaaagagag ctcagaagac ctcgtctatt acgacggtac ggaaaaatca 252120
atggcaccgg gggaaactca gtccagagaa gaaaatgtca gttaggaaag agtagtcaga 252180
cgcagaccag cgcaggtggg cgccacagct gtcttcctcc atatgatatc acgcaagagg 252240
cgaaagaatc cctttacctt atttacaaaa taagaacccg gtcgatcgga gtacccttcc 252300
tcctttttga ggcttttagg cctccggtca gtcaggggtt gacatgagac cggatttttt 252360
ggggaatcca ttctttgccc tactgtctgt ggtaagtcag tctgctttgc cttctcgctc 252420
gaattctttt caatgtaatt gaattcaata gtatgacttc tatttcattg ggaacttgat 252480
gagtcgatcc gcctacacgt cttgctttta ctgctatatc gggtcttact ccacgtattg 252540

-continued

```
cttgacgtaa aagagagagt ggatttcttt ctgtcttttg ttgaatcgct cgatagagaa 252600
tttgataagc cagtatccgc ggtaagttcc aatgcttgat agagtaaagt aaagaaaggg 252660
cttttttttaa agagtaagtc agtcccccttg aaagatgcat ccaaatctgc actcggggta 252720
cgcataaggc ttcagaacag ggttggaaac gaaattagat gttatagata gttatcggga 252780
aagaaagact tgatgacggc tgcacatact caaagggttc cttagctctt tacagagaat 252840
ctcccagtat gctaaacagt gacatctctc gttatatcga gaatgtgcat cccgttatgg 252900
atgatgcagc ttctcggttt ggcgaagtgt tctgtagcgg agtcgccgcc acacctgccg 252960
gggcgggtaa gctacgactg ttcatcatag gtaactatgt gaagcagagg ctgttgaagc 253020
cttatcacga ctgggcgatg tcagttttgc gtcgcttaga ttgtgatggt acttacaatc 253080
aaacaaaacc ccctagagcg ggttggtccg ctttccaatt tattcttctc tttttctata 253140
tttctaggtc gaaggaatcg gggcagagaa ggtttttatc cctaaaaaaa gccttttttcc 253200
gttgctcgac tcgaagcaac cacgagctct aacttaaagt aggtctagaa ccactgagat 253260
taagttgttt tctattttct ctccaggcta tgaaagatct gggatttcgt tccaggaaat 253320
ccgtatattg ttttaacata tctaataggg agaggaggag acagacagta aggtatggcg 253380
agatcacatc tcccgttact atagtagagc ctatacgggg aataagatat agtgatgccg 253440
acaattcaat aactaatcaa gaaagtaact cactgaactg aaccagctcc cactaaacaa 253500
aacaagctta aaatggggct tattcttgaa caaaccttac tgtagaaaaa aggagatttt 253560
ctttctcggc ttgactaaac tttctttttc ttatactccc ctttgagaag agaaggaata 253620
gaaatagaga aagagatatt cgtgggccgt taaacgacca cctatgaacc tttttaataa 253680
gcttttcctc gcgggaatta catgaataaa gaatcatcct tttcgtatac atttcataga 253740
cctccctatt agcctactaa taaagaaagt aaagcactaa tgggtttccg atgaaaagaa 253800
ggaacaagga agttccgagt taagcgatag aaattggtcc acagtgagaa actcaagcga 253860
agcaagagag aagatgcccg gccgagagga agttcaagtc gctgaggtaa tttcagatag 253920
agctacgttc cgggtattcc taccatcttt tcttataggt tactctttga actcttaatt 253980
aaagcactgg aagagaatcg ctatcgtctt tctaaaggac ggggatttac gtgtattgct 254040
tatgcccgat ttgctgacgc tagcttgact tcactcactt cagagacgga aaaaaagaat 254100
aagaaagggg cgtagcagcc ggaaagaggg agaaatcccc tcttccgctt aaggcaccga 254160
agtcccacag ctaatatcaa tagctgttga ttaaagggaa gttctttcta gagcagtaag 254220
agcctattct gtcttgcttt ctgattcaat tccgctgcta gggcgagcta actccaaaaa 254280
accgtcctca gttcggattg cgggctgcaa ctcgcctgca tgaagccgga atcgctagta 254340
atcgccggtc agccatacgg ctgtgaattc gttccaggat ctctcgctcg ccctcaaaga 254400
ccaactcttc tggaaagagt tctatctccc taggttttaa ttccttccgg agataagcaa 254460
ccatcttccc tttaagatag ggttaagag gatttcccct ccctaaccaa tattctaaag 254520
gtagttgctg tgaaccgtgg ggtttgccag cagccgcttt cagtcgttcc catcgctttg 254580
tttggattga catcaagcga gaccgaacgc gatagcctgc acctgctaag ggttgtaaaa 254640
cagacatctt ttggatgcca tatttacaag ccagctggca caaaccaatg gtcgacctac 254700
aacctgttaa agcacgaaga gatattgggg acaaatcctt ttgcatgtcc ttagtccagt 254760
acctcttcgc gaactcgaga gtaccattct ctgaaataat ggattttgac agagaaatag 254820
taactccgag tctttccagt aacaggctat actctctggc taccaactca tcggcgataa 254880
gaatatcatc gccaaggaga gcgtagtcat agaaaggggt ggccctctgc gggtaggcct 254940
```

-continued tcttcgctgc caaccatacc agataatggt gtgacagggc gaaaagcgac caagagccgt 255000
agtaacccaa aggctgtcca gtcaagaaag ccacttcact tatcccttta acaaaaggtt 255060
ttgttaaaag gaaagtgtta agaccaagag tactgttgac gattgatgat gccaaagtac 255120
ttccccacat acaagacatg agggagtcta tgacactcaa tggccaacag tccgtagcag 255180
acttcaagtc aaaggaagaa agtttcctca atttcttgac ccgaagccta tgtaaatgta 255240
aggctttctc ttggttgaag gtaccgtcct tccgtattgg tttcctcttg gactccggcg 255300
taatcccgag cctgtaaggt gtctttttaa accggatggt aagattgttc caatccaccc 255360
ggaagtgact taccacctct actactttta tacgagatgg atcggcgtac tgggactcaa 255420
accagtctgt atcggcccaa gctttagcgg gacccttgaa cttgactaca ggctcggcct 255480
ccccttttagg ttggtaccaa gaggctttcg gtgctaaaaa tagacctttc tctattttgt 255540
cttcaagctt aaacttacct aagacagaag gagaaaccag ctcgtcaggg agtggatgac 255600
caagcacaac agagtcggtg tcggtatagt aacacttctt attacggata atggggtcca 255660
tatgcatcct agcgtaggca gcagccgctg ccgccatctg gaccgcagcg ttcctcaggg 255720
ggcgccattt ttctatggtc gggccagtgt agctagggta ggtagcgagg ttggtgtttt 255780
ctttaagctc tacaccgtgc aggaactcct catgggagtg aatcaattct ttccagcgtg 255840
cattatcgca gatctcggca gtcgtgcttt ctgggctaat accgaatctg ccgtagaggg 255900
cattcatcag gatctttaac acataggcta tcgcctcatt accttcttcg cgcgccctca 255960
gcctactctc agagagagag ctaacaaagt ctttaaatgg gcttctttcg cccttctcaa 256020
agaggtagcc ctgggttggg actacagtgt accccagggt tctagcatac tttaactcct 256080
cgctaaagta gacccctata aacctcccgg tagggaagac ccagaggtcc accccgcgat 256140
cgataaggca gaaagggctt cttgatagtc ttggggcact ccacatatgc ctcgataaag 256200
ccaaagaggc tatctaagtc ctcgccaccc agatcctcac gccagacagg cttcccggcg 256260
ggcatggggc gctccgccat tacaaaggga tagagtgagt tcacatcgta gtagtatagg 256320
tccttaccta ttggtatgta ggcatccaca tgaccaccgt agtagccacg ccttataaac 256380
ctctcttcat tcgtgttggg gatgtggatc cgccctttag cgggatcgtg gaacttcata 256440
cgaaagaggt acattgccaa tgaggaaatg ggaattttgt ttactatgtc aacctcgtat 256500
acctcccaaa atatctcctg cgccctttgc atcacaccgc caaggagaag gacgtccttc 256560
ttcagatagt ctatcaactc ctctctcata ctgctaagat tctcgagagt cactctctca 256620
tgatcaatag accccttatt cccaagttcg gggcatagac tacgcgaaag tgaatcaagc 256680
gaacccagga gtagagccat agagtctctg aagcggaata agagcctccc ccgctcggaa 256740
tagaggctta gctcgtaaag cctattccct ctcgacagcg gtcttatcct gcccggccac 256800
ttaccggcca ggtgctctag caagagaatt ccatcgaatc tctgaaggtt atgaaagtag 256860
acggttatag acgacctatg cttgatagct atatcattta tcctggatac taaatcgcta 256920
agtaccttag tactcctttc atcaaattct tttaaggtcc tgtactcctc actgaagtag 256980
gtttcaacct tattatattt gaccggctcg ccggggcgaa caatcattag acctgcagca 257040
taagtctttt gaaccccatc ccttattact gtctcgaggt ccgctacaat gaaaggtttc 257100
cgcgccccgg gacgtggttt ggccgctgtc atatagacgg gggggctacg cccatgatgt 257160
ttgatcgccc ttgctggggt ggggccgccc ctaattaatc gggtgccgat acggagggcc 257220
gattgttgta agtcatttct ctcatcaaaa gacggggctg gcccttccgc cctagactcc 257280
cccatataga ctcgtatgtt gagtcgaact agctcggcgt tcttgtactc ttcgcaacga 257340
tctacaatag cttgatatat tttagggtag actacaccca tcgggagtgg cttaccgtca 257400
ttttcggtta atggaatagc ggggcccgcg gtaaatatta gaacatccac agcgggtggt 257460
cgccgcgcct caaagccaat cgtgaacttt ccgacgcccg ctagagcggg gtaagcaaac 257520
cggcataata ggtccacgac cgcgagactg agtagctcag tctcgcccaa aagaggcgag 257580
gggggtgtga aagtcatgga cgcagcgacc aacttagtat ccttactatc cttcttcctt 257640
ttcttattct tattattact tataacgtgc agcacggctt ccccaatcct cccataatac 257700
tcgtccagca ctcggctgcc agtttttaat cctccttgat tttcatgggg tgcacgctcc 257760
aatttatcac cccctcatca gaggcccccct caagggtagg ggcaagctgg ccccggaaga 257820
ctttccacct taagaaatgc atttcataat cctagttagg gccgcatacc tcaccagtat 257880
aggcctcata cgccttaacc aggttttgga tccttccaga ccaatctttc atcaatttcc 257940
ggttaaccgt gccaggtata ccctcatgta agcactccgc caggtccgta ctagaaaaga 258000
cccggtcaag gtcaaaagca ccggcgcggc gccatgacgg gccggtgtcc ctactaaaca 258060
ggccggcggg cctaccaagg accggactaa tcacattttc gtatatgaac tggttgatga 258120
ccctaagtgg agggtccaag cgcgaaaagg aaagggtata aagaccaggg agcatccagc 258180
tatggtgagc tgtacttaca aagttgtcgt gtacagtgta tataggtgca tcgcgctgcc 258240
gcatttcctt taccacactc atagcaatat aggcgtcctt ctgatggatg aagttggcga 258300
agctagccac ttctgccttc ctacgatctc tcttatcggt aggaactttg agagtgattt 258360
gccgtctttc aatgcctgtg ccccaaaaga gggctaggtt caagggtagg cacctagtag 258420
ctgcgagcct aagatcaaag gcagttccaa aaaggagttc cctatttcca gcttgataaa 258480
gtaaagtctc agtgccagtt gtaaggttag gaaagccagg tatgatgaaa tcctcttttc 258540
gaataggaat tgattcgatc ttattattat tatatgaaga tgaaactgaa tatactcttt 258600
ttcaagaagg aatcgccatc accagtggaa gttgaacccg gcgatctctt cctcctgaag 258660
tatggaaaaa ggaagaaaaa gcagtcaacc acagggaagg aaggaggtat agctcaactt 258720
tcttgcctct tcctcaatcc agtagcgagg tttcaacgag ttctttgtac gcgtgtaacg 258780
aaaagtatat atactttttc tcccgaattc cctattactc tcggtccttg ttcttggtct 258840
ctgtgaaaga tccagtcgat gggaatgaat ccatgttcaa atcttattac cgggttcgat 258900
tacattgctc gatgtaattg agtcttaaag gggaattgca taaggaatct cttttcttat 258960
gagaactacg aatcatcctc atgaataagc tctactctac cttaaggaga tgtggaggca 259020
ataggtcccg tgcagcttta actaactcga ctcctccata cgcctatcct ttagtttagt 259080
gggccaggtc ctccagcctt ccattagctt tcgatttagt ttgcattcaa agtcttggaa 259140
tgcgagctta tgtgctttca ggtataggca tcctattccc cgttttgact ttcttttgga 259200
atcgtcttct tttaaataag atcttctccc ttgttcttcc ctctgcctat gatcttgacc 259260
tgctaagtga tttccgaaag ctcccactat gactaaaaag ctcccaatag gccacgtagc 259320
agcttaagct tatattataa taaagtaagt aggaaggagc gaaagctact cgaccagacg 259380
ggagaggcga ccaaaggaag ctggttcacc ttctctcctc cgttacaaca taggtcgttc 259440
caatcccgga tgaaaatatt ccaaaacgga agtcaaggag gaaagttcca tcctgtcctt 259500
caaagatcga ctcgaaggta gccatactta tcttacgata taagtggact acccgcgata 259560
tcgaaaacca tgagagataa agcagaaccg gtcagccttt gcatcacgac gtcgaatcat 259620
ctttcgatga aaggacggta tgatgcgagg aagccccggc ctggtatttt gaccggctga 259680
agcagcggca gaagctgaac ccgaaccaaa ccctaagcaa agaagggatg tgccttagtt 259740
cagtctcgag gacgggataa taggggcgta gcaccgaata tgtcggagta gtcccaccca 259800
gtagatggac aagccagtag taccaatcaa ggaagccttt cactgtagag ctttctttcc 259860
tgatggggac taagaaaagg agacgaatat agctaaacag ctgcagcaga aagaacgaaa 259920
agccaaaagt caaggtgcat agcggtctat tcaagaatag gggagtacag aataaggggt 259980
ttgcaagaca aaagagaatc cgctggaact acggacaagg atattttact caattcccct 260040
cttactattt aaaaaagcgg aaaaaaatga aattccacca gtgtgtatgt aagacaacct 260100
taattctcta tgttcaacgc tttgggcaag ccagagcaag acttctctgt gggaataccc 260160
ggctatctcc tactttaaat agagaaaatc cctggagtca aagagttatc acccgctgta 260220
tcattgacgc ggacggggct ttctttcctg cggtttccga tattgcaatg gcaagcaaac 260280
agaaggtttc cctctttcgg gtataggctt tcccgattga ttggaaagat tttatactgc 260340
cagagaaaaa aaagctatct aaccctgata tccttggtac tgtccctgct gagaaagatc 260400
ctaatttccc agagagtgct tttccggtgc ggtgtaacca acaactcaag gctatcaagg 260460
gaaggagttg caggaccgga gttctatctc ggatccacag aatgacctgt ttttgtctcg 260520
aaaaccgctc ttagggcagg ttccacgtgg gattggatat cgaaggttcc ttccgagcat 260580
tttggatatg gaatctgtat tgccggaaag gttctccctg tcccgggcaa cctctcttct 260640
tataggattc atagagtgga gtttaccttt aaggttggat tctgattgag aagccgcatc 260700
ggatagagaa cacgagatct tgccccccatt gttgaagatt tgctcttctc aggcgtctcc 260760
agggagatga agtatttgtc tttgtcgatt ccactagatc tgagcatgct acgtgtcatc 260820
gggccagtgc gatcacgttc aacggacgca acagcgtaga tattgttgca tgggatgttg 260880
ttgctcttcc ttgaggccat cacagcagtt ggctccagag tctgcagatc tgatttgtga 260940
gagaaagaga tgaagggcag agttggtccc accgggcgtg ccagaaattt gttcgtgaca 261000
aaaatggaat atagaaaata aataactgca atcacaaaac aaatatgaga aaaaatcatt 261060
tttttgataa atgtttgagt acaactccaa gtatcccctg attcttgtct ccaagttgtt 261120
cgccttgatt cgagggctga agcagcgtgt ttctcgaatg aaggatgatg tggacctcct 261180
cgtgatgtat ttgatctccg agaaagtcgg gcagcacttc gggttgatct tgaggaagaa 261240
cttctcttga tcacttcacc cttgctagag aactttgaga aagacgatgt agtcgatgtc 261300
ttgatctcct tgtgaatctt ccaagatgtt atggaatttt caagatgcct ccaaagagaa 261360
tatgtagccc ctttatatag gcatggatta ggcttttagg gtagcctcca agtaatccta 261420
atggaccctt gggcttgaaa tatgtgggtg ggccattttg tagaggccca acctagccca 261480
atgtagttgg atttgactta agtcatgcaa ttttgactta aataatgaat ccggctttat 261540
taacccaaaa tgttgacttg ggtcaatatg tcttgaattt agaacttagt ccaaattttg 261600
tatggactta atcccataaa attttgcatg tctacactta ccaaactagg taagctagtc 261660
atatagcttg cttagcacaa agtttagctt gcttgctcct ttaaattact cgtagcgtaa 261720
gcgagcgtag aggaacgaac ggagcatctc tcgtagcacc gtaaggcaac gaagttgctg 261780
cattgcatag aggtcgctaa gattgctggt aagaatcgct attgcaagtc tatcgaagcc 261840
tacgctactt attgattatc aaaaagcgaa ccccccggcc cttcccacct ggggctaccc 261900
ctaccctaag ataagacggt tcccgccctc aggtcaggga atagagctaa ctgcatcgga 261960
aaaaatagca attcctagtc cgaatcctgg acctggttca cgcttgaaag cagcaattct 262020

-continued

```
tcttccaatt tcgtacatca aattgtgtat ataaagaaga gttcgtcctt cttcaaagag 262080
ataaagtcac gcggcccttc aagatagagg cttcagtcat cgttagaatc ccggggcggg 262140
ccaaattaca taaagaaagg agacttattt caaagtggtt caggtagctc agctggactg 262200
aaaatccttg tgtggttcga atccacatcc acttcacagc aaagaaagag aatgcggggt 262260
agaggaattg gtcaactcat caggctcatg acctgaagat ggtgcaccat ctatccatgg 262320
gagtagcgaa agatacctcc ttcagggcaa tgaatgccat ggtttctaat gaactttatc 262380
cagaaggagc tgcagcgatt gagcggccag ctggttaaag aatttttatt ctccgctccg 262440
actctcaaga aaccccatat ctcccttact ggtcgcggtc tcggaagaga cacagcgctg 262500
ccgaccttct gagctacgca aagccttcta atatcagggt ggctgtacac gcaattgaga 262560
gtacttcttg ctacttcatc gtccgtcaaa accatcagct attggccgga gaacctaaca 262620
gaactttttt ttctttcagg agttggttgg tggcatggtt ttcttattta tagtatttgt 262680
ttgtttgctg gcacaggtag tctagtcatt atcagtagca gatgtagaat ctgaaaggtg 262740
ggattaccgg tttcatttaa acctagctta caatcactag tgaaagagtg cccattgacc 262800
caactagcga atctgtttag aaccaggttc agaaagatag ctgaaagtgc tagcataagg 262860
aagagattct atggttttcg gcattcaaag tcaaacgatt cttttcattc aaggaaatcg 262920
tctctattga actatggaaa gcactttcta gtagcgacac ggattcacca tttcgccaat 262980
ggggcaaacg aaggctaacc cgttctggtt gttatgaaat cagtaggttc tttcagtctt 263040
gctttccttc ttacagagat aagagagata agtaagtata agtaatgatc catccaagga 263100
atgagcttcc ccagagtcca atcccgtgga ctaagaacct cgcccggcaa cagcagatgg 263160
ttaacctttc attcgatgct tctgattcaa accaaggtac agagattagg tcgaggtacg 263220
aagtctctgc ggggctaccg cagaggtacg aagtgactcg accaaaggga gaggggctac 263280
cgctcgtttc actatgttac ctatgttcag tttcacatag tgaaacgaat cgttacactc 263340
tcatttcgta ccttttccct gcgagcagaa gctctccgct cgtgcttcat tggagcgaga 263400
cagtcgcttc cacacagaat acttggctac ctacctagct cgcatttgtt tatcctctcg 263460
tgggttgatg acatagcaag gggataagcg gtgtggggcg aagtgagctt ggccgctctg 263520
agtagaagtg ctctctagca gcctagatct agctcagctt gagactttcg tactgaaagg 263580
atgacttcgc tagtcgcgag taagcacccg tacgggaacg gctttcggca gacaagttgc 263640
agcagcaaag agtgcgccct ttcgtttcaa tgtagattct cctctcagag aactagaaga 263700
aggggcctaa gcacggtaca cttgagtgga actcaactcg accaaaggta cgaccaacgt 263760
acgaagttgc tagagattcg ttgaacatag ttcaactcat tcgactgaaa ggagagggga 263820
gaggaattcc cggaaatcct tcttgacgac gcatccagca ggaatcgaac ctacgaattt 263880
gggcgcttta accattcagc catggatgca aagagactca gcgagtgaac taggttttgg 263940
tattccttct cgagcttcta tttcttccgt taaaggagat tcgagaaaag atgaaatagg 264000
aagacgtgtt tccagaacga aaaagatacg gggagttagc aaagttagac aagattggaa 264060
tgggcatagg aacatgtatt ggtatatcga tcggtccagc ccaggcttgt gcggttaagg 264120
ttgttgtaca cgatggaagc tgttacgtgt gggattcggt gtcgccatcg gatcggagcc 264180
aaagcatacg ctgctttaaa gcagttactg ttgtggcgtc cccgctcaca actccatccc 264240
ttagtcgcaa taggttctcc agggaatcct cgcccgttaa ggtacgagga ttcgcgagcg 264300
cccaggcacc ccgtcccatc caatccccat ctgggtgaag acccgccatg acccgacaga 264360
tatctacctt ggcctcgaag aggtcttcgg cgtcaatccg ggccatttga atggcatggg 264420
```

cggagggaaa gggggatccc cccaaaagcc tccgctgaat ggattccaca caatcccccc 264480
ctatcaattc attatgggga tagggatagg ggactggggc tgcttgatta gcagctgctt 264540
cctgcataac aggaagagca gcttgttccc ccggaagcgg ctgattgacc gttgaggtac 264600
ttccagaacg ctgggaatcc tccaacatat cggttgtata agtaaacaac tccgtgctgg 264660
tggatccgtg aggaatcatg ctgctcccga tggagagacc cccatcggcg gcactgaata 264720
gtgctcgcac caggcaccca atggcccagg caagtccacc cgtgaggccc aaccctctaa 264780
gagcaaagga gagggcccga cccaaccata aatatgaaat caaggatgca aatgattgac 264840
ccaaggttgt attaaagttt cgatcggtta ataacaagct tgctyrsamm tygctttata 264900
ttgaaagagg tcttcctcct tgagaaggya gcctttctat catttagtgg ataactcctt 264960
gctccattcc gcttaaggtg gcgcgcctta gtcccataag cttatgccta tacctgcttt 265020
cccttgaaat aaacatagta aaccacttta aactcgcagt tagtcttggc ccaactctgc 265080
ccgggggttg gccttttaag gcttatttca cttctttttt tatttttctc ttattgctaa 265140
ttggaactcc ggctccggta acctcctgaa ccttatccat tacgtcaacc cttcttcaac 265200
aaggggaaga taggagggaa ttcccttttt caaggcccct aacctagtcc tggtttggtt 265260
ctccagtgga aagatttgag ataccttctc ctaccctata aagtaaggga gactgacact 265320
ttatgcttta tagaaagcga aatagtgata aggagttgcg gaaaagtccc gaaaaaagga 265380
agcgactttt cccggaagag caggggacag tctttagccc aggtaaaata aaacctggcc 265440
tccccttcca ccaaattgga ctattctctc atatggagtc taagaaagag atatccttgc 265500
gcaaggcgaa agatcgatgt ccttcagaat tctaaaagat caagattgcg tgcctttaga 265560
tccgtctttc ttgattcata atcaagacag aaaggtcgga tgtacttgtt caggtcaagg 265620
tctacttttg gtcattcttc tctctgaaaa atagaatatt gctcaaagaa ggtgactcat 265680
gtagtccctt ttcgagtatt atcttcgctg tggatgatca gtcggtgtgc gtatgaacga 265740
acggattcca cctctttatg ggctgtatat gccctgcttg tccccatacc cctttcagca 265800
agggttgacg tggtctcaag aatcttcttc cgacctctga ggtggtcgtc aagtcctcta 265860
gcctaggagt gagtcaataa aaggcaggat tctcgtcttt tttttttttt tctgagagag 265920
atgtcgtcct tcagttcctg atgaattgag tccgccatct atttcatagt aatcacgaac 265980
aagccctatg tgtcacaaag caccacgggt tctttacttt tttggtgggg gtggaggctt 266040
ttgtgcatta tagcacagcc gtgactacct ttaccttgat tgttgctgca tatcgcccgc 266100
ttgttctata gaaactaagt gcctatcaat tggttcaaag cggccggggt ctaactagaa 266160
cttcatttct cgatattgtt ggaattggtc tcgaagaagc gattgcccgc gaagccggta 266220
gccccttaag cttaggggaa tcggccttct ttagtaaaag ctttttcttg cttaatgctt 266280
tcctatctcg actgattccc cgtgatccac ctatgagatc gtttgcaccg gctttggatt 266340
caagaagatc ggccatagaa taaggaatgg gaagaggcga gactctcgat tcgctgctct 266400
acatttcgat aaagtggaat aagaaaggcc gtagtaccct aggcccgaca gaataatgaa 266460
gaaagaggcc gattggagaa gttttgtttg agaggctaag ggactagacc catcaaaagc 266520
agaaagaaaa tgcgtgacta agaaggagta accctagaac aagttgtcaa gacttgaccc 266580
ctgaagaact ggccaaaacg caggacattc cggaagttgg tcggtcaaga cgggcactcc 266640
cttcgctcct ttcgacctga tctcccacaa aaccaataca aagaaggtgg aagtgggtca 266700
ccccatataa gtaatatggg caaagtacgc gagatatgac caatagtttt tttttcaac 266760

-continued agagtccttc tttcagcaaa atcaaagctc cttagtgcaa tcgatttcag tatgccagtt 266820
taatttgaag agaaagaggg cagaaatcct tacaatctca gaaccaaaag gagagaaggt 266880
ggcgaaggat ccggattcac tttttttatt tgattcatac ccgcgtaaag gcttttcctg 266940
attaaggaag aagcctgaag gaaactctga actaagccca aaggctagat cccatccact 267000
tcgaacttta tgtttcaagc acgttggcat ttgattttca ccataaagag gaaccccggt 267060
aaaaaaaaag gcttgcttct ttcttgatgg ttgaacggaa tcaagcccaa gggcaatagc 267120
tgacattgtt gaattagctg acagaagaag cgaaaggtat tctgatttaa gttcatactc 267180
ctaagccctt attcttgaaa aaataggcat atgggtgatc tttttataag caaggagcta 267240
tctataggaa gatacttctt tgccaggtca gtctggtcgg aaagaagctt gcttacacct 267300
tgctttatat tgaaagaggt cttcctcctt gagaaggtag cctttctatc atttagtgga 267360
taactccttg ctccattccg cttaaggtgg cgcgccttag tcccataagc ttatgcctat 267420
acctgctttc ccttgaaata aacatagtaa accactttaa actcgcagtt agtcttggcc 267480
caactctgcc cgggggttgg ccttttaagg cttatttcac ttcttttttt atttttctct 267540
tattgctaat tggaactccg gctccggtaa cctcctgaac cttatccatt acgtcaaccc 267600
ttcttcaaca aggggaagat aggagggaat tccctttttc aaggccccta acctagtcct 267660
ggtttggttc tccagtggaa agatttgaga taccttctcc taccctataa agtaagggag 267720
actgacacta tgctttatag aaagcgaaat agtgataagg agttgcggaa aagtccccga 267780
aaaaaggaag cgacttttcc cggaagagca gaggggacag tctttggccc aggtaaaata 267840
aaacctggcc tccccttcca cccaagtgga ctattctctc cttatggagt ctaagaaaag 267900
agagatatcc ttgcgcaagg cgaaagatcg atgtccttca gaattctaaa aagatcaaga 267960
attgcgtgcc tttagatccc gtctttcttg attcataatc aagacgaaag gtcggatgta 268020
cttgttcagg tcaggtctac ttttggtcat tcttctctct gaaaaataga atattgctca 268080
aagaaggtga ctcgtagtcc cttttcgagt attatcttcg ctgtggatga tccagtcggt 268140
gtgcgtatga acgaacggat tccacctctt tatgggctat atgccctgct tgtcccccat 268200 accccttca gcaagggttg acgtggtctc caagaatctt cttccgacct ctgaggtggt 268260
ccgtcaagtc ctctagccta gggtagtcaa aataaaggca ggattctctc gtcttttatt 268320 tcccttttt ctgagagaga tgtcgtcctt ccagttcctg atgaattgag tccgccatct 268380
atttcatagt aatcacgaaa agcaagccct atgtgtcaca agcaggcacc acgggttctt 268440
tactttttgg tggggtggag ggcttttgtg cattatagca caggccgtga ctaccttttt 268500
accttgattg ttgctgcata tcgcccgctt gttctataga aaactaagtg cctatcaatt 268560
agttccaaga aagcggccgg ggtctaacta gaacttcatt ccaatctcga tattgttgga 268620
attggtctcg aagaagcgat tgcccgcgaa agccgtagcc ctttaattgc ttaggggaat 268680
cggccttctt tagtaaaagc tttttcttgc ttaatgcttt cctatctcga ctgattcccc 268740
gtgatccacc tatgagatcg tttgcaccgg ctttggattc aagaagatcg gccatagaat 268800
aaggaatggg aagagagcga gagactctcg attcgctgct ctacatttcg ataaagtgga 268860
ataagaaagg ccgtagtacc ctaggcccga cagaataatg agaagaaaga ggccgattgg 268920
agaagttttg tttgagaggc taagggacta gacccatcaa aaagcagaaa gaaaatgcgt 268980
gactaagaaa ggtaacccta gaacaagttg tcaaaagact tgacccctga agaactgacc 269040
caagcaagga cattccggaa gttggtcggt caagacgggc actttccctt cgctcctttc 269100
gacctgatct cccacaaaaa ccaatacaaa gaaggtggaa gtgggtcacc ccatataagt 269160
aatatgggca agtacgcgag atgtaaccaa tagatttcca tttttcaacg aagtccttct 269220
ttcagcaaaa tcgaagctcc ttagtgcaat cgatttcagt atgccggttt aatttgaaga 269280
gaaagagggc agaaatcctt acaatctcag aaccaaggag agaaggtggc gaaggatccg 269340
gattcacttt tttttatttg attcataccc gcgtaaaggc ttttcctgat taaggaagaa 269400
gcctagaagg cagaactctg aactaagccc aaaggctaga tcccatccca cttcgaactt 269460
tatgtttcaa gcacgttggc atttgatttt caccataaag agggaacccc ggtaaaaaaa 269520
aaaggcttgc ttctttcttg atggttgaac ggaatcaagc ccaagggcaa tagctgacat 269580
tgttgaatta gctgacagaa gaagcgaaag gtattctgat ttaagttcac ccaatactct 269640
aagcccttat tcttgaaaaa taggcatatg ggtgataagg aacttgaaac aggcatggac 269700
agaagtatgc ccctcctttt gatggtgaat gtcggaaatc ctcttcccgg atcacctttg 269760
atggacattc aaaaggatct gctaggctgt cttacatgtc ccaaaaagca agcaaaaggg 269820
ctcctttcct tccccatgtg gaagaagtgt acacacaggg ggcctctcga cctcagtatg 269880
aaaagcatga cggaatcgac ggtggtcaat cttccttctt ctttggcatc tcgactgggg 269940
agcatgaaaa caagactgga agagggctca ggtatcaacg tccttagccc gcattgatca 270000
atatcaataa gaatagcagt cgtataggta taggttagcg cttccttgct tgcatccttt 270060
cctctctttc ttaatgaaat agatatagat gtctcgactg ccgaatcctt atcctgcaaa 270120
caactcgatt ctgttgattc actgtccatt tgtccttaaa ccggatgttt ggtcaacgac 270180
tttgacagcc tttccttcac acaaggtttt taatccttct cccccgctta ggacagaaag 270240
gggaagtagc gagattacga ttccttggtg ggaaatcaac gaaggcagtc gctccagcag 270300
ctttagtact tagttaaggc cccagccctt cgcccggttc ttctccggct ccaccagcag 270360
cctttatcag ctgctatggt tcccttcccg caatgcgaat ctctatctct ttgcggctac 270420
agcctattct aataggaccc atattcaatc ttttaagtga cttctgaaga ctagctagct 270480
ctggacctac ctatattagc catgagcgat caccaagcgg agttgaaaga aaagagactt 270540
gacatgccaa aacttcgctc gcgagctcgg aacgaacgga gcggaaggga tcaaaagttc 270600
cagggagaaa aaaaagacga gcactttggg ccacggagcc aacgtttaag acaaggctaa 270660
aggaggccat acgtgtagta aactcctctc gttgtgaaga gagtgagtct atagagccta 270720
cgagccggcc gatccactgt agtggaatct tgtaggctag cgggcggtcc cgcgcggttt 270780
gcattagagg ggcccgcttt catcatcctt ccccagatct cttctattct gtgatctggg 270840
atgattagat gaggtttcca tgtgtgtgtc ttcgggagca tcttctcctg tgggatcata 270900
gccagttttt cactgcgagt ggttatctaa agtaaaggta aaggagggtg acagatcgat 270960
gagggcgctc ctgcttatcg gttataccct tcgacccctg ttttagcagc tagcgaaaag 271020
gcttcgttct gctgttcccc gtgagtggtc taaatcagct gcggtagtta aggtttggaa 271080
caaatgagcc taagggaacg aagttgtgag cctttagtaa tatatgaata agagatattc 271140
gaaataatca aacctgatgg ttcctgtcct gaaacgaagg atgcgaagaa agtactgccg 271200
cctgtcatca tgctcaatca gtaataagtt ggcttcacct ccggggatca gtccagcctt 271260
gtgaagggag aggactctgt tatcttgctt tcctcattcg catgagagac agacacattg 271320
tgcactcaag atgatgaatg ccacaagaga gatagaagaa agaagatctg tctcgattct 271380
atctctatct ttcgacatct catctctata atagagataa tagtgggtgg agaatccttg 271440
tgtattctac tggtatagaa tctttgtgga aggcgggaaa cttccgtcta gcggtcatgg 271500
gaaagccaaa acttgtatat aataagtcaa tactgggtcg gtcgagactc tttcttagtg 271560
aagtgggaag acagcaccga atcagacggg cacagaagaa gaagtggttt catccgaccg 271620
gcgagataat tcgatttcta gtcagctaac tgagaatcca atagagaaaa ttgcttttct 271680
aatgatttct cgatagaacg atttcttgtg agccacgaaa cagataatcc aagtcgtaag 271740
tacgaaccac tcaatggaga atctcaggcc aataagctac gactacgaaa cgaattggat 271800
cgggttcagc gcttgaaagc tatcgaagaa gagtcaattc aatgctcaag tcaaaggggg 271860
gagtccactt attcaataga agagaagcct atatctgccg accctacttc acttccaact 271920
agtgccttgc ctactgtctt tgaataatgc ttcattccag ggcgtaaaag aaagcttagt 271980
atagcaattg aattgacctt ttgtactgag gacgacctat gagatggttt gaaccggttc 272040
tcaaacctac tactatacga acagtcttct tcggctaagg ctggcaaatc caactatttt 272100
ttgttaaaaa gagatctcgg atcaagggct atcgacccga cagtgctccg ttggtccatt 272160
tagtggatcc tccccccaaa aacaagatca tattgagcag caacttcgag gaagatagca 272220
ttgggacatg ctattaccta tgtatggtga cgggtgtcat gccagagtct gtccgggtgg 272280
gctcaagcta aagcaggaga agagagttag ctttctgctg agtgagcccg aacaggagcg 272340
gacgcacact agatcagagc aagtttagct ggcccaatgg cgcagacacc tactaggatg 272400
aggcatagcg ggaatggaac ccacatctcg ttgagctgct ccagcaagca cccctttcgg 272460
aagctcaatt tgtaggaccg gggagaacac tcgcaggcgt gcaggcgttt tgagagagcg 272520
caaaactcta acttgagtaa gtgccagcca ggcaaaaggg ttagcctgaa gtggtggttt 272580
agccaaaggg agaacgtgca acggttggat tcagcacgct cttagaatag ctgttccaat 272640
ccgaacgcct atcccaacac ggagagctta tccactacat ctacataagg aatagtctag 272700
tccaatattt cttgtcctta aaatagaata tatgcaccgc tgctgatcct ttctaaatcc 272760
agcttcaacc gagcatacgt ctgccgcggg aacaggaaga acggaaattg acttttatgt 272820
tgaagtcttt ccccttggaa ggctgggggg cgccttgcac gtcttggaaa aataatgctt 272880
tgtatctgaa gttattggcc catggtcctc agtgaggaaa ggacctagaa cagagaagag 272940
ggccgatagg aagttaaaag caattcttat ttcttctttc tcgaaaacct gatgtgaggg 273000
ggcccactgg gatgtccata attgaagcat ttttcttcat cgactgtcgg tttttttacta 273060 ggtggccgat gtctttgatg ctttggtttt cgcaggaaag ggtaaggagc tttagccctt 273120
agcgtgtgag ctttgatgaa gacttgcatc actattcgtt tcctcgtggc tcgattgctc 273180
atttgcttct tcctttgggc atgaagtgtt tggtgaggcc tttcttcgcc tgttgaaaag 273240
ctagcccttg ctcaaagatc ttttttattt agcactagag ggagccctcc aatcttaaaa 273300
aaccgatgga atgcgatctc ataggcaatt tgctatgagg gctggacccc ctgcatctgt 273360
agaagaaagg ggaaactcaa tcatgaaact gaatttccaa gcggaaggat gagaaaaaaa 273420
aaatccacta ttgcaaaaaa tctttccttc ttttttagta agggtgtcag ccgcaagtat 273480
gagggggcat tccccatcat agagaaagta ggacaagttg cctaaaaact tcagcttctt 273540
tccaagctaa agatccaccc tgtcttccat gtggggtgtc taaagacata ccatccagac 273600
atggaagacc ctacaagagg cgttcccaag aggccaccgg aaaggatgac gactttcttg 273660
tcgaaggaat atgtgatggc ggaacgcaaa gttaatcgac gtggtgtccc agcttaaact 273720
tttgacttgg taaagtagaa ggttctaccg aagcagggaa gctctagggt tttgctaacc 273780
agtgtgaagt tgagttctat ctttccctag ttcatgcaag gctaaccttc gggtttttgc 273840
tttctggaaa aacctcttac cagatggttg ttcgctacag cctttaagtc tcgcctagcc 273900
tctcccgccg ttctccagga aactagcggc tcgcagctgt tcagccgctt ctctaggaga 273960
taggagatgt gccgctgact gggttcagga cacaaccatc gtccgaaccg tctgctacca 274020
agtccatggg ttggaaccca taagaaactg aaaaagcact tctgccggtc gacgaatgcg 274080
tgctccggtt gtagcagtgt tgaatgaacg gctgatttgg aaccagaccg ggtaacttta 274140
aaggtggtcc cgatgttaga ttctgaagaa ccgacggttc tattggtgac ccattcaaaa 274200
gaagctggcc gctttgactt tgattagcca atcgagtgcg gagggtgctg tgctcctctt 274260
catttgttcc cgttaacgac cacaaagccc ttaactgctc ctgctcgcta cttgcccact 274320
tgcccttttt tactactttg actagcgccc ggcaaaggaa tgattttttc ccaaagccga 274380
cttcctttat cgagcggctc tctctgttga cgataaaagc gatggtccgg gctgggctgt 274440
ctgaaataag cggtaatttt ggtcagtcct aatcctaata aataccacgt gaagcgcgtg 274500
atcacccaga ttcctaatgc cttaattatc ttatatatat aataacttat cgacgtcagc 274560
ccccttccta ctccagctaa tggaaaaatg cctttgaatg gtcgtaatcg tcgacaaccc 274620
aaccgacgtc caccataggc tcggcgagct gtcctcctag atttcccgaa ggtaatgcca 274680
gggccttttc agtactgacg actcttgatg ccaagaagga gaccaactag acgagacaga 274740
ccattgttca taggttggtt ataagcccgg agatcgaatc ttattcttcc cctttgagag 274800
ggattctcgt gccaaccata ggaagaagaa ctcggttact catcttggat cggattggat 274860
taatagcttt gtgctgatct acgaacgagc cttctatttg atttatacta tacttcttca 274920
agtctccatc atcccgatct ctctttccgg gtttgcctgt ccaaagaaaa cagaacctct 274980
tctagttcaa ggtcgaaatc ctcaaaccaa tcaaaatatg atttctagtt cactattctt 275040
atgaatagaa gttatgtctc attcatgtga tgagaaagct gagaatgaaa attagcaaat 275100
ttcacatcta cggcagattc tgtgccccaa atcatttaga cttattaaac taagcgggcg 275160
gggaaggtat gacccctccc ccattgaaca aaggggatcc gtagggcggg ctcactcaca 275220
tactggatag gtgactcgga attatagtgc tagttccgtt ccctcgggga agagaaagca 275280
cgaatctatt acaatcttag tagagaacag aggaggaata aaaacgttgg ttcttcgttc 275340
cgtccttgac ctatgatatg atcaatggct taatccatcc actggaccac ctggaattct 275400
taattaaacc tttacccgaa aaaggaaatt ggattttctt tttaaatctt cttttcttag 275460
attaagatat catcagaccg gtaagtttaa gaaggaatgc attgattttg tgatttcttc 275520
tttccgctct tcgcttagct acaccggctt acagatgccc atgtccttca tggatctagg 275580
agttcatacg aataatggct agcgggattt cgcattcaat cggagttgcc ttagttggtt 275640
tccgaaggga aggcactcaa gactctatat agtggtttat gcccttattt ggcttcaaga 275700
agcattagaa tcccttattt aacttgcggg gcaatcaagg aatagaagct accatcctag 275760
ggggaggatc tattatctct ctacccagct cctcgtctag cagccaagaa caagagagct 275820
acaacactca ggttgttgaa tgatttagga tcagatgaga aaaccaaccc taggagagag 275880
gctcaataag ataagttaat cggagttccc ggaaggaggt cccaccattt acttgactct 275940
tagaaccttt gttggttttg ggcaacgggg atcaacttcc aggacaggaa agggcgatcc 276000
atctatttat ttgactgaac ctagttcacg agaaagagtc ctagggatag accccttttgt 276060 tttgcaccga gaagaaatca atagaatcgt ctaacgaatc gtctgatact agatgaagag 276120
gtaccccgga aagcaggaat agaggaggca caggcctgcc attagaagaa accaaaggca 276180
attagttcat ctttgaatag gtagcccggt taaccagaca agctggaggg acttcctgcc 276240

-continued atacaggaaa ggaaagacct gggacctgta ctccccaact tgggaactca gcttatagcg 276300
aagggaagga gccgctttgt atgcgacact actatggtga agagtgaacc gagactcttt 276360
ttattgagat ttcccccggg tttctgcttc attcaagtct taattcaagt aaggacaagt 276420
ccttatcatc ccgatcggga tagacgggcc tgcctcgctg cgggtcagca cctcgggctc 276480
tctttctgct ttctgtctgt ctacaagcgg aaggcgttaa tgaaaatgtt caagtaaaat 276540
agccatcaaa tgcgaattga tgttgagatg gagtccttac ggaggtactt ctattatcag 276600
atgaggcaga atcagaacct ggagatcaac cccaaggact gactgcggga gcaaggattg 276660
gattggagac tgcatgactt gattcctctg ataagatcca tccatttagc agcaccttag 276720
gatggcatag ccttaaaagt gaagggcgag gttcaaacga ggaaaggctt acggtggata 276780
cctaggcacc cagagacgag gaagggcgta gtaatcgacg aaatgcttcg gggagttgaa 276840
aataagcata gatccggaga ttcccgaata gggcaacctt tcgaactgct gctgaatcca 276900
tgggcaggca agagacaacc tggcgaactg aaacatctta gtagccagag gaaaagaaag 276960
caaaagcgat tcccgtagta gcggcgagcg aaatgggagc agcctaaacc gtgaaaacgg 277020
ggttgtggga gagcaataca agcgtcgtgc tgctaggcga agcagcctga atgctgcacc 277080
ctagatggcg aaagtccagt agccgaaagc atcactagct tacgctctga cccgagtagc 277140
atggggcacg tggaatcccg tgtgaatcag caaggaccac cttgcaaggc taaatactcc 277200
tgggtgaccg atagcgaagt agtaccgtga gggaagggtg aaaagaaccc ccatcgggga 277260
gtgaaataga acatgaaacc gtaagctccc aagcagtggg aggagccagg gctctgaccg 277320
cgtgcctgtt gaagaatgag ccggcgactc ataggcagtg gcttggttaa gggaacccac 277380
cggagccgta gcgaaagcga gtcttcatag ggcaattgtc actgcttatg gacccgaacc 277440
tgggtgatct atccatgacc aggatgaagc ttgggtgaaa ctaagtggag gtccgaaccg 277500
actgatgttg aagaatcagc ggatgagttg tggttagggg tgaaatgcca ctcgaaccca 277560
gagctagctg gttctccccg aaatgcgttg aggcgcagca gttgactgga catctagggg 277620
taaagcactg tttcggtgcg ggccgcgaga gcggtaccaa atcgaggcaa actctgaata 277680
ctagatatga cctcaaaata acaggggtca aggtcggcta gtgagacgat gggggataag 277740
cttcatcgtc gagagggaaa cagcccggat caccagctaa ggcccctaaa tgaccgctca 277800
gtgataaagg aggtaggggt gcagagacag ccaggaggtt tgcctagaag cagccaccct 277860
tgaaagagtg cgtaatagct cactgatcga gcgctcttgc gccgaagatg aacggggcta 277920
agcgatctgc cgaagctgtg ggatgtcwac tcttttcttt gcagtatttt tattgtgatt 277980
atttttgagt attctatttt acgcgtcaca gcaattagga attgagaatc tatatcttta 278040
gatcaaagaa gggtctagct gttggaataa tggtatccat tgctatttga tcccttgttg 278100
ttagtaaaat tggtgaatta agcgaaggta cggaaagaga gggattcgaa ccctcggtaa 278160
acaaaagcct acatagcagt tccaatgcta cgccttcaac cactcggcca tctctcctac 278220
ataatgatta tgaccccaaa accgagtgaa tagcgagtca gtcataatcc atattccatt 278280
attggatagg tacgaccaat ccattttaac tttaactgaa aatttttcat caaagtcaaa 278340
gcaaagaacg atttttcttt ccttcgaggc tccggtatat atcctccttc cttggattag 278400
tactgggacg catatatcaa aagctcagtg tgaaatttga atgagatata tctttctttt 278460
ttcaaattca aaatttgagt aatagaggtt acacaaaatc ggagccagaa aaggaaaaag 278520
tggaatctgg aaaagtattc tctaagggta atgtaattga gtgaaattca ttttgtatcg 278580
tacaagaaag gaattccatt tgtgtatgtg ctcccgataa aaagaaataa ggtactctat 278640
tccattacat acatggatcg ggttgaaaaa ccagacccag tctctcttgg aatcctgaat 278700
atgccaataa ataattaatt gtactaatcc acatatgtct ctctcccatc aatcggtact 278760
agttgaagta atgaaaaaat cccctatttg tttgatgaga aatgcgaaac gaaaaagaaa 278820
aaaaaaaaag atcccccgtt gggaatgaaa ttatgctccc tgtcccccctt ttcacagaaa 278880 atggagagat gaattgatat atttattgaa tccgtcggga ctgacggggc tcgaacccgc 278940
agcttccgcc ttgacagggc ggtgctctga ccgattgaac tacaatccca ggaaaattag 279000
gtgtacagcc taaaatcaat ttagattcga accatttagt ttcgctgtgt tgtaacagag 279060
acacgaatga tatacttttt tattattatt atctaattat atataattat tagatatata 279120
aaatatagta gactcatagt gggctaattc atgaattgaa tcaaatgggg ccttttaatt 279180
taacaaattt gaacttaatt aaactaaaga gccacgctct ttaaacgccc tataagaaga 279240
agaaagaggc ttaagtcatc gcttccaatc cgataaaggg ctttttttatt ttccacgaaa 279300 gtccgtccct taaatttaag cagaggatat aaatatgaat atgaaaaaaa aaggtaaccg 279360
cctggagagt cgttttttag tttttaagtg gaatgttcat tatcataata agtagtcgat 279420
taggagaaca gctatctcac tacagagtat actcttcctc atctttcatt attcatattt 279480
tatgtcctgg gacatagata ttctagatac cccttctat tatgaatcgc caaagtcttc 279540
ctacttctcc attgttacaa tcagatccga aaaatgagaa atcaatcaaa atggacctga 279600
attgaatcat gactatataa gctattctga tattaagaga ttgaatatag atttcattcg 279660
tggaagcgga cttttgattt ccttggacca cgtaagaatt cgtcgtccga ttgaatctgc 279720
tttttcctgg atgctctata ggaatccatc gctattcctt tcctccaccg ataaaggttc 279780
atcccgagtc acaagagcaa tctcttttttt ttttttgaat tcttttttct tttcgttatg 279840
gtaatgcaat gcaagaggtc ggaaatctgg ttgtttctga tgatgaaaag agcttttatc 279900
ttatgtgaaa tttatgaaaa cccgaaatgt cggtaatgtt agaagacgac ctacggcatc 279960
tgatggtcag atgcctacgg tcggtatatc tttgaaagct cagacggaga gaataaacgg 280020
actcctcgag ggctacttaa gccactttag tgcaaaccag aaggactgga gctgttggat 280080
gttgctcagt cctgctataa cttaacaacc aaaaagctct gcgtcgaact tcagcccctt 280140
cgagttggcc acggggtaac agcctctgac gccccacacc attgcgacag gagggggctt 280200
gcccatcagc ctactttacc aagaggtggc aggagcgcaa cgaccttagc ccaaacctac 280260
ttaaacaacc taaaggcttg gcccggtctg aaagtagacc ttgtagaaaa gcggatagga 280320
aaggtagcct atagactcaa gcgaccagct cggtgaaaac gaaccccgta ttccatgtga 280380
gtcagttgac ttcgattaga ccagaccgcc ccagagagga acgtgcccac gagggcacca 280440
ccagatgttg tagataaacc tactaaagaa gaagttgatt atatcatagc tgaccgcacc 280500
atgggctagc ccatagaccc actgcacgag tggaatacta cttagtcaag tagaaaggcc 280560
aacctgagag cgaggcaagc cgggaacggg ctgagactta cgattcgaag accaagtcag 280620
agactactag acgtctcgca gagcgactct caacgaggac gttgagactg ttcgaaaaaa 280680
aaaagatttt ttggcttaat ccgcctttac taaagaaaaa agagtacact tgtactccgg 280740
ctaataaggg aaaggttttt ttttcaaatc caagtttgac tctgattaga tccttagcgc 280800
aagcgctaag taagcaagct accttatgta aaaaccgagg aaaataaaga aggtcaagta 280860
gaaaggaaca aggtcttacg gcacgatcac tatatctttt ctttttcttt ctctctcctc 280920
tatggaaaga ggggatgata cgtggcgtgg tatacctgat cgtttagtca acaagacgta 280980

-continued cgtaagtcga catagctcca tgtatatgtt ctttggagct agaaccaatc aatagaatga 281040
aatgaaataa tggtaagcct agggcgacga acatggctca agagtgtcta tacaaagccc 281100
ctctcttctt cactcaaaga ggcaatgcac cctttgtttg aatggtactt gattcataaa 281160
gaatgattct tttgaagttc tacggacttt ctaaaaaaaa atgccacgcg gagcgtgtca 281220
cgagatatat cgctctcgga cttcttacgg taaggccaat gcaccagcca gccagtgtgg 281280
tggcgaacac gctgtgctct aagctaagct gtttaccttg tagacggagg agatatagaa 281340
agtgtgccgt gcttgattca taagattcta taatcaatag caccagtata ttattttact 281400
tagcctgcct ctcccatgac tttccggacc aaccaacccg gatctgcctt cgcgagtctc 281460
tctgcatttt gggagcagag catgcagcaa aatcgagcaa tggatcttag aagaattcaa 281520
ctttgaagca cgactctttc tatttctgtg ctggcatttg acttgtctcc cttcctcttt 281580
caatcgaaag actcgacgca gatagctccg gtggcccccg tttctgcctc tatcaggcgg 281640
cgacagcccc cccctccaca cccacagcat agaggagctg ctccttaatc cgcactacaa 281700
ccaatccaaa ttctctccag agcgatatat gatgctaaac cgagaccgag atatagagag 281760
ggctgtcctt ttgttttgtt gtctcgaaga gagaaaagca ctcatatgaa tggtgctaat 281820
tcccatgttc tttctagtct cgtttggttt cgagagcctc cctctccccg tcccttactc 281880
gtcttttgaa agccgtcatc ctggatttga tttccgtatg ccggggaaag taccccaccc 281940
tcacctttct acatttatta ttatatagaa tttcctcggg tctctataaa acagaatgaa 282000
aagcccgggt ggaagcacaa acaaaaggag agagaaaaag tcgaaaagaa aggggggaag 282060
aagtctagtg ctagttctta ctaacacttc tttatctaac tttcattttt gagtgctttc 282120
tttgttctct tatttggatt gaaagaaaga aaaaacttcc ctttctttct cttctttatt 282180
tttgttttat cccttcgacg aatttcggct atgaccaatg ccccactagc taaataggcg 282240
taagaaaaag ctacctgaaa aaagagcaag gtgcaccttg aattgaactc gacgaattgc 282300
gttttgccag agagattttt ttagaaagat tctccattgg taattcaaaa atagaaagaa 282360
tataaataaa ggcgcatacg cgggaagggg cccccactac ttcttcattc agggggagg 282420
gggggagact agcctcatta cttcccactg ggcgagaggt gcacctaacc cacctaccca 282480
ctcatcaatc acggtgttca gctgacttgc actgatagac ccctattgta ttggaatttg 282540
gcgcccatct ttttactgtt gtcaatgaat ctcttccatg ttcgattcta ctctatgtta 282600
gaacatttct gtgaatgcta ttctgatcta agtggtctta ttctttgtcc cgtgctagga 282660
agcattactc ctcttttcat tccaaattca agaatacgac cgatacgatt aattggtctg 282720
tgcgcctctc ttattacttt tttgtatccc cctgttcttc ggatacaatt cgatccttct 282780
acggccaaat ctcaatttgt ggaaagcctt cgatggcttc cttatgaaaa catcaatttt 282840
tatttgggta tagacggtat ctctttattc ttcgtgatat tgaccacatt tctgatccct 282900
atttgcattt cagtgggttg gtctggtatg agaagttatg ggaaagagta tattacagca 282960
tttctaattc gtgaatttat aatgatcgcc gtgttctgca tgctggatct tctactattc 283020
tatgttcttc ccgaaagtgt gctaatccct atgttgtgcg gagctgagta tcttctattc 283080
gctgggataa agcctttcct ctgcaggggc cttgtgcagt aaaccccccta cgggcggtcg 283140
tccgtcgtcc taaagtagtc cccgcgaagc tttcgggaag aggggtagtc ttgtgtgtaa 283200
gcatagcatt tctggtcgaa cccgcccaac ccaactaaga agaaccgaac ctgacagaca 283260
catctttttc cttttgggag ggtactccga gtagtgggta cctcgtagga cctcgacccg 283320
cctactcggg tcttgtatgg atatgcagga aggggtgctc ctaggtgtgt gtaggggttg 283380
tgtttgttcg cgagaaagga ttcctcgtca agtaagtttg gggggtgtgg acacacttgc 283440
gcgaattcgg gtaacggcta caagggagaa atcgaaagga aactgtaccc gaccagggat 283500
ggacgtaaac tcgtaagcta ccgaaggtag ggataatcgt ccaggtctta ttgtgaaaga 283560
aaaaagccgc cccgccacag cagacgggtt gcttcctctg tcgtcgccgg ggagctcttg 283620
gcgaggagac cttaggataa gttgctaaaa caaaggggat gggaggatcg acccgttcag 283680
ataattccga agaaagactg ttggcagcag gtagagagat tttttttcc tcttcaaaac 283740
acaaggaaat gcgggcaggg tagagctcgg cagagggttc gagaataggg tagggtcctg 283800
tccttaagat tcagataaga aaagagttcc aaacctttat gcatgcacct ccgtacaagt 283860
gctgcataca agttccggcc aggatgattg agaaagattc aaccaatttg aaccgctcac 283920
atcacaatag tagtagcgta aaggccgtaa gtcgggggc ggccataaca taaggctatt 283980
actttcacac ctctctctct atctatagat agagagagat ccgctgcgtg agcaacccga 284040
ctgtgcctta catgtgctct acaggccgca ctccatcttt cttcccaacg agcccttttt 284100
ttgatttgga agacgggcat tgcgttcggt tcgaaaggca tggttttcag tatgtctcca 284160
gatagggccc ccactagtcc ggctagctag tgagcggttc tttcgggcgg gaagcaggcc 284220
gggccctacg ggcgggcatc tcccgcaacg caagcaccat tgttcgacac cacccgagaa 284280
gcaaaagatt ctagagtcca ggctgaaaat acatgcatag atagtggttt aatgccaagg 284340
ccgacgacgg aagctcggga cggagccgta tgaggcggaa gtctcacgta cggttctctg 284400
agaagggagt ggctacctac tggagcttcg accaagcacc accggtcaat tccgctttgg 284460
ggccacccct gactctacca ttattatagg ggtatggggt tcgagacaaa gaaagatcaa 284520
ggcagcatat cagttgttcc tttatacttt acttggatct gtttttatgc tattagctat 284580
tctgttgatt cttctccaaa caggaacaac cgatttacaa atctcattaa ccacagaatt 284640
tagtgagcgg cgccaaatct ttctatggat tgcttctttc gcctctttcg ccgtcaaagt 284700
gcctatggta ccagttcata tttggttacc cgaagctcat gtagaggcac ctacggcagg 284760
atccgtcatc ttggcaggaa ttgctttaaa attgggaacc tacgggtttt taagattttc 284820
aatacccatg tttcccgaag cgacactttg ttccactcct ttcatttata ctttaagcgc 284880
gattgctata atatatactt cctcgaccac tttaaggcag atcgatctta agaagatcat 284940
tgcttactcc tcagtagctc atatgaatct ggtgactatt ggtatgttta gtcgggcggc 285000
ggccgttagg tcacctattt tgagttatgg acacacaagg ccaaaacatg tgtgccgggc 285060
gcgcgaccca tcaacctact agcaatgggg gagaaagcat agcatgtcgc aataaaagct 285120
tgattcgagg cgtcagcaaa acactgccgt ctgttccaaa aacaaaagcc ccttagcgcc 285180
ccgggacggg agtgggggac ggccctacgc gcaggcaaca gcagcaccgg ctctacgaag 285240
tcagaatcga atctttctgt tggctttccc aattcattcg tgaataataa ttcaagggcg 285300
tgaagcgagt acttctagct gcttcgcctg cttcttatta tggcggctat gttttcgtgg 285360
cgaaaatgaa cgaaaagcga gatgagcgtg ctattttcaa atcgattgat agatagcctg 285420
atctgttctg atagatcgaa agagatagag agggaatctc tcaagaataa ggggaaatct 285480
cctatttcta tctattgatg agacaactat ctattcttga tccatcagaa agaaatcgat 285540
atgtatctga tggagtctac atcgtacgta gagcgcccaa gcttaggccg gctcagttct 285600
cttatccatc ggtccaatgc actgggctca tctcatggaa ggaaaagcca aaatgtagtt 285660
gtcttgttcg ccgcctcgac gcattccctt ctctccccgg tatcgtccca cacagaaaga 285720
aagagcgcag agccccggcc cgacctgtag gtccgctaac gtaaagcgag gagttgagcc 285780
tgaactggcg aaccgaagtc actttcggaa ccatacttcc tacagctaac atgtgtccag 285840
tccagcggga acgcgcagcg caaacgaacc tgagctgcta taccgaatcc cccgctgacc 285900
atcggggacc gagtggtaag gccatgatcc gcaggggaac agatcactca ttcttccatt 285960
ggggacaggt gcacgaacga caactccaaa cgtcacacat ccgccgccta cctaccgttt 286020
aggtggcacc agcgagatcc agctaaggta aggaacttcg tgtcgcggct gctccactcc 286080
gctgcgctgc ggtctcatga actgaacttc gttgccttcc cgcgcgcgaa gcgaatgggc 286140
gctgtgccgt gggtcagttt cggggtgggg agcgaagaga gaccagaaga atgattcatt 286200
tggatcgacg agctttttca gcccaaaaac taagaatcaa tggaatgtcc gtctatccat 286260
gaacatctat tctatctgta tatctagggg atctctctat acatatagat ttttttatg 286320
gaatgatatg atcggctagc cgtagccgca tatcagctac gctcaatgcg ggatttctgt 286380
tggatcagat cttttgggaa gcttttggac ctagcgaaaa gggctctaag ccttcacgca 286440
agcaagcgcg agaggagcgg agcacgaagc taccgcttcc cccgaccgac taaaatacaa 286500
cagtcgcgac ctactttgat tcaaaagaaa ggcgaagggt taggcaacaa gcaaacggct 286560
ttctatcata gttgcaaggg ttccaaacct taactactta agtaccaaag gctgctttcg 286620
gttggtttca taatggggct gttcactaca agctatcagc gctcagcgct gtcttagatt 286680
gaacgttgac ttatcttatt gccgttcaat ctctaaggcg ggtttccgct gagaacggaa 286740
tagtgttcgt gtccaaaggt gaacaaagcc ctagcttcta gagttcgctg cttttcccag 286800
gccggagaag ggcttatact gctcgccttt gtttgatatg ttcattcagt accaatacaa 286860
actaaaacta caccaaagtg gaagggccag tatagaagct agaagtagct agcctatagt 286920
agtcggccta accaaagcct cacgacaaca taaaattagc cttatgaatt gaatcttaag 286980
tagggggctt agcccgcccg cctaccaatc aaagaggctg agagtaagcg taagctcacc 287040
cggaagctcg aagagcttcc cttcattcgc ttcgcgggag ccgcacagca catagctgga 287100
agtcagaggg cccatactac ctgcctaacc cctcgctccg agggaccgta gatcggaaag 287160
cgccttctaa accaccccat tcatccaaaa gagaagggaa ggggcctatg tatttgcatg 287220
acccctgcag atttaaccct atctataccc ggagccactc ccctagcggt cctgccacca 287280
cgccgcagaa cgggagctcg tgtggaacct tttattctgg cgtaacagcg gtagaacgta 287340
acaaaatatt acggccgcct aacatagggg acggaggtac ggtaaactcg gccaaaatat 287400
gagacccgaa gggcccggcg cgcacaatcc tatcctatcc gaggccgagt ttaccccttg 287460
cacttcggac agccgtccgt agcatcataa ggaggacccc cctttcgagg tacaaaaaga 287520
gtacggtaca taggaggttg gtctttctca acgtggtgta tagcacgaaa aacctttcga 287580
tacaagatag ggccgttcac atgaaagaaa aaaatgaatc ctttcttatc ttctttcccg 287640
agagggaaag agaaagaggg tcttatggag ggaggggaaa ggcttgggcc tacctatccc 287700
gataggaccc cataaaagaa cgggagctgt tgagaggttc catattgccg agacgaagga 287760
cagcacttct gtacgtgatc gtagtatgtc acctcgtctc gtccccgctg catcgaagag 287820
tacctatgca ctatgttccg gttcactgat aaggaagata gcgttggggt gggggtctac 287880
gatgtgatac taaagtatga ccgggggaga tacatgctaa ctatgggtag gaagcaggaa 287940
ccattatgta aaaaatttcg gggggttaca gatctcttat actaccatcg atcgacagag 288000
cggaacgacc agaaaaagaa gttaagttag aaagccgtat gataggtggt aactatcttg 288060
tacggttcgg ggggtaatcg gcgtactccg atcagtgggg gggaatcttt ggctctatcg 288120
aacatacagg gaattggagg tagcattcta ccgatgtcaa gtcatggact ggtttcttca 288180 gcccttttc tatgtgttgg tgttctatat gaccgacata agactcgact tgttagatat 288240
tacggaggtt cagtgagcac catgccgaat ctctctacca ttttcttctc ttccactttg 288300
gccaatatga gttcacctgg tactagcagc tttatcgggg aatttctcat cttagtagga 288360
gctttccaaa gaaatagctt agtagccaca ttagcagcgc ttgggatgat tttaggcgcg 288420
gcctattccc tttggctata taatcgtgcg gtttctggga atttaaaacc cgatttcctc 288480
cataaattct ccgatccaaa tggcagagaa gtttccatat ttataccttt tcttgttgga 288540
ggggcgaccg tacgttaaac taccaaagaa actagggtaa accaatgtga tcatgacatt 288600
gtaggtgctt gcgatgggac ggatgcgact tccctcagtt ggtttgggtg gcatagcccg 288660
ttgcataagt cccccccttt ttttttttcc attttttag tctttaggga gccaaagctt 288720
gactttacta aactaataaa taaggctcgc gctaggcgct taccttttt ggctgagccc 288780 tatcttgctg ggtgagactg atagaaagaa aggacggggg gaaaccatgc atggtacttc 288840
tcgaccctgt ctccgaggga cagttgaact agcgactcat gaatgctgcc gggttggacg 288900
agccaataac tcgaaggcgt tcggtctgtt ttttgagcaa gaatcacagc cttaccttat 288960
cttcaccagg atacggactc caagttctta tggcagagca cgaggagatt tatcatcaat 289020
atgatgattg gaatggaaac cagaagcacg actggggtct tcgtggtcca agataatcaa 289080
accatcaata agagtaacgt aagcatgaga ctttttggta gtaccggtga accggatggc 289140
cgcggcgatg gaatctggga cggaggactt gtagtatctc tctagatctg gcaaaagcga 289200 aagacccccct aacataattc gaatggaggc tgaccgctga gcccactctg gcctcgcggg 289260
gcgggcccct gtggttgcga gctggagctg ccatagctta tggctatagc aatgggaggg 289320
ccccagcaga gagaaaagtc aggataacga gcgctccgcc cgccaagcgg gcggcaggag 289380
cagcgggcaa gtgcttggta agccaacagc ccagtgaacc gggcggggca ctcgaagaaa 289440
ggggggcaca ctgagcaagt acgagaaatt ggccccgctc cgctttctta aaagcaagga 289500
ccactacggg aggtcaaacc aaggatctat ggaagtgggg gctcgtcccc ggtcaatatt 289560
ggatcaaaca atagggggcc gtaacactga cctcttttt tttttgatt caatacaata 289620 ggggaaaaga tcgtacagtt ccctaccgag acaaactctc aacggatcct ccgcgcgctg 289680
ggaatacctc ttccgtgcgt ctttctcgtg gcgggaacag aacaacaggg aaagacccgg 289740
cccagggcga gctttattta tttaagagag aatggggagt gaatcgaaag gcttccgttt 289800
ccgttctttg ggggctttcg ggcccctctc gatcttttc gtagttgaga agggggaagg 289860
agtctaaatc aatggacatt aatgaaccat cattgatgga cgttgcacat gacacgatca 289920
attcgactca aggtccggcg ctaatagaag ttgcttactt tcctagtagc gaaggaaagg 289980
gcagggcttt tttcgtagta atagtgggcg ggtctcatga gatctatgcc ggccgtcgga 290040
atcaaacgaa ggtcgaagga ccattcgatt cattaagggg catagcggcg ccctcgcctg 290100
gcgccatttc cgggcctagc agcagacggg cgggccgtgc ctgaattcag accggaccag 290160
actcttcttt gtttgagctg ctcccaggca cgcagaccga agatctcact tgtcctggac 290220
aagtacgtag agatcttcgt gggaccgtgg agggagtctc aatcgatctt ttctaggatt 290280
ccttatcacg ccacacatgg agatctttcc attgatagat cagagggtcc cccttgaac 290340 aaattcttaa aggttaggtt actacctgct tctacggaag aggtttactt tataccgccc 290400
ggaggtcata tagatcggaa tccggagcga taagaacgaa agggttggtg tggccacagc 290460

-continued tacaactact ggcgcttcaa aaggcttaga ttctaagggc gctactgaaa gccttttttt 290520
aggtcctgta atagggaggt gtaagcctcg aaagcctttg gtacttcggt agggcgagca 290580
gcccttaaac caaaaaaaaa gggttggaac ccttccccta ttttttttat gcatttcatt 290640
ctctatttgg cccgcttcaa acaaaatgag aaaaaagggt ccggtcaata gcatagctct 290700
ttctttcccc ggtctccttt cgaaggagag gccttcgcat tcctaatccg gtagggtcgg 290760
acggctttct ttgccccagc ttggcgaatc gcatccccgc acaacgacat tctttgtttg 290820
tgcgcccctt accgttctcg ctcagtcttt caacggctgg gaaggcagtc gtagaaagga 290880
agcctatcgc cacgccgacc atcaaatacg agattgggcc ccttctcaaa gatttgatgg 290940
aatggcccac cccacccaag agcgcttatg tcatagggga actcatggct ggaaacaatc 291000
cttatggttt gttttgatat ccggtaggaa taataaaaaa aaagtccagg ttggttggtg 291060
agcctagtga taggagacta tctagcttgg ttcggagagc acttgttggg ttaaatattt 291120
tttggttgct aaatgttacg gcctaaatgc tgaactattg accctacttg ttcggatggg 291180
tgttcacccc aaagtgttcc cggaccgcat gcatacatcc gtaagtaact tagtgcaaca 291240
tggaaaattt cattgagagg aatcagcaaa gaaaagaaaa acgggtcaac aacatcaaca 291300
tgtgtatttg agagattgtc ctcgggctga ggagtgtcca catgagttcg ttgaggtgtt 291360
tacacaggcc tgtggtcctc ttttctattc tgtcgagagt tcggattgct ccacctaagt 291420
agaacgaaaa gaaggaattg gaaaagaaag gggggagcta ttgtgaagcc tagtaaaggc 291480
ggaagcggca aatcgcttat accgagttcc ccaacagcag cttagcttag tagcaacact 291540
ctttctactg gcgtggcgct gctggatgct tctgatcaat agaacacgaa gaggaggaaa 291600
aaaaaagctt atgatgagca tctatttgag tcgatcattt ccaagatcta attccagttt 291660
tttcttatgt agtggaaacg ccttacaatc tgaagtttta cgcttaaggg aagaaatgtt 291720
cttggtggat gcaggacttg ggacccccag aatttgtatg caagatgagc ctacaggagt 291780
gccaatcaac cgagccacca ggtttgagaa taaggtggga ttcctggatc tagtggccgg 291840
tgaatcactg atcaaagaga agattttgga gagattcttc atcgatctag tggccggtga 291900
atcactgatc aaagagcgag cagccgccag gtttaatgat ttggtgggat ctacagatgt 291960
agtggctggt gaaccgcttc ttcttcttcc acgaagattc agacaaaacc gagcttggat 292020
ggaactgaac aagatttggc gaacgaatac aaaggtcaaa ggctttatta ttgagaaagt 292080
aaaaggaggt tattcagtag ccatcgcagg tttcattact tttcttccat tccgtcgcag 292140
aaggaaaagg atatcgaatg atcgattcac cattgagaac attaacccca aaaagacgaa 292200
tattgtggtg ttctaacagc ggcagatcaa acaagaactg gatgagcgaa atccgctgac 292260
aaaaaaaaag agaacttttt gaattccgat gcctagcgtc ccctgataac ctaggattag 292320
tggtaatagg gctgatgtgg tatctcggaa actgggattt gatggtatct gtagagcgga 292380
tcccatgggc ttctcgggtg gaggttggtt gaagatgatg tgatgcaagt gaacgtctac 292440
gaaaaagctg tcgtaaagtt tcgttcttcg ttccgtcgtc gatcaatcta tcactcaatc 292500
acaggccgct ctgtcattgt ctgatttttg gttgtctgat cacactcgaa attatgtatc 292560
tacttatcgt atttttaccc ctgctcggta gttttgtagc aggttgtttc ggacgttttc 292620
taggaaaaga aggaaccgct ataataacca ctacgtgcgt ttcattctct tcgatcttct 292680
ctttgattgc tttttatgaa gtcgcaccgg gagctagtgc ttgctatcta agaattgctc 292740
catggatctc atcggaaatg tttgatgctt cttggggctt ctttggcgac cgtgaagtca 292800
ccggatgaat tgccgagtca atagatcaga tccggacgcg gctgttgctc cgcggcgata 292860
cggactcgac ccgctcctac ccactccggg gtaccatagc atgtcgggaa taagggggga 292920
catactggac gtaaccactc ccttggttgg gggctgtgcc gccctgcctt tcgatcgata 292980
cacagttgag gaggccgatc acgaacgcta caggtgtggg agcgatcctg gtcagggaag 293040
gctaagvcgv hdcntcgtat atgggtagca agagggcgct tatgccccga cggtgdgdch 293100
ctcttggatt tbttgvaata tgagahggva tdccadddbb cytctckkgt cgtgvtctgt 293160
atcgwctgwa tmacwcwttt ggtctagtcg gtggaaccgg tgaaccacgc gagctggtta 293220
gatgcgtggg gcagagggct cgtagtaccc cctttgattg atccagcctt ttcttcgctt 293280
cggtagtgaa tcacctacta aaggggcagg cctgcacgcc ttatttgaga ctactaaggc 293340
aggcggtgga ctctttcatt aggtaaggga agaaggggcc taagcacggc agatgccgta 293400
cacttgagtg gcaaaggaaa gcgagacctt acctttttc caggcctgtt cggacatacg 293460
gttcccgcgg aagatcaagt tggtgagccg tgtgatggga aaccttcccg cacggttcgg 293520
agagcactga attagaatga gaggtttacc accacatcat tgcatgcaag gggagctcgc 293580
tcgattcgca gattggtccg actcgtaatt cacttctgac cccgtgttcg atagcccgac 293640
cgtagtgatg ttaattgtgg ttacattcat aagtagcttg gtccatcttt attccatttc 293700
atatatgtct gaggatccgc atagccctcg atttatgtgt tatttatcca ttcctacttt 293760
ttttatgcca atgttggtga ctggagataa ctctcttcaa ttattcctgg gatgggaggg 293820
agtaggtctt gcttcatatt tgttaattca tttctggttt acacgacttc aggcagataa 293880
agcagctata aaagctatgc ttgtcaatcg agtaggtgat tttggattag ctcctgggat 293940
tttgggttgt tttactctat ttcaaacagt agacttttga gccantttta ctacttyttt 294000
tttycarbrs agtctcyscy wtrwratwwk cymaagtrts rcrtggtmkc cgatatgtaa 294060
ttanactttt tattggtgct gttgggaaat ctgcacagat aggatcgcat acttggtcac 294120
ctgatgctat ggagggtccc actccagtat ccgctttgat tcatgcagct actatggtaa 294180
cagctggcgt tttcatgata gcaaggtgct ccccttttatt tgaataccca cctacggctt 294240
tgattgttat tacttttgca ggagctatga cgtcattcct tgcggcaacc actggaatat 294300
tacagaatga tctaaagagg gtcatagctt attcaacttg cagtcaatta ggctatatga 294360
tctttgcttc gnraatcwgg cgatsntckg ataygktgdb bccchtaatg anthacgcct 294420
tttcaaagca ttactattcc tgagtgcagg ttcggtgatt catgccatgt cggatgagca 294480
agatatgcgg aagatggggg gcttgcctcc tcgttccctt tacctatgcc atgatgctca 294540
tgggcagctt atctctaatt ggatttcctt ttctaactgg attttattcc aaagatgtga 294600
tcttagagct cgcttacact aagtatacca tcagtgggaa ctttgctttc tggttgggaa 294660
gtgtctctgt ccttttcact tcttattact cctttcgttc actttttcta acatttctag 294720
taccaactaa ttcattcggg cgagacatct tacgatgtca tgatgcgcca ttcctatggc 294780
cattccttta atacttctgg ctctcaggag tctctttgta ggatacttgg ccaaagtgtg 294840
acctgttagc ccataagtaa gtactgtgac gaagcggctg ttgctcaccc gacacgatcg 294900
tacgaggtca caattcaccc gacacgatca tccggggtga acaagaattg gggatcggat 294960
gcgggcgaaa ttcccgccaa tggctgagat gttcagtcga ctccctcccc tttgtggggt 295020
cccgacccta cgagtgagca gaaagggagg aggaaagagg ccctggtgaa ccgtcataat 295080
tagtgaacaa gtgtaagctt cgctgcccga cagtatggag tactgaccac accgagggac 295140
aggccctgaa gcgaaggacg ggaacgagcg gaatcaatgt gttccaattt ctggccttgc 295200
accgaccatc caatggacca tggactaaac ggccactgcc tgaaaggact atgtccaggg 295260
gaccgccgcc ccacaaggta catctcgcgc ctatgggccg ctataactat caagaagaca 295320
ctcgaaactg gaaggataaa caaacccacc cggtggactg ccgagctaca agtcctacga 295380
cacaggagcg ggattctcta aaagccaagg tcgtgggtgg ccaagagggc ccacttggag 295440
acttgggatc tcagcaggaa atgcgaaggt tgcttaaagc cggccggcca aagagaatca 295500
actagtttag ttctgatctg agtaggctca taatagggaa taccctaacc ctgggaaccg 295560
gggcctggcc atccttcgtt tgcggtcgac gttccggctt tgtccgtcga cagctgaatg 295620
tttcgatctg gttcgattca tgatcgcatc tgcaaacctt atcccgtggg ctttagcgga 295680
cgttttcatt cttcacccgg tccttagtag cctttccaaa gtcaacctaa ccggttacct 295740
ttggaaaggc gctaaataaa ccttcgcctt tacgcctttc tatataattg aagaaaatta 295800
gatagttgta tatagaatta gccagatcgt ctgaagcatg aacagaatcg cctttgttct 295860
gaaggcctag cgagttcctt ttttttcaaa ggcggtcctt ttctttcctc ggaccgatga 295920
ctcgcttgtt cagtactgct aactattata ggaggatgcc gcccctcagg actaccagta 295980
gcttcggttg ttgaatctcg tgcaagttag gttgtggttg tattggctgc aagcggaacg 296040
taggcgcttt aggtgtgtgt tgaccatgca ctctcgcttc gtgtaatgtc gtatgtatga 296100
tagaggtagt gtggtgattg acctcaatgc taatggtgat ccccaaggtt caacgaatga 296160
atgaagctat gatcgtaccc ggatagagat gatggtcttc ctctgatgtc tccaagccgg 296220
ccataataga atagataggc gaagcagtca atagcagtct gttctcgcct atcgatagat 296280
agcaggttgc ttccaagctc aaaccatttg aaagggaatt gctacttttt tcttgttatt 296340
gatagagtgg tattctccgc ccctgtcaaa taaagtagag gggagaactg gaagagaaag 296400
gaaaagagca aaggattgac aagtctaatg gggaagaatg gctgacacgt tgactgcctt 296460
cgatactaga aaaaaaccaa gcggtctaac ctaaccccag ggcggacccc aaccgaaagg 296520
cgctagacgg actaagggca agcgagataa agaaagcagc tggccctatg tgtaaaacct 296580
tgccgcggga gagtctttct ccaatgagaa taaagaaagt tttgggcaag acaagaaagg 296640
aactcgccct ttgacaccaa gggataagag ctgattgctg gcgatgactt ggtaaaggga 296700
atctatgaga gaaggttctc gaaccgggtt acgaccgaat agagcgcgga accaacgagt 296760
tcagtcgaac aaggtaacga gtctaaggga aggatcaagc ttgaaaggaa tggacgggcg 296820
taggcttaat agtgaacgca gaccccctgc ttatagatat gagatcaatg acttaaaaaa 296880
aagaaagatg caggaaagga aaatgaaaga agaaatccaa atttgctttg ggagtgtgag 296940
ataggcagac ggggagtacg cagccgaaca accgctgggg tttccagcag tgatagctga 297000
actaatcaga tgggccgccc caaacctgga gctgacattt aaatcggaaa tcaacatcgg 297060
gtcccggcta tccgaaaacg cagactgaag cggaagatca caaaatgcaa cacaacaagg 297120
ggtcgttaga ccgtagcttg cgcgaaggaa gaagctaatc aatcagaatt gagacaggga 297180
ggagaaagag attttcgagc ctgcaagcag caagcaacaa cggcttttca gcccttgcgc 297240
gctagcttgt agtttagggg tatagtaggg tgcccctttc tcaaactttt ctataatata 297300
aggtaatttg gaaccctagt tttggagttt tccccaacca acctatacct tactaataaa 297360
aggggcttcc ctttttcagc tgcattgcac tgccgcataa acaatggatc cgctgggctg 297420
gatgagcaac cttctatctg gcctctgtac caatagtcga gtggcttgca actttcaatc 297480
agaaaaggaa gattgagcaa ggcaaaggag aaagaagttg tcccctcttc tctggtaacc 297540
cgccgccgca tatgtagaaa agaaggagcg gagaaggaag aacaaccctt tgactttggc 297600

```
acatgaggtg gcgggtttgg ctaggtaaca taatggaaat gtatcggact gcaaatcctg 297660
gaatgacggt tcgaccccgt ccttggcctc gaggagtggt gagcagcacg gaactttaat 297720
caatcaaatg gcatagtatt agggtaggag gctttccttt gttatagaaa tccacagaca 297780
acattctgga acttccaaac caaagaaatg caagatgaga aggagctttt accttacgct 297840
tcaatagaat gaattcggta agggtagaat aggccctatg gtcgatcgaa ggtgctgtgc 297900
cacttgaact caaatctatc tgaccttcaa tccatctttg tccagccagc tcataacaaa 297960
atgttagacc aatctcaggg ctgacacaac cgaattggtt ggggaaaagg aaaccccagc 298020
gaccaagcac tcccgccccc aaaagcggag accgaagaac cgccaggttg tcgaggaccc 298080
gtctgaagag gaggcgggcg cccbctaagd bbavcrcsmt wcccgywwry sgtctkyykc 298140
ttrwacamaw aaccvhvhct ayvmkaaawa gayavcgcty athnnncbcc ttcadhbtvc 298200
aatvadaaag gttggggatg gctggaacca atcagaagtg caaatcgcgc aagcgaagcc 298260
gggaaacgga ccgcagcgca acgactagga ctcgtgtcgg aggagttttg agcgtgagct 298320
aacactcatg cagcggcaag gacccgcaac tctcgaaggg gccaccaacc gcccgaatca 298380
ctgtagcaaa ccctctcttt actcaatgga tagcgcttat tctctttcaa ttaacaaaat 298440
gtgaaatggg rasaaagaaa aaaaagaggt ctttatttaa gaggctttgc accggaaata 298500
gghmtaatgc agatccagaa gaatggtctg ggctttagaa aagatgaaga tggaaggggt 298560
aaagagacag tcttttgaac aaccaagctg acataaggat tctagctcgc gcccacttag 298620
agcagatgga gattctcgga cggggaaaag cggcactcga catctattaa acaagaccaa 298680
gaacaaagcc ataccatgcc ctcgggagaa agtagtgatg attgccatga atgctgccct 298740
cgaggacgtg tacaagaagg tctttgccga ttcctatcaa catggtgcat ctcttagtag 298800
aggggcgtga aaagtggaga ctttgaccga atgaataggg atcaattgat agccattttc 298860
ttgaggaaga gaatccagga tgaacgcttt ttcattcgct atgcgctgac tggatgcgta 298920
ctcgcgtgat caatcgatgg acggggaatt gcgtgaatga tgagaccggc ctaacctaaa 298980
gtcaaggctc ttccctctct tgatggcgaa tcttgattga ctgacactag aaaccgattc 299040
ggagaaagaa gaagcatggc atgagatagg cggcggatca atttccgata gcgaattact 299100
tgactcgatg gatggatgga ggagagccct ccaactcaag cacgaaatca atgttgagtc 299160
aacaatcatc gagagggtac caccaagcga gatcgagacc agccccttgt ataggtatag 299220
ggttccaaac ctgcccttct tcaaatatcc cataaatcta aataaagtag ggacttcaaa 299280
gcttgactaa caagcgagaa agttgacttt gagaaagaaa ggggcgccct agctgcaatc 299340
aaaagagcgc taacgagcaa gaaagggccc ttactataga tagggcgtta gcgctttact 299400
aataacatat atagggctta ctttttttcag cttgatcgga atcgattcta tgattgaata 299460
gcagaagtgc tacttagtag tagaaactcg gagagacaga cagagagggg actctttcat 299520
acctgctaac tcctaggatg agaagtaggt cccttgtttt tggcaggaag agttccagcc 299580
tttgttgccc ctcggtagag tgagtctact tagcgaactg gcaggacgcg gagatctatt 299640
gatcaatatg aatctcgaga gtggatggtt gatcgccgcc tccttgtcct ggaggctctc 299700
cggccgggga ggggcttgct atcgtaacct tttctcccgg tgtatgtgaa aaagagtgac 299760
gaactcattt ttcttcggtc ataggttggt ccaaagaacg agagtcggct tccttaatta 299820
agtccgttgt tcctcagtag ctcagtggta gagcggtcgg ctgttaaccg attggtcgta 299880
ggttcgaatc ctacttgggg agatttttga gttatcgctt ttctgaccta gcgacccctg 299940
```

```
tccttctcct tagtttctaa actagcagaa tcgtgggaca tcaaaagcgg taagttgatt 300000
gttggttttt attcctcact ctcgtatagg ttaacttggt tcgttccatt cttagggata 300060
aaaaggatcc actggaaaga ctggagtagt atcttcatta gccggaagga attagtctcc 300120
actagcgtca ttcgaagaac gaacaagaaa agggttacag tttaggtagg atagatggat 300180
gtggcccaat ggctaaagct ctgccagctt cttgtagact gaactctctt taggctccga 300240
gttctttttt gggggatgg tctaatttac tagtggcaac gaagttcttg gtaattagca 300300
agggggaagg aggatctcca ctcatttcat tcattcagtg cctgcggtga ggcgcgaccc 300360
acaacaaacg aagggggaaa gcttgctttg cttgctgtag ccctatttta gtagattagg 300420
cttggtaagc gtaagctata tttaagtagg ctcgcagctt cgctcagcag aagagcctga 300480
ctttttatta tattagtaaa gcgctagcgc ccaacctata caagggcttt gaagggatag 300540
gggaagaaaa gaaaacaaag agggtcattt tcttttagga acatggctcg ttcattcact 300600
tgctcatgaa ctcgcagctt cgccagaagc gacgaggggg ggctggggaa ggccgacgac 300660
tacatgaggg ggaagctttc gtagaagctt taccccttgc tttacagaga tagttatgaa 300720
ctgactaaat gactagattc tcccggaacg ctagctaagc taatcgtctt agttcccttc 300780
aattaaatca ataaggcttt ttgattgatt cagggcgacg ccccccttct tagaattaga 300840
acccattgag gggggcctcg gcccgggaag gggagagtgg ccgagtggtc aaaagcggca 300900
gactgtaaat ctgttgaagt ttttctacgt aggttcgaat cctgcctctc ccacttgttt 300960
gttgtagact tcagagaaga gaaaagaggc attcgtcagc gtaggaaggc caaccgagcg 301020
aagctctttc ttttttttgg ccgtgccgtg aagtgaaatt gtatcgtatg ttagttagag 301080
aggttggcga actactacga tctatagatt tcccatctat atccaatccc aacgagaata 301140
gaagcgagtc gcttccggcc tgtcttgtag tcgtagtctt ttagcttatg tagtcgtcgg 301200
ccttcctaca cgcgtgcgtc cgccagaatg cctccttggt tcgggacgaa gccaagccga 301260
tacatacgat aggcgaagga aagacccccca tttcatagcg cctggggaac gcaagtttga 301320
tcgaggattg gagaggagag gtggaagaaa gggctcggga tggatttagg agtctttgtg 301380
cgagccgtat gcggtgagag tcgcacgtac ggtaacgagg ggggttcgcg tctatacgtg 301440
tagtgtggtg cttaggccta cccaccctat ttgttccatg atctatgggt ctactggagc 301500
tacccacttc gatcaattag ccaagatttt gaccggatac gaaatcactg gtgctcgatc 301560
tagtggtatt tttatgggga ttctatttat cgctgtagga tccctattca agatcactgc 301620
agttcctttt cgggcggctg taggacggac ggccgcctat aggtggtagg gtagggtggg 301680
tggtaccgct cagattgcgg ccaatcttcc taaccgcgcg cgggccgggc ttagagcgcg 301740
tgaaactcat cactacctcg taagggcgtt gagaccatag catgttacac gaaagcgccg 301800
ctttctctgt agtgttgtca cacagctgcc cgcctagaag agcaactcgc tctgtagtgt 301860
tgtcacacaa gataagcacg ccgcccgcct gctggccggg cgaatcgaag ttatcttccg 301920
gtcaactgtc cacccagtca agtgcaaaaa acacagtaga atcacgcaac gcacgctgct 301980
ggtgtgcttc ctgctcgcga ggaaagaaag aagagcgaca gggttcagtt cagatttgac 302040
tgtttgcagc atgggagcag attccccaaa aaatccctgg gaacaatgaa aaaaaaaaga 302100
tatctcggta acgaaaacta tagggggctg tattggcgag atccaacggt gaacagctgc 302160
ccaaaagaaa gaccgcctgg aagtccgagg acctttagta ctgtactcta cccccgaacc 302220
agcagccttc gcgccaagca agaccgccct tgtccctttc ctttctccat tccgcctcct 302280
tctttgcttt gttccaatag agtctaaggc taagtggttc gtatgcctac tttacctact 302340
```

tgacgaaagg gaacgaactt tgtttcattt ccgggtttat ggattggatt cagtcagcct 302400
cacgacataa tcagagtgag gctttggtta ccggcaaacg cttctccaaa ggcgaccctc 302460
tcgagtttcc ggctctttcc tagattgaag tagcctttcg tcgccctacc aaacgaaaga 302520
agtaactatc aaacagctcg ccctattgaa gtaccaaagg tgcgctcagc ctggtgacta 302580
ggaaatgggt ttgcccttga attgaagtga tgaggtcgga aagagggaag tagggctcct 302640
attgactaaa ggttggttct tcgctttcct ttagaatgaa agttgctatg aagcccctac 302700
tacttacttt gtttgattca aaaggcgaac agcccccca actagttgta tggggtgggg 302760
tgcttgtgaa aagctgcttt ggatatgagt aattcctaaa aaaaggcaaa gtccggtatt 302820
tgacgaagat ctttctatca atagatagga atgagtgttc gatatagggg ataggatcca 302880
tctgctcttt atctctccat ttttttaga gagagcagat ataacgatag aaaaaagaat 302940
cgggagatga taaaggatag atagacatct aaagggatgt ctattctatt cctctttttt 303000
tttttagaaa tatatatata tatcgtttat ctatctcttg tctatctatc attgattctc 303060
aagtcaaaag acttcgtttt tgggttcccc gaagccccga atggaatgga tcgtttctgc 303120
caacgaaatg aacgcggagc ccgttccgaa tgcttctacg atccggaagt tctcgcgaag 303180
agaataagat gctgctcccc ttccctcttt cttttcccgc tttgctaatc ttcccctcta 303240
acgcgggccg ggcggcgacg ggcgcgggag gaagaaacct aagagaagac gctcgtctct 303300
taggtccttt ttttcagtgc aacacaggaa agcgccctct ttttgtcatc cctgcagctt 303360
tccagatttt gtattgaacg catggcgtag ctaggaccct tccaattctg tttgagccta 303420
tgttcaagcc aaaaccaccc ccaatttgac taaggctgga aagaatgccc accaagttca 303480
gataagggaa tgctttcccc aaccattaaa ggaaaggctc gacgaaggga gggaggtgcg 303540
gcgggggaag gaaaacgctt tcggagatca agattttttt ttcatcgaaa acgaagaagg 303600
ccgaggatgg cctacggtgc gtcttatctg aagggaacac gctttttga ccgccgtggt 303660 atgattgccg ggccctctcc tcgttccgcc cttcctattg ggatagcagc cttcgggctt 303720
tgcctgccct ttataataaa aaattccggc tcggcccggg aaagcgctgg caacaacaga 303780
aaggaagggg tccatgtagc tgctgtgtcc gcccccttct tagtcaatgg ggcacagcag 303840
gttcggcatc tactacaaaa gagagaatcc acttcagata accacgtctc tgctaggcag 303900
cgtgtggaat ggccgagagc ggaccttttt ggatatataa tccaagtcga gagtagagtt 303960
agaggaaaag ccgtctgatg gaaaactact ttcacgttcg gttcagagag cacttttttc 304020
gttgagaatt cctcgttccc tttcgtgtga attccccagc ggcgaattca aaacttgtgg 304080
ggccctatct attccatctc tcgagccccg aagaaaaccc cctacccttc ggactccata 304140
tatcttttga ctctatatat gtgggcacct gatatctatg agggttcacc caccccggtt 304200
acagcattcc tttctattgc gcctaaaatc tctatttctg ctaatatttc acgtgtttct 304260
atttatggtt cttatggagc tacattgcaa caaatcttct ttttctgcag cattgcttct 304320
atgatcttag gagcactggc cgccatggcc caaacgaaag taaaaagact tctagctcat 304380
agttcaattg gacatgtagg ttatattcgt actggtttct catgtggaac catagaagga 304440
attcaatcac tactaattgg tatctttatt tatgcatcaa tgacgataga tgcattcgcc 304500
atagttttag cattacggca aacccgtgtc aaatatatag cagatttggg cgctctagcc 304560
aaaacgaatc ctattttggc tattaccttc tccattacta tgttctcata cgcaggaata 304620
cccccgttag ccggcttttg tagcaaattc tatttgttct tcgccgcttt gggttgtggg 304680
gcttacttcc tagccccagt gggagtagtg actagcgtta taggttgttg ggcggccgga 304740
aggttgccac gagtaagtaa gtttggggga ccgaaggcag ttctccgtgc accggacacg 304800
tagcttaccg aatcagttgc gacacggatg ggaatgcatg ctacgaaaga tagggtcgag 304860
tctgatacat caaccgtcta ctcaatatcc ttgtacgagt ccacaatgac tacacgagat 304920
gaaccttggt ttggtgaatt gaagttggcc ttaggtgtaa taggactccc agttactgcg 304980
cgcgatcgta tactgaggtg ctccccgccg gttgttggaa cgacgcgagc cgggccgggt 305040
ctcgattcag aaagatgaag ggcccaaaag tctaaatagg gggttacaaa ttccccatct 305100
cattgggggc ggaaaacgaa tcgacatctc gatgtgatac agccctttcg attttagttg 305160
ggaaagaacg gcgaagtcca tccgaaccgt ccaatgaaga ataagaggag agcaaagcgc 305220
caatggcgcg cgaagcgcat gcggaacggg cacggagaaa aagaagtgtg gaggagaagc 305280
agccgagctc attcccttcg cttcctgggc ccaaagcagt gcagtctttc ctggccaaat 305340
caaggatttg gggcttcttg ctacgctact taactatata aatccatttt ttttagtaat 305400
atatatgaat agaaagatag atccatccat ctatcctatc cgatttcgat tttgatatct 305460
aaaaaagaat cgatttcatt caacgtttga ttcaaagaac tgcgcttagc ccccccgctc 305520
atgaaacggc tctgctgcaa tggatggcag agggtccgta gtacccgaag cactggagtg 305580
atccagtagc cgggaagggg cctagaagtg cctactacta caccacacta cacttggctc 305640
tacacattta cagagctaac ccctgtccag tgcctggcag agctaagggg gcttcaatcc 305700
ttactcttta tccccatctt cgcccaggct aacggggcct tacttattca ggggggagag 305760
tggagcctcg aaaagcactg ttgagaggaa gatccttggc cctcttcat tctctacagg 305820 gttccaaccc tttcttcaac ataggtgaca acgagccagg cagagatgga agagatcaaa 305880
gacgggaata agaagcaagc tcgccttcct ttttgatcat tttgatagag ggggatgaag 305940
aaagtggaca aaacagactc gcatttctca tcgaacaaat acaggaaagg aatcatattg 306000
aaaacgctcc taacccaacc ccttccttcg tagagcccgt gtattgtaag tgatccgaac 306060
ctgcccggag cgagcctccc atagaggcaa gtgaagttgg tgagccgtat gatgggcaac 306120
tatctcctgc ggttcggaga ggactcagct gttagttagt accccccttgg tttcggggtg 306180 gaccttttca ctctatttta ttatatacgc ttagcgaaaa gaatgttttt tgatacacct 306240
aggacatgga ttctatatga accaatggat cgtgacaagt cgttactact agcaatgact 306300
tcctctttca ttacttcatt ctttccatat ccctctcctt tgttctcagt tactcatcaa 306360
atggcactca gttcatatct ttaagttcga tcattgacaa ggttcaaaga aagggtgggc 306420
cattgataaa gaatcgattc caaaccacaa tgctagcaga tggcgggcct ccgcttttct 306480
tttcattaat gaaacccgcc agttattctt attaggaact caaataaaag gactttcact 306540
tagagtttga ttagcataaa gtgccagccc agctaggctg agttccgttc cattgctttc 306600
ccaataagtg aagtagcgaa acctccctct gaatgaacag aagcggaatg caactcaaaa 306660
aaagttctag gatcacaatg aggtcccacg aaaaaatgag ctgaaacgga gcaaaaggga 306720
aagcccgcgc gcgggaagca aagtaccatc gtgcacactc atcaaaccaa tgatcgctgc 306780
caaaaagacg gtgagttcga agccacttcc tatatccgat atccgaggag atggaattgt 306840
gaagaacctg acgaagatga tgatgtccaa aacccggtag aactaaggta gttcagttct 306900
ccgaggttta atctcctacc ttgcttccat tctttaatgg cattctgcag ttcaatgtcg 306960
gcgaagcctt gcattgaata ggttgttata agcctgactt ggctctagaa agcagattca 307020
ttattatagc cttataatct aagaaggtca ggcattgtgc tgtggcataa gctttgtctt 307080
cctctacctt tggattgaga gttcatctgg actgagtaag cactttaaag aaaggaagta 307140
aaagattcaa tcagatcaga agaagactga cttcagcttt gacttcctcc cgagcgagag 307200
cgatcaaagg actggcggag ggaaagcaaa atcagaaaga aaaaggatcg agacaggact 307260
ctcttagcat aggctttcag ccatttcttc ctatagtaag tggaagtcat aaatcctatc 307320
catcttgctc aaaccctttg cacgagtcag aaagcagtct acttatggca tcggaaccac 307380
taatgccgca tctctcggtg agaaggaatc aaggaaagaa gagaaacttc ttccttcttt 307440
gatcttctgc cccggaaatt ggaaacgtaa aagtaggctg tgggactgat tcttttcctt 307500
ctttcaggca aaataagcgt ctgccagcgg tcagagtgtc aatttgtact catgattgca 307560
catcgcagtc gttgcgtgct tgctttgcgc accggcacag cagaattcga atccgctggc 307620
ttagatgagt ggctcttggc ttactgagaa gggctttctg taactaagaa atgagaattg 307680
ttgatccata tgatctcagg caactttcgt tgatgaaact gacaatttaa cacttagaga 307740
ttgagctact cagtcttgct tccatggata tcttaaacaa gtttgcttac ccatcgttat 307800
ctggcgggaa gtgagccacc tagcctacct tctctctttc tcttaagcaa tttcatgtca 307860
ccttaactct gcccttggga aacttctctc ccttaaggta gcattcatag ttttgagtca 307920
acaagacttt gattttctcc atcgcctctg aagttcaggt caaaatcaga actggaattt 307980
gaaatccagt aggaaaaaga aatgcagact ttttcttgac ttttgaatct attagaaaga 308040
gagtctctga agcctttgct ttcgacccta ctaggatagg acttagaaag cctccttgaa 308100
ctacggttta cagttcacta agatcattct ggccttttct cttctagcct ggttagttac 308160
ttctatttac caagaagtgg aattagatag aggagaccga gcatagaaat agaaaaggat 308220
tggatttgac ttcgaatgga tggttctcgc taatccccat ttctcagatt gtgcttcgtg 308280
gggggagtcg gatattggtc cgtaaaaggg tcaataaccg agctgggttt atgctccgtt 308340
tttccaagaa cggatctagt aaggcgaaag gtattcccca atgcaaagga gtctaatcaa 308400
agcaatcctc gagtaagaaa agagaaggcg ctacttagcg ctattaaata aagaatgaag 308460
ctccgtgcga cacccggctc ccaaagaagg aaatgctaac cacagtttca atggtaacgg 308520
gaatacgcct gacggcgaaa cacagagagt gacgcttcca tcgcttagat ttagggcgat 308580
agggcgcccc acagatacga actagaaagc accattgcat agggaaggct tgctctgaca 308640
atgagtaggc tacactagtc tacgggtacc tagtctttaa agtgggcgag gctaacccta 308700
tactttcttc tcaaaaagag gtcgatcttc cgctctagat ctttcaaaca attgatttcc 308760
atattggtat ggtacccttt cttcatagaa agggcatttg gcttccttta gtatactcct 308820
aacaacgaaa acaaggaaaa ggtaagtgaa aaataggaca gagattctga aagagggcac 308880
taagagaaga agaatgaata actgttaccg aggcccaagg agatgcagcc tagcccttac 308940
ttcaccagat tcaatagcag ctcctattgc gatgtggtaa ggctatggca tcggtttaca 309000
cattcttgac ttgaaaagag ttagaaggat tttcgccata taggaagggt ctgagaacaa 309060
gagccattcg tggtcacatg aaagcggcaa tagagaatcc tcctactgct aggctaaggg 309120
caaagatcac agcagtactt gctaaagtcc cctatcctga acgtgtgcta tgtagaaagt 309180
agttagctag gcatcataat agccatcaac cgtcagcctt cgaaattagc actcgattag 309240
ccggcaaaag cgctcttctt tccattttat gtgattttaa gatggatata gatagaactc 309300
gatcgaacta aatgctattg tggcaaactc gtgggaaaag agatcggggg tatcgatgtg 309360
gatgaaaggc agagatgaga gcgacagaag aggagtggaa caactacctt cccagtctat 309420
cgggaccttt ttggtttatt tttgccctgg gctgaactcc ctgaatcccg ggactcgctc 309480
cttcgctctc cggacttctt ccttcaacaa aacaaggttt ttctgatgag catctttcgg 309540
gactttctct tgttgttttc ggggagctgg ctgggaactc ccactcaaaa tcaaaacaaa 309600
aaaatcctta ctacccccttt aattttcaag gagcctccaa cctacgaact ctgaattcgg 309660
ataacataac tatatttagc tgaactccct ttcgctttag agaagacagt tcgagcagaa 309720
tcataagaag aaggtaaggg acaaggtgcc aatctattaa tctcaagcct gcaaaagtca 309780
aagtcactct tcttcagaag aaattttcct tgtagcctta gaggctaaac ttcagtttca 309840
tacgttctat tagtaggtct cttgaaagca gtttcagcat atcgtctaaa tgtatccttt 309900
ttttacctct tccctagtac tgatctcaat ccttatgtca tctaatgcgg ctttttcact 309960
ggctagcttg ctggatggat tgcacctctg aaaagaacta actatagggt ctaatcctga 310020
aaaacttcta cttatacggg gtcgggtttg tgaactactg ctactggtac actaaaacga 310080
aatttaggga ctctcataat ccatcaagtt ctttttttagg ccatccgcct atttagccac 310140
attacacgct ctcttacaag cccttacata agacataagg aacaataagt gtcttcttca 310200
tcaaattcaa atcaaagaaa ttgagtacta ctatggatgc tgcaaacagg ctttctttct 310260
agttaagttc ttagaagagc gattggtgta ggctcgggag gcatacgaac atggtgcact 310320
tcgctttggt ttaaaagcgc ttaaactaga tagctgggaa tgcgttaggt tatggtaatt 310380
tatatagaat ataggctgaa aaagtatcta ttaccttgaa ttctcagttt taaaatgtct 310440
taattaataa aataaaaggt aggcccttag acagactgtt agcgcttgtt aggaagggga 310500
agtcttgcat tgcaagcaac ctaattccta tgttatagcc ttcgttccct tctctgtcgg 310560
tgtgctccga cagtgaaccc gagatatctg gttcataagg ttgccaatgg ggctagcggc 310620
gtccccgcct catgaaaggg aagcgatatc attttgtcgc ccgatggaag tcaataagag 310680
agaaagcacg aactaggatc gacctgcatg tgaggcaagt aaaagctgcg agtgaggaaa 310740
gctggttgtc aaagaagtta tggtgtgccc ttcattaaga gtaagagcgc aaacttggca 310800
tttccggtcc ggaaaactct cttatttttt agaagtttgc caggaggtga ggtttaaata 310860
ggcttccaac tgtgttggag tttcagactc actactaacg aatgggcttc gaacagctct 310920
tttttttcca acaggctgca aatcataagg ataagcctga acctaaagct caaggagcat 310980
agttccaatt caaactacct agagagaaac ctatcatagt cctagctata aggggttttc 311040
agcgaaagcg cgtgttctta gattcgtaag aatatgaatc gtcaaaagga agatgctggt 311100
ctttcattcc tttatcattg aaggccttac ccataggata ggaatcccgg agcccataat 311160
agtcatcgta ggcccagaac tatagttcag aggaaaccgc cggaagactt tgtttaggaa 311220
aagaaagacg aagaacgcca ttcctttgcc ctatgccctt catttacctg ctcaaaggaa 311280
gaaactaaac tataagatca gagaaagcaa gagccttcga tttaactaca tcagtagaac 311340
cggccttaac tttctttcca tttgaagaat tcctgatgat ggttgataaa ggctttcctt 311400
ccacttaccg tagttctatc aaagtcagcc ttaaattaaa gcttcttgcg aaggccctgc 311460
ctttttaatt tgattttttta tttgatcgaa aatctagcta aactaaagag cttcttttaa 311520
agattccccg ctagagcacg gaaacctaga gaatagctag cggattcgcc aacatcgaaa 311580
gcaatcagac ttggtttgga aatctccgcg cttgctatgt tatatcaatc tcaattgccg 311640
attcactgat attggcaact ttcagatcat ctagttatta tccttcaagg catagggccg 311700
tgaggtactt acttttagcg cagccgggat tgattaaggt agttgttcag ccgagggaaa 311760
gaatcattca atgctagtga aagaggaagc tgttcccttc gttgattacc gtggtggctt 311820
ctgtatcatg atacagagaa gacagaagca gcactcttgt cgaccgttca tggctagctt 311880
cgaacaaaag aaaggctagg cgaagaatcc atcccttacc gaaggaagat tgcatcgcta 311940
gttgactcct cctcgtcgac agctagcagt ttccggactc gcttttgttg ccttaaggct 312000
tcctcctaaa ggggaagacc tgctaaggca ctaataagag caacagtagc aacagcgacc 312060
cccctatctc ttaaagcttc tgccttcaga cgggatgatg gctaaacaat catttggtaa 312120
gtagggtggg tggactggtg agccgcttac gctttaagcg aggagacagg agctatcaag 312180
cttaaagtag tccctagacc agacagaggt tctagggggg gtccggatag aggattcctt 312240
taagcggtct gcccgcagat gtaggatagg aaggcggcct gcctgctaac cgaactgcgt 312300
aactaaagcg actccttctt ggtgtaagat aggtcttggt ccgattcacc tatgtcagtt 312360
cgaacctgac gggtcgttcg tgtggagaat ctctctcctt actcaggatt tctttatctt 312420
cgaggcgagg catattcata tatatgtcga agaaggagga agtgtctcca tattctattt 312480
atgctcatag aacccgaaaa aaaagaatat accgtcgttt aagggccaag gatacgatgt 312540
gagaagcgta ggtcggagta gcaggagtat gcgacaagca gttgcatgtt cgatgtggga 312600
gatcttctgc acttaataca cactctttcg tgccttggtt cgccatcatt tggttaaaca 312660
agaccacatg gggtgattga agttggaaac ccttgtcggt ggaactaacg aagcaaagcg 312720
tgcttggtta tcctagccta ggtggaatgg aattagggac gcttgcttgt gcgcctaaga 312780
ctcctagtta aagagccttt ttctgatgaa cctttaatgg ggatttctag caaattttta 312840
ggctatccct tcggggatct agcatggttc ccctagtccg aaatctagac tctgtcttta 312900
accttcgctc gagcgatgga aagagtcttt acacaggact ggtattctaa gttttcttcg 312960
ttctctgata tcttactata gaaggctcga agagctatgc ttgataagaa gagttagcag 313020
gcgagacatc atctcgtgtt aacaataact cgtaaagact agtttcataa gctagctttg 313080
aataagagaa atcgtagcct agaaagtctt gccaacggaa agaacagcag actcaatagc 313140
cgctctagac gccctaaagg gaagtttggc gctagcttcc taaacaggat tttctatgag 313200
gtagaggccc ggccgcgcaa agcaagagga aataggtata ggctggatca ataaaagaaa 313260
gataaggaaa gtgtacaaga ttccaatctt rctgtacagc aattggggca ttggtctttg 313320
cagcgttaat gctttttgct ggttggtttc attaccataa agcggcgcca aaattggctt 313380
ggtttcaaga tgtagaatct atgctgaatc accatttggc agggctacta ggacttgggt 313440
ctctctcttg ggcggggcat caagtacatg tatctttacc gattaaccaa tttctaaacg 313500
ctggagtaga tcctaaagag ataccacttc ctcatgaatt tatcttgaat cgagatcttt 313560
tggctcaact ttatccaagt tttgccgagg gagcaacccc atttttcacc ttgaattggt 313620
caaaatatgc ggaatttctt acttttcgtg gagggttaga tccagtaacg gggggtctgt 313680
ggctgactga tattgcccat caccatttag ctattgcaat tcttttcctg atagcgggtc 313740
acatgtatag gaccaactgg ggtattggtc atggactaaa agatatttta gaagctcata 313800
aaggtccatt tacaggtcag ggccataaag gcctatatga gatcctaaca acgtcatggc 313860
atgctcaatt atctcttaac ttagctatgt taggctcttt aaccatccct tactatgaag 313920
ggattaagcc actatcaaag caggaaagag aacaactagg atgaaaggta ttactaatat 313980
tgatatagtg acacaggatg atagaatgta actaggataa gcgtccggtt agaaccatgg 314040
gaagattaga atgacctcac taggaacctc attaaagata gatagctacc ttagagagct 314100
tacacagtca attgatctat cctaggttga ggaatcaggg aagaaggctt tcaagtcaag 314160

-continued aagagattcg ctcctaagga ggaaataagg gactcatatc gaaagggctt acaggactaa 314220
aacctatatc tgagagcttg aaccgacagc agccccatgg gagaaccttt catcttcatc 314280
tctctcactt aaaaaaggct tagcttgggc cttagcctaa aaaagagaat caatggctgc 314340
agatcgtgcc tttcttgcag ctttggctac tgaacttatg aacagaggac agagccttaa 314400
gttaagccgc agagagaact ctttgttccg tctttcgggt tgtagggcgt agggagtagg 314460
cgagtcagtc tatagagcta gttaaagtcg aaaacacgtt cagctccagt gtcttaggga 314520
aatccatctt gtcgctagtt gagttacggg tgccagtatt cttggtctcg tcgtagaaag 314580
tctttttttg ctgtccggta gtcgtagtcc aattcttctt tctcgggctt tttttaagat 314640
ttgaatctga aggttcgtaa accaaagctc tttacgatcc aaaagaatct ttctcttccc 314700
ttatccgcga ttccggttct cgatcgaagg ccgggctttg aatcgtttta ttttagtaca 314760
caacactcgc aacaaaaggc ttatagccga actgaggcag caagcggatt agaaaagata 314820
gagtttcctt gattgggaag gaaggaagga actagtaatc cattcaagag gaccttacct 314880
ttgagttctc gagtgaaagg gtccaagcca taggaaaata tccagtttat ctcgcaacat 314940
atctagttta tcctgaagca gcatttctcg aagtagcatt cccataagta gaggatgaaa 315000
cccttgcttc tttatcccga cgagggttta tgaatcactc aaacgagcct ttctagccgc 315060
atctgaatcg gcatccctat ccatatgttt atgcgcaggg gcatccaaat ccgaatctgt 315120
agaatctatt ggggaatccc catccgcacc cgaattggct aaatctagta tagtgggtct 315180
tgttccgatg cgggaaaaaa tctttttaaa aggcatctcg gcgaaagagg actgagaacc 315240
ataaggcgag cgccaaaacg ctagcacaaa ctgctcccac agacacgcat gataaggggg 315300
tgtggggaca accaggccac cacttttacc agatatgggt ccggacgacc caagagcccg 315360
ccactagaac ccaaccctta agaggctaag gtccaagggg ctaccgcagg aagtcagctt 315420
cacctgtaac cttaaggaat acagaaagtt acccggaatt cctagcaagg actttgcctg 315480
ctattcattc ctaaatccct ttcaccctta actagctaac tcgatgggac gtcaacagcg 315540
ggaatgccaa atgcaagacc tggacctggt tcacgcagtc aagcagcaaa gacctctttc 315600
tcttcgggag ctttcgtaac ggctataaag aatgggtctt tcccctcgtg aaaggctatt 315660
gggatcgatc ccttcaaccc tccttggcgt ggaaggtcgc aagagaaaag aaaactattc 315720
ttcttagctg ctttttcaac ctacccgagg taaggaagta aagcaaccaa tagccttttt 315780
acctactatg cctttcaccg ggtgagcaaa aagtagttac ctttagccgg gtcttcctta 315840
ttaattattg ataaggcaca ggggaagcat tatccttata agactgttgc taaacaaaag 315900
caattctttt tcacattcaa ccatgagagg gcaacttgag caatcaaagc taccccctct 315960
tccactgctg actatgaaca gttgacagct aatgatttct actttactaa gccagttcgg 316020
taagttaagg tccatgcttg aaacgataaa aaagaggaag gggaaggggt cgcccaaagc 316080
tgtggagata aggtggaaga taaaaaagct atatttaaaa taataaagag aatctcttca 316140
aattcatatt caaaaatggg attctcaact atacttgact ggaaaaacca gccaatctac 316200
tctccttttt ttggtctccc ccctgtaact ttataaatca taagagaaga agaaatcgtt 316260
gcgtagaaag tcgtgcttac tatctcctcc atctaagtta tgtaagagga aaagagcgaa 316320
aagcttactt ttaggtagtg gcctaagcgc taagaagctc caatcatgct actcagacta 316380
tatgcttaac acatgcaagt cgaaccttgg ttttcggagt tcgaaagaga aggggaagaa 316440
gcggggtaga ggaattggtc gactcatcag gctcatgacc tgaagactgc aggttcgaat 316500
cctgtccccg cctaatccat ctgaggcccg gcctcaagat ttgagattcc gtaagtaact 316560
cagtgactgc tttctaagaa gggcttggaa gaagaaaatg aaataggaac aaccgcgctg 316620
gtcgtagagc taatgaagag aaatcttacc taatatgagg atcctttttg ctctttctcg 316680
gctctgtgtt cgtggtaata gtgttactta tctttcgaaa gtccctacag gtcatagtag 316740
ttcgcgtctc cttgatcttg gttatacttg tgaattagca gctagtaagt ttttgatttt 316800
gcttcttttt tggaagcaaa gaatgttgcg acgatttccc gtcttaaaga aaatatcgcc 316860
caagatgtat atatcgatat gccttttcat ttatctaatt ttccttaaag taggagtatc 316920
gcttggatac ctcttgatgg acgagcttca aagggctgtc gctccatttc ttcatgcatc 316980 gggggggga atgtctgggt ctgaaggaaa cctgggggt agcagtggag gccccggttg 317040
gccgtccttc ggtgtaggcc tatttgcgga taatagtagt tgttattcaa atgacgaaga 317100
gttcgcccag ccaaaccccc aaaacgcccc taatgcagtg gaggcagtcc ttccagaacc 317160
ggatatggat tctgtgaggg gtgtcatcaa gcagaggtta cttgtgcacc gcttgggtca 317220
gaaaaatttc tcggtttccg agaaagaaat tgaccaaatc gtggagctca agaacgacat 317280
tctaaataga atgggcgaac tggaccccga ccccttctgg actagccatc gaaggaggct 317340
cattcgggac tacatacgac cgcacatggg cggggagtat agaataaagg ttttgactaa 317400
aaatttaaac ttattattgg gggaaagtcc aaccagctcc ttgatttata accaactgat 317460
gaaagagaaa gactggttct ttttagatgc tccatttcaa ggccctagat agagctgaat 317520
catatgtggt tggtctgttc cgatcggtcc ggagggtgga gggtggaggt tggaggttgg 317580
ttgaagatga tgtgatgcaa gtgaacgtct acgaaaaagc tgtcgtaaag tttcgttctt 317640
cgttccgtcg tcgatcttcc tttcctattt cttccggtat gccgctccgc caacaaggag 317700
cgaaagaacc aagttttctg tggtgatgtc agaatttgca cctatttgta tctatttagt 317760
gatcagtccg ctagtttctt tgatcccact cggtcttcct tttctatttt cttccaatag 317820
ttcgacctat ccagaaaaat tgtcggccta cgaatgtggt ttcgatcctt ccggtgatgc 317880
cagaagtcgt tttgatataa gattttatct tgtttccatt ttatttatta ttcctgatcc 317940
ggaagtaacc ttttcctttc cttgggcagt acctcccaac aagattgatc cgtttggatc 318000
ttggtccatg atggcctttt tattgatttt gacgattgga tctctctatg aatggaaaag 318060
gggtgcttcg gatcgggagt aaccactagt gagagggcaa aaataggggg gaaggacaaa 318120
ggaaagagcg atgcctacac taaatcaatt gattcgtcat ggtagagaag aaaaacggcg 318180
cacggaccgt actcgagctt tggatcaatg tccccagaag caaggagtat gcccgcgtgt 318240
ttcaacgaga acaccgaaaa aacctaattc agctccacgt aagatagcca aagtacggtt 318300
gagcaatcga catgatatat ttgctcacat tccaggcgaa ggtcataatt tgcaggaaca 318360
ttctatggtc ttaataagag gaggtagagt gaaagattcg ccaggtgtga aatcccattg 318420
tattcgagga gtcaaggatt tgctgggaat tccggatcga agaagaggca gatcaaaata 318480
tggtgcggaa aaacccaaat cgatatgaat ggaagatgcc tctggaactt gtttttctcg 318540
gtaaggatag gtacgaagtc actcgactga aaggagaggg aacaaccaca acgttacacc 318600
ccaaaactat acggagccct tccgaatgac ctagaatata gtctactaaa ctagccaaga 318660
aagagtctag tagactatat tcgcccgtgg aggtgagtgg aggaagctgt gaagcttcta 318720
actctaatta ccaactcggg actaaattag taaaaagcgg cattatccct ttactcaatc 318780
ccccctcgct taccaccttt cccgatcaat tggtttttaa ttatttaata agaaagatgg 318840
caaatcctac cattgtattt ccttttttca tttggatcct atcaactttt agagtgtcta 318900
gattaagaca cttctcgtat tcggactatc aagatcgact aaatgagagt gtggctgaca 318960
tggtaaaaga agaaataagc cacacttttc tggacccctt tttctcttta caacgtctta 319020
ctaccacagc tattccactc tggtagatac gaatagtcca aacacgtatc ttcgggcgaa 319080
tagcctttaa ttaagcaagg gcgagaccaa agcacttaac tatagaaatt acttagaata 319140
gtgaaaatcg gcactactca agccttctta tccgcgagtg ctactcgccc aaggaagtct 319200
ctagcggttc aattcaatta ggtgaaaact gtctcggatg ccccttcctc ctcaacccgg 319260
gagaagaccg ggctttagcc gcttgagcgc actcgtctct ctctttaggg gcctttggga 319320
atcttgttca atggggaatt ctgcatccac tttccagccg gttgacgatg tggcatttct 319380
tcctaaacct tcagtcttgt cctaagcgaa aggggaatcg gattcttgca caagccattc 319440
taagaactga ttctagcaag acctattcgt gcacaaggga atctgtccat ttacagcaag 319500
caagccgcaa aaccaaaaga gtaagacatg gtaattgcta cgctactcta gccagtcgaa 319560
tgataaaggg gagtggaaat ggaattgatt taaaaaaaac agctagttcc gcatcaagac 319620
cgctttcacc tgaggaagga gcaaaataag acatactttt attaaccttt ctgtgctatt 319680
attcacttgc ccaagaaagg gctatgcaaa atgaaatggt actggcactt cgtcaaacct 319740
tccatgagca gcagattcaa tagcaattgc agctacttct atcatcctta tttgatttag 319800
ctgcggttac gtcgacgcgc acggcaaaaa cgctttcagt caagtgtcag ttccttgtct 319860
gattcttggc atctagatcg attaccaaca gtggaaagct agtagccttt gacagaagat 319920
cttgatttct ttctcacccc cgtcctatgt tcttgtcgtc tactcaggaa gaacccaacc 319980
aatacagttc gctgggcctt cccaacttga ctagtgagca ctgctcgact ataagagcgt 320040
cgcaatgcta tctatacaaa gcgtcatagc gtagtcgttc ttgttcgttg tcgtagtgag 320100
ctggttgggc tccgttacgc ttgctttcga gccttcttgc tattagaaag gagcgtccta 320160
agacctaaga cgaggataag gaagtttcat atggggccgg ggatatacct acgaatgagt 320220
ggttcagtcc agtcctgaaa taattggact aaccttcaat aatgacttcc gcaacatcga 320280
catgatggtg acacctttta cataaggaat gcaccctaag gtgtcaatct aaggtctcgt 320340
gttaatcctt ccattaattt cgttatcatt tgaatttctc atacctatct ctttgatcat 320400
gggctatcaa gatacactca tacccaccta agaaaggtgg tattctatct cccaccagac 320460
tgcctatcca gattaccata ctcactaaga gacttgattg cttactctcc ctttcttgct 320520
tgttcttttt ctacatttgc ttcctccgca ctcaatgaac aatcagatgc gggattacct 320580
gttgattgcg gtgtgcttgt cttggttgat ttcgcatatc tctttcttgt ttttgggcaa 320640
gctgctcttg ctcaagtgga atcagttgca gttggcatat ataaagaagt ctaatatcct 320700
gtcttctttt attaaggaat ttctagagag gaatcccctg gccttagctc atctagccgt 320760
agctcattgg gcggattgct ttgaatagcc aaagtctttt gaaagagaag aatcaacatt 320820
cttggattag gctggtgcta tctcttattt aagagaaata ataaggagaa aggctgcctt 320880
aggtttagga gtttcgagtt ttctctgctt tcataggcta tcgcttcttg gtgcctagcc 320940
ttctgcttct gatcccggga gaataataag aatggccgtt gttgaatcag ctgtgaaaga 321000
cgctcttgcc tcagtttttg ttggtggaat agaccctacg ggagccccgt gaaggctaat 321060
ttctctgtcc ggctatcccc cctatgtcac caattgttgc aacgagggtg acgtcattga 321120
ggccctcaag gacatgctta gcaaaggtat gataaaatgt cgccagttct ataaagtcaa 321180
gggctggaga gtcgaagagc gcactttggg actgaaaaag ttccaccctt catcaatgct 321240
tcaaatacgt tgatgagaag gggtatttg ccgacaagaa gcccttttt aaaggagtct 321300

-continued aggcatactt tctgtacgga tgcgcgtctt tacaacgacg gcccagccca gacagtgatg 321360
gatgacaaaa gcccgccagc gaaagccgaa gcacaggttc gtagacctct ccgaatccca 321420
aagtcgaaag ctaagggatt gacggtcaac gctatctcaa agagcatgac cccgttgacg 321480
aaatctctaa actggggctg agggagaatt acttcaactc tcggtaaaga tgccacttcc 321540
tgcattacag caaccttctc aggcagaggt gtttataaaa ctggagcgac attcgtcctc 321600
tcaatggaag gtttttttcct catctttcac agggtagccc ggaagtattc ttctacgttg 321660
gaaagaatcg tcaccgtcac cgatggtgag ataagaaaga gaaagtacag tccgattgca 321720
aagaagcgaa ggacatgggc tatatgacct tgaggagcct gtcgggctga agtgaagaac 321780
ggtcgaggca gaaaagtacc cctcgagccg catctaagtg aagaagaaag ggaagcttgg 321840
ctagccggcc agtacgtcga tctcagaaaa cataggcttg ggctacctgc caactccgct 321900
ccctgcgcca aaaactttgt ctgacgccga aagttctgga gatctttctt tcagatctct 321960
tccaattgtc tataaactct gtctccgtaa aacaaagagc aaagagacga gagtaagttc 322020
aagaatagga tgtagagcct gtgcccccta cagaggacga ggtcaagtaa atggatctcg 322080
ggactgttga caatcctcgc cctgtattcc taagtgcaag cttctcaaat gaaagagatt 322140
tgacagtaca tggatctact cagagaattc ttttatgttt tcgcttggag ctacgccgaa 322200
ctggactaga ccgaaagata aatgagttag ctcaggctca gggcgtgaaa gaaaatagat 322260
aagaaaggcg attcctgatc tgaagagttt agttgctata gtggaatctg ttgaatttgg 322320
gaaggctcag gtttggtggt atatccttac atatataagt agttttgatc ccggctccgg 322380
tcaaatggat ttaggaaagc ttccacgtga catcctcaag ttagtcttct gcttgaactg 322440
tcttatcgaa agctaaaggt agttaaccta ggggaagaat ccgactaagc tttgccttga 322500
acttggcacc ttaccttcta atcctttgct tgggaattcg attcaataaa gaggaatcac 322560
tgattggaca gtggcactgg aatgatagca agcatccctt cttctctttc ttggtatgag 322620
aagttggtta tgtaggctga caacctttcc taggttgttt cgatcaggcc aaataatcta 322680
ttttgagtat gcctgagatt gccagaagaa cttccccctc ttgaaaactg actaatcaaa 322740
caaagggggt aactttttttt tatgagggta gggagtttgg gttggtgttc agtgtaccgc 322800
actttgggta caagatcgga aattccattc tcttttttac catccaaaat cgaagaaaag 322860
aaagaagggc gagataaaca aataaagagc taactttctt taaactttct ttattattat 322920
gtaagattag aaagttcaaa atgaatcggc gcaggagctg ctacaattgc ttcagcggga 322980
gctgctgccg gtattggaaa tgttttcagt tccttaattc tgttgcgaga aatcattcat 323040
tggcaaaaca attttttggt tatgctattt tgggatttgc tttaaccgaa gctattgcct 323100
tgttttcctt aatgatggcc ttcttaatcc tccttgtctt ttagaaaaaa aaaaaagaaa 323160
agagtggaag cgggctagtc cccgaaaatg cccggtactt tagcgttggg gacaagtaag 323220
attattatct ggtttatccg ccatcgttat cacaaattga atatcctgtt aatgtgccag 323280
ccctagcccg tcttgctctt ccaattccat ttcgagagtc atcatagctc ttttggactt 323340
atacatgcag caccctttta tctttcggca tagacccttc ttcctccttg cgatgcaaag 323400
gcaatgtcag ggagggcgag aggagagaag gagagcacgt atgggtggta tgaaagccat 323460
aagcggaggc atgggtcttt ctcacgaaga tgcgaagcct agagatgagt ctattcaaaa 323520
ttgactgaaa aatccggggt aggaggcttg atgacaggtg ataaggtgag gaaaagcgaa 323580
gtcaagcctg acctaagaaa agactggttc tcaaccacag cagaatgagg ttttttcctt 323640

-continued taccgatacc tatttttgcg tctttcttcc tcgtctaaga agcagaatca gccttctcct 323700
ccttatagaa tctcattcat ctatggaagg aaggaataat cgttgggtac cctgaacggg 323760
tgagagatcc tggaaaaggg agtcttctgg ttgcgggatc tccggcataa gctttcttcc 323820
cttgtcggcc ctccaatttt catgcccgat agtcaaagta aagcacgcac ttcaagtggc 323880
gcgatttatg tcgttgcgca gggatgctct tcccgtagtg ccccttcttc ctccttctct 323940
ctttctctgc ggcctgcgtg ggactgatcc ggactgataa cccgaaccct tcgtagactg 324000
aactctcttc tctttaggct cgcgtaggtt agggaactcg cctccttcac tgcttccact 324060
ccaactcgaa ctaaaaacct cttcctcatc ttgactcatg gcgtcttcat cagtgagtaa 324120
atcctcatca tcatcctccg taagataaaa gaacctaact cctgggcctg tgcagactct 324180
tggtgaggct gttccaagtg tgtaggcccc acatgttgct catctccccc tgttggtggt 324240
cttacagtag caatggacgt agaaggaatt ctttgcatgg cttttaacgt ttgggttcaa 324300
taacattcac cttagtggga ccccccagca ccatctttcc ttagtaaata ctagatggat 324360
tccctattgc tatgctagct tccttgggaa tactaccttg cactggttta ggcggtatcc 324420
gggccctttt agaggcaaca gttgacttct ccttatttat tgtggtccca agaggcgtaa 324480
taacctaaaa gttgtccagt cctaaacaag acaggaaaac ctttaggctt cttcagaaaa 324540
ggaacatcaa acgtttactt ggaaaacacg ttatacacgt atgatccaag taaacgtcca 324600
aacatccttt ctagcatacc cgtccgaaga gtcaaaggcc atctatcagt ggccgacttt 324660
aaatcaatca tacgagtatg ctatctcact acccgtcaat ctgagttctc gaaagcgact 324720
gaaccagcca cccagatgag actcccgctg aaaaacattc tttttccgac aaaacctgcc 324780
actaagcttt gacaagtcgc taacttgctc attttgtaat agggcccagt cacctccctt 324840
cttcccaacc tctggcagtc aaaagggaga cgtgcttcgg tctttccatc gatagaagca 324900
gtaggtatat aacgcatgca gctagtaggt gataggagga tgtaagccct ggtggcagtg 324960
gtactttggc gaatcaggcg tcgcttctat ttcgtttttg attattattt ttgaccctac 325020
aatggcagaa cctagaaagc tgctcttttt tccctgtccc gtgatttgat accgtctagc 325080
ctctagctag gaagtcttgg attcgtatac catgtaggtg agaaaatcgt ccgtgactag 325140
ctatccttat tctcctccca gggatgttta ggaatatggg tgcgggaggc tgagggacga 325200
ccacgatgag tacgcgtttt tatataggat caaacggttt ttgttcgatc gaaagttagc 325260
ttgactcaag tcgacaagcg agagagaagg ttgggtgagg gtacaaggca tcatgtggga 325320
tctacgatcg actgtgcccg ttgttggctt tgcagatgct ttcaaatact ctagcagtat 325380
attccattca ttgtatatat cccttttttcg tgtcattgac atcagagatt gcattcaatc 325440
gaatggtttg acataagaaa tgttctagtc tatctgtagt agttctcttt gtttatagta 325500
gagtaatgag ggtggcgact cacaagagga gtgtagacca gagcaagagg gagccaagcc 325560
agctactgtg gttgtgccat ttggtgggcc aaagtagtct agtggcggtg aaaagacgat 325620
agtagaccag acggggacac caccagaaca cccgaacaag gatctatttt ctttttaagc 325680
tatagtacat atgcacttta tacgtctgtc ttactaataa tattccttag cgtacatctg 325740
tactataacc ctcccctctg ggaggtgttt tcaagggaag gcggactccg cagctgcgga 325800
ccgggcacta tcactatact atgcgatgct ttttaccaaa aaaatggaaa ctgtcaagat 325860
tagcgtacta aacgattcga tctatcacct acgtcatttc tactttgaat aaatccatac 325920
ttgttgcact cagtcatcgt tccgtcatcc aacatgcttc tatctaagtg atttcataac 325980
atatggatat gtaaggaata agctaaagaa ggccgcacct ccctattcat tacatcacaa 326040
tatccgcacc atttgcttaa aacacagttt ttgcatttgt gtagcttact cacttgccaa 326100
gaaaaattca tcacatactt cgtggcttta tgcttcgaac tgtgatcaga acgagaggag 326160
tgggcaccga agatgccaaa gaagctagcc actatcattg tatatatttt taaaacaaac 326220
ctgacttctg tggtttgaaa cctgtgccta gcctttctgg cttgcctttt gaatgggcgt 326280
gccaatattc aatatattta cccttttcct gcttcatcgc tttggcctat tgaatccgca 326340
gctgtctcag taggagtagc acgttttcga ccaggcttgg cttattctat agcatttgtg 326400
ccatctatat ctataagaga ctcctctctg catttacagg taaaaactca catgctttcc 326460
tttcttgctt tcctaagtcc ctttctccat atggattgaa aaagagttat tcggcccgtc 326520
atggaaagaa actacacctg gctcgctaga tcaaggaaag ggctcgcgta gatcaattac 326580
ctgaatcatg cttttcccaa gctgagttct aagacccttt cgtttcggaa gcaaaaccca 326640
aagcaaagaa agcagcaaga gtggagagaa caagctcttc aagctcagct tcggcaacag 326700
caactcgaga aagcaattca gtttgtgagg aaccgtccac ttatttatat acgtcgccct 326760
ttgacgatct gtctgttcag gcaggtgcca cggaagtgag tacggaatca gataatgggg 326820
aacgtaaaag actgagggaa tttagttccg agactcatct aagttcccat cggccgtttg 326880
aagccacggg atggggaaag gagcgtttac actcgacaag aggtctcaga gcaaccccta 326940
tggtatggct aagctccgtt catagcctga aaaacactga cgatctgtcc tcatcgtggt 327000
cttttggtga tagaaccagg atggaaagaa ctgaaaaaca taactcttct tttccgaatt 327060
ttctagcctg gcccatagtc atggtaaact ataaggattc cctagcccgc tttctggatt 327120
ttcggcttta tccgaagact ttggtagatg tgcggggtca gggggcagga tggtcgaaat 327180
ggatttcaag gatcagtaaa attcgccaaa aggaggggaa ttttctcgat cctttggtaa 327240
accgaattca gttcggaaag gtgggaaagc agttcttcgg gtgagcagtt tcaaaggatc 327300
aaggaataat aaaaggtacc ctagctggat agctaagaca ctaagaaggc ttaggccgaa 327360
tgcttacctt atgcttacgt accggccgta gagaaggtag gtaggaatag atgggctgac 327420
ggattagggg aatggaccac tggcaagact gaaaactcaa agaagaagca aaaaaaaaaa 327480
aagaaactaa gaaagagaac ccttttagct acggcaaatg ctgcccaatt cacattcact 327540
cgatctacgt cgagcaaaaa gccttgaaac tgactgacac gctaccgaaa tgccaagcca 327600
aaggatttga attcagttta gcaaggtacc tgatacgatt agaaggatag ctaagagaga 327660
agtcaactaa aggttgcttg cttccttaca ctaagaccac tatcaggctt agagccaagg 327720
ggccactgct tgcacggaca taggggcata cgaacatagg ggtagagtag aggtttttcc 327780
aacgcaggac ggaatggatt agatggacag ctagcactgc cccctcactt cccacttcca 327840
agagaggacc gaatcgagga ctcgaagact tagacggaaa ccccctttata tcgctcctgc 327900 aacagaaaga ctcaatcaac agccgtataa tcaagcaaaa aagaaagaga aatattcgag 327960
ggaggaagat gctctccctt acggtcgagt tactttgttc cttcctctcg cttcgctcga 328020
gcatcttcaa acctcactcc ggcgaatggg tacctaggct tctcttgcca atgtatacaa 328080
atagacagac ctggcgaact atctttccaa agccccctgc aagtataatg attagacgaa 328140
gaagaggccg tcagaccaga aagaaagcta ccctttgaag ctagattgag atttaggtaa 328200
tgggctgtca gacagagact gagcgcagac gcacccgagg agtttgattt ctacgcttct 328260
tcttcctttc tgaagggcac tttctttctc ttgaaagatt tgatgcgcca cacgacttac 328320
ccaatagctt ttcgattgtt ggcgccgact tccctttca aagtaagata gtttcgaaca 328380
acatatatga tattgtaact tcactctttt catccaactc gaaatatcgt aagagaagca 328440
cttttacgcc caaaaagccc catgtctttc cggaccaacc accggcgatt tccgacaagt 328500
ctttccccgg gggagcagaa aaagaaaaga aaatgaatca aaggaatgga cttgctaatt 328560
taagaataca tcacatctct agggttaacc ctgtctatcg cccttcttgt ggcttttagg 328620
gctggacagg ccagaaatct aaattccatt aatatggaga ataagctcaa tcaattgagt 328680
atagacacgc taaaagaaag aatcgtatcc aaagtagaaa tgcttgtacg ggtttctaaa 328740
gaaactaccc caggtttgga ctttgagctg cctcccatag aacctattgc tcagcagatc 328800
ctttttacag aggaaagtat tccctatctt aattccctat atacgagtct cattgagaac 328860
gggacccaag gggaatactt ggaaaaagta ttcactttgg cttccatgat ccacaagatc 328920
catatagata tggtttagcc agtgaatgtt gtcgacgcta aaaagaacac gttcagatac 328980
accatggaaa tcgaccgctg ctggtaagtc accatctccc gtaggagtag tgtccctata 329040
gactttatat acaatataca gttgatcaac cactttttct ttaacaacat ctactgcaac 329100
ttttgttaga gcagtttcca tattgatact atttaaagtt gggagaattt gaccagcact 329160
aacggccacc agaatagcta caggcaaagg caaagccatt ttcaatatga aatcagcaac 329220
tagttcaccc attccataca taataccgag tcttagattc cagttttctt agaccggcaa 329280
ctcctatccc gaatatacaa gacaagtaag cgcccggtcc tcttgcgtcg aagtgaagtg 329340
tagtgtggtg aggttttgcc tcacagaagg cgtgggaaat tggggaaaaa gccgaaactg 329400
attcggccag tacaatactg agtcttattg aggccatgaa gacggacagc acttggttta 329460
gagctgacca acgaaaaaag actccaattc attccgttgg tcaacaacca accagtgatt 329520
tcaatagctg tttattcgtt ccctcaatcc tctgatgtaa acctgagact agtgaaagaa 329580
aataagtgac ttgttctcct ctctttcttc attcaatatc tgtctagcct actaacgacg 329640
ccctttctta tctacgctat ttacccttca ttacttcccc agctttgagt tcagttcctt 329700
tatttgatct tgtctcctag tggtaccatc tctgcttact ctttcttctt tccatctact 329760
aagtttgcgg aaaagagaga gcagacggtt ctcggcatca tgatgcaaga atgacatctg 329820
agatcgctca ttccattgct ttacagtcat gatgggaatg attctattta ctagaaagag 329880
acaacaccct attcttagca tcgaagaggg aattttgtgt agactgcttt ttgaaagtga 329940
aatagagact ttcactaaag agtgagattg aggagtgaaa gaacccggta ttcacataag 330000
aaagtggcag tagtctaggc ggacaccttt tcttttgcct tacccgcaac gccccctttc 330060
taagtagcag cttagggttt gacaaacctt aattcaaaag ctggaaactc atatgctagt 330120
acacttgccc tgtatgcccc atctccatga aagtcttagc cagtgcttct ttccgccttc 330180
caacttaata gattctctct atctctattt cactttcagg ggtgagtatt aaaacgccat 330240
aggaaaaaaa aggggttagc tcttagctcg ctggtagtac tgatacaatc aatatgtaca 330300
cacatattag gaaactaaaa agcagaaaga tcctttcaaa agggggttgg atactaaaac 330360
tcgggaactt ctcccaatct ctcttcaaac ttaccttttc ataaaggtta gaaccttcct 330420
aaaattcagg agagctatgc cgcactctca aatccactca taaaagcata gcgagagata 330480
gcagcttctg attccggaga ttctatctag gttctagtta aactcccaaa ctccctggtt 330540
atagggggctt ataatagtac tggaaagaaa aaggagtatt gtataacgta tcctaataca 330600
ggaaaaaaat atattataag gaaagattct atgttagtac tccaggtact ttcttattcg 330660
agacgagaat aggcccaact cgcctgcatc gacagcaaag gaaactggca gggaaataga 330720
tgccattttt tctcaatggc aactggtact taaactagat atccctcagc cagagactct 330780

-continued gggatgaaat gactcttatg atagtcagat ggcgaagact tagaacgtgg ctaatccgct 330840
ttctcccatt tctctctact ctatctatta aggctatgaa ggaattcgtt catagaatgc 330900
gattgcacta ctttttgaaa acaaccgtac gggatatagt cggccgaggt accaaagcct 330960
tttacggatc cggctctgtc cttaggaagc ttacccaact catttttaa ctcccaagaa 331020 aggaagacaa ccccagtaaa tcgtgcataa tggaagagga aagacctgtt aacaacagga 331080
taagggaata gcaaaagtta ggaaccaagg gatatgagaa tgtgaaaagc gatacgataa 331140
gacagtcatc tcacacgcta ggcccaaaac ctattccgga tctgattttt tctttcctgg 331200
gtgtggaaaa gacaaagtct tcttagtctt ccgctttttc ggtgatatct ataagaagga 331260 ataccttct caaggtaaac aggagttccc ggctcaagcg aaatgatacc ggcgcaaggt 331320
cagtcaattc tttctttagg atagattcct agtgctatcg atttagctct tggaagaagg 331380
gaagtttcat tttgaagagt aggcataaga ggtcttggag tcggcattag ccccgttgtt 331440
gtaggagaga tgaaagccat aactctgccc taagcattga gcttacgcga accaagcccc 331500
ccggtctttc atcaggctac ccccactcct tggtcttctt ctttacgctt ttctctgtct 331560
tctatagtaa gttcccccac gggtgcagag atgcgaatcc ctagtttatt aatagaatag 331620
caggtattag gtcctagcgg gcgtaacctc tttgtcctct actgcctttc ccacatttaa 331680
agatgcagga agcgcccaca gagatgttag ctctttcaac tctttatccg gactggaaag 331740
caactctata gaaattggat gcttgtaaag ctgctcattc tgatgaagct gggaactgct 331800
tgctttaaac tcaatcacac agtccggtcg ggctgccctt tgcccgcatt cctaactccc 331860
ctggtaactc aatagaattc tctcccggaa ggggcttaca ccaaaatagt aactgggaaa 331920
gatcaattat tccttactct tcctacgggt tcaaagaaga tagggacaaa gctccatagc 331980
gggataaagt gttattgtgc ccgtaaggcc tttgtctgca ttgcctccca attgtgtatt 332040
ggaagagatt ctaagggcat agtaagaaat tctataggat aagggcctaa cttccccatg 332100
aatcccaggt catttgaatt tcatatgggt aaagacccag tcctctaact tctaaccaga 332160
taaagagcag ccagcgggaa gaggattagg atcagatgac ctaaaagggc ttttcctcat 332220
cagtatgttg ttccccgtga atcacaggga agagtcagat cttaggcttt cgggtcctta 332280
gtctctcttt gccgctaaag tctaagaatc cattcaactg caactgcgga ctcaagagaa 332340
gatgccctct aacttacaat caattcctaa ctttcggctt gcacaacaat agacagagga 332400
tgctccgctt tttctcaatc aatgggcaga ggcaggttaa tccccgaggg ttattggatt 332460
gatttctctt cggtagttaa ttgttatagt taaaagggcg attaggagaa ccaaaggttc 332520
tttgaagttc ttagtccccg ctttcctgaa agagttctct ctgctcgggc ttctgtctgg 332580
acttacgtcc ttttcaatca caggaagagc ggtgtaaaac gaaatcataa tattctgcct 332640
tcaatggctt tgcctgcgac gtatcatctt acctcagtct gttacgggcc tacctgtcat 332700
agcctaccag atcatcagct ggaggaggat gggattgaaa gaactaaaga gaactagttt 332760
tcccgggctc ttctaagtat taactgtccg atagcgtagt taagtgactt ctggggtcag 332820
acagatagga atccacacca agcttttcat atgtaatttc gccagtaaat aaagaaagac 332880
ttcttgaact cggtgttccg gtgaagaggc tttccgtctg ttcgctgcta aagtctcatc 332940
agaaagattc gtacttgact tcctcttctt tctaacttac aggcctagca gaaaagtcgg 333000
ttttatagac tgacaaagct gggtaatgca ccctaatatc aatacttcct ggctgatcaa 333060
ttttaggaag ctggggaaag gacagacttg ctttcttcag actgacttca gggtatcaaa 333120
atattatgat tcatactttt gcccaccttt aaagagaagg gatgggattg taccaacaat 333180
agatcgatct aaagaacggg cttttaccaa cctagaaata ctaattcatt ctaattctgg 333240
tcggacgttt aagtcaaagc cgcatctctt ttatcacaaa gttaccattt agcaataaag 333300
gataagctcc gattgaaagg atcttcttct ctttaaggca ttttctcctg ctttgtctat 333360
ttaatttcta ctttgaagtc aagattagcc tactgcagga agggcttcat tcacctcaag 333420
cactaattct tttcgaactc ttattacgga ctctaatgca ataccaagag atagagtaat 333480
tcaatcctcc gctcgtggga actcaatcta aacacactaa ctcctcaagc actaagtcca 333540
tacatcaatc ctcaagagaa tgcctttcaa cggcagcatt tactctagct tctacttccg 333600
aagtcagttc cgggaaagag gcagaaattg cttatatagt agttcagtgg ggaagacccg 333660
tgagggaata gtaaaagaat tacagggttt cggaattgat taacagggat ggggaactcc 333720
gccttcaaag gtcgtagtgc tttcctaatc aaatgacttg tttacggctc taagatgcca 333780
tgctttaact atttcccgtg taaatatcat gagttcttgc ttgattcatt ctcaggacgt 333840
aatgctactg ctttctcaga ctttgcagag aataaagaga cttgcaagga tagattcccc 333900
tacttcagat acttcttagg gctttcaata ctgactacaa ggaagtctgg gaacacagtc 333960
gaaatctatt cccctatcaa gaaaagaaag agtcgaaagc tagagctgac aaaggaaaga 334020
aagcctctaa cttctaactc aacttcctcc gagagggctg cgtcagtctt taaagttgct 334080
ttcgtagttg ctaccttctt ttaggcctaa ggaatgaaat cctggaagag tcagagaata 334140
tcgaaatcaa actacgcacc tcgggttaag acttccaaga gcctacaggg gaatctaagg 334200
gaatagctca agagagatcc tgatcttggt ccctagagga agtaaataaa tacatgaatt 334260
aggattttat ttcccgggga acttcttaat ggggagtttg cagatctggg tgtaggggat 334320
tcggaagtaa atactgacta gacttccctc ctggggataa agactgagaa tctgtaagtc 334380
ttgaagctct aactctttat aagactaggc cagcccgtca acctttagag ttgcatttat 334440
gcccttgctt ttggttggaa gttcagaagc tgtcagatcc cctacggctc tgttagcaga 334500
taatggactt gattcaattc aatggcattt catcacaggc attagacttc cagactttcc 334560
ttgcttttta gcaatgaact ccgaaacttc agatactgct tacgcctgat caactcataa 334620
ggttgggatt gtattgaaat agtaggcatc tcttccggac aggcgtgtaa caacaaaaga 334680
ttaatcgtaa actgcttttc tttcctacgt aatttcccag tgaagaagcg ggagttgata 334740
tgatcttctt tacctaactg cccgggaaag acagcataat taggaattga atcaatgggc 334800
atagtaattt catcatcggg attatctcaa atagacccaa aggtaagcaa taaagactac 334860
aaagactaca aggaattcaa tccttgcact acgcatctac gggaaattta gaagtcaaga 334920
ttgaaacgaa atcaaggact tcatctacgg attatgcctc tactttttat atgatatttt 334980
tcttgctttt ttcctattct ctttcggatg cagctttgac tctagcagag ctaaagtaac 335040
tgattccact caactacact aattgaggaa gaggatgaaa atctagggga atatcctact 335100
gcaaaagact tagatcaatg aagctcagcc ggccttgttg tatggcgtat tggtcctatt 335160
tgccccttgt attagtataa gtaggccttt ttcctcaatc taacaaggac tcattaggac 335220
cactacacac taaccatagg cctgatcccg tagatgaacc gctaagttaa gtttaggatt 335280
atgagttaga tcttagggtt taagccgccc ataaaggcag agaatcgtct tcgccctgac 335340
ttccgggagg cgaggtagtt taaagcagtg gaaatctcat atgattgggt ttcgactctg 335400
tcccgcagtc ttgactaaaa ttgtttgtcc ctgcagctga aactgctaga tactgacttg 335460
agtttaaaac ctcagatata ggaggaatga caatctaaaa ccatggaagt tcttatgaat 335520
ggtaggctta ttgagttacc ggggaaagac ttagttagga aagcatcata tcttcccctc 335580
tactcactgg aaagtctgac tgatgaaatg caggagtaga atgaagtcaa ggacttttct 335640
ttctttatgg ctttagtcga gccgtaagta gttgaattca gtaatggaga gagtgatagt 335700
tgtctagggt aaagttagtg cgtagttaga caggctttct agatctaagg aaagcaacgt 335760
ctttgctgtt gtgattcctc attgctggag taattcatgc tttctccaga gcgggatcaa 335820
gctttctaat gaaagcctat gttcacacaa tggttaactc attcgatttg gggattgggt 335880
tagtgttcta ggagtgaatt gtagtgcccc tggtggctta ttgcgtagtt aactctttat 335940
atacgacctt actactcctc aattcccatc aagtgttgtc ttatttccca agccactgct 336000
caatcctcct tttctgattg attgaaagta gcaaggaaag acaagcaaaa actttgttgg 336060
ctcaagaagc aactgaggag agacaaagag tagtaaagga aatacaagta gcagtctcag 336120
gtcaaaggaa tcaaggaaga atttcttctg atattgcggt tactcttcca gaatctcatc 336180
ctgagaccta agtatgccat tctcttcgtc aagaaagatc gagcagcata gaagccttga 336240
cttcaagctt aggtcttttt tttgaaaaag ggaactaagg caacttttag gtgcagggaa 336300
agaggttcgc tagccttttc cctagctttt tttgtcaact atctatcttt ccgaactaga 336360
ttagacggac ttacttaaaa tgaaaaaagg gctaaaaaag aaggacgaag taatttcgta 336420
tataaagata tggctttccg ggtttagatc gaaatggaat ccccgaaaac cagggctgga 336480
gtcttagact tcttctgctt cgatagaggg actgacagcc taagtggaat aagaatcatt 336540
cggccgattg ctctgactct tatccttcct tcgctgacag agaagagagc actcccaagc 336600
caaggatgag tgccaaagag aagatgggca agcaatgccc actcccatgc tttccgttgg 336660
tcaacaacca accaaagtgc tctatacttc ttcactactc gtacaggctt gacggagtta 336720
agctgtattg agggaatcgt tttgtctcaa tcaatcaata tgtttccgaa aattccacgt 336780
atcttttctt tgatgaagag agtctaaatt ccagtgctac atcctctcaa actcgagtca 336840
atccacgaca actattagcg attttagtct tcaatcgtcc gatactcaag gttcttctaa 336900
tggtattttg aggatcatcc aggtcttaac ccttccagtg aacgtatagt agagcttcaa 336960
tgttgtatac gcgaaagatt cgaagagttg ctgcctaaca acaatgccga agcccaagcc 337020
caagaggctc tggtagcggc cgaagtttta catggcgaaa gcaacgatat cgccgagctg 337080
gaacaccttt gacagatttg aatcttcacg gagtactaag tgaagccttt ctagaggcga 337140
tgcatctagt gaaggagctc accagccccc aacccaccta ccgtccccag cccacttgaa 337200
caatttgaaa taatcccatt gattcctatg aaaataggaa acttatattt ctcattcaca 337260
aatccatctt tgtttatgct actaactctc agtttggtcc tacttttggt ttattttgtt 337320
actaaaaggg aggaggaaac tcagtaccaa atgcttggca atccttggta gagcttattt 337380
atgatttcgt gctgaacccg gtaaacgaac aaataggtgg tctttccgga aatgttaaac 337440 aaaagtttc ccctcgcatc tcggtcactt ttacttttcg ttattttgta atccccaggg 337500
tatgatacct tatagcttca cagttacaag tcattttctc attactttgg gtctctcatt 337560
ttcgattttt attggcatta ctatagtggg atttcaaaaa atgggcttca ttttttaagc 337620
ttcttattac ctgcaggagt cccactgcca ttagcaccct ttttagtact ccttgagcta 337680
atcccttatt gttttcgagc attaagctca ggaatacgtt tatttgctaa tatgatggcc 337740
ggtcatagtt cagtaaagat tttaagtggg ttcgcttgga ctatgctatg tatgaatgat 337800
cttttatatt tcatagggga tcttggtcct ttatttatag ttcttgcatt aaccggtctg 337860

-continued gaattaggtg tagctatatc acaagctcat gtttctacga tcttaatctg tatttacttg 337920
aatgatgcta taaatcttca tcaaagtgct tattttttta taattgaaca aaagcgagtc 337980
tgaatgggta tacttagtcg tggagcattc cgagtatttg ctttagggat cgttcctgcg 338040
catctcctta ctttatagca gttattgctc cggttccaga aggtatagct cttggctcag 338100
cttttcttag aaattggaga ctgttccaat ttcctactga gataggcaag cggagggaga 338160
actagacgta tcttgctagg caaagacagg ttagaatgga tagctcgcgg gtgggattga 338220
cgggatagat cactattgca gaaggaggta gaaccgggga agaattatgg ctataaaggt 338280
cctcgccctc ttaggcacat ggttctaaag attcaatctc aaagcggtac taaagattag 338340
gcagaagcag aactagaact agaattcttc gcccctccct tgtaccaaga agcaagttca 338400
gaacataagg ataatgggct cgtctattag aagttattag tttacggagc tatctcagat 338460
atctcgagta aggagacggg gcgggtttga tagttagagt tctatttcta ggaaggaaga 338520
gactatcggg aagctcactc tcggccgggc tcgaagcaga aggtagaacg taatatctct 338580
tgttggttca gctcatcaag ctattacaaa agagtccagc ggagacaaag aaagaagcca 338640
ttttacggta ttttcgcttc cagtccgtaa ttagatcttc aagcttagtc cagtccggat 338700
ccatcctaaa ccaaagagcg gggctaagcg aggggcatag cgatacagtg ttcatactcg 338760
agttgctcaa atccagtagg aatatcagga atagtaggat ctagtaggag cttgccttgg 338820
aatgcagtga gggagcccgg agctattgaa ttctttcata acccaaggag aagaatagga 338880
ctctttacca gtatcataac ctctcgatgg gaaatggaac ttagatcacg atgtgaacct 338940
acttatgagt ggaatttcgt tgacaagcaa attccccgga aaacgaactt ttctccaatt 339000
gagatgcttt cttcatttat ggattctatg cgagattcgg ttagtgtgaa gtgtgatcct 339060
ggctcagaag gaagagctat atgcttaaca catagagttc gatgtaggta aggatgtgct 339120
ccaaagtttt caattccacc ttatcaacct gaaaagagct aatacgggct tagcctgcct 339180
tttatcttat ccttctattc taggcgagga ggtttatttt taaatagtaa atagccccat 339240
aaaaacaaca aactagtcaa aggacagcct gccttattct tctcccgttc gggaccccta 339300
ttttctcgga gatagcctgg tctgagctag aacagcagat tcgtgagcaa gagcgtattt 339360
cacagctgat tcaacaacag ccatttttc tggggaactt tcatatgagt ctgttctttc 339420
ttttaatcca ctataaaggt tcttaatttt ctctttaata tgaaggagaa ttacattctt 339480
gaaaggatca agggctctac cctctcgcat aaagtcttac gctcttatcg tcaaccttcg 339540
tggcttttgc tcctttggtc tcgctatttc attcctggtt ctctctttca agcttctttc 339600
catcctgggg atttcttctc attccgtccg ttctgctagc tggtgtcgcc ttctctctta 339660
cttatctatt cccatccatc tttacctctc ctactccact acttccctcc ttcaaagcgt 339720
gattaatgcg ccttaaacct ctctcttgaa aagagcattt tttagtggag ccttagcacg 339780
tgaacccata ggaacagggc ccttcttctt tgcaaaaaag cttctgaatt atcatcacat 339840
cagtaggcgc agaaagcaaa tcttggtatt gacttattga aaatctcttt gagattgctt 339900
agacaaatct tttgtgtgag gccgctgttc ccccaccttc ttaccttgtt ttttgggctt 339960
aaaattctgt gactcataag ccctccatat ctaaagatag atggctaaag ggcgggttcc 340020
gcagttaact aagaaggcga tcgattggct tggagaggaa acgaaacccg gactgaaaac 340080
aaaaggatag gaatgaattg aataaagaaa gaatatatag aaccttgagc attttctctt 340140
ctcggcaatg gttgagagta aaaaagggta tccgcataga aggattgctg gtataccggg 340200
tagatgttta tcttttcgac ttcagcgaaa atgtaaaagc acaaatttcg taaatttttct 340260 ttctgtcgaa agggaagagg acagggtctt acttacttaa aagtaaaaaa aaaaatggaa 340320
gtttcctgtc ttagtttcac ttccttgaac tggctactac cgcgcaacgt gcccttgctt 340380
ggtgggtcgt taattaatca gttttaaaag agggatggat ttcgaccttg ctttgagtcg 340440
tcaggctagt aaagcgctac ttctaaaacg atcgttaagg tcattcactc gattccctcg 340500
gtggctctgc taccgatgga tcaagatatg ctgcctgcct atcatgccaa aggcgctgct 340560
ggtggatatg ccaaagatgt cctggctctg aaccgggtac ttgaaatgct aaaggtactt 340620
cttatggtcc tgcttcaacc acccttcctt ctctaccttt tcttcaaaac ttaagctact 340680
tagactgatg ctggcgatct cgaagggaga tatctggacc tggagctact catcttgatc 340740
tttattatat taggatgcga ggaaagggaa agaaggtgat aagcaagaag aggaaagaag 340800
aatgttaaag aagtccctat aagtacttca cttagccttt ctatagtctg tctttcttcc 340860
ctcttccctc aaagcgctct ttcatccatg cgcatggttc ttactttcat ttcccctcct 340920
cacgtaggag cgcatcttgt tttcaaagat gagttgtaga tgagtcggtt cgatcacccc 340980
acatatcgac ggtttttaat gccttatcct aagcccatct agttgatcga gggatagacg 341040
agtataaaga agggatggag aatcttttat ttgatcttga tttgatgtat atgttacgat 341100
gccttcgtat tcaggaggat tggggtacgg cagataagaa gagcgaccca aaacggaaag 341160
aagagtatga ggggcagcgg ctcaccgata ataagaagaa ctcacattct cgtcctgaca 341220
gatgaccaac ctgttaaggc atctttctca atgaccatcc tctcccattc cagttctttc 341280
tcttttttta gggacaagtt cattttcatt ccctcgatat ggccaggtgt gaagcaactt 341340
cacgatccaa tgaattccct aaaatcggat gacacaaggc gaactagaat aggctgattt 341400
atccacaaga atgtcataaa ggttttctcc ggtcttcctc aaaagacagc tttagagcgc 341460
aagtcaaact catgataggc gagaaatcac gcgcacatgg tttagcggtt tgctgtgctc 341520
tgtgatctta ttcttctcaa gacccgatgc ttcatctgct tctttagttt agtaggactt 341580
ctttcacgct attgcgtgaa acatttgttt ggtctcccac tgctactgct atctatgcta 341640
acttgaaagg tatggctact ctcttgtttc ctgctgaacc tccttcccaa tacaggcttc 341700
gcagccatcc ctgcttgcat tttttaaaaa agtttggtag ggctgccaa gcttgactaa 341760
tagaataggg tcccettaaa aggagaatgc ctgccctgtg ccaccttggt agcacaaaca 341820
aaggtcctgt gtaccaggga tgtacgaatc atagtaataa actttacaaa ctttattagt 341880
tgcaaggcga ctttgctgta aagtttatta tactcttaaa gtatattcta aagtaaaagt 341940
cttcttagta ttcaaatttt tgactatgaa tattcctacc cttgcagtgc taatatattc 342000
attagtctga gtcttagtct actaaaagca taggaaagga agagtcaact cttatgttgc 342060
aaggttccac cccaaccaag taataagcac taaactgaac tctataagga tagacggggt 342120
gatttctcac tacaaagaaa aaggctgagg atttgaaata gatagaaagg agtccaatct 342180
aagcaagcgt agtggaggaa aaaaatccta aaagtaagca agtagttgaa ttagtccctg 342240
ctagtattgg ttggtcttac tttattatac aaagsthhgd ggcaacgcgt htghvgtcad 342300
chgcdtdbgv vgtacdvhvc gaaggcccct cgaatcttcc ttgagttgac gtcactggga 342360
catctaccgc ttggatcctg ccttgttagt catccgtaga gctaaaggga attttttgaa 342420
gccattccca ttcccacaca ccaataccaa ccagggtggc tgttcagtaa gtcctacccc 342480
taatagaaag gataaattgc ttgcgcgctt cgtcaagtaa gagagggatc ttaggccgaa 342540
cagatcaccg gctccgaagg cctgcaatcg tgactttagt tccggtggtt cgctttgctg 342600
ccggggtgca acagcctttg tgacacttcg aatggagtgg tccgtacgcc cctcccctcg 342660
ccaagcctga agaaaggagc aacttagata cctctttgtt aactagattc ctggtttgct 342720
aaaagggtcc ttgggcccaa tcaatctcta tactcttgat gcaatggact ccccaaagcc 342780
actaaaccgc tctcttccac ccgatttgaa cagaacctcg ttctagtgag attttatccc 342840
ttttaaacgg aaactcagtt gcctatctga tccttggtct aattgggcct ttctctatag 342900
ctcgaatcga atagctgggc taccccttcc cttggcttgg ttggttatat aagagaatcc 342960
caggagaaag caagttagac cttacttagg gcgaaagatt ttttggatgg ttcattccag 343020
tctgaagtca gtcaagtcat ggaattggca gaagttcccc ttaaccaacc ctaagaggga 343080
attcttctat tcattaagat gaagccattc agtcagctct gaatctgaac tcaatgattg 343140
cttttcaaga agggcatgaa gctttggctc agtacagtag catttgactt tgggaaagag 343200
aatcgataga atcgatcgct taccttgctt tggcatgcca gaagcatttc gctgtggttc 343260
tcattgattg agtcgatccc gagacaaagc aaagggagtt ccgtgggttc agtttgctta 343320
gaggcagaaa gcctagaaga ggcctagaag tcataaggaa taggcaatgt accggcaact 343380
ctaaggtttg gctttttctt ttattgactt ttgagtcaat gtcgcatttc gcgtgcttgg 343440
ttagatctcc taacctaatg taatgaagga gaaggcagaa aaaaagatgc ctttatccct 343500
agagatgcag gagcttgcct taggacagaa atgatatccg aatggcgtac ggagctgctt 343560
accctaagac ttcaactcca tcttacatcg aagtcagttc ggctggatcg agagaatctg 343620
gataggcatg atcgaaagag gggcaactct gtctccgcct ctgctcgtgc actcgttaaa 343680
gtcatggcct agcctagttg gtgaaggagc ctacaagtgg taaccgctct gtatccgtca 343740
tctctttgaa gaagcagttg ggctacaagc ggcgctttca aaatcccgtg actctcagtc 343800
atctatcttc ttttcacctg aaaattttgg attggggaag cagagaatca aaaaaaaaaa 343860
aaagtcatgc ttactataag aaggaagcgg gcggagaccc gtgcgtgcag caggtgtaga 343920
gtcagtcgaa ctagtcctgc gaatatgcga aaatgttctt tatgaatgga gaccagacac 343980
aattgcttta gcggggactg aaatcgtgac tatgtgttca tgctttcgaa aagaaaacaa 344040
ccatctacac ggggcgctat ttgtctactt attgcattag tcacgtctat tttgaagtct 344100
tatttaactc gttcgatgtg aagcccttcc acacctgtat gaagcatctc ctctcgggat 344160
tcaccggact tcgtagcttg aaacaacctg tccttttcct atgctgaggc agcaccaaca 344220
aatcaatcca tcgaagttcc tattgacata cataaaaata tagggatgcc cttgatgatt 344280
cggatcatct caatcaattg attgggaaga gattacttat gagcaaaggg aggacgaagt 344340
cgcaggagat taggtattat ttaaactgtc aaaataaggg atatcgttga ctggtacaag 344400
aatagaattc cttgcttaca ctttctttct actggttggc ttaccctgta tttcaagagt 344460
aaataccgca gtgaggaata gcggttcctc tctttgtttg gtctaataaa aagattattc 344520
atcaccgcaa ccactctcgc ttagctacca cttgtctttg cttgcttact tctaaagcaa 344580
accagactga agacagtaga gaaagacttt tattacgtta tccagaatgc gatgccccaa 344640
ggcaagaaag tagcaatcgg ctttcaatcc tatgatttta ctcgaatagc taatatcaga 344700
gtagcagata tggttttagc ggaagctgct ttccccggat gcggaattga aagaaccatg 344760
ccttttttct tataaaagcc tcctcatcaa ctctctatct ttcgaaccca cctcaccgag 344820
cttaacgccc tgtggacttt tttacgaagg cctaacttga caggcccgga cggccgattc 344880
ataagggtct gagccttggt cggctgccct actaggtaag gcaagcgctc accgatttct 344940
ttacgtcttt tcgatcgtgc tttccgtgaa ttgaaagggg aattaattat ccagcagaga 345000

-continued tggcatccat tagcttattg tcggctctca ctctggctca tcatccagag gcgggttgag 345060
ccccttgcac agcttttagc agatgattcc aggcaagaca agatcagggt caatgaagtg 345120
tttaaggaca atcaatggca ctgggattgt ctgcacactc aacctccaga ctttgtgaag 345180
aacatcatct cctctatgca gcttacactc agtccagatg aagatgattt ggcaattttg 345240
tctccaactg catcaggtaa attctctctt gcttcagcct ggaatatgct taaacataaa 345300
aaagggtgtc cttttagatt caaagatatg gcataaggat gtgcctttta aaatggcatt 345360
tcttacctgg agagcagtcc atgataaact cccaactgat gggagagtgt ccaggtttgg 345420
tcattctctt tccctaaatg ttattgctgt gttgactcta ctgtgaactc aagcttagaa 345480
tctgttgagc atctcttttg ctctggtgtt tttgctcaac tggtttggga acatcaattg 345540
ttgaatgcta cttcttaatt ggtggaacca caaggtcctt aatcctgtgg cttcatatat 345600
tactaaggtc atgcctcctt tggtttgctg ggagctgtgg aggtccagat gcagcaataa 345660
atatggttct gagaaaccat cactcaatag atccaaggca ttgatcacat actccttatc 345720
tcacctgctg cattctcagt ttggcaaggt tagagtaggt gagagctggg agagtatctg 345780
tcatctgtgt gatgcttcaa tgacttagaa atctgtggct ttggttaggt ggatcaagcc 345840
accactgctt ttgtcaagct taatagtgat ggtagctgta gagatggtat ttgtggaggt 345900
ggtggtgttg tcagagatag tatgggtgct cttattatgg cttactccat tcccttgggt 345960
gctggaacca gcaactgggc agaagcaaag gccatgcttt tggccttaaa tggtgcattg 346020
aaagaaggta caggttggtg atagggagac tgattcctta ttgctgtcaa gctgcatttc 346080
aggagaagtg aagtgatccc cacccgggaa tcacgaacgg gaatctaaat agaaaagaag 346140
gccctggcaa agcctctcct aggcacctaa gggcggataa tagcagcgga tatatcgctt 346200
tctgtttccg ctctatctgc caagggaaat cccggtaaag ggaaccccga ccccgagaag 346260
accgtactca tgtgcaacta attcaatagg accggttatg aacccaagag aagagcggat 346320
aggagtactc atactcaagg acaggaagct ctcacagcgt gaaggcaaag aataactcct 346380
attggaagaa gagcgtttac gatcagagct ggaagagtgg gagggaatga aatagcaata 346440
gccgctactt ctgtctgcgg ctatcttctc ctattgatta agcccttcaa aggaatttct 346500
tctatttctt ctttctaaag gcaaggctaa gccatccgcc cttcattgct gggtaaaagg 346560
ggagacggtt cccaaggggt ggctagttcg agtaagagag acggatacag ataaggtcct 346620
ttttctgaga gacccgctct tgacttttat catacccact agtaagcgca gtggatgctc 346680
cttcatacag ggacagagag gcgagtgatg ggcactactc atcataagaa agcagtcatg 346740
cagatagaaa gagtaaaaca atgactctga ctaagtaaag agatgaggtt tttttctcat 346800
ctattttcca taccacagct ctagacatgc gccccgattc aaactatgtt tcaatcatac 346860
cacccttgtg gggtgttcgc aattcacatt aaagaccctt tccaaaggtt gagtaccttg 346920
gctcgggtag gtggtgctgg gttccgtgtc cttggcaggc tcgaccatcg gagatccgtt 346980
cattacgaac gttttttctc gatgtggacc aagctccgac ttccttttag ctttggctcg 347040
gaagaggccg gcctttgagc ccgtattgga agggatcttg gtttctttta gaaaagaaac 347100
cccaagagtt acgtcttatt cccgaggaga tgtttgatct cctagtctag ggacttcttg 347160
taagggcccc ttatttatgg aatgggtaat gtgttaaagg atagcttagg tactgcagta 347220
ggtttggaat tagactacct taatatcaga catcaaagac aacacagaat ccaagtccaa 347280
gacttgagtg ataatgctag agaacgtatc cttcttggca aggcaaacaa cctttgccaa 347340

-continued ggttccgaag gaaagataga tctgaactaa cacaatcact ataatcatcc ctcttgtatg 347400
tatataagtt ttcgatgaaa gaggggatta tcctacgata ccctaggagc gtgtcagaaa 347460
gatgggtacg cgaagtgagt aatggtgaaa ttctccgcca caagccctct gaagcgagga 347520
tgcacactgc tttaaataga aagcgcaatg caacatcccc gaacgtcggg ccgtcctcat 347580
taccgtaaga gcaaacaggt aagctccaat acagaactcc ttagtaagac cgtcagcggc 347640
tatcaagatc gctttgttaa gcagtgacct taagaaccga gagtcttcta aaactctctg 347700
ccacaaacta aagaattgaa ttaccttgcg ccggtatcat ttcgcttgag ccgggaactc 347760
ctgtttacct tgcgacaggt attccttctt atagatacca ccgaaaaagc ggaagactaa 347820
gaagactttt ctttgtctcg tccacaccca ggaaagaaaa gatcagatca gcaacggctt 347880
tcgagtagag gattttttgc ttttaattat tccctcggag ttgagttaga gttagcagat 347940
gggatctaat tcattagagg aagggatggt gattaactga tagaacctct tctcttcttt 348000
caaatcgcat ctctcaagtg agaagaaaag gccccacgga gcggtgggaa agcaagggcg 348060
tagcaggaag aagaagtatg aaagcagcaa atctttcctc ctcgggctgg gatcacgaac 348120
gggaatctaa atagaaaaga aggcccaggt cgagvgttcg ctccctctct ctcagctaag 348180
gaaagagata gagaattcat gtacatcgct atttcctgcg gatctatcgt atccttactt 348240
ctctctgatt gtgatttccc ttgtgccgta ctataccgct aaggaaaaca aacaagaacc 348300
aggctaggct actcctcttc ccctttctga atcaacttgt ccttgcgctt accacttctt 348360
aaaacttgcg agcgagtgtc gatcgctcct ttgcctgggc aagatctgac gactcctgcc 348420
caaggcgggt tacgaattca gattagctac tgccaaagag gccaggaacg agcttccgct 348480
ttatctaaag aaaaacctct tcctttctct cttcctgatc agcggattca gagtgatcag 348540
gtgaagcccc ttctcgttgg atgaccggcc ctttcttaga cttggtgaac tcctgtcgcg 348600
atgaattaaa ctccgttcca tgccccgctg cttgtcaatc acatcggaaa gtcgttgggt 348660
cggcggagac ctctttcggc aaagaattat atcacaaaga aagccccaac tagggactac 348720
cacttatagg agtcttcttt gctagtagaa tgccccccacg agaagaaaga atagtgggat 348780
gctcacgctc tcgttggacg tgacagtcag ttacagtggg taaactaacg aagggaagaa 348840
ttttatttca tcacagaatt gaatcgggtc tcatcccttc gattcctcgc tgcatacttc 348900
aatgagaaag gaaaagagct ttgttgcgtg cttcttcggg tgtggttgca agatctcgct 348960
ttcagttcga aaatgtgtac gtagcttcct tgtacaatag ctctctctct gagagagtga 349020
tcgggaagca ttctctcttc ccctccgtat ctgaccctga cccacgctct agccctcttt 349080
cgtcgtccaa gtcgcatacc tcctaaacag tctatttggt tttaaacgcg atctatttaa 349140
ctgattaact gtgaactagg tgggacttga ttcttttgct gaaaagagaa ggtacgtagg 349200
cagctctcct aaaagagtga agttccgccc gcgtttgaag gctagctcct gcttcggagc 349260
ttcatcccca catctcacat attggaaaag gcaaacaaaa aggggaactc agtcaataga 349320
caaagaaaaa acggatatgt tacacaaaac aatccaatct ttgtctttct aaggattgat 349380
ttttcttgtc gtagttcata ttcatattca agttggaaaa attcttcttt tcttcttatt 349440
gtggaaacgg agggaaggca aaggtccgta gaagctagct ctcttatccg cttgcctctt 349500
ttaatgaaga agggttggtt taattgatag ctttggaata ggtagtccta tggactgctc 349560
ttttcttatg ccccggagtg gcgagaatac gaagctagat cagcaggaat gacagcggtc 349620
tcttccaaaa gtgggtacag gactcggatc ccatttccaa ggtgaattgg aggagaaatg 349680
gatactggta ttatagttgt tgaaagacct attaattaca tgccaaaaga gcaaaagttg 349740

-continued aatcatcggc ttggccacct tatcctttta tacaaagatt ttccttgttg atataccgtc 349800
cgatgcgctt ggtgtcgact ctgatcttcc ttcacttgac aatggggcga aggaacgacg 349860
tcctgactaa acaaaagttt ctttcttcaa taatggcttg gtcgaaagtc gtaaagaagg 349920
caccggataa gcagctaaca taaacaacta ccgtacagcg catcccgtgg gcggccttca 349980
aaggctatca ttcgtaggac gagacgctaa cctacgcccg tacattccaa cctgcctcct 350040
tgggacttag ctctgaagat gaattcccgg ttagccgatt accttgcccg gttaggagaa 350100
cagttagaag taggaaaaga tgccgacacc gaacagttaa agaattctcc gttgcttcaa 350160
gactgccagc ctattcgctt tgagccgaag cagacgctgc ccatggagag cctttttcctt 350220 tgtgaacatt tgtgtgcgtg cccataagac atgacaaaaa atacaaaaat tgggcttcta 350280
gacgccttac aataaagaag ccccggcccc tcggtgtctt acacgtcttc ttcgatcctg 350340
ccgaagctgc tttctttctt caggtagtga agtcactccg gtttgtgtat gacttgacgc 350400
tctaaagtct ctatcttgcc cctagttact taatcgtatt cgacttctat cgcagatctt 350460
ttatttctta cgcatttctt tccattagct ctccaagctt cctatctttc cattcctcta 350520
gctctcattt cgcgcatgcg ctttgcgctc ttggcttaat aacatcaaag aggaatcgaa 350580
cctcttccag ttctgtgaga acaaaaatcc atttgatgtg tagagtagag actgttagat 350640
aatcttctct ctcactagaa agtatatgtg tatatatact ttaacaaagc cgacctggac 350700
gtccacgacc ctgagtacca tgaggaacag ctctaactgg ctatgtatgc tggaggaggt 350760
gcggtaacca tagtaccctg ctgctgcgtg cctgtctgac cagtaccact atctcgaggg 350820
caaaacctcg taatgtgacc aacctctctg caagtgtagc aactttgaga tgtaccccaa 350880
cactcgccac gatgagtgcg gccacaagta gaacatgaac gtgaccctgt ctgagatgat 350940
ccacctctct atctctgagt ctgctgctgg ccctgctggg ctgggggtgc ctcggaagta 351000
acctgaagtg ctatctgagt aggtctagac tgaccacgac catgcttgcc cttgctccca 351060
gatggagcac cactctgtcc tcctgtagtc ttgacctctt gctctccctc tcggctatgt 351120
cccgcctctt agatgccttg cacctaaggg tggtatccaa cacgtcggca taagaaccgg 351180
tccgaacaat cccagcaatt gccatacggt aagccctcct tttcttgaaa aaaaaaatga 351240
agcttagaac tgccagagcc aattattgtg ctttttaacc ctgttttcgt gatactctca 351300
cattaaaccc tactgttcct taaggtaacg gaaagcaaaa ctgaattcct aaggtggaga 351360
gcaaaagcaa taaagaaaag aagttaaaga acatttcaaa tgcgtcgaca taaatatgac 351420
tgattctgtg tcaatacatt gtaaattttc tcaagttgta ctgtgacaaa cagctcaatc 351480
aatagccgac atgtttatcc aaaaaggatt ctgatgaaaa atgttattac ctcattttga 351540
tttctggtct actggaaatt tagttaatag tagagcttca aagtggaatt gatgtgcacc 351600
caattccacg gacattgttg atatagtttg ctactacttg tgtagcttgt tttttagtgc 351660
cgcttactct actctattgg gtaattttag agtgtcttta ttgatgtttc cttgacagga 351720
ttagaataga ttcatactca acatgacaat gatgaaaata tctttatgaa atttctcgaa 351780
atctttgaat gaatcttcat tttggacagt tcttaggcta ccctaacaga cgtgtgggaa 351840
tgaagctact actatctttt ttacacgcat aaatatacat agtaaaaatt catcgcaatt 351900
cattcttgaa cccgttgtgt ttagtctaaa tccgccacta gaagaatccc aacgtatcag 351960
cctctttagt aacttgataa taactataag gtattttgtg tatcataaaa acctatacgt 352020
agctcaagac gaggggtcat ctttggcaac tgaatagggt cagggaggta tctccttgat 352080
taatagttga acatgcttga tgaacttagg gacatgtata tacaatacct cgaggtacaa 352140
gcactaaaat ggcaattttt tgttgtgttg ttctatgata gtggtttcat cttctagatt 352200
aggcactgaa actgatcatt tttttattcc ttcaaatctt ttattcaggg gcctggattt 352260
ttggctgtat tctgtaatgg ttttactacc tttttttttt caactcttat tcattttttc 352320
agatttaaca ctaacttact gtccacggat tcagatattc aatcccacaa tgattggaaa 352380
tttttgcttt cagtacccca ctcttttgaa aaataggctt ctgtgcaaaa aatggggtgt 352440
agaatgtgga accaaatccc actagcaaga gcctattcca taataaggtt tctagaggat 352500
tttaagtgct tgttaattgc tttgcctctg tgggcattgg aagagccata ttttacctct 352560
cattttggaa aatgacagct tcagatattt tctcttactc cctcttctat cttatccctt 352620
atagtcgaaa ttttcttggg gcagtggtac atgcccataa gctacagtac taacagcaaa 352680
aacaatacca atttatttaa gggaagaaca actaaagtat cttgacatgg aaaagaaatc 352740
actttagaaa ccaaacagtc attcaactag atcaaaacct gtaagtagtt aaataggaga 352800
aatagaacaa atcgcttaac acattactct tgttagtgaa tagtgaatct ccatcttttt 352860
tttttgaatt caaacgttta agtaccttct cctttgctga gctagacctg atttgaatac 352920
cggttttatg gcctcttctc ctgggacctg cttcgtcaaa ttcagcaacg ggagcccgag 352980
agggttaagc agcgtcagga gcattggaag tttcattcct gaaatgaaca aatcattaat 353040
gggcactttg aagcaagttg atcctagaag actaacctcg tagctcactt agatcaatca 353100
gttcaagcat tgacaaaccc gccttccttc tgtgttcagg acggagactc tttctgcctt 353160
tgtcgaactg ccttgacgcc ttggcaggct ttgacctgct ttccttcgct taccggagag 353220
cggattcttt attactgact tttcgcggtt gatcgcacct cgcacctaaa ggagccggtc 353280
cttgtgagga ggaggactct tctcttgctg tcaaaagtgc ttactcatgg tctatcgtgc 353340
agttgatgat atcattctgg actagtttcc aggcatacgc caaccataca taccgctttc 353400
tcgttcagga atttcttaag attaaggttc gaaaggacca ggcggcgatg aagtatgagt 353460
ctaaaacact atatgcagag ctgccttagc tcaatagatc aacgaatcag gagatgactt 353520
cttaaacgtt cgcgaatgga aaagagttgc tttaggcacg gaccacaaac ccacgaacct 353580
aatagttgga tccatgagga gacaggagaa agccattcat tccggtcatt gagcccggat 353640
tgaggattga ttgatctaaa ccaaagactt gattatatag gagaaaggcg ttctcatacc 353700
ctgataccgc tttgtggaaa cctagaacag aagaaagtct ctttaggatg gctctgtcct 353760
agctagaccg agtcacaact acttattata gaagactcag gcacacttcc ctatacttct 353820
cctaagtgac atcaaaatcc tctttcagcc gattcgaaag cagtaataga tgagattgaa 353880
tcagacagaa ggttcacccc tcaccctggg ggattgggga gttgagaggg atttggacgc 353940
ggtagtatcc tactattcgt tggcgctccg taaggcccaa agtcaacgag atcttcttta 354000
tccggtgcgg ggcatgtact atcttctgcc ttctgctagg ggttgaaggt cttctctctc 354060
gtttgatgat ttgagaagcc atcttctctc cctcccaatg cttcattctc tgctttttgt 354120
actcgttcga taacacgaaa cgaagaaaac tcttagcccc aacgaactga ttcatgttct 354180
tgacaggctt cttgactcca ctgctaccca cccggagtcg actattgatc cgtcgcccga 354240
gccccttttc ctttcgtcct tgcctgaggt acgttgttct tatttgtgac acccatatgg 354300
tttgtgtctg acccagcata gtgcttttct ttccattgtt cattcttctt tgaagccgca 354360
aaatgatagt gaggcagcaa ggatccctca gtgtcagcag gccatatctg aggaattgcc 354420
agtcttgcag aagacgtcgt tcattaccat atcagataga gaggggttcc aaacctcttc 354480
ctgacggaaa gaccactatt gaggtgaggg aaattcagac tcactcttgg tatcgatctg 354540
agaatacttt tgccccactg taaaaggtta cttttgtagg gctctgattg aagttgccac 354600
ggaaagaaag tagcctttgt tccagtgaga tgtggggaat ctttttctga attgaaaact 354660
acatgagggg atttacatgc caccttcgcc agggcgatca gtttcttcac atctagttag 354720
tcgactcagg aaggcgttgt atggactaaa acaagcaaac tccggctcga aagcaaggga 354780
aggccctatt attggggatc ttccttgacc gggtggaaag gtctcttttt tctatgtgtt 354840
tcgcccattc gagtgttctt tgacgatgac atcataggca ccagaccctc ggtccgtctg 354900
tgctgcttcg aatgatcggg tttcaacggc ttccctagct gtactgatct atctggcagt 354960
tcactacgcg ccgaatgatt ctttgctatt tcctctttct cctccctatt atttgattgg 355020
tgctgcctga aaagagttcc ctgtaagagg gacagtcata acaagattat tatttgcggt 355080
ttcatcagac gggatcaaag atttcgaaat tcgccgatca taggtaagcg gttctacaaa 355140
ggtgaagaga attcctaaaa ttctcggagg aaatttttg cttagaatgg ggattctgta 355200
gggccttggc ggcccgtaag gggttcatcc ctgtggtata aatatattcc actcttttt 355260
ttttttcttc tgggtcggca acttgaattc cgttcctttg aaggaattgg tcggcttcct 355320
cgctttcgcg agtgtctagc tgttctaact tggtgacctc tactttcgag agattgttag 355380
gctccatggc attcctagac taactatcac ttctgatcgg gattccaagt tcatgagtca 355440
ctttttgtgc acactttgga gaaagcttgg aactcgtctt caatttagct caacttgtca 355500
cccacaaacg gatggccaaa ctgaggttgt taataggatt ttggggattc ttttacggag 355560
ctttgggggt gaaaatattc ggcaatggga cttgctttta gctcaaatag aatttgctta 355620
caatcagtcc actagccaaa ctactggttt tagtcctttt taagctgttt atggccaaaa 355680
tcccgagagt cctctggact tagctccact tccagctact cacaacttta gtggagatgc 355740
gggtgaagaa aatgaagaag ttgcatgagc gagaaaattt ctaagcaaaa tgagaagtat 355800
caagctcaag ctaacaagca tcgcaagttt tctgagttca aagaaggtga tctggtctag 355860
gttcatcttc gaaaggagcc tttcccgcga ggacaatttg ctaagctcaa gcctagagct 355920
gatggaccat tcaaagttct caaacgcatt ggtgaaaatg cctacaagat tgaactacca 355980
gctgagtatg aggtttcaga aactttcaat ctttctgatc tttctcctta ttatggtgaa 356040
gaaagcacta acgactcggg ggcgagtctt cttcaacttg acggggagaa ctagaaataa 356100
aggaagttgt tttggctgta gtttttccag gttgggtaaa tttctttaga aatgtcataa 356160
aagagagggg ctttctttct tcagcatgtg agggaaatgc cccgggtacc gaagttagcg 356220
gatagagagg gcggcgggtg ggcacggtag cagatacgtg aaatgagatc ttcttggaac 356280
aaggtcagag gcgttggacg gaccagtttc ttcagattcc aatgatagat ggatggtcag 356340
gtcggtaaca tatggatgga ggacttctac agggtcttct cgtgcgctcg actagaaagg 356400
tggttttgta ggcgaacgaa ataagttttt ggaggcgagc ggagtgaggc aatgaaattg 356460
tttaggcgaa agaaaggaga gaacgagtgg agtatactcc acgaggtagg tgggcatgga 356520
agcacgagag gtgttggtga gtggggaagg taaggtagtc gacctacggg agtcgcgagc 356580
gttagtgagt tgacaaactc gccatgcatt cattcgtggt tggaacttct ctctgcagag 356640
tagccttgtg catagaggct cgcgcccttg attgattgat tgaccgggcc cctaaagctg 356700
cacagctatg gcctgtaccg ctaactctca tgatgcttct ttctgggaaa ggaagaaaac 356760
taaagcaagc tacctttact ttttgaaaga ggaagacata aaacaaagcc gcttctcctg 356820
attgaatagc tcgtcatgca gcaagactaa agaaggctct gaatggccgc taaattaagt 356880
caaagactaa gtaagctggt acgtcaggtc ttgacctatc attctgttat cgtgctttga 356940
cagctataaa atagcccttt cttaaagatt gtgagagctt ccgttttagt tgttgatttt 357000
gaagcattat aataagaatc atcctttcca caaatagatc ctcaaacata gaatcatggg 357060
cagctagcga taggcagggt ggtcacgtca aagtgtgcca atcatggtga tcaaaccctc 357120
tttttgttag agctcccagc cttgctaagc taagaaagat gcccttcatc ctcctttctt 357180
ccctttaccc ttccctctcg ttccttctct ctttctcgtc tggcttggtc tggtggttcg 357240
cctagttgga ggctttcagc tccatgccgt aggtcagggg tcggtgctaa ttttcctgat 357300
ctttctgatc ttgttgattt ttctttcgat agagtgtgaa tcatacgccg gatctaatta 357360
gatatatatc ataccataat ctagagtctt gtggagtagc ctccgtgcca catatactgg 357420
gcgatttagt tcgttcggga cacgtgggcc aagaagctct aggcaattct cacgatcacg 357480
gtcgatcatg gttcaactcc atgtcgtgaa agtgaaagca atcatttctt tcatcaacat 357540
caacgaatca ctatctctct ttcatcggta gggcgatcag tcttttcttt ttgtgtctaa 357600
tcggagtcta gtacctctct ggcccttatg ggcctccaca gatgtaacca aaaaaagaaa 357660
gtctaaaaag ttttttatcc tcgttggtct ataagcttgt gacttgatcc gctagcgcag 357720
gttcgattcc tgcttgcgag aaacgaaaaa tgaaacgatc tacagggatt tcatgcttct 357780
catccattct ttgagtgagt cgggtcatcg gtaggcttgc ttcaccggta tggctcatcg 357840
gcttattaat gactaagcgg agtcaggagt cgatcgagcc tttattagat atgttctatt 357900
tcattggcag ttccgatccg attaagactg gaaaatccat caataagaga gagaagctac 357960
cagcaagaat catatcaatg ttgggcaaag gaaggtactt tggacaagct tatatctccg 358020
aattcactgc cgattctgat gcccccagtt tcctcggcca ctgggacaag gagatccgat 358080
cttcataatc aatgggacga atgttttgat acctcaaaga gcgaacgaat tcctgccttt 358140
gcaataacag cccatcttgt gccacagaat cggttgtgct ctgcctcttc ccctctatca 358200
gaagattgcc ttgtgtggaa ggttgactct gaacttcagt caatgggagg tatcccctta 358260
tctaaggttc tttgtatggc actctaaact ctctttctta cgcgagacag aaagtctaac 358320
taccgaagct ctttcaactt gtcctgtctt tggataagta ttgcgcttaa gtcagttaac 358380
aagatgagag tcggaaaatg gaaataagaa ctgtaaagtg attcttgaat ccttctactt 358440
atgtagatgg agtccagtac gctactatat agactgaaaa ttcccaagac aatatcggga 358500
gtacccatct tatcagatat ttaaatatat cgtcaaactc tttcccgctg tacccagccg 358560
attctcaagg acaaaaggta tagcattaca ttttaacaga cagatgaaag ctaggtctct 358620
actccttctt catgaggaag aaaggccttc ttatcatcta gatcgacgta aggtgcgtag 358680
cggtctagag tccaactaag acttccatga aaggtctcat tcatgttgat tgaggagttt 358740
cttactgacc gctaaacctt ctctacttta gaagatagac tggaaagcaa gctcagagaa 358800
tagctaagtg gaagtcagag actccctttt ttaggaactt agactaccta tgtgctggta 358860
aactccacct agactgagat tcatcagttc gatcatttag tttgtgtcct aagtcctata 358920
tccttcagga aaggatcaat tccttctcta acttctactt ggggtcactc ctcggaaaga 358980
ttcttcattc gagttagctt ctttcgctcc ttcacccttg actgcattcc cggaaatgcc 359040
attcccatcc gctaaacctg ctccttctga gaatggtttt accccgctcc tcaatcttat 359100
tcagtttccg atcctgcttc agattctctt tcagttgtgg aaacaaaccc ctattcctat 359160
cggttgagta gcccaagctc cttaagagcg tattgtcccc tctcctgtga aagaaagagg 359220
ttgatgcacc cagctacccg aagtagagct ttctttgtcc cacctttcct tactgacttt 359280
cctagtttag atagcgtatt gagaatcatg tcaaaataca ccaagacctg ggcccaggtt 359340
ctctttcttc aagaaagggt tgctttaaac aacccggttc caaacacacc aaacaagcaa 359400
gcgactcccc ttccttagcg tacccgtcca ttaaggcatt cttccttctt gcgtatgtgt 359460
tatagctcat agctctaagc cccaattcct tggctcataa ctggaaaaca taacaacaat 359520
gtctcctagc tgcaaaagaa tggctcccaa ctgaaaatct ctcttgatca ctctctaaca 359580
gaaagccatt ttccctttcg caaaaagtaa acttggactt ctttcctaag cggagatttg 359640
gactacatgg acctaagcaa cccgccgaca ggggcagcct ttcactgttg gaaactttga 359700
ttttgattgg taggattctg tctaatcttt cctaatttag aaattgcact caatcaacat 359760
agtttccact cattccttct cgaccgcctc ttttctagtc acttttgatc aaatctttct 359820
tgtgattttc tattatctta tgagaaatgg tttgcttcgt ttgagccgtc gtcgcttaat 359880
gcatgtaggg gggctggggc ttttccccca cgaccccttt taaaggagaa ccagaagaac 359940
aacaatgaac tcaaagctaa tgaaggagat ccgcaacttg aacaaggtac acgggatctt 360000
tcctacccct ttctatttcg acttctttga aaggtgaaag agtaagaagc tagaccgact 360060
tgctcttaaa ttaaaagcag caagagcaag taagtaggct tttctccgca agaacaatct 360120
tgactttctt tatactttag aatataaggc cctttaaacg atcgtaaatg gcctgaaatg 360180
taacgaccta tgagagaagg gtttttagaa aagaaagcgt accaatccgg caaacaaagc 360240
aaaaacaacg gctcctacat aaatacaata gaattgaaat gctgtcacta gaacggacca 360300
cacaaataac atctttctag ccgcctaaag gaagtattca aagataagat aacgctatgc 360360
gcacacaagc aaacttcagg tatgcagtta gttctcaagc gattccttcg gatcttaggt 360420
gcgaccttag ggagcttgtt ttggcagcta ctctcttata gttatgtgtc ctggtttccg 360480
agttctagtt caaggcaggg caggacggga ctcacggggg ttggggggag ccttccccca 360540
gggaaaacct aataagactc attcgaatac ttgagttcaa gctcctactt cgaagtaagc 360600
ctatgggttg tttcgaagct tagcagctaa agcgtacttg cgtgttaaag tgggtacgcg 360660
gatttaggct actaagtgga accagaccat tcaacttgcc atttgcactc tcctagggtg 360720
cgatcgtagg aagctctatt agcgaatgca attccccgcc cgataagact gatcatgccc 360780
tgctgcttgg cttggaatca aactagccta tcatgccctt tcttcattcc tatatggacc 360840
catattccta tgttcttcca atgtttactg tattactggg attcctattt actgaaccat 360900
atcaaagaag ctactttctt tctggctttt atacccaggt ataaagggat agacagtcta 360960
agagagtgcc aagaaagaac acatacctat cacttttgga aggtttggaa ccctcgattc 361020
atccgactca aggagaaaaa gagaacaaga tgggtttggc tcgctgtgcc tccctcttgc 361080
cttaagcgac tcctagtgag cttttgaata atttaatagc tctgcccttc tctcttatac 361140
ctttatcgct tatttccacc ctttgacttt tgagccagcg acacctctcc acgaatcaag 361200
cctataccgt gcaataaaga cttttcctta tctttcttct tcaaattacg agtagagatt 361260
tggggagagt ggataggaca gggtggtgga tgacgtaaag gaagggaagg cccatcccgt 361320
gctttcgagc gattcttccc gcaaaaggca gatctttttc tttccgtccc aaatagaaca 361380
atagaatagg gacttagatg tgaccaaggt gcttgcaagc ttagggttag caggttgttg 361440
gctgggagag ctggtaaaag aatgaaacct tcaagagacc gtggttaaca agccagctga 361500
ggaagaacaa tctcccccag caataccgat cctccctagt tcaatcagaa tcgagaactg 361560
cggagaggtt ctaaccggcc tagcctaacc aaccgctaca agcgggcagg aaatagatgt 361620
ggtggagact caagtcaagg cgatggatca ctatcactat agatagatgc tttccctgga 361680
ctgtgttcaa tggcacctga tatgccaaca agggcttact aagagatctt gcatgtttta 361740
tagggtgctt cttatgtctt tccataagca gaagtctgag tagagcagct cttcccctat 361800
tcttaatccc acttcttatg tctgtcaaca agagcccagc ccctggttca atcgatagat 361860
aggccgaaaa cttctttctg gacaaatgaa cagacctttc cttacttgac ttgccaacaa 361920
agcggtcaaa ccagtaagca agttcatgcg tcagtaccac gtccaggatc ttaggaaagg 361980
ggaagctcaa atgatatcta atgggatggg catgctcccc actgctctat gatttattat 362040
agtcatactc agtttcgtac ctggtagcta gcctttcgct tcctccttgt actagatttt 362100
gacttgaatt ccccctgaaa gcgagaacgc actatatgcc tttaaaataa aaagaaggct 362160
ggaaaaaaga gagagctcct ttcttttcta gctttggcgg gaggaatgaa aatcctatcc 362220
tatacgaagg cctatataca aaaaaagcac tttgcctaga atcccaagtt gcctcccctc 362280
tcctctgagg ccgatcgcat ccacttttgg agcccctcgc cagtacggca gcagcccaga 362340
catagaccga attaggggcc taaactcttg agtagattgc ccatggaaag gagcttactc 362400
caagatctga ctccccccgt gtaggagttc gggaaggcca gaagtaaaga aagagcggta 362460
gaagagaata aagtgttgcg cccattcttc tttttcatag ctggagcaaa tggaaggaga 362520
cgtcgtgcaa gccgaagact ttgacaggtg tcggtaggca cgcctctgat aagggctcga 362580
tcctgagaat caatcccaat cgaatctatg gaagggagac cctctatcct cttaatctgt 362640
agagtatata tttattttag gataatcagt ccactgcggt gcccaagaca aggcaagatg 362700
aataggaatg ttgaagggac ataaggctca gctaaggtaa ggaaagaccc tgaccatcta 362760
ggtcaccaag tactcttctt ttttagggag ttggagacga tcgaagaggc agcaaaatag 362820
gaactttcga tcagggagag ctcaacaagg tcgagaccaa gatgatggat attccaagga 362880
agatcgaaga agatgaatga aggtttatac ctacccctaa ctggcactat gaatccaatc 362940
ccatctacat agatgttcct agccacgaga tgagggggtt ctctcttact gttaagccgt 363000
cttcaactct tctttcttta ctcctttccg catcggggct gataattgga tagaatctcc 363060
ttaaataaag aaagggggcg taaaaatagg gtttttggct cgcaataaag ctagggtcct 363120
gatcgagcaa ctagtagtcc tatctatcca cctctccaga cacaatatct tgagtaccta 363180
tgatggtgac cacatctgct ggcatgtgat gtttggacat agaatcgagt ccttgtgaat 363240
gggcaaagcc aggtgctctt attttacgac ggtagggacg attgcttcca ttactgacca 363300
gaaagacacc aaattctcct ttaggtgctt caactgcggt ataggtagaa ggagctggta 363360
cggaaaaacc ttctgtataa ggttcgaaat ggtgaattga ggtagagtag accgatgatc 363420
ctgtagtcat ttggccggct attgaaagaa aaagcttgca tctgcttccc ctattatata 363480
accggtccca tctctctcca aacctaacgt ggtagtttcc catcataggg ctttctatct 363540
atagattaag ccattaccaa ggagctaatt cgttcagaac tcagttgact gcttctatag 363600
agaaggcgga gcgtccttgg ctcagcatta tagcacatag ggcttcggcg ctactacagc 363660
gcttcgctaa ctcgaagcgc ctcgctatga gaatctagct tcgctaacgc tcggctaagt 363720
cttgaacctt cgcgctgacc gttcgctttc tcagtagcaa aagcgcttct ctttgcccct 363780
taaccttaag tagaaggaca agaaagatat tattggtttt cttgcccccg cttcctcatc 363840
tgcgctcatc aagccaactt tgctctttgg gaggtgaaac agcggttgaa gcggacattt 363900
cgaaatgaca gcatcgaaga tagatttcta tatatacacg gttagggtta tctcggactg 363960
cgttccggaa aaagcagcct acttgtgggg cactgtgtac ttacagcctc tacgataagc 364020
aagtgaatgt ggccggtgcg tggcgaacgg ttcatcaagc catttttcgc ctcaactccc 364080
taaataggaa taggggttgt ttacaaaaag ggtaagaat gactgtgata gccctctcga 364140
taccttattg gagctttgta actagtggcc ggtttcccgt cgcgtcagcc ttttcccagt 364200
gcgcggagcc ccaacgagga aggtgttagt gctttatcat tgggtcaata atgctaatcc 364260
ctctttttgt gctactccta gggcgggaag aagataagaa aacgcgaagc gttctcttgc 364320
tttcccaacc tgttctttct aaagactgcc ctctctcggc tggatcttgg tccagcctac 364380
tacgaggatc ccgtatccag caacccaacc tatacaaagg gcatcaaagc cccttgacta 364440
ggttggagct ataaagctta ccttatttat tattattaaa aggggaaagg gccttttcag 364500
ctggtgcgca ggagcgcact tccgttttcc ctttacgagt agggggtccc gtggttccta 364560
tgccgccgcg tttcccggtc cttttctttt agtgcttcga cccgaagcga tagcttctag 364620
ctagttcagt ggataagatg gctgcgctcc agctcactca agaatgggac ggcagtggtc 364680
cgccggcaag ctcgttctga tcttggacgc agtacattgg aatcctgaag caccaccacg 364740
aacgctaccg cgcgtccgcc tgcggtgcgg taaggcacca ccctcttgtg ccagcagcca 364800
actccggcgt gtcagcttag ttatcctcat caaaccactt acttgatgtc tagcttccca 364860
actggtagac ggttcctttt cccccaaatc aatgaagaag ggagacataa gttgattctt 364920
ccgaagaacc ggaagcgaag cgctatgccg gggcgggggg acggaaaaag aaacggctcc 364980
gaagaaaaaa attggggttc ccaatgcttc tccacgctca acgagatgcg ccaacctcgg 365040
gatgctttac tcctaacccc acaaggttcc gagacggagc ttaacctgag tctcggttaa 365100
gaacggcgat gatatacgtt tcacacggcg cacgattcca tggatagttt cattcgagat 365160
cgtgatggag gacatagctt acgatcatcg gctttgatca tgccactagg catttgatta 365220
agacattgca caatgatccg aacactttgt cgcatctctt cgatacgaat acagtaacga 365280
tcatagcgat ctcctctggt acctactggt atgtcaggat ccaattggtc atgaacatcg 365340
taaggtgctg cttttcgcaa atcccagcat accccagaac ctcttaacat tacaccactg 365400
aatccccaat cctttgcttg ctgtgcagtg acagtaccaa tatccactaa tcgttgtttc 365460
cagatacggt tgccggttga catctcttct aattcgtcga tacgagaagc aaattgttgt 365520
gtgaatgaat caatatctat acataagcca agaggcagat cttgtgccac tccaccaggt 365580
cgtatgaaac tggcatgcat cctggctccc gagactcttt catagaattc caacaatttc 365640
tcccgctcct caaaagccca caggaacgga gttgatgctc ctacatccat agcatgagta 365700
gttaaagcaa gtgaatgatt tgaaattcga gttatttcac ggaataacac tcgtatatat 365760
tgagctcgta atggtacctc gcaattcaaa agtctctcta cggctgaaga atgagcgtgt 365820
tcttgggcca tcatagaaac atagataggg tcgacgacgg aacgaagaac gaaactttac 365880
gacagctttt tcgtagacgt tcacttgcat cacatacaca agtgctctct gaaccgtgca 365940
ataaggtcac ccataacacg gctctcccac ttgagttatc ttagccccag gccatgctat 366000
tcaataatct aggaaaaatg gcagcgtaag gtaacaacga gtatggaaag ctggtcgcct 366060
ttggaagcct tcgccggtaa ccaaagcgta tcgttcccgc aaccactttg gtactttgtt 366120
tctagctttt ttaagttatg caatagaagg gggggcttgc gcttgaattg aagtagcgcc 366180
tttggaatat gagtagggct cctaagtggc gcgttcgtgg aggcaaaccg aaggaagagc 366240
aaaaggaagg ttgggtgctt gtggggcgag gccatccggc ctcgaatagg agggggctta 366300
gctctggagc ctccctgctt gcagaaatga atggatcaga aaggggcttg gttctctatt 366360
tccgggcggg gggtgaaggc cataagagaa gattgcccta ccggtaagga agaggggaaa 366420
aaggtgctgt catctatctc gaccagtttc ccgaggcgtt ggaaatccag accggctcag 366480
agaatcactg tcgctattta gcccttcgtt ccgccaacaa agaagtcatc cttgacgatt 366540
tcccattcct tccccgccga gccgcctctc ttcgccattc gatgcttctg ccttcccttt 366600
ctataacata cccaggcgcc ctcctttcca atcactaaga aaaaaaaaat accaataaaa 366660
gccctatcta agtaaagctt cgtctgttat ttttccggcc ccaggggagt ttattcgacc 366720
cattccccag tctcccgcac tgctcaagta agtgtgcgac tccgtatgag gacctccttc 366780
tcttctgccc actctccgtt cacacggttc tcaaagcaga ggaggaaggg tgggcagcag 366840
gtaccacgag ccctctgtcc cacacatcta tccagaagca agtgtagttc accggttcca 366900
ccgaatgctc ctatctctcg gcaaagatcg tgtgagtgtg cagttatgct tcggatgctt 366960
caccatagaa tagatcgatc cagttcccgt tcttttccgg tgcactcgct ttatatctcc 367020
gacacacaag gaaggacgcg gtgggaagga agcagcccta gcctctgtcc ggccgatcat 367080
tccgctggca tctcgcattc acgcccccgt ttgactgccg ctcggggatg tagttgtaga 367140
taggttagtc ttagtgggtc gttggctcca cctgttatct ccttctacga catgctgttg 367200
tcgtcgccat attctatatg tcacttagtc atctctgcct cgctgcgggt cagcacctcc 367260
gaaagaaacg gaggacttca ttcagtgacc ccgcgatcgc cctctgaacg atcagaataa 367320
ggtaaagctt gaagataagt tttgtactca attaatttct cagttcctct agtcgggtgg 367380
gcgccggccg gtttttcgac cagatccccc taaaaaccgt acgtgcgggt ctccccgcat 367440
gcggctcacg ccattcgagg tggcccagcc cagcattcat tcgcaaatcc tgtagtgaaa 367500
ttgagactgc tcaacctcgg aagctaattc gcgtgtaggc agcgctgtct gtcgtaccgt 367560
tgactctatc tattcatgga atttctttt tttttttca ttttcgattt tatataggct 367620
cgctccctct ttttccaaga attcatccac ttccctttac tccatagggc cttctctaat 367680
agggaaaagc cttccatttc cgtcaaatga cccggcctcc cctggctctt ccaccgtccg 367740
ggctcccttt cttccctatg gtatgctcct ccggcgcagg cctaccacgc ttcgcgcctg 367800
cggcgttttc gccagacggt ctttgccagt agtgccatcc tccccgctgg ctgtatgggc 367860
gggttgtccc tcgctgctgc gttcttttaa gctatggatt aaaggaacaa atgtagttga 367920
atggaacagc aggcgggtta cacgttccac tgtgccgaga tgtgaggtgc aggtggtgat 367980
gatcaccccg gggtatgcgc tagcgccctt gacaggcact ccagaacccg ccaacgctcg 368040
tgaaaacccg ggtcggtcgg tcctccattc atccgaccgg aggtatggat aacgaggcca 368100
ccttcacaac cttctccctt ctgtccctat gttggaataa ggtaaggcgg ttcgcttgag 368160
ttgctcaacc gcccccttagc ccggtgctca tgacgtgcta cggaacctcc accgtgccgg 368220
gggaggggga ccaagcaggg catagctagc ggcataggag ccgactcggc atcagcggct 368280
tcgtgccgca ctggagtaat ccaatatgtg gttccgcacg ttccaccact tctccgttca 368340
tttccaatac tgatcgtgaa acaccatgag cagcaggatg ttgaggtccg aaattcgaag 368400
tgaaattttt gatttgcctg ttcttagtcg tcatgggaaa gaaatacaga aataagaaag 368460
agattattcc cttagagctt gtccaatacc accagtacca gaaatgcatc tccttcgccc 368520
gcgcgagaga cttctatgcc agccgggaat aacggctctg ttatgaaaga aagcggcaga 368580
cagagtaatt tggccggtat tccctaatga gtagctttag gagataaagg tccccttat 368640
attctccacc catctgcgga gggtttccgt atccgtctcc gcggagatct ccagatcata 368700
agacattatc gccttcgcgg cactggacta tatttccgtc atttccggaa agtgcacgga 368760
cagccgccat ttccccccttt cacaatgttc tcgtgaagtt gctcacgaat caaagtgtga 368820
atgtcccttc gaagtctcgc atgctctttt tgatcgggag cggggtgggc tatttatgtc 368880
ggtgctggcg cctgcggcag cgcctctgga gccgcccccc cgttatggag ccagcgggtt 368940
ctgaatgacc tccctctcac ggttaaaaaa gtggttaact atctcgaaaa aatccatatc 369000
gtccatccga aaaacgtgtc tcaattacag ccaactcccc ctcccctgtc tctttaccta 369060
tcgaaaaacc agccctactt attttgttct acaaatgcta accaagtgac acactggggc 369120
catgggtcat gaaagaggtt gacccccatc ctccttaact atgtatggct aatgaactcc 369180
tcgctttagt ccgttctttt ccttctttgg gctcgggtcg atagtcgccg tggtagtaat 369240
gccccggagc ccagctaccg acctgaggcg ccgatcggga aagtcataaa gggacgttaa 369300
acgtaattct agaagggcct tcccgcaaaa aaaccgagtc ttggcagttc aagtgaaagt 369360
tttttagact agtcccacta agatggcgag gaaactgact tccgagagag ctgctttcgc 369420
ctcggtaatt acctaacgag agagagccga tgcaaaagtt gtcctttacg cgaggaaacg 369480
ccagacagac tgacctctgc taactacgtt ttctatagac tggaagctag agagatacta 369540
aggtatagtg ctgctaccag agaaggctct ttcatgctag gcgtccagac ctactatacc 369600
cccccggcac atttgctata tctactaacg cttcatccta accaactata cctgatagaa 369660
agccgttcta taaaaattca agacaagaag aaagcaagaa aaggatagcg atcgctttgg 369720
gaacgtcacg ggggaggaag atagaaaggt aacctatgac accggggaat taggcttttt 369780
ctcccgcctc agcttcgcgg atggaaggag ggcgagagcg tagcacgcac gctctatgct 369840
tttcgccagc tttccctcta gtaaaagatt agctcgtacc ctctctctgt gtctagggat 369900
tcctggggca tgagttaagg ttaagcatat agttgattgc tctttctttc gattgagcgt 369960
cggtactttt ggagtctctc tctgtaggcg tgcaaaacaa cagagccact gctcttcggg 370020
gtgatgaggt ggacaattcc ttactccagc ttcaaaggag catctttgca tgaatcaata 370080
ctaactcctc agtcagctga ccttcgattt cggagattag agcagaagaa ctccgtaagg 370140
gcggagaggg gtttcgcctc gaatccaaat gatttctctt cttctcttaa gatatttcta 370200
gttaggactt gatcgaggga tcaattgact ccgaaagata aagtaacaag accataaccc 370260
cgtgcccccg ccttaaagga tcccaactca tcaccctcat ctccaactta ttcgtggttt 370320
taaggtgctt ttgactattc taaaaactta tttggagacc aaggcgaggg gtcatcttcg 370380
gcaaccaacc ggggtcatgg agccggcctc cccgccgtcc cccctgcccg caccctccat 370440
aacggaagta cgtagaaacc ttgatctgtt tacttcctcc tttaataaga tcgggatgag 370500
gagtgacctt ttactggacc tcgaggatcg gcttaaactt gaaactgcct cagaagcaaa 370560
gagacgcaaa ataattgaat tcatggagat cttggccttt gatgaagatg aactgatata 370620
ctggcattct cttccaactc cgtatcctaa ctcagggcaa actatctcta gatggcaaag 370680
tgaaaagtcg aattgatctg cacatccctc tattccaata gaaaacgtta gccttcatcc 370740
atgagatcgg ggtatcacta ccagtagggg cccgcttcca taatagactt tgaaacctcg 370800
ccttcccttt cgatgtccga tcccggatac catgacttgc cttcaaacgg gcttcacctt 370860
caaaggagag taatcgatct gcggacagca aggccaatga agatcaaatt gaccggggtc 370920
tgagtcgtgt cttgtccttg agtcctctct atgcctctca tgtccttctt tccttcgctt 370980
gggactcact agcacactcc ttgctgcttt cgtgcttgat ggcttctgat gaaccaatga 371040

-continued

```
tagagatcct tccctaacag ctgctgttca atccgtccct gagagtgaga ggagtcgtag 371100
gaattcacat tgccttttac ggcttggaat tcctattgta tagaataaat gtattgggca 371160
atgtcttttc ttgaattcaa aaattctccg ccttttctca gcttgacacc tactttagaa 371220
ccatcctttt ctaagtacga caaagcttcc ttgtaaacta aggctaaggc acgctcgata 371280
gcaagaagct agtgacttct ttcaggtcat taactagaac ttgcacgagg tatcacagtg 371340
gggtctgtct tctgtccggt tcttggggcc ggtcgagcct ctttgaaatt acatccctgc 371400
ctctcgtctt gccccgctcc tttggcagtt aaagtagctc gcttcaagaa gtaagattat 371460
atccctaggg gtatgttacg agcagaagtt ctcttgctag tggaagtaag agtagcaagg 371520
ttaggaccgc atataaatag aatagggggt tcgaaagaaa tttgattccc tagaagtttt 371580
gtccggttgg gaaagccaga actcttgtaa accagcttga taaagggtag tggtagggac 371640
agtctcagta ccactgaaag tgcgatagtg cttcaagcaa gggacttggg caaacaaagt 371700
ccttactcgt attccaccaa caactcgcgt atcgtataga gctttttcct atcctttccg 371760
catagacttg cttcgcacct gtgtaaaaag ccagtttagt tttactcaag agtaagaatg 371820
ataaagcatt tcgtaagctt gaatccctat aaaaagtccg tcccttaaat ttagcctgaa 371880
aagaaaaaaa gggggctaac ctcccctcca aactattcta ggccagtccc agtgagtgag 371940
tcagtcaatc ctgttcaaaa actagcgccc gctctcgctc caatatacgt gtagggggaa 372000
gcaccaatga aagtgaacct ttattctttc gtttcctttt ctcttcgaac cgattggaag 372060
gaaggcagta gctcctccta catacgagta gggagatcct gaactaaggt atgattccat 372120
tttcctttga cgacaaagaa agttatagta gcttattcca tttggaaggt tttttgttta 372180
agacagcttt tcgtgccctt acttttgagt ctatcagctg caacaagggc tgcgggaacg 372240
agtgctgtgc ttgccccgac cgagaccacc attcattacc gtgaaccggc cttggccttc 372300
acttaaaagt cagatgagtc ctctgatgaa cttgggtcca tactctagtg aaaaaaggaa 372360
attaggcttc tctttccgct tcttaacttc tatccttttt cgtacttagc ccttctttgg 372420
catccttccc tatgaatctc tcaatctcgg gagttcctgc cgattggtta gtccctcgcg 372480
ttttcttctt tcctttcttt ttcactcttg ttaggttagg aaggagcaag ccttttagac 372540
tatggaaggc aagccagctg aagaagtcaa gcctgcagag cagtcacaaa gaagaggttg 372600
tattcactgg aacaagagtc accttcatct tctcgggtca ggccactgcc cttccatagt 372660
gaagactctt tccaggccta acgataagat tccctggtag agctccagat attcgaatat 372720
agaaatatct ttatccggtg gggacaaacc tataagtaga agatcatggt aataggctat 372780
aagatagcta tataatagac tattctaata gttactgact ctaataaaag taattgccgt 372840
tcaaagggca agctcacccc agtcactact ttcttcccct atccctaaac aaatagtcag 372900
aatagtgact agtctcagtc ctacttacat ccattgctct ttcctctcct tgcttagggc 372960
ggcttcgttc cccgctagcc agttcctgta agctgaacta tatcttagtc atactctaag 373020
cccgtggtag ttccattcca tcccgcctag tgcccagtca tgcatttttt gtcttaagct 373080
aagcgctttt cattccttct gcaagccatc cagttctaag gtcagccctg cccttttgt 373140
tgggttagag cgagtatgaa gtcagggagg aagaagaaga gagggaagaa ataatatagt 373200
aatatttacc tttcccagct ctcagaaatg gagaaggaat caaaaatcta gtcaacccct 373260
caaactccgt aggtaattcg agacaattca agaagaataa gataagctaa cacaaagaac 373320
ttgaacattg acaatagaaa gttgaatact accattcttt cgcgttgact cttccgcgga 373380
gtagcctaaa gaatcccctt tcgcttatta ctcctataga gcgagagatt cggcaacatt 373440
```

cactgagtaa aaacaaacct ccactttctt tcataagaaa acttcttgta aactaagatt 373500
agtcttagat taggtaggaa aggggatcgc atcaccgacc atatctatta ttagtaggaa 373560
ggtaagtaca aaaaactaga tttctctatt tgattgacaa tgtaaatcta ttcggatgat 373620
gtgataattt atgtagccga gtcacgagga cttcttcttc tactcccttc ccggaagata 373680
gagggaactt agcctctgac aaagtagtag ctgacatagg aatagctggc aaaggaagag 373740
cttccgctaa gattctgact tatttggaaa ctagatttgc tgcccctgca gactcttctt 373800
ttgaagaatc tgattcgcta acattggttg aattttcggc atggcataga atagaacatg 373860
aatgggtctt ccttgccaac cttcgcttct agaaggaagt aagtagaagc tgaccctcca 373920
acatacattg cagggaagga cccctccagt ggcatacttt atggagaaag gcttccatca 373980
gcaggcaggt atttactttt ctgatacctt cacgtcttgt tgtcaaacca taaactattc 374040
gtattattca ttctctcgcg cttgcacata taattgggct cttaagcaac tggaggtctg 374100
taatgccttt ttacacggaa ctcttgagga ggaggtctat atgtctcaac ctcctggttt 374160
tctggatacc gctcatccag gatatgtctg ccgacttcac aaagctcttt atggactgaa 374220
gcaagctccc agagcttttt tcacttgttt cagcactata ttgtgctcta aagggattcc 374280
gtggcagtgc ctgtgatacc tctttattca ttcgtcacac atctggggat agtatctacc 374340
ttcttttta tgtcgaagat atttttatca caggtagtga tcaacaggga atacttgctc 374400
ttctttcgtt cttgcatgct catgaaaata tgaaagactt gggccttctc cactactttc 374460
ttggtatgga agtgtatcgg caggggcgca ctcttatcct tcgtcagcag aaatatgccc 374520
tagatctctt gcctcgtgca gacatgcttg attctcgtcc tttggccact cctcttacta 374580
gtggtaccga gcttcccaag ttggatgtca cttccctctc tgatcccacc aatttcattc 374640
ttctattgag tcggctaact gtaactataa gctacacgcc tcgaactcgt ataaagattc 374700
ttcctctagg gcctcctttc accttttgtt agcgaccctt aaacgggttc cagcagtgcc 374760
agttcaagcc ttaccttttt cgtttagtct gactattttc cgaattctat atatgaatga 374820
aagctacgtt tcggcaaata ggtctattta tataaactat catcctaagg aagaaactga 374880
aaaacattag tttcacagcc gaggtcagag cttcaagtca gtaatgtctc tttagcgccc 374940
cataccctac tacaattctt attcaaataa tattactaca atgtcgtgcc gatgtctccc 375000
ttacgaaatt gaagataagt cttttgatta cgggggtgac aaccgaggct tttaagagaa 375060
gttgccatag aggctataaa gagctatctc atatctaata ggaataatca aattgttatg 375120
tctactgtgg gaaatggggt cccaagaccc tctcttcgac gacgtagaca aggggtccca 375180
tcatgggcga tctgagaaga gagatgcaga agaagatgtc ctcctcaacg ggtcaagccc 375240
tcgctcagaa ctaaaggatc cttaacatcg gcactcactg cataagctca tagggcaaga 375300
tgaagatccg gaaaaaggtt aaacagatcg tcaacttcac cttggcatgc ttccatcagc 375360
gctgaaaaga cagcattgaa cgagaagaga actaaggcaa ggctggtgat gtgccactgt 375420
atggagggct cagagagagt agaagcactt tctttcacgc tgagtgtgaa cttccgattt 375480
caggctgctc ttagaccagg aagattgctt atgacatcaa tcagctaggt ccgtcgtatg 375540
tcgaatagtt tgtcaatgca tgcttccctt tcttatgcta aagttagtct ttagaaagtt 375600
ttctgatgag caaactcttt ttcttcagat cccttttagt aataaagaaa tgtttgaggc 375660
cttttatctc gtccaaggcc tcaaacctga tatctgagag gagatgtctt tgggagcagc 375720
taaagaaagt gtctaaacgc atccagggac catggttggt caccggggac ttcaattggt 375780

-continued cctttctctc tcctctttca ccagtgagtg gtgagtttcc cttttttttt ctaggtaggt 375840
acctcttgga ttcggacttt gttccaacag ctgccatacg tgagatcctg atcgtcttcc 375900
tcccagtgtt gttgcctgct gggggaagga aggaaagtag ggcttccttc caggaccgga 375960
gaaggtcaaa ctctgggcgg gctgccaggt ttcgcctacg caacggtttc acaagattga 376020
acctttttg ttcaacccaa gtgttggagt tccagagcac gagggaatgg actttcattc 376080
ccaggaccgc ctcgtctatg tattcggcgc ctccccgat tgcttgaaga taggcgcgcg 376140
atacgataaa ggcccctggg agaaaccaat gaaaagccag ggtagagcct cggagccgac 376200
ccaagcgaag atcggcactc gattgaggag cagcccgaaa aagggaaagc cgtggagacg 376260
gcagactcgc cagtcaggca cagcgtgagg ctgactacag tagaccggga ggttacaatt 376320
cctgtttcaa tttccgggag tgaatgtagt aagtgcagac ggtggatcag gtgtaaacat 376380
caaccaaagg cgtcttgggg atcggcaata gctaaacatt gtggccatca cagttcaagc 376440
tacgtatggc tggcgtacaa cctacgggct ttttagccaa aataaaaaga acaaaaaagg 376500
atgcctgctt tggtaccttt agtccaatct tagacaaaga gcaatttgga tatgaagcac 376560
tgctgggtag accatggctc caaccaggtg attcatgact gggctaataa aaaaagtctc 376620
aagcagggaa aggcgggatg gaaggcggaa aaggcttggc tttgtttcac agaaaaagga 376680
ctaaggaaat ttcctttccc tagtgttgga gctggctcat tcatgctagt catcttagag 376740
ctatgagtca gaacaatgtt caccaactcc tccatagtaa tcttgttcat atatcgaaaa 376800
agctttagaa tattcgtttt tttatattaa agtgttatat ctcctcccca aggtagcatt 376860
gacgagcggg cgatccctgt cttgtttatc cagctagctt ttttccgtgg tactcaaatt 376920
cgatttgtga gagctctttc ggctcggcta ctctttttt ttaaggtaag gtaggacctt 376980
taaaccgaca aaagtaataa aaaaaaaaat gcctatctat aaagcgctga gttgaagagg 377040
gaacaagtcc cacagagaga tgataagtgg gagaaagagt gaaattacaa tctcttctgg 377100
aatggaagac ctcccatcca ctgactacaa gactgcagcc taacacccaa gttagcctga 377160
cggtcagcta aatgagtccc ttacctcttc acatgatgaa tttgaactca acatatattg 377220
agaaatgttt tatcaggaga aagcataggc accaaggttc ttgattatta ccattcgccc 377280
atctaatcat tgttaagaga accccttttt gtttgatatg atgacttgaa aagaatcaat 377340
agtttggaca aaactatggc catgcaggag agtttctgct tctgcaaagg ttgcatcttt 377400
aatccctaga ggagatctgt tcaattccac atgacagcac cattgccatc tcttatgacc 377460
cccaccataa tccgaattcc cagagtagcc ttccctactc cttcaaagtt catcttgatg 377520
tgatttgaag aggaaattgc cgcaagattg agatagatat gtttgaattt tttttctttt 377580
taattaagta atgcaataaa acctcgtcat gttcatcctt actaacatcc catacaaaaa 377640
agaaaatctt ttatggtctg gattttttca atcaccttaa cgcttaacga aggaggtgga 377700
cttcaaccaa atcagccctt cttatgaagt ggctatggaa atttccaaaa gaaaagaaaa 377760
agccatggtg ctcatatttg gctgctaagt gcctctccaa tggcaaaaat ggattgacca 377820
acccacctct taaatattct gcatctaaaa aggtattatt tttaatagag agactttcag 377880
gcagaacttg ggctagactt tggttgggca atggtaagct gattcgcttc tgggatgatg 377940
tttggccgcg ccactctcct cagagatgca tgccataatt tatatcaaat cacaaggttc 378000
tcatgacctc aaagtgattg actacattca atataaagga gaaaaaagga tttatccccc 378060
tattcaacta cccatccaag agcatttggc ttcagaatac tttcttcttt ttcttttttct 378120
atggactgcg taaatcttct cttccagccc aaaggaggat aatctctttt ggcagctcaa 378180

-continued tcctcacggt aataattatg ccaattctgc ctaaaaatct cttcaggtga tcaagggggc 378240
tcccttttc agtagatgag attaggatga aaggtattat ctaaacgctt cttttctctg 378300
gcttgctctt tcaaatccaa ttttggcctg cagtaatgta atcgggattt catctcctaa 378360
attcttttt ctatgaaagc aagaggtgga aagttttgtt aaaaattctg ccttattcca 378420
tgagatctag aagcacttct gcaactttct ctcttcccta gcgctagcgc tcttttttt 378480
tttactttt tcaaagggca atgaaggcct tccttataag ttctcgctcg atcgaaagga 378540
tataacacat acgaaacctt agcttcgctg actttatgag gtctaacctt cgccacgaca 378600
ttagtggctt agctcttcgc gcttcccgca ggctttttta tagagagaga gtaagggggg 378660
ggggcggtac ggaagattgg tccgctccga aaagctgagt ttttcggttc gcccccccta 378720
tgtggtcggc cttcttacca gtctgcctcc tttctcttga tggaatatat caatacccga 378780
gctccagctt tgcttgcgtt cttcaccggc gctcgccaga tgtatcactc atcccgctcc 378840
taaggtaagg agtcttcttg tgtgttataa tctttacggg aatgaatcgc atatgttggt 378900
tgagaattgc tcgggaattc attgataatg actttgccag gttctaggga ggctactctt 378960
ctttttgtc gatcgagccg ctttccctca ttccactcgt ccagccctct tcacgaactt 379020
gtacaatcga tgccacaaag atagccaact ctattatcaa agaaataagg aaaggggcga 379080
caatttggca ccagatatcc ggaggtgtgg aaagagcagc tgtgagaagc ggaaaaacca 379140
tcaaaaaacg acgattgttc gtggaggttt ctacagaaag acccccttggt tctggcaaac 379200
ggatcacaat tacaggtacc tgggagcata ccgatggaat gaacgaaata cgaacagtta 379260
acataatatg gtcatagatc ttaggttgta acttgatcat gagcgaattt gttgatgttg 379320
cacccatgaa gtatggaaag tgccaaacat tgggaactac ccggggagga gttaggaaca 379380
ggaacaagga gaagcgagaa ccacttaaat ggaggaatcg attgtatttc gtcctttgtt 379440
ccccatagca actggggatc aaaaagcacc aaatttgatg acttattaag ggaaagacga 379500
agtaagagca tgctattgga gacgttgcaa catatgtagg gaaggcctcc gttgattgtg 379560
tacgaacaaa atacgaatcc aaaggcaggg taagaaaggg tttagctaat ggagatatta 379620
actcttccgg gaaccagtaa cgcgtaaacc atgtcaaacc aagaccaatc aatatccgaa 379680
cggaacggat tcgaacttct cctagaatag tttccggtgc gaaatgaaat tcataggata 379740
tatatgagta attcaaagga taaatataaa tatttgatag gattcgattc attttagtaa 379800
tgaacaaaac aaataggatt ttttatgtat cacaatttca tcactacatc gaaggctctt 379860
ttgtaaatat attgataaga tagcttggta tccaaactaa aataattatg atccttattg 379920
tgtacataag aaattgggtg ggtatagggc atataacaaa aaggtttcct cggtcataaa 379980
atgaaaaaag aaaaagcaga caggaacagt ttgattcttt aaacaagcag gttttggctt 380040
ctttttagc accctaattc tcttgttggc tttgatacca tgaaataaaa tagagaaaaa 380100
gaccttcaag agaataaata aataaaacca ttttcaagag acaaactcca gtgaacccct 380160
ttcctcccat tcattgccct ttgaaagaag taaaaaaaaa aaaaagaatc taacgctcta 380220
gtcgaattga agactttcaa cgctcatgct atttgaaaga gctttcaaca tggagtggag 380280
actccataac gtacacaaag agtaagcgat ctatgaatat catcccaatt caggtcttgt 380340
tccgcactta aatggataac tcaaaccctt accttgacca gtttgtagtg gaaaacctca 380400
atgacataat cgtttatagt cactcactgg aggtttggaa ccctgagtac agtgttccgg 380460
gtgtagcagg aaaagaggct gtacgtgaaa cagtactcag acgaaagtgc tatttcttgg 380520
ccattggatc agcaagggtg tgattcagat ggatcaagag aagaccaggt ctgttgtgga 380580
ctgggaagtg ccgaagaagg agagagcagg cagcagtggt gaagctggat gctcgaagtc 380640
attttagata cggcaagaca gctcaggagg agtcgaaagt tgccacaacc taggaggggt 380700
ttctaggaag ccaaaaaagg ggagcctttt tacatacttc ttaaaggggg agagcgccag 380760
gagaatgtcg agacgccatc agtttggagc gcgaggccag cagagcttgc tgcagaggag 380820
ataagaaaag gctcagcaga ggggatctgg taactgttat gaatgtggag gagtggggca 380880
tttttctcgt tactcttcca atgttcagac ggacgaatgc tgctagggga gtgcagaata 380940
gaccagctga agatggaaga gtgaacgttg tcgagcctag agcccgggaa gctctaaagg 381000
taagttcaag tcggaaacat agcgggggtt ctcaagctta ggagaggaga ctgtttcgct 381060
gtcgttagat tgtgtggcaa cgtgagccaa cgtcagcaga aaggaggaga agacggaagg 381120
ctgtattcaa aatctatgtc ggaattggcc agtgcaaaga taatcattga tgctgggagt 381180
ttggataaga tagcgtccac ggagatggta gatcagttgg ggctgaagcc cttttaagta 381240
agggcctcat ccagagccct atcgaatcag atcaaaaagg gcatgagcgg cgggccctat 381300
gttgagtaag gggggagaag gtgccccttc tgctaagttg gagctaggga agttaaagca 381360
ggacgtctgg tgtgacgtcg tccttatgga cgtattacat atcctactcg gaagaccttg 381420
gtaatacgag tagggttcta cctgcgtaga gagaacaccg gtttactttt aaggggaaag 381480
gcggttattg ccatcagaag actttggttg gctaaggaga aagggtgttt gttggcatac 381540
catttctgga cgtgggaaag agtccataga atgctatgcc ttgatagcaa caaagccaac 381600
tagcagagcc gattcgggga tcggtgggat gccgtagctt taagagatag gggcggaggc 381660
aatcagaaag gctttttagg aacgaggccc cctccctcct atgttgtaaa agggaagtgc 381720
agatctttat ctttctgcaa cactcttccg acttgatgcc gcccctgaat ccacaagtac 381780
cggcttgatt accctctaag ataagaggag gatatagaag cagatttagt tgcaggtagg 381840
agcgagtcta ccctgcaaag cggcttctcg cttatcccca ttttcaaatg aggagatccg 381900
acgtcaagtg caggaattgc tgtcaaaggg gcgggagagt ctcagtccgt gttcaacgcc 381960
tgcttgacta gctcaaaagg aagcagctgg agtgtgtaga tgggctttga ataagagttg 382020
ggtgatttat ttccaataat gccaacgatg gatgatatta tggattaatt gcctgtcggg 382080
agcgtgttac ttttcaaagc ttaccttatt tagaaaaggg gaaagggctt ttttttatag 382140
agagagagta agggggggttt tctggggctt tgaagaaggg ccacttatat tgcaaaactt 382200
tcagagacgg gatggaaagt ctttcgtgag aagagatggt aggcttgata cggatacagc 382260
tgcttatcac ccaccttaga atcaagcagt tcagttcgac tatacccgcc ttaattccct 382320
cattcaggac agatggaagc aggttatgga tctgttcaag ttggtcgatc aatccctccc 382380
ttctttcccc tgcctccgga caccttagaa tagatttgat tggaaggagg gtgaggaacg 382440
aacacagtgg cttgactgct gggatcccaa tcggcctgca tcagcagaaa atggaactat 382500
cgaatcacgg gtgactcgct ttatcgggat gggaagaatt gcttaattgg catttctttc 382560
cttccctaaa tcgatccact agtaggtagc ggtagtagag atccattatg gtgggatgga 382620
ccgttctcga attccggccg gcatttctgt caatcggcgg aagactcacg catactggga 382680
gggtacgact tcaagggatg gactcgatcg aacggccaac cacttgccat ttttgtagga 382740
gatgaaatcc aaaagaccat tattagcgtg tagtagattg gcccgagtgc gtaataggcc 382800
agtcgagaag aaattcaatc aatagattga acggtagata aaggatcaga ggatgagagg 382860
ggtagatcta cccaatatgg accgataacg gatggtcccc gccaactgct tatctctctt 382920
cctcgcattc cattcatgac ctaacgacta tccctgtttc ggggagggaa tcacttgctg 382980
gatcgaaccc aaggataggt ttgatcggcc gggtgttggg tcgaatgaac actcaaccgc 383040
gtcatcacgg cagcgatgga tgtccaacct ttagatctct tctttctcaa taaaggcggg 383100
taaggaaagt ccgaaggcta atccggcaac tgctggctag aaggcgaaaa ccgcttttgc 383160
caatcaaagc cccaaaacta gtaagggcac tcgtgcccca gcaagccacc ccaaccctac 383220
cgccaaagct tgactttact aaacaagcga gaaaggctct ttctatctta ttagtcaagc 383280
gctaacgagc aagaaaacgg atatgcccta agaagcaagg gctttcgtgc agctgctgcg 383340
cccttgcttc ttgctttaga aagattgctc gttagctagg ccgttttcaa taaggctcgc 383400
gctaggcgct cacctttttt ggctgagccg tatcgtatct tgctggtaat ggattgattc 383460
ttgaatcttg cttggtttag gcaggtaagt gttaagaggc tctttaaggc tttcgttagg 383520
tacacatagg actttcttgc aatacatagt ggttggcttc gaatcacatg aagcccatat 383580
agatgtccac tcctatttcc tctaaagctc tccctgtggg gaacacaatc agtccataca 383640
aggacctact gagtcatcca cccttgcatc tatttgatgc atcatcacat ggccgtcgtc 383700
taactcctcg agaatcatgt cattcgcctg tcacgtgttg ccaccagagt cataaatact 383760
cgaagtaagc tcctggctcg cccctatctc taaaggggct tacgaacgag cggagtgctt 383820
acggccgtgg tagctgcgag cctcctgggt cttgctctct cgtctttttt cctccgcctt 383880
cctcttgtaa ttgacccttt cttttctgct acgcctatcc atccgtcaga ttgacatcca 383940
gccgggtgag cgatagcggc tcctgtttac taatagatct gccgccgcta gtataacaaa 384000
aaaaagcaca taaggatcca gaatattcaa atatactgat cactgatcag gatcatataa 384060
agcccggtat taccagaaag gatagtcgtg atgtcccttc atggccggcg ttttcagtat 384120
agagccgaag gcgagggttt ccagcaggcc cccttctctg gctttccctt taagtgacaa 384180
ggggggtgag gtaaggagta gtataagagt ggttcggtca tcgataagcc tctccttatt 384240
cattctatag ggcggggctg cggaccaaca atccagcaaa agggctgaaa agctccttta 384300
ttaaaccttc cccttttaat aataagaagg taagcatcaa agcccagaaa acccaaccta 384360
tacaaagagc tcttttcagc ccctactcct aacaagtgaa agttgctggc acccaccata 384420
tcttgcttcg gggccgatct cttgtatcgg agcaaagaaa ttcaatgatt ttctatattc 384480
tatttctttc ttttttgtt gagtttttc caccacaaac agatttgccg catggattgg 384540
atagagtccc ctgatctcga cattcaagca cgaatccctt gagcgcttcg gcggcggata 384600
gcagcatggg caaagcactc tgctgcggcg agcagccggt tcttattgca ttcaccaaga 384660
tagtcttgct cgctcctgaa ctctgcggcg agttcagcca ccacctccgg gtctgagctc 384720
tgctcgagcg tagtcagcca gcttcgtgac tttgcttagc ttccagcctt gcaaagggat 384780
aacctttcac tatctaggcg ccctcgaagg aggggtccca cggacttctt ccccgaaggt 384840
caagccgtag ttcctgtccc tgggagaagt ggaaggagtt aggaggatgg agcgcccttt 384900
gccctaagaa ataggcggct tcgccttcaa gccgtcaata aaatcgagct aatatgtggt 384960
catgacagta cactgatgca taggtcttct ttactttacg gccttttgat tatgatgcat 385020
catgaacgtg ccaatatgtg atcggggtgc gcggtggtta gatatagggg cggcttcgcc 385080
ggcttggatt ggaaggaagg gcttcgcttt ccgatcgctt tttgaggccg ctttggatga 385140
gcgtgggcaa gttagggatt cactatcgct ttccgcttgg agcggctcac ccccttgtca 385200
cttaaagggc gaagtcgccg aagcgagtct aaaggccaaa gagtcatctt tgaaggctac 385260

-continued tatgcatcct tattcatagt agagtgtaag gtaggtttgg gtatagcagg acttgaacct 385320
gcgaccatta ggttaaaagc ccaatgctct accaactgag ctatacaccc aaaaaaagat 385380
gtagtagtaa ataaggattg gtacggaaaa gaggccggcc ccccttcttc tcatcatatt 385440
aaaggagcgc ggctctgtat gaggctcgta ctgcagagca ggcggaagaa aacgtaaggt 385500
cgcgcgttag cactcctgca agaaaacgga tgcgctaagg cgcaagggct ttcgcgcagc 385560
tgctacgccc ttgcttcttg ccccttattt caaactcttg atcgatatga gaaagatgcg 385620
ctcaagcacc caacctatac aaggggcttg ggctcgaaag ccggccttac tcaacaagca 385680
cctttcttag taaggttgct tctttccact cattgaagat tctatctaca aaagaaggtc 385740
aacgggggat actcaaattg ctctcactga caccagagaa ggtgaggtcg tctttctttc 385800
cagccgccat acggttcgcc ttaaagcctt aaggagaagg ggaggagcag ttatctatgt 385860
aattacggtc tttgttggcc gttgttccgg tcgagcactc tcttttcttt gtccaattcc 385920
gtcttaccaa acaagactga cttcttacca acccgcgaag ggttgtgagg ctggaccagg 385980
tacgaagaat gaatctatat ctgtgcacgg aagttgctgg ccggcggccg ctcaactgtt 386040
cgagcgcaat gcagtggtgt tggttccgat tcgacaaagg tggaatgcct ggtcgaaggt 386100
ccagtacagt aggtagcagg cgtgttcgtt ttggctcccg agcgagaacg ataaataggc 386160
gatgcaccat ccttgctgct acgtacgttt tccttgactt gacagattca ttcaattgaa 386220
cccacactca aaggaggacc acaagctcgg ggctcgacga aacagaaagt ttcagcatgt 386280
tgaaacctct tggggttagc agtgaaagaa agagcccggc attcatttct tcatgaatat 386340
tcatagctga gtctactaaa agagggacca gcctcgtcgt ggtgattaga ggacacctct 386400
gatcgttcac ctctaatgtg acacgttccc tcccagttat atgatcaacg ggatcagtcg 386460
gctagagagc ggggctattc ttcttccggg gagacaaagt cgtcccttct actgaccgaa 386520
ccctcagttc gggggccttc gtcaacatgt tacgaagctc cagtcttcgg tgggtcacca 386580
ttacttgact tcgaaaggcg aacatctggg caagggaaag cgcagtgcgc ctggtgcaaa 386640
tggctttctt ttttcatgat ataccaatca gaatggaggg tcctacctac gtacatgatt 386700
gatagaatca ctacgtaggg ggggcggtca acttgatgcg ggagaggcat gagtgcagtt 386760
cgatcttgtg gtgtattcgt ttgtagtgag tagggcctct ttctcgttga tcagtccgcc 386820
tccgctctat tgaaaagtcg gaattcctac ggcggttttg tcaacgaacg cgtctcgggc 386880
cggattgact aacctaaccc acccttaagg aggcttttcc atagttgggt gtccgcttta 386940
gtgtgattta cgaaggctag gctaggtttg gtaatatcca aaacaaatga aaagagatcg 387000
gggtcgatag gtggcagctg gcaaggaact tgatcccccc caaaaaaagg gggaagccgc 387060
ggtcgaactc gaattctgga aataagtcgg ggccctttta ccaagtctac cagatagaag 387120
atgatagagg gccaactatc gttgccttgc acaagacggt gccctttcac ttcgagttcc 387180
ttccttcgta gtcaaatctg atgatacgct ttggcgatgt tacctaccaa ataaaaggcc 387240
tgctaggtga tcgaaatcgc tcaggtcagt gaggactcac tcactcacct actccttatc 387300
tatttaatac tttcttctat ctacttaatt taaaaggcga cccgccgcgc cgggctataa 387360
gataagatac agttcttgta ctacttgatt gactggtaag aaagagcttc cgtaagaact 387420
ggaagactct tgtatgtacg gtaaccctct cttccgctac tggtggactg ttgcacagaa 387480
agggcgacag aagcaacctt tcttagcgcg cttttcaagc gcttagcttc tgctagtggc 387540
ggggcggcaa ggccattaag ttcagttgga agcctaagcc aagaaggtac gaacgaagtg 387600
acgggcccct ttagaagata gggggcggct ttcttgtggt agtaattgcg aacatctctc 387660
ctcttctctt agcgtgcaca gtttgcttac atgccgcctt aggcacatct ctctttctta 387720
gtttcacgct ggactaatga taatgaatga aagtcagtct tttagtaaac gtatataagc 387780
agctgtttag tgtataagca attctttagt ggtcgcaccg aaagtacggt ggaggttggt 387840
tgaagatgat cttacgcggc gttcagaacc agtcttgaag tgaatgaatt agaaagaacg 387900
aagaagtaag gaaatgagac gactctttct tgaactatat cataaacaga tcttcccctc 387960
cacaccaatc acgagttttt ctctattcct ctcgtatatc gtcgtaacgc ccttaatgct 388020
aggttttgaa aaagactttt tatgtcattc ccatttaggt ccgattcgga tccctccgtt 388080
gtttcctttt ccttccgcac cttttcctcg aaatgagaaa gaagatggta cacttgaatt 388140
gtattattta agtgcttatt gcttgccaaa aatcctactt ctacaattgg taggccaccg 388200
ggttattcaa ataagtcgtg ttttccgtgg ctttcccatg ttacaacttc cgtaccaatt 388260
cggtcgatcc ggaatggatc ggttaaacat tccattaggg agcctggtct tgactcttct 388320
gtgtggtatt cattctcgtt cggctcttgg aatcacatcc agcagtggtt ggaacagctc 388380
gcaaaatcca accacttcac ctacttcatt gcccccaacc gtttctcgta cctctattga 388440
aacagaatgg tttcatgttc tttcatcgat tggttattcc tctccgttcg tatctctttt 388500
tccaatttcg gtctcgatta gttcacaaga ttgaatggcc aattctcctc cgaaccctcg 388560
attcgattgt tttccaagaa tgttgagccg ggtatgtaag ccatgtatct gggaggaact 388620
taataaaaag aagggctttc ggtttttgc accccgtttt ggtcttgcag ctatttttaa 388680
aatatacata aaagtctctt ttttttatta aaatgattat atatatgtcc aatctctagt 388740
ggtggtggaa ccaaccaaga tgtatgtcgt ccgacccgac ctcagactcc ttcttcccga 388800
cctatttgac tctctggccg tagttattta ggtggtattc cgagatcgaa ttcctcccag 388860
gaacacacga aacaaagata tgaactgggt aaatagaaat ggaaaagaga tctttctatt 388920
tcatccaaat tagaagcttt ttctacatcc atatgatcta ctaaagtaga tcggtattga 388980
ccatataata aaagcagatc ttggtccatg gagtcccaag aaggtaagaa ctccaacctg 389040
tccgatgctt cttcggccaa atacgatata caagtgggac ctgcactatg agcaagctgt 389100
gcgaaaaacc gcttcttttt tccggttccg aaagaacttg ggcgaaatag ggttctaccg 389160
ggaaaccatg aatttttgag ttttcgccat tggttactgg ttgagccact ggaatggaat 389220
gagataagaa tctctggaga tctttcctct ccacttactc gtaacaggct tttcttctgt 389280
agaagacttt ttccgaatgg cataattgtc cgacactacg ttcctcgatc ttcaaagaaa 389340
actgactcct cctactccac cttctccttt aggataggat cctccttggt ccttctttca 389400
ctaatggtct caccattttc tagtagtagt tcgcgcgagg gactatcctt tctatcgctt 389460
gcccttgcct ttcactctca tttggtctct ttcttataga aaataaagcg aagcaaagcg 389520
catggcaaag aagcagccag ctgactgccc ccttccactc ggcctttctt cgctgtgtga 389580
ataaggtctt agtctgtatg ggcattctgg gcaggtcgca ataagtcgct agtcgaaggt 389640
ttagaccaat cgcaattcat caccatcttg cccgcttcca attgatgact ggctattata 389700
taagtgttga cctaagcccc tgcgcagggg ctcggctccc gaaccgtacg tgagctgtct 389760
cgtacggctc ttcctaagaa cttgaagccc cctctctcta aatagaaaaa aatgaattta 389820
caaaacaaaa aagacttttt caaaaagcct tcgccctcct attcaagggg gctattagag 389880
aagcagcttc gttccttgac ttcttttctc agtcaagctt ccttgttcct tagtgtagtc 389940
tcggtccata gtttaagact ccgttcctta tagcctagtc tatatccaca gctgacgtga 390000

```
ctccgtaccg acgcctttcc ctttgtatag tatacggcta agtgacttcg taaccttaac 390060
gtactttttt tcttactgta gcataggcct tcgtcgggct ttcgtccctt cgcctataga 390120
cggcggcttg gcttctagca ctaaataata ggcattaggc attctgagct gaaaggaggc 390180
aagcaaatga agggaggcat tacgggccga ctacaagaaa agcaaagctt cgtagactcg 390240
gtcaagtcgc ttatagaatg ccgacgacga ttttccactt aataagtgaa ggggagaggg 390300
aagcgaggct tagcgagctt tataaggccg accactacat aagccgctgg cggagaaagc 390360
tcgaagagct tcccttcatt cattactaag ccaaggtccc aggtctccga gtcagcccgc 390420
gctttttcga agaatcctgc acccatgggc atacggcctg gcaggccttc cctttccgcc 390480
ggagcttcat gggcgttgcc ccgttcccca atcagatgtt tggatgtgag ctatactccg 390540
cgaggagcca aacgggcgta tggccttgcc ttgccatttg acctcttttc ccgtgtgact 390600
aggaatgctc agtgacaacc tctcaattgt caccgcctgg cctctcttgc taccacggta 390660
gcacctagtg tggtcagcac caatcgtgtt cgggcaacga agcttacact cattcacatt 390720
ggttcatcct gctatgccct gggccttttg ctcttctaac gtaaaaggtg gccggccatt 390780
cgtcaaggcc caggaatccg ctggacatct cagcggcggg atttgatacc cgcatccgat 390840
cgaagttgca ttttagtgct cccctaacat aaaggggagc tttttcaaag tgggtcgctt 390900
cgcgcaagac attgcttagg accaacgggt cacacgacag gtgcacgatc tactttgcac 390960
gttccatcct tcagcccttc gcctatcggc ttggcaggca agctaccttg atccgtcttc 391020
ggcttcgatt cgttacgctc agaagctcca acaagcccta aagtctcttg ccgcctaaaa 391080
ctctgccaag agagcgctgc tttacgtttg atcctatgta cccatagaat gctatgcgtt 391140
ctccactttc ggatctcgca aagagataac gtgtttttc ctctgacttt ctctctcatt 391200
cgcggagcga agaaagcggg ctttgcccca gctaccgcta tccttgggaa accaaaagag 391260
ctaccgaagg aaagggatgc agtctctccc ttggcctttg gagaggagag ggcagagaag 391320
aaaacgtcct tcgcgcaagt ttttttgctt cctgcgtcct tactagtaaa aaaggggctc 391380
ttcgagcaag aaggcatttt ggtaggaagg ccgaccacta cataagtcgc catccgtcca 391440
ggagagaagc aagctacctt tctttgatcc cccttttcgg gcagggaaga gaacgaaaat 391500
ggaccgcaga tggtagtcgt ggttgattcg aggatcttac gcggcggagc gaactcttct 391560
atcgtgttgc attttctctg gcggaccccc cccccggtcc atcgtactgg agcgattcga 391620
gaagaacgat taggctcata ttctatcctt tctacaatgc ctatagacga agtgcttcgt 391680
ttcagatcaa ttcttcgctg caatcgcttc gatccacccc ctcggtgaaa aaccgtaata 391740
cgccctgagg aattcctacc agcagacttc cctgtactca aagtgaattg tctaagtgct 391800
ctcctttgtc tcattgttta tctcgtaatc attcgattcc gcccctaaag ctagcgccta 391860
ctcctcctcc ttctcctcct gaatcctcct tggtcctttt tacataacac tctcggccgc 391920
ccaagaggac tggctatctt tctctttata cgcacaatat cttgaaaggc aaagaaaaag 391980
atctaccttg gcaacgaaga cgtcattgac tgatatattc attgcatgga atgccacact 392040
caattgtcag cgactgggga cccggtcttc attagcaatt tatggcatga gctctttcgt 392100
ttacaaggga cacaatttaa catgagtact gctttacact cttttcccgg gtggggcttc 392160
ttatacctaa acgcagcagg ccccgcgagt agtcgaacaa atgagaggtt gtcgacgaag 392220
gggtcaaagg ttgcgcttgc gagaatccga aggttgcgca agaccccttc aacctcgccc 392280
gcgtcttagc ttgcttgtac tatcgctcgc ctgcctgacc tgctttctgg ctagcttctt 392340
tatggcaagc gctaccgtaa cctagctagc gctacatctt gctaacgtcg tctgaattgc 392400
```

-continued cttgcaagcg ctacatctat atggcaagcg ctacccgtcg cttgcactac attgtctgac 392460
gataaccttg cctgaccgct tccgctctga ctgagctgac cgccgcacct gacttctata 392520
tcccattatc catagatctc cttccttatc gttgccggtc taagcagaag gttgctaagt 392580
cagatgtctg gtgaacacat tcgtaatgag tatgggtcta gtaggtgtac tagtaaggaa 392640
gcgaggtact gagtttagcg tcgacaaggc aagtagtgga tctttattct cgaatgatat 392700
gggagacagt caaagcatca gtctcagcat caacagaaga aaaggactga ccgaccgccg 392760
ttcaagagag atcccgaagg ctcgaacttt ttgctagctt tgaaacatgg gccgaaggaa 392820
agaggaagac caaacaaagt cgcggtcaaa gcaaagaaaa agatgccaaa aaagattcac 392880
tttagcttct agctcgctta gtgtaggttg cttgcaagac tttcgatagc tggctcggcc 392940
gaacggaatc accgatctag atagaagggt cgttcactcc ctattctttg agaggttgct 393000
tgcgacggta gcattagcta ggcaatcaag gcaggtcgaa cagagtcagt cctagggtga 393060
agatcatcgg atggaaaaat ggattgagct ggctaatcac ttgatgaccc ggtggagaat 393120
gggaacagag agtcgctccc ataaacgaat gaatgggact cctggtcctg atcgaaccag 393180
agattccgac aacccgggga atcggcagaa agagatggtt cggatactgg aatctgccca 393240
aaagtcctga ctttttcgag gcagggcttc gacccgtatc tggccaactc ctcgaactgc 393300
tgggtgcggc atattcatgg actggcaaag cgaactctca atttgatcag gagagcctag 393360
agagctctct atctttcccc aaattccgac tagcgcggtt ctttttctcg accaatttga 393420
attccatttc attttttatt ttaagttaag tagagtagta agtagctagg cggatttcag 393480
cgcatgctgc attgagaatc tccaaagaaa ttagaagggc ctatgagagc gtattattct 393540
tcccatttgt gaccgacggt tgcttgcaag aggtggcgat cggcagtgtt ccaaagcgcc 393600
ataacgacgt gcgttagagc gttatgccaa acgatcccca gcaccagtag ttatggggat 393660
cgccttcggc ttgctatact ctttccctaa cgcatgctgg ttaccataaa gacaccgagg 393720
gatatcgcat gcgctagttt cggggatgtt gtttacacta ctattggtaa caactcaaag 393780
tgccggaacg actctagtgg tgcaagcgaa ggtttcagtc ttgtcgagcg aagcaaccac 393840
tagtcgccct tagtgctcca aaacaccctt tcgcttgcgt gagcaacggc ccctagcgcc 393900
cagagcaagc gcctttagtg ttcccgaccg cctgcctttc ggccttagcg ttccaaacaa 393960
ccagtagtgt gaccgatctg tgttcaaaac aaccgatgac gctagcgacg actcgtgggg 394020
ccccctaacg ccgaacaaaa aggactagtg ctataacgac gagtggtgtg gtcctaacaa 394080
ccgactacgg taacgacaac tcgtagtggt cctaactact agcaacaacc actacggcaa 394140
gcgccacaac gacgataggt gaggctagac cgtaatatag gcttgcgaag caagcactcg 394200
ttgtccttta gttgtccgtc actcgtagtc tctgcgtcag aggtggttgt tcggaagggt 394260
ttgacaaggc aacagacagc caggcagtta ctacgcaaca cacattgggg tggtgcaaca 394320
atggaacgac tagtagtcta cgactagtgg tgttacggaa caactacccg acgagtggta 394380
ataacgacaa ctacagtagg tttgacagta gcgttaggac gactggttct cgtagttgta 394440
ttgccctaag gcaacgactc aaacaacaac gagtgctccc aagacgatga gacgcatgcg 394500
ctataccgtc gagtattgct tgcgaagcaa ccgcaactcg ttgtaggtcc tctccaacca 394560
ttacagtcga gtagctttca ctccttcgct tgaaatgtgc ggttggttta cctaacgcat 394620
ggcttcccca acgccaatag tcgcatgagt tctcctaggc cataacccat gcgttgaaag 394680
aaagcgcatg atgcgttccg gagttgccgt agttccgtta ccgccttgtc gtcttgggtt 394740
gggaaggata cgacaggctc aattcaagga cactcaattt caagctcaat ttcaggcttt 394800
cgaagctctg acgctttctg tcgcatttgt tctctctttt gtttaccttt cattttcact 394860
ttctttaacc gtacttaggt agctcttcgt tcggtagagg cgtagagtcc tagaacgcta 394920
tctacttggt cgcgactggc tctgctacgc taggttctcc ctatggcgct acgcatcgtt 394980
cccttcggtc gagcgaatcc cgttgttccg gtccgagaat ccctatgtct gaggtcgagc 395040
agctaggctc tcgttggtcg aggttagatc ctcgtatgtc gccactctcg tcactgggcg 395100
ttgtcactga tgtcttgtta tctcaggaca ctctgccagg ttgttccttg ttgaccggcc 395160
ttgtgattct cgttatagaa tgtagtgccc aacagtttaa aggaacgggt gaagtctcgg 395220
gatccgctct agtcgagttg ttagatgtct ctctccggag tcgctcctct atctttcgtg 395280
aaagcatacg agtcgttatg ttaagcatct aatcctagtc tttatgttat ctgtgttaga 395340
ggagttagat gtccctcatg ttgaacagtc tgacatcaag ttgttaggac cttagtcgct 395400
atgcgaacac ttaacacaag actgaaagcg ttagtggttt atgaatcagt catcaaggat 395460
cttagccaaa cggtgaccgg ctacgtaagc actttgggcg caggtttctc gatcggactt 395520
gacgaattgt cataaagaca tcactctgct atatatataa gaaaattgga ttctaaaaaa 395580
agattcaatt aattagaagc attcgcagtt ttcagttcgt ttgtcatcat ctaaaagaaa 395640
agagaaaacg aaagtcattt tgaaagacaa aactgctaag ctataagtag aagttgttga 395700
agtagaaaat gcttgctgct cgcttagcgc acggatcata ggctatctca tcactcacta 395760
aggctagcga aaagtgatcg aataaagcat ttgttcgtac agctctcgaa cctcacgctc 395820
tatcacgcac ggaaaagaag ctgactcaaa gaaactagct ctcgcttaat ccgcatatct 395880
ggaactcctt gatttgaact actccgaatc cggcgatgaa ctcacatttc ccccctgggg 395940
ggactcttgc ttctgtcttc ctctttctgg catctggtgg aaatgttatc tcgatcgatc 396000
agtttcttct actctatgcc tactaaaagc ttaaccatgc cctaccacca agaacagatt 396060
ctcgccatct atttatagga aaaacttcgc aatatgccag agctatcatt acctttagtt 396120
gattatgtcc agactgggaa caagaggcct ggtttttttc ctgtgtctga ttccagagta 396180
tcagcaccag ttgttcttgt aatagacgag tgtttagatg aacctcatct ccagcatcta 396240
caaagctcct tgcatgcatt tgtagattca ttacccccaa caacaagact cgggattgtc 396300
acgtatggca gcacagtgtc agtttatgat ttctcagaag agtctatggc atcagcagat 396360
gtatttccag gtaaaaaatc accaaatttg gagtcattga aggcattgat ttatgggacc 396420
gggatatact tgtctcctat gcacgcatca cttcctgtcg cacactcaat attctcatca 396480
ttgaggccat atagactgaa tatcccggaa gcttctagag accgttgcct gggtacagca 396540
gttgaagttg ctttggcaat tattcaaggt ccatcggcag aaatgtcaca gggtgttgtt 396600
aaaaggcccg gtggaaatag cagaattctt gtttgtgctg gtggacccaa tacttgtggc 396660
cctggttcgg ttcctcattc tttcactcat ccaaactatg cccatatgga gaaaactgca 396720
ttgaagtgga tggaaaacct aggtcgtgag gcttttagga agaagaagac tttgatttac 396780
atattttgtg caggcacatg tcctgtaaga gtgcctgtcc tgcaacctct tgccaaagcc 396840
tccgggggtg tacttatact ccacgatgac tttggagagg cttttggtgt gaacttgcag 396900
agagcatctg ggagggctgc aggttcacat ggtttattgg aggtccgctg ttctgaggat 396960
atttttgtta gtcaagttat aggccctggt gaagaggcac atgtggacag caatgaaact 397020
tttcaaaatg acgagactct tgtcatacaa atgttaagca tcgaagaaac acagagcttt 397080
gcattatcca tggaaaccaa gagagacatt aagcgcgatt ttgtgtattt ccagtttgca 397140
tttcaatttt ctgatgtcta ccaatcggat atcaccagag tcattactgt tagattgcct 397200
actgtagaca gtgtttcatc ataccttgag agtgttcaag atgaagtggc tgctgttctt 397260
atcttattgc caagaggaca ggagagccaa gaatgccaat gatgcacttg atatgcgagt 397320
cacggtcgat gaaagaatca aagatattgc aagcaaattt ggttctcaaa tgcccaaatc 397380
aaaactctat cggttcccta gggagctctc attgttacca gaactcttat tccatcttag 397440
aagggggcca cttttaggaa gcattcttgg tcatgaagac gagagatctg tgctgcggaa 397500
cttgtttctg aatgcagcat ttgatttgtc ccttcgaatg gtggcatctc gctgtctgaa 397560
aaaaaaaaag ttcctattgt aagaacataa aagaagcatt ccacagtcgt aggttcttct 397620
ctttctctgg cataaacaat aaaaagcttc aactaatccg atctttcaac cgcacttcat 397680
ggcaaagcgg tcttctttca aagaatctcc gtccctagtc catacccacg tctggggaac 397740
ttcttcactt catgttcaca tctttgtctc cctctttcaa gtgagttcag ttagccctta 397800
gggtcagaag agagctcatc tttacttcct ttcctataga aagctactga ttctcttata 397860
gccttcgttc attttgttta agaaggctgc gacatataca gcatctttcc ttatactttt 397920
tcttgcctgg atgaaaatac aatagatgaa tagtcattcc ctcacaaatt ctttatttga 397980
atatctttgc tttgttcgtt ctacagatat agattcaact tcctttcttg gcaccatccc 398040
tattctgatg gctcagtaca agaccgacgg aagagaaggg gtgaaaaggc tagcgaggca 398100
gaattctttt tctctttcat agcgccgcac aatggagaca ttgtagtgct agaccagatt 398160
taccagcgga cagttgaaaa acgatacgac ccaggacctc cctccactcg tgggacgggg 398220
ttcttctttc tatcaaaata aatcgaattc gaaagcgcac caccccttctt tactttacaa 398280
ccagcctccg acccaaggtg cttttagaaa aggtcagcgg ggcaatcaaa aaagacttgc 398340
ttttgacgcc ccgctgtgcc gaccagcagc gggatgctac ttacgagctg gtcagggaca 398400
ggttccggtc actctttcga tgccatgcca ttgtggtggc acgggaacca ctgaatgggg 398460
gctgttttca tctcatcgct ggcgtgtgga agactagtgc atccaagcac agcgcagcca 398520
agagggtcca agattgcttc gtcgaatggg acggacatcg atcttcgctt ctacaaggcc 398580
tggtcgactc tttgtaggag ccttttttta tcaaggggtg acctggcttc ctttccttta 398640
cctttaaaca gttagagcct cttctcttat cagtcctttc agtcagttcc ttttcggtta 398700
gctacttagg atgaatcaca cagaggcgat ctctaacata agaatacaat attttcaaga 398760
gacagaaggc ttaagagaga tggggaactt ctctcctata aatcttcttt gcacgagctt 398820
ctgtaagccc cgaaacagac tccaattaca tgtgttaagc atcgtgccat ttcaaaaaaa 398880
atcaaataat agagaaaaaa cggctagaaa gaaggtcaag tgaggaagcc ataatcttca 398940
taagcagacg tgtgagtcta gctttcaatt agcgaagaag gaaggaggca aagcaaggct 399000
ttcttctttc tttcagagtg agaaacgaat cgaagcgggg aggcttgaaa ggtccttcga 399060
ggctcgtcaa tggcttggct tcaggtcgcg aatggaagcg cggattagcg ggtgtccgct 399120
tgactcagtc atagtctcgc ctggtacgca ctcgaagcct atgttcacta gaaaaatgga 399180
aaaaaaaaaa aagtgtgaag atccgcccat gattcatgga accattcctt cgcgtgccgt 399240
agcttaggat tcgtgctatt gctattgttt aggggcgtca agaccgggtt ccgacttttt 399300
ctttttgaga aagaagaggt tactggacaa gcgaaagaga tgccgaaaga gcagatgctt 399360
ttatttgaaa caaaagcatt agccgagaca tacctcccgc taaagaacac tattgacaat 399420
ggggtccggg aggccctcaa aaaaagcgat agagcaagaa agaaagaaag gatcaaaaca 399480
tcacgcacgg gccgcacgca aaagaagaga gaggatagcc agaattgtat tgaggccgca 399540
gcagcaagaa aacaagaaga gcacgtcttc ccaaacaaag cagccttcag caggagctgc 399600
actacaatgc ctcagctctg ggaacaggaa ggaactgagc gccccggcga ataaagaaaa 399660
cctagaacaa aaatggaagc ctaagccttc acatccgaaa ctgaaaaatc atcagttgga 399720
gaatcgtttt tacagggtag gcatggtgaa ggcagaatgg aaatagaaaa caactaaatg 399780
acttagtctt ggcttcttct tcctttatgg agagaggccc ctttagcttc agggggaaat 399840
tcctatgtct ttctttcatc ctctctgtct atggcctatg ccaattggtc ttattcggat 399900
gagttgcatt tcgttttcct tttgttagtt tctcagtcag ggccaaatcc ttctccctaa 399960
aaattccaga ttttctttcc tcggcgagtg aagtttctgc ccttgttgag tgagtaaggc 400020
ccgatcgagc ttatgtgctt gccaggtctt tcaccatctg cttttcctcg agaatgtgag 400080
actgctcacc ctcagtaatc gtattgtccg ctcttttcat tgattgtaca gctttctcta 400140
aacaaggaat ttctagggag tcctcccagt cggctaaagg cgcaatggct tttggttttg 400200
aatccggcta aggttgaatt tgcttttgct ttagttgttg tcgtagagcg accttctgtt 400260
ctttcagttg tgtaagcctt ccacctctct cttagctttg catcttttcc attcggtcca 400320
agaactaaga gcggtcgaag tcctgtctca gggaatgggc ttgaaggcta gtggtcatat 400380
tagtcgtcta aggggaaatg ccttttccgg gcctatcccc attcgcctat cgctttcttg 400440
agttgatgtt taacttgcac ctaggggatt aaatcttcct tgaggtttta gtgggagttc 400500
ctttttgatg cccattcgcg agtggctaaa gggaaatttg cttgttccga tagttagtct 400560 aaccccttc ccgcagcatt ccattcgaag tcgtcgaaaa agtctaagac ggagaaagtg 400620
gtgatgctct ttgattgcat ccgcttgctt gatctttgat cgtctagctg tcccctaagc 400680
ccctctcttt agcctatgtt gtctcagtct tggatagagt ccattaccta tctttctttg 400740
tttgaatgag actatctgat gtcctttcat ctcaaactga atgtaataag agtgaaaaat 400800
taggaaattt cgtacgaaaa ggaggctatg tagtatggcc cctatccctt ctttttacgc 400860
cagttgctct gctccttatc cctttggggc tagacctcag ttcagatcat ccttggatgc 400920
tagcgatcct ttcaccgaag aactcttcaa agaggacact ggctttctat ctttgaaggg 400980
tttacccaca gaccagaggg ttaaggctct caccttcttt tcaaatcaaa gaaagaagag 401040
cccttcgatt cgggcccttt cccacctcct tagtatgaat ttgatttatc ctttttcttt 401100
gttgcgtact taacctgaac cctgtctatg agtatagcaa tcctttgaat ctttcctaat 401160
ccgctttctc tttttcttat gccttgggag cccagtcttt aggagaagca gctgctcact 401220
cgtgacaatg gatgcctgct tatgtcaaac tatcctcaat ctctttcccc taaagctagg 401280 attttttct tagcttccgc tatttcaaga gtttgctgag cttcttgtgg atcaatgtca 401340
ctacccttct ccgcatcatt tactaaaaca gtgatctcat tattgcctat tctagcaaaa 401400
ccacccatca gagccatcgt taaccattgg tcgttaaggc gtattctcaa aatccctata 401460
tctacagctg tggcaatagg ggcgtgactt ggtaatatgc caatttgacc actatttgta 401520
gataaaatga tttcttccac ttctgaatcc caaacaattc gattaggggt cagtacacta 401580
agatttaagg tcatttcttc gcattgctct ccatttctaa gttcatagcc ttcgcggtag 401640
cttcatcgat attacctacc aaataaaagg cctgttcagg aagaccatct aattctccgg 401700
aaaggatcaa ttgaaatcct cgaattgttt ctgctagacc aacatatttc cctggcgaac 401760
cggtaaacac ttctgctacg aaaaagggtt gtgataagaa acgctcaatt tttcgcgctc 401820
ttgctacgac taaacgatct tcttcggata attcgtccaa cccaaggata gctataatgt 401880
cctgaagttc tttgtaacgt tgtaaagttt gcttaactct ttgggcagtt tcgtaatgtt 401940
cctcaccaac gatccgaggt tgcagcatgg ttgacgttga atctaaagga tctactgctg 402000
gataaatacc tttggcggcc aatcctcttg atagtacggt agtagcatct aaatgtgcaa 402060
atgtcgtagc aggagcaggg tcggttgata acccacagcg gaaggcattc tacccaataa 402120
ggccgatact tcggatcctg cttggacgaa acggaagata ttgtcaataa atagaagtac 402180
gtcttgttca ttaacatctc ggaaatattc cgccatagtt agggcagtca aaccaactct 402240
catacgagct cccggcggtt cattcatctg accgtaaact agggccactt tagattctgc 402300
aatattttct tcattaatca ccccagattc tttcatttcc atgtaaagat catttccttc 402360
ccgagtacgt tcacccactc cgccaaatac ggatacaccc ccgtgagctt tagcaatatt 402420
gttaatcaat tccataatga gtactgtttt acccactcca gctcccccga atagtccgat 402480
ttttcctcca cgacgataag gggctaaaag atctactact ttaattcctg tttcaaaaat 402540
cgctaatttt gtatccaact gtataaaggc gggcgcagat ctatgaatag gagacgttgt 402600
actagtatct acaggcccta aattatcaac aggctctccg agcacgttaa aaatccgtcc 402660
cagagtcgct ccaccgaccg gaacacttat agcagctcct gtgtcaatca cttccattcc 402720
tctcgttaga ccgtctgtag cactcatagc tacagcccta actcgattat ttcctaataa 402780
ttgctgtacc tcacaactca cattaattgg ttgaccaaca ctatctcgac cttgaactac 402840
cagagcgtta taaatattcg gcatcttgcc cgggggaaag gctacatcta gtaccggacc 402900
gctsgtaacc tcgctcctga ctattcatat tcacggctta ttcataataa aggctgtaac 402960
ctcctaatca aggagtggaa ttctctgctc ccctcggaaa accccattgc tttgaccatc 403020
ctcaatgacc tgaggatgct tctagccttc aaagaagagc aattgaccac tactactata 403080
atggagaaag gacaatctgc cttctaaccc gaggtccagg tattccggcc ccagagagag 403140
agcgtgccaa agcccgatga atagacaggg gatggacagt cctcccgttc agggaagagg 403200
aagggggga agtccttggc attcctgcct ttctgtcaaa aagacaataa acatagaaga 403260
gaaaaagact ggcgtcctcc cggaggtcta gccggtgaag gccaacttaa gtactgacct 403320
ggcttactta acttaatagg cttgcagagg aaaggcctag cccttggagc cgtaccacca 403380
agaagaagat caggggaatc tctaccatca ggcttcgaat ctgaggttga ggtctagcct 403440
ctcttttcag tggaagttga gctcgtcgga tctgctgccc gtgacgtgag tgatcgttga 403500
ccctgcccct tcttattgct atttgtgaca tcgagtgctt aagtgagatc agcggtctgg 403560
caggtccttg gacgctggcc cttatagtct agtctactcg gacctctact agggctagag 403620
ctagccggaa aaagaaaaga cttagccaaa aagaagtaca taataagaaa atgctccacg 403680
ctctaccttc cgtcctcctt aaactaggct ttcttgcaca gtagcctacc tttggtctca 403740
ggttcgctac ttgctagcct agagctgacc ctggctgtga tcaagaagtc tgcagctaat 403800
tctagtttcg gggtcgccaa agcattgaga gatggaagga atgctctgtc taaccgcaat 403860
gcttgtctgg cctctccagc caaattgaga aattctgaga gaaattcatc cttccttcta 403920
tcttttttt ctgaaaggcg ggtcttccta gtgggctcgt cgccactagg cagtcatctt 403980
tgatcctgat cggccgacct ttccgatccc gaaacaaaga gagttcggct ctctttttc 404040
gctcattcag atgaataaat tccgtgaaga cgacgagaga tgccgcctgc tctttccgtt 404100
ccttctcttt cggagtggag cactcctctt tgttctgttc ctttctaata aaagcttggt 404160
acgtgttctg agcgagcctt cacgtgacgt gaacggtacc tatgaagtgg aatccgtttg 404220
tcttggcttc caactcataa gggagttgcg ttctgaggga ctcaaaatat ccacagctat 404280
tgtcaagctt gggcatacta aagaatgacc caattgagac cgtggccaca ccttgataaa 404340
acagtgatga tgtggtcaac cctggatacg tggctcttcg atgggggaag gaccacgcta 404400
gtcgtctgag tgtgtggtgt gtagtgggtg cgtcttagtg tcttcttact acgaaaaaga 404460
aatgagaaaa tagatgattc tcgttctcga aactccactc tttttctctt tcaaaccagg 404520
aggattggca tttggccaag atgtgatcta tctctttcct tggccttctt tctatttaga 404580
tccccgttcg tgatcccagc cctggaatca cttcactctt tattcaagag aataataaag 404640
taaagaagag gttcaagaca gaactgtgag cagggatatt tagctattta gccttagaga 404700
aaggctgact tgagagccct agtcccttac ttttagagaa gaaggacaac tccgttcgtg 404760
attcccgggt ggggatcact tcactcctgc gcctgtagag tctttaagca tctttccttg 404820
aaaatcgact aagcgggaag cctacttgtg aagtgggcta ttgcagagtg aaggaaggtg 404880
ggttccagag aggattgcgc ctaccaaagc tttgactctg agagtgagag ttgttctgtt 404940
tgagttctga actagaggag agatttcgat tatcttcgat tctagggtct tgtgcttacc 405000
taagtgttga agcgtggaag cggaagatca ccctaggtga cttagtttaa gagcttcggt 405060
atatagaaag caaaagcata ttttttttta gaaatttctt tcactttccc ccctccaaaa 405120
gagttctttc ttcctccatt agcatagttc caaacctcta ttgcttggat gaagagcttg 405180
atgccaaagc aatagtgcaa taggagacga tggccagtat gaagagattc aaaaaggatg 405240
cttcccgaga aagctttttg ctttctttac tcaactcgtc gcggcgagct aggagcatct 405300
agaatagcat aatggctatc ttttatttat aggcttcaaa caaagagtcc aaagattgaa 405360
agggcaccaa aggtgaaata gccgggataa gggctttggc tttctctcta atatgccaga 405420
tgccggtgaa aggaagggaa tgaaagatgg catgaacaca aaaaactgcc atttcccccct 405480
agttggagtc ttagcataaa atagaaaagg aatggctgcc ttaactttac taaaagtaaa 405540
gttaagaggc agattccgga ctggagcatt aaaaggaaga cttgaagccg ctttagaata 405600
aagaaatttt ttctatgggg aaagcatcga atcctctctt ttcacgaatc cgcagcaaaa 405660
agacgcagat attttcatga agaataagct cttagatgta gcattaccgg acgtgaatct 405720
aaaggttaga actaataatc tagctctttg caataagggc ttttttcagg acaaatgcca 405780
aacgcaaaga aagcagaaga tgcggcttag ccagctcgct ctagtcccct acaataagga 405840
tgagaaaagg ccaaggagtg aataggaggg aataggggca atataggggc atcagtctta 405900
gctcttactg ttcgagaatc aactgtacat gaatgcccat ttataggctc ttccttaggc 405960
catcaaggag gaagcgaggg tgggacaagt gaatccgatg tgagggaagg attgcagcta 406020
gagtcgaaac tagggcttat gcaattgaat cagaaaaggc tgcacatgta atataagaat 406080
gggaggagac agccaaagct gggattgatt gatctattcc aaaaccacta ggaagggacc 406140
tattcctaag ccattttcag tagacagaca gggaaaagga ctaaaaagat tcttcgcaag 406200
atgagagcaa gcattagatg aagccgactt tgtccatctc gcatatcaac atcctctatc 406260
gatagcctaa tatagcccca cacagagaac gaagatggtc ggtaggtcct tcctctattt 406320
caagagttct agtacttgca ttgcggtccg tccattagtt cgatgattct tcttcgcctt 406380
taagttaagg ctttttcaat caatctcata ggttcctata gctcgtccta taagaaagtg 406440
ttggattcaa agctggtgtt aaagagtaca aattgactta ttatactcct gagtaccaaa 406500
ccaaggatac tgatatattg gcagcattcc gagtaactcc tcaacctgga gttccacctg 406560
aagaagcagg ggccgcagta gctgccgaat cttctactgg tacatggaca actgtatgga 406620
ccgatggact taccagcctt gatcgttaca aagggcgatg ctaccgcatc gagcgtgtta 406680
ttggagaaaa agatcaatat attgcttatg tagcttaccc tttagacctt tttgaagaag 406740
gttctgttac caacatgttt acttccattg taggtaacgt atttgggttc aaagcccttc 406800
gcgctctacg tctggaagat ctgcgaatcc ctgttgctta tgttaaaact ttccaagggc 406860
cgcctcatgg tatccaagtt gaaagagata aattgaacaa gtatggtcgt cccctactgg 406920
gatgtactat taaacctaaa ttggggttat ctgctaaaaa ctacggtaga gctgtttatg 406980
aatgtcttcg cggtggactt gattttacca aagatgatga gaacgtgaac tcacaaccat 407040
ttatgcgttg gagagaccgt ttcttgtttt gtgccgaagc aatttataaa tcacaggctg 407100
aaacaggtga aatcaaaggg cattacttga atgctactgc aggtacatgc gaagaaatga 407160
tgaaagkaat gttgtgttgt aatggcttgt gctaaaggaa ctgagagatg ccatgccacg 407220
atctttagta ttcctgctat cccaaagggc gggaaggaag agagcattac gaattgccct 407280
atttgagata gtctctataa ttaccaagac ccgtacatac taagatcgtt ctagcgaagt 407340
acgagtttac gaggcaattt ccttccgagc tcacattcgt tctagactct atttagatta 407400
ttatatctca taagagaaga aagatcgtag gaaaggtgaa gattcgagaa aacgtccgtt 407460
cacgtcaggc aatgtttcgt ttcgagattg gcttcagcct tctgcttaac acatgcaagt 407520
ctactagttg atcgaccgat tcccccgagc ttaggggtca attacggggg aatcggaaac 407580
tattgtatct tttctaaagt ggcattctcc cttttgagga ccggctttcc tattgatttg 407640
acttttgcgg gattatgaat atatcaatcg actcttgcat tcctcccttg ctttccaccg 407700
gccttggcct gaaaatgaag agtcttctct gctgacctat agagaggtag gaaagatttt 407760
ccctacactg gcttcctccc ctagctactg aggaagaggg atctcgaatc aatcaattcc 407820
tgggttgttg tattaaagaa agcttttagt gcgcgttgca tgctttgtaa tagtacgaac 407880
tcattatgct cgtcaactag gtcaagcagg tgaacccccct tacgctgtct gtgacttttt 407940
ttgccttcaa aaaccgatgc ttaaaacata gaattctatc ttctcagtcg tcgatcgatc 408000
attctctgcg gccaactaaa aaggatggaa aatataggca aattctgaaa tggaccgaga 408060
tggcctatac accaattgac tgagaaagga agattgttgc aagcccttaa aagtactcta 408120
aagcaagcct tgttccaggc agaggcccac ggaacggtaa tgaaattccc tgcctgcttc 408180
acttctttct ttattccaaa aaaaggtcca atcagaactt ttgctaaagc tgtcgatcag 408240
gtcggtcagg caacgataag ccaataggcg atcctaagag ccagatttct ttcttcgagc 408300
taaagaaggt tcacctaaga aaagacaatg tctgagattt ccgtcaattg acttttggtt 408360
ggctaatagc tcgtcaattt ctagattttc catggtaccc gctcattgat ggaattgatg 408420
cgtggaatgc taaacccaag agagtgatac cagcgagtcg ggcaagagag ctaggaatag 408480
ttagttagcc attcaagtgt gctattccta tggggaagga taactccttt ctctgacgag 408540
aagaaggttt gctttcgaat aaataagccg ataggcgaaa gaatagcacg agcgctagag 408600
cggtagggac ggggactaac ccaccatctt tagattttgg cattctttct tgtgacctaa 408660
caatttagat agtgtggaag agcaggacta tggtcaagtg atccctcgca taagagcgtg 408720
ttaccagggt cccccagttg gagaagaaaa ggcttgcatt cacccattcg attcgactcg 408780
aagcagacag ttcaattgaa gcgcgaactt cattttcacc gcctaaaggc cgaaaaatag 408840
gactttgtta ccggaaaggc gggaacaggc gcctaagaaa gagagccatc tttgttgaca 408900
gtagcatata cctcaatctg acctaccagc cttcgtattt aaacggatgc gtaaagaaag 408960
aaaaaagaca gacgacgctt gtagtaagcc gaaggagcta gcccaaccaa agtctgcctt 409020
tattcgctag gctcagtctc atatgtaacg atacctggct gacaatccat tctctctcat 409080
gggatataaa gaatatgtga attagaagca tccgaggcaa aaagaggtca aatcccctag 409140
ttgggctttc ttcgagcaag ctcttagcga cgaagggact cgttttctat taattgttgg 409200
tgtgatcgta tcagctgtga ttgagtatgt cagtgtgaaa gaaacccctg cagatctgat 409260
cgtatcgggt gctttagtat gagtacgagt aggaactcct gcagttgccg ttgctagtgt 409320
tttcgtaacc ggtcttcttc ttagagtaag cgctgaaatt gaatctactc ttggcctatc 409380
agctcttgtg cactcattgg cagttctcga agaagcagct cttgaggaag catccaattc 409440
ccagtctcta tccaatccat gcggcaaatc tatttgtggt ggaaaaaagt caacaataaa 409500
atataggaac ttattctatt ttgagaataa caataaaaag aattgcttaa gtaaggtagt 409560
cgtttctttt tttcggtata ccccgctctg cgagtagagc gaatgaagat aaatcttacc 409620
taatctcatg aatatccttc actcaatttc tcgtctttgt ctgcatgtgt caaaaaacct 409680
acttgttcca accaatctat tttttagaaa gaatatcgtc cgttgtttct ccccctgtct 409740
cctccttctt gtctttctaa ctatcatctt tctagttctt ggcaaaagtg acctctttca 409800
cttttacctt tcgaaggcat tcatagccgc ggtaagccgc accctctcgt ctttattaat 409860
caagatgggc ttctcgggcg tgctagcctt ggccgttgca tggtctctga aatttttttt 409920
cattgcagac tcatgtaaca tgatggctcc ttcgggggcc tctggctcag gatcagggga 409980
gagcgctgga ggaaggggct tcaggtggac tgatttattt ggaagcagtt cccctgctaa 410040
ttccgaagcg agtctggacc aaccggcccc ggactctccc aaccctggtg aacccgcagc 410100
gcctattgct gaggtttatc atccgttaca ggaggacgaa cagaggcgtc gggagctcag 410160
tgatcgtctt gcactgaata caattaagga gcccttgagc gaagagattt ttgaggcaat 410220
tatagaaact caattccaaa cggaattgaa aattgagaaa gctcttcgct cggacatggt 410280
tcaggagggt tccattttag agaagaggca caaaattaga ggggcgctct tctattctaa 410340
aggaaggcca ttatcattgg cgacctattt ggaccacctt aaccaaatgg agaaccaggg 410400
gacccaccgt agcccgcctt ataaaaacct tatgaaagcc atttttgata agatggaatt 410460
tgacctggat tttaaaggaa tcaaaaaaag gagatactgg tagagctcat ctttgtcagc 410520
ggcattctcc ctttactttc taataattag atagattatt atggaacttt ctccccgagc 410580
tgcggaacta acgagtctat tagaaagtcg aattagcaac ttttacacga attttcaagt 410640
ggatgagatc ggtcgagtgg tctcagttgg agatgggatt gcacgtgttt atggattgaa 410700
cgagattcaa gctggggaaa tggttgaatt tgccagcggt gtgaaaggaa tagccttgaa 410760
tcttgagaat gagaatgtag ggattgttgt ctttggtagc gatactgcta ttaaagaagg 410820
agatcttgtc aagcgcactg gatctattgt ggatgttcct gcgggaaagg ctatgctagg 410880
gcgtgtggtc gacggcttgg gactacctat tgatggaaag gggctctaa gcgatcacga 410940
gcgaagacgt gtcgaagtga aagcccctgg gattatagaa cgtaaatctg tgcacgagcc 411000
tatgcaaaca gggttaaaag cggtagatag cctggttcct ataggtcgtg gtcaacgaga 411060
acttataatc ggggaccgac aaactggaaa aacagctatt gctatcgata ccatattaaa 411120
ccaaaagcaa ctgaactcaa gggccacctc tgagagtgag acattgtatt gtgtctatgt 411180
agcgattgga cagaaacgct caactgtggc acaattagtt caaattcttt cagaagcgaa 411240
tgctttggaa tattctattc ttgtagcagc caccgcttcg gatcctgctc ctctacaatt 411300
tttggcccca tattctgggt gtgccatggg ggaatatttc cgtgataatg gaatgcacgc 411360
attaataatc tatgatgatc ttagtaaaca ggcggtagca tatcgacaaa tgtcattatt 411420
gttacgccga ccaccaggtc gtgaggcttt cccaggggat gttttctatt tacattcccg 411480
tctcttagaa agagcggcta aacgatcgga ccagacaggc gcaggtagct tgaccgcctt 411540
acccgtcatt gaaacacaag ctggagacgt atcggcctat attcccacca atgtgatccc 411600
cattactgat ggacaaatct gtttggaaac agagctcttt tatcgcggaa ttagacctgc 411660
tattaacgtc ggcttatctg tcagtcgcgt cgggtctgcc gctcagttga aaactatgaa 411720
acaagtctgc ggtagttcaa aactggaatt ggcacaatat cgcgaagtgg ccgccccttgc 411780
tcaatttggc tcagaccttg atgctgcgac tcaggcatta ctcaatagag gtgcaaggct 411840
gacagaagta ccgaaacaac cacaatatgc accactgcca attgaaaaac aaattctagt 411900
catttatgca gctgtcaatg gattctgtga tcgaatgcca ctagacagaa tttctcaata 411960
tgagagagcc attccaaata gtgtcaaacc agaattacta caatcctttt tagaaaaagg 412020
tggcttaact aacgaaagaa agatggaacc agatacattc ttaaaagaaa gtgctttagc 412080
ttttatttaa tacaatacaa gaaaaagcaa aaatagctaa aaacagcctg cctcctttat 412140
catatatatg agatgggcgg gcctttttaa gcaaaagatg atccgatcca ctatcggttg 412200
taatcttctt gacatagaaa gtcctttttt tccaattgat cgtttatgaa atggaagagt 412260
agctcatgtt agactgatgt gatgagcgag gcccctagcg atggggggaa aggggagtgg 412320
gtaagcgggc tcctttcact tgactgctta gttaggagtg atctttccca tgctttccgt 412380
tggtcaacaa ccaaccaaag tgctctatac ttcttcacta ctcgtacagg cttgacgggg 412440
ttaagctgta ttgagggaat cgttttgtct caatcaatca agaatgcctc aactggataa 412500
attcacttat ttcacacaat tcttctggtc atgccttttc ctctttactt tctattttgc 412560
gtgttccatt tttaatattc aatataggct ttactttctc tatgtgatag atcctagatt 412620
tcagcggatc attttctact tgaaattttt tttctttttc tttttagtgg tgcgcgctgg 412680
ctttctcctt tgggaaaaca tccatctcct tctttttcca cgtacctgtt ttggtattct 412740
tccctctgaa ctaagccttc ttcatttctg cttaaaccaa ccgcatcaag accctgagtg 412800
ggtggaatat gtacatcaag tgctaagaac cacccccagg atgtcggcca catatgaggt 412860
catggtccga aacgtcctaa acacagagat gtgtttttcg acgcgagaac agatttactc 412920
tatatacaaa cttattttct atggtcgaga ggacccttcc ctctttcttg atcctctcga 412980
cctggaaggc atccttcaag tccatctaga aaagatggag tttgatcaag ccgctctgaa 413040
cgaagtatta cgaagtctat gtaccgagag ggatgattcc cccttttatc aagaggtaaa 413100
gacgactcaa gctcattatt ttcgggactt tataaactta aagaagaaag ccgaattgga 413160
gatgggggaa aagctcaatt tgcatagaga gtgggaatct ctctcgagga agacagactt 413220
cttagagaag gagaactcct ctctcagaga aaaacttttg cttctcgaga gggggccagt 413280
cggaaaaaaa gaataataaa gtaatataaa gcaataaagt agagaaagaa agtcccggtt 413340
tttttgttgt atagagagaa ttctccaatt tccctttcgt tattactttt ttttatgtca 413400
aagaccagaa gctggaaaca tagttttttt cattcttttc ttatgaggtc gtgtacaaca 413460
accttaaccg cacaagcctg ggctgggcct acctccatcc ctagaggagc cgtatgaggc 413520
ggaagctcca cgtacggttt tgaagccgag cctttccagc aatggggcct agggaccgat 413580
atgatgattg gtttaggtag ggcggccggc ctactacggg cacctgtagg gattagtgtg 413640
tgagaccgcg atccacaaac tgacgcatgg gactcacccc tttacttggg aatagagagg 413700
ggaaacatag catgtcacaa gagcgaggcg aggtttggaa ccctactgcg agagggacgc 413760
ctcgcgagcc gggcttttag agatgaggcc ttttggcgaa gccaagtcaa tttcgggcca 413820
ccaaaccctg caactgatga gaaggcccta tggagtaaag ggaagcgtgt acgttgtcac 413880
actccctgcc ttccaaaggt gcctagagga cgggccagac gcagcagagc gacgaccggg 413940
gagcgggttc cccactggaa gggggacagg agacggccat ctcaaggcac atcacgacct 414000
acaggcaaca ccggcgagac ctgggaaggc aacccgattg ggtgtcagag gatccatagt 414060
acctgcagcc tcccggactt catattcatc atttttgaaa gcgaggggaa gggatctctt 414120
ttctgcaacg gaaaaaaacg gagcagattt gactcggcac aacctaacga tacatccaat 414180
accaatgatc tgtgcctaga atgcgttgct agatctctgc tctagaaagc tatacaggca 414240
acaacgaagg cgctttgacc ccgggcttcc ctttcattac ttctttcacg acgagagaac 414300
cgcgtccgca tcagtcgaag tggtggaagg ccccctgagt caaagggaga gcttctgcac 414360
ttctctccaa gagatacgat tcggtatctg aataggctga aggagagtga agaggcggct 414420
actttcccag cccacgggaa agcctcttct ttctggtatt ctttctttgg ctttggagat 414480
cgagagcggg gtccggaaga gcatgatgtc ttcgtctgga acttcctgcc catcaagctc 414540
ttcggggcga ccgcctatcg atttgaattt gcctcctcag ccggaggcgg aaccggctcc 414600
ccctgaacca tcctcggaag agtaagaaag gagaaggaaa cgggagtttc tcgcctccaa 414660
agagtataaa gaagcggagt gtcaccccaa aaactagacg cacgcatcaa ggcgttctgc 414720
caacgagcga aggcgatcgc tcaagaaagg ggattcagcc ccggcaaatg cgatgcagtg 414780
aaagacgctg cggactatgt ggccggtgac gtaaaagata tgccggcagc tagccaactc 414840
cgctttctaa cgaggttaag gcatgaccta gaaaacggaa acagcgagac ctggggtctc 414900
atcgaacgag aagttcgaag atggagacca ggttcggcac gaaatcataa aggtttgagg 414960
acccgttggt caaaggaaag ggaaggtcct gcttccggga cggagccgta tgacgcgaga 415020
gtgtcacgta cggttccttt gagaagggtg tgataccacc acctatcagg cccgacgagc 415080
ggtccacgga gctgcatccc tactcacctg gtctatgcac atcgctctct ccaggaggtt 415140
ggccgcctat cctagatctt cccatttcca agaagatccc gggctcgatc tggtttagta 415200
tcaaggtgat tctttttctg ttcctatata tatgggtccg tgcagcattt ccacgatatc 415260
gttatgatca attaatggga cttggccgga aagtgttctt gcctctatca ttagctcggg 415320
tagtccccgt ttctggtgtt ttagtcacct ttcaatggct cccttaatta tgtgcgagga 415380
attgccctat tgagtaatgg gaagcgggct agtccccgaa aatgccccgc ccgtaagttc 415440
gtttgtcgtt ggggaaaaaa aaagatcttt ttcaataaat aagcccctct ctgataagga 415500
aagaaacaaa aaacctaata tcatgaatat ccttcgcccc ctatctcctc ctgcattgcg 415560
ccacttcatt ctttctgtga ttcttcttgc aaggcttatc ttgtgtactt ggctcttctg 415620
tcatttgatc ggctttgacc cctaccttat tattgagaaa gtcaaaggtt ctttttttcct 415680
ccttgggtta cgtgcaattt ttaggctctt tggtttgcgg attccttctg tacttcttct 415740
ttcgatcgtc cctttggtac tagattgctg cttgcacatg caggatcccg caggaggtca 415800
acctgcagcg gagcaaccct ccaacctgcc ttcgggcgaa tccagcgaag ctagcgtgaa 415860
tcagcagcct gtgattcccg aactgcagcc tccccttctc gatgacaaca cccgtcgagc 415920
ggagctcgct agccgattga ggactcattt ttggggggta gcttatacca accgaatttt 415980
agactctttt gttcatactc aagtgcaaat tgaaaaagat ctcgaagccg cacttgtgga 416040
cgacggctat tctcgtgatt ctcttcttgc gaagagagat cagatcaggg gattcatttt 416100
ctacccgaat ggacaggcgc ttagtgaaga cacttacgct ttgcatctga agcaaattct 416160
caattcgggt acacgccaaa gcattccata ccatcggatt gaaagagcca tcaatgacta 416220
gaatctcctt ttagattcga aattcttcgt ttttttctcc caatttccca ctctttctgt 416280
gaggcaaaac ctcaccacac tacactacac ttcgacacaa gagaagagga ccgggcgctt 416340
tgtatcttcg ggataggagt tggcggtctt ctttaagaga acttcaatct aatactcatt 416400
atggatcaac tcatgtttcc actctatttt cattacgaag atgtatcacg tcaggatccg 416460
ttgctcaaac cgaatcacgc caacgttatg gaagttcctg gatcgtgtaa aataatagta 416520
gtaccgaaga cagcaccttc tatcaaaaat ggaaaattgg ctatggagat tccgtgcggt 416580
cagaaattaa tacagacaca aagggcttca acaggaaagt cgtttcgatc caatccattc 416640
ttggggtcaa ataaagacaa aaaaggatat gtcagtgacc tagcacgaca aagcactctc 416700
cgagggcatg gaatgtctaa ttttttggtc agaatatcca cagtaatgtc tctgttagat 416760
tctccggtcg aaataaggga aaggtcaatt caattctcga tggaaacgga attttgcgaa 416820
ttctccccccg aactggaaga tcatttcgag atcttcgaac atattcgagg gttcaatgtt 416880
actattgtaa cttcggccaa cacacaagat gagactttac caccgtggag cggctttttg 416940
caaaaagatg agggggaaac tcagtaagat gtcggagaag agaagcgaaa tataggagat 417000
cacaaacgta gattgctcgc ggctaaatat gaattgagac gaaagcttta taaagccctt 417060
tgtaaagatc ccgatcttcc tagtgatatg cgggacaaac atcgttataa gttgtccaag 417120
ttgccaagaa atagttcctt tgcacgagta agaaaccgat gtatttacac gggtcgccct 417180
cgttccgtat atgagttcta aaaaatttct cgtatccttt ttcgtggatt agcatctcga 417240
ggtcctttga tgggcataaa gaaatcgtct tggtagcaac caccaaacca atagaacaag 417300
gggtagctcc gcagcaggtc tacaagcaag gtaagtaggt ccattaccag ccggctccgg 417360
accgaaaaga cctaacggac taatccctta tctcggatcg tagatgctaa cggggcggga 417420
atcgaagtgg gggacccctc taccgcctgt gtctatctcc tgtcaagtat gctccccaga 417480
catagactac gtacagggta gtactcttgg aaagatagaa tatcaccgcg tgaacataac 417540
attacattaa gttacgaatg taactcccga aggatcgacc acttttctaa atatagtaag 417600
gcggagaact gttgttcagt ggagcgccgg agtgcggagg ttgttcccat cattgaagtc 417660
agggtgtggg actgagcctt ccgaatgaga aagaagaaaa gtgcttagtt tcgttggaaa 417720
aaccaacgca aatatcatat tgactttctc tcgccctact tctaaagata gatagaaaag 417780
gttggaaaga atgactttct gaaattctct cctttctaaa gctgcgcaag gycgtggggc 417840
cccagaacaa aagcccaccc ctcttttccc ctttaatgaa ggaccctcgw rkwctattca 417900
tttgtgggtc tggatbcgvd gtctbtddtt ttttttttth btnnaggtga tttcgaaaat 417960
caaccaacgg aaaaatccgt agcccaggtg actcacagcc tccctctcgc ccaaataaat 418020
gaaatgggat gaatcaaatc aataagcttt ttgattgatt cagggcgcag cgaagccaaa 418080
ttcaatcaag gcaagggggc ttacttttcc tgaggctgat tcatcctatt caaatttagc 418140
tatgctaatg gaagaggaaa agttttcaga tgagatggac ccccaagaga tgagcgagaa 418200
cccccaattg cttaggggtc gcactctgtc ccgcttggtg gacgaaatct tctctccttt 418260
tagaattctt tctcccacac acctttttttg ccctctttca cttcaccgag gaggaaagaa 418320
taatcttcca agcggacaga gacctaaatt tccattagat tcattcctaa gcttgctttg 418380
ttgcagcaag atgatcagtc cgagagtgct ggagagaaga gaaagcggta aaaacctctc 418440

-continued ttattcggtc accgagaagt cggacgactc ttcagtaacc cagggtgatc cgacccccttc 418500 gacgcttttt tcgctgtata ccccctccat ccttcggagg tggaagaaag ggtactctaa 418560
ttttaataat agtagggccc cagaacgcta aaaggtgggg gaacaagagt tgtcacgata 418620
gaaaagataa aaaaataaat gactataagg aaccaacgac tctctcttct taaacaacct 418680
atatcctcca cacttaatca gcatttgata gattatccaa ccccgagcaa tcttagttat 418740
tggtggggtt tcggttcgtt agctggtatt tgtttagtca ttcagatagt gactggcgtt 418800
tttttagcta tgcattacac acctcatgtg gatctagctt tcaacagcgt agaacacatt 418860
atgagagatg ttgaaggggg ctggttgctc cgttatatgc atgctaatgg ggcaagtatg 418920
tttttcattg tggttcacct tcatattttt cgtggtctat atcatgccag ttatagcagt 418980
cctagggaat ttgttcggtg tctcggagtt gtaatcttcc tattaatgat tgtgacagct 419040
tttataggat atgtactacc ttggggtcag atgagctttt ggggagctac agtaattaca 419100
agcttagcta gcgccatacc tgtagtagga gataccatag tgacttggct ttggggtggg 419160
ttctccgtgg acaatgccac cttaaatcgt ttttttagtc ttcatcattt actccccttt 419220
attttagtag gcgccagtct tcttcatctg gccgcattgc atcaatatgg atccaataat 419280
ccattgggtg tacattcaga gatggataaa atagcttctt acccttattt ttatgtaaag 419340
gatctagtag gttgggtagc ttttgctatc ttttttttcca tttggatttt ttatgctcct 419400
aatgttttgg ggcatcccga caattatata cctgctaatc cgatgtccac cccgcctcat 419460
attgtgccag aatggtattt cctaccgatc catgccattc ttcgtagtat acctgacaaa 419520
gcgggaggtg tagccgcaat agcaccagtt tttatatgtc tgttggcttt accctttttt 419580
aaaagtatgt atgtacgtag ttcaagtttt cgcccgattc accaaggaat attttggttg 419640
cttttggcgg attgcttact actaggttgg atcggatgtc aacctgtgga ggcacccttt 419700
gttactattg gacaaatttc tcctttagtt ttcttcttgt tctttgccat aacgcccatt 419760
ctgggacgag ttggaagagg aattcctaat tcttacacgg atgagactga tcacacctga 419820
ttagtgagaa attctgacac caatcattta cgagtgagta ttacaccaag aatttacaag 419880
cggatcgagg aatgaaggga gaggaattag aatagaaaga aagagaggga tttcgaatta 419940
gagtaagggc acgctaagac attccttttc gtgctttcga tctgcttact ttgaataaag 420000
agaaaaaaaa gaatagaata gataggcgga aaggctttac acaagaccac agagcgagag 420060
agagagcctt cgcttacctg cttaaccgta ccctcctatc gtacctatat agcctttcct 420120
tcagttatat ccagtttcag ttctgcttcc aactaccgat gggagaaggc ttggacgtat 420180
agcaagatta aataagaggt attgcatacg ggaatgataa aaaaaaaggt tggaaacaga 420240
gctggagatg agcgctagcc aatggttaag acttcagaaa gcaccttagc aattaccagt 420300
aatgccccta tcgacctcag tcttgttttt tgctagcttg agttcataac tttactattt 420360
ttcattaaac gtagaatatc ccgacttcgc tagccagaac gaaatggaca taggagcgat 420420
cgattacgag agctcgaccg atcagaccgg gaagaagaga aagaaaggtc aatctccgaa 420480
aggccttcgc agagctgagc tttagggggg aatacttttt gtggtcttgc acatggaaaa 420540
gtcaagtatt ctacgcaggc ttgatttacc ggaatttttg cttcaaagaa tgctttcaag 420600
ctaggaattt aagcacggat agctttattt gacaattagc tggaagtcgg gtatgccata 420660
aactaaggcg ctgggtagat cgtagattgc cgggtatgaa ttcgattcta agtcggagaa 420720
tgcccatgaa tagggtctta ttacagaatc cgcagttttg aaagtagccc tagacagatc 420780
attgctaaga ggagagcagg gaatttcttg ctaatctggt gctatcatcg tattctaatg 420840
attattccga cgtcagagca gacgggacta ccaatcccag agtgaattaa ccttgtctgc 420900
actaccacct tagtttacta gaccttgggg aattggctag ttaccttcac tccgcgtggc 420960
agcctaccta cgttttgtct ttttcctacg agaccttaga gtttcccagc ctttctccgc 421020
ctacatgccc cccgaaatca gattgggttt tttcttgagg aaggtccatc tgcttttgtt 421080
ttcgaataag actaaggcgt gagcgagggt ctctttgtgg tggtctttca ccatcttcct 421140
tttgattggc ctatatcttg gaataaggtc tttagctatt cccacagtac cttagtcccg 421200
taccggctgt cggtctatct catattcgca gaagaaggaa cttgcttaat gccatgccgg 421260
aagtgtaatt aagtaggcgg ctggtcgtag aatagtcttt tcagtaagtg ctgttgcagt 421320
tgtagaacca ttggccattg attcttcctc gcaaaccttt catccccgct gtctagctct 421380
ctcgtagtcc aaagcgaatt caatcgtatc cgcctttgag gaaaagaccg aatcagtctt 421440
tgagccatcc taataaatcc tcgtaggtaa tgctcttggt ctgccttcaa tcagtttatc 421500
agcctaaggc ttcgctctat tacctgtgtt gtaagctttc cagtctttga agtaaggttc 421560
aatgctagga aaaatgcttt tgcttcgcgg gtctatcgcc ccaataggtt ttgttaggaa 421620
attttttata tgagtatgcc cctatcccgt aagccttcca tcgttgcaag ccccttccat 421680
tcggcccaag ctttctttcg attacgtctg cttccgattc tgttattccg ttagcctgag 421740
ttagtcgttt agtcaaagcc gtacgtatgc ccctttcgaa tcgttctatc attcgaagta 421800
ggagctgggg ttgcgggcag agaactattg gtatagcgag ttcatgtgct tgcagttggg 421860
ttactaccat ccccctaacc attagtatca cactctgtga agtgtctctc tggtattggg 421920
ataacttcaa gccccttagc tcgcttgtat cggggggagc ttacttcact tgttttcttt 421980
tagtcacttg ccaggaggga aagcagcaga taaagagcac catcacctta cttaacaaag 422040
ggcttatgcg aaagagagca ccgcttcccc gataagataa tccgctttcc taaaatccct 422100
actttattgc tctagctctt gactcatatg gcactgaaat tggataggtt cacgcttagg 422160
cctggttatg gaaactcttt aagcatagga aatttttcct tttccataag aaactccaac 422220
ttaaacagga actggcctgg aactatatgt aagggcactc tcatccactg gctgcaagga 422280
aacaactgga ttggcctttc taactctctt taaaagagac tgctttcaaa ttcacttgcc 422340
ctagaacctg ctttttattg agattgatct agaatccgct attcctagtt tttttattat 422400
tcctagccag agaaataaaa caaatctcga gatccagaaa cctatctata cgcctagcct 422460
taagcaaaag aaatctcctt agccctacca tagaaactat tacctcgact tggattgaaa 422520
ggaagaactt aggactttgg gacttcccct aggactccaa cccctagcat tccaattgaa 422580
actcaaggag atggaactaa acaggcttag gccctttttcc tctttcaagg agactagagg 422640
gaatgcaact actgagacag caactcaaac aaaatcccga gagaaaataa aagattagtg 422700
aggtaaggtc tatagactgt aaggcagaag gcttgaaagg aagagcactc ctacttactt 422760
ttcttttggg agaaatccta gacaccttag acaccggatc ctcggtagga ctcttatttg 422820
ataggcatta ggggatttga ggttttgggg tttcacttgc agacccagcc ctgctgcttc 422880
cataagtctc ctatcctaag tttctttctc tgcatgaatc aagttcttcg acaggaccat 422940
cccgaccgag ggctaatcat agatctacta tggtcttttt ttttttttta ttcttttatc 423000
ttatttccgg ttaaaagcct tttctggaag cattatgttg agtcactcca agagtagaat 423060
cagcagctca cctcacgttt taggaaccaa atgaggaatc acacgtagac ggacctgagc 423120
attctcctgc tctacggagc cctctggagc tagagttggg gctgcttgac gctcttctcc 423180
tttcgagtga attgaattac ttcggctcgg atgcctttga tcaaatggaa ggatggatgc 423240
ctgcctttag cgacttcgtt cggtcattcc ttctttactt gttcgctatg gcttgagagt 423300
taatcgcacg agagagtaag taagagattg aaaggaggat cattggacct cgctctcggg 423360
cccagaggca gagcaaagaa agccttagat ctttgcttgt ttcgtggtat ggaccaaagc 423420
aaaggttctg ctgctatcga cacctaccca attaaccaaa agtataatcg atcgagaccg 423480
aagcttatgc aattgtggaa ttccgttcaa atagaaagct ttttggccag ttcaaggtca 423540
gtcgtgagct gtaggaaaag atagtagcga accagaagaa attcccgtag ttgcataagg 423600
gggacgttga aaacattcca gcagatagta tgtaatactc ttctcaaaac gagcactata 423660
ctctttctta gtttagggca gaaacatact caaggaatgc aaagctaacc ctaaaaatgg 423720
aatattacct cagctcaaag gttgtttact cagatatttc ttatcaaagc gagggattcg 423780
tttcaggcga aatcaaatca gaagctattt ccgctctacc attaattgtt gctatttccg 423840
cacccctgtc cggtggtttg agaaagaaag tcgagacatt cagaaagaga gttatggcat 423900
ttctaggatt ctaatatggt cctattgatt caatctttat gcttggcccg gaactcttgt 423960
ttcgagtgaa agggagagca gtggcccgca ccgcattcac cggtaaattt ccctctacgg 424020
ggcggggtgt ggaaagcact ataagttagt tgacttctcg accaaaggta gtctagctca 424080
acctccaagt aggaatagat tctatgagtc gtgatccagt taagataggg ggcatttcta 424140
gcattgaaaa tccctattct tattgaatag ttcaaataac tagttgaaca tacctattct 424200
tttcaagaat agcctcccct tatcgaaaag aagggtccga agaagacaga actggccatc 424260
cttctcatcc ccctaaggaa gtagagcgcg gtgaaagaat tccgtcgttc agtcgaaggg 424320
gacaggttag cagcttcagg ataacccgag cagtgaaaga gaagtagggt tcagkytgwt 424380
agatttttat ttattattta tcgtgaatgg gggaatcatt acacatagta tatcaaaccg 424440
gcgtattttt ttgttttacg ccccgtaact cttcctcagc caggcttggg cagaatagca 424500
gagcaagtat tagtagcata acaaaaaggc cttcctcatc aaagatgcag tgctagtaca 424560
tctgagactt cttaattggc tagttgtaaa tagccccagg gctatggaac aaaggattat 424620
ctcggaccta gaccgaggca ttgatggtga ttttctaatc tcgcagaaca gaatgtgata 424680
cgatgagata gaatgcaata gaaacaaaga ctgggaacgg gttacctact cttaacgggc 424740
aaagcgagcc cctttatttt attctgaatt ctttaattca gaatcaatca aatctcccca 424800
agtaggattc gaacctacga ccaatcggtt aacagccgac cgctctacca ctgagctact 424860
gaggaacaac aggagattcg atctcataga gttcaattcc cgttcccaac ccatgaccaa 424920
tatgagctcg aagcttcctt cgtaactccc ggaacttctt cgtagtggct cccttacatg 424980
cctcatttca gagcatcymg gacaasgagg cggcgatsaa ccatccrctc tcgagattca 425040
tattgatcaa tagatctccg cgtcctgcca gttcgctaag tagactcact ctaccgaggg 425100
gcaacaaagg ctggaactct tcctgccaaa aacaagggac ctacttctca tcctaggagt 425160
tagcaggtat gaaagagtcc cctctctgtc tgtctctccg agtttctact actaagtagc 425220
acttctgcta ttcaatcata gaatcgattc cgatcaagct gaaaaaagta agccctatat 425280
atgttattag taaagcgcta acgccctatc tatagtaagg ggccctttct tgctcgttag 425340
cgctcttttt tgattgcagc tagggcgccc cttttctttc tcaaagtcaa ctttctcgct 425400
tgttagtcaa gctttgaagt ccctacttta tttagattta tgggatattt gaagaagggc 425460
aggtttggaa ccctatacct atacaagggg ctggtctcga tctcgcttgg tggtacccct 425520
ctcgatgatt gttgactcaa cattgatttc gtgcttgagt tggagggctc tccctccatc 425580
catccatcga gtcaagtaat tcgctatcgg aaattgatcc gccgcctatc tcatgccatg 425640
cttcttcttt ctccgaatcg gtttctagtg tcagtcaatc aagattcgcc atcaagagag 425700
ggaagagcct tgactttagg ttaggccggt ctcatcattc acgcaattcc cccgtccatc 425760
gattgatcac gcgagtacgc atccagtcag cgcatagcga atgaaaaaag cgttcatcct 425820
ggattctctt cctcaagaaa aatggctatc aattgatccc tattcattcg gtcaaagtct 425880
ccacttttca cgcccctcta ctaagagatg caccatgttg ataggaatcg gcaaagacct 425940
tcttgtacac gtcctcgagg gcagcattca tggcaatcat cactactttc tcccgagggc 426000
atggtatggc tttgttcttg gtcttgttta atagatgtcg agtgccgctt ttccccgtcc 426060
gagaatctcc atctgctcta agtgggcgcg agctagaatc cttatgtcag cttggttgtt 426120
caaaagactg tctctttacc ccttccatct tcatcttttc taaagcccag accattcttc 426180
tggatctgca ttagtcctat ttcaggtgca aagcctcttc aataaagacc tcttttttt 426240
ctttctcccc catttctcat tttgttgatt gaaagagaat aagcgctatc cattgagtaa 426300
agagagggtt tgctacagtg attcgggcgg ttggtggccc cttcgagagt tgcgggtcct 426360
tgccgctgca tgagtgttag ctcacgctca aaactcctcc gacacgagtc ctagtcgttg 426420
cgctgcggtc cgtttcccgg cttcgcttgc gcgatttgca cttctgattg gttccagcca 426480
tccccaacct taatgaatgg actatgaagg ggttagtcaa gcggttcggg ttttcggtcg 426540
gttcccgttc gccttccccc cccctcatag tccattagtg ggtagggtgg tcaacttaga 426600
gggcgcccgc ctcctcttca gacgtgtcct cgacaacctg gcggttcttc ggtctccgct 426660
tttgggggcg ggagtgcttg gtcgctgggg tttccttttc cccaaccaat tcggttgtgt 426720
cagccctgag attggtctaa cattttgtta tgagctggct ggacaaagat ggattgaagg 426780
tcagatagat ttgagttcaa gtggcacagc accttcgatc gaccataggg cctattctac 426840
ccttaccgaa ttcattctat tgaagcgtaa ggtaaaaagc tccttctcat cttgcatttc 426900
tttggtttgg aagttccaga atgttgtctg tggatttcta taacaaagga aagcctccta 426960
ccctaatact atgccatttg attgattaaa gttccgtgct gctcaccact cctcgaggcc 427020
aaggacgggg tcgaaccgtc attccaggat ttgcagtccg atacatttcc attatgttac 427080
ctagccaaac ccgccacctc atgtgccaaa gtcaaagggt tgttcttcct tctccgctcc 427140
ttctttttct acatatgcgg cggcgggtta ccagagaaga ggggacaact tctttctcct 427200
ttgccttgct caatcttcct tttctgattg aaagttgcaa gccactcgac tattggtaca 427260
gaggccagat agaaggttgc tcatccagcc cagcggatcc attgtttatg cggcagtgca 427320
atgcagctga aaaagggaag cccctttttta ttagtaaggt ataggttggt tggggaaaac 427380
tccaaaacta gggttccaaa ttaccttata ttatagaaaa gtttgagaaa ggggcacccc 427440
tactataccc ctaaactaca agctagcgcg caagggctga aaagccgttg ttgcttgctg 427500
cttgcaggct cgaaaatctc tctttctcct ccctgtctca attctgattg attagcttct 427560
tccttcgcgc aagctacggt ctaacgaccc ccttgttgtg ttgcattttg tgatcttccg 427620
cttcagtctg cgtttttcgg atagccggga cccgatgttg atttccgatt taaatgtcag 427680
ctccaggttt ggggcggccc atctgattag ttcagctatc actgctggaa accccagcgg 427740
ttgttcggct gcgtactccc cgtctgccta tctcacactc ccaaagcaaa tttggatttc 427800
ttctttcatt ttcctttcct gcatctttct tttttttaag tcattgatct catatctata 427860
agcagggggg tctgcgttca ctattaagcc tacgcccgtc cattcctttc aagcttgatc 427920

-continued cttcccttag actcgttacc ttgttcgact gaactcgttg gttccgcgct ctattcggtc 427980
gtaacccggt tcgagaacct tctctcatag attcccttta ccaagtcatc gccagcaatc 428040
agctcttatc ccttggtgtc aaagggcgag ttcctttctt gtcttgccca aaaactttct 428100
ttattctcat tggagaaaga ctctcccgcg gcaaggtttt acacataggg ccagctgctt 428160
tctttatctc gcttgccctt agtccgtcta gcgcctttcg gttggggtcc gccctggggg 428220
ttaggttaga ccgcttgggt ttttttctag tatcgaaggc agtcaacgtg tcagccattc 428280
ttccccccatt agacttgtca atcctttgct ctttttcctt ttctcttcca gttctccccc 428340
tctactttat ttgacagggg cggagaatac cactctatca ataacaagaa aaaagtagca 428400
attccctttc aaatggtttg agcttggaag caacctgcta tctatcgata ggcgagaaca 428460
gactgctatt gactgcttcg cctatctatt ctattatggc cggcttggag acatcagagg 428520
aagaccatca tctctatccg ggtacgatca tagcttcatt cattcgttga accttgggga 428580
tcaccattag cattgaggtc aatcaccaca ctacctctat catacatacg acattacacg 428640
aagcgagagt gcatggtcaa cacacaccta aagcgcctac gttccgcttg cagccaatac 428700
aaccacaacc taacttgcac gagattcaac aaccgaagct actggtagtc ccgagggggc 428760
ggcatcctcc tataatagtt agcagtactg aacaagcgag tcatcggtcc gaggaaagaa 428820
aaggaccgcc tttgaaaaaa aaaaggaact cgctaggcct tcagaacaaa ggcgattctg 428880
ttcatgcttc agacgatctg gctaattcta tatacaacta tctaattttc ttcaattata 428940
tagaaaggcg taaaggcgaa ggcctattta gcgcctttcc aaaggtaacc ggttaggttg 429000
actttggaaa ggctactaag gaccgggtga agaatgaaaa acgtccgcta aagcccacgg 429060
gataaggttt gcagatgcga tcatgaatcg aaccagatcg aaacattcag ctgtcgacgg 429120
acaaagccgg aacgtcgacc gcaaacgaag gatggccagg ccccggttcc cagggttagg 429180
gtattcccta ttatgagcct actcagatca gaactaaact agttgattct ctttggccgg 429240
ccggctttaa gcaaccttcg catttcctgc tgagatccca agtctccaag tgggccctct 429300
tggccaccca cgaccttggc tttttagaga atcccgctcc tgtgtcgtag gacttgtagc 429360
tcggcagtcc accgggtggg tttgtttatc cttccagttt cgagtgtctt cttggatagt 429420
tatagcggcc cataggcgcg agatgtacct tgtggggggg ggcggcggtc ccctggacat 429480
agtcctttca ggcagtggcc gtttagtcca tggtccattg gatggtcggt gcaaggccag 429540
aaattggaac acattgattc cgctcgttcc cgtccttcgc ttcagggcct gtccctcggt 429600
gtggtcagta ctccatactg tcgggcagcg aagcttacac ttgttcacta attatgacgg 429660
ttcaccaggg cctctttcct cctccctttt ctgctcactc gtaggggtcg ggacccccac 429720
aaagggggag ggagtcgact gaacatctca gccattggcg ggaatttcgc ccgcatccga 429780
tccccaattc ttgttcaccc cggatgatcg tgtcgggtga attgtgacct cgtacgatcg 429840
tgtcgggtga gcaacagccg cttcgtcaca gtacttactt atgggctaac aggtcacact 429900
ttggccaagt atcctacaaa gagactcccg agagccagaa gtattaaagg aatggccata 429960
ggaatgggcg catcatgaca tcgtaagatg tctcgcccga atgaattagt tggtactaga 430020
aatgttagaa aaagtgaacg aaaggagtaa taagaagtga aaaggacaga gacacttccc 430080
aaccagaaag caaagttccc actgatggta tacttagtgt aagcgagctc taagatcaca 430140
tctttggaat aaaatccagt tagaaaagga aatccaatta gagataagct gcccatgagc 430200
atcatggcat aggtaaaagg gaacgaggag gcaagccccc ccatcttccg catatcttgc 430260
tcatccgaca tggcatgaat caccgaacct gcactcagga atagtaatgc tttgaaaaag 430320
gcgtgattca ttaagtgaaa gacgctaacc gaatagttag agatgccgca agcaaagatc 430380
atatagccta attgactgca agttgaataa gctatgaccc tctttagatc attctgtaat 430440
attccagtgg ttgccgcaag gaatgacgtc atagctcctg caaaagtaat aacaatcaaa 430500
gccgtaggtg ggtattcaaa taaaggggag caccttgcta tcatgaaaac gccagctgtt 430560
accatagtag ctgcatgaat caaagcggat actggagtgg gaccctccat agcatcaggt 430620
gaccaagtat gcgatcctat ctgtgcagat ttcccaacag caccaataaa aagtaaaata 430680
caaataagag ttatggcatt caatctcata ttgcaagaaa tccaagaatt tctgggggca 430740
ctagcacgag caaaaatggt tgaaaagtct actgtttgaa atagagtaaa acaacccaaa 430800
atcccaggag ctaatccaaa atcacctact cgattgacaa gcatagcttt tatagctgct 430860
ttatctgcct gaagtcgtgt aaaccagaaa tgaattaaca aatatgaagc aagacctact 430920
ccctcccatc ccaggaataa ttgaagagag ttatctccag tcaccaacat tggcataaaa 430980
aaagtaggaa tggataaata acacataaat cgagggctat gcggatcctc agacatatat 431040
gaaatggaat aaagatggac caagctactt atgaatgtaa ccacaattaa catcactacg 431100
gtcgggctat cgaacacggg gtcagaagtg aattacgagt cggaccaatc tgcgaatcga 431160
gcgagctccc cttgcatgca atgatgtggt ggtaaacctc tcattctaat tcagtgctct 431220
ccgaaccgtg cgggaaggtt tcccatcaca cggctcacca acttgatctt ccgcgggaac 431280
cgtatgtccg aacaggcctg gaaaaaaagg taaggtctcg ctttcctttg ccactcaagt 431340
gtacggcatc tgccgtgctt aggccccttc ttcccttacc taatgaaaga gtccaccgcc 431400
tgccttagta gtctcaaata aggcgtgcag gcctgcccct ttagtaggtg attcactacc 431460
gaagcgaaga aaaggctgga tcaatcaaag ggggtactac gagccctctg ccccacgcat 431520
ctaaccagct cgcgtggttc accggttcca ccgactagac caaaagagtg attcagtcga 431580
tacagaggtg cgcttgaagt ggggggtgtg ctgtccctat tgggctgggc ccttccccat 431640
aaggccccac cgtcggggca taagcgccct cttgctaccc atatgcgagg cgccgtctta 431700
gccttccctg accaggatcg ctcccacacc tgtagcgttc gtgatcggcc tcctcaactg 431760
tgtatcgatc gaaaggcagg gcggcacagc ccccaaccaa gggagtggtt acgtccagta 431820
tgtcccccct tattcccgac atgctatggt accccggagt gggtaggagc gggtcgagtc 431880
cgtatcgccg cggagcaaca gccgcgtccg gatctgatct attgactcgg caattcatcc 431940
ggtgacttca cggtcgccaa agaagcccca agaagcatca aacatttccg atgagatcca 432000
tggagcaatt cttagatagc aagcactagc tcccggtgcg acttcataaa aagcaatcaa 432060
agagaagatc gaagagaatg aaacgcacgt agtggttatt atagcggttc cttcttttcc 432120
tagaaaacgt ccgaaacaac ctgctacaaa actaccgagc aggggtaaaa atacgataag 432180
tagatacata atttcgagtg tgatcagaca accaaaaatc agacaatgac agagcggcct 432240
ttatacaagc tgtatattgg tttggtatat tatcctatgg ctcgctagct tgacggtcat 432300
aaaatgcgag tcttcttcag agggggaaaa ggcaagtcaa ggtcatattg ggaccgtgct 432360
tttagaatgc acgcatataa tttgctacgg tgggccccac agttctctat ttgattcagg 432420
tggttcaagt acgtacccaa tgtaagaggt tttccttgag gatagaagag gatacctcta 432480
atctggtgcc ttttcgcgac aagttgatcg tcggacacca agtcagaacg aagtgctctt 432540
tctatatgaa gttctgcttt cgcttgggcc tcaattattt gatcaaaaat actatcgggc 432600
aagggacgcc ctatagtatt tatgctcaga cgatctgtca gctccagacg cctctcccct 432660
tcttcctgta atgggtggta aacctcagcc tcgggcaaaa taggcgccgc gggttcgcta 432720
ggtgtttcgc cggtttcagt ggaactgcta ccgaataaat cgctccacct taattcacct 432780
gagccagagg aagccatcat gttacacatg ttacaatccc caatgaagaa tttttgggac 432840
aatgtaatgg ccaaggctag tccgcctgag aagcccatct tgatcaataa agacgagatg 432900
gtgcgccttc ccacggctat gaaccctttc caaaagaaaa agtgaaaaac ttcaccttcc 432960
ataaagatta gagctataat tagcacaatg gctattatta gcacaatacg gtaaaaaaaa 433020
accgctttta aacctgtttg catcggctcg tgcacagatt tacgttctat aatcccaggg 433080
gctttcactt cgacacgtct tcgctcgtaa tcgcttagag cccctcttcc atcaataggt 433140
actcccaacg cgtcgaccac acgtcctagc atagcctttc ccgcaggaac atccacaata 433200
gatccagtgc gcttgacaag atctccttcc ttaatagcag tatcactacc aaagacaaca 433260
atccctacat tctcattctc aagattcaag gctattcctt tcacaccgct ggcaaattca 433320
accatttccc caacttgaat ctcgttcaat ccataaacac gtgcaatccc atctccaact 433380
gagaccactc gaccgatctc atccacttga aaattcgtgt aaaagttgct aattcgactt 433440
tctaatagac tcgttagttc cgcagctcgg ggagaaagtt ccataataat ctatctaatt 433500
attagaaagt aaagggagaa tgccgctgac gaaaagattt ctcttagaga gtaggtactg 433560
tctatgccat tggtaagtag atctaaatag atcttttgta gtccgagaaa tttttcttgc 433620
caagactcgt ctccatttg cttcaaatcc ggagtttcgt ttcactggtt gtgttaaaat 433680
aatctttcaa tcctattagt aaactattag cgtaccaaag ctcaagcgag cggccacttc 433740
ttcctctatt cgatttttct tcttcccagg cccgggtagc tttggctctt gttgaagcat 433800
tgccggaagc ttcactctgt gtaaagtaag gacttagctt ttacggggaa atccccgaat 433860
ggggacctta ggagctttgt tcagcactga ccttttctag accgatccct gcgtagaagt 433920
gaagtttcaa agcgctaata atcccatctt ttcacgaata aactgattct ctgcttgctt 433980
ttggggaagc ccctgcttgg ccctttactg gcagtccttt gtaatgcccg aacccgggct 434040
actaccgatt ctaaattcta cgggtaaccc ttcccatgac tacttcttgt cgtaagacag 434100
ttcgcttacc cgattggctg gggcttagac aagacttaaa aacaatcact aaaggcctgg 434160
tgaagctcca ccttttccat ccgctgtctc tcttctcgct accatgttga aaaagaaaat 434220
tcgtatttga gagaatcgta aacagaggat ttcggtggca ccatctatcc atgaggaaaa 434280
cctttaacag tagactagtt ccatagtatg gtcagtcact catgaattcc ttctcgaatc 434340
actactggaa tatagcaaca aagcttgaag caagtggaaa tgcgtcaagg gcatttcttt 434400
ctcactggaa gcctacttga gtagtgcgtt ggatctacac ttggacagct tcatcgagac 434460
ttcacatacg tagcatacgt agattgccat gtttatatcc gaacgaaaac accttactga 434520
tgtttttgtt tccagactta aatctttaac tataagaagg gaatcgattc aagccagatt 434580
acttgaccgg tcttaagctt aagctaacta agtatatgta tgtgaggacg gccatccggt 434640
tagctgcctc tgctgttctt ccagtccttc tatttacttt tttgcctttt ataatctata 434700
tcgtatatcg gccttataaa cttctaaagc ggtaaagatc taaaaagata taaatagaac 434760
ctcgtttgga gagtaattgc ttgttaatgc agtaagcagt tcgttcgact cgctcaaaga 434820
ttcgtctcac taataaggaa tagtcacttc gtacctcttc gaggaacgaa gtcccgcgac 434880
caaatgagtt gaactatgtt caacgaattc ccgtagggag agggaatgtg gtaccgaacg 434940
gttattgtgt gtcaccaagt acttccactt gtcactgagt aaggtaaagc cacgagggta 435000
ggtgggaatc tttcctcaag gcgcaaccaa cccagtaaga agcagctccg gggaacctct 435060
agctagttat gaaactacgt ttcataatta caatgaatca acaccaaccc agaatgtgga 435120
caacgtcttt tccgaccgga gaatacgtta ttaggtaact agagtcaagt gaggaatgag 435180
aggtactcgc tcttatccaa agacgatcta gctgcttatc cgggccttca agcaagttca 435240
aaaactctca ctatgtgaaa tcaacgaatc gttacactct agccacttcg tacctagtcg 435300
ctagagattc ctctcccgtt ggtcgagaga cttcgtacct ctcccgttgg tcgaattcgt 435360
tgttcgttga actatgtgaa acgaacttcg tacgttggtc gtacctcttt cgatagatag 435420
tcagagttct tatttctttg acctttgaca cttgctggat tccttctggt tgtcacatct 435480
tgtcaccctg tctgctttgg ctatctgttc gtaatgcttc cttcttttct tcgatccttc 435540
ttaacttgaa tcatgaattg gattcgaacc aatatctctc caggatctcg gcatccctcc 435600
cacctttcgg cgagatattt gccgtgagca atgcgacatt cccaagacct aacgagagat 435660
ctctctctcc ctctcttttt gggcagagat tactgctttt agtttccatt gccctaagcc 435720
tgtcgctcgg cccgggcgcc catgaggtgt ggttcgggtt cctcctcagg cgaacatgaa 435780
aaaaaaaaag gggtttagtc aagggccaaa atttggtttt atgccatgtt gtctttacac 435840
agctctgaaa taccccccac ctaatatata tataatatat atatatagaa acaaccaacc 435900
aaagagtacc agacagataa cgtcttgcaa atgcaagtag catgtaaaac aatcaaagat 435960
aagatcgaag agaatgaaac gcacgtagtg gtcattatga atgaatctcc cagaaaacga 436020
ttgactatat atactggtga taggaaacaa gtcaaattca tgacgaaggc tatcatatag 436080
agtcgaacaa atttggggca aagccacatc ggggctatgg gagtcgaacc caattcaatt 436140
cttccgcgac cctttctctt ttctacgaaa atttctgttt cgctgctttt ctaaactaga 436200
cagagtgcgg taaaatcaat ctcgactgtt cactacgtac gatatttctt gaaattttgc 436260
atgaagatgt gatcaaagct acatgttccg cttttcctca atgaaattac agagagagtg 436320
gaattggaat ttagcactgt gcggagctct cgctccttct ttgcttttct gatctcattc 436380
tggacatata gaggagatag gaaccttacc ttatctatga aattatgaaa taatgatctc 436440
acactcttca agacagattc gtgaaaggta tatctacgcc atggaagttt catggctgaa 436500
tgatttgtct gctaccaact ccttcctcta tgtctatgct atgggcagga tctctctctc 436560
tacatgtgaa atcttgtata ataatttctc acataccaga ttcccgagga agaaagcaag 436620
caagcctata aagatacgag gtttcaccag attacaggta tggatccggt atgaaataga 436680
tccctccttt tttttatccc ttaggagcta actaagaggg caggcggaca cttctcttcg 436740
ttagacaagg aaatgctttc aaaataaaag cattatgtga ttggttgtcc ttcttcactt 436800
caattcttca agaaggacct cgccaactta tgttgttcac ccaccccctt cggataggcg 436860
cttccgttct tttttcatat ccgcgagaat gggaggtaag taagaagtaa ggtggagact 436920
tacatatatt atattatgca acttatgcaa ctcagtgacc tatcctgttc ttgggatgag 436980
gcttgacttc tcagatgctg cttctccttt cttgtcttgt ggcaggggaa agacggaaaa 437040
aaaccttctt cgcgaacctc tcttcgatgc cgtcttcttt gcgcccctct cccgttggtc 437100
gaatgagttt cactatgtga aacgttggtc gagtgacttc gtacctccta ttagggacat 437160
ctttgtgaat ttaactcacg agatggcctc atttatgttt catttaaaca aaaccctgat 437220
ccctctattc tatgggccga gtggatcata tatccattcg atcccaggaa tacggctata 437280
gctaattggt gccttgattg gtttgagcga cggaaaccta tcaaggtatc ccattagtta 437340
caggtaggtt agcgcagaca ctctcagggg ctgggaactt tgctatatgt aactatatca 437400
agcaaagact tcttgctccc gtcaatgaat gtattatcta caatagagat ggatagtacg 437460
tatgaccaag agcggcccat tcttaggtta gctcgtaagg gttaaagggt tataataata 437520
cttattgtta tgttgttatg acctgaaaag tgcgaccgac agatggttat ctatcatttt 437580
gattcgggac aacatatggt caactatccg ttgactaaga agattcatga gatttcattc 437640
ttggcaggtc aacctttagg ttacctcggc tcctggtcat ttctcaccac tttgtcatgt 437700
gattggcagc acaaatgacg tatccagaac ggtcaaggac tatgccatat taggtgatga 437760
tgttcttatc actgatgatg gggaattata ggatgagctt ggtgtgtcta tctctgatag 437820
gaaatctatt attatatcaa atggcgtacg gagctgctta ccctctttgg atcgacagcg 437880
ggggggaaac tggctctggc tttgttgtaa tgagcatttt ttctacaatt gcctctacgg 437940
atacaacttt cgccatctag ggtgggctgc ttcgcctagc agcacgtttt cacggttttc 438000
gctcgccgct actattttcc tctagatctt cctgcccatg gattcagcag ttgccctatt 438060
cgggaatctc cggatctatg cttcagatac ccgttttggt ctcctttgga ggtctgacga 438120
cttggtcgcg ttgaagggta tagatttcaa agtgctttct cgatgtgaat catagctaga 438180
aattacatta tttctcattc actcggactc ttagatcaaa cggaacgatt cgttgaacat 438240
agttcaactc atttcgtacc ttcttttttt ctgatttttt agcaaaaacc tgttgataaa 438300
cggttgataa acggttgata aacgaccggt cgactcacgg agttggcact ccaggagatc 438360
gaggagtccc ctttgactga ttcgtgattc cgtacaacgg gacggcgggt ccaactgacc 438420
atcttctcca ctacaggaat atcatggatc agaagactat ctgatgtgcc gtgtctccca 438480
gccagcctac gcgggatccc agcgaaatct tcctagctgt aaccggagga tcttgactac 438540
ctcttcaacc tgaagaagag gattccacta agcgattctg agcttcagcc cttcgggttg 438600
acaactgcaa cgagcagcca gcagtggtag cctacaagaa agggctaccc gtagagtcca 438660
agctctacca gtctctggtc gattcttgac cagagaccct ttaaggccct ccccaacagc 438720
tgtcccttct taagcaatga atatgcatct ttgactaaac ggttaataga aatattctta 438780
atgaaccttt agtgggatgg ggcaaagccc tgggataacc ctatccatga gctgcaagat 438840
caattgtcca gtacgggtta ctccagccgg ttattcatat tattcatact agtaatggaa 438900
ctctagtgcc ctatatactt tgacacatac atctctgtct gaacgagcaa tttcgatgct 438960
tcttctggcc caacctttag gtttaggtac gaagtcacta atatagtaat atagctagta 439020
tagctagcta tattaggaag agatcccatt cgtaggaatc tccactccat tcaccgaagc 439080
agaagcgcct gatcccacag gatctggggt aatttgtcag cttgccttta catggaaaaa 439140
ccccattcct tagctgagag tgatgcagct ggcgcagaag acgtcgttca ttaccttatc 439200
agatagagct gacggaaaga ccactttggt atcgattctg agaagacgcc ccactggcca 439260
gttgccacgg aaaactacat gaggttcgcc gagggcgaga ggaggcaaat cactgagatt 439320
tccgagacaa agtcttcttc ggatgatttc actgtcttct cgaattgtat ttgctgttgg 439380
ctcttgccta ttatatcagt catgccattc tggtcttcct ttcctgcctt tagttctcta 439440
tcgaaatcac aagcagaggg gaactcggac tatgacactt tgtttggacc ggggaattgc 439500
accgacaagt cacctgctct gcttagtttt cataatatct ggaagtagga aagacattcc 439560
cttgtcgttt actgcgcgaa ctcatacgca tactttgatg ctaactcgaa tgatggatgt 439620
ctcgggataa ttcctttttc aaggacctcc tgcaggactg gatcctcatt ctggacaaaa 439680
agcaatctca aaataggaaa tctactctta gagtaactag gatctcgcct tgaccactaa 439740
ctagacttgc ctattcttcg ctaaccacct actgtctagt gtacgcttag ttaacgaata 439800

-continued aatccttttg caataacagg gaatagcaat ctaaatattg cctccccctt taacatcttt 439860
caattcccga ctccatcagt attcactgga atgcggctat gaagtgtgac ctgacgggcg 439920
aacatgatct ttacaatctt tacataacca agagtttggt cggttctccg atccaccttg 439980
aatgagctaa acaaagactg ggaacgggtt acctactctt aacgggcaaa gcgagcccct 440040
ttattttatt ctgaattctt taattcagaa tcaatcaaat ctccccaagt aggattcgaa 440100
cctacgacca atcggttaac agccgaccgc tctaccactg agctactgag gaacaacagg 440160
agattcgatc tcatagagtt caattcccgt tcccaaccca tgaccaatat gagctcgaag 440220
cttccttcgt aactcccgga acttcttcgt agtggctccc ttacatgcct catttcagag 440280
ggaacctcaa agtggctcta tttcattata ttccatccat atcccaattc cattcattta 440340
atatcccttt ggtgtcattg acataacaga tgtcgtttct agtctatctc tttctatttc 440400
gtttctatat atggaaagtt caaaaatcat catataataa tccagaaatt gcaatagaaa 440460
agaaataagg gaggtttgtg atgatttttc aatcttttct actaggtaat ctagtatcct 440520
tatgcatgaa gataatcaat tcggtcgttg tggtcggact ctattatgga tttctgacca 440580
cattctccat agggccctct tatctcttcc ttctccgagc tctggttatg gaagaaggaa 440640
ccgagaagaa ggtatcagca acaactggtt ttattacggg acagctcatg atgttcatat 440700
cgatctatta tgcgcctctg catctagcat tgggtagacc tcatacaata actgtcctag 440760
ctctaccata tcttttgttt catttcttct ggaacaatca caaacacttt tttgattatg 440820
gatctactac cagaaattca atgcgtaatc tcagcattca atgtgtattc ctgaataatc 440880
tcatttttca attattcaac catttcattt taccaagttc aatgttagcc agattagtca 440940
acatttatct ctttcgatgc aacaacaaga tcttatttgt aacaagtggt tttgttggtt 441000
ggttaattgg tcacatttta ttcatgaaat ggcttggatt ggtattagtc tggatacggc 441060
aaaatcattc tattagatcg aataagtaca ttcgatctaa taagtacctt gtgttagaat 441120
tgagaaattc tatggctcgg atctttagta ttctcttatt tattacctgt gtctactatt 441180
taggcagaat accctcaccc attcttacta agaaactgaa agaagcctca aaaacagaag 441240
aaagggtgga aagtgaggaa gaaagagats acggtctggg gctggagttc taaggttgaa 441300
ttctgggcat gtggataatc cgaatcttaa acaactgacc tggaaggctt tactaccact 441360
ggggaactaa tccctgaaaa gagctcttgc gaactctgac ttagaaagca ttgtactact 441420
cagctgttag agtccattag agtgtttgaa atccctgaat ccttactctg tacagagcag 441480
taggcttgag ttagaagtcc gtatcccgtt ggagtgtgga gtcttttacc aggccgtttt 441540
ctagccttta cagctggtgt aagagtagtg gcattctcac cagcctgaat agcaagattt 441600
cctccagtag agggctatag ataagattat aaggtagggt tatacggtag aatcattaaa 441660
atgtgaattc cttgtgagga tctaaggtag taatagaata tcatagcgct agagctgggt 441720
caagagtaag gggcaagtgc ctatagaaag ccaatttctt ttattagaac cctgggaaaa 441780
ttcatatttt gcatttctac ttcctccatc agacaaggga gctgatgggt tttaaatcag 441840
agcagaagta cctctttcag ccagttttct tacaccccgg ccagcctttt tttcatctct 441900
ctcttttgta agacgccctg cctgaaaata ataccttatc ctggcctgtt ggagtggtag 441960
ttcacagttt tccaagcgca tctagctcca ttctttcttg ttggaaggct acctcgggat 442020
atggcaatga agcctatctg tggctatagt ttcctgagtg aggggattgg agagtacgac 442080
atatcctttg aggcagctta ttttcagata tttaatttcc taaaagataa gcctatctag 442140
ttgaagtgta agtccccccc tttttttcca gttggagttt ctttccccgg tataactatg 442200
accggctata aagcagttga ttagggcaga ggttttctag taggcgctat ctggctgaaa 442260
ttctaagtca aaagagatcc tggtgtgcag tccatcatct ttgttagagg gctcccagcg 442320
gatttgttag ctgctacaaa tagggaagaa atcacgaaat ggaataggat cgagagtttt 442380
cgttctcttt agccacagtc ttagtcttag acttttgagt tcttctcctc gcgatccagt 442440
gccgttgcag caaatgataa acccagtgaa agaaagtttg ccattcctgc gcgtgtaatt 442500
ccttcttcct actaggattt tcagtcctaa gctaagcaca tgcagtctaa gtttcggagg 442560
aatctacttg aagtgcttcc ccatcttgct tgactcaagt ttgaactttc ttactttact 442620
tatggataaa atagaatcta tcttacccta cttcatatga atagaggaga gggatgaaga 442680
tgaagacgag atttctttta cgatatgtct ctgggttgcc ctacatagag ggattctaat 442740
gggatttcta aagcgagaaa cctatccaat tgctgcagtt tcttattctg tagttgcctg 442800
ccgctgtata acgagttgtt tccgatgggt aagccgtgga aagaagactc tggctaaggc 442860
atttgactac tccttccgaa cagctataga acagcttatt caatagcagc agattcgaga 442920
gaatttccta ttatggaaag gtagtcttca gactcccaga tattggaatg ccctaggatt 442980
ggattcatat ggaagtcaag ctcgacaaca agaagagaaa gtcactgaac acaaactatc 443040
tttctcatgt cttgcaatag acgattcaaa atgaaacaaa cgatagaaca cttatatacc 443100
gaactttcca tcaacttctt atttcttcaa ctactatatt acatactata ctatatgtat 443160
atatgtttga gatttgctcc gagatgatag attgtatgaa aacaaaagag aaagggcatc 443220
accccagctc cggttccggc aacgctaggc gattcatctc tctcaattcc tgaaccaaag 443280
ctaattcaac taccttcccc ctcctgttta gacatctagc agccagaaaa tttgataact 443340
aagaaataag ggatcctttt gcaaaaatag caattggatt gagatggatg gttgtgcttt 443400
cagtcttttc catgccgaat agacaactgc ctcttatgag tgattgctct acagccaagg 443460
cagactgagg aatcccctaa aaagagatct ccatagtaaa tagaatcgta catccaagaa 443520
gcaagactga cagagcgagc tgtaaatgcc ataccattga ttcttgcttt tttacttatt 443580
agcattaagt ggactaaggg caccaatcaa tttgaaccca acgctcggga atccattctt 443640
ctatagcagc ttgccggaat gccttcaagc ctttgaaact acccgggaat ttaaaaacct 443700
tccttccttc aagtcttcta tgagggatcg atcttgggta aatacactag gggatggtcc 443760
cataccaaag agaacctcga gcggacggct tttccgcagt caaatgactt attgcttgac 443820
agcttcaaca atagattgcc ttttcttttt tctttagtga ctcagtccct ccgcagcccc 443880
ttacttagtc taattttttg atagaatcgt ggtaatggct gaagatcgag ttcacgcttt 443940
tgggcttgtg taaggatttc cctatcagtt agccggagaa ggtaatcaag gagttccgtc 444000
ttctacgatg tatgctcttt aactggttca tactggaaga atggatggcg caggagtctc 444060
tcttctgaga cttggactga tgaactctgt aacctatatt ctccaacctt cctcgatacc 444120
ctagaggtcg actcttgcca caaggaatgt catcgctttt cggctgttct acgatattcc 444180
ttggaggatg aaacttttct gttgacctaa ctttccagtg agcggaccta ctcgaaggaa 444240
ggaaaaaaaa gggggttggg ggtgcttcta tataatctct aatccgagtc ttacccctat 444300
atatgtggaa attctgctac aaatggattg gatgcacgga actcacctaa aaaccccaac 444360
ctgcgtgcag tcgaactgct ttattcaact tggcaaagac aaagcatgac ctctggaacc 444420
aaatcgttct tgtctctgga ttgcctcaac tcgaagcatg aggcctggac ccatcggtgg 444480
ataagatcac ctcttcatga caaaaggtgt acacgttagg cctcactcaa ggtaatgggc 444540
caaacctaac gagtccaaac aaattggatc tttttgtatg acaaaaccac agattgggct 444600
taattcaaag cccacaacca atggaagagc ctacaacttg accatgcact tacacatacc 444660
aacactaggt tctattcgaa ggtctcgacc accgatgggt cttgttctaa gcccaatcct 444720
ctcgtcttag gataggatat ccataaaccg ggaacttctc ctttttagtt gacaacctat 444780
gttgggctga ctaagcccac tatcctaata gggtcccagg gttaaggctc cacctcatct 444840
tgggttaagg gcttagttga acccaatttc ttcttttcct atgattgttc cgtgatgggt 444900
tttctccttc taggattagc tttctatccc cgtgttgtgc taagctcatt tctcttatta 444960
ggtatgacct tttgtactct gtggatgttc agattgcata ccttgcaagt cattcattat 445020
ccacacatgt catacatctt tcatatagga tgattttaga aagcacctaa gtgttggaca 445080
tttgtcaccc ctacactcag ctgaggccac aggtctagtc gacgtggcca ttcatattct 445140
acagtaaact actagtcaca ccaccatctt tctttcagct ctctctcttc tgtcatgtgc 445200
ttaaagaatt taaagtcaaa aagacgtgat caactttctc gatctggttc agactcatca 445260
ctctaactaa tgtctcgtcc aggtcggggg gtgaattggg ccctctgaat gaatggtgaa 445320
ccagtcctac gagtgggtgg atccgccgca attattgtta tatatatata taagtcctga 445380
cccggaaagg taccgccacc ttgttcaggc tttccaaaga aagcccatca agtgaatgaa 445440
gtctaattcc cattccgggc cggcccaggc ctgctcgcta tccgagtgta gtcagcaaaa 445500
gctagtttag aactaccatc cggccttaaa aaaaaaccac tcgacatgtg ctcttattct 445560
tctgtcaaaa gtagggaaca gcaagtgtct gatcagatca atcaagcgat aggggcagag 445620
actttacttc gctaggacgg agctgctgtc gattgaggat tggccgaggg gccctttttc 445680
ttttctaagg gaatagattg tagctgggta caaataggcc gggacgagta ggcagggtac 445740
gacgaagccc gcggggtgac acatggttgt actggtcagc tttgggctgg agattgacga 445800
ttgactgagc gtgctttggc agctcgtggt ggagtactct ctgacggatt cgctctatta 445860
ttgcctccta ttcttgaggg agtgatcggg attaagccgc gtggcgaaaa agcactattc 445920
gctctttggg gtgggccttt cgtactcaaa tccgtacggg gaaaggacaa ttattcagcg 445980
cactaaaatc tagtgaatgg ggttccatat tcatgaaaag ccaggtttga aatgatccat 446040
gttacggaac caagacaacc tatcttacta ataataagaa agggttaagg gcctccaacg 446100
cctataaata gaagcttctt tcagtctcta tttggcaaag ggagacggag aggaacttag 446160
aagtcggcaa aaaaaagctt tgagtgtagc catggattct tttataagac ttcaagaaat 446220
ttcgcaagaa atctctcaag tggaagagga gaagctccaa tcggagcaaa ccctggctgc 446280
cttttgggag cacctgcctc ccatcgatcc tgcacttgtg gctgcagcca tgcagcggat 446340
ccgggaccgc attagcgtcc tggaagacag gaaacgggcc ctcctccaaa aacaggaaga 446400
cctaattgtg ggtgctgtca cccgtggtcg ccagggagac tagaatagaa gagtccgtcg 446460
actcttttta gttttagaag gtttaaataa gtgtctgtag acgcaaagta gtgtgtttct 446520
tctttttctt tgtttggtgg agatctactc ctatcctaag tagattgctt tttttgggtg 446580
tgtttgcatg tatcactagt agtcttcaat gcttccgttg ttaactttgt aatgttgtct 446640
ttagttgtgt ggctggtcta tgtgtgtgta agcttcctat ttgatgtatt cccatgtaac 446700
ggctattaat gaataaaaag tgctggtctg ctttgttaaa tattccttat gtatacgtaa 446760
ttaataatcc cagagggaat ccggatcttg agtgaacctc aaagccatgc cagcctggag 446820
ttaattcttt ctatggacag cctttttttt aagacctaat ctaggcatta gccatttaaa 446880

-continued aagatggatt taggtttcgg aggtagatcg aaaacctcag cgaaggtcac cgaacacgaa 446940
caagatacga aagatgttag acagcggacc acttaaacta cttagttaga gattctttgc 447000
tattgcttat gcctcagcag agaagtaaag ttctgctctc ctctctttct cttgcgtatc 447060
tagttctata gcttaaccct gacttttacg atgtaagggc ggaacgtaat agtaataaag 447120
gaaaagcaag gtgtggcggt aagtcaaaac tttttggtct ccatgttccg gtcccggaag 447180
aagcttattt ttatcgctat aaggcataag tagtgaaaga agtagaccta taaagagaaa 447240
aggaagcgct atccctccta cttatgattc aacatttagc tcgatctatt ctagatgtct 447300
tttttacatc aatggcatca gctggagctt gcaccgaatt gcttacccgc ggaactcatt 447360
taacccgacc ctgcataagt accaatgccc cttccccttt cacctctagg aaaaacttct 447420
gggatgagcc cttctactcg tcatttttat attagaggga aaattctcga tcccagacca 447480
ggctccgatc aaggcttata aaagcatcaa cctcatccta aaaggactcc tttagctttg 447540
gggttgattt acgtggctca agactttgag tcaagaggtc aggtgttcag aaaggtggtg 447600
atgcggcatt ggcattttca gcaaattcat cagatagctt gccttctttt cgtttacgtg 447660
gctacatact tgtagcgatc aaagggcata tttattcttt tttattattt atataaggaa 447720
aaggtaattg tatgggcctt tgcttcgaga acaatcgtat tagcgccttc gcagcctgcc 447780
tttccattct tcgagtgcag ttccttcttg agccttttct ttttgactcc taccgaagca 447840
agcctctcaa gtgctgacct ttcttcccac ccggaaatcg tagtaagccg ggagaaagac 447900
attcatatat tccccaggca cgggataaag agagagccga gagccgggaa cgcaacaaaa 447960
agaatttccc tctccctgta ggtcgagcct ccttttcagt cgccctctca cgggaatctt 448020
cttctttata atacgtacga gactaccaaa gaaaatgaaa cttctttccc cggagcagca 448080
actgaaagag aaaataccgc tttcttcatc tgcaccggaa aagagctaag cccggaagtc 448140
acggagctct cttctctttc aatggcagca gctagtttaa gttcaatgtc agccggattt 448200
ctaagcacta gtctttcctt ctcacctgct aactcataga aagaaataga gtcaacccat 448260
gcgcctttcg cggggtgagc aaaaagcctt tccctggatc ctggtatgaa ctcaaaaaaa 448320
gcatttaccc gtcgcctgct tcatctgcag agcttcctct tgttcacagc aaagagagcg 448380
gattcgttca agcaagctaa tcacattacc ctttctaggg taggggtagg ctacgatgtc 448440
attactctcg ctccctcact ccttaaaggg atcaaacgac tttgagcttt ggcattaagt 448500
acgcgtggga aggaattcca ttcaactagt tcaatgaccc tagagggaat gaacgcatta 448560
agcttgaaag cattaaattt agttgctagc tggactgact gtcttctctc tctttcggtt 448620
tctagtcttt gcttcagaaa gtcatttaga aagacccgct tttaacagag aggatttcct 448680
tacattacat acgatatttg agtggggatt cactaagcgt aagttcttaa cccggtatga 448740
tgcgacgatg acttcttgct ttgtttccgt ctctcctgcc tttgttagtc tttaatcgtc 448800
tctaaagcga gtgaagtcac ctgagggtta gaatccgatg tgatcttaga gctattgacc 448860
ctacccaact aactctctct aagtaagagc tcgccctgac ttattagtct tatcgaagtc 448920
gatagggaaa agagaaaagg tcagtgcttc tcctgtgagc gactccgaag tgggctcctt 448980
tcacttgact atttctcttt tttaggaggg agagactgaa tccacctaaa agctaaggga 449040
agcccggaag tattcgaagg ctgataaaaa gagacgtgta ctacgagacc accaagactg 449100
ataggcattc cgaccaaaag gggcaagttt cttataggat ccaccctccc aacaaaaaaa 449160
gaattccttg ctgtggaaaa gctgttcaag ttgaaaagca taaaggttga aggaaatgca 449220
ccttctccga ttagaagggt acgggactcc ttttcctacg caatttccta cgatagggta 449280
gggatgaatt gaatgagaga ctacgaaagt gaggcaaacc cacataagga aagaaatcaa 449340
tctaatcact ccatttcaag ccttagagaa tccgactaaa aagcctaaat tagcgaattc 449400
acctccctct gagtccgatt agaaaaacag ggatgaaagg cctagttttc ggtgagctag 449460
tgggattcaa gtatgaattt gaattttcct cgatccggac ttattaccgt gatcaattca 449520
ctaccagtgc ccatgtggcc gaggttgtcc cgaagcggat caccccgatg cctgtaatga 449580
aaggacagac tttcatcagc tgcaaactgg aagcggtttt tcgttagtgc gttaaggttg 449640
caagaaccta ctcctaacta aacaaagact catccgagga gccaccatcg gtactagtcc 449700
aggaggtcaa tactagcgag agtcccacag ctacgctagt tatttaggta taacgtgttt 449760
cggtcagctt taaaggccaa actaacccag tcgctttttt gcagccctgt ggagtcaagg 449820
cgaatcgaat ggtcaggaag gaagcaagca attcggacag aattaagagg gcttgaaaga 449880
ataagatacg tagagcgtga accaaggttc ataggcggat caaagtcgaa aggcaaagct 449940
gttggttaga cgtagacgaa gccaaagtat agttagacga agccgtagga actcttgcaa 450000
cgcaatccca gctacaggaa gctaactccc taagacgaat gagtcacttt ctgatcctta 450060
ctccccgaag gaactcttag cctcatagct acatgagcta cattaggttc cgtagggtta 450120
gcaatacaag aatctcgatt ggaaaatacc tgaggtagga ttactcaacg atccttgtta 450180
ccttaactcc cttctcccgg gatgaagcct tagaaggaaa agtatagggg accccaaaaa 450240
ctctttagct ttagatgtta tatgaacccc taacaaggaa ccgtaggcat agagctatcg 450300
ggtcataact cttctcactc tggccttagg gttcttcttt caacaatcta aaatcctttc 450360
ttcatttgca aacacttatg tgataatatt cctaacaaag attccgtttg acttgaccgt 450420
aggacatcgc gttcctcaat gcaatggaaa actaggagcg cggaagcgat gaaagcatgc 450480
ccactttcgc cggctaacac aatggatcaa tacaggggaa actggccgag aagcctaagc 450540
tagctatcag ctgccctagc gaacgaagtc tagtcttctt atcgagatga gcatgagtgg 450600
tcaagccctg caatgagatc atgcgcccta acctaagcct gggctactgt tgtgtgttcc 450660
gatccttcta gtgagagctt gtgaccatcg cagtgaccgc agtatgctta atcgactgtc 450720
tctctacctt cttgatcgtt gcatcacaag ttcgcacgac aagccgcatt gtgcactcaa 450780
gatgatgaat gcctttgaaa gatagaggat ttgaacctgt aatgtgtacc taagggctag 450840
atacacagat gccttcctat cttccttctt tactggacca atcgaagact gaaaagacaa 450900
agagatttcg cttagccaat gcttactgat agactagatg gagagcctgg tgcaaggtgg 450960
gaagactgag tgagaactag ccctttgagg agctctctaa gctgtctaac tctctattac 451020
cataggcaga gggaaaccag gttcaatagc cggatagagt aagaaaacaa gaaatttgac 451080
gatcaactat gtaaaccccc cgaaggggga aggtaagccc gccgctgatc ccgctttacc 451140
ttcgcctacc gtgaaaagag agtcccctat cacgataggc cctcccagct cccgaacgtg 451200
tctttctatc aatcgagaga ggtacataaa agaagagcaa ctaaactgtg aaactaaaag 451260
catgggaaaa agaaagcggt gaaaagcata catctactaa ggaccctcat actagaagac 451320
atagtttata ctatcgagaa aattacagag atcttctaca agccaactcg aacccccccct 451380
taaaagaaca tcgtaataga tatcttggag gtgtcctgga atttgaaaag cctcgtctcc 451440
cataacagcc tgaacaagat ctgctatgtt ccactccgga ggtaattccc tacctctgag 451500
tcgaagcaac tccgcgctat tttggcagat tctatcaaat acctgttcta actcaggtgg 451560
agcgctttgc gcgtccgacc tagttgagga aagagtggaa gtgctactag cagaagggaa 451620
cgaagaagtg gaactttgca aaaagtgaag atcactaggg gtaggatctc catagagtat 451680
tacagcatta tttcgaagaa tcatttggtt tggttcattc tttcactgct ctgctccccc 451740
aaaaaaagaa gagagactga atttcttcca ccttccctgt acgagtagtg aagaagtata 451800
gagcacttta gttggttgtt gaccaacgga aagcatggga gaaaaaaaga tgcacaaagg 451860
aaaaggagtc tcattaacag ctgaatgtgc caaactagta gcccgaaata gagatctgat 451920
ttaaaggacc aggtacagcg agttcgatcc attaggttct tttttttttt cagaaaagaa 451980
acgagagaca agaaaacatc tttgattacg attaaaagga acaatctcaa atagaccaag 452040
atccaatttc gggtcatttc ttggtgaaca tgatctgcca taatctcttc gatcccttca 452100
tttatgtgcc agaatagaga gagatttggt aggaaagtgg aagagacctt tttgtatatg 452160
ataatcaaag ggagtgggaa agctgcagta attctttgga aaagcccggt tctctttgtc 452220
ttcgaacttt cattcctcaa tccactgatt ccttccttca tatacctccc caccaataga 452280
tagagacaaa tgggaataac cgaaccacgt ctacaaaatg ccagtaccat gcagctgctt 452340
caaagccaac gtgatgctcc ttggtcagat gaccaagata ttggcgaatg ccacatatga 452400
tcaagaaaat agtacctata atcacatgaa aaccatgaaa gccagttgct aagaaaaagg 452460
tagaaccata aatactatcc gaaatagtga agggtgcttg ataatattcc attccttgaa 452520
agcctgtgaa tactagagcc agtgaaacgg tagctactaa agcgtaaact gctcgttttt 452580
ccttccccgc gagtatagca tgatgagccc aagttacggc agctccggat gaaaggggaa 452640
taagggtatt aagaaaaggg atttcccaag gatctaaaac tgcaatccct ttcgggggcc 452700
aaatacctcc gatctctacc gtaggcgcca aggaagaatg agaagaagcc cgaaaaagag 452760
caaaaaagaa cataacctcc gatacgataa acagaataaa accatatcga ggtcctaatt 452820
gtacgacttt ggtatgatgt ccttcgaacg tggattcacg tagaacatcg cgccaccata 452880
cgaacatggt atataggata aatatgaggc ccaaactgag aagtgttgca ccccccttgaa 452940 atgagtgcat gtacatcaca cctcctacgg ttgttgccaa agctccgagt gaacccgaaa 453000
taggccatgg acttggatct accaaatgat aagaatgcct ctgagattca atcataaacc 453060
actttgcctc ggttctatgt aaaccccccc ttcaccccca cccccctaaag tagtaaagta 453120 aagaagggct ctttggggtc ttattttctt tctatctgac aggacaaaca aagaaatagg 453180
aagggagggt tctttcattc cattgataga agtctaacta gaaaaagact ctctctatta 453240
ctttgagaag agaatcgttg gtttgaccga cgaactacgt gggaaaatag accttctttc 453300
tttgatttga agcaagattt ttggcaagta acaattccat tcagttcgct ttcggaaaac 453360
ttgctggtcg cggattagtt cgttctgcgc cgccagcggc ctcaactcaa aggcgcaggt 453420
tgaactctct ggttgaggct gcattcattt attcatattc aacttgacac gtgggaaggg 453480
cttactctac tagtggctcg gcttggtctc gctcccttcc cgcactattc ctccccacta 453540
aaaagagcga ttgagaatct cgagaacctt tccgaacgtc tgtcttcgcg gggcgattgg 453600
aaaagaaagg agtcttcaat tcttttactg ccttccattc cactattttg atcgaattaa 453660
ttgctcttcc gaacgaccaa gtcataatga gattaaaaac cgatgcttcc ttggccgtgt 453720
ggaacatgga ttagcattat gtcattccta caagtgatga cccacccagg attgctatgt 453780
acggacttag agatcaaata taatatgttt ctttccattc ctcgtgagcc acttatttct 453840
ccgaaacaag agattaaagt catcttcctc ctttttccca agaagtcgac ggccttacac 453900
cattgggata cttcgaataa acttgagtac atataggaaa caccggtgct aaaacctttt 453960
ctcaagatat cttccaaact gttggggtcg ttgctccgga tcttgttctc ccggtgtgaa 454020
accagttggt tccgtagttt tagaattctg ctgatcccaa gtactccatc tccatcattg 454080
catataggaa tatagaaagt aaagaggaaa aggcatgacc agaagaattg tgtgaaataa 454140
gtgaatttat ccagttgagg cattcttgat tgattgagac aaaacgattc cctcaataca 454200
gcttaacccc gtcaagcctg tacgagtagt gaagaagtat agagcacttt ggttggttgt 454260
tgaccaacgg aaagcatggg aaagatcact cctaactaag cagtcaagtg aaaggagccc 454320
gcttacccac tccccttcc ccccatcgct aggggcctcg ctcatcacat cagtctaaca 454380
tgagctactc ttccatttca taaacgatca attggaaaaa aaggactttc cttttccttt 454440
ctggtggaaa aacgaaagaa aaggtgttcc ccttattgt aatgctccag ttgaagtgct 454500
tccactcttg aaagcagagc tttagaaaag ccaactgtcg cattattcaa gtgaaggggt 454560
tcaatatagg tcgaaaacat ttcatcggac agcgtttttt ttcgacctat attgaatagg 454620
tatcgcaatt gttcgttaat atgtcttaac agacagtccg gcgctagttg attctcggga 454680
agagaaagcg ccgtttccca ttccggcttg gcttggaaaa ggaggtagag gcttccgagc 454740
ttgatgggca ggaagttcca gacgaagaca tcatgctctt ccggaccccg ctctcgatct 454800
ccaaagccaa agaaagaata ccaagaagaa tgagacttgc gcccccctcc catccaaaag 454860
ccctactaca aaataaggcg agggatcgcc tccccacaga gaacccaacc ctttcaagta 454920
gggcctgaaa gaaatcaatt gaagccattt tcaaacaaag aagataaaat aagaaaacta 454980
tagtggctag gaacagtaac ggaatacggc gttttttcat aatcgaaccg agatgcatca 455040
tattaggtaa gatgtatctt cattcgctct gcgagcagag cggtataccg aaaaaaagaa 455100
aagccttatg gccactacct tacttaagca attctgctta ttcttattct atcttagaat 455160
aagaataagt tccccctctc cggatcccga taagaatgga agatggtgca agatcgaatc 455220
ctgttacctt acttcgaatg gaatcttagc ccgcctcact tgctttcttt actgcataaa 455280
taagggcata agcgaagtca agggatttcc gtctaactag tgtctgagag taagcaagct 455340
accttcattc aacagatttg tggttgagtc aataacatgc tctgctctgg gtcgggaatc 455400
tttgctcttc tcttttgcat ttccgctgcc tgcctaaagg cttattgcta gctcttaggt 455460
tctctgtcag tagagtgatt gccaaaacct aggtatgttt tcggagaata ataagaagag 455520
acggttgtag cttttagaga ctatcctctg cagctgtagc tacgtggaag ccagctgctt 455580
aaagacaagc cccctaacca ttctgctatt cctgccctaa agcaagggaa tccgctctga 455640
cccaccaccc tggtaggaat tgccagattt acagtttatg aatccttgta atacaagttc 455700
tttcctctaa cgatggctac gaactacgcg aactgaactg tcaaggcttt caaaccaaga 455760
ctgagaaagc tcaatcaaaa aagagtattt tagtggaatg gcttaacgaa gttactcccc 455820
atacgagacc ggaaaggaag ctagcgaacc tagggtcaac accaaggtag gggcgaaagg 455880
gaaaagaacg atgtttgatg tgaacggaag caagcatttc gctaagaaag caaaacagga 455940
agcggcgata gcaaacatta ccctgactca gaacaatatg ctcttgggag acatgaagca 456000
caatcaacct ctctacctta agacttctaa catggtcgat tctagataga gcacggtaac 456060
ccacaacccc ctactctaca aaacaaagag tggaaaatct cttcataggg tactgtagct 456120
gtacagccat agtaccatag ggatggtgag agttcataag agcccgaatt tagataggtg 456180
aaagatcctt actcaaatta cgaaccctga acctctttgc gaattcacag ctgaaccttg 456240
atgggaaatc atagatttct gataggaaag aaaaagccca attacccaca attttttcat 456300
atacacgagc gtcctcctac attgtcccct agtacagcat acttaataaa gcggtttcca 456360

-continued gggtcaacct gtttaactgc atgccagacc actaagtgat gagaccatgc aaacaaaggc 456420
aacgaggagc gctagccgga actggacaat gggtgggtgt ccaacaaaca ttccttagct 456480
aagaaggatt cattcaccgc agcttctctt actagcagat gaaactagca acatcacatc 456540
atatagaata ccgattgaca ggcattccag tctatcttat agtttatgtt gatgatctca 456600
ttgtttccgc gagcgcatcc ttcatttcca agctttattt ctatcgtaat ttttccatgc 456660
ctattcattc ttttttgggg tgtataatat aaagccacgg agcgattcag gcatctatct 456720
tattgtattg acgcaattgg aagatcagga tttctcccta ccgctcaagc gggatcagat 456780
cgggctttag cgagaacagc tgtaattgaa tcgggaacgg aaagacttca cttcaactca 456840
ataaatgacg tctacttcgt aagtgctaag gcaaaatata tcaccgaaag gaaaggtgat 456900
aggggagcct agccatttca ctctacctga gtaataaagt ggaaaccccc ctcacgatcg 456960
attaaaagga aagtcgccca gagatatttg ttcaaatcca attcgtgaag acagagtaaa 457020
ttcaacaaat ctaagaaagc aagtcctagg cctcactatc tatcaatcaa gaaggtaaag 457080
gagagaaggt ttgattgaaa gtagtacgtc tgcagggatc tgtcgttaac gatttgaccg 457140
ggacacatcc aattgaaagt ctaatcccaa cctctttgga aggagctcca aaaaagactt 457200
gacttcagag cggggaatct tcctacaagt gagcaccaag tcaaatgtat gaaaaaaggg 457260
ctatacctct gcctagacaa agaggacttt aagacagcct cgtaggagac attggatgta 457320
accagccttc aaaggcggag gagtcaaaag cgactttcga ttcaaattag agaaatgctg 457380
agctttatcc gcttcaattc attaaggtat tattttttcc ttctaaatag tcagagtggg 457440
aactcaaaag caagaactct taaccatcat tccttaactc taaagggcgt gaatgtgtgg 457500
atcaaggaag aagggtggga tagcgcccga ttgattgagc gtcttacagc ccgtcatgca 457560
agctagcaaa gccagcgcag aagcagccct ttccatcgtc tttcgctgac cctggttcta 457620
tcaaaccagc ttcttcaatc ctggtgtgaa cttcttcctg ccttcttacc caagagctct 457680
gattccgctt aaataaaagc agcccttctt ccttactctt tcgagtaagc attttgaaac 457740
ttccttaaac atctgcttca aagagctaag ccccggtctc actgaactgg gtcaaagaac 457800
taccttcctg gagctacctc cttacttaga tcgttcgttc cccaattcaa actcggatca 457860
gttggcaagt ggattccatg cctgggtacg aaactcgaaa ttcgatcttg aaagagtgaa 457920
atctagcctt ttgtctttat cctttatagg tctgggctaa ttcttgaaag cagcaactcc 457980
tacacctacc gaaactttaa cagaacaact acggattctc accctcgagt caggagctcg 458040
ctttcaatct ctaagagccg attcgatggc atcttttttt atgatctttc tagttagcac 458100
gtagtgggaa tagtccctca tcgacacggg aagagagctt caagcaaaaa gggcttgtgc 458160
aagcaagtga cactttactt caagcgaata gtgctgcctc actttcttta gctaggctga 458220
gaagccgatt cccgacatag actatttcct tctcatcgaa agatgcctaa gaccttttca 458280
ccaaaacaaa acctctaccc cctactctag tcagctttct atctctttct ccaaccttcg 458340
atgatcctcc tgcaggcaaa tcatcgaagt caagaagaag tgatgggcct gatcttccga 458400
tatcgatatc tgatccctaa gctgagctcc aaagtctaga tttcttccta aagctaaagt 458460
aagggcaagg ccccggtcgg ttctcccttt ctttctttcc tggttctctg ttctctagtc 458520
gtataatcat accattctgc catactattt tcagaattca ttccacgtgg aaaatcgtct 458580
agctagggaa ctcttcatca gacgatttct catatgatta ttttcgtgaa ttcgacgtag 458640
aagaagttcg ccttgcctcc ctttattaag tactgggcta agggcggacc ccccttcta 458700
tctgggtcct agtctcgtcc cttgttagtg caataaagag aagtgtatta aattccaatt 458760 ctttttccgcc cttcctaacc ttgctcgatc caatagcccg atcctagccc actcaccttt 458820
ctccaagatt gaagttagaa ctaggagtcc taaaatctta atgaaaagga gcttggcatc 458880
catgtgttcg agaggtagaa aacgacccct gtggcggggt ttaccaggta ggtataattc 458940
aatgggaccc tatcccgtcc tgtggtcctg aacaaaggtt ccatcctaaa aagaaaagag 459000
agccttcacg gaaaaactgt tggaacgaga tctctcatac aaaaagacct gaactaacta 459060
ctcgctcaat gcgcattgaa attctaatga atgcccttat ttagcatctt tgagttgagc 459120
ttagccctct tcctatccta aatccctaga atcataagga acgattgatg gttgatctgg 459180
caattctttt tagtaattag ttagtctatc aagcagaaaa ctatgactga ggaagtctca 459240
gggagggcac cccctttttaa ggtaattata tgccatttgt ggccccccac gttagaactc 459300
tctttaaccg gaatctttat ggctaaacct tttttttaa ccgatttaat cgtaagttgc 459360
atcctcaact tctggacggg ttcgagagtt tggttcgact gagactgatg tctcatcggg 459420
ttcagaaggg gatgggaatg cagattttga tgcctcgtat cgtatgacaa agaagagagt 459480
ttttacaaag ccctagagct agagcttgtt gagaaagtag ctttgaagat gggcttccta 459540
tgggaaatag ggaagtttaa agcgataaca aaggccttag ggaataggat ctctttctgc 459600
gtctactgat gcttttgaaa aaagcctttg gtttggcttg tttaattgat tcgtacgtaa 459660
tccgagagct tcatacgtgg gatttttttg gcaaaggaaa gtcaagagaa aaggtggtag 459720
ctattctagc aagtcttctg tggaggagta gcactaggct agtaacttat tacactagtc 459780
tcgattcctc aaggttgtac gagctgtaat agtagttgaa aaacctcccg tcccgagttg 459840
gcttaagcca tgcctttact aaagaattct cgccatctct gataaaatct ggtgtggagc 459900
ccaggctagc caacaatgag aaatgccttc ctcttttttg ttgatttagg tgacgtagtc 459960
ttatccgatg aatggcagtg agaaggcgga aaaggtcgta aagggctaag ctaagggagg 460020
ttggcattcc gaagtcaagt gggcttttct cacaccgcat ggggtggttt cctacgcata 460080
tgcaacaagc tcttatttgg atctccctaa tctagagggt tctcacgcca aggttccttt 460140
gtttcgggca agtccaatta caaacaaaag agaaggtcgg tcccgtccca cgggttaggt 460200
gcttagctga aggtggaagt ccaaagctta ataaggtgga aggcgaagcc gaggcaagag 460260
caagggttga aagacaagag agaagaattc aatctcccct atttgttcca ttctcaatgg 460320
ttggccagga tgctttggtt tatcggatcg atcgcagtgg tcaagtgcgc tggacgacac 460380
ggcattctcg tttaaatagt accatcgact ggagaccgga ttgctaccag agagaggaat 460440
gactataggc acggaactta cttttgaccc tttctttgcc ccttggttcg ctagctgact 460500
tgccagcgct tggattctcg aactctaaga gcggatttca ggaatttgtt cacatccgat 460560
tcgatggcat ctgtctgctt tccacccttt gcaagcgtgc tactgactcg atggacaaac 460620
tcaaggaact gctttgcctc taggttgact tggatcacat catcctgaac ttttgatcgt 460680
atgtcgtcca gctttgttgg tgctgtgggt gtcagtcttc taatgtcagc tctctggtag 460740
gccaatcgat ctctgcttga ttggccgtaa ctgcatgatc gatctgacga agattcccat 460800
gtagatctat gaaactacag ccgaaccaaa tgggaatcct aggtataggc aaaggtggga 460860
gggatgagag agcaagctgg cgtgggggca agggcaataa catccgagca aggcaagccc 460920
tagaaatcgg cagggtatga tgaaaagctc tcaccaggat tgtgtttcca gatcgattga 460980
tcaacatttc cctctttgtg atagctgaga agcgttctaa atacttttcg acaaggagag 461040
agttccaaca aagacgcgat cttctgcaac ggaagctaac gtggatgttc caccggcacc 461100
ggggttcgaa ggtcacgatc atcggagcaa tcaacggagt gtttccttca gtcagtaagg 461160
ggagaaatcc cttattctaa ggaaatgttt ttggtaagaa agcctgtcct agaaggaagc 461220
ctgcccgcaa gaactctggt taagtgccct ccaccgcaac cgacataaca taaagaaaga 461280
aggaaccggt ccccatggtc gccttcgttc gtaaggtaaa aacgaataga cattcttgtc 461340
ttggcccagg tgacgcacat gaccggtcaa gaaagttctt atttttggat ttcgctttcg 461400
ctacggctac agtcaagtgg ctcccccttt acaagactcc ctcccaccag aagaaagatt 461460
gatcgctttc ggtaacccag ggctccattg cgtgtgctcg aggtagaagt tttttttttt 461520
tttagatgtg aatgggaaaa aattctgacc accggtagcg aatgcttttg aaaagatttg 461580
aaggtagaag gctgtttcag tctagctccg gaagcattgt ctgaagtaat aagaagaagg 461640
aagtgaccac tctgaagttc tttttctttg attccaatga ccgatatcgt acaagacgga 461700
agtcatgagc gatagcgaag ataggtatag gtcttagatt agagtgccag tgcccctcgg 461760
gaaaaaggaa acctagctat tctttttgtt cttaagaaag gttgcggtaa gggtgggcgt 461820
caatcggcca ttcctccatc ataacctttg gaactctacg cccgcgcttg gttctcatgc 461880
actaggtgca cccgagtcga ctatagcact aaccaacttg ccattgatta caacatcgac 461940
ctttgaatcg tatcatccat ggtgagtggt atcatatata agtataagag caacctttag 462000
gaaggatctt tctctctaac tagaaatttt agaagaaagc gtagaaaatc aaggttttga 462060
ttcaacaacg gataaccccg aaaggcaaaa aaactcgaac tgaatcaaag tacaaggctg 462120
acgtacttat ataagtgatg aatatgtagt taatcagata tttccatttg gagactgatt 462180
catgtattct atctttatct accgctacgc cctggaaaag cagtgaaact tctaaagctt 462240
attagcacag aaaaaaggat ttgaataccc tagtttataa gggaatcacc aatccctcta 462300
tataagctat cgttcgaaac tacattcatc agttgtccaa ggaggcaaac atggaatgga 462360
gatagaaaga ttcagtcggt ctatccctgt ggatcggtat atgcacctat agttgagttg 462420
agttggttga ttcaatccac aacaccgcca accagagggg aatcaaactc gcttagcaaa 462480
gtgcaaaaag aaaaggaatc gaaagtatga atatcataaa gcagcagctg ctcccctagc 462540
cttctaaaga gctagtcccg aagtagcaac agagctcttc ttccctatta gtctatgaac 462600
tatggatgct actaactagc aatgtatata ggtaagctac taaccttatg gatgatatct 462660
actctttgct gtataagtct ttctcattcc tcttctctta ataagcctag cagctttctt 462720
ttcttcactg ggaaatatcc ataggaataa gaatctctat atatcaaaga tcttaaaatc 462780
cctctacaac gggaaagcga cggaaaagcc gtttcaccac cgaagcgaac taccttaggc 462840
caatgggaaa tgccagagta gagcgcaaaa gaaagggatt ttcaatccac ttcaggtggg 462900
actaagaaaa gaaaatctga acctgggaag cagatttaca ggttgtactt ttcccgttag 462960
tccataagga tcggacaccc atattccagg accatacaag cctgttacat gaaatgcacc 463020
aaaaccaaag caagccaagt agccttccat taatagcctc tctttcaggc tcttctgtgg 463080
gaatactttc aatcgttggc attcccctag gcggagacag ttttcgcaat agctagattc 463140
tcaagctctg attcacttgc acccttcttc ttgaaatggc attagctgct ctttctattc 463200
catcaaagat ccaagcagga gattctgtaa gaaaaagatc gcttaggccg acataacata 463260
tgtcacttcc acttccttta ggagatgttt ttcagggacc aaagagaagg cgatttggtc 463320
aaattgatcc tttttcattt ccatgccatg acatgagaca gatctctcgc aactagttcc 463380
tttgctgatg aaatgcctta gtcagtagcc tgccttacga ctgaaaatgg ttcacgttca 463440
cagccctata gcgctagtct tgctaaagga atggtgaaga aaatccccct atagctagtg 463500

-continued

```
agcatcttta cttttagtag gtaaagagcc tcaatgaaag gggaattgcc gccctcaagg 463560
gagaactaag atagtggttg attgtctacg gtctcgttac aggatgaagc tacagataga 463620
acagatagag tagaagagtc ggtggggctt acctttcttg ttgaactaga gtagagggtg 463680
agcagagaaa tcccttgaag aaagagctta ttccacctcc tggatcggta agggcttcgg 463740
ttccatcaat tcgatgttgc tcgataagca ggattacgat tctagtttag ttcatcagat 463800
ctacgctctc aggcacaccc accaacgtaa gacaggatca aagtccaata gaatagctcg 463860
ggcatgaata aagataggaa tcgacgagac cttttcctac ttaaaacaat tcgaaatctc 463920
gaacccctgg tatttcattg aggagacaag acaaataggg acctaaaaac gccctgagtg 463980
ggacgccccc ttcgggctga gatgctttcc ggacatgcta ttctttttat ataagacttc 464040
gctacacggc ttagccgacc tttccgagag aacttcaaga catactttga gtattctata 464100
aatatcctaa gtcgagttat aggccaaatg ccctaccaga tcagtctcga agaaatagca 464160
aaaggatggc tacgggatcc cactctacct ttccaggatg aacttccctt cctgcttctg 464220
tagcactgga agtgacccgt gtttggatct aggattcaat tcatccagct ttcatttaaa 464280
gtaaactctt taagataagg ctttttccct cgcctaagtt atgaatctat tgcaattgaa 464340
aactccctcg cgactgattt gccatttgga tcgatttgag atatagagag ttgtgtcttt 464400
ctaacgctaa cgatgctaag cttaagctct ttcctttagc ttaaacagga atagctcttc 464460
cagcttgttc gttgcactca ccctcaccct gaccttctcc cagaaacaaa ggaaaaaacc 464520
taacattcgc tccttcaccc gcgagggatt ctcttcatcg ctactaacta gaaaaagttc 464580
ctgggctaag aagagctccg ttaaaggata tctatagctg cggagaggga agcgcttaga 464640
agctatgctc ttcttcagct ttctaagctt ctactttcgt gagctcttat tgctctttta 464700
gtcgagaatg ctaccattca tccctaaaag aggaagatag tgaatcagtg cttactttag 464760
aggaagagta gtttagctag acagattata tagagaaagg gaaggggctt gcttactcgg 464820
aagagaaagg actgaaggtg aatgtattca tggatatgat tcgattctct gatcggagaa 464880
tgtaaggtat gaactcctaa gaggaggaga gggaagatct acatttttaa aagaaagatg 464940
tatatcagac attatgctgt gcttactaag gtctttagtc tttactttag atagaggttc 465000
atctgtcctt tctttcctct agcaaagcct acttcctgat taaggatttg aagcttcatg 465060
gccttctttt cttcctcaga aacacagaaa gaaagattta aaaaagcaac aaaatctgta 465120
tttaacacaa aacggaaact aaggagagag ctggtcttac tgttagacac agtaaacata 465180
ggagacacct tatacacgtt aggaatttag gaagagtagt accgatagcc ttagtatgag 465240
ttgaaccttt cttattctta gtcctcttat acaagctagc tctcttatcc gcttgcctct 465300
tttaatgaag aagggttggt ttaattgata gctttggaat aggtagtcct atggactgct 465360
cttttcttat gccccggagt ggcgagaata cgaagctaga tcagcaggaa tgacagcggt 465420
ctcttccaaa agtgggtaca ggactcggat cccatttcca aggtgaattg gaggagaaat 465480
ggatactggt attatagttg ttgaaagacc tattaattac atgccaaaag agcaaaagtt 465540
gaatcatcgg cttggccacc ttatcctttt atacaaaaat tttcyttgat gatataccgy 465600
ycraggsgaw ttstcwcgac ntcctctgcy agamaaagaa aahagaaacc cvscagbtsc 465660
cwcctcwsat camwgaaraa accaaawcac yacamwavac haaccgcaaa ahgctcccac 465720
tcbtstdtgt yctmgratsc tgcttgtatt caancttatr tttnygkaan cctctnchdc 465780
tyswtmwac                                                         465789
```